United States Patent
Thastrup et al.

(10) Patent No.: US 6,518,021 B1
(45) Date of Patent: Feb. 11, 2003

(54) METHOD FOR EXTRACTING QUANTITATIVE INFORMATION RELATING TO AN INFLUENCE ON A CELLULAR RESPONSE

(75) Inventors: Ole Thastrup, Birkerod; Sara Petersen Bjørn, Lyngby; Soren Tullin, Soborg; Kasper Almholt, Copenhagen; Kurt Scudder, Virum, all of (DK)

(73) Assignee: BioImage A/S, Soeborg (DK)

( * ) Notice: Subject to any disclaimer, the term of this patent is extended or adjusted under 35 U.S.C. 154(b) by 0 days.

(21) Appl. No.: 09/417,197

(22) Filed: Oct. 7, 1999

Related U.S. Application Data

(63) Continuation of application No. PCT/DK98/00145, filed on Apr. 7, 1998.

(30) Foreign Application Priority Data

Apr. 7, 1997 (DK) .............................................. 0392/97

(51) Int. Cl.$^7$ ................................................ C12Q 1/68

(52) U.S. Cl. ........................ 435/6; 435/366; 435/320.1; 435/325; 435/354; 435/357; 435/358; 435/365; 435/367; 800/13; 536/23.1; 536/23.5

(58) Field of Search ................................ 800/13; 435/6, 435/366, 320.1, 325, 354, 357, 358, 365, 367; 536/23.1, 23.5

(56) References Cited

U.S. PATENT DOCUMENTS

| | | | |
|---|---|---|---|
| 5,874,304 A | * | 2/1999 | Zolotukhin ................. 435/366 |
| 5,958,713 A | | 9/1999 | Thastrup et al. |

FOREIGN PATENT DOCUMENTS

| | | |
|---|---|---|
| WO | WO 91/01305 | 2/1991 |
| WO | WO 94/23039 | 10/1994 |
| WO | WO 95/07463 | 3/1995 |
| WO | WO 96/03649 | 2/1996 |
| WO | WO 96/23898 | 8/1996 |
| WO | WO 97/11094 | 3/1997 |
| WO | WO 97/20931 | 6/1997 |
| WO | WO 97/30074 | 8/1997 |
| WO | WO 98/02571 | 1/1998 |
| WO | WO 98/30715 | 7/1998 |

OTHER PUBLICATIONS

Sakai, N. et al., "Direct Visualization of the Translocation of the γ–Subspecies of Protein Kinase C in Living Cells Using Fusion Proteins With Green Fluorescent Protein", Journal of Cell Biology, vol. 139, No. 6, 1997, pp. 1465–1476.

Schmidt, D.J. et al., "Dynamic analysis of alpha–PKC–GFP chimera translocation events in smooth muscle with ultra–high speed 3D fluorescence microscopy", FASEB Journal, 1997, p. A505.

Gerisch, Günther et al., "Chemoattractant–controlled accumulation of coronin at the leading edge of Dictyostelium cells monitored using a green fluorescent protein–coronin fusion protein", Curr. Biol., vol. 5, 1995, pp. 1280–1285.

Sidorova, J.M., et al. "Cell cycle–regulated phosphorylatoin of Swi6 controls its nuclear localization", Mol. Biol. Cell., vol. 6, 1995, pp. 1641–1658.

Htun, H. et al., "Visulation of glucocorticoid receptor translocation and intranuclear organizationin living cells with a green fluorescent protein chimera", Proc. Natl. Acad. Sci. USA, vol. 93, 1996, pp. 4845–4850.

Carey, K.L., et al., Evidence Using a Green Fluorescent Protein–Glucocorticoid Receptor Chimera tht the RAN/TC 4 GTPase Mediates an Essential Function Independent of Nuclear Protein Import, Journal of Cell Biology, Vo. 133, 1996, pp. 985–996.

Ogawa H., et al., "Localization, trafficking, and temperature–dependence of the Aequorea green fluorescent protein in cultured vetebrate cells", Proc. Natl. Acad. Sci. USA, vol. 92, 1995, pp. 11899–11903.

Sakai, N., et al., "Translocation of γ–subtype of protein kinase c–direct visulation in living cells using fusion protein with green fluorescent protein", Society for Neuroscience, vol. 22, 1996, p. 371, Abstract 150.1.

Sakai, N., et al., "Translocation of protein kinase C–γ and –∈– Direct visualization in living cells using fusion protein with green fluorescent protein", Japanese J. Pharmacology, vol. 73, 1997, p. 69 (Abstract of meeting held Mar. 22–23, 1997).

(List continued on next page.)

*Primary Examiner*—Janell Taylor Cleveland
(74) *Attorney, Agent, or Firm*—Birch, Stewart, Kolasch & Birch, LLP

(57) ABSTRACT

Cells are genetically modified to express a luminophore, e.g., a modified (F64L, S65T, Y66H) Green Flourescent Protein (GFP, EGFP) coupled to a component of an intracellular signalling pathway such as a transcription factor, a cGMP- or cAMP-dependent protein kinase, a cyclin-, calmodulin- or phospholipid-dependent or mitogen-activated serine/threonin protein kinase, a tryosine protein kinase, or a protein phosphatase (e.g. PKA, PKC, Erk, Smad, VASP, actin, p38, Jnkl, PKG, IkappaB, CDK2, Grk5, Zap70, p85, protein-tyrosine phosphatase 1C, Stat5, NFAT, NFkappaB, RhoA, PKB). An influence modulates the intracellular signaling pathway in such a way that the luminophore is being redistributed or translocated with the component in living cells in a manner experimentally determined to be correlated to the degree of influence. Measurement of redistribution is performed by recording of light intensity, flourescence lifetime, polarization, wavelength shift, resonance energy transfer, or other properties by an apparatus consisting of e.g. a flourescence microscope and a CCD camera. Data stored as digital images are processed to numbers representing the degree of redistribution. The method can be used as a screening program for identifying a compound that modulates a component and is capable of treating a disease related to the function of the component.

88 Claims, 12 Drawing Sheets

OTHER PUBLICATIONS

Fulop, et al., "Cellular distribution of protein kinase C isozymes in CD3–mediated stimulation of human T lymphocytes with aging", FEBS Letters, vol. 375, 1995, pp. 69–74.

Bastiaens, P.I.H., et al., Miscospectroscopic imaging tracks the intracellular processing of a signal transduction protein: fluorescent–labeled protein kinase CβI, Proc. Natl. Acad. Sci. USA, Vo. 93, Aug. 1996, pp. 8407–8612.

Sano, M., et al. "The activation and nuclear translocation of extracellular signal–regulated kinases (ERK–1 and –2) appear not to be required for elongation of neurites in PC12D cells", Brain Res., vol. 688, 1995, pp. 213–218.

Godson, C., et al. "Isoform–specific redistribution of protein kinase C in living cells", Biochimica et Biophysica Acta, vol. 1313, 1996, pp. 69–71.

Farese, R. et al., Effects of insulin and phorbol esters on subcellular distribution of protein kinase C isoforms in rat adipocytes, Biochem, J., vol. 288, 1992, pp. 319–323.

Khalil, R. A., et al., "$Ca^{2+}$–independent isoforms of protein kinase C differentially translocate in smooth muscle", American Physiological Society, vol. 263 (3 Pt. 1), 1992, C714.

Westphal, M., et al., "Microfilament dynamics during cell movement and chemotaxis monitored using a GFP–action fusion protein", Curr. Biol., vol. 7, 1997, pp. 176–183.

Toda, T. et al., "The fission yeast sts 5+ gene is required for maintenance of growth polarity and functionally interacts with protein kinace C and an osmosensing MAP–kinase pathway", J. Cell Sci., vol. 109, 1996, pp. 2231–2342.

Webb, C.D., et al., "Use of Green Fluorescent Protein for Visulation of Cell–Specific Gene Expression and Subcellular Protein Localization during Sporulation in *Bacillus subtilis*", J. Bacteriol., vol. 177, 1995, pp. 5906–5911.

Adams, S. R., et al., Fluorescence ratio imaging of cyclic AMP in single cells, Nature, vol. 349, Feb. 21, 1991, pp. 694–697.

Blobe, G. C., et al., Protein kinase C βII specifically binds to and is activated by F–actin, J. Biol. Chem., vol. 271, No. 26, Jun. 28, 1996, pp. 15823–15830.

Chalfie, M. et al., "Green Fluorescent protein as a marker for gene expression", Science, vol. 263, Feb. 11, 1994, pp. 802–805.

Cossette, L. J., et al. "Localization and down–regulating role of the protein tyrosine phosphatase PTP2C in membrane ruffles of PDGF–stimulated cells", Experimental Cell Research, vol. 223, 1996, pp. 459–466.

Debernardi, M. et al., "Single cell $Ca^{2+}$/cAMP cross–talk monitored by simultaneous $Ca^{2+}$/cAMP fluorescence ratio imaging", Proc. Natl. Acad. Sci. USA, vol. 93, May 1996, pp. 4577–4582.

Waggoner, Alan et al., "Muliparameter fluorescence imaging . . . ", Human Pathology, (May 1996) vol. 27, No. 5, pp. 494–502.

Mochly–Rosen, Daria, "Localizing of protein kinases . . . ", Science, (Apr. 14, 1995) vol. 268, pp. 247–251.

Giuliano, Kenneth A. et al., "High–content screening . . . ", Journal of Biomolecular Screening, (1997) vol. 2, No. 4, pp. 249–259.

* cited by examiner a)

| [forskolin]μM | $t_{1/2max}$ / s | $t_{max}$ / s |
|---|---|---|
| 1 | 115±21 | 310±31 |
| 10 | 69±14 | 224±47 |
| 50 | 47±10 | 125±28 | a)

b)

c)

a)　　　　　　　　　　　　　　b)

c)

d)

METHOD FOR EXTRACTING QUANTITATIVE INFORMATION RELATING TO AN INFLUENCE ON A CELLULAR RESPONSE

RELATED APPLICATIONS

This application is a continuation of International Application No. PCT/DK98/00145, filed Apr. 7, 1998, which in turn claims priority to Denmark Application No. 0392/97, filed Apr. 7, 1997 both of which are incorporated herein by reference.

FIELD OF INVENTION

The present invention relates to a method and tools for extracting quantitative information relating to an influence, on a cellular response, in particular an influence caused by contacting or incubating the cell with a substance influencing a cellular response, where the cellular response is manifested in redistribution of at least one component in the cell. In particular, the invention relates to a method for extracting quantitative information relating to an influence on an intracellular pathway involving redistribution of at least one component associated with the pathway. The method of the invention may be used as a very efficient procedure for testing or discovering the influence of a substance on a physiological process, for example in connection with screening for new drugs, testing of substances for toxicity, identifying drug targets for known or novel drugs. Other valuable uses of the method and technology of the invention will be apparent to the skilled person on the basis of the following disclosure. In a particular embodiment of the invention, the present invention relates to a method of detecting intracellular translocation or redistribution of biologically active polypeptides, preferably an enzyme, affecting intracellular processes, and a DNA construct and a cell for use in the method.

BACKGROUND OF THE INVENTION

Intracellular pathways are tightly regulated by a cascade of components that undergo modulation in a temporally and spatially characteristic manner. Several disease states can be attributed to altered activity of individual signalling components (i.e. protein kinases, protein phosphatases, transcription factors). These components therefore render themselves as attractive targets for therapeutic intervention.

Protein kinases and phosphatases are well described components of several intracellular signalling pathways. The catalytic activity of protein kinases and phosphatases are assumed to play a role in virtually all regulatable cellular processes. Although the involvement of protein kinases in cellular signalling and regulation have been subjected to extensive studies, detailed knowledge on e.g. the exact timing and spatial characteristics of signalling events is often difficult to obtain due to lack of a convenient technology.

Novel ways of monitoring specific modulation of intracellular pathways in intact, living cells is assumed to provide new opportunities in drug discovery, functional genomics, toxicology, patient monitoring etc.

The spatial orchestration of protein kinase activity is likely to be essential for the high degree of specificity of individual protein kinases. The phosphorylation mediated by protein kinases is balanced by phosphatase activity. Also within the family of phosphatases translocation has been observed, e.g. translocation of PTP2C to membrane ruffles [(Cossette et al. 1996)], and likewise is likely to be indicative of phosphatase activity.

Protein kinases often show a specific intracellular distribution before, during and after activation. Monitoring the translocation processes and/or redistribution of individual protein kinases or subunits thereof is thus likely to be indicative of their functional activity. A connection between translocation and catalytic activation has been shown for protein kinases like the diacyl glycerol (DAG)-dependent protein kinase C (PKC), the cAMP-dependent protein kinase (PKA) [(DeBernardi et al. 1996)] and the mitogen-activated-protein kinase Erk-1 [(Sano et al. 1995)].

Commonly used methods of detection of intracellular localisation/activity of protein kinases and phosphatases are immunoprecipitation, Western blotting and immunocytochemical detection.

Taking the family of diacyl glycerol (DAG)-dependent protein kinase Cs (PKCs) as an example, it has been shown that individual PKC isoforms that are distributed among different tissues and cells have different activator requirements and undergo differential translocation in response to activation. Catalytically inactive DAG-dependent PKCs are generally distributed throughout the cytoplasm, whereas they upon activation translocate to become associated with different cellular components, e.g. plasma membrane [(Farese, 1992),(Fulop Jr. et al. 1995)] nucleus [(Khalil et al. 1992)], cytoskeleton [(Blobe et al. 1996)]. The translocation phenomenon being indicative of PKC activation has been monitored using different approaches: a) immunocytochemistry where the localisation of individual isoforms can be detected after permeabilisation and fixation of the cells [(Khalil et al. 1992)]; and b) tagging all DAG-dependent PKC isoforms with a fluorescently labelled phorbol myristate acetate (PMA) [(Godson et al. 1996)]; and c) chemical tagging PKC b1 with the fluorophore Cy3 [(Bastiaens & Jovin 1996)] and d) genetic tagging of PKCα ([Schmidt et al. 1997]) and of PKCγ and PKC ε ([Sakai et at 1996]). The first method does not provide dynamic information whereas the latter methods will. Tagging PKC with fluorescently labelled phorbol myristate acetate cannot distinguish between different DAG-dependent isoforms of PKC but will label and show movement of all isoforms. Chemical and genetic labelling of specific DAG-dependent PKCs confirmed that they in an isoform specific manner upon activation move to cell periphery or nucleus.

In an alternative method, protein kinase A activity has been measured in living cells by chemical labelling one of the kinase's subunit (Adams et al. 1991). The basis of the methodology is that the regulatory and catalytic subunit of purified protein kinase A is labelled with fluorescein and rhodamine, respectively. At low cAMP levels protein kinase A is assembled in a heterotetrameric form which enables fluorescence resonance energy transfer between the two fluorescent dyes. Activation of protein kinase A leads to dissociation of the complex, thereby eliminating the energy transfer. A disadvantage of this technology is that the labelled protein kinase A has to be microinjected into the cells of interest. This highly invasive technique is cumbersome and not applicable to large scale screening of biologically active substances. A further disadvantage of this technique as compared to the presented invention is that the labelled protein kinase A cannot be inserted into organisms/animals as a transgene. Recently it was discovered that Green Fluorescent Protein (GFP) expressed in many different cell types, including mammalian cells, became highly fluorescent [(Chalfie et al. 1994)]. WO95/07463 describes a cell capable of expressing GFP and a method for detecting a protein of interest in a cell based on introducing into a cell a DNA molecule having DNA sequence encoding the protein of interest linked to DNA sequence encoding a GFP such that the protein produced by the DNA molecule will have the protein of interest fused to the GFP, then culturing the cells in conditions permitting expression of the fused protein and detecting the location of the fluorescence in the cell, thereby localizing the protein of interest in the cell. However, examples of such fused proteins are not provided, and the use of fusion proteins with GFP for detection or quantitation of translocation or redistribution of biologically active polypeptides affecting intracellular processes upon activation, such as proteins involved in signalling pathways, e.g. protein kinases or phosphatases, has not been suggested. WO 95/07463 further describes cells useful for the detection of molecules, such as hormones or heavy metals, in a biological sample, by operatively linking a regulatory element of the gene which is affected by the molecule of interest to a GFP, the presence of the molecules will affect the regulatory element which in turn will affect the expression of the GFP. In this way the gene encoding GFP is used as a reporter gene in a cell which is constructed for monitoring the presence of a specific molecular identity.

Green Fluorescent Protein has been used in an assay for the detection of translocation of the glucocorticoid receptor (GR) [Carey, K L et al., The Journal of Cell Biology, Vol. 133, No. 5, p. 985–996 (1996)]. A GR-S65TGFP fusion has been used to study the mechanisms involved in translocation of the glucocorticoid receptor (GR) in response to the agonist dexamethasone from the cytosol, where it is present in the absence of a ligand, through the nuclear pore to the nucleus where it remains after ligand binding. The use of a GR-GFP fusion enables real-time imaging and quantitation of nuclear/cytoplasmic ratios of the fluorescence signal.

Many currently used screening programmes designed to find compounds that affect protein kinase activity are based on measurements of kinase phosphorylation of artificial or natural substrates, receptor binding and/or reporter gene expression.

DISCLOSURE OF THE INVENTION

The present invention provides an important new dimension in the investigation of cellular systems involving redistribution in that the invention provides quantification of the redistribution responses or events caused by an influence, typically contact with a chemical substance or mixture of chemical substances, but also changes in the physical environment. The quantification makes it possible to set up meaningful relationships, expressed numerically, or as curves or graphs, between the influences (or the degree of influences) on cellular systems and the redistribution response. This is highly advantageous because, as has been found, the quantification can be achieved in both a fast and reproducible manner, and—what is perhaps even more important—the systems which become quantifiable utilizing the method of the invention are systems from which enormous amounts of new information and insight can be derived.

The present screening assays have the distinct advantage over other screening assays, e.g., receptor binding assays, enzymatic assays, and reporter gene assays, in providing a system in which biologically active substances with completely novel modes of action, e.g. inhibition or promotion of redistribution/translocation of a biologically active polypeptide as a way of regulating its action rather than inhibition/activation of enzymatic activity, can be identified in a way that insures very high selectivity to the particular isoform of the biologically active polypeptide and further development of compound selectivity versus other isoforms of the same biologically active polypeptide or other components of the same signalling pathway.

In its broadest aspect, the invention relates to a method for extracting quantitative information relating to an influence on a cellular response, the method comprising recording variation, caused by the influence on a mechanically intact living cell or mechanically intact living cells, in spatially distributed light emitted from a luminophore, the luminophore being present in the cell or cells and being capable of being redistributed in a manner which is related with the degree of the influence, and/or of being modulated by a component which is capable of being redistributed in a manner which is related to the degree of the influence, the association resulting in a modulation of the luminescence characteristics of the luminophore, detecting and recording the spatially distributed light from the luminophore, and processing the recorded variation in the spatially distributed light to provide quantitative information correlating the spatial distribution or change in the spatial distribution to the degree of the influence. In a preferred embodiment of the invention the luminophore, which is present in the cell or cells, is capable of being redistributed by modulation of an intracellular pathway, in a manner which is related to the redistribution of at least one component of the intracellular pathway. In another preferred embodiment of the invention, the luminophore is a fluorophore.

The Cells

In the invention the cell and/or cells are mechanically intact and alive throughout the experiment. In another embodiment of the invention, the cell or cells is/are fixed at a point in time after the application of the influence at which the response has been predetermined to be significant, and the recording is made at an arbitrary later time.

The mechanically intact living cell or cells could be selected from the group consisting of fungal cell or cells, such as a yeast cell or cells; invertebrate cell or cells including insect cell or cells; and vertebrate cell or cells, such as mammalian cell or cells. This cell or these cells is/are incubated at a temperature of 30° C. or above, preferably at a temperature of from 32° C. to 39° C., more preferably at a temperature of from 35° C. to 38° C., and most preferably at a temperature of about 37° C. during the time period over which the influence is observed. In one aspect of the invention the mechanically intact living cell is part of a matrix of identical or non-identical cells.

A cell used in the present invention should contain a nucleic acid construct encoding a fusion polypeptide as defined herein and be capable of expressing the sequence encoded by the construct. The cell is a eukaryotic cell selected from the group consisting of fungal cells, such as yeast cells; invertebrate cells including insect cells; vertebrate cells such as mammalian cells. The preferred cells are mammalian cells.

In another aspect of the invention the cells could be from an organism carrying in at least one of its component cells a nucleic acid sequence encoding a fusion polypeptide as defined herein and be capable of expressing said nucleic acid sequence. The organism is selected from the group consisting of unicellular and multicellular organisms, such as a mammal.

The Luminophore

The luminophore is the component which allows the redistribution to be visualised and/or recorded by emitting light in a spatial distribution related to the degree of influence. In one embodiment of the invention, the luminophore is capable of being redistributed in a manner which is physiologically relevant to the degree of the influence. In another embodiment, the luminophore is capable of associating with a component which is capable of being redistributed in a manner which is physiologically relevant to the degree of the influence. In another embodiment, the luminophore correlation between the redistribution of the luminophore and the degree of the influence could be determined experimentally. In a preferred aspect of the invention, the luminophore is capable of being redistributed in substantially the same manner as the at least one component of an intracellular pathway. In yet another embodiment of the invention, the luminophore is capable of being quenched upon spatial association with a component which is redistributed by modulation of the pathway, the quenching being measured as a change in the intensity of the luminescence.

The luminophore could be a fluorophore. In a preferred embodiment of the invention, the luminophore could be a polypeptide encoded by and expressed from a nucleotide sequence harboured in the cell or cells. The luminophore could be a hybrid polypeptide comprising a fusion of at least a portion of each of two polypeptides one of which comprises a luminescent polypeptide and the other one of which comprises a biologically active polypeptide, as defined herein.

The luminescent polypeptide could be a GFP as defined herein or could be selected from the group consisting of green fluorescent proteins having the F64L mutation as defined herein such as F64L-GFP, F64L-Y66H-GFP, F64L-S65T-GFP, and EGFP. The GFP could be N- or C-terminally tagged, optionally via a peptide linker, to the biologically active polypeptide or a part or a subunit thereof. The fluorescent probe could be a component of a intracellular signalling pathway. The probe is coded for by a nucleic acid construct.

The pathway of investigation in the present invention could be an intracellular signalling pathway.

The Influence

In a preferred embodiment of the invention, the influence could be contact between the mechanically intact living cell or the group of mechanically intact living cells with a chemical substance and/or incubation of the mechanically intact living cell or the group of mechanically intact living cells with a chemical substance. The influence will modulate the intracellular processes. In one aspect the modulation could be an activation of the intracellular processes. In another aspect the modulation could be an deactivation of the intracellular processes. In yet another aspect, the influence could inhibit or promote the redistribution without directly affecting the metabolic activity of the component of the intracellular processes.

In one embodiment the invention is used as a basis for a screening program, where the effect of unknown influences such as a compound library, can be compared to influence of known reference compounds under standardised conditions.

The Recording

In addition to the intensity, there are several parameters of fluorescence or luminescence which can be modulated by the effect of the influence on the underlying cellular phenomena, and can therefore be used in the invention. Some examples are resonance energy transfer, fluorescence lifetime, polarisation, wavelength shift. Each of these methods requires a particular kind of filter in the emission light path to select the component of the light desired and reject other components. The recording of property of light could be in the form of an ordered array of values such as a CCD array or a vacuum tube device such as a vidicon tube.

In one embodiment of the invention, the spatially distributed light emitted by a luminophore could be detected by a change in the resonance energy transfer between the luminophore and another luminescent entity capable of delivering energy to the luminophore, each of which has been selected or engineered to become part of, bound to or associated with particular components of the intracellular pathway. In this embodiment, either the luminophore or the luminescent entity capable of delivering energy to the luminophore undergoes redistribution in response to an influence. The resonance energy transfer would be measured as a change in the intensity of emission from the luminophore, preferably sensed by a single channel photodetector which responds only to the average intensity of the luminophore in a non-spatially resolved fashion.

In one embodiment of the invention, the recording of the spatially distributed light could be made at a single point in time after the application of the influence. In another embodiment, the recording could be made at two points in time, one point being before, and the other point being after the application of the influence. The result or variation is determined from the change in fluorescence compared to the fluorescence measured prior to the influence or modulation. In another embodiment of the invention, the recording could be performed at a series of points in time, in which the application of the influence occurs at some time after the first time point in the series of recordings, the recording being performed, e.g., with a predetermined time spacing of from 0.1 seconds to 1 hour, preferably from 1 to 60 seconds, more preferably from 1 to 30 seconds, in particular from 1 to 10 seconds, over a time span of from 1 second to 12 hours, such as from 10 seconds to 12 hours, e.g., from 10 seconds to one hour, such as from 60 seconds to 30 minutes or 20 minutes. The result or variation is determined from the change in fluorescence over time. The result or variation could also be determined as a change in the spatial distribution of the fluorescence over time.

Apparatus

The recording of spatially distributed luminescence emitted from the luminophore is performed by an apparatus for measuring the distribution of fluorescence in the cell or cells, and thereby any change in the distribution of fluorescence in the cell or cells, which includes at a minimum the following component parts: (a) a light source, (b) a method for selecting the wavelength(s) of light from the source which will excite the fluorescence of the protein, (c) a device which can rapidly block or pass the excitation light into the rest of the system, (d) a series of optical elements for conveying the excitation light to the specimen, collecting the emitted fluorescence in a spatially resolved fashion, and forming an image from this fluorescence emission, (e) a bench or stand which holds the container of the cells being measured in a predetermined geometry with respect to the series of optical elements, (f) a detector to record the spatially resolved fluorescence in the form of an image, (g) a computer or electronic system and associated software to acquire and store the recorded images, and to compute the degree of redistribution from the recorded images.

In a preferred embodiment of the invention the apparatus system is automated. In one embodiment the components in d and e mentioned above comprise a fluorescence microscope.

In one embodiment the component in f mentioned above is a CCD camera.

In one embodiment the image is formed and recorded by an optical scanning system.

In one embodiment a liquid addition system is used to add a known or unknown compound to any or all of the cells in the cell holder at a time determined in advance. Preferably, the liquid addition system is under the control of the computer or electronic system. Such an automated system can be used for a screening program due to its ability to generate results from a larger number of test compounds than a human operator could generate using the apparatus in a manual fashion.

Quantitation of the Influence

The recording of the variation or result with respect to light emitted from the luminophore is performed by recording the spatially distributed light as one or more digital images, and the processing of the recorded variation to reduce it to one or more numbers representative of the degree of redistribution comprises a digital image processing procedure or combination of digital image processing procedures. The quantitative information which is indicative of the degree of the cellular response to the influence or the result of the influence on the intracellular pathway is extracted from the recording or recordings according to a predetermined calibration based on responses or results, recorded in the same manner, to known degrees of a relevant specific influence. This calibration procedure is developed according to principles described below (Developing an Image-based Assay Technique). Specific descriptions of the procedures for particular assays are given in the examples.

While the stepwise procedure necessary to reduce the image or images to the value representative of the is particular to each assay, the individual steps are generally well-known methods of image processing. Some examples of the individual steps are point operations such as subtraction, ratioing, and thresholding, digital filtering methods such as smoothing, sharpening, and edge detection, spatial frequency methods such as Fourier filtering, image cross-correlation and image autocorrelation, object finding and classification (blob analysis), and colour space manipulations for visualisation. In addition to the algorithmic procedures, heuristic methods such as neural networks may also be used.

Nucleic Acid Constructs

The nucleic acid constructs used in the present invention encode in their nucleic acid sequences fusion polypeptides comprising a biologically active polypeptide that is a component of an intracellular signalling pathway, or a part thereof, and a GFP, preferably an F64L mutant of GFP, N- or C-terminally fused, optionally via a peptide linker, to the biologically active polypeptide or part thereof.

In one embodiment the biologically active polypeptide encoded by the nucleic acid construct is a protein kinase or a phosphatase.

In one embodiment the biologically active polypeptide encoded by the nucleic acid construct is a transcription factor or a part thereof which changes cellular localisation upon activation.

In one embodiment the biologically active polypeptide encoded by the nucleic acid construct is a protein, or a part thereof, which is associated with the cytoskeletal network and which changes cellular localisation upon activation.

In one embodiment the biologically active polypeptide encoded by the nucleic acid construct is a protein kinase or a part thereof which changes cellular localisation upon activation.

In one embodiment the biologically active polypeptide encoded by the nucleic acid construct is a serine/threonine protein kinase or a part thereof capable of changing intracellular localisation upon activation.

In one embodiment the biologically active polypeptide encoded by the nucleic acid construct is a tyrosine protein kinase or a part thereof capable of changing intracellular localisation upon activation.

In one embodiment the biologically active polypeptide encoded by the nucleic acid construct is a phospholipid-dependent serine/threonine protein kinase or a part thereof capable of changing intracellular localisation upon activation.

In one embodiment the biologically active polypeptide encoded by the nucleic acid construct is a cAMP-dependent protein kinase or a part thereof capable of changing cellular localisation upon activation. In a preferred embodiment the biologically active polypeptide encoded by the nucleic acid construct is a PKAc-F64L-S65T-GFP fusion.

In one embodiment the biologically active polypeptide encoded by the nucleic acid construct is a cGMP-dependent protein kinase or a part thereof capable of changing cellular localisation upon activation.

In one embodiment the biologically active polypeptide encoded by the nucleic acid construct is a calmodulin-dependent serine/threonine protein kinase or a part thereof capable of changing cellular localisation upon activation.

In one embodiment the biologically active polypeptide encoded by the nucleic acid construct is a mitogen-activate serine/threonine protein kinase or a part thereof capable of changing cellular localisation upon activation. In preferred embodiments the biologically active polypeptide encoded by the nucleic acid constructs are an ERK1-F64L-S65T-GFP fusion or an EGFP-ERK1 fusion.

In one embodiment the biologically active polypeptide encoded by the nucleic acid construct is a cyclin-dependent serine/threonine protein kinase or a part thereof capable of changing cellular localisation upon activation.

In one embodiment the biologically active polypeptide encoded by the nucleic acid construct is a protein phosphatase or a part thereof capable of changing cellular localisation upon activation.

In one preferred embodiment of the invention the nucleic acid constructs may be DNA constructs.

In one embodiment the biologically active polypeptide encoded by the nucleic acid construct In one embodiment the gene encoding GFP in the nucleic acid construct is derived from *Aequorea victoria*. In a preferred embodiment the gene encoding GFP in the nucleic acid construct is EGFP or a GFP variant selected from F64L-GFP, F64L-Y66H-GFP and F64L-S65T-GFP.

In preferred embodiments of the invention the DNA constructs which can be identified by any of the DNA sequences shown in SEQ ID NO: 38, 40, 42, 44, 46, 48, 50, 52, 54, 56, 58, 60, 62, 64, 66, 68, 70, 72, 74, 76, 78, 108, 110, 112, 114, 116, 118, 120, 122, 124, 126, 128, 130, 132, 134, 136, 138, 140, 142 or are variants of these sequences capable of encoding the same fusion polypeptide or a fusion polypeptide which is biologically equivalent thereto, e.g. an isoform, or a splice variant or a homologue from another species.

Screening Program

The present invention describes a method that may be used to establish a screening program for the identification of biologically active substances that directly or indirectly affects intracellular signalling pathways and because of this property are potentially useful as medicaments. Based on measurements in living cells of the redistribution of spatially resolved luminescence from luminophores which undergo a change in distribution upon activation or deactivation of an intracellular signalling pathway the result of the individual measurement of each substance being screened indicates its potential biological activity.

In one embodiment of the invention the screening program is used for the identification of a biologically toxic substance as defined herein that exerts its toxic effect by interfering with an intracellular signalling pathway. Based on measurements in living cells of the redistribution of spatially resolved luminescence from luminophores which undergo a change in distribution upon activation or deactivation of an intracellular signalling pathway the result of the individual measurement of each substance being screened indicates its potential biologically toxic activity. In one embodiment of a screening program a compound that modulates a component of an intracellular pathway as defined herein, can be found and the therapeutic amount of the compound estimated by a method according to the method of the invention. In a preferred embodiment the present invention leads to the discovery of a new way of treating a condition or disease related to the intracellular function of a biologically active polypeptide comprising administration to a patient suffering from said condition or disease of an effective amount of a compound which has been discovered by any method according to the invention. In another preferred embodiment of the invention a method is established for identification of a new drug target or several new drug targets among the group of biologically active polypeptides which are components of intracellular signalling pathways.

In another embodiment of the invention an individual treatment regimen is established for the selective treatment of a selected patient suffering from an ailment where the available medicaments used for treatment of the ailment are tested on a relevant primary cell or cells obtained from said patient from one or several tissues, using a method comprising transfecting the cell or cells with at least one DNA sequence encoding a fluorescent probe according to the invention, transferring the transfected cell or cells back the said patient, or culturing the cell or cells under conditions permitting the expression of said probes and exposing it to an array of the available medicaments, then comparing changes in fluorescence patterns or redistribution patterns of the fluorescent probes in the intact living cell or cells to detect the cellular response to the specific medicaments (obtaining a cellular action profile), then selecting one or more medicament or medicaments based on the desired activity and acceptable level of side effects and administering an effective amount of these medicaments to the selected patient.

Back-tracking of a Signal Transduction Pathway

The present invention describes a method that may be used to establish a screening program for back-tracking signal transduction pathways as defined herein. In one embodiment the screening program is used to establish more precisely at which level one or several compounds affect a specific signal transduction pathway by successively or in parallel testing the influence of the compound or compounds on the redistribution of spatially resolved luminescence from several of the luminophores which undergo a change in distribution upon activation or deactivation of the intracellular signalling pathway under study.

Construction and Testing of Probes

In general, a probe, i.e. a "GeneX"-GFP fusion or a GFP-"GeneX" fusion, is constructed using PCR with "GeneX"-specific primers followed by a cloning step to fuse "GeneX" in frame with GFP. The fusion may contain a short vector derived sequence between "GeneX" and GFP (e.g. part of a multiple cloning site region in the plasmid) resulting in a peptide linker between "GeneX" and GFP in the resulting fusion protein.

Detailed Stepwise Procedure:

Identifying the sequence of the gene. This is most readily done by searching a depository of genetic information, e.g. the GenBank Sequence Database, which is widely available and routinely used by molecular biologists. In the specific examples below the GenBank Accession number of the gene in question is provided.

Design of gene-specific primers. Inspection of the sequence of the gene allows design of gene-specific primers to be used in a PCR reaction. Typically, the top-strand primer encompasses the ATG start codon of the gene and the following ca. 20 nucleotides, while the bottom-strand primer encompasses the stop codon and the ca. 20 preceding nucleotides, if the gene is to be fused behind GFP, i.e. a GFP-"GeneX" fusion. If the gene is to be fused in front of GFP, i.e. a "GeneX"-GFP fusion, a stop codon must be avoided. Optionally, the full length sequence of GeneX may not be used in the fusion, but merely the part which localizes and redistributes like GeneX in response to a signal.

In addition to gene-specific sequences, the primers contain at least one recognition sequence for a restriction enzyme, to allow subsequent cloning of the PCR product. The sites are chosen so that they are unique in the PCR product and compatible with sites in the cloning vector. Furthermore, it may be necessary to include an exact number of nucleotides between the restriction enzyme site and the gene-specific sequence in order to establish the correct reading frame of the fusion gene and/or a translation initiation consensus sequence. Lastly, the primers always contain a few nucleotides in front of the restriction enzyme site to allow efficient digestion with the enzyme.

Identifying a source of the gene to be amplified. In order for a PCR reaction to produce a product with gene-specific primers, the gene-sequence must initially be present in the reaction, e.g. in the form of cDNA. Information in GenBank or the scientific literature will usually indicate in which tissue(s) the gene is expressed, and cDNA libraries from a great variety of tissues or cell types from various species are commercially available, e.g. from Clontech (Palo Alto), Stratagene (La Jolla) and Invitrogen (San Diego). Many genes are also available in cloned form from The American Type Tissue Collection (Virginia).

Optimizing the PCR reaction. Several factors are known to influence the efficiency and specificity of a PCR reaction, including the annealing temperature of the primers, the concentration of ions, notably $Mg^{2+}$ and $K^+$, present in the reaction, as well as pH of the reaction. If the result of a PCR reaction is deemed unsatisfactory, it might be because the parameters mentioned above are not optimal. Various annealing temperatures should be tested, e.g. in a PCR machine with a built-in temperature gradient, available from e.g. Stratagene (La Jolla), and/or various buffer compositions should be tried, e.g. the OptiPrime buffer system from Stratagene (La Jolla).

Cloning the PCR product. The vector into which the amplified gene product will be cloned and fused with GFP will already have been taken into consideration when the primers were designed. When choosing a vector, one should at least consider in which cell types the probe subsequently will be expressed, so that the promoter controlling expression of the probe is compatible with the cells. Most expression vectors also contain one or more selective markers, e.g. conferring resistance to a drug, which is a useful feature when one wants to make stable transfectants. The selective marker should also be compatible with the cells to be used.

The actual cloning of the PCR product should present no difficulty as it typically will be a one-step cloning of a fragment digested with two different restriction enzymes into a vector digested with the same two enzymes. If the cloning proves to be problematic, it may be because the restriction enzymes did not work well with the PCR fragment. In this case one could add longer extensions to the end of the primers to overcome a possible difficulty of digestion close to a fragment end, or one could introduce an intermediate cloning step not based on restriction enzyme digestion. Several companies offer systems for this approach, e.g. Invitrogen (San Diego) and Clontech (Palo Alto).

Once the gene has been cloned and, in the process, fused with the GFP gene, the resulting product, usually a plasmid, should be carefully checked to make sure it is as expected. The most exact test would be to obtain the nucleotide sequence of the fusion-gene.

Testing the Probe

Once a DNA construct for a probe has been generated, its functionality and usefulness may be tested by subjecting it to the following tests:

Transfecting it into cells capable of expressing the probe. The fluorescence of the cell is inspected soon after, typically the next day. At this point, two features of cellular fluorescence are noted: the intensity and the sub-cellular localization.

The intensity should usually be at least as strong as that of unfused GFP in the cells. If it is not, the sequence or quality of the probe-DNA might be faulty, and should be carefully checked.

The sub-cellular localization is an indication of whether the probe is likely to perform well. If it localizes as expected for the gene in question, e.g. is excluded from the nucleus, it can immediately go on to a functional test. If the probe is not localized soon after the transfection procedure, it may be because of overexpression at this point in time, as the cell typically will have taken of very many copies of the plasmid, and localization will occur in time, e.g. within a few weeks, as plasmid copy number and expression level decreases. If localization does not occur after prolonged time, it may be because the fusion to GFP has destroyed a localization function, e.g. masked a protein sequence essential for interaction with its normal cellular anchor-protein. In this case the opposite fusion might work, e.g. if GeneX-GFP does not work, GFP-GeneX might, as two different parts of GeneX will be affected by the proximity to GFP. If this does not work, the proximity of GFP at either end might be a problem, and it could be attempted to increase the distance by incorporating a longer linker between GeneX and GFP in the DNA construct.

If there is no prior knowledge of localization, and no localization is observed, it may be because the probe should not be localized at this point, because such is the nature of the protein fused to GFP. It should then be subjected to a functional test.

In a functional test, the cells expressing the probe are treated with at least one compound known to perturb, usually by activating, the signalling pathway on which the probe is expected to report by redistributing itself within the cell. If the redistribution is as expected, e.g. if prior knowledge tell that it should translocate from location X to location Y, it has passed the first critical test. In this case it can go on to further characterization and quantification of the response.

If it does not perform as expected, it may be because the cell lacks at least one component of the signalling pathway, e.g. a cell surface receptor, or there is species incompatibility, e.g. if the probe is modelled on sequence information of a human geneproduct, and the cell is of hamster origin. In both instances one should identify other cell types for the testing process where these potential problems would not apply.

If there is no prior knowledge about the pattern of redistribution, the analysis of the redistribution will have to be done in greater depth to identify what the essential and indicative features are, and when this is clear, it can go on to further characterization and quantification of the response. If no feature of redistribution can be identified, the problem might be as mentioned above, and the probe should be retested under more optimal cellular conditions.

If the probe does not perform under optimal cellular conditions it's back to the drawing board.

Developing an Image-based Assay Technique

The process of developing an image-based redistribution assay begins with either the unplanned experimental observation that a redistribution phenomenon can be visualised, or the design of a probe specifically to follow a redistribution phenomenon already known to occur. In either event, the first and best exploratory technique is for a trained scientist or technician to observe the phenomenon. Even with the rapid advances in computing technology, the human eye-brain combination is still the most powerful pattern recognition system known, and requires no advance knowledge of the system in order to detect potentially interesting and useful patterns in raw data. This is especially if those data are presented in the form of images, which are the natural "data type" for human visual processing. Because human visual processing operates most effectively in a relatively narrow frequency range, i.e., we cannot see either very fast or very slow changes in our visual field, it may be necessary to record the data and play it back with either time dilation or time compression.

Some luminescence phenomena cannot be seen directly by the human eye. Examples include polarization and fluorescence lifetime. However, with suitable filters or detectors, these signals can be recorded as images or sequences of images and displayed to the human in the fashion just described. In this way, patterns can be detected and the same methods can be applied.

Once the redistribution has been determined to be a reproducible phenomenon, one or more data sets are generated for the purpose of developing a procedure for extracting the quantitative information from the data. In parallel, the biological and optical conditions are determined which will give the best quality raw data for the assay. This can become an iterative process; it may be necessary to develop a quantitative procedure in order to assess the effect on the assay of manipulating the assay conditions.

The data sets are examined by a person or persons with knowledge of the biological phenomenon and skill in the application of image processing techniques. The goal of this exercise is to determine or at least propose a method which will reduce the image or sequence of images constituting the record of a "response" to a value corresponding to the degree of the response. Using either interactive image processing software or an image processing toolbox and a programming language, the method is encoded as a procedure or algorithm which takes the image or images as input and generates the degree of response (in any units) as its output. Some of the criteria for evaluating the validity of a particular procedure are:

Does the degree of the response vary in a biologically significant fashion, i.e., does it show the known or putative dependence on the concentration of the stimulating agent or condition?

Is the degree of response reproducible, i.e., does the same concentration or level of stimulating agent or condition give the same response with an acceptable variance?

Is the dynamic range of the response sufficient for the purpose of the assay? If not, can a change in the procedure or one of its parameters improve the dynamic range?

Does the procedure exhibit any clear "pathologies", i.e., does it give ridiculous values for the response if there are commonly occurring imperfections in the imaging process? Can these pathologies be eliminated, controlled, or accounted for?

Can the procedure deal with the normal variation in the number and/or size of cells in an image?

In some cases the method may be obvious; in others, a number of possible procedures may suggest themselves. Even if one method appears clearly superior to others, optimisation of parameters may be required. The various procedures are applied to the data set and the criteria suggested above are determined, or the single procedure is applied repeatedly with adjustment of the parameter or parameters until the most satisfactory combination of signal, noise, range, etc. are arrived at. This is equivalent to the calibration of any type of single-channel sensor.

The number of ways of extracting a single value from an image are extremely large, and thus an intelligent approach must be taken to the initial step of reducing this number to a small, finite number of possible procedures. This is not to say that the procedure arrived at is necessarily the best procedure—but a global search for the best procedure is simply out of the question due to the sheer number of possibilities involved.

Image-based assays are no different than other assay techniques in that their usefulness is characterised by parameters such as the specificity for the desired component of the sample, the dynamic range, the variance, the sensitivity, the concentration range over which the assay will work, and other such parameters. While it is not necessary to characterise each and every one of these before using the assay, they represent the only way to compare one assay with another.

Example: Developing a Quantitative Assay for GLUT4 Translocation

GLUT4 is a member of the class of glucose transporter molecules which are important in cellular glucose uptake. It is known to translocate to the plasma membrane under some conditions of stimulation of glucose uptake. The ability to visualize the glucose uptake response noninvasively, without actually measuring glucose uptake, would be a very useful assay for anyone looking for, for example, treatments for type II diabetes.

A CHO cell line which stably expressed the human insulin receptor was used as the basis for a new cell line which stably expressed a fusion between GLUT4 and GFP. This cell line was expected to show translocation of GLUT4 to the plasma membrane as visualized by the movement of the GFP. The translocation could definitely be seen in the form of the appearance of local increases in the fluorescence in regions of the plasma membrane which had a characteristic shape or pattern. This is shown in FIG. 12.

These objects became known as "snircles", and the phenomenon of their appearance as "snircling". In order to quantitate their appearance, a method had to be found to isolate them as objects in the image field, and then enumerate them, measure their area, or determine some parameter about them which correlated in a dose-dependent fashion with the concentration of insulin to which the cells had been exposed. In order to separate the snircles, a binarization procedure was applied in which one copy of the image smoothed with a relatively severe gaussian kernel (sigma= 2.5) was subtracted from another copy to which only a relatively light gaussian smooth had been applied (sigma= 0.5). The resultant image was rescaled to its min/max range, and an automatic threshold was applied to divide the image into two levels. The thresholded image contains a background of one value all found object with another value. The found objects were first filtered through a filter to remove objects far too large and far too small to be snircles. The remaining objects, which represent snircles and other artifacts from the image with approximately the same size and intensity characteristics as snircles, are passed into a classification procedure which has been previously trained with many images of snircles to recognize snircles and exclude the other artifacts. The result of this procedure is a binary image which shows only the found snircles to the degree to which the classification procedure can accurately identify them. The total area of the snircles is then summed and this value is the quantitative measure of the degree of snircling for that image.

Definitions

In the present specification and claims, the term "an influence" covers any influence to which the cellular response comprises a redistribution. Thus, e.g., heating, cooling, high pressure, low pressure, humidifying, or drying are influences on the cellular response on which the resulting redistribution can be quantified, but as mentioned above, perhaps the most important influences are the influences of contacting or incubating the cell or cells with substances which are known or suspected to exert and influence on the cellular response involving a redistribution contribution. In another embodiment of the invention the influence could be substances from a compound drug library.

In the present context, the term "green fluorescent protein" is intended to indicate a protein which, when expressed by a cell, emits fluorescence upon exposure to light of the correct excitation wavelength (cf. [(Chalfie et al. 1994)]). In the following, GFP in which one or more amino acids have been substituted, inserted or deleted is most often termed "modified GFP". "GFP" as used herein includes wild-type GFP derived from the jelly fish *Aequorea victoria* and modifications of GFP, such as the blue fluorescent variant of GFP disclosed by Heim et al. (1994). Proc.Natl.Acad.Sci. 91:12501, and other modifications that change the spectral properties of the GFP fluorescence, or modifications that exhibit increased fluorescence when expressed in cells at a temperature above about 30° C. described in PCT/DK96/00051, published as WO 97/11094 on Mar. 27, 1997 and hereby incorporated by reference, and which comprises a fluorescent protein derived from Aequorea Green Fluorescent Protein (GFP) or any functional analogue thereof, wherein the amino acid in position 1 upstream from the chromophore has been mutated to provide an increase of fluorescence intensity when the fluorescent protein of the invention is expressed in cells. Preferred GFP variants are F64L-GFP, F64L-Y66H-GFP and F64L-S65T-GFP. An especially preferred variant of GFP for use in all the aspects of this invention is EGFP (DNA encoding EGFP which is a F64L-S65T variant with codons optimized for expression in mammalian cells is available from Clontech, Palo Alto, plasmids containing the EGFP DNA sequence, cf. GenBank Acc. Nos. U55762, U55763).

The term "intracellular signalling pathway" and "signal transduction pathway" are intended to indicate the coordinated intracellular processes whereby a living cell transduce an external or internal signal into cellular responses. Said signal transduction will involve an enzymatic reaction said enzymes include but are not limited to protein kinases, GTPases, ATPases, protein phosphatases, phospholipases. The cellular responses include but are not limited to gene transcription, secretion, proliferation, mechanical activity, metabolic activity, cell death.

The term "second messenger" is used to indicate a low molecular weight component involved in the early events of intracellular signal transduction pathways.

The term "luminophore" is used to indicate a chemical substance which has the property of emitting light either inherently or upon stimulation with chemical or physical means. This includes but is not limited to fluorescence, bioluminescence, phosphorescence, chemiluminescence.

The term "mechanically intact living cell" is used to indicate a cell which is considered living according to standard criteria for that particular type of cell such as maintenance of normal membrane potential, energy metabolism, proliferative capability, and has not experienced any physically invasive treatment designed to introduce external substances into the cell such as microinjection.

The term "physiologically relevant", when applied to an experimentally determined redistribution of an intracellular component, as measured by a change in the luminescence properties or distribution, is used to indicate that said redistribution can be explained in terms of the underlying biological phenomenon which gives rise to the redistribution.

The terms "image processing" and "image analysis" are used to describe a large family of digital data analysis techniques or combination of such techniques which reduce ordered arrays of numbers (images) to quantitative information describing those ordered arrays of numbers. When said ordered arrays of numbers represent measured values from a physical process, the quantitative information derived is therefore a measure of the physical process.

The term "fluorescent probe" is used to indicate a fluorescent fusion polypeptide comprising a GFP or any functional part thereof which is N- or C-terminally fused to a biologically active polypeptide as defined herein, optionally via a peptide linker consisting of one or more amino acid residues, where the size of the linker peptide in itself is not critical as long as the desired functionality of the fluorescent probe is maintained. A fluorescent probe according to the invention is expressed in a cell and basically mimics the physiological behaviour of the biologically active polypeptide moiety of the fusion polypeptide.

The term "mammalian cell" is intended to indicate any living cell of mammalian origin. The cell may be an established cell line, many of which are available from The American Type Culture Collection (ATCC, Virginia, USA) or a primary cell with a limited life span derived from a mammalian tissue, including tissues derived from a transgenic animal, or a newly established immortal cell line derived from a mammalian tissue including transgenic tissues, or a hybrid cell or cell line derived by fusing different cell types of mammalian origin e.g. hybridoma cell lines. The cells may optionally express one or more non-native gene products, e.g. receptors, enzymes, enzyme substrates, prior to or in addition to the fluorescent probe. Preferred cell lines include but are not limited to those of fibroblast origin, e.g. BHK, CHO, BALB, or of endothelial origin, e.g. HUVEC, BAE (bovine artery endothelial), CPAE (cow pulmonary artery endothelial) or of pancreatic origin, e.g. RIN, INS-1, MIN6, bTC3, aTC6, bTC6, HIT, or of hematopoietic origin, e.g. adipocyte origin, e.g. 3T3-L1, neuronal/neuroendocrine origin, e.g. AtT20, PC12, GH3, muscle origin, e.g. SKMC, A10, C2C12, renal origin, e.g. HEK 293, LLC-PK1.

The term "hybrid polypeptide" is intended to indicate a polypeptide which is a fusion of at least a portion of each of two proteins, in this case at least a portion of the green fluorescent protein, and at least a portion of a catalytic and/or regulatory domain of a protein kinase. Furthermore a hybrid polypeptide is intended to indicate a fusion polypeptide comprising a GFP or at least a portion of the green fluorescent protein that contains a functional fluorophore, and at least a portion of a biologically active polypeptide as defined herein provided that said fusion is not the PKCα-GFP, PKCγ-GFP, and PKCε-GFP disclosed by Schmidt et al. and Sakai et al., respectively. Thus, GFP may be N- or C-terminally tagged to a biologically active polypeptide, optionally via a linker portion or linker peptide consisting of a sequence of one or more amino acids. The hybrid polypeptide or fusion polypeptide may act as a fluorescent probe in intact living cells carrying a DNA sequence encoding the hybrid polypeptide under conditions permitting expression of said hybrid polypeptide.

The term "kinase" is intended to indicate an enzyme that is capable of phosphorylating a cellular component.

The term "protein kinase" is intended to indicate an enzyme that is capable of phosphorylating serine and/or threonine and/or tyrosine in peptides and/or proteins.

The term "phosphatase" is intended to indicate an enzyme that is capable of dephosphorylating phosphoserine and/or phosphothreonine and/or phosphotyrosine in peptides and/or proteins.

In the present context, the term "biologically active polypeptide" is intended to indicate a polypeptide affecting intracellular processes upon activation, such as an enzyme which is active in intracellular processes or a portion thereof comprising a desired amino acid sequence which has a biological function or exerts a biological effect in a cellular system. In the polypeptide one or several aminoacids may have been deleted, inserted or replaced to alter its biological function, e.g. by rendering a catalytic site inactive. Preferably, the biologically active polypeptide is selected from the group consisting of proteins taking part in an intracellular signalling pathway, such as enzymes involved in the intracellular phosphorylation and dephosphorylation processes including kinases, protein kinases and phosphorylases as defined herein, but also proteins making up the cytoskeleton play important roles in intracellular signal transduction and are therefore included in the meaning of "biologically active polypeptide" herein. More preferably, the biologically active polypeptide is a protein which according to its state as activated or non-activated changes localisation within the cell, preferably as an intermediary component in a signal transduction pathway. Included in this preferred group of biologically active polypeptides are cAMP dependent protein kinase A.

The term "a substance having biological activity" is intended to indicate any sample which has a biological function or exerts a biological effect in a cellular system. The sample may be a sample of a biological material such as a sample of a body fluid including blood, plasma, saliva, milk, urine, or a microbial or plant extract, an environmental sample containing pollutants including heavy metals or toxins, or it may be a sample containing a compound or mixture of compounds prepared by organic synthesis or genetic techniques.

The phrase "any change in fluorescence" means any change in absorption properties, such as wavelength and intensity, or any change in spectral properties of the emitted light, such as a change of wavelength, fluorescence lifetime, intensity or polarisation, or any change in the intracellular localisation of the fluorophore. It may thus be localised to a specific cellular component (e.g. organelle, membrane, cytoskeleton, molecular structure) or it may be evenly distributed throughout the cell or parts of the cell.

The phrase "back-tracking of a signal transduction pathway" is intended to indicate.

The term "organism" as used herein indicates any unicellular or multicellular organism preferably originating from the animal kingdom including protozoans, but also organisms that are members of the plant kingdoms, such as algae, fungi, bryophytes, and vascular plants are included in this definition.

The term "nucleic acid" is intended to indicate any type of poly- or oligonucleic acid sequence, such as a DNA sequence, a cDNA sequence, or an RNA sequence.

The term "biologically equivalent" as it relates to proteins is intended to mean that a first protein is equivalent to a second protein if the cellular functions of the two proteins may substitute for each other, e.g. if the two proteins are closely related isoforms encoded by different genes, if they are splicing variants, or allelic variants derived from the same gene, if they perform identical cellular functions in different cell types, or in different species. The term "biologically equivalent" as it relates to DNA is intended to mean that a first DNA sequence encoding a polypeptide is equivalent to a second DNA sequence encoding a polypeptide if the functional proteins encoded by the two genes are biologically equivalent.

The phrase "back-tracking of a signal transduction pathway" is intended to indicate a process for defining more precisely at what level a signal transduction pathway is affected, either by the influence of chemical compounds or a disease state in an organism. Consider a specific signal transduction pathway represented by the bioactive polypeptides A-B-C-D, with signal transduction from A towards D. When investigating all components of this signal transduction pathway compounds or disease states that influence the activity or redistribution of only D can be considered to act on C or downstream of C whereas compounds or disease states that influence the activity or redistribution of C and D, but not of A and B can be considered to act downstream of B.

The term "fixed cells" is used to mean cells treated with a cytological fixative such as glutaraldehyde or formaldehyde, treatments which serve to chemically cross-link and stabilize soluble and insoluble proteins within the structure of the cell. Once in this state, such proteins cannot be lost from the structure of the now-dead cell.

BRIEF DESCRIPTION OF THE DRAWINGS

in FIG. 3H the x-axis counts the image numbers, with 12 seconds between images. The raw data of each experiment consisted of 60 fluorescence micrographs acquired at regular intervals including several images acquired before the addition of buffer or agonist. The charts (A–G) each show a quantification of the response seen through all the 60 images, performed as described in analysis method 2. The change in total area of the highly fluorescent aggregates, relative to the initial area of fluorescent aggregates is plotted as the ordinate in all graphs in FIG. 3, versus time for each experiment. Scale bar 10 mm.

FIG. 5. Time from initiation of a response to half maximal ($t_{1/2}$max) and maximal ($t_{max}$) PKAc-F64L-S65T-GFP redistribution. The data was extracted from curves such as that shown in "FIG. 2." All $t_{1/2}$max and $t_{max}$ values are given as mean±SD and are based on a total of 26–30 cells from 2–3 independent experiments for each forskolin concentration. Since the observed redistribution is sustained over time, the $t_{max}$ values were taken as the earliest time point at which complete redistribution is reached. Note that the values do not relate to the degree of redistribution.

b) The same cells as in (a) following treatment with 10% foetal calf serum for 15 minutes at 37° C.

c) Time profiles for the redistribution of GFP fluorescence in HEK293 cells following treatment with various concentrations of EGF in Hepes buffer (HAM F-12 replaced with Hepes buffer directly before the experiment). Redistribution of fluorescence is expressed as the change in the ratio value between areas in nucleus and cytoplasm of single cells. Each time profile is the mean for the changes seen in six single cells.

d) Bar chart for the end-point measurements, 600 seconds after start of EGF treatments, of fluorescence change (nucleus:cytoplasm) following various concentrations of EGF.

Figure 10:
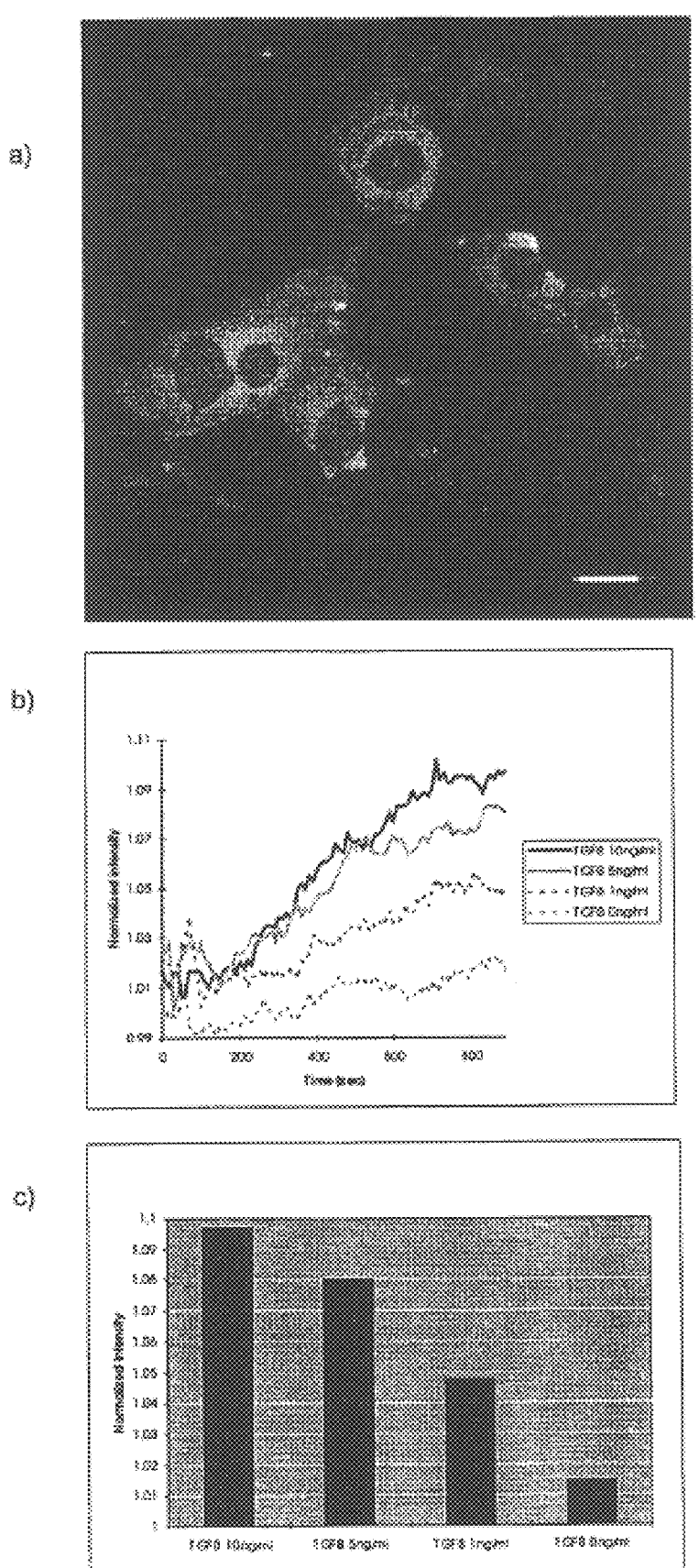

FIG. 10. a) The SMAD2-EGFP fusion expressed in HEK293 cells starved of serum overnight in HAM F-12. HAM F-12 was then replaced with Hepes buffer pH 7.2 immediately before the experiment. Scale bar is 10 mm.

b) HEK 293 cells expressing the SMAD2-EGFP fusion were treated with various concentration of TGF-beta as indicated, and the redistribution of fluorescence monitored against time. The time profile plots represent increases in fluorescence within the nucleus, normalised to starting values in each cell measured. Each trace is the time profile for a single cell nucleus.

c) A bar chart representing the end-point change in fluorescence within nuclei (after 850 seconds of treatment) for different concentrations of TGF-beta. Each bar is the value for a single nucleus in each treatment.

Figure 11:
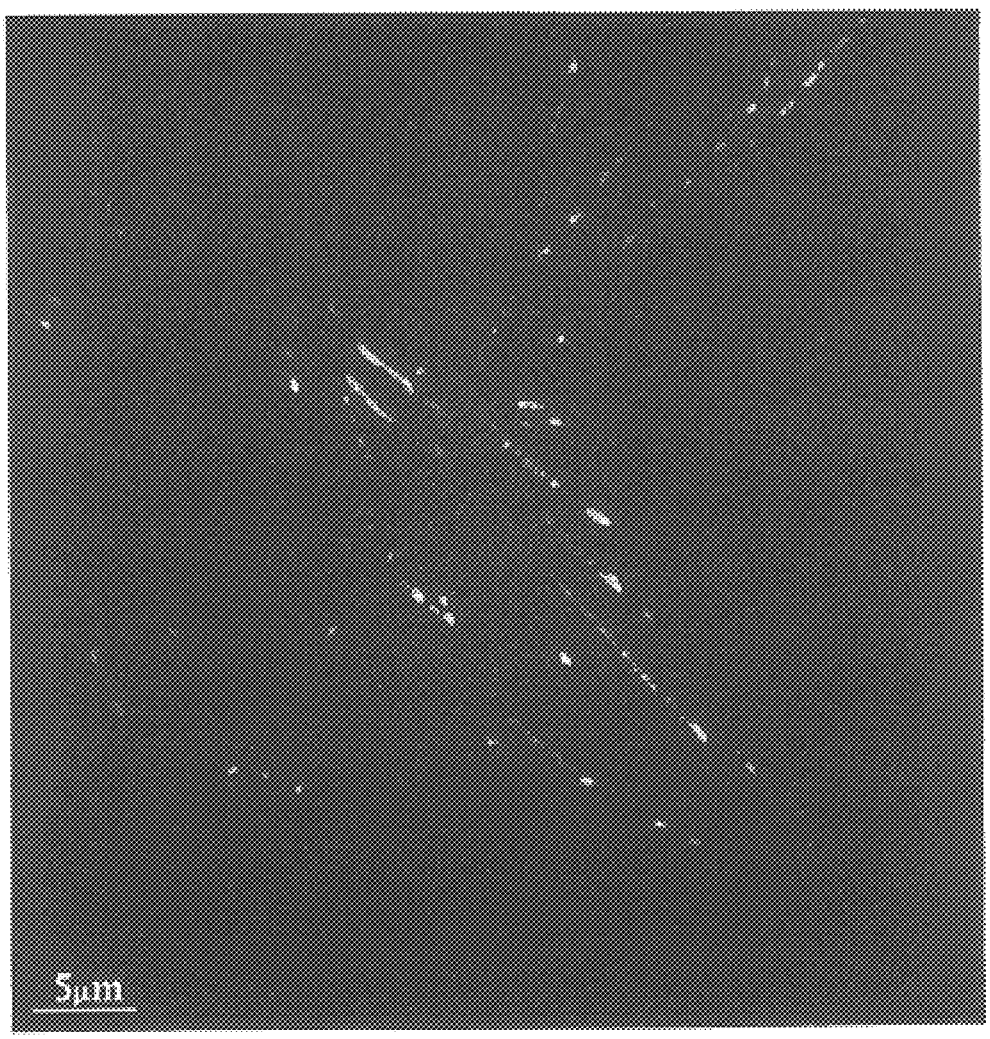

FIG. 11. The VASP-F64L-S65T-GFP fusion in CHO cells stably transfected with the human insulin receptor. The cells were starved for two hours in HAM F-12 without serum, then treated with 10% foetal calf serum. The image shows the resulting redistribution of fluorescence after 15 minutes of treatment. GFP fluorescence becomes localised in structures identified as focal adhesions along the length of actin stress fibres.

Figure 12:
Figure 12:
Figure 12:
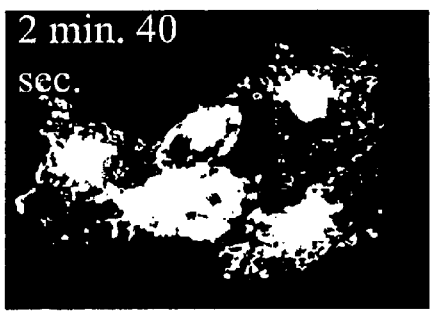
Figure 12:
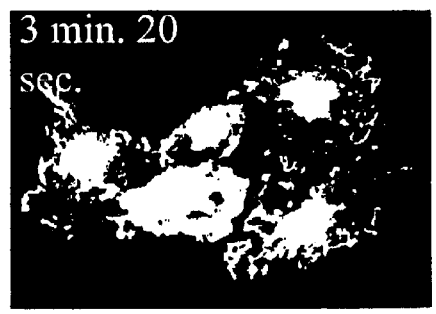
Figure 12:
Figure 12:

FIG. 12. Time lapse recording GLUT4-GFP redistribution in CHO-HIR cells. Time indicates minutes after the addition of 100 nM insulin.

EXAMPLE 1

Construction, Testing and Implementation of an Assay for cAMP Based on PKA Activation in Real Time within Living Cells Useful for monitoring the activity of signalling pathways which lead to altered concentrations of cAMP, e.g. activation of G-protein coupled receptors which couple to G-proteins of the $G_s$ or $G_i$ class.

The catalytic subunit of the murine cAMP dependent protein kinase (PKAc) was fused C-terminally to a F64L-S65T derivative of GFP. The resulting fusion (PKAc-F64L-S65T-GFP) was used for monitoring in vivo the translocation and thereby the activation of PKA.

Construction of the PKAc-F64L-S65T-GFP Fusion

Convenient restriction endonuclease sites were introduced into the cDNAs encoding murine PKAc (Gen Bank Accession number: M12303) and F64L-S65T-GFP (sequence disclosed in WO 97/11094) by polymerase chain reaction (PCR). The PCR reactions were performed according to standard protocols with the following primers:

5'PKAc: TTggACACAAgCTTTggACACCCTCAg-gATATgggCAACgCCgCCgCCgCCAAg (SEQ ID NO:3),

3'PKAc: gTCATCTTCTCgAgTCTTTCAggCgCgC-CCAAACTCAgTAAACTCCTTgCCACAC (SEQ ID NO:4),

5'GFP: TTggACACAAgCTTTggACACggCgCgC-CATgAgTAAAggAgAAgAACTTTTC (SEQ ID NO:1),

3'GFP: gTCATCTTCTCgAgTCTTACTCCTgAg-gTTTgTATAgTTCATCCATgCCATgT (SEQ ID NO:2).

The PKAc amplification product was then digested with HindIII+AscI and the F64L-S65T-GFP product with AscI+XhoI. The two digested PCR products were subsequently ligated with a HindIII+XhoI digested plasmid (pZeoSV® mammalian expression vector, Invitrogen, San Diego, Calif., USA). The resulting fusion construct (SEQ ID NO:68 & 69) was under control of the SV40 promoter.

Transfection and Cell Culture Conditions

Chinese hamster ovary cells (CHO), were transfected with the plasmid containing the PKAc-F64L-S65T-GFP fusion using the calcium phosphate precipitate method in HEPES-buffered saline (Sambrook et al., 1989). Stable transfectants were selected using 1000 mg Zeocin/ml (Invitrogen) in the growth medium (DMEM with 1000 mg glucose/l, 10% fetal bovine serum (FBS), 100 mg penicillin-streptomycin mixture ml$^{-1}$, 2 mM L-glutamine purchased from Life Technologies Inc., Gaithersburg, Md., USA). Untransfected CHO cells were used as the control. To assess the effect of glucagon on fusion protein translocation, the PKAc-F64L-S65T-GFP fusion was stably expressed in baby hamster kidney cells overexpressing the human glucagon receptor (BHK/GR cells) Untransfected BHK/GR cells were used as the control. Expression of GR was maintained with 500 mg G41 8/ml (Neo marker) and PKAc-F64L-S65T-GFP was maintained with 500 mg Zeocin/ml (Sh ble marker). CHO cells were also. simultaneously co-transfected with vectors containing the PKAc-F64L-S65T-GFP fusion and the human a2a adrenoceptor (hARa2a).

For fluorescence microscopy, cells were allowed to adhere to Lab-Tek chambered cover-glasses (Nalge Nunc Int., Naperville, Ill., USA) for at least 24 hours and cultured to about 80% confluence. Prior to experiments, the cells were cultured over night without selection pressure in HAM F-12 medium with glutamax (Life Technologies), 100 mg penicillin-streptomycin mixture $ml^{-1}$ and 0.3% FBS. This medium has low autofluorescence enabling fluorescence microscopy of cells straight from the incubator.

Monitoring Activity of PKA Activity in Real Time

Image aquisition of live cells were gathered using a Zeiss Axiovert 135M fluorescence microscope fitted with a Fluar 40X, NA: 1.3 oil immersion objective and coupled to a Photometrics CH250 charged coupled device (CCD) camera. The cells were illuminated with a 100 W HBO arc lamp. In the light path was a 470±20 nm excitation filter, a 510 nm dichroic mirror and a 515±15 nm emission filter for minimal image background. The cells were kept and monitored to be at 37° C. with a custom built stage heater.

Images were processed and analyzed in the following manner

Method 1

Stepwise procedure for quantitation of translocation of PKA:
1. The image was corrected for dark current by performing a pixel-by-pixel subtraction of a dark image (an image taken under the same conditions as the actual image, except the camera shutter is not allowed to open).
2. The image was corrected for non-uniformity of the illumination by performing a pixel-by-pixel ratio with a flat field correction image (an image taken under the same conditions as the actual image of a uniformly fluorescent specimen).
3. The image histogram, i.e., the frequency of occurrence of each intensity value in the image, was calculated.
4. A smoothed, second derivative of the histogram was calculated and the second zero is determined. This zero corresponds to the inflection point of the histogram on the high side of the main peak representing the bulk of the image pixel values.
5. The value determined in step 4 was subtracted from the image. All negative values were discarded.
6. The variance (square of the standard deviation) of the remaining pixel values was determined. This value represents the "response" for that image.
7. Scintillation proximity assay (SPA) for independent quantitation of cAMP:

Method 2

Alternative method for quantitation of PKA redistribution:
1. The fluorescent aggregates are segmented from each image using an automatically found threshold based on the maximisation of the information measure between the object and background. The a priori entropy of the image histogram is used as the information measure.
2. The area of each image occupied by the aggregates is calculated by counting pixels in the segmented areas.
3. The value obtained in step 2 for each image in a series, or treatment pair, is normalised to the value found for the first (unstimulated) image collected. A value of zero (0) indicates no redistribution of fluorescence from the starting condition. A value of one (1) by this method equals full redistribution.

Cells were cultured in HAM F-12 medium as described above, but in 96-well plates. The medium was exchanged with $Ca^{2+}$-HEPES buffer including 100 mM IBMX and the cells were stimulated with different concentrations of forskolin for 10 min. Reactions were stopped with addition of NaOH to 0.14 M and the amount of cAMP produced was measured with the cAMP-SPA kit, RPA538 (Amersham) as described by the manufacturer.

Manipulating Intracellular Levels of cAMP to Test the PKAc-F64L-S65T-GFP Fusion

The following compounds were used to vary cAMP levels: Forskolin, an activator of adenylate cyclase; dbcAMP, a membrane permeable cAMP analog which is not degraded by phosphodiesterase; IBMX, an inhibitor of phosphodiesterase.

Figure 1:
FIG. 1. CHO cells expressing the PKAc-F64L-S65T-GFP hybrid protein have been treated in HAM's F12 medium with 50 mM forskolin at 37° C. The images of the GFP fluorescence in these cells have been taken at different time intervals after treatment, which were: a) 40 seconds b) 60 seconds c) 70 seconds d) 80 seconds. The fluorescence changes from a punctate to a more even distribution within the (non-nuclear) cytoplasm.
Figure 1:
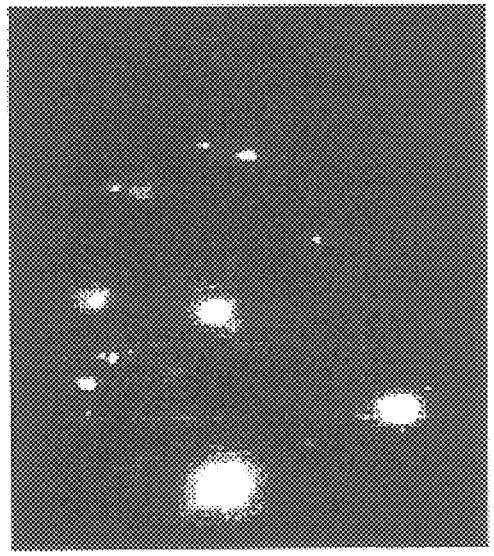
Figure 1:
Figure 1:
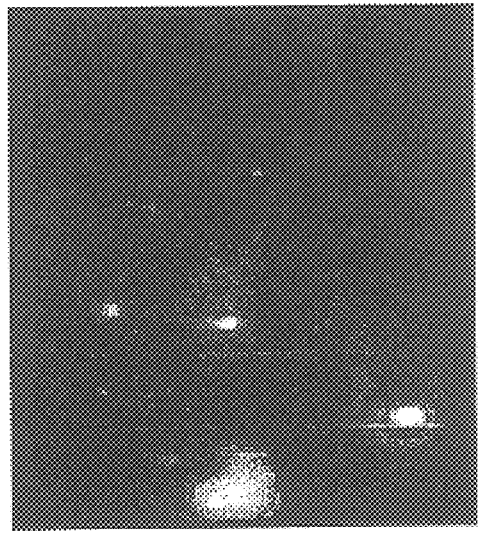

CHO cells stably expressing the PKAc-F64L-S65T-GFP, showed a dramatic translocation of the fusion protein from a punctate distribution to an even distribution throughout the cytoplasm following stimulation with 1 mM forskolin (n=3), 10 mM forskolin (n=4) and 50 mM forskolin (n=4) (FIG. 1), or dbcAMP at 1 mM (n=6).

Figure 2:
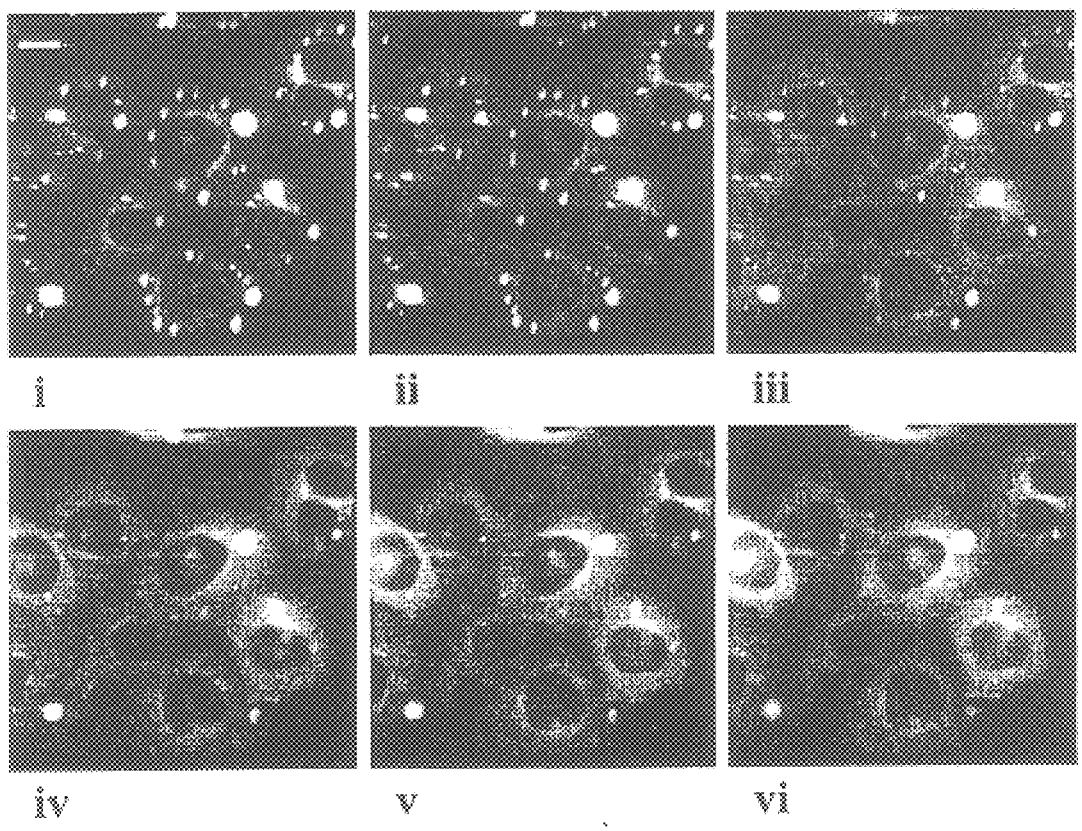
FIG. 2. Time-lapse analysis of forskolin induced PKAc-F64L-S65T-GFP redistribution. CHO cells, expressing the PKAc-F64L-S65T-GFP fusion protein were analysed by time-lapse fluorescence microscopy. Fluorescence micrographs were acquired at regular intervals from 2 min before to 8 min after the addition of agonist. The cells were challenged with 1 mM forskolin immediately after the upper left image was acquired (t=0). Frames were collected at the following times: i) 0, ii) 1, iii) 2, iv) 3, v) 4 and vi) 5 minutes. Scale bar 10 mm.

FIG. 2 shows the progression of response in time following treatment with 1 mM forskolin.

Figure 3:
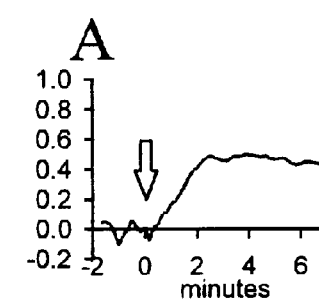
FIG. 3. Time-lapse analyses of PKAc-F64L-S65T-GFP redistribution in response to various agonists. The effects of 1 mM forskolin (A), 50 mM forskolin (B), 1 mM dbcAMP (C) and 100 mM IBMX (D) (additions indicated by open arrows) on the localisation of the PKAc-F64L-S65T-GFP fusion protein were analysed by time-lapse fluorescence microscopy of CHO/PKAc-F64L-S65T-GFP cells. The effect of addition of 10 mM forskolin (open arrow), followed shortly by repeated washing with buffer (solid arrow), on the localisation of the PKAc-F64L-S65T-GFP fusion protein was analysed in the same cells (E). In a parallel experiment, the effect of adding 10 mM forskolin and 100 mM IBMX (open arrow) followed by repeated washing with buffer containing 100 mM IBMX (solid arrow) was analysed (F). Removing forskolin caused PKAc-F64L-S65T-GFP fusion protein to return to the cytoplasmic aggregates while this is prevented by the continued presence of IBMX (F). The effect of 100 nM glucagon (FIG. 3G, open arrow) on the localisation of the PKAc-F64L-S65T-GFP fusion protein is also shown for BHK/GR, PKAc-F64L-S65T-GFP cells. The effect of 10 mM norepinephrine (H), solid arrow, on the localisation of the PKAc-F64L-S65T-GFP fusion protein was analysed similarly, in transiently transfected CHO, PKAc-F64L-S65T-GFP cells, pretreated with 10 mM forskolin, open arrow, to increase $[cAMP]_i$. N.B.
Figure 3:
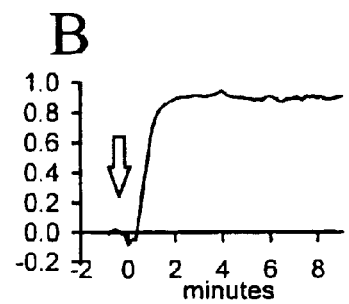
Figure 3:
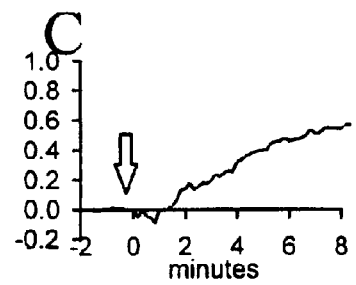
Figure 3:
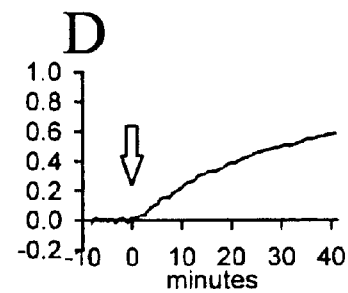
Figure 3:
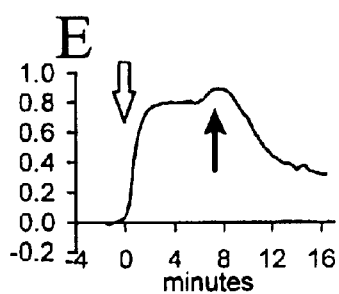
Figure 3:
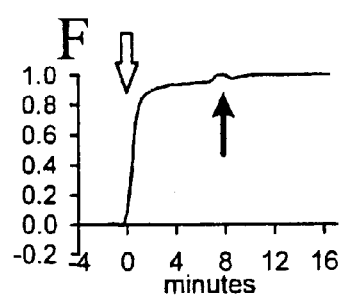
Figure 3:
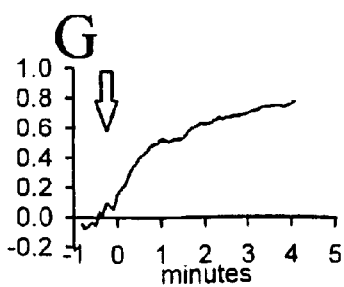
Figure 3:
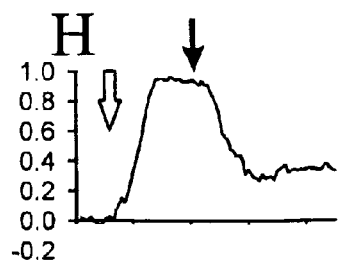

FIG. 3 gives a comparison of the average temporal profiles of fusion protein redistribution and a measure of the extent of each response to the three forskolin concentrations (FIGS. 3A, E, B), and to 1 mM dbcAMP (FIG. 3C) which caused a similar but slower response, and to addition of 100 mM IBMX (n=4, FIG. 3D) which also caused a slow response, even in the absence of adenylate cyclase stimulation. Addition of buffer (n=2) had no effect (data not shown).

As a control for the behavior of the fusion protein, F64L-S65T-GFP alone was expressed in CHO cells and these were also given 50 mM forskolin (n=5); the uniform diffuse distribution characteristic of GFP in these cells was unaffected by such treatment (data not shown).

Figure 4:
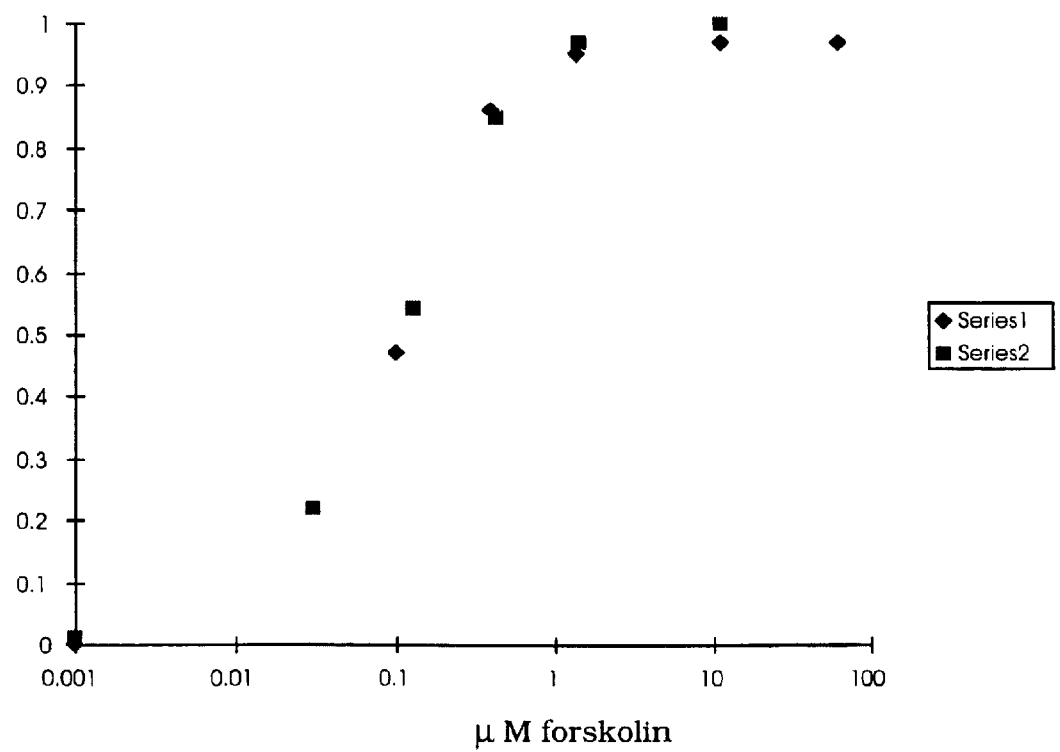
FIG. 4. Dose response curve (two experiments) for forskolin-induced redistribution of the PKAc-F64L-S65T-GFP fusion.

The forskolin induced translocation of PKAc-F64L-S65T-GFP showed a dose-response relationship (FIGS. 4 and 6), see quantitative procedures above.

Reversibility of PKAc-F64L-S65T-GFP Translocation

The release of the PKAc probe from its cytoplasmic anchoring hotspots was reversible. Washing the cells repeatedly (5–8 times) with buffer after 10 $\mu$M forskolin treatment completely restored the punctate pattern within 2–5 min (n=2, FIG. 3E). In fact the fusion protein returned to a pattern of fluorescent cytoplasmic aggregates virtually indistinguishable from that observed before forskolin stimulation.

To test whether the return of fusion protein to the cytoplasmic aggregates reflected a decreased $[cAMP]_i$, cells were treated with a combination of 10 mM forskolin and 100 mM IBMX (n=2) then washed repeatedly (5–8 times) with buffer containing 100 mM IBMX (FIG. 3F). In these experiments, the fusion protein did not return to its pre-stimulatory localization after removal of forskolin.

Testing the PKA-F64L-S65T-GFP Probe with Physiologically Relevant Agents

To test the probe's response to receptor activation of adenylate cyclase, BHK cells stably transfected with the glucagon receptor and the PKA-F64L-S65T-GFP probe were exposed to glucagon stimulation. The glucagon receptor is coupled to a $G_s$ protein which activates adenylate cyclase, thereby increasing the cAMP level. In these cells, addition of 100 nM glucagon (n=2) caused the release of the PKA-F64L-S65T-GFP probe from the cytoplasmic aggregates and a resulting translocation of the fusion protein to a more even cytoplasmic distribution within 2–3 min (FIG. 3G). Similar but less pronounced effects were seen at lower glucagon concentrations (n=2, data not shown). Addition of buffer (n=2) had no effect over time (data not shown).

Transiently transfected CHO cells expressing hARa2a and the PKA-F64L-S65T-GFP probe were treated with 10 mM forskolin for 7.5 minutes, then, in the continued presence of forskolin, exposed to 10 mM norepinephrine to stimulate the exogenous adrenoreceptors, which couple to a $G_1$ protein, which inhibit adenylate cyclase. This treatment led to reappearance of fluorescence in the cytoplasmic aggregates indicative of a decrease in $[cAMP]_i$, (FIG. 3H).

Fusion Protein Translocation Correlated with $[cAMP]_i$

Figure 6:
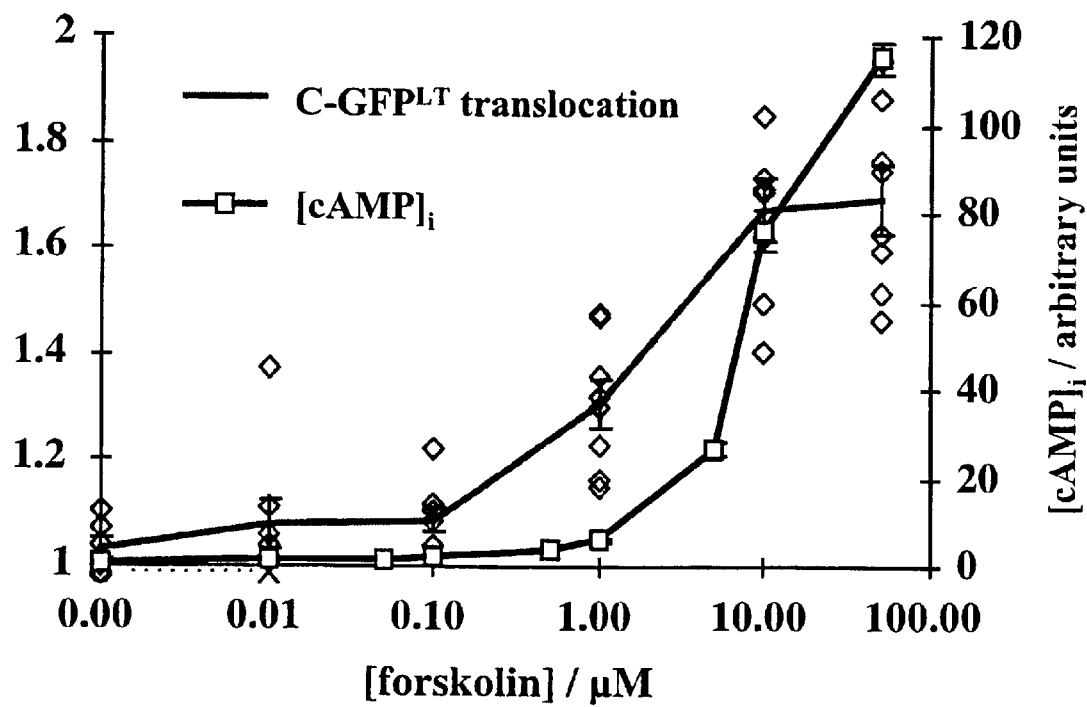
FIG. 6. Parallel dose response analyses of forskolin induced cAMP elevation and PKAc-F64L-S65T-GFP redistribution. The effects of buffer or 5 increasing concentrations of forskolin on the localisation of the PKAc-F64L-S65T-GFP fusion protein in CHO/PKAc-F64L-S65T-GFP cells, grown in a 96 well plate, were analysed as described above. Computing the ratio of the SD's of fluorescence micrographs taken of the same field of cells, prior to and 30 min after the addition of forskolin, gave a reproducible measure of PKAc-F64L-S65T-GFP redistribution. The graph shows the individual 48 measurements and a trace of their mean±s.e.m at each forskolin concentration. For comparison, the effects of buffer or 8 increasing concentrations of forskolin on [cAMP]$_i$ was analysed by a scintillation proximity assay of cells grown under the same conditions. The graph shows a trace of the mean±s.e.m of 4 experiments expressed in arbitrary units.

As described above, the time it took for a response to come to completion was dependent on the forskolin dose (FIG. 5) In addition the degree of responses was also dose dependent. To test the PKA-F64L-S65T-GFP fusion protein translocation in a semi high through-put system, CHO cells stably transfected with the PKA-F64L-S65T-GFP fusion was stimulated with buffer and 5 increasing doses of forskolin (n=8). Using the image analysis algorithm described above (Method 1), a dose response relationship was observed in the range from 0.01–50 mM forskolin (FIG. 6). A half maximal stimulation was observed at about 2 mM forskolin. In parallel, cells were stimulated with buffer and 8 increasing concentrations of forskolin (n=4) in the range 0.01–50 mM. The amount of cAMP produced was measured in an SPA assay. A steep increase was observed between 1 and 5 mM forskolin coincident with the steepest part of the curve for fusion protein translocation (also FIG. 6).

EXAMPLE 2

Quantitation of Redistribution in Real-time within Living Cells

Probe for Detection of PKC Activity in Real Time within Living Cells

Construction of PKC-GFP Fusion

The probe was constructed by ligating two restriction enzyme treated polymerase chain reaction (PCR) amplification products of the cDNA for murine PKCα (GenBank Accession number: M25811) and F64L-S65T-GFP (sequence disclosed in WO 97/11094) respectively. Taq® polymerase and the following oligonucleotide primers were used for PCR;

5'mPKCa: TTggACACAAgCTTTggACACCCTCAg-gATATggCTgACgTTTACCCggCCAACg (SEQ ID NO:5),

3'mPKCa: gTCATCTTCTCgAgTCTTTCAggCgCgC-CCTACTgCACTTgCMgATTgggTgC (SEQ ID NO:6),

5'F64L-S65T-GFP: TTggACACAAgCTTTggACACg-gCgCgCCATgAgTA
AAggAgMgMCTT-TTC (SEQ ID NO:1),

3'F64L-S65T-GFP: gTCATCTTCTCgAgTCTTACTCCT-gAggTTTgTATAg
TTCATCCATgC-CATgT (SEQ ID NO:2).

The hybrid DNA strand was inserted into the pZeoSV® mammalian expression vector as a HindIII-XhoI casette as described in example 1.

Cell Culture

BHK cells expressing the human M1 receptor under the control of the inducible metal-lothionine promoter and maintained with the dihydrofolate reductase marker were transfected with the PKCα-F64L-S65T-GFP probe using the calcium phosphate precipitate method in HEPES buffered saline (HBS [pH 7.10]). Stable transfectants were selected using 1000 μg Zeocin®/ml in the growth medium (DMEM with 1000 mg glucose/l, 10% foetal bovine serum (FBS) 100 mg penicillin-streptomycin mixture ml-1, 2 mM 1-glutamine). The hM1 receptor and PKCα-F64L-S65T-GFP fusion protein were maintained with 500 nM methotrexate and 500 μg Zeocin®/ml respectively. 24 hours prior to any experiment, the cells were transferred to HAM F-12 medium with glutamax, 100 μg penicillin-streptomycin mixture ml$^{-1}$ and 0.3% FBS. This medium relieves selection pressure, gives a low induction of signal transduction pathways and has a low autofluorescence at the relevant wavelength enabling fluorescence microscopy of cells straight from the incubator.

Monitoring the PKC Activity in Real Time

Digital images of live cells were gathered using a Zeiss Axiovert 135M fluorescence microscope fitted with a 40×, NA: 1.3 oil immersion objective and coupled to a Photometrics CH250 charged coupled device (CCD) camera. The cells were illuminated with a 100 W arc lamp. In the light path was a 470±20 nm excitation filter, a 510 nm dichroic mirror and a 515±15 nm emission filter for minimal image background. The cells were kept and monitored to be at 37° C. with a custom built stage heater.

Images were analyzed using the IPLab software package for Macintosh.

Figure 7:
FIG. 7. BHK cells stably transfected with the human muscarinic (hM1) receptor and the PKCa-F64L-S65T-GFP fusion. Carbachol (100 mM added at 1.0 second) induced a transient redistribution of PKCa-F64L-S65T-GFP from the cytoplasm to the plasma membrane. Images were taken at the following times: a) 1 second before carbachol addition, b) 8.8 seconds after addition and c) 52.8 seconds after addition.
Figure 7:
Figure 7:
Figure 8:
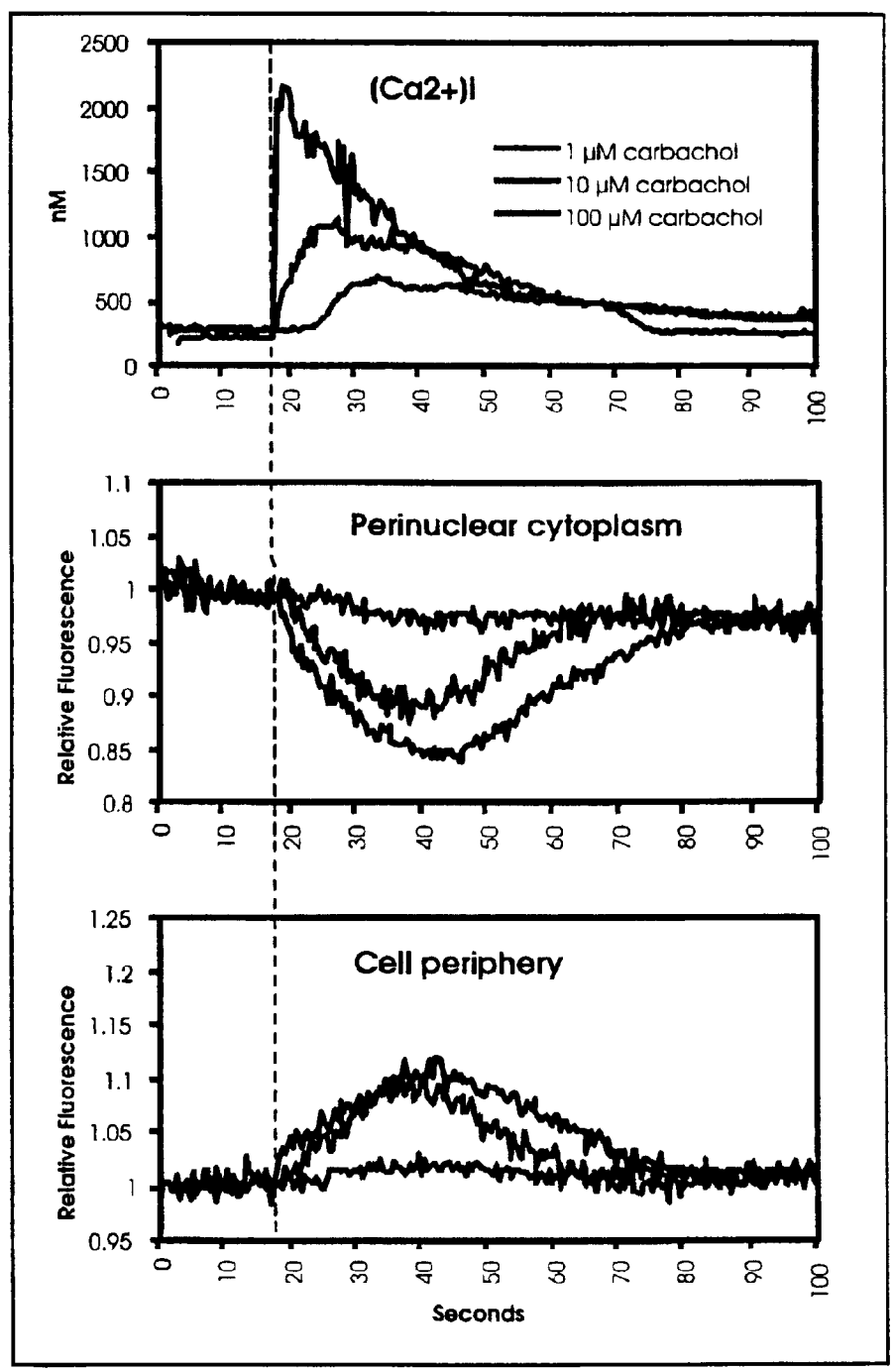
FIG. 8. BHK cells stably transfected with the hM1 receptor and PKCa-F64L-S65T-GFP fusion were treated with carbachol (1 mM, 10 mM, 100 mM). In single cells intracellular [$Ca^{2+}$] was monitored simultaneously with the redistribution of PKCa-F64L-S65T-GFP. shed line indicates the addition times of carbachol. The top panel shows changes in the intracellular $Ca^{2+}$ concentration of individual cells with time for each treatment. The middle panel shows changes in the average cytoplasmic GFP fluorescence for individual cells against time for each treatment. The bottom panel shows changes in the fluorescence of the periphery of single cells, within regions that specifically include the circumferential edge of a cell as seen in normal projection, the regions which offers best chance to monitor changes in the fluorescence intensity of the plasma membrane.

Upon stimulation of the M1-BHK cells, stably expressing the PKCα-F64L-S65T-GFP fusion, with carbachol we observed a dose-dependent transient translocation from the cytoplasm to the plasma membrane (FIGS. 7a,b,c). Simultaneous measurement of the cytosolic free calcium concentration shows that the carbachol-induced calcium mobilisation precedes the translocation (FIG. 8).

Stepwise Procedure for Quantitation of Translocation of PKC

1. The image was corrected for dark current by performing a pixel-by-pixel subtraction of a dark image (an image taken under the same conditions as the actual image, except the camera shutter is not allowed to open).
2. The image was corrected for non-uniformity of the illumination by performing a pixel-by-pixel ratio with a flat field correction image (an image taken under the same conditions as the actual image of a uniformly fluorescent specimen).
3. A copy of the image was made in which the edges are identified. The edges in the image are found by a standard edge-detection procedure—convolving the image with a kernel which removes any large-scale unchanging components (i.e., background) and accentuates any small-scale changes (i.e., sharp edges). This image was then converted to a binary image by threshholding. Objects in the binary image which are too small to represent the edges of cells were discarded. A dilation of the binary image was performed to close any gaps in the image edges. Any edge objects in the image which were in contact with the borders of the image are discarded. This binary image represents the edge mask.
4. Another copy of image was made via the procedure in step 3. This copy was further processed to detect objects which enclose "holes" and setting all pixels inside the holes to the binary value of the edge, i.e., one. This image represents the whole cell mask.
5. The original image was masked with the edge mask from step 3 and the sum total of all pixel values is determined.
6. The original image was masked with the whole cell mask from step 4 and the sum total of all pixel values was determined.
7. The value from step 5 was divided by the value from step 6 to give the final result, the fraction of fluorescence intensity in the cells which was localized in the edges.

EXAMPLE 3

Probes for Detection of Mitogen Activated Protein Kinase Erk1 Redistribution

Useful for monitoring signalling pathways involving MAPK, e.g. to identify compounds which modulate the activity of the pathway in living cells.

Erk1, a serine/threonine protein kinase, is a component of a signalling pathway which is activated by e.g. many growth factors.

Probes for Detection of ERK-1 Activity in Real Time within Living Cells

The extracellular signal regulated kinase (ERK-1, a mitogen activated protein kinase, MAPK) is fused N- or C-terminally to a derivative of GFP. The resulting fusions expressed in different mammalian cells are used for monitoring in vivo the nuclear translocation, and thereby the activation, of ERK1 in response to stimuli that activate the MAPK pathway.

a) Construction of Murine ERK1-F64L-S65T-GFP Fusion

Convenient restriction endonuclease sites are introduced into the cDNAs encoding murine ERK1 (GenBank Accession number: Z14249) and F64L-S65T-GFP (sequence disclosed in WO 97/11094) by polymerase chain reaction (PCR). The PCR reactions are performed according to standard protocols with the following primers:

5'ERK1: TTggACACAAgCTTTggACACCCTCAg-gATATgg
CggCggCggCggCggCTCCggggg-gCgggg (SEQ ID NO:7),
3'ERK1: gTCATCTTCTCgAgTCTTTCAggCgCgC-CCggggCCCTCTggCgCCCCTggCTgg (SEQ ID NO:8),
5'F64L-S65T-GFP: TTggACACAAgCTTTggACACg-gCgCgCCATgAgTA
AAggAgAgAACTT-TTC (SEQ ID NO:1)
3'F64L-S65T-GFP: gTCATCTTCTCgAgTCTTACTCCT-gAggTTTgTAT
AgTTCATCCATgC-CATgT (SEQ ID NO:2)

To generate the mERK1-F64L-S65T-GFP (SEQ ID NO:56 & 57) fusion the ERK1 amplification product is digested with HindIII+AscI and the F64L-S65T-GFP product with AscI+XhoI. To generate the F64L-S65T-GFP-mERK1 fusion the ERK1 amplification product is then digested with HindIII+Bsu36I and the F64L-S65T-GFP product with Bsu36I+XhoI. The two pairs of digested PCR products are subsequently ligated with a HindIII+XhoI digested plasmid (pZeoSV® mammalian expression vector, Invitrogen, San Diego, Calif., USA). The resulting fusion constructs are under control of the SV40 promoter.

b) The human Erk1 gene (GenBank Accession number: X60188) was amplified using PCR according to standard protocols with primers Erk1-top (SEQ ID NO:9) and Erk1-bottom/+stop (SEQ ID NO:10). The PCR product was digested with restriction enzymes EcoR1 and BamH1, and ligated into pEGFP-C1 (Clontech, Palo Alto; GenBank Accession number U55763) digested with EcoR1 and BamH1. This produces an EGFP-Erk1 fusion (SEQ ID NO:38 &39) under the control of a CMV promoter.

The plasmid containing the EGFP-Erk1 fusion was transfected into HEK293 cells employing the FUGENE transfection reagent (Boehringer Mannheim). Prior to experiments the cells were grown to 80%–90% confluency 8 well chambers in DMEM with 10% FCS. The cells were washed in plain HAM F-12 medium (without FCS), and then incubated for 30–60 minutes in plain HAM F-12 (without FCS) with 100 micromolar PD98059, an inhibitor of MEK1, a kinase which activates Erk1; this step effectively empties the nucleus of EGFP-Erk1. Just before starting the experiment, the HAM F-12 was replaced with Hepes buffer following a wash with Hepes buffer. This removes the PD98059 inhibitor; if blocking of MEK1 is still wanted (e.g. in control experiments), the inhibitor is included in the Hepes buffer.

The experimental setup of the microscope was as described in example 1.

60 images were collected with 10 seconds between each, and with the test compound added after image number 10.

Figure 9:
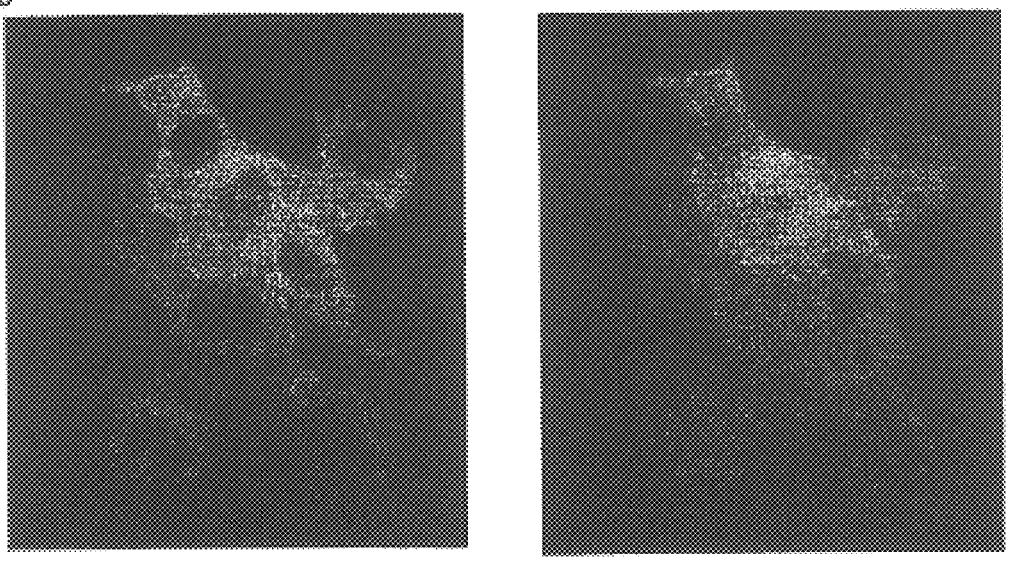
FIG. 9. a) The hERK1-F64L-S65T-GFP fusion expressed in HEK293 cells treated with 100 mM of the MEK1 inhibitor PD98059 in HAM F-12 (without serum) for 30 minutes at 37° C. The nuclei empty of fluorescence during this treatment.
Figure 9:
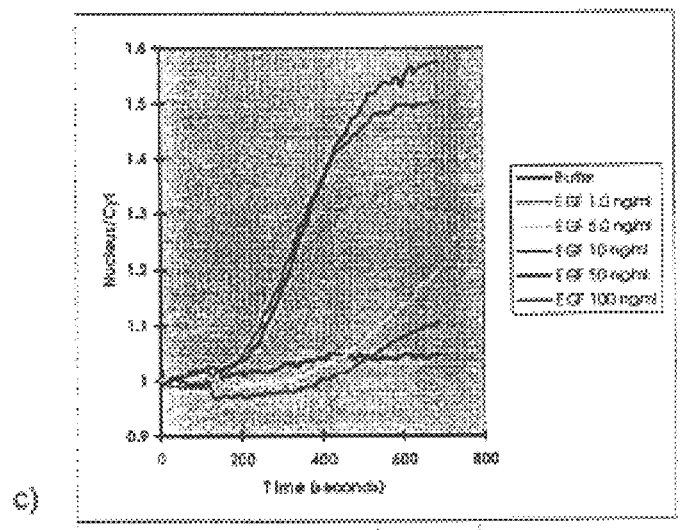
Figure 9:
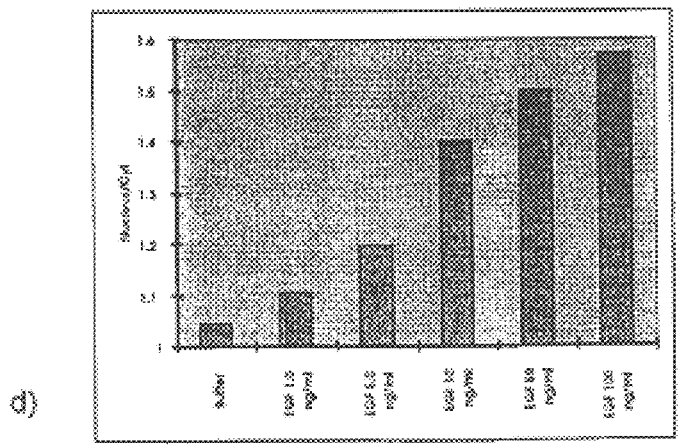

Addition of EGF (1–100 nM) caused within minutes a redistribution of EGFP-Erk1 from the cytoplasm into the nucleus (FIGS. 9a,b).

The response was quantitated as described below and a dose-dependent relationship between EGF concentration and nuclear translocation of EGFP-Erk1 was found (FIGS. 9c,d). Redistribution of GFP fluorescence is expressed in this example as the change in the ratio value between areas in nuclear versus cytoplasmic compartments of the cell. Each time profile is the average of nuclear to cytoplasmic ratios from six cells in each treatment.

EXAMPLE 4

Probes for Detection of Erk2 Redistribution

Useful for monitoring signalling pathways involving MAPK, e.g. to identify compounds which modulate the activity of the pathway in living cells.

Erk2, a serine/threonine protein kinase, is closely related to Erk1 but not identical; it is a component of a signalling pathway which is activated by e.g. many growth factors.

a) The rat Erk2 gene (GenBank Accession number: M64300) was amplified using PCR according to standard protocols with primers Erk2-top (SEQ ID NO:11) and Erk2-bottom/+stop (SEQ ID NO:13) The PCR product was digested with restriction enzymes Xho1 and BamH1, and ligated into pEGFP-C1 (Clontech, Palo Alto; GenBank Accession number U55763) digested with Xho1 and BamH1. This produces an EGFP-Erk2 fusion (SEQ ID NO:40 &41) under the control of a CMV promoter.

b) The rat Erk2 gene (GenBank Accession number: M64300) was amplified using PCR according to standard protocols with primers (SEQ ID NO:11) Erk2-top and Erk2-bottom/–stop (SEQ ID NO:12). The PCR product was digested with restriction enzymes Xho1 and BamH1, and ligated into pEGFP-N1 (Clontech, Palo Alto; GenBank Accession number U55762) digested with Xho1 and BamH1. This produces an Erk2-EGFP fusion (SEQ ID NO:58 &59) under the control of a CMV promoter.

The resulting plasmids were transfected into CHO cells and BHK cells. The cells were grown under standard conditions. Prior to experiments, the cells were starved in medium without serum for 48–72 hours. This led to a predominantly cytoplasmic localization of both probes, especially in BHK cells. 10% fetal calf serum was added to the cells and the fluorescence of the cells was recorded as explained in example 3. Addition of serum caused the probes to redistribute into the nucleus within minutes of addition of serum.

EXAMPLE 5

Probes for Detection of Smad2 Redistribution

Useful for monitoring signalling pathways activated by some members of the transforming growth factor-beta family, e.g. to identify compounds which modulate the activity of the pathway in living cells.

Smad 2, a signal transducer, is a component of a signalling pathway which is induced by some members of the TGFbeta family of cytokines.

a) The human Smad2 gene (GenBank Accession number: AF027964) was amplified using PCR according to standard protocols with primers Smad2-top (SEQ ID NO:24) and Smad2-bottom/+stop (SEQ ID NO:26). The PCR product was digested with restriction enzymes EcoR1 and Acc65I, and ligated into pEGFP-C1 (Clontech; Palo Alto; GenBank Accession number U55763) digested with EcoR1 and Acc65I. This produces an EGFP-Smad2 fusion (SEQ ID NO:50&51) under the control of a CMV promoter.

b) The human Smad2 gene (GenBank Accession number: AF027964) was amplified using PCR according to standard protocols with primers Smad2-top (SEQ ID NO:24) and Smad2-bottom/–stop (SEQ ID NO:25). The PCR product was digested with restriction enzymes EcoR1 and Acc65I, and ligated into pEGFP-N1 (Clontech, Palo Alto; GenBank Accession number U55762) digested with EcoR1 and Acc65I. This produces a Smad2-EGFP fusion (SEQ ID NO:74 &75) under the control of a CMV promoter.

The plasmid containing the EGFP-Smad2 fusion was transfected into HEK293 cells, where it showed a cytoplasmic distribution. Prior to experiments the cells were grown in 8 well Nunc chambers in DMEM with 10% FCS to 80% confluency and starved overnight in HAM F-12 medium without FCS.

For experiments, the HAM F-12 medium was replaced with Hepes buffer pH 7.2.

The experimental setup of the microscope was as described in example 1.

90 images were collected with 10 seconds between each, and with the test compound added after image number 5.

After serum starvation of cells, each nucleus contains less GFP fluorescence than the surrounding cytoplasm (FIG. 10a). Addition of TGFbeta caused within minutes a redistribution of EGFP-Smad2 from the cytoplasma into the nucleus (FIG. 10b).

The redistribution of fluorescence within the treated cells was quantified simply as the fractional increase in nuclear fluorescence normalised to the starting value of GFP fluorescence in the nucleus of each unstimulated cell.

EXAMPLE 6
Probe for Detection of VASP Redistribution

Useful for monitoring signalling pathways involving rearrangement of cytoskeletal elements, e.g. to identify compounds which modulate the activity of the pathway in living cells.

VASP, a phosphoprotein, is a component of cytoskeletal structures, which redistributes in response to signals which affect focal adhesions.

a) The human VASP gene (GenBank Accession number: Z46389) was amplified using PCR according to standard protocols with primers VASP-top (SEQ ID NO:94) and VASP-bottom/+stop (SEQ ID NO:95). The PCR product was digested with restriction enzymes Hind3 and BamH1, and ligated into pEGFP-C1 (Clontech, Palo Alto; GenBank Accession number U55763) digested with Hind3 and BamH1. This produces an EGFP-VASP fusion (SEQ ID NO:124 &125) under the control of a CMV promoter.

The resulting plasmid was transfected into CHO cells expressing the human insulin receptor using the calcium-phosphate transfection method. Prior to experiments, cells were grown in 8 well Nunc chambers and starved overnight in medium without FCS.

Experiments are performed in a microscope setup as described in example 1.

10% FCS was added to the cells and images were collected. The EGFP-VASP fusion was redistributed from a somewhat even distribution near the periphery into more localized structures, identified as focal adhesion points (FIG. 11).

A large number of further GFP fusions have been made or are in the process of being made, as apparent from the following Examples 7–22 which also suggest suitable host cells and substances for activation of the cellular signalling pathways to be monitored and analyzed.

EXAMPLE 7
Probe for Detection of Actin Redistribution

Useful for monitoring signalling pathways involving rearrangement or formation of actin filaments, e.g. to identify compounds which modulate the activity of pathways leading to cytoskeletal rearrangements in living cells.

Actin is a component of cytoskeletal structures, which redistributes in response to very many cellular signals.

The actin binding domain of the human alpha-actinin gene (GenBank Accession number: X15804) was amplified using PCR according to standard protocols with primers ABD-top (SEQ ID NO:90) and ABD-bottom/−stop (SEQ ID NO:91). The PCR product was digested with restriction enzymes Hind3 and BamH1, and ligated into pEGFP-N1 (Clontech, Palo Alto; GenBank Accession number U55762) digested with Hind3 and BamH1. This produced an actin-binding-domain-EGFP fusion (SEQ ID NO:128 &129) under the control of a CMV promoter.

The resulting plasmid was transfected into CHO cells expressing the human insulin receptor. Cells were stimulated with insulin which caused the actin binding domain-EGFP probe to become redistributed into morphologically distinct membrane-associated structures.

EXAMPLE 8
Probes for Detection of p38 Redistribution

Useful for monitoring signalling pathways responding to various cellular stress situations, e.g. to identify compounds which modulate the activity of the pathway in living cells, or as a counterscreen.

p38, a serine/threonine protein kinase, is a component of a stress-induced signalling pathway which is activated by many types of cellular stress, e.g. TNFalpha, anisomycin, UV and mitomycin C.

a) The human p38 gene (GenBank Accession number: L35253) was amplified using PCR according to standard protocols with primers p38-top (SEQ ID NO:14) and p38-bottom/+stop (SEQ ID NO: 16). The PCR product was digested with restriction enzymes Xho1 and BamH1, and ligated into pEGFP-C1 (Clontech, Palo Alto; GenBank Accession number U55763) digested with Xho1 and BamH1. This produced an EGFP-p38 fusion (SEQ ID NO:46 &47) under the control of a CMV promoter.

b) The human p38 gene (GenBank Accession number: L35253) was amplified using PCR according to standard protocols with primers p38-top (SEQ ID NO:13) and p38-bottom/−stop (SEQ ID NO:15). The PCR product was digested with restriction enzymes Xho1 and BamH1, and ligated into pEGFP-N1 (Clontech, Palo Alto; GenBank Accession number U55762) digested with Xho1 and BamH1. This produced a p38-EGFP fusion (SEQ ID NO:64 &65) under the control of a CMV promoter.

The resulting plasmids are transfected into a suitable cell line, e.g. HEK293, in which the EGFP-p38 probe and/or the p38-EGFP probe should change its cellular distribution from predominantly cytoplasmic to nuclear within minutes in response to activation of the signalling pathway with e.g. anisomycin.

EXAMPLE 9
Probes for Detection of Jnk1 Redistribution

Useful for monitoring signalling pathways responding to various cellular stress situations, e.g. to identify compounds which modulate the activity of the pathway in living cells, or as a counterscreen.

Jnk1, a serine/threonine protein kinase, is a component of a stress-induced signalling pathway different from the p38 described above, though it also is activated by many types of cellular stress, e.g. TNFalpha, anisomycin and UV.

a) The human Jnk1 gene (GenBank Accession number: L26318) was amplified using PCR according to standard protocols with primers Jnk-top (SEQ ID NO: 17) and Jnk-bottom/+stop (SEQ ID NO:19). The PCR product was digested with restriction enzymes Xho1 and BamH1, and ligated into pEGFP-C1 (Clontech, Palo Alto; GenBank Accession number U55763) digested with Xho1 and BamH1. This produced an EGFP-Jnk1 fusion (SEQ ID NO:44 &45) under the control of a CMV promoter.

b) The human Jnk1 gene (GenBank Accession number L2631 8) was amplified using PCR according to standard protocols with primers Jnk-top (SEQ ID NO:17) and Jnk-bottom/–stop (SEQ ID NO:18). The PCR product was digested with restriction enzymes Xho1 and BamH1, and ligated into pEGFP-N1 (Clontech, Palo Alto; GenBank Accession number U55762) digested with Xho1 and BamH1. This produced a Jnk1-EGFP fusion (SEQ ID NO:62 &63) under the control of a CMV promoter.

The resulting plasmids are transfected into a suitable cell line, e.g. HEK293, in which the EGFP-Jnk1 probe and/or the Jnk1-EGFP probe should change its cellular distribution from predominantly cytoplasmic to nuclear in response to activation of the signalling pathway with e.g. anisomycin.

EXAMPLE 10
Probes for Detection of PKG Redistribution

Useful for monitoring signalling pathways involving changes in cyclic GMP levels, e.g. to identify compounds which modulate the activity of the pathway in living cells.

PGK, a cGMP-dependent serine/threonine protein kinase, mediates the guanylyl-cyclase/cGMP signal.

a) The human PKG gene (GenBank Accession number: Y07512) is amplified using PCR according to standard protocols with primers PKG-top (SEQ ID NO:81) and PKG-bottom/+stop (SEQ ID NO:83). The PCR product is digested with restriction enzymes Xho1 and BamH1, and ligated into pEGFP-C1 (Clontech, Palo Alto; GenBank Accession number U55763) digested with Xho1 and BamH1. This produces an EGFP-PKG fusion (SEQ ID NO:134 &135) under the control of a CMV promoter.

b) The human PKG gene (GenBank Accession number: Y07512) is amplified using PCR according to standard protocols with primers PKG-top (SEQ ID NO:81) and PKG-bottom/–stop (SEQ ID NO: 82). The PCR product is digested with restriction enzymes Xho1 and BamH1, and ligated into pEGFP-N1 (Clontech, Palo Alto; GenBank Accession number U55762) digested with Xho1 and BamH1. This produces a PKG-EGFP fusion (SEQ ID NO:136 &137) under the control of a CMV promoter.

The resulting plasmids are transfected into a suitable cell line, e.g. A10, in which the EGFP-PKG probe and/or the PKG-EGFP probe should change its cellular distribution from cytoplasmic to one associated with cytoskeletal elements within minutes in response to treatment with agents which raise nitric oxide (NO) levels.

EXAMPLE 11
Probes for Detection of IkappaB Kinase Redistribution

Useful for monitoring signalling pathways leading to NFkappaB activation, e.g. to identify compounds which modulate the activity of the pathway in living cells.

IkappaB kinase, a serine/threonine kinase, is a component of a signalling pathway which is activated by a variety of inducers including cytokines, lymphokines, growth factors and stress.

a) The alpha subunit of the human IkappaB kinase gene (GenBank Accession number: AF009225) is amplified using PCR according to standard protocols with primers IKK-top (SEQ ID NO:96) and IKK-bottom/+stop (SEQ ID NO:98). The PCR product is digested with restriction enzymes EcoR1 and Acc65I, and ligated into pEGFP-C1 (Clontech, Palo Alto; GenBank Accession number U55763) digested with EcoR1 and Acc65I. This produces an EGFP-IkappaB-kinase fusion (SEQ ID NO:120 &121) under the control of a CMV promoter.

b) The alpha subunit of the human IkappaB kinase gene (GenBank Accession number: AF009225) is amplified using PCR according to standard protocols with primers IKK-top (SEQ ID NO:96) and IKK-bottom/–stop (SEQ ID NO:97). The PCR product is digested with restriction enzymes EcoR1 and Acc65I, and ligated into pEGFP-N1 (Clontech, Palo Alto; GenBank Accession number U55762) digested with EcoR1 and Acc65I. This produces an IkappaB-kinase-EGFP fusion (SEQ ID NO:122 &123) under the control of a CMV promoter.

The resulting plasmids are transfected into a suitable cell line, e.g. Jurkat, in which the EGFP-IkappaB-kinase probe and/or the IkappaB-kinase-EGFP probe should achieve a more cytoplasmic distribution within seconds following stimulation with e.g. TNFalpha.

EXAMPLE 12
Probes for Detection of CDK2 Redistribution

Useful for monitoring signalling pathways of the cell cycle, e.g. to identify compounds which modulate the activity of the pathway in living cells.

CDK2, a cyclin-dependent serine/threonine kinase, is a component of the signalling system which regulates the cell cycle.

a) The human CDK2 gene (GenBank Accession number: X61622) is amplified using PCR according to standard protocols with primers CDK2-top (SEQ ID NO:102) and CDK2-bottom/+stop (SEQ ID NO: 104). The PCR product is digested with restriction enzymes Xho1 and BamH1, and ligated into pEGFP-C1 (Clontech, Palo Alto; GenBank Accession number U55763) digested with Xho1 and BamH1. This produces an EGFP-CDK2 fusion (SEQ ID NO:114 & 115) under the control of a CMV promoter.

b) The human CDK2 gene (GenBank Accession number: X61622) is amplified using PCR according to standard protocols with primers CDK2-top (SEQ ID NO:102) and CDK2-bottom/–stop (SEQ ID NO:103), The PCR product is digested with restriction enzymes Xho1 and BamH1, and ligated into pEGFP-N1 (Clontech, Palo Alto; GenBank Accession number U55762) digested with Xho1 and BamH1. This produces a CDK2-EGFP fusion (SEQ ID NO:112 & 113) under the control of a CMV promoter.

The resulting plasmids are transfected into a suitable cell line, e.g. HEK293 in which the EGFP-CDK2 probe and/or the CDK2-EGFP probe should change its cellular distribution from cytoplasmic in contact-inhibited cells, to nuclear location in response to activation with a number of growth factors, e.g. IGF.

EXAMPLE 13
Probes for Detection of Grk5 Redistribution

Useful for monitoring signalling pathways involving desensitization of G-protein coupled receptors, e.g. to identify compounds which modulate the activity of the pathway in living cells.

Grk5, a G-protein coupled receptor kinase, is a component of signalling pathways involving membrane bound G-protein coupled receptors.

a) The human Grk5 gene (GenBank Accession number: L15388) is amplified using PCR according to standard protocols with primers Grk5-top (SEQ ID NO:27) and Grk5-bottom/+stop (SEQ ID NO:29). The PCR product is digested with restriction enzymes EcoR1 and BamH1, and ligated into pEGFP-C1 (Clontech, Palo Alto; GenBank Accession number U55763) digested with EcoR1 and BamH1. This produces an EGFP-Grk5 fusion (SEQ ID NO:42 &43) under the control of a CMV promoter.

b) The human Grk5 gene (GenBank Accession number: L15388) is amplified using PCR according to standard protocols with primers Grk5-top (SEQ ID NO:27) and Grk5-bottom/–stop (SEQ ID NO:28). The PCR product is digested with restriction enzymes EcoR1 and BamH1, and ligated into pEGFP-N1 (Clontech, Palo Alto; GenBank Accession number U55762) digested with EcoR1 and BamH1. This produces a Grk5-EGFP fusion (SEQ ID NO:60 &61) under the control of a CMV promoter.

The resulting plasmids are transfected into a suitable cell line, e.g. HEK293 expressing a rat dopamine D1A receptor, in which the EGFP-Grk5 probe and/or the Grk5-EGFP probe should change its cellular distribution from predominantly cytoplasmic to peripheral in response to activation of the signalling pathway with e.g. dopamine.

EXAMPLE 14
Probes for Detection of Zap70 Redistribution

Useful for monitoring signalling pathways involving the T cell receptor, e.g. to identify compounds which modulate the activity of the pathway in living cells.

Zap70, a tyrosine kinase, is a component of a signalling pathway which is active in e.g. T-cell differentiation.

a) The human Zap70 gene (GenBank Accession number: L05148) is amplified using PCR according to standard protocols with primers Zap70-top (SEQ ID NO:105) and Zap70-bottom/+stop (SEQ ID NO:107). The PCR product is digested with restriction enzymes EcoR1 and BamH1, and ligated into pEGFP-C1 (GenBank Accession number U55763) digested with EcoR1 and BamH1. This produces an EGFP-Zap70 fusion (SEQ ID NO:108 &109) under the control of a CMV promoter.

b) The human Zap70 gene (GenBank Accession number: L05148) is amplified using PCR according to standard protocols with primers Zap70-top (SEQ ID NO:105) and Zap70-bottom/–stop (SEQ ID NO:106). The PCR product is digested with restriction enzymes EcoR1 and BamH1, and ligated into pEGFP-N1 (Clontech, Palo Alto; GenBank Accession number U55762) digested with EcoR1 and BamH1. This produces a Zap70-EGFP fusion (SEQ ID NO:110 &111) under the control of a CMV promoter.

The resulting plasmids are transfected into a suitable cell line, e.g. Jurkat, in which the EGFP-Zap70 probe and/or the Zap70-EGFP probe should change its cellular distribution from cytoplasmic to membrane-associated within seconds in response to activation of the T cell receptor signalling pathway with e.g. antibodies to CD3epsilon.

EXAMPLE 15
Probes for Detection of p85 Redistribution

Useful for monitoring signalling pathways involving PI-3 kinase, e.g. to identify compounds which modulate the activity of the pathway in living cells.

p85alpha is the regulatory subunit of P13-kinase which is a component of many pathways involving membrane-bound tyrosine kinase receptors and G-protein-coupled receptors.

a) The human p85alpha gene (GenBank Accession number: M61906) was amplified using PCR according to standard protocols with primers p85-top-C (SEQ ID NO:22) and p85-bottom/+stop (SEQ ID NO:23). The PCR product was digested with restriction enzymes Bgl2 and BamH1, and ligated into pEGFP-C1 (Clontech, Palo Alto; GenBank Accession number U55763) digested with Bgl2 and BamH1. This produced an EGFP-p85alpha fusion (SEQ ID NO:48 &49) under the control of a CMV promoter.

b) The human p85alpha gene (GenBank Accession number: M61906) was amplified using PCR according to standard protocols with primers p85-top-N (SEQ ID NO:20) and p85-bottom/–stop (SEQ ID NO:21). The PCR product was digested with restriction enzymes EcoR1 and BamH1, and ligated into pEGFP-N1 (Clontech, Palo Alto; GenBank Accession number U55762) digested with EcoR1 and BamH1. This produced a p85alpha-EGFP fusion (SEQ ID NO:66 &67) under the control of a CMV promoter.

The resulting plasmids are transfected into a suitable cell line, e.g. CHO expressing the human insulin receptor, in which the EGFP-p85 probe and/or the p85-EGFP probe may change its cellular distribution from cytoplasmic to membrane-associated within minutes in response to activation of the receptor with insulin.

EXAMPLE 16
Probes for Detection of Protein-tyrosine Phosphatase Redistribution Useful for monitoring signalling pathways involving tyrosine kinases, e.g. to identify compounds which modulate the activity of the pathway in living cells.

Protein-tyrosine phosphatase 1C, a tyrosine-specific phosphatase, is an inhibitory component in signalling pathways involving e.g. some growth factors.

a) The human protein-tyrosine phosphatase 1C gene (GenBank Accession number: X62055) is amplified using PCR according to standard protocols with primers PTP-top (SEQ ID NO:99) and PTP-bottom/+stop (SEQ ID NO:101). The PCR product is digested with restriction enzymes Xho1 and EcoR1, and ligated into pEGFP-C1 (Clontech, Palo Alto; GenBank Accession number U55763) digested with Xho1 and EcoR1. This produces an EGFP-PTP fusion (SEQ ID NO:116 &117) under the control of a CMV promoter.

b) The human protein-tyrosine phosphatase 1C gene (GenBank Accession number: X62055) is amplified using PCR according to standard protocols with primers PTP-top (SEQ ID NO:99) and PTP-bottom/–stop (SEQ ID NO:100). The PCR product is digested with restriction enzymes Xho1 and EcoR1, and ligated into pEGFP-N1 (Clontech, Palo Alto; GenBank Accession number U55762) digested with Xho1 and EcoR1. This produces a PTP-EGFP fusion (SEQ ID NO:118 &119) under the control of a CMV promoter.

The resulting plasmids are transfected into a suitable cell line, e.g. MCF-7 in which the EGFP-PTP probe and/or the PTP-EGFP probe should change its cellular distribution from cytoplasm to the plasma membrane within minutes in response to activation of the growth inhibitory signalling pathway with e.g. somatostatin.

EXAMPLE 17
Probes for Detection of Smad4 Redistribution

Useful for monitoring signalling pathways involving most members of the transforming growth factor-beta family, e.g. to identify compounds which modulate the activity of the pathway in living cells.

Smad4, a signal transducer, is a common component of signalling pathways induced by various members of the TGFbeta family of cytokines.

a) The human Smad4 gene (GenBank Accession number: U44378) was amplified using PCR according to standard protocols with primers Smad4-top and Smad4-bottom/+stop (SEQ ID NO:35). The PCR product was digested with restriction enzymes EcoR1 and BamH1, and ligated into pEGFP-C1 (Clontech, Palo Alto; GenBank Accession number U55763) digested with EcoR1 and BamH1. This produce an EGFP-Smad4 fusion (SEQ ID NO:52 &53) under the control of a CMV promoter.

b) The human Smad4 gene (GenBank Accession number: U44378) was amplified using PCR according to standard protocols with primers Smad4-top (SEQ ID NO:33) and Smad4-bottom/–stop (SEQ ID NO:34). The PCR product was digested with restriction enzymes EcoR1 and BamH1, and ligated into pEGFP-N1 (Clontech, Palo Alto; GenBank Accession number U55762) digested with EcoR1 and BamH1. This produced a Smad4-EGFP fusion (SEQ ID NO:76 &77) under the control of a CMV promoter.

The resulting plasmids are transfected into a cell line, e.g. HEK293 in which the EGFP-Smad4 probe and/or the Smad4-EGFP probe should change its cellular distribution within minutes from cytoplasmic to nuclear in response to activation of the signalling pathway with e.g. TGFbeta.

EXAMPLE 18
Probes for Detection of Stat5 Redistribution

Useful for monitoring signalling pathways involving the activation of tyrosine kinases of the Jak family, e.g. to identify compounds which modulate the activity of the pathway in living cells.

Stat5, signal transducer and activator of transcription, is a component of signalling pathways which are induced by e.g. many cytokines and growth factors.

a) The human Stat5 gene (GenBank Accession number: L41142) was amplified using PCR according to standard protocols with primers Stat5-top (SEQ ID NO:30) and Stat5-bottom/+stop (SEQ ID NO:32). The PCR product was digested with restriction enzymes Bgl2 and Acc65I, and ligated into pEGFP-C1 (Clontech; Palo Alto; GenBank Accession number U55763) digested with Bgl2 and Acc65I. This produced an EGFP-Stat5 fusion (SEQ ID NO:54 &55) under the control of a CMV promoter.

b) The human Stat5 gene (GenBank Accession number: L41142) was amplified using PCR according to standard protocols with primers Stat5-top (SEQ ID NO:30) and Stat5bottom/–stop (SEQ ID NO:331). The PCR product was digested with restriction enzymes Bgl2 and Acc65I, and ligated into pEGFP-N1 (Clontech, Palo Alto; GenBank Accession number U55762) digested with Bgl2 and Acc65I. This produced a Stat5-EGFP fusion (SEQ ID NO:78 &79) under the control of a CMV promoter.

The resulting plasmids are transfected into a suitable cell line, e.g. MIN6 in which the EGFP-Stat5 probe and/or the Stat5-EGFP probe should change its cellular distribution from cytoplasmic to nuclear within minutes in response to activation signalling pathway with e.g. prolactin.

EXAMPLE 19
Probes for Detection of NFAT Redistribution

Useful for monitoring signalling pathways involving activation of NFAT, e.g. to identify compounds which modulate the activity of the pathway in living cells.

NFAT, an activator of transcription, is a component of signalling pathways which is involved in e.g. immune responses.

a) The human NFAT1 gene (GenBank Accession number: U43342) is amplified using PCR according to standard protocols with primers NFAT-top (SEQ ID NO:84) and NFAT-bottom/+stop (SEQ ID NO:86). The PCR product is digested with restriction enzymes Xho1 and EcoR1, and ligated into pEGFP-C1 (Clontech, Palo Alto; GenBank Accession number U55763) digested with Xho1 and EcoR1. This produces an EGFP-NFAT fusion (SEQ ID NO:130 &131) under the control of a CMV promoter.

b) The human NFAT gene (GenBank Accession number: U43342) is amplified using PCR according to standard protocols with primers NFAT-top (SEQ ID NO:84) and NFAT-bottom/–stop (SEQ ID NO:85). The PCR product is digested with restriction enzymes Xho1 and EcoR1, and ligated into pEGFP-N1 (Clontech, Palo Alto; GenBank Accession number U55762) digested with Xho1 and EcoR1. This produces an NFAT-EGFP fusion (SEQ ID NO:132 &133) under the control of a CMV promoter.

The resulting plasmids are transfected into a suitable cell line, e.g. Jurkat, in which the EGFP-NFAT probe and/or the NFAT-EGFP probe should change its cellular distribution from cytoplasmic to nuclear within minutes in response to activation of the signalling pathway with e.g. antibodies to CD3epsilon.

EXAMPLE 20
Probes for Detection of NFkappaB Redistribution

Useful for monitoring signalling pathways leading to activation of NFkappaB, e.g. to identify compounds which modulate the activity of the pathway in living cells.

NFkappaB, an activator of transcription, is a component of signalling pathways which are responsive to a varity of inducers including cytokines, lymphokines, some immunosuppressive agents.

a) The human NFkappaB p65 subunit gene (GenBank Accession number: M62399) is amplified using PCR according to standard protocols with primers NFkappaB-top (SEQ ID NO:87) and NFkappaB-bottom/+stop (SEQ ID NO:89). The PCR product is digested with restriction enzymes Xho1 and BamH1, and ligated into pEGFP-C1 (Clontech, Palo Alto; GenBank Accession number U55763) digested with Xho1 and BamH1. This produces an EGFP-NFkappaB fusion (SEQ ID NO:142 & 143) under the control of a CMV promoter.

b) The human NFkappaB p65 subunit gene (GenBank Accession number: M62399) is amplified using PCR according to standard protocols with primers NFkappaB-top (SEQ ID NO:87) and NFkappaB-bottom/–stop (SEQ ID NO:88). The PCR product is digested with restriction enzymes Xho1 and BamH1, and ligated into pEGFP-N1 (Clontech, Palo Alto; GenBank Accession number U55762) digested with Xho1 and BamH1. This produces an NFkappaB-EGFP fusion (SEQ ID NO:140 & 141) under the control of a CMV promoter.

The resulting plasmids are transfected into a suitable cell line, e.g. Jurkat, in which the EGFP-NFkappaB probe and/or the NFkappaB-EGFP probe should change its cellular distribution from cytoplasmic to nuclear in response to activation of the signalling pathway with e.g. TNFalpha.

EXAMPLE 21
Probe for Detection of RhoA Redistribution

Useful for monitoring signalling pathways involving RhoA, e.g. to identify compounds which modulate the activity of the pathway in living cells.

RhoA, a small GTPase, is a component of many signalling pathways, e.g. LPA induced cytoskeletal rearrangements.

The human RhoA gene (GenBank Accession number: L25080) was amplified using PCR according to standard protocols with primers RhoA-top (SEQ ID NO:92) and RhoA-bottom/+stop (SEQ ID NO:93). The PCR product was digested with restriction enzymes Hind3 and BamH1, and ligated into pEGFP-C1 (Clontech, Palo Alto; GenBank Accession number U55763) digested with Hind3and BamH1. This produced an EGFP-RhoA fusion (SEQ ID NO:126 &127) under the control of a CMV promoter.

The resulting plasmid is transfected into a suitable cell line, e.g. Swiss3T3, in which the EGFP-RhoA probe should change its cellular distribution from a reasonably homogenous to a peripheral distribution within minutes of activation of the signalling pathway with e.g. LPA.

EXAMPLE 22

Probes for Detection of PKB RedistributionUseful for monitoring signalling pathways involving PKB e.g. to identify compounds which modulate the activity of the pathway in living cells.

PKB, a serine/threonine kinase, is a component in various signalling pathways, many of which are activated by growth factors.

a) The human PKB gene (GenBank Accession number: M63167) is amplified using PCR according to standard protocols with primers PKB-top (SEQ ID NO:36) and PKB-bottom/+stop (SEQ ID NO:80). The PCR product is digested with restriction enzymes Xho1 and BamH1, and ligated into pEGFP-C1 (Clontech, Palo Alto; GenBank Accession number U55763) digested with Xho1 and BamH1. This produces an EGFP-PKB fusion (SEQ ID NO:138 & 139) under the control of a CMV promoter.

b) The human PKB gene (GenBank Accession number: M63167) was amplified using PCR according to standard protocols with primers PKB-top (SEQ ID NO:36) and PKB-bottom/-stop (SEQ ID NO:37). The PCR product was digested with restriction enzymes Xho1 and BamH1, and ligated into pEGFP-N1(Clontech, Palo Alto; GenBank Accession number U55762) digested with Xho1 and BamH1. This produced a PKB-EGFP fusion (SEQ ID NO:70 &71) under the control of a CMV promoter.

The resulting plasmids are transfected into a suitable cell line, e.g. CHO expressing the human insulin receptor, in which the EGFP-PKB probe and/or the PKB-EGFP probe cycles between cytoplasmic and membrane locations during the activation-deactivation process following addition of insulin. The transition should be apparent within minutes.

REFERENCES

Adams, S. R., Harootunian, A. T., Buechler, Y. J., Taylor, S. S. & Tsien, R. Y. (1991) Nature 349, 694–697

Blobe, G. C., Stribling, D. S., Fabbro, D., Stabel, S & Hannun, Y. A. (1996) J. Biol. Chem. 271, 15823–15830

Chalfie, M., Tu, Y., Euskirchen, G., Ward, W. W. & Prasher, D. C. (1994) Science 263, 802–805

Cossette, L. J., Hoglinger, O., Mou, L. J. & Shen, S. H. (1997) Exp. Cell Res. 223, 459–466

DeBernardi, M. A. & Brooker, G. (1996) Proc. Natl. Acad. Sci. USA 93, 4577–4582

Farese, R. V. (1992) Biochem. J. 288, 319–323

Fulop Jr., T., Leblanc, C., Lacombe, G. & Dupuis, G. (1995) FEBS Lett. 375, 69–74

Godson, C., Masliah, E., Balboa, M. A., Ellisman, M. H. & Insel, P. A. (1996) Biochem. Biophys. Acta 1313, 63–71

Khalil, R. A., Lajoie, C., Resnick, M. S. & Morgan, K. G. (1992) American Physiol. Society c, 714–719

Sano, M., Kohno, M. & Iwanaga, M. (1995) Brain Res. 688, 213–218

Bastiaens, P. I. H. & Jovin, T. M. (1996) Proc. Natl. Acad. Sci. USA 93, 8407–8412

Schmidt, D. J., Ikebe, M., Kitamura, K., & Fay, F. S. (1997) FASEB J. 11, 2924 (Abstract)

Sakai, N., Sasaki, K., Hasegawa, C., Ohkura, M., Suminka, K., Shirai, Y. & Saito, N. (1996) Soc. Neuroscience 22, 69P (Abstract)

Sakai, N., Sasaki, K. Hasegawa, C., Ohkura, M., Sumioka, ., Shirai, Y., & Naoaki, S. (1997) Japanese Journal of Pharmacology 73, 69P (Abstract of a meeting held March 22–23)

What is claimed is:

1. A method for detecting intracellular translocation of a component of an intracellular pathway affecting intracellular processes comprising:
   (a) culturing one or more cells containing a nucleotide sequence coding for a hybrid polypeptide comprising a luminophore linked to the component under conditions permitting expression of the nucleotide sequence,
   (b) incubating the cell or cells with a substance to be screened for biological function or biological effect, and
   (c) measuring the light emitted from the luminophore in the incubated cell or cells and determining the result or variation with respect to the emitted light from said luminophore, such variation being indicative of the translocation of the component in said cell or cells.

2. A method for detecting intracellular translocation of a component of an intracellular pathway affecting intracellular processes comprising:
   (a) culturing one or more cells containing a nucleotide sequence coding for a hybrid polypeptide comprising a luminophore linked to the component under conditions permitting expression of the nucleotide sequence,
   (b) incubating the cell or cells with a substance to be screened for biological function or biological effect, and
   (c) extracting quantitative information relating to the translocation of said component by recording variation in spatially distributed light emitted from said luminophore, such variation being indicative of the translocation of the component in said cell or cells.

3. A method according to claim 2, wherein the quantitative information relating to the translocation of the component is extracted from the recording or recordings according to a predetermined calibration.

4. A method according to claim 1 or 2, wherein the substance to be screened for biological function or biological effect is a chemical substance.

5. A method according to claim 1 or 2, wherein the substance is a substance whose affect on an intracellular pathway is to be determined.

6. A method according to claim 1 or 2, wherein the step (c) is made at a single point in time after the application of the substance.

7. A method according to claim 1 or 2, wherein the step (c) is made at two points in time, one point being before, and the other point being after the application of the substance.

8. A method according to claim 1 or 2, wherein the step (c) is performed at a series of points in time, in which the application of the substance occurs at some time after the first time point in the series of recordings, the recording being performed within a predetermined time spacing from about 0.1 seconds to 1 hour over a time span of from 1 second to 12 hours.

9. A method according to claim 8, wherein the predetermined time spacing from 1 to 60 seconds.

10. A method according to claim 8, wherein the predetermined time spacing from 1 to 30 seconds.

11. A method according to claim 8, wherein the predetermined time spacing from 1 to 10 seconds.

12. A method according to claim 8, wherein the time span is from 10 seconds to 1 hour.

13. A method according to claim 8, wherein the time span is from 60 seconds to 30 minutes.

14. A method according to claim 8, wherein the time span is from 60 seconds to 20 minutes.

15. A method according to claim 2, wherein the cell or cells is/are fixed at a point in time after the application of the substance at which the response has been predetermined to be significant, and the recording is made at an arbitrary later time.

16. A method according to claim 1 or 2, wherein the luminophore is a luminophore which is capable of being translocated in a manner which is physiologically relevant to the degree of the substance.

17. A method according to claim 1 or 2, wherein the luminophore is a luminophore which is capable of associating with a component which is capable of being translocated in manner which is physiologically relevant to the degree of the substance.

18. A method according to claim 1 or 2, wherein the luminophore is a luminophore which is capable of being translocated in a manner which is experimentally determined to be correlated to the degree of the substance.

19. A method according to claim 1 or 2, wherein the luminophore is a luminophore which is capable of being translocated, by modulation of the intracellular pathway, in substantially the same manner as the at least one component of the intracellular pathway.

20. A method according to claim 1 or 2, wherein the luminophore is a luminophore which is capable of being quenched upon spatial association with a component which is translocated by modulation of the pathway, the quenching being measured as a decrease in the intensity of the luminescence.

21. A method according to claim 1 or 2, wherein the variation or result with respect to the spatially distributed light emitted by the luminophore is detected by a change in the resonance energy transfer between the luminophore and another luminescent entity capable of delivering energy to the luminophore, each of which has been selected or engineered to become part of, bound to or associated with particular components of the intracellular pathway, and one of which undergoes translocation in response to the influence, thereby changing the amount of resonance energy transfer, the change in the resonance energy transfer being measured as a change in the intensity of emission from the luminophore.

22. A method according to claim 21, wherein the change in the intensity of the emission from the luminophore is sensed by a single channel photodetector which responds only to the average intensity of the luminophore in a non-spatially resolved fashion.

23. A method according to claim 1, wherein the property of the light being recorded is intensity, fluorescence lifetime, polarization, wavelength shift, or other property which is modulated as a result of the underlying cellular response.

24. A method according to claim 1 or 2, wherein the recording of the spatially distributed light is performed using a recording system which records the spatial distribution of a recordable property of the light in the form of an ordered array of values.

25. A method according to claim 24, wherein the recording of the spatial distribution of the recordable property of the light is performed using a charge transfer device or a vacuum tube device.

26. A method according to claim 25, wherein the charge transfer device is a CCD array.

27. A method according to claim 25, wherein the vacuum tube device is a vidicon tube.

28. A method according to claim 1 or 2, wherein the light to be measured passes through a filter which selects the desired component of the light to be measured and rejects other components.

29. A method according to claim 1 or 2, wherein the step (c) is performed by fluorescence microscopy.

30. A method according to claim 2, wherein the recording of the variation or result with respect to light emitted from the luminophore is performed by recording the spatially distributed light as one or more digital images, and processing of the recorded variation to reduce it to one or more numbers representative of the degree of redistribution comprises a digital image processing procedure or combination of digital image processing procedures.

31. A method according to claim 1 or 2, wherein the intracellular pathway is an intracellular signaling pathway.

32. A method according to claim 1 or 2, wherein the luminophore is a fluorophore.

33. A method according to claim 1 or 2, wherein the luminophore is a Green Fluorescent Protein (GFP).

34. A method according to claim 33, wherein the GFP is selected from the group of GFPs having the F64L mutation.

35. A method according to claim 34, wherein the GFP is a GFP variant selected from the group consisting of F64L-GFP, F64L-Y66H-GFP, F64L-S65T-GFP, and EGFP.

36. A method for detecting intracellular translocation of a biologically active polypeptide affecting intracellular processes comprising:
   a) culturing one or more cells containing a nucleotide sequence coding for a hybrid polypeptide comprising a luminophore linked to a biologically active polypeptide under conditions permitting expression of the nucleotide sequence,
   b) incubating the cell or cells with a substance to be screened for biological function or biological effect,
   c) measuring the light emitted by the luminophore in the incubated cell or cells and determining the result or variation with respect to the emitted light, such result or variation being indicative of the translocation of a biologically active polypeptide in said cell or cells, and
   d) measuring the effect of said substance on the inhibition/activation of enzymatic activity of said biologically active polypeptide.

37. A method according to claim 1, 2 or 36, wherein the nucleotide sequence is a DNA sequence.

38. A method according to claim 1, 2 or 36 wherein the biological function or biological effect is an activation.

39. A method according to claim 1, 2 or 36, wherein the biological function or biological effect is a deactivation.

40. A method according to claim 36, wherein the emitted light of the cell or cells is measured prior to the incubation of the cells or cells with said substance, and the result or variation determined in step (c) is a change in the emitted light compared to the emitted light measured prior to the incubation of the cell or cells with said substance.

41. A method according to claim 36, wherein the intracellular processes are intracellular signalling pathways.

42. A method according to claim 36, wherein the change in the emitted light measured in step (c) comprises determining a change in the spatial distribution of the emitted light.

43. A method according to claim 1, 2 or 36, wherein the cell or cells is/are a mammalian cell/mammalian cells which, during the time peroid over which the influence is observed, is/are incubated at a temperature of 30° C. or above.

44. A method according to claim 43, wherein the cells or cells is/are incubated at a temperature of from 32° C. to 39° C.

45. A method according to claim 43, wherein the cells or cells is/are incubated at a temperature of from 35° C. to 38° C.

46. A method according to claim 43, wherein the cell or cells is/are incubated at a temperature of about 37° C.

47. A method according to claim 1, 2 or 36, wherein at least one cell is part of a matrix of identical or non-identical cells.

48. A method according to claim 1, 2 or 36, wherein the cell or cells is/are selected from the group consisting of fungal cells, invertebrate cells and vertebrate cells.

49. A method according to claim 48, wherein the fungal cell or cells is/are a yeast cell.

50. A method according to claim 48, wherein the invertebrate cell or cells is/are an insect cell.

51. A method according to claim 48, wherein the vertebrate cell or cells is/are a mammalian cell.

52. A method according to claim 36, wherein the fusion polypeptide comprising a biologically active polypeptide affecting intracellular processes and a luminophore is encoded for by a nucleic acid construct wherein the construct is not a construct coding for a fusion polypeptide in which the biologically active polypeptide is not selected from the group consisting of PKC-alpha, PKC-gamma and PKC-epsilon.

53. A method according to claim 1, 2 or 36, in which the method of the invention is used as a screening program.

54. A method according to claim 1, 2 or 36, wherein the method is a screening program for the identification of a biologically active substance that directly or indirectly affects an intracellular signaling pathway and is potentially useful as a medicament, wherein the result of the individual measurement of each substance being screened which indicates its potential biological activity is based on measurement of the redistribution of spatially resolved luminescence in living cells and which undergoes a change in distribution upon activation of an intracellular signaling pathway.

55. A method according to claim 1, 2 or 36, wherein the method is a screening program for the identification of a biologically toxic substance as defined herein that exerts its toxic effect by interfering with an intracellular signaling pathway, wherein the result of the individual measurement of each substance being screened which indicates its potential biologically toxic activity is based on measurement of the redistribution of said luminophore in living cells and which undergoes a change in distribution upon activation of an intracellular signaling pathway.

56. A method according to claim 1, 2 or 36, wherein the luminophore is used in backtracking of signal transduction pathways.

57. A method according to claim 1, 2 or 36 of identifying a drug target among the group of biologically active polypeptides which are components of intracellular signalling pathways.

58. A method according to claim 36, wherein the luminophore is a fluorophore.

59. A method according to claim 36, wherein the luminophore is a Green Fluorescent Protein (GFP).

60. A method according to claim 59, wherein the GFP is selected from the group of GFPs having the F64L mutation.

61. A method according to claim 60, wherein the GFP is a GFP variant selected from the group consisting of F64L-GFP, F64L-Y66H-GFP, F64L-S65T-GFP, and EGFP.

62. A method according to claim 36, wherein the step (c) is made at a single point in time after the application of the substance.

63. A method according to claim 36, wherein the step (c) is made at two points in time, one point being before, and the other point being after the application of the substance.

64. A method according to claim 36, wherein the step (c) is performed at a series of points in time, in which the application of the substance occurs at some time after the first time point in the series of recordings, the recording being performed within a predetermined time spacing from about 0.1 seconds to 1 hour over a time span of from 1 second to 12 hours.

65. A method according to claim 64, wherein the predetermined time spacing from 1 to 60 seconds.

66. A method according to claim 64, wherein the predetermined time spacing from 1 to 30 seconds.

67. A method according to claim 64, wherein the predetermined time spacing from 1 to 10 seconds.

68. A method according to claim 64, wherein the time span is from 10 seconds to 1 hour.

69. A method according to claim 64, wherein the time span is from 60 seconds to 30 minutes.

70. A method according to claim 64, wherein the time span is from 60 seconds to 20 minutes.

71. A method according to claim 36, wherein the cell or cells is/are fixed at a point in time after the application of the substance at which the response has been predetermined to be significant, and the recording is made at an arbitrary later time.

72. A method according to claim 36, wherein the luminophore is a luminophore which is capable of being translocated in a manner which is physiologically relevant to the degree of the substance.

73. A method according to claim 36, wherein the luminophore is a luminophore which is capable of associating with a biologically active polypeptide which is capable of being translocated in manner which is physiologically relevant to the degree of the substance.

74. A method according to claim 36, wherein the luminophore is a luminophore which is capable of being translocated in a manner which is experimentally determined to be correlated to the degree of the substance.

75. A method according to claim 36, wherein the luminophore is a luminophore which is capable of being translocated, by modulation of the intracellular pathway, in substantially the same manner as the at least one component of the intracellular pathway.

76. A method according to claim 36, wherein the luminophore is a luminophore which is capable of being quenched upon spatial association with a component which is translocated by modulation of the pathway, the quenching being measured as a decrease in the intensity of the luminescence.

77. A method according to claim 36, wherein the variation or result with respect to the spatially distributed light emitted by the luminophore is detected by a change in the resonance energy transfer between the luminophore and another luminescent entity capable of delivering energy to the luminophore, each of which has been selected or engineered to become part of, bound to or associated with particular components of the intracellular pathway, and one of which undergoes translocation in response to the influence, thereby changing the amount of resonance energy transfer, the change in the resonance energy transfer being measured as a change in the intensity of emission from the luminophore.

78. A method according to claim 77, wherein the change in the intensity of the emission from the luminophore is sensed by a single channel photodetector which responds only to the average intensity of the luminophore in a non-spatially resolved fashion.

79. A method according to claim 36, wherein the property of the light being recorded is intensity, fluorescence lifetime, polarization, wavelength shift, or other property which is modulated as a result of the underlying cellular response.

80. A method according to claim 36, wherein the recording of the spatially distributed light is performed using a recording system which records the spatial distribution of a recordable property of the light in the form of an ordered array of values.

81. A method according to claim 36, wherein the recording of the spatial distribution of the recordable property of the light is performed using a charge transfer device or a vacuum tube device.

82. A method according to claim 81, wherein the charge transfer device is a CCD array.

83. A method according to claim 81, wherein the vacuum tube device is a vidicon tube.

84. A method according to claim 36, wherein the light to be measured passes through a filter which selects the desired component of the light to be measured and rejects other components.

85. A method according to claim 36, wherein the step (c) is performed by fluorescence microscopy.

86. A method according to claim 52, wherein the intracellular process is an intracellular signalling pathway.

87. A method according to claim 52 or 86, wherein the biologically active polypeptide is selected from the group consisting of a protein kinase, a phosphatase, a transcription factor and a protein associated with the cytoskeletal network which change cellular localization upon activation.

88. A method according to claim 1 or 2, wherein the fusion polypeptide comprising a luminophore linked to a component of an intracellular pathway affecting intracellular processes is encoded for by a nucleic acid construct.

* * * * *

SEQUENCE LISTING

```
<160> NUMBER OF SEQ ID NOS: 143

<210> SEQ ID NO 1
<211> LENGTH: 53
<212> TYPE: DNA
<213> ORGANISM: Artificial Sequence
<220> FEATURE:
<223> OTHER INFORMATION: 5' GFP Primer

<400> SEQUENCE: 1
ttggacacaa gctttggaca cggcgcgcca tgagtaaagg agaagaactt ttc        53

<210> SEQ ID NO 2
<211> LENGTH: 53
<212> TYPE: DNA
<213> ORGANISM: Artificial Sequence
<220> FEATURE:
<223> OTHER INFORMATION: 3' GFP Primer

<400> SEQUENCE: 2
gtcatcttct cgagtcttac tcctgaggtt tgtatagttc atccatgcca tgt        53

<210> SEQ ID NO 3
<211> LENGTH: 54
<212> TYPE: DNA
<213> ORGANISM: Artificial Sequence
<220> FEATURE:
<223> OTHER INFORMATION: 5' PKAc Primer

<400> SEQUENCE: 3
```
ttggacacaa gctttggaca ccctcaggat atgggcaacg ccgccgccgc caag        54

<210> SEQ ID NO 4
<211> LENGTH: 55
<212> TYPE: DNA
<213> ORGANISM: Artificial Sequence
<220> FEATURE:
<223> OTHER INFORMATION: 3' PKAc Primer

<400> SEQUENCE: 4
gtcatcttct cgagtctttc aggcgcgccc aaactcagta aactccttgc cacac        55

<210> SEQ ID NO 5
<211> LENGTH: 55
<212> TYPE: DNA
<213> ORGANISM: Artificial Sequence
<220> FEATURE:
<223> OTHER INFORMATION: 5' mPKCa Primer

<400> SEQUENCE: 5
ttggacacaa gctttggaca ccctcaggat atggctgacg tttacccggc caacg        55

<210> SEQ ID NO 6
<211> LENGTH: 55
<212> TYPE: DNA
<213> ORGANISM: Artificial Sequence
<220> FEATURE:
<223> OTHER INFORMATION: 3' mPKCa Primer

<400> SEQUENCE: 6
gtcatcttct cgagtctttc aggcgcgccc tactgcactt tgcaagattg ggtgc        55

<210> SEQ ID NO 7
<211> LENGTH: 64
<212> TYPE: DNA
<213> ORGANISM: Artificial Sequence
<220> FEATURE:
<223> OTHER INFORMATION: 5' ERK1 Primer

<400> SEQUENCE: 7
ttggacacaa gctttggaca ccctcaggat atggcggcgg cggcggcggc tccgggggc   60 gggg                                                              64

<210> SEQ ID NO 8
<211> LENGTH: 55
<212> TYPE: DNA
<213> ORGANISM: Artificial Sequence
<220> FEATURE:
<223> OTHER INFORMATION: 3' ERK1 Primer

<400> SEQUENCE: 8
gtcatcttct cgagtctttc aggcgcgccc ggggccctct ggcgcccctg gctgg        55

<210> SEQ ID NO 9
<211> LENGTH: 30
<212> TYPE: DNA
<213> ORGANISM: Artificial Sequence
<220> FEATURE:
<223> OTHER INFORMATION: Erk-1 Top Primer

<400> SEQUENCE: 9
tagaattcaa ccatggcggc ggcggcggcg                                   30

<210> SEQ ID NO 10
<211> LENGTH: 29

```
<212> TYPE: DNA
<213> ORGANISM: Artificial Sequence
<220> FEATURE:
<223> OTHER INFORMATION: Erk-1 Bottom/+Stop Primer

<400> SEQUENCE: 10
taggatccct aggggcctc cagcactcc                                     29

<210> SEQ ID NO 11
<211> LENGTH: 31
<212> TYPE: DNA
<213> ORGANISM: Artificial Sequence
<220> FEATURE:
<223> OTHER INFORMATION: Erk2-top Primer

<400> SEQUENCE: 11
tactcgagta accatggcgg cggcggcggc g                                 31

<210> SEQ ID NO 12
<211> LENGTH: 25
<212> TYPE: DNA
<213> ORGANISM: Artificial Sequence
<220> FEATURE:
<223> OTHER INFORMATION: Erk2-bottom/-stop Primer

<400> SEQUENCE: 12
taggatccat agatctgtat cctgg                                        25

<210> SEQ ID NO 13
<211> LENGTH: 26
<212> TYPE: DNA
<213> ORGANISM: Artificial Sequence
<220> FEATURE:
<223> OTHER INFORMATION: Erk2-bottom/+stop Primer

<400> SEQUENCE: 13
taggatcctt aagatctgta tcctgg                                       26

<210> SEQ ID NO 14
<211> LENGTH: 28
<212> TYPE: DNA
<213> ORGANISM: Artificial Sequence
<220> FEATURE:
<223> OTHER INFORMATION: p38-top Primer

<400> SEQUENCE: 14
atctcgaggg aaaatgtctc aggagagg                                     28

<210> SEQ ID NO 15
<211> LENGTH: 28
<212> TYPE: DNA
<213> ORGANISM: Artificial Sequence
<220> FEATURE:
<223> OTHER INFORMATION: p38-bottom/-stop Primer

<400> SEQUENCE: 15
atggatcctc ggactccatc tcttcttg                                     28

<210> SEQ ID NO 16
<211> LENGTH: 29
<212> TYPE: DNA
<213> ORGANISM: Artificial Sequence
<220> FEATURE:
<223> OTHER INFORMATION: p38bottom/+stop Primer

<400> SEQUENCE: 16
```

```
atggatcctc aggactccat ctcttcttg                                                29

<210> SEQ ID NO 17
<211> LENGTH: 28
<212> TYPE: DNA
<213> ORGANISM: Artificial Sequence
<220> FEATURE:
<223> OTHER INFORMATION: Jnk-top Primer

<400> SEQUENCE: 17
gtctcgagcc atcatgagca gaagcaag                                                 28

<210> SEQ ID NO 18
<211> LENGTH: 27
<212> TYPE: DNA
<213> ORGANISM: Artificial Sequence
<220> FEATURE:
<223> OTHER INFORMATION: Jnk-bottom/-stop Primer

<400> SEQUENCE: 18
gtggatccca ctgctgcacc tgtgcta                                                  27

<210> SEQ ID NO 19
<211> LENGTH: 28
<212> TYPE: DNA
<213> ORGANISM: Artificial Sequence
<220> FEATURE:
<223> OTHER INFORMATION: Jnk-bottom/+stop Primer

<400> SEQUENCE: 19
gtggatcctc actgctgcac ctgtgcta                                                 28

<210> SEQ ID NO 20
<211> LENGTH: 40
<212> TYPE: DNA
<213> ORGANISM: Artificial Sequence
<220> FEATURE:
<223> OTHER INFORMATION: p85-top-N Primer

<400> SEQUENCE: 20
cgcgaattcc gccaccatga gtgctgaggg gtaccagtac                                    40

<210> SEQ ID NO 21
<211> LENGTH: 32
<212> TYPE: DNA
<213> ORGANISM: Artificial Sequence
<220> FEATURE:
<223> OTHER INFORMATION: p85bottom/-stop Primer

<400> SEQUENCE: 21
cgcggatcct gtcgcctctg ctgtgcatat ac                                            32

<210> SEQ ID NO 22
<211> LENGTH: 30
<212> TYPE: DNA
<213> ORGANISM: Artificial Sequence
<220> FEATURE:
<223> OTHER INFORMATION: p85-top-C Primer

<400> SEQUENCE: 22
gggagatcta tgagtgctga ggggtaccag                                               30

<210> SEQ ID NO 23
<211> LENGTH: 34
<212> TYPE: DNA
<213> ORGANISM: Artificial Sequence
```

```
<220> FEATURE:
<223> OTHER INFORMATION: p85bottom/+stop Primer

<400> SEQUENCE: 23
gggcggatcc tcatcgcctc tgctgtgcat atac                          34

<210> SEQ ID NO 24
<211> LENGTH: 33
<212> TYPE: DNA
<213> ORGANISM: Artificial Sequence
<220> FEATURE:
<223> OTHER INFORMATION: Smad2-top Primer

<400> SEQUENCE: 24
gtgaattcga ccatgtcgtc catcttgcca ttc                           33

<210> SEQ ID NO 25
<211> LENGTH: 31
<212> TYPE: DNA
<213> ORGANISM: Artificial Sequence
<220> FEATURE:
<223> OTHER INFORMATION: Smad2bottom/-stop Primer

<400> SEQUENCE: 25
gtggtaccca tgacatgctt gagcaacgca c                             31

<210> SEQ ID NO 26
<211> LENGTH: 32
<212> TYPE: DNA
<213> ORGANISM: Artificial Sequence
<220> FEATURE:
<223> OTHER INFORMATION: Smad2bottom/+stop Primer

<400> SEQUENCE: 26
gtggtacctt atgacatgct tgagcaacgc ac                            32

<210> SEQ ID NO 27
<211> LENGTH: 31
<212> TYPE: DNA
<213> ORGANISM: Artificial Sequence
<220> FEATURE:
<223> OTHER INFORMATION: Grk5-top Primer

<400> SEQUENCE: 27
gtgaattcgt caatggagct ggaaaacatc g                             31

<210> SEQ ID NO 28
<211> LENGTH: 30
<212> TYPE: DNA
<213> ORGANISM: Artificial Sequence
<220> FEATURE:
<223> OTHER INFORMATION: Grk5-bottom/-stop Primer

<400> SEQUENCE: 28
gtggatccct gctgcttccg gtggagttcg                               30

<210> SEQ ID NO 29
<211> LENGTH: 31
<212> TYPE: DNA
<213> ORGANISM: Artificial Sequence
<220> FEATURE:
<223> OTHER INFORMATION: Grk5bottom/+stop Primer

<400> SEQUENCE: 29
gtggatccct agctgcttcc ggtggagttc g                             31
```

```
<210> SEQ ID NO 30
<211> LENGTH: 32
<212> TYPE: DNA
<213> ORGANISM: Artificial Sequence
<220> FEATURE:
<223> OTHER INFORMATION: Stat5-top Primer

<400> SEQUENCE: 30
gtagatctac catggcgggc tggatccagg cc                                32

<210> SEQ ID NO 31
<211> LENGTH: 31
<212> TYPE: DNA
<213> ORGANISM: Artificial Sequence
<220> FEATURE:
<223> OTHER INFORMATION: Stat5-bottom/-stop Primer

<400> SEQUENCE: 31
gtggtaccca tgagagggag cctctggcag a                                 31

<210> SEQ ID NO 32
<211> LENGTH: 31
<212> TYPE: DNA
<213> ORGANISM: Artificial Sequence
<220> FEATURE:
<223> OTHER INFORMATION: Stat5bottom/+stop Primer

<400> SEQUENCE: 32
gtggtacctc atgagaggga gcctctggca g                                 31

<210> SEQ ID NO 33
<211> LENGTH: 33
<212> TYPE: DNA
<213> ORGANISM: Artificial Sequence
<220> FEATURE:
<223> OTHER INFORMATION: Smad4-top Primer

<400> SEQUENCE: 33
gtgaattcaa ccatggacaa tatgtctatt acg                               33

<210> SEQ ID NO 34
<211> LENGTH: 31
<212> TYPE: DNA
<213> ORGANISM: Artificial Sequence
<220> FEATURE:
<223> OTHER INFORMATION: Smad4bottom/-stop Primer

<400> SEQUENCE: 34
gtggatccca gtctaaaggt tgtgggtctg c                                 31

<210> SEQ ID NO 35
<211> LENGTH: 32
<212> TYPE: DNA
<213> ORGANISM: Artificial Sequence
<220> FEATURE:
<223> OTHER INFORMATION: Smad4-bottom/+stop Primer

<400> SEQUENCE: 35
gtggatcctc agtctaaagg ttgtgggtct gc                                32

<210> SEQ ID NO 36
<211> LENGTH: 27
<212> TYPE: DNA
<213> ORGANISM: Artificial Sequence
<220> FEATURE:
<223> OTHER INFORMATION: PKB-top Primer
```

-continued

```
<400> SEQUENCE: 36
gtctcgaggc accatgagcg acgtggc                                          27

<210> SEQ ID NO 37
<211> LENGTH: 27
<212> TYPE: DNA
<213> ORGANISM: Artificial Sequence
<220> FEATURE:
<223> OTHER INFORMATION: PKB-bottom/stop Primer

<400> SEQUENCE: 37
tgggatccga ggccgtgctg ctggccg                                          27

<210> SEQ ID NO 38
<211> LENGTH: 1896
<212> TYPE: DNA
<213> ORGANISM: Artificial Sequence
<220> FEATURE:
<223> OTHER INFORMATION: EGFP-Erk1 fusion construct
<220> FEATURE:
<221> NAME/KEY: CDS
<222> LOCATION: (1)..(1893)

<400> SEQUENCE: 38 atg gtg agc aag ggc gag gag ctg ttc acc ggg gtg gtg ccc atc ctg       48
Met Val Ser Lys Gly Glu Glu Leu Phe Thr Gly Val Val Pro Ile Leu
1               5                   10                  15 gtc gag ctg gac ggc gac gta aac ggc cac aag ttc agc gtg tcc ggc       96
Val Glu Leu Asp Gly Asp Val Asn Gly His Lys Phe Ser Val Ser Gly
            20                  25                  30 gag ggc gag ggc gat gcc acc tac ggc aag ctg acc ctg aag ttc atc      144
Glu Gly Glu Gly Asp Ala Thr Tyr Gly Lys Leu Thr Leu Lys Phe Ile
        35                  40                  45 tgc acc acc ggc aag ctg ccc gtg ccc tgg ccc acc ctc gtg acc acc      192
Cys Thr Thr Gly Lys Leu Pro Val Pro Trp Pro Thr Leu Val Thr Thr
    50                  55                  60 ctg acc tac ggc gtg cag tgc ttc agc cgc tac ccc gac cac atg aag      240
Leu Thr Tyr Gly Val Gln Cys Phe Ser Arg Tyr Pro Asp His Met Lys
65                  70                  75                  80 cag cac gac ttc ttc aag tcc gcc atg ccc gaa ggc tac gtc cag gag      288
Gln His Asp Phe Phe Lys Ser Ala Met Pro Glu Gly Tyr Val Gln Glu
                85                  90                  95 cgc acc atc ttc ttc aag gac gac ggc aac tac aag acc cgc gcc gag      336
Arg Thr Ile Phe Phe Lys Asp Asp Gly Asn Tyr Lys Thr Arg Ala Glu
            100                 105                 110 gtg aag ttc gag ggc gac acc ctg gtg aac cgc atc gag ctg aag ggc      384
Val Lys Phe Glu Gly Asp Thr Leu Val Asn Arg Ile Glu Leu Lys Gly
        115                 120                 125 atc gac ttc aag gag gac ggc aac atc ctg ggg cac aag ctg gag tac      432
Ile Asp Phe Lys Glu Asp Gly Asn Ile Leu Gly His Lys Leu Glu Tyr
    130                 135                 140 aac tac aac agc cac aac gtc tat atc atg gcc gac aag cag aag aac      480
Asn Tyr Asn Ser His Asn Val Tyr Ile Met Ala Asp Lys Gln Lys Asn
145                 150                 155                 160 ggc atc aag gtg aac ttc aag atc cgc cac aac atc gag gac ggc agc      528
Gly Ile Lys Val Asn Phe Lys Ile Arg His Asn Ile Glu Asp Gly Ser
                165                 170                 175 gtg cag ctc gcc gac cac tac cag cag aac acc ccc atc ggc gac ggc      576
Val Gln Leu Ala Asp His Tyr Gln Gln Asn Thr Pro Ile Gly Asp Gly
            180                 185                 190 ccc gtg ctg ctg ccc gac aac cac tac ctg agc acc cag tcc gcc ctg      624
```

```
Pro Val Leu Leu Pro Asp Asn His Tyr Leu Ser Thr Gln Ser Ala Leu
        195                 200                 205 agc aaa gac ccc aac gag aag cgc gat cac atg gtc ctg ctg gag ttc        672
Ser Lys Asp Pro Asn Glu Lys Arg Asp His Met Val Leu Leu Glu Phe
    210                 215                 220 gtg acc gcc gcc ggg atc act ctc ggc atg gac gag ctg tac aag tcc        720
Val Thr Ala Ala Gly Ile Thr Leu Gly Met Asp Glu Leu Tyr Lys Ser
225                 230                 235                 240 gga ctc aga tct cga gct caa gct tcg aat tca acc atg gcg gcg gcg        768
Gly Leu Arg Ser Arg Ala Gln Ala Ser Asn Ser Thr Met Ala Ala Ala
                245                 250                 255 gcg gct cag ggg ggc ggg ggc ggg gag ccc cgt aga acc gag ggg gtc        816
Ala Ala Gln Gly Gly Gly Gly Gly Glu Pro Arg Arg Thr Glu Gly Val
            260                 265                 270 ggc ccg ggg gtc ccg ggg gag gtg gag atg gtg aag ggg cag ccg ttc        864
Gly Pro Gly Val Pro Gly Glu Val Glu Met Val Lys Gly Gln Pro Phe
        275                 280                 285 gac gtg ggc ccg cgc tac acg cag ttg cag tac atc ggc gag ggc gcg        912
Asp Val Gly Pro Arg Tyr Thr Gln Leu Gln Tyr Ile Gly Glu Gly Ala
    290                 295                 300 tac ggc atg gtc agc tcg gcc tat gac cac gtg cgc aag act cgc gtg        960
Tyr Gly Met Val Ser Ser Ala Tyr Asp His Val Arg Lys Thr Arg Val
305                 310                 315                 320 gcc atc aag aag atc agc ccc ttc gaa cat cag acc tac tgc cag cgc       1008
Ala Ile Lys Lys Ile Ser Pro Phe Glu His Gln Thr Tyr Cys Gln Arg
                325                 330                 335 acg ctc cgg gag atc cag atc ctg ctg cgc ttc cgc cat gag aat gtc       1056
Thr Leu Arg Glu Ile Gln Ile Leu Leu Arg Phe Arg His Glu Asn Val
            340                 345                 350 atc ggc atc cga gac att ctg cgg gcg tcc acc ctg gaa gcc atg aga       1104
Ile Gly Ile Arg Asp Ile Leu Arg Ala Ser Thr Leu Glu Ala Met Arg
        355                 360                 365 gat gtc tac att gtg cag gac ctg atg gag act gac ctg tac aag ttg       1152
Asp Val Tyr Ile Val Gln Asp Leu Met Glu Thr Asp Leu Tyr Lys Leu
    370                 375                 380 ctg aaa agc cag cag ctg agc aat gac cat atc tgc tac ttc ctc tac       1200
Leu Lys Ser Gln Gln Leu Ser Asn Asp His Ile Cys Tyr Phe Leu Tyr
385                 390                 395                 400 cag atc ctg cgg ggc ctc aag tac atc cac tcc gcc aac gtg ctc cac       1248
Gln Ile Leu Arg Gly Leu Lys Tyr Ile His Ser Ala Asn Val Leu His
                405                 410                 415 cga gat cta aag ccc tcc aac ctg ctc agc aac acc acc tgc gac ctt       1296
Arg Asp Leu Lys Pro Ser Asn Leu Leu Ser Asn Thr Thr Cys Asp Leu
            420                 425                 430 aag att tgt gat ttc ggc ctg gcc cgg att gcc gat cct gag cat gac       1344
Lys Ile Cys Asp Phe Gly Leu Ala Arg Ile Ala Asp Pro Glu His Asp
        435                 440                 445 cac acc ggc ttc ctg acg gag tat gtg gct acg cgc tgg tac cgg gcc       1392
His Thr Gly Phe Leu Thr Glu Tyr Val Ala Thr Arg Trp Tyr Arg Ala
    450                 455                 460 cca gag atc atg ctg aac tcc aag ggc tat acc aag tcc atc gac atc       1440
Pro Glu Ile Met Leu Asn Ser Lys Gly Tyr Thr Lys Ser Ile Asp Ile
465                 470                 475                 480 tgg tct gtg ggc tgc att ctg gct gag atg ctc tct aac cgg ccc atc       1488
Trp Ser Val Gly Cys Ile Leu Ala Glu Met Leu Ser Asn Arg Pro Ile
                485                 490                 495 ttc cct ggc aag cac tac ctg gat cag ctc aac cac att ctg ggc atc       1536
Phe Pro Gly Lys His Tyr Leu Asp Gln Leu Asn His Ile Leu Gly Ile
            500                 505                 510
```

```
ctg ggc tcc cca tcc cag gag gac ctg aat tgt atc atc aac atg aag      1584
Leu Gly Ser Pro Ser Gln Glu Asp Leu Asn Cys Ile Ile Asn Met Lys
        515                 520                 525 gcc cga aac tac cta cag tct ctg ccc tcc aag acc aag gtg gct tgg      1632
Ala Arg Asn Tyr Leu Gln Ser Leu Pro Ser Lys Thr Lys Val Ala Trp
    530                 535                 540 gcc aag ctt ttc ccc aag tca gac tcc aaa gcc ctt gac ctg ctg gac      1680
Ala Lys Leu Phe Pro Lys Ser Asp Ser Lys Ala Leu Asp Leu Leu Asp
545                 550                 555                 560 cgg atg tta acc ttt aac ccc aat aaa cgg atc aca gtg gag gaa gcg      1728
Arg Met Leu Thr Phe Asn Pro Asn Lys Arg Ile Thr Val Glu Glu Ala
                565                 570                 575 ctg gct cac ccc tac ctg gag cag tac tat gac ccg acg gat gag cca      1776
Leu Ala His Pro Tyr Leu Glu Gln Tyr Tyr Asp Pro Thr Asp Glu Pro
            580                 585                 590 gtg gcc gag gag ccc ttc acc ttc gcc atg gag ctg gat gac cta cct      1824
Val Ala Glu Glu Pro Phe Thr Phe Ala Met Glu Leu Asp Asp Leu Pro
        595                 600                 605 aag gag cgg ctg aag gag ctc atc ttc cag gag aca gca cgc ttc cag      1872
Lys Glu Arg Leu Lys Glu Leu Ile Phe Gln Glu Thr Ala Arg Phe Gln
    610                 615                 620 ccc gga gtg ctg gag gcc ccc tag                                       1896
Pro Gly Val Leu Glu Ala Pro
625                 630

<210> SEQ ID NO 39
<211> LENGTH: 631
<212> TYPE: PRT
<213> ORGANISM: Artificial Sequence
<220> FEATURE:
<223> OTHER INFORMATION: EGFP-Erk1 fusion construct

<400> SEQUENCE: 39

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
```

-continued

```
            195                 200                 205
Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Ser
225                 230                 235                 240

Gly Leu Arg Ser Arg Ala Gln Ala Ser Asn Ser Thr Met Ala Ala Ala
                245                 250                 255

Ala Ala Gln Gly Gly Gly Gly Glu Pro Arg Arg Thr Glu Gly Val
            260                 265                 270

Gly Pro Gly Val Pro Gly Glu Val Glu Met Val Lys Gly Gln Pro Phe
            275                 280                 285

Asp Val Gly Pro Arg Tyr Thr Gln Leu Gln Tyr Ile Gly Glu Gly Ala
290                 295                 300

Tyr Gly Met Val Ser Ser Ala Tyr Asp His Val Arg Lys Thr Arg Val
305                 310                 315                 320

Ala Ile Lys Lys Ile Ser Pro Phe Glu His Gln Thr Tyr Cys Gln Arg
                325                 330                 335

Thr Leu Arg Glu Ile Gln Ile Leu Leu Arg Phe Arg His Glu Asn Val
            340                 345                 350

Ile Gly Ile Arg Asp Ile Leu Arg Ala Ser Thr Leu Glu Ala Met Arg
            355                 360                 365

Asp Val Tyr Ile Val Gln Asp Leu Met Glu Thr Asp Leu Tyr Lys Leu
370                 375                 380

Leu Lys Ser Gln Gln Leu Ser Asn Asp His Ile Cys Tyr Phe Leu Tyr
385                 390                 395                 400

Gln Ile Leu Arg Gly Leu Lys Tyr Ile His Ser Ala Asn Val Leu His
                405                 410                 415

Arg Asp Leu Lys Pro Ser Asn Leu Leu Ser Asn Thr Thr Cys Asp Leu
            420                 425                 430

Lys Ile Cys Asp Phe Gly Leu Ala Arg Ile Ala Asp Pro Glu His Asp
            435                 440                 445

His Thr Gly Phe Leu Thr Glu Tyr Val Ala Thr Arg Trp Tyr Arg Ala
    450                 455                 460

Pro Glu Ile Met Leu Asn Ser Lys Gly Tyr Thr Lys Ser Ile Asp Ile
465                 470                 475                 480

Trp Ser Val Gly Cys Ile Leu Ala Glu Met Leu Ser Asn Arg Pro Ile
                485                 490                 495

Phe Pro Gly Lys His Tyr Leu Asp Gln Leu Asn His Ile Leu Gly Ile
            500                 505                 510

Leu Gly Ser Pro Ser Gln Glu Asp Leu Asn Cys Ile Ile Asn Met Lys
            515                 520                 525

Ala Arg Asn Tyr Leu Gln Ser Leu Pro Ser Lys Thr Lys Val Ala Trp
    530                 535                 540

Ala Lys Leu Phe Pro Lys Ser Asp Ser Lys Ala Leu Asp Leu Leu Asp
545                 550                 555                 560

Arg Met Leu Thr Phe Asn Pro Asn Lys Arg Ile Thr Val Glu Glu Ala
                565                 570                 575

Leu Ala His Pro Tyr Leu Glu Gln Tyr Tyr Asp Pro Thr Asp Glu Pro
            580                 585                 590

Val Ala Glu Glu Pro Phe Thr Phe Ala Met Glu Leu Asp Asp Leu Pro
            595                 600                 605

Lys Glu Arg Leu Lys Glu Leu Ile Phe Gln Glu Thr Ala Arg Phe Gln
    610                 615                 620
```

```
Pro Gly Val Leu Glu Ala Pro
625                 630

<210> SEQ ID NO 40
<211> LENGTH: 1818
<212> TYPE: DNA
<213> ORGANISM: Artificial Sequence
<220> FEATURE:
<223> OTHER INFORMATION: EGFP-Erk2 fusion
<220> FEATURE:
<221> NAME/KEY: CDS
<222> LOCATION: (1)..(1815)

<400> SEQUENCE: 40 atg gtg agc aag ggc gag gag ctg ttc acc ggg gtg gtg ccc atc ctg      48
Met Val Ser Lys Gly Glu Glu Leu Phe Thr Gly Val Val Pro Ile Leu
1               5                   10                  15 gtc gag ctg gac ggc gac gta aac ggc cac aag ttc agc gtg tcc ggc      96
Val Glu Leu Asp Gly Asp Val Asn Gly His Lys Phe Ser Val Ser Gly
            20                  25                  30 gag ggc gag ggc gat gcc acc tac ggc aag ctg acc ctg aag ttc atc     144
Glu Gly Glu Gly Asp Ala Thr Tyr Gly Lys Leu Thr Leu Lys Phe Ile
        35                  40                  45 tgc acc acc ggc aag ctg ccc gtg ccc tgg ccc acc ctc gtg acc acc     192
Cys Thr Thr Gly Lys Leu Pro Val Pro Trp Pro Thr Leu Val Thr Thr
    50                  55                  60 ctg acc tac ggc gtg cag tgc ttc agc cgc tac ccc gac cac atg aag     240
Leu Thr Tyr Gly Val Gln Cys Phe Ser Arg Tyr Pro Asp His Met Lys
65                  70                  75                  80 cag cac gac ttc ttc aag tcc gcc atg ccc gaa ggc tac gtc cag gag     288
Gln His Asp Phe Phe Lys Ser Ala Met Pro Glu Gly Tyr Val Gln Glu
                85                  90                  95 cgc acc atc ttc ttc aag gac gac ggc aac tac aag acc cgc gcc gag     336
Arg Thr Ile Phe Phe Lys Asp Asp Gly Asn Tyr Lys Thr Arg Ala Glu
            100                 105                 110 gtg aag ttc gag ggc gac acc ctg gtg aac cgc atc gag ctg aag ggc     384
Val Lys Phe Glu Gly Asp Thr Leu Val Asn Arg Ile Glu Leu Lys Gly
        115                 120                 125 atc gac ttc aag gag gac ggc aac atc ctg ggg cac aag ctg gag tac     432
Ile Asp Phe Lys Glu Asp Gly Asn Ile Leu Gly His Lys Leu Glu Tyr
    130                 135                 140 aac tac aac agc cac aac gtc tat atc atg gcc gac aag cag aag aac     480
Asn Tyr Asn Ser His Asn Val Tyr Ile Met Ala Asp Lys Gln Lys Asn
145                 150                 155                 160 ggc atc aag gtg aac ttc aag atc cgc cac aac atc gag gac ggc agc     528
Gly Ile Lys Val Asn Phe Lys Ile Arg His Asn Ile Glu Asp Gly Ser
                165                 170                 175 gtg cag ctc gcc gac cac tac cag cag aac acc ccc atc ggc gac ggc     576
Val Gln Leu Ala Asp His Tyr Gln Gln Asn Thr Pro Ile Gly Asp Gly
            180                 185                 190 ccc gtg ctg ctg ccc gac aac cac tac ctg agc acc cag tcc gcc ctg     624
Pro Val Leu Leu Pro Asp Asn His Tyr Leu Ser Thr Gln Ser Ala Leu
        195                 200                 205 agc aaa gac ccc aac gag aag cgc gat cac atg gtc ctg ctg gag ttc     672
Ser Lys Asp Pro Asn Glu Lys Arg Asp His Met Val Leu Leu Glu Phe
    210                 215                 220 gtg acc gcc gcc ggg atc act ctc ggc atg gac gag ctg tac aag tcc     720
Val Thr Ala Ala Gly Ile Thr Leu Gly Met Asp Glu Leu Tyr Lys Ser
225                 230                 235                 240 gga ctc aga tct cga gta acc atg gcg gcg gcg gcg gcg gcg ggc ccg     768
Gly Leu Arg Ser Arg Val Thr Met Ala Ala Ala Ala Ala Ala Gly Pro
```

-continued

|   |   |   |   |   |   |   |   |   |   |   |   |   |   |   |   |   |
|---|---|---|---|---|---|---|---|---|---|---|---|---|---|---|---|---|
|   |   |   | 245 |   |   |   |   | 250 |   |   |   |   | 255 |   |   |   |
| gag | atg | gtc | cgc | ggg | cag | gtg | ttc | gac | gtg | ggg | ccg | cgc | tac | act | aat | 816 |
| Glu | Met | Val | Arg | Gly | Gln | Val | Phe | Asp | Val | Gly | Pro | Arg | Tyr | Thr | Asn |   |
|   |   |   | 260 |   |   |   |   | 265 |   |   |   |   | 270 |   |   |   |
| ctc | tcg | tac | atc | gga | gaa | ggc | gcc | tac | ggc | atg | gtt | tgt | tct | gct | tat | 864 |
| Leu | Ser | Tyr | Ile | Gly | Glu | Gly | Ala | Tyr | Gly | Met | Val | Cys | Ser | Ala | Tyr |   |
|   |   | 275 |   |   |   |   | 280 |   |   |   |   | 285 |   |   |   |   |
| gat | aat | ctc | aac | aaa | gtt | cga | gtt | gct | atc | aag | aaa | atc | agt | cct | ttt | 912 |
| Asp | Asn | Leu | Asn | Lys | Val | Arg | Val | Ala | Ile | Lys | Lys | Ile | Ser | Pro | Phe |   |
|   | 290 |   |   |   |   | 295 |   |   |   |   | 300 |   |   |   |   |   |
| gag | cac | cag | acc | tac | tgt | cag | aga | acc | ctg | aga | gag | ata | aaa | atc | cta | 960 |
| Glu | His | Gln | Thr | Tyr | Cys | Gln | Arg | Thr | Leu | Arg | Glu | Ile | Lys | Ile | Leu |   |
| 305 |   |   |   |   | 310 |   |   |   |   | 315 |   |   |   |   | 320 |   |
| ctg | cgc | ttc | aga | cat | gag | aac | atc | atc | ggc | atc | aat | gac | atc | atc | cgg | 1008 |
| Leu | Arg | Phe | Arg | His | Glu | Asn | Ile | Ile | Gly | Ile | Asn | Asp | Ile | Ile | Arg |   |
|   |   |   |   | 325 |   |   |   |   | 330 |   |   |   |   | 335 |   |   |
| gca | cca | acc | att | gag | cag | atg | aaa | gat | gta | tat | ata | gta | cag | gac | ctc | 1056 |
| Ala | Pro | Thr | Ile | Glu | Gln | Met | Lys | Asp | Val | Tyr | Ile | Val | Gln | Asp | Leu |   |
|   |   |   | 340 |   |   |   |   | 345 |   |   |   |   | 350 |   |   |   |
| atg | gag | aca | gat | ctt | tac | aag | ctc | ttg | aag | aca | cag | cac | ctc | agc | aat | 1104 |
| Met | Glu | Thr | Asp | Leu | Tyr | Lys | Leu | Leu | Lys | Thr | Gln | His | Leu | Ser | Asn |   |
|   |   | 355 |   |   |   |   | 360 |   |   |   |   | 365 |   |   |   |   |
| gat | cat | atc | tgc | tat | ttt | ctt | tat | cag | atc | ctg | aga | gga | tta | aag | tat | 1152 |
| Asp | His | Ile | Cys | Tyr | Phe | Leu | Tyr | Gln | Ile | Leu | Arg | Gly | Leu | Lys | Tyr |   |
|   | 370 |   |   |   |   | 375 |   |   |   |   | 380 |   |   |   |   |   |
| ata | cat | tca | gct | aat | gtt | ctg | cac | cgt | gac | ctc | aag | cct | tcc | aac | ctc | 1200 |
| Ile | His | Ser | Ala | Asn | Val | Leu | His | Arg | Asp | Leu | Lys | Pro | Ser | Asn | Leu |   |
| 385 |   |   |   |   | 390 |   |   |   |   | 395 |   |   |   |   | 400 |   |
| ctg | ctg | aac | acc | act | tgt | gat | ctc | aag | atc | tgt | gac | ttt | ggc | ctt | gcc | 1248 |
| Leu | Leu | Asn | Thr | Thr | Cys | Asp | Leu | Lys | Ile | Cys | Asp | Phe | Gly | Leu | Ala |   |
|   |   |   |   | 405 |   |   |   |   | 410 |   |   |   |   | 415 |   |   |
| cgt | gtt | gca | gat | cca | gac | cat | gat | cat | aca | ggg | ttc | ttg | aca | gag | tat | 1296 |
| Arg | Val | Ala | Asp | Pro | Asp | His | Asp | His | Thr | Gly | Phe | Leu | Thr | Glu | Tyr |   |
|   |   |   | 420 |   |   |   |   | 425 |   |   |   |   | 430 |   |   |   |
| gta | gcc | acg | cgt | tgg | tac | aga | gct | cca | gaa | att | atg | ttg | aat | tcc | aag | 1344 |
| Val | Ala | Thr | Arg | Trp | Tyr | Arg | Ala | Pro | Glu | Ile | Met | Leu | Asn | Ser | Lys |   |
|   |   | 435 |   |   |   |   | 440 |   |   |   |   | 445 |   |   |   |   |
| ggt | tat | acc | aag | tcc | att | gat | att | tgg | tct | gtg | ggc | tgc | atc | ctg | gca | 1392 |
| Gly | Tyr | Thr | Lys | Ser | Ile | Asp | Ile | Trp | Ser | Val | Gly | Cys | Ile | Leu | Ala |   |
|   | 450 |   |   |   |   | 455 |   |   |   |   | 460 |   |   |   |   |   |
| gag | atg | cta | tcc | aac | agg | cct | atc | ttc | cca | gga | aag | cat | tac | ctt | gac | 1440 |
| Glu | Met | Leu | Ser | Asn | Arg | Pro | Ile | Phe | Pro | Gly | Lys | His | Tyr | Leu | Asp |   |
| 465 |   |   |   |   | 470 |   |   |   |   | 475 |   |   |   |   | 480 |   |
| cag | ctg | aat | cac | atc | ctg | ggt | att | ctt | gga | tct | cca | tca | cag | gaa | gat | 1488 |
| Gln | Leu | Asn | His | Ile | Leu | Gly | Ile | Leu | Gly | Ser | Pro | Ser | Gln | Glu | Asp |   |
|   |   |   |   | 485 |   |   |   |   | 490 |   |   |   |   | 495 |   |   |
| ctg | aat | tgt | ata | ata | aat | tta | aaa | gct | aga | aac | tat | ttg | ctt | tct | ctc | 1536 |
| Leu | Asn | Cys | Ile | Ile | Asn | Leu | Lys | Ala | Arg | Asn | Tyr | Leu | Leu | Ser | Leu |   |
|   |   |   | 500 |   |   |   |   | 505 |   |   |   |   | 510 |   |   |   |
| ccg | cac | aaa | aat | aag | gtg | ccg | tgg | aac | agg | ttg | ttc | cca | aac | gct | gac | 1584 |
| Pro | His | Lys | Asn | Lys | Val | Pro | Trp | Asn | Arg | Leu | Phe | Pro | Asn | Ala | Asp |   |
|   |   | 515 |   |   |   |   | 520 |   |   |   |   | 525 |   |   |   |   |
| tcc | aaa | gct | ctg | gat | tta | ctg | gat | aaa | atg | ttg | aca | ttt | aac | cct | cac | 1632 |
| Ser | Lys | Ala | Leu | Asp | Leu | Leu | Asp | Lys | Met | Leu | Thr | Phe | Asn | Pro | His |   |
|   | 530 |   |   |   |   | 535 |   |   |   |   | 540 |   |   |   |   |   |
| aag | agg | att | gaa | gtt | gaa | cag | gct | ctg | gcc | cac | ccg | tac | ctg | gag | cag | 1680 |
| Lys | Arg | Ile | Glu | Val | Glu | Gln | Ala | Leu | Ala | His | Pro | Tyr | Leu | Glu | Gln |   |
| 545 |   |   |   |   | 550 |   |   |   |   | 555 |   |   |   |   | 560 |   |
| tat | tat | gac | cca | agt | gat | gag | ccc | att | gct | gaa | gca | cca | ttc | aag | ttt | 1728 |

```
Tyr Tyr Asp Pro Ser Asp Glu Pro Ile Ala Glu Ala Pro Phe Lys Phe
                565                 570                 575 gac atg gag ctg gac gac tta cct aag gag aag ctc aaa gaa ctc att    1776
Asp Met Glu Leu Asp Asp Leu Pro Lys Glu Lys Leu Lys Glu Leu Ile
            580                 585                 590 ttt gaa gag act gct cga ttc cag cca gga tac aga tct taa            1818
Phe Glu Glu Thr Ala Arg Phe Gln Pro Gly Tyr Arg Ser
        595                 600                 605

<210> SEQ ID NO 41
<211> LENGTH: 605
<212> TYPE: PRT
<213> ORGANISM: Artificial Sequence
<220> FEATURE:
<223> OTHER INFORMATION: EGFP-Erk2 fusion

<400> SEQUENCE: 41

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys Ser
225                 230                 235                 240

Gly Leu Arg Ser Arg Val Thr Met Ala Ala Ala Ala Ala Ala Gly Pro
                245                 250                 255

Glu Met Val Arg Gly Gln Val Phe Asp Val Gly Pro Arg Tyr Thr Asn
            260                 265                 270

Leu Ser Tyr Ile Gly Glu Gly Ala Tyr Gly Met Val Cys Ser Ala Tyr
        275                 280                 285

Asp Asn Leu Asn Lys Val Arg Val Ala Ile Lys Lys Ile Ser Pro Phe
290                 295                 300

Glu His Gln Thr Tyr Cys Gln Arg Thr Leu Arg Glu Ile Lys Ile Leu
```

-continued

```
305                 310                 315                 320
Leu Arg Phe Arg His Glu Asn Ile Ile Gly Ile Asn Asp Ile Ile Arg
                325                 330                 335

Ala Pro Thr Ile Glu Gln Met Lys Asp Val Tyr Ile Val Gln Asp Leu
                340                 345                 350

Met Glu Thr Asp Leu Tyr Lys Leu Leu Lys Thr Gln His Leu Ser Asn
                355                 360                 365

Asp His Ile Cys Tyr Phe Leu Tyr Gln Ile Leu Arg Gly Leu Lys Tyr
            370                 375                 380

Ile His Ser Ala Asn Val Leu His Arg Asp Leu Lys Pro Ser Asn Leu
385                 390                 395                 400

Leu Leu Asn Thr Thr Cys Asp Leu Lys Ile Cys Asp Phe Gly Leu Ala
                405                 410                 415

Arg Val Ala Asp Pro Asp His Asp His Thr Gly Phe Leu Thr Glu Tyr
                420                 425                 430

Val Ala Thr Arg Trp Tyr Arg Ala Pro Glu Ile Met Leu Asn Ser Lys
            435                 440                 445

Gly Tyr Thr Lys Ser Ile Asp Ile Trp Ser Val Gly Cys Ile Leu Ala
            450                 455                 460

Glu Met Leu Ser Asn Arg Pro Ile Phe Pro Gly Lys His Tyr Leu Asp
465                 470                 475                 480

Gln Leu Asn His Ile Leu Gly Ile Leu Gly Ser Pro Ser Gln Glu Asp
                485                 490                 495

Leu Asn Cys Ile Ile Asn Leu Lys Ala Arg Asn Tyr Leu Leu Ser Leu
                500                 505                 510

Pro His Lys Asn Lys Val Pro Trp Asn Arg Leu Phe Pro Asn Ala Asp
                515                 520                 525

Ser Lys Ala Leu Asp Leu Leu Asp Lys Met Leu Thr Phe Asn Pro His
530                 535                 540

Lys Arg Ile Glu Val Glu Gln Ala Leu Ala His Pro Tyr Leu Glu Gln
545                 550                 555                 560

Tyr Tyr Asp Pro Ser Asp Glu Pro Ile Ala Glu Ala Pro Phe Lys Phe
                565                 570                 575

Asp Met Glu Leu Asp Asp Leu Pro Lys Glu Lys Leu Lys Glu Leu Ile
                580                 585                 590

Phe Glu Glu Thr Ala Arg Phe Gln Pro Gly Tyr Arg Ser
                595                 600                 605

<210> SEQ ID NO 42
<211> LENGTH: 2529
<212> TYPE: DNA
<213> ORGANISM: Artificial Sequence
<220> FEATURE:
<223> OTHER INFORMATION: EGFP-Grk5 fusion
<220> FEATURE:
<221> NAME/KEY: CDS
<222> LOCATION: (1)..(2526)

<400> SEQUENCE: 42 atg gtg agc aag ggc gag gag ctg ttc acc ggg gtg gtg ccc atc ctg      48
Met Val Ser Lys Gly Glu Glu Leu Phe Thr Gly Val Val Pro Ile Leu
1               5                   10                  15 gtc gag ctg gac ggc gac gta aac ggc cac aag ttc agc gtg tcc ggc      96
Val Glu Leu Asp Gly Asp Val Asn Gly His Lys Phe Ser Val Ser Gly
                20                  25                  30 gag ggc gag ggc gat gcc acc tac ggc aag ctg acc ctg aag ttc atc     144
Glu Gly Glu Gly Asp Ala Thr Tyr Gly Lys Leu Thr Leu Lys Phe Ile
```

-continued

| | 35 | | | | 40 | | | | | 45 | | | | |
|---|---|---|---|---|---|---|---|---|---|---|---|---|---|---|
| tgc | acc | acc | ggc | aag | ctg | ccc | gtg | ccc | tgg | ccc | acc | ctc | gtg | acc | acc | 192 |
| Cys | Thr | Thr | Gly | Lys | Leu | Pro | Val | Pro | Trp | Pro | Thr | Leu | Val | Thr | Thr | |
| | 50 | | | | 55 | | | | | 60 | | | | | |

| ctg | acc | tac | ggc | gtg | cag | tgc | ttc | agc | cgc | tac | ccc | gac | cac | atg | aag | 240 |
|---|---|---|---|---|---|---|---|---|---|---|---|---|---|---|---|---|
| Leu | Thr | Tyr | Gly | Val | Gln | Cys | Phe | Ser | Arg | Tyr | Pro | Asp | His | Met | Lys | |
| 65 | | | | | 70 | | | | | 75 | | | | | 80 | |

| cag | cac | gac | ttc | ttc | aag | tcc | gcc | atg | ccc | gaa | ggc | tac | gtc | cag | gag | 288 |
|---|---|---|---|---|---|---|---|---|---|---|---|---|---|---|---|---|
| Gln | His | Asp | Phe | Phe | Lys | Ser | Ala | Met | Pro | Glu | Gly | Tyr | Val | Gln | Glu | |
| | | | | 85 | | | | | 90 | | | | | 95 | | |

| cgc | acc | atc | ttc | ttc | aag | gac | gac | ggc | aac | tac | aag | acc | cgc | gcc | gag | 336 |
|---|---|---|---|---|---|---|---|---|---|---|---|---|---|---|---|---|
| Arg | Thr | Ile | Phe | Phe | Lys | Asp | Asp | Gly | Asn | Tyr | Lys | Thr | Arg | Ala | Glu | |
| | | | 100 | | | | | 105 | | | | | 110 | | | |

| gtg | aag | ttc | gag | ggc | gac | acc | ctg | gtg | aac | cgc | atc | gag | ctg | aag | ggc | 384 |
|---|---|---|---|---|---|---|---|---|---|---|---|---|---|---|---|---|
| Val | Lys | Phe | Glu | Gly | Asp | Thr | Leu | Val | Asn | Arg | Ile | Glu | Leu | Lys | Gly | |
| | | 115 | | | | | 120 | | | | | 125 | | | | |

| atc | gac | ttc | aag | gag | gac | ggc | aac | atc | ctg | ggg | cac | aag | ctg | gag | tac | 432 |
|---|---|---|---|---|---|---|---|---|---|---|---|---|---|---|---|---|
| Ile | Asp | Phe | Lys | Glu | Asp | Gly | Asn | Ile | Leu | Gly | His | Lys | Leu | Glu | Tyr | |
| 130 | | | | | 135 | | | | | 140 | | | | | | |

| aac | tac | aac | agc | cac | aac | gtc | tat | atc | atg | gcc | gac | aag | cag | aag | aac | 480 |
|---|---|---|---|---|---|---|---|---|---|---|---|---|---|---|---|---|
| Asn | Tyr | Asn | Ser | His | Asn | Val | Tyr | Ile | Met | Ala | Asp | Lys | Gln | Lys | Asn | |
| 145 | | | | | 150 | | | | | 155 | | | | | 160 | |

| ggc | atc | aag | gtg | aac | ttc | aag | atc | cgc | cac | aac | atc | gag | gac | ggc | agc | 528 |
|---|---|---|---|---|---|---|---|---|---|---|---|---|---|---|---|---|
| Gly | Ile | Lys | Val | Asn | Phe | Lys | Ile | Arg | His | Asn | Ile | Glu | Asp | Gly | Ser | |
| | | | | 165 | | | | | 170 | | | | | 175 | | |

| gtg | cag | ctc | gcc | gac | cac | tac | cag | cag | aac | acc | ccc | atc | ggc | gac | ggc | 576 |
|---|---|---|---|---|---|---|---|---|---|---|---|---|---|---|---|---|
| Val | Gln | Leu | Ala | Asp | His | Tyr | Gln | Gln | Asn | Thr | Pro | Ile | Gly | Asp | Gly | |
| | | | 180 | | | | | 185 | | | | | 190 | | | |

| ccc | gtg | ctg | ctg | ccc | gac | aac | cac | tac | ctg | agc | acc | cag | tcc | gcc | ctg | 624 |
|---|---|---|---|---|---|---|---|---|---|---|---|---|---|---|---|---|
| Pro | Val | Leu | Leu | Pro | Asp | Asn | His | Tyr | Leu | Ser | Thr | Gln | Ser | Ala | Leu | |
| | | 195 | | | | | 200 | | | | | 205 | | | | |

| agc | aaa | gac | ccc | aac | gag | aag | cgc | gat | cac | atg | gtc | ctg | ctg | gag | ttc | 672 |
|---|---|---|---|---|---|---|---|---|---|---|---|---|---|---|---|---|
| Ser | Lys | Asp | Pro | Asn | Glu | Lys | Arg | Asp | His | Met | Val | Leu | Leu | Glu | Phe | |
| | 210 | | | | | 215 | | | | | 220 | | | | | |

| gtg | acc | gcc | gcc | ggg | atc | act | ctc | ggc | atg | gac | gag | ctg | tac | aag | tcc | 720 |
|---|---|---|---|---|---|---|---|---|---|---|---|---|---|---|---|---|
| Val | Thr | Ala | Ala | Gly | Ile | Thr | Leu | Gly | Met | Asp | Glu | Leu | Tyr | Lys | Ser | |
| 225 | | | | | 230 | | | | | 235 | | | | | 240 | |

| gga | ctc | aga | tct | cga | gct | caa | gct | tcg | aat | tcg | tca | atg | gag | ctg | gaa | 768 |
|---|---|---|---|---|---|---|---|---|---|---|---|---|---|---|---|---|
| Gly | Leu | Arg | Ser | Arg | Ala | Gln | Ala | Ser | Asn | Ser | Ser | Met | Glu | Leu | Glu | |
| | | | | 245 | | | | | 250 | | | | | 255 | | |

| aac | atc | gtg | gcc | aac | acg | gtc | ttg | ctg | aaa | gcc | agg | gaa | ggg | ggc | gga | 816 |
|---|---|---|---|---|---|---|---|---|---|---|---|---|---|---|---|---|
| Asn | Ile | Val | Ala | Asn | Thr | Val | Leu | Leu | Lys | Ala | Arg | Glu | Gly | Gly | Gly | |
| | | | | 260 | | | | | 265 | | | | | 270 | | |

| gga | aag | cgc | aaa | ggg | aaa | agc | aag | aag | tgg | aaa | gaa | atc | ctg | aag | ttc | 864 |
|---|---|---|---|---|---|---|---|---|---|---|---|---|---|---|---|---|
| Gly | Lys | Arg | Lys | Gly | Lys | Ser | Lys | Lys | Trp | Lys | Glu | Ile | Leu | Lys | Phe | |
| | | 275 | | | | | 280 | | | | | 285 | | | | |

| cct | cac | att | agc | cag | tgt | gaa | gac | ctc | cga | agg | acc | ata | gac | aga | gat | 912 |
|---|---|---|---|---|---|---|---|---|---|---|---|---|---|---|---|---|
| Pro | His | Ile | Ser | Gln | Cys | Glu | Asp | Leu | Arg | Arg | Thr | Ile | Asp | Arg | Asp | |
| | 290 | | | | | 295 | | | | | 300 | | | | | |

| tac | tgc | agt | tta | tgt | gac | aag | cag | cca | atc | ggg | agg | ctg | ctt | ttc | cgg | 960 |
|---|---|---|---|---|---|---|---|---|---|---|---|---|---|---|---|---|
| Tyr | Cys | Ser | Leu | Cys | Asp | Lys | Gln | Pro | Ile | Gly | Arg | Leu | Leu | Phe | Arg | |
| 305 | | | | | 310 | | | | | 315 | | | | | 320 | |

| cag | ttt | tgt | gaa | acc | agg | cct | ggg | ctg | gag | tgt | tac | att | cag | ttc | ctg | 1008 |
|---|---|---|---|---|---|---|---|---|---|---|---|---|---|---|---|---|
| Gln | Phe | Cys | Glu | Thr | Arg | Pro | Gly | Leu | Glu | Cys | Tyr | Ile | Gln | Phe | Leu | |
| | | | | 325 | | | | | 330 | | | | | 335 | | |

| gac | tcc | gtg | gca | gaa | tat | gaa | gtt | act | cca | gat | gaa | aaa | ctg | gga | gag | 1056 |
|---|---|---|---|---|---|---|---|---|---|---|---|---|---|---|---|---|
| Asp | Ser | Val | Ala | Glu | Tyr | Glu | Val | Thr | Pro | Asp | Glu | Lys | Leu | Gly | Glu | |
| | | | 340 | | | | | 345 | | | | | 350 | | | |

| aaa | ggg | aag | gaa | att | atg | acc | aag | tac | ctc | acc | cca | aag | tcc | cct | gtt | 1104 |

```
                                                         -continued

Lys Gly Lys Glu Ile Met Thr Lys Tyr Leu Thr Pro Lys Ser Pro Val
            355                 360                 365 ttc ata gcc caa gtt ggc caa gac ctg gtc tcc cag acg gag gag aag      1152
Phe Ile Ala Gln Val Gly Gln Asp Leu Val Ser Gln Thr Glu Glu Lys
370                 375                 380 ctc cta cag aag ccg tgc aaa gaa ctc ttt tct gcc tgt gca cag tct      1200
Leu Leu Gln Lys Pro Cys Lys Glu Leu Phe Ser Ala Cys Ala Gln Ser
385                 390                 395                 400 gtc cac gag tac ctg agg gga gaa cca ttc cac gaa tat ctg gac agc      1248
Val His Glu Tyr Leu Arg Gly Glu Pro Phe His Glu Tyr Leu Asp Ser
                405                 410                 415 atg ttt ttt gac cgc ttt ctc cag tgg aag tgg ttg gaa agg caa ccg      1296
Met Phe Phe Asp Arg Phe Leu Gln Trp Lys Trp Leu Glu Arg Gln Pro
            420                 425                 430 gtg acc aaa aac act ttc agg cag tat cga gtg cta gga aaa ggg ggc      1344
Val Thr Lys Asn Thr Phe Arg Gln Tyr Arg Val Leu Gly Lys Gly Gly
        435                 440                 445 ttc ggg gag gtc tgt gcc tgc cag gtt cgg gcc acg gtt aaa atg tat      1392
Phe Gly Glu Val Cys Ala Cys Gln Val Arg Ala Thr Gly Lys Met Tyr
450                 455                 460 gcc tgc aag cgc ttg gag aag aag agg atc aaa aag agg aaa ggg gag      1440
Ala Cys Lys Arg Leu Glu Lys Lys Arg Ile Lys Lys Arg Lys Gly Glu
465                 470                 475                 480 tcc atg gcc ctc aat gag aag cag atc ctc gag aag gtc aac agt cag      1488
Ser Met Ala Leu Asn Glu Lys Gln Ile Leu Glu Lys Val Asn Ser Gln
                485                 490                 495 ttt gtg gtc aac ctg gcc tat gcc tac gag acc aag gat gca ctg tgc      1536
Phe Val Val Asn Leu Ala Tyr Ala Tyr Glu Thr Lys Asp Ala Leu Cys
            500                 505                 510 ttg gtc ctg acc atc atg aat ggg ggt gac ctg aag ttc cac atc tac      1584
Leu Val Leu Thr Ile Met Asn Gly Gly Asp Leu Lys Phe His Ile Tyr
        515                 520                 525 aac atg ggc aac cct ggc ttc gag gag gag cgg gcc ttg ttt tat gcg      1632
Asn Met Gly Asn Pro Gly Phe Glu Glu Glu Arg Ala Leu Phe Tyr Ala
530                 535                 540 gca gag atc ctc tgc ggc tta gaa gac ctc cac cgt gag aac acc gtc      1680
Ala Glu Ile Leu Cys Gly Leu Glu Asp Leu His Arg Glu Asn Thr Val
545                 550                 555                 560 tac cga gat ctg aaa cct gaa aac atc ctg tta gat gat tat ggc cac      1728
Tyr Arg Asp Leu Lys Pro Glu Asn Ile Leu Leu Asp Asp Tyr Gly His
                565                 570                 575 att agg atc tca gac ctg ggc ttg gct gtg aag atc ccc gag gga gac      1776
Ile Arg Ile Ser Asp Leu Gly Leu Ala Val Lys Ile Pro Glu Gly Asp
            580                 585                 590 ctg atc cgc ggc cgg gtg ggc act gtt ggc tac atg gcc ccc gaa gtc      1824
Leu Ile Arg Gly Arg Val Gly Thr Val Gly Tyr Met Ala Pro Glu Val
        595                 600                 605 ctg aac aac cag agg tac ggc ctg agc ccc gac tac tgg ggc ctt ggc      1872
Leu Asn Asn Gln Arg Tyr Gly Leu Ser Pro Asp Tyr Trp Gly Leu Gly
610                 615                 620 tgc ctc atc tat gag atg atc gag ggc cag tcg ccg ttc cgc ggc cgt      1920
Cys Leu Ile Tyr Glu Met Ile Glu Gly Gln Ser Pro Phe Arg Gly Arg
625                 630                 635                 640 aag gag aag gtg aag cgg gag gag gtg gac cgc cgg gtc ctg gag acg      1968
Lys Glu Lys Val Lys Arg Glu Glu Val Asp Arg Arg Val Leu Glu Thr
                645                 650                 655 gag gag gtg tac tcc cac aag ttc tcc gag gag gcc aag tcc atc tgc      2016
Glu Glu Val Tyr Ser His Lys Phe Ser Glu Glu Ala Lys Ser Ile Cys
            660                 665                 670
```

-continued

```
aag atg ctg ctc acg aaa gat gcg aag cag agg ctg ggc tgc cag gag      2064
Lys Met Leu Leu Thr Lys Asp Ala Lys Gln Arg Leu Gly Cys Gln Glu
            675                 680                 685 gag ggg gct gca gag gtc aag aga cac ccc ttc ttc agg aac atg aac      2112
Glu Gly Ala Ala Glu Val Lys Arg His Pro Phe Phe Arg Asn Met Asn
690                 695                 700 ttc aag cgc tta gaa gcc ggg atg ttg gac cct ccc ttc gtt cca gac      2160
Phe Lys Arg Leu Glu Ala Gly Met Leu Asp Pro Pro Phe Val Pro Asp
705                 710                 715                 720 ccc cgc gct gtg tac tgt aag gac gtg ctg gac atc gag cag ttc tcc      2208
Pro Arg Ala Val Tyr Cys Lys Asp Val Leu Asp Ile Glu Gln Phe Ser
                725                 730                 735 act gtg aag ggc gtc aat ctg gac cac aca gac gac gac ttc tac tcc      2256
Thr Val Lys Gly Val Asn Leu Asp His Thr Asp Asp Asp Phe Tyr Ser
            740                 745                 750 aag ttc tcc acg ggc tct gtg tcc atc cca tgg caa aac gag atg ata      2304
Lys Phe Ser Thr Gly Ser Val Ser Ile Pro Trp Gln Asn Glu Met Ile
        755                 760                 765 gaa aca gaa tgc ttt aag gag ctg aac gtg ttt gga cct aat ggt acc      2352
Glu Thr Glu Cys Phe Lys Glu Leu Asn Val Phe Gly Pro Asn Gly Thr
770                 775                 780 ctc ccg cca gat ctg aac aga aac cac cct ccg gaa ccg ccc aag aaa      2400
Leu Pro Pro Asp Leu Asn Arg Asn His Pro Pro Glu Pro Pro Lys Lys
785                 790                 795                 800 ggg ctg ctc cag aga ctc ttc aag cgg cag cat cag aac aat tcc aag      2448
Gly Leu Leu Gln Arg Leu Phe Lys Arg Gln His Gln Asn Asn Ser Lys
                805                 810                 815 agt tcg ccc agc tcc aag acc agt ttt aac cac cac ata aac tca aac      2496
Ser Ser Pro Ser Ser Lys Thr Ser Phe Asn His His Ile Asn Ser Asn
            820                 825                 830 cat gtc agc tcg aac tcc acc gga agc agc tag                          2529
His Val Ser Ser Asn Ser Thr Gly Ser Ser
        835                 840
```

<210> SEQ ID NO 43
<211> LENGTH: 842
<212> TYPE: PRT
<213> ORGANISM: Artificial Sequence
<220> FEATURE:
<223> OTHER INFORMATION: EGFP-Grk5 fusion

<400> SEQUENCE: 43

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
```

-continued

```
            130                 135                 140
Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
                180                 185                 190

Pro Val Leu Leu Pro Asp Asn His Tyr Leu Ser Thr Gln Ser Ala Leu
                195                 200                 205

Ser Lys Asp Pro Asn Glu Lys Arg Asp His Met Val Leu Leu Glu Phe
                210                 215                 220

Val Thr Ala Ala Gly Ile Thr Leu Gly Met Asp Glu Leu Tyr Lys Ser
225                 230                 235                 240

Gly Leu Arg Ser Arg Ala Gln Ala Ser Asn Ser Ser Met Glu Leu Glu
                245                 250                 255

Asn Ile Val Ala Asn Thr Val Leu Leu Lys Ala Arg Glu Gly Gly Gly
                260                 265                 270

Gly Lys Arg Lys Gly Lys Ser Lys Lys Trp Lys Glu Ile Leu Lys Phe
                275                 280                 285

Pro His Ile Ser Gln Cys Glu Asp Leu Arg Arg Thr Ile Asp Arg Asp
                290                 295                 300

Tyr Cys Ser Leu Cys Asp Lys Gln Pro Ile Gly Arg Leu Leu Phe Arg
305                 310                 315                 320

Gln Phe Cys Glu Thr Arg Pro Gly Leu Glu Cys Tyr Ile Gln Phe Leu
                325                 330                 335

Asp Ser Val Ala Glu Tyr Glu Val Thr Pro Asp Glu Lys Leu Gly Glu
                340                 345                 350

Lys Gly Lys Glu Ile Met Thr Lys Tyr Leu Thr Pro Lys Ser Pro Val
                355                 360                 365

Phe Ile Ala Gln Val Gly Gln Asp Leu Val Ser Gln Thr Glu Glu Lys
370                 375                 380

Leu Leu Gln Lys Pro Cys Lys Glu Leu Phe Ser Ala Cys Ala Gln Ser
385                 390                 395                 400

Val His Glu Tyr Leu Arg Gly Glu Pro Phe His Glu Tyr Leu Asp Ser
                405                 410                 415

Met Phe Phe Asp Arg Phe Leu Gln Trp Lys Trp Leu Glu Arg Gln Pro
                420                 425                 430

Val Thr Lys Asn Thr Phe Arg Gln Tyr Arg Val Leu Gly Lys Gly Gly
                435                 440                 445

Phe Gly Glu Val Cys Ala Cys Gln Val Arg Ala Thr Gly Lys Met Tyr
                450                 455                 460

Ala Cys Lys Arg Leu Glu Lys Lys Arg Ile Lys Lys Arg Lys Gly Glu
465                 470                 475                 480

Ser Met Ala Leu Asn Glu Lys Gln Ile Leu Glu Lys Val Asn Ser Gln
                485                 490                 495

Phe Val Val Asn Leu Ala Tyr Ala Tyr Glu Thr Lys Asp Ala Leu Cys
                500                 505                 510

Leu Val Leu Thr Ile Met Asn Gly Gly Asp Leu Lys Phe His Ile Tyr
                515                 520                 525

Asn Met Gly Asn Pro Gly Phe Glu Glu Glu Arg Ala Leu Phe Tyr Ala
                530                 535                 540

Ala Glu Ile Leu Cys Gly Leu Glu Asp Leu His Arg Glu Asn Thr Val
545                 550                 555                 560
```

```
                Tyr Arg Asp Leu Lys Pro Glu Asn Ile Leu Leu Asp Asp Tyr Gly His
                            565                 570                 575

Ile Arg Ile Ser Asp Leu Gly Leu Ala Val Lys Ile Pro Glu Gly Asp
                            580                 585                 590

Leu Ile Arg Gly Arg Val Gly Thr Val Gly Tyr Met Ala Pro Glu Val
                            595                 600                 605

Leu Asn Asn Gln Arg Tyr Gly Leu Ser Pro Asp Tyr Trp Gly Leu Gly
                            610                 615                 620

Cys Leu Ile Tyr Glu Met Ile Glu Gly Gln Ser Pro Phe Arg Gly Arg
                625                 630                 635                 640

Lys Glu Lys Val Lys Arg Glu Glu Val Asp Arg Arg Val Leu Glu Thr
                            645                 650                 655

Glu Glu Val Tyr Ser His Lys Phe Ser Glu Glu Ala Lys Ser Ile Cys
                            660                 665                 670

Lys Met Leu Leu Thr Lys Asp Ala Lys Gln Arg Leu Gly Cys Gln Glu
                            675                 680                 685

Glu Gly Ala Ala Glu Val Lys Arg His Pro Phe Phe Arg Asn Met Asn
                            690                 695                 700

Phe Lys Arg Leu Glu Ala Gly Met Leu Asp Pro Pro Phe Val Pro Asp
                705                 710                 715                 720

Pro Arg Ala Val Tyr Cys Lys Asp Val Leu Asp Ile Glu Gln Phe Ser
                            725                 730                 735

Thr Val Lys Gly Val Asn Leu Asp His Thr Asp Asp Phe Tyr Ser
                            740                 745                 750

Lys Phe Ser Thr Gly Ser Val Ser Ile Pro Trp Gln Asn Glu Met Ile
                            755                 760                 765

Glu Thr Glu Cys Phe Lys Glu Leu Asn Val Phe Gly Pro Asn Gly Thr
                            770                 775                 780

Leu Pro Pro Asp Leu Asn Arg Asn His Pro Pro Glu Pro Pro Lys Lys
                785                 790                 795                 800

Gly Leu Leu Gln Arg Leu Phe Lys Arg Gln His Gln Asn Asn Ser Lys
                            805                 810                 815

Ser Ser Pro Ser Ser Lys Thr Ser Phe Asn His His Ile Asn Ser Asn
                            820                 825                 830

His Val Ser Ser Asn Ser Thr Gly Ser Ser
                            835                 840

<210> SEQ ID NO 44
<211> LENGTH: 1902
<212> TYPE: DNA
<213> ORGANISM: Artificial Sequence
<220> FEATURE:
<223> OTHER INFORMATION: EGFP-Jnk1 fusion
<220> FEATURE:
<221> NAME/KEY: CDS
<222> LOCATION: (1)..(1899)

<400> SEQUENCE: 44 atg gtg agc aag ggc gag gag ctg ttc acc ggg gtg gtg ccc atc ctg      48
Met Val Ser Lys Gly Glu Glu Leu Phe Thr Gly Val Val Pro Ile Leu
1               5                   10                  15 gtc gag ctg gac ggc gac gta aac ggc cac aag ttc agc gtg tcc ggc      96
Val Glu Leu Asp Gly Asp Val Asn Gly His Lys Phe Ser Val Ser Gly
                20                  25                  30 gag ggc gag ggc gat gcc acc tac ggc aag ctg acc ctg aag ttc atc     144
Glu Gly Glu Gly Asp Ala Thr Tyr Gly Lys Leu Thr Leu Lys Phe Ile
            35                  40                  45
```

-continued

| | |
|---|---|
| tgc acc acc ggc aag ctg ccc gtg ccc tgg ccc acc ctc gtg acc acc<br>Cys Thr Thr Gly Lys Leu Pro Val Pro Trp Pro Thr Leu Val Thr Thr<br>50                            55                        60 | 192 |
| ctg acc tac ggc gtg cag tgc ttc agc cgc tac ccc gac cac atg aag<br>Leu Thr Tyr Gly Val Gln Cys Phe Ser Arg Tyr Pro Asp His Met Lys<br>65                            70                        75                        80 | 240 |
| cag cac gac ttc ttc aag tcc gcc atg ccc gaa ggc tac gtc cag gag<br>Gln His Asp Phe Phe Lys Ser Ala Met Pro Glu Gly Tyr Val Gln Glu<br>                        85                        90                        95 | 288 |
| cgc acc atc ttc ttc aag gac gac ggc aac tac aag acc cgc gcc gag<br>Arg Thr Ile Phe Phe Lys Asp Asp Gly Asn Tyr Lys Thr Arg Ala Glu<br>                100                      105                      110 | 336 |
| gtg aag ttc gag ggc gac acc ctg gtg aac cgc atc gag ctg aag ggc<br>Val Lys Phe Glu Gly Asp Thr Leu Val Asn Arg Ile Glu Leu Lys Gly<br>          115                      120                      125 | 384 |
| atc gac ttc aag gag gac ggc aac atc ctg ggg cac aag ctg gag tac<br>Ile Asp Phe Lys Glu Asp Gly Asn Ile Leu Gly His Lys Leu Glu Tyr<br>130                          135                      140 | 432 |
| aac tac aac agc cac aac gtc tat atc atg gcc gac aag cag aag aac<br>Asn Tyr Asn Ser His Asn Val Tyr Ile Met Ala Asp Lys Gln Lys Asn<br>145                          150                      155                      160 | 480 |
| ggc atc aag gtg aac ttc aag atc cgc cac aac atc gag gac ggc agc<br>Gly Ile Lys Val Asn Phe Lys Ile Arg His Asn Ile Glu Asp Gly Ser<br>          165                      170                      175 | 528 |
| gtg cag ctc gcc gac cac tac cag cag aac acc ccc atc ggc gac ggc<br>Val Gln Leu Ala Asp His Tyr Gln Gln Asn Thr Pro Ile Gly Asp Gly<br>                180                      185                      190 | 576 |
| ccc gtg ctg ctg ccc gac aac cac tac ctg agc acc cag tcc gcc ctg<br>Pro Val Leu Leu Pro Asp Asn His Tyr Leu Ser Thr Gln Ser Ala Leu<br>          195                      200                      205 | 624 |
| agc aaa gac ccc aac gag aag cgc gat cac atg gtc ctg ctg gag ttc<br>Ser Lys Asp Pro Asn Glu Lys Arg Asp His Met Val Leu Leu Glu Phe<br>210                          215                      220 | 672 |
| gtg acc gcc gcc ggg atc act ctc ggc atg gac gag ctg tac aag tcc<br>Val Thr Ala Ala Gly Ile Thr Leu Gly Met Asp Glu Leu Tyr Lys Ser<br>225                          230                      235                      240 | 720 |
| gga ctc aga tct cga gct cga gcc atc atg agc aga agc aag cgt gac<br>Gly Leu Arg Ser Arg Ala Arg Ala Ile Met Ser Arg Ser Lys Arg Asp<br>                245                      250                      255 | 768 |
| aac aat ttt tat agt gta gag att gga gat tct aca ttc aca gtc ctg<br>Asn Asn Phe Tyr Ser Val Glu Ile Gly Asp Ser Thr Phe Thr Val Leu<br>          260                      265                      270 | 816 |
| aaa cga tat cag aat tta aaa cct ata ggc tca gga gct caa gga ata<br>Lys Arg Tyr Gln Asn Leu Lys Pro Ile Gly Ser Gly Ala Gln Gly Ile<br>275                          280                      285 | 864 |
| gta tgc gca gct tat gat gcc att ctt gaa aga aat gtt gca atc aag<br>Val Cys Ala Ala Tyr Asp Ala Ile Leu Glu Arg Asn Val Ala Ile Lys<br>290                          295                      300 | 912 |
| aag cta agc cga cca ttt cag aat cag act cat gcc aag cgg gcc tac<br>Lys Leu Ser Arg Pro Phe Gln Asn Gln Thr His Ala Lys Arg Ala Tyr<br>305                          310                      315                      320 | 960 |
| aga gag cta gtt ctt atg aaa tgt gtt aat cac aaa aat ata att ggc<br>Arg Glu Leu Val Leu Met Lys Cys Val Asn His Lys Asn Ile Ile Gly<br>                325                      330                      335 | 1008 |
| ctt ttg aat gtt ttc aca cca cag aaa tcc cta gaa gaa ttt caa gat<br>Leu Leu Asn Val Phe Thr Pro Gln Lys Ser Leu Glu Glu Phe Gln Asp<br>          340                      345                      350 | 1056 |
| gtt tac ata gtc atg gag ctc atg gat gca aat ctt tgc caa gtg att<br>Val Tyr Ile Val Met Glu Leu Met Asp Ala Asn Leu Cys Gln Val Ile | 1104 |

|  |  |  |  |  |  |  |  |  |  |  |  |  |  |  |  |
|---|---|---|---|---|---|---|---|---|---|---|---|---|---|---|---|
|  | 355 |  |  |  | 360 |  |  |  |  | 365 |  |  |  |  |  |
| cag | atg | gag | cta | gat | cat | gaa | aga | atg | tcc | tac | ctt | ctc | tat | cag | atg | 1152 |
| Gln | Met | Glu | Leu | Asp | His | Glu | Arg | Met | Ser | Tyr | Leu | Leu | Tyr | Gln | Met |
|  | 370 |  |  |  | 375 |  |  |  |  | 380 |  |  |  |  |  |
| ctg | tgt | gga | atc | aag | cac | ctt | cat | tct | gct | gga | att | att | cat | cgg | gac | 1200 |
| Leu | Cys | Gly | Ile | Lys | His | Leu | His | Ser | Ala | Gly | Ile | Ile | His | Arg | Asp |
| 385 |  |  |  |  | 390 |  |  |  |  | 395 |  |  |  |  | 400 |
| tta | aag | ccc | agt | aat | ata | gta | gta | aaa | tct | gat | tgc | act | ttg | aag | att | 1248 |
| Leu | Lys | Pro | Ser | Asn | Ile | Val | Val | Lys | Ser | Asp | Cys | Thr | Leu | Lys | Ile |
|  |  |  |  | 405 |  |  |  |  | 410 |  |  |  |  | 415 |  |
| ctt | gac | ttc | ggt | ctg | gcc | agg | act | gca | gga | acg | agt | ttt | atg | atg | acg | 1296 |
| Leu | Asp | Phe | Gly | Leu | Ala | Arg | Thr | Ala | Gly | Thr | Ser | Phe | Met | Met | Thr |
|  |  |  | 420 |  |  |  |  | 425 |  |  |  |  | 430 |  |  |
| cct | tat | gta | gtg | act | cgc | tac | tac | aga | gca | ccc | gag | gtc | atc | ctt | ggc | 1344 |
| Pro | Tyr | Val | Val | Thr | Arg | Tyr | Tyr | Arg | Ala | Pro | Glu | Val | Ile | Leu | Gly |
|  |  | 435 |  |  |  |  | 440 |  |  |  |  | 445 |  |  |  |
| atg | ggc | tac | aag | gaa | aac | gtg | gat | tta | tgg | tct | gtg | ggg | tgc | att | atg | 1392 |
| Met | Gly | Tyr | Lys | Glu | Asn | Val | Asp | Leu | Trp | Ser | Val | Gly | Cys | Ile | Met |
|  | 450 |  |  |  |  | 455 |  |  |  |  | 460 |  |  |  |  |
| gga | gaa | atg | gtt | tgc | cac | aaa | atc | ctc | ttt | cca | gga | agg | gac | tat | att | 1440 |
| Gly | Glu | Met | Val | Cys | His | Lys | Ile | Leu | Phe | Pro | Gly | Arg | Asp | Tyr | Ile |
| 465 |  |  |  |  | 470 |  |  |  |  | 475 |  |  |  |  | 480 |
| gat | cag | tgg | aat | aaa | gtt | att | gaa | cag | ctt | gga | aca | cca | tgt | cct | gaa | 1488 |
| Asp | Gln | Trp | Asn | Lys | Val | Ile | Glu | Gln | Leu | Gly | Thr | Pro | Cys | Pro | Glu |
|  |  |  |  | 485 |  |  |  |  | 490 |  |  |  |  | 495 |  |
| ttc | atg | aag | aaa | ctg | caa | cca | aca | gta | agg | act | tac | gtt | gaa | aac | aga | 1536 |
| Phe | Met | Lys | Lys | Leu | Gln | Pro | Thr | Val | Arg | Thr | Tyr | Val | Glu | Asn | Arg |
|  |  |  | 500 |  |  |  |  | 505 |  |  |  |  | 510 |  |  |
| cct | aaa | tat | gct | gga | tat | agc | ttt | gag | aaa | ctc | ttc | cct | gat | gtc | ctt | 1584 |
| Pro | Lys | Tyr | Ala | Gly | Tyr | Ser | Phe | Glu | Lys | Leu | Phe | Pro | Asp | Val | Leu |
|  |  | 515 |  |  |  |  | 520 |  |  |  |  | 525 |  |  |  |
| ttc | cca | gct | gac | tca | gaa | cac | aac | aaa | ctt | aaa | gcc | agt | cag | gca | agg | 1632 |
| Phe | Pro | Ala | Asp | Ser | Glu | His | Asn | Lys | Leu | Lys | Ala | Ser | Gln | Ala | Arg |
|  | 530 |  |  |  |  | 535 |  |  |  |  | 540 |  |  |  |  |
| gat | ttg | tta | tcc | aaa | atg | ctg | gta | ata | gat | gca | tct | aaa | agg | atc | tct | 1680 |
| Asp | Leu | Leu | Ser | Lys | Met | Leu | Val | Ile | Asp | Ala | Ser | Lys | Arg | Ile | Ser |
| 545 |  |  |  |  | 550 |  |  |  |  | 555 |  |  |  |  | 560 |
| gta | gat | gaa | gct | ctc | caa | cac | ccg | tac | atc | aat | gtc | tgg | tat | gat | cct | 1728 |
| Val | Asp | Glu | Ala | Leu | Gln | His | Pro | Tyr | Ile | Asn | Val | Trp | Tyr | Asp | Pro |
|  |  |  |  | 565 |  |  |  |  | 570 |  |  |  |  | 575 |  |
| tct | gaa | gca | gaa | gct | cca | cca | cca | aag | atc | cct | gac | aag | cag | tta | gat | 1776 |
| Ser | Glu | Ala | Glu | Ala | Pro | Pro | Pro | Lys | Ile | Pro | Asp | Lys | Gln | Leu | Asp |
|  |  |  | 580 |  |  |  |  | 585 |  |  |  |  | 590 |  |  |
| gaa | agg | gaa | cac | aca | ata | gaa | gag | tgg | aaa | gaa | ttg | ata | tat | aag | gaa | 1824 |
| Glu | Arg | Glu | His | Thr | Ile | Glu | Glu | Trp | Lys | Glu | Leu | Ile | Tyr | Lys | Glu |
|  |  | 595 |  |  |  |  | 600 |  |  |  |  | 605 |  |  |  |
| gtt | atg | gac | ttg | gag | gag | aga | acc | aag | aat | gga | gtt | ata | cgg | ggg | cag | 1872 |
| Val | Met | Asp | Leu | Glu | Glu | Arg | Thr | Lys | Asn | Gly | Val | Ile | Arg | Gly | Gln |
|  | 610 |  |  |  |  | 615 |  |  |  |  | 620 |  |  |  |  |
| ccc | tct | cct | tta | gca | cag | gtg | cag | cag | tga |  |  |  |  |  |  | 1902 |
| Pro | Ser | Pro | Leu | Ala | Gln | Val | Gln | Gln |  |  |  |  |  |  |  |
| 625 |  |  |  | 630 |  |  |  |  |  |  |  |  |  |  |  |

<210> SEQ ID NO 45
<211> LENGTH: 633
<212> TYPE: PRT
<213> ORGANISM: Artificial Sequence
<220> FEATURE:
<223> OTHER INFORMATION: EGFP-Jnk1 fusion

<400> SEQUENCE: 45

-continued

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys Ser
225                 230                 235                 240

Gly Leu Arg Ser Arg Ala Arg Ala Ile Met Ser Arg Ser Lys Arg Asp
                245                 250                 255

Asn Asn Phe Tyr Ser Val Glu Ile Gly Asp Ser Thr Phe Thr Val Leu
            260                 265                 270

Lys Arg Tyr Gln Asn Leu Lys Pro Ile Gly Ser Gly Ala Gln Gly Ile
        275                 280                 285

Val Cys Ala Ala Tyr Asp Ala Ile Leu Glu Arg Asn Val Ala Ile Lys
    290                 295                 300

Lys Leu Ser Arg Pro Phe Gln Asn Gln Thr His Ala Lys Arg Ala Tyr
305                 310                 315                 320

Arg Glu Leu Val Leu Met Lys Cys Val Asn His Lys Asn Ile Ile Gly
                325                 330                 335

Leu Leu Asn Val Phe Thr Pro Gln Lys Ser Leu Glu Glu Phe Gln Asp
            340                 345                 350

Val Tyr Ile Val Met Glu Leu Met Asp Ala Asn Leu Cys Gln Val Ile
        355                 360                 365

Gln Met Glu Leu Asp His Glu Arg Met Ser Tyr Leu Leu Tyr Gln Met
    370                 375                 380

Leu Cys Gly Ile Lys His Leu His Ser Ala Gly Ile Ile His Arg Asp
385                 390                 395                 400

Leu Lys Pro Ser Asn Ile Val Val Lys Ser Asp Cys Thr Leu Lys Ile
                405                 410                 415
```

```
Leu Asp Phe Gly Leu Ala Arg Thr Ala Gly Thr Ser Phe Met Met Thr
            420                 425                 430

Pro Tyr Val Val Thr Arg Tyr Tyr Arg Ala Pro Glu Val Ile Leu Gly
        435                 440                 445

Met Gly Tyr Lys Glu Asn Val Asp Leu Trp Ser Val Gly Cys Ile Met
        450                 455                 460

Gly Glu Met Val Cys His Lys Ile Leu Phe Pro Gly Arg Asp Tyr Ile
465                 470                 475                 480

Asp Gln Trp Asn Lys Val Ile Glu Gln Leu Gly Thr Pro Cys Pro Glu
                485                 490                 495

Phe Met Lys Lys Leu Gln Pro Thr Val Arg Thr Tyr Val Glu Asn Arg
                500                 505                 510

Pro Lys Tyr Ala Gly Tyr Ser Phe Glu Lys Leu Phe Pro Asp Val Leu
            515                 520                 525

Phe Pro Ala Asp Ser Glu His Asn Lys Leu Lys Ala Ser Gln Ala Arg
        530                 535                 540

Asp Leu Leu Ser Lys Met Leu Val Ile Asp Ala Ser Lys Arg Ile Ser
545                 550                 555                 560

Val Asp Glu Ala Leu Gln His Pro Tyr Ile Asn Val Trp Tyr Asp Pro
                565                 570                 575

Ser Glu Ala Glu Ala Pro Pro Pro Lys Ile Pro Asp Lys Gln Leu Asp
            580                 585                 590

Glu Arg Glu His Thr Ile Glu Glu Trp Lys Glu Leu Ile Tyr Lys Glu
        595                 600                 605

Val Met Asp Leu Glu Glu Arg Thr Lys Asn Gly Val Ile Arg Gly Gln
    610                 615                 620

Pro Ser Pro Leu Ala Gln Val Gln Gln
625                 630

<210> SEQ ID NO 46
<211> LENGTH: 1824
<212> TYPE: DNA
<213> ORGANISM: Artificial Sequence
<220> FEATURE:
<223> OTHER INFORMATION: EGFP-p38 fusion
<220> FEATURE:
<221> NAME/KEY: CDS
<222> LOCATION: (1)..(1821)

<400> SEQUENCE: 46 atg gtg agc aag ggc gag gag ctg ttc acc ggg gtg gtg ccc atc ctg    48
Met Val Ser Lys Gly Glu Glu Leu Phe Thr Gly Val Val Pro Ile Leu
1               5                   10                  15 gtc gag ctg gac ggc gac gta aac ggc cac aag ttc agc gtg tcc ggc    96
Val Glu Leu Asp Gly Asp Val Asn Gly His Lys Phe Ser Val Ser Gly
                20                  25                  30 gag ggc gag ggc gat gcc acc tac ggc aag ctg acc ctg aag ttc atc    144
Glu Gly Glu Gly Asp Ala Thr Tyr Gly Lys Leu Thr Leu Lys Phe Ile
            35                  40                  45 tgc acc acc ggc aag ctg ccc gtg ccc tgg ccc acc ctc gtg acc acc    192
Cys Thr Thr Gly Lys Leu Pro Val Pro Trp Pro Thr Leu Val Thr Thr
        50                  55                  60 ctg acc tac ggc gtg cag tgc ttc agc cgc tac ccc gac cac atg aag    240
Leu Thr Tyr Gly Val Gln Cys Phe Ser Arg Tyr Pro Asp His Met Lys
65                  70                  75                  80 cag cac gac ttc ttc aag tcc gcc atg ccc gaa ggc tac gtc cag gag    288
Gln His Asp Phe Phe Lys Ser Ala Met Pro Glu Gly Tyr Val Gln Glu
                85                  90                  95
```

| | |
|---|---|
| cgc acc atc ttc ttc aag gac gac ggc aac tac aag acc cgc gcc gag<br>Arg Thr Ile Phe Phe Lys Asp Asp Gly Asn Tyr Lys Thr Arg Ala Glu<br>100 105 110 | 336 |
| gtg aag ttc gag ggc gac acc ctg gtg aac cgc atc gag ctg aag ggc<br>Val Lys Phe Glu Gly Asp Thr Leu Val Asn Arg Ile Glu Leu Lys Gly<br>115 120 125 | 384 |
| atc gac ttc aag gag gac ggc aac atc ctg ggg cac aag ctg gag tac<br>Ile Asp Phe Lys Glu Asp Gly Asn Ile Leu Gly His Lys Leu Glu Tyr<br>130 135 140 | 432 |
| aac tac aac agc cac aac gtc tat atc atg gcc gac aag cag aag aac<br>Asn Tyr Asn Ser His Asn Val Tyr Ile Met Ala Asp Lys Gln Lys Asn<br>145 150 155 160 | 480 |
| ggc atc aag gtg aac ttc aag atc cgc cac aac atc gag gac ggc agc<br>Gly Ile Lys Val Asn Phe Lys Ile Arg His Asn Ile Glu Asp Gly Ser<br>165 170 175 | 528 |
| gtg cag ctc gcc gac cac tac cag cag aac acc ccc atc ggc gac ggc<br>Val Gln Leu Ala Asp His Tyr Gln Gln Asn Thr Pro Ile Gly Asp Gly<br>180 185 190 | 576 |
| ccc gtg ctg ctg ccc gac aac cac tac ctg agc acc cag tcc gcc ctg<br>Pro Val Leu Leu Pro Asp Asn His Tyr Leu Ser Thr Gln Ser Ala Leu<br>195 200 205 | 624 |
| agc aaa gac ccc aac gag aag cgc gat cac atg gtc ctg ctg gag ttc<br>Ser Lys Asp Pro Asn Glu Lys Arg Asp His Met Val Leu Leu Glu Phe<br>210 215 220 | 672 |
| gtg acc gcc gcc ggg atc act ctc ggc atg gac gag ctg tac aag tcc<br>Val Thr Ala Ala Gly Ile Thr Leu Gly Met Asp Glu Leu Tyr Lys Ser<br>225 230 235 240 | 720 |
| gga ctc aga tct cga ggg aaa atg tct cag gag agg ccc acg ttc tac<br>Gly Leu Arg Ser Arg Gly Lys Met Ser Gln Glu Arg Pro Thr Phe Tyr<br>245 250 255 | 768 |
| cgg cag gag ctg aac aag aca atc tgg gag gtg ccc gag cgt tac cag<br>Arg Gln Glu Leu Asn Lys Thr Ile Trp Glu Val Pro Glu Arg Tyr Gln<br>260 265 270 | 816 |
| aac ctg tct cca gtg ggc tct ggc gcc tat ggc tct gtg tgt gct gct<br>Asn Leu Ser Pro Val Gly Ser Gly Ala Tyr Gly Ser Val Cys Ala Ala<br>275 280 285 | 864 |
| ttt gac aca aaa acg ggg tta cgt gtg gca gtg aag aag ctc tcc aga<br>Phe Asp Thr Lys Thr Gly Leu Arg Val Ala Val Lys Lys Leu Ser Arg<br>290 295 300 | 912 |
| cca ttt cag tcc atc att cat gcg aaa aga acc tac aga gaa ctg cgg<br>Pro Phe Gln Ser Ile Ile His Ala Lys Arg Thr Tyr Arg Glu Leu Arg<br>305 310 315 320 | 960 |
| tta ctt aaa cat atg aaa cat gaa aat gtg att ggt ctg ttg gac gtt<br>Leu Leu Lys His Met Lys His Glu Asn Val Ile Gly Leu Leu Asp Val<br>325 330 335 | 1008 |
| ttt aca cct gca agg tct ctg gag gaa ttc aat gat gtg tat ctg gtg<br>Phe Thr Pro Ala Arg Ser Leu Glu Glu Phe Asn Asp Val Tyr Leu Val<br>340 345 350 | 1056 |
| acc cat ctc atg ggg gca gat ctg aac aac att gtg aaa tgt cag aag<br>Thr His Leu Met Gly Ala Asp Leu Asn Asn Ile Val Lys Cys Gln Lys<br>355 360 365 | 1104 |
| ctt aca gat gac cat gtt cag ttc ctt atc tac caa att ctc cga ggt<br>Leu Thr Asp Asp His Val Gln Phe Leu Ile Tyr Gln Ile Leu Arg Gly<br>370 375 380 | 1152 |
| cta aag tat ata cat tca gct gac ata att cac agg gac cta aaa cct<br>Leu Lys Tyr Ile His Ser Ala Asp Ile Ile His Arg Asp Leu Lys Pro<br>385 390 395 400 | 1200 |
| agt aat cta gct gtg aat gaa gac tgt gag ctg aag att ctg gat ttt<br>Ser Asn Leu Ala Val Asn Glu Asp Cys Glu Leu Lys Ile Leu Asp Phe<br>405 410 415 | 1248 |

-continued

```
gga ctg gct cgg cac aca gat gat gaa atg aca ggc tac gtg gcc act    1296
Gly Leu Ala Arg His Thr Asp Asp Glu Met Thr Gly Tyr Val Ala Thr
            420                 425                 430 agg tgg tac agg gct cct gag atc atg ctg aac tgg atg cat tac aac    1344
Arg Trp Tyr Arg Ala Pro Glu Ile Met Leu Asn Trp Met His Tyr Asn
        435                 440                 445 cag aca gtt gat att tgg tca gtg gga tgc ata atg gcc gag ctg ttg    1392
Gln Thr Val Asp Ile Trp Ser Val Gly Cys Ile Met Ala Glu Leu Leu
    450                 455                 460 act gga aga aca ttg ttt cct ggt aca gac cat att gat cag ttg aag    1440
Thr Gly Arg Thr Leu Phe Pro Gly Thr Asp His Ile Asp Gln Leu Lys
465                 470                 475                 480 ctc att tta aga ctc gtt gga acc cca ggg gct gag ctt ttg aag aaa    1488
Leu Ile Leu Arg Leu Val Gly Thr Pro Gly Ala Glu Leu Leu Lys Lys
                485                 490                 495 atc tcc tca gag tct gca aga aac tat att cag tct ttg act cag atg    1536
Ile Ser Ser Glu Ser Ala Arg Asn Tyr Ile Gln Ser Leu Thr Gln Met
            500                 505                 510 ccg aag atg aac ttt gcg aat gta ttt att ggt gcc aat ccc ctg gct    1584
Pro Lys Met Asn Phe Ala Asn Val Phe Ile Gly Ala Asn Pro Leu Ala
        515                 520                 525 gtc gac ttg ctg gag aag atg ctt gta ttg gac tca gat aag aga att    1632
Val Asp Leu Leu Glu Lys Met Leu Val Leu Asp Ser Asp Lys Arg Ile
    530                 535                 540 aca gcg gcc caa gcc ctt gca cat gcc tac ttt gct cag tac cac gat    1680
Thr Ala Ala Gln Ala Leu Ala His Ala Tyr Phe Ala Gln Tyr His Asp
545                 550                 555                 560 cct gat gat gaa cca gtg gcc gat cct tat gat cag tcc ttt gaa agc    1728
Pro Asp Asp Glu Pro Val Ala Asp Pro Tyr Asp Gln Ser Phe Glu Ser
                565                 570                 575 agg gac ctc ctt ata gat gag tgg aaa agc ctg acc tat gat gaa gtc    1776
Arg Asp Leu Leu Ile Asp Glu Trp Lys Ser Leu Thr Tyr Asp Glu Val
            580                 585                 590 atc agc ttt gtg cca cca ccc ctt gac caa gaa gag atg gag tcc tga    1824
Ile Ser Phe Val Pro Pro Pro Leu Asp Gln Glu Glu Met Glu Ser
        595                 600                 605
```

<210> SEQ ID NO 47
<211> LENGTH: 607
<212> TYPE: PRT
<213> ORGANISM: Artificial Sequence
<220> FEATURE:
<223> OTHER INFORMATION: EGFP-p38 fusion

<400> SEQUENCE: 47

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110
```

```
Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
        130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys Ser
225                 230                 235                 240

Gly Leu Arg Ser Arg Gly Lys Met Ser Gln Glu Arg Pro Thr Phe Tyr
                245                 250                 255

Arg Gln Glu Leu Asn Lys Thr Ile Trp Glu Val Pro Glu Arg Tyr Gln
            260                 265                 270

Asn Leu Ser Pro Val Gly Ser Gly Ala Tyr Gly Ser Val Cys Ala Ala
        275                 280                 285

Phe Asp Thr Lys Thr Gly Leu Arg Val Ala Val Lys Lys Leu Ser Arg
        290                 295                 300

Pro Phe Gln Ser Ile Ile His Ala Lys Arg Thr Tyr Arg Glu Leu Arg
305                 310                 315                 320

Leu Leu Lys His Met Lys His Glu Asn Val Ile Gly Leu Leu Asp Val
                325                 330                 335

Phe Thr Pro Ala Arg Ser Leu Glu Glu Phe Asn Asp Val Tyr Leu Val
            340                 345                 350

Thr His Leu Met Gly Ala Asp Leu Asn Asn Ile Val Lys Cys Gln Lys
        355                 360                 365

Leu Thr Asp Asp His Val Gln Phe Leu Ile Tyr Gln Ile Leu Arg Gly
370                 375                 380

Leu Lys Tyr Ile His Ser Ala Asp Ile Ile His Arg Asp Leu Lys Pro
385                 390                 395                 400

Ser Asn Leu Ala Val Asn Glu Asp Cys Glu Leu Lys Ile Leu Asp Phe
                405                 410                 415

Gly Leu Ala Arg His Thr Asp Asp Glu Met Thr Gly Tyr Val Ala Thr
            420                 425                 430

Arg Trp Tyr Arg Ala Pro Glu Ile Met Leu Asn Trp Met His Tyr Asn
        435                 440                 445

Gln Thr Val Asp Ile Trp Ser Val Gly Cys Ile Met Ala Glu Leu Leu
        450                 455                 460

Thr Gly Arg Thr Leu Phe Pro Gly Thr Asp His Ile Asp Gln Leu Lys
465                 470                 475                 480

Leu Ile Leu Arg Leu Val Gly Thr Pro Gly Ala Glu Leu Leu Lys Lys
                485                 490                 495

Ile Ser Ser Glu Ser Ala Arg Asn Tyr Ile Gln Ser Leu Thr Gln Met
            500                 505                 510

Pro Lys Met Asn Phe Ala Asn Val Phe Ile Gly Ala Asn Pro Leu Ala
        515                 520                 525
```

```
Val Asp Leu Leu Glu Lys Met Leu Val Leu Asp Ser Asp Lys Arg Ile
    530                 535                 540

Thr Ala Gln Ala Leu Ala His Ala Tyr Phe Ala Gln Tyr His Asp
545                 550                 555                 560

Pro Asp Asp Glu Pro Val Ala Asp Pro Tyr Asp Gln Ser Phe Glu Ser
                565                 570                 575

Arg Asp Leu Leu Ile Asp Glu Trp Lys Ser Leu Thr Tyr Asp Glu Val
            580                 585                 590

Ile Ser Phe Val Pro Pro Leu Asp Gln Glu Glu Met Glu Ser
            595                 600                 605

<210> SEQ ID NO 48
<211> LENGTH: 2907
<212> TYPE: DNA
<213> ORGANISM: Artificial Sequence
<220> FEATURE:
<223> OTHER INFORMATION: EGFP-p85alpha fusion
<220> FEATURE:
<221> NAME/KEY: CDS
<222> LOCATION: (1)..(2904)

<400> SEQUENCE: 48
```

| | |
|---|---:|
| atg gtg agc aag ggc gag gag ctg ttc acc ggg gtg gtg ccc atc ctg<br>Met Val Ser Lys Gly Glu Glu Leu Phe Thr Gly Val Val Pro Ile Leu<br>1               5                   10                  15 | 48 |
| gtc gag ctg gac ggc gac gta aac ggc cac aag ttc agc gtg tcc ggc<br>Val Glu Leu Asp Gly Asp Val Asn Gly His Lys Phe Ser Val Ser Gly<br>            20                  25                  30 | 96 |
| gag ggc gag ggc gat gcc acc tac ggc aag ctg acc ctg aag ttc atc<br>Glu Gly Glu Gly Asp Ala Thr Tyr Gly Lys Leu Thr Leu Lys Phe Ile<br>        35                  40                  45 | 144 |
| tgc acc acc ggc aag ctg ccc gtg ccc tgg ccc acc ctc gtg acc acc<br>Cys Thr Thr Gly Lys Leu Pro Val Pro Trp Pro Thr Leu Val Thr Thr<br>50                  55                  60 | 192 |
| ctg acc tac ggc gtg cag tgc ttc agc cgc tac ccc gac cac atg aag<br>Leu Thr Tyr Gly Val Gln Cys Phe Ser Arg Tyr Pro Asp His Met Lys<br>65                  70                  75                  80 | 240 |
| cag cac gac ttc ttc aag tcc gcc atg ccc gaa ggc tac gtc cag gag<br>Gln His Asp Phe Phe Lys Ser Ala Met Pro Glu Gly Tyr Val Gln Glu<br>                85                  90                  95 | 288 |
| cgc acc atc ttc ttc aag gac gac ggc aac tac aag acc cgc gcc gag<br>Arg Thr Ile Phe Phe Lys Asp Asp Gly Asn Tyr Lys Thr Arg Ala Glu<br>            100                 105                 110 | 336 |
| gtg aag ttc gag ggc gac acc ctg gtg aac cgc atc gag ctg aag ggc<br>Val Lys Phe Glu Gly Asp Thr Leu Val Asn Arg Ile Glu Leu Lys Gly<br>        115                 120                 125 | 384 |
| atc gac ttc aag gag gac ggc aac atc ctg ggg cac aag ctg gag tac<br>Ile Asp Phe Lys Glu Asp Gly Asn Ile Leu Gly His Lys Leu Glu Tyr<br>    130                 135                 140 | 432 |
| aac tac aac agc cac aac gtc tat atc atg gcc gac aag cag aag aac<br>Asn Tyr Asn Ser His Asn Val Tyr Ile Met Ala Asp Lys Gln Lys Asn<br>145                 150                 155                 160 | 480 |
| ggc atc aag gtg aac ttc aag atc cgc cac aac atc gag gac ggc agc<br>Gly Ile Lys Val Asn Phe Lys Ile Arg His Asn Ile Glu Asp Gly Ser<br>                165                 170                 175 | 528 |
| gtg cag ctc gcc gac cac tac cag cag aac acc ccc atc ggc gac ggc<br>Val Gln Leu Ala Asp His Tyr Gln Gln Asn Thr Pro Ile Gly Asp Gly<br>            180                 185                 190 | 576 |
| ccc gtg ctg ctg ccc gac aac cac tac ctg agc acc cag tcc gcc ctg<br>Pro Val Leu Leu Pro Asp Asn His Tyr Leu Ser Thr Gln Ser Ala Leu<br>        195                 200                 205 | 624 |

```
agc aaa gac ccc aac gag aag cgc gat cac atg gtc ctg ctg gag ttc        672
Ser Lys Asp Pro Asn Glu Lys Arg Asp His Met Val Leu Leu Glu Phe
    210             215                 220 gtg acc gcc gcc ggg atc act ctc ggc atg gac gag ctg tac aag tcc        720
Val Thr Ala Ala Gly Ile Thr Leu Gly Met Asp Glu Leu Tyr Lys Ser
225             230                 235                 240 gga ctc aga tct atg agt gct gag ggg tac cag tac aga gcg ctg tat        768
Gly Leu Arg Ser Met Ser Ala Glu Gly Tyr Gln Tyr Arg Ala Leu Tyr
                245                 250                 255 gat tat aaa aag gaa aga gaa gaa gat att gac ttg cac ttg ggt gac        816
Asp Tyr Lys Lys Glu Arg Glu Glu Asp Ile Asp Leu His Leu Gly Asp
            260                 265                 270 ata ttg act gtg aat aaa ggg tcc tta gta gct ctt gga ttc agt gat        864
Ile Leu Thr Val Asn Lys Gly Ser Leu Val Ala Leu Gly Phe Ser Asp
        275                 280                 285 gga cag gaa gcc agg cct gaa gaa att ggc tgg tta aat ggc tat aat        912
Gly Gln Glu Ala Arg Pro Glu Glu Ile Gly Trp Leu Asn Gly Tyr Asn
    290                 295                 300 gaa acc aca ggg gaa agg ggg gac ttt ccg gga act tac gta gaa tat        960
Glu Thr Thr Gly Glu Arg Gly Asp Phe Pro Gly Thr Tyr Val Glu Tyr
305             310                 315                 320 att gga agg aaa aaa atc tcg cct ccc aca cca aag ccc cgg cca cct       1008
Ile Gly Arg Lys Lys Ile Ser Pro Pro Thr Pro Lys Pro Arg Pro Pro
                325                 330                 335 cgg cct ctt cct gtt gca cca ggt tct tcg aaa act gaa gca gat gtt       1056
Arg Pro Leu Pro Val Ala Pro Gly Ser Ser Lys Thr Glu Ala Asp Val
            340                 345                 350 gaa caa caa gct ttg act ctc ccg gat ctt gca gag cag ttt gcc cct       1104
Glu Gln Gln Ala Leu Thr Leu Pro Asp Leu Ala Glu Gln Phe Ala Pro
        355                 360                 365 cct gac att gcc ccg cct ctt ctt atc aag ctc gtg gaa gcc att gaa       1152
Pro Asp Ile Ala Pro Pro Leu Leu Ile Lys Leu Val Glu Ala Ile Glu
    370                 375                 380 aag aaa ggt ctg gaa tgt tca act cta tac aga aca cag agc tcc agc       1200
Lys Lys Gly Leu Glu Cys Ser Thr Leu Tyr Arg Thr Gln Ser Ser Ser
385             390                 395                 400 aac ctg gca gaa tta cga cag ctt ctt gat tgt gat aca ccc tcc gtg       1248
Asn Leu Ala Glu Leu Arg Gln Leu Leu Asp Cys Asp Thr Pro Ser Val
                405                 410                 415 gac ttg gaa atg atc gat gtg cac gtt ttg gct gac gct ttc aaa cgc       1296
Asp Leu Glu Met Ile Asp Val His Val Leu Ala Asp Ala Phe Lys Arg
            420                 425                 430 tat ctc ctg gac tta cca aat cct gtc att cca gca gcc gtt tac agt       1344
Tyr Leu Leu Asp Leu Pro Asn Pro Val Ile Pro Ala Ala Val Tyr Ser
        435                 440                 445 gaa atg att tct tta gct cca gaa gta caa agc tcc gaa gaa tat att       1392
Glu Met Ile Ser Leu Ala Pro Glu Val Gln Ser Ser Glu Glu Tyr Ile
    450                 455                 460 cag cta ttg aag aag ctt att agg tcg cct agc ata cct cat cag tat       1440
Gln Leu Leu Lys Lys Leu Ile Arg Ser Pro Ser Ile Pro His Gln Tyr
465             470                 475                 480 tgg ctt acg ctt cag tat ttg tta aaa cat ttc ttc aag ctc tct caa       1488
Trp Leu Thr Leu Gln Tyr Leu Leu Lys His Phe Phe Lys Leu Ser Gln
                485                 490                 495 acc tcc agc aaa aat ctg ttg aat gca aga gta ctc tct gaa att ttc       1536
Thr Ser Ser Lys Asn Leu Leu Asn Ala Arg Val Leu Ser Glu Ile Phe
            500                 505                 510 agc cct atg ctt ttc aga ttc tca gca gcc agc tct gat aat act gaa       1584
Ser Pro Met Leu Phe Arg Phe Ser Ala Ala Ser Ser Asp Asn Thr Glu
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     | 515 |     |     |     |     | 520 |     |     |     |     | 525 |     |     |     |      |
| aac | ctc | ata | aaa | gtt | ata | gaa | att | tta | atc | tca | act | gaa | tgg | aat | gaa | 1632 |
| Asn | Leu | Ile | Lys | Val | Ile | Glu | Ile | Leu | Ile | Ser | Thr | Glu | Trp | Asn | Glu |      |
|     |     | 530 |     |     |     |     | 535 |     |     |     |     | 540 |     |     |     |      |
| cga | cag | cct | gca | cca | gca | ctg | cct | cct | aaa | cca | cca | aaa | cct | act | act | 1680 |
| Arg | Gln | Pro | Ala | Pro | Ala | Leu | Pro | Pro | Lys | Pro | Pro | Lys | Pro | Thr | Thr |      |
| 545 |     |     |     |     | 550 |     |     |     |     | 555 |     |     |     |     | 560 |      |
| gta | gcc | aac | aac | ggt | atg | aat | aac | aat | atg | tcc | tta | caa | aat | gct | gaa | 1728 |
| Val | Ala | Asn | Asn | Gly | Met | Asn | Asn | Asn | Met | Ser | Leu | Gln | Asn | Ala | Glu |      |
|     |     |     |     | 565 |     |     |     |     | 570 |     |     |     |     | 575 |     |      |
| tgg | tac | tgg | gga | gat | atc | tcg | agg | gaa | gaa | gtg | aat | gaa | aaa | ctt | cga | 1776 |
| Trp | Tyr | Trp | Gly | Asp | Ile | Ser | Arg | Glu | Glu | Val | Asn | Glu | Lys | Leu | Arg |      |
|     |     |     | 580 |     |     |     |     | 585 |     |     |     |     | 590 |     |     |      |
| gat | aca | gca | gac | ggg | acc | ttt | ttg | gta | cga | gat | gcg | tct | act | aaa | atg | 1824 |
| Asp | Thr | Ala | Asp | Gly | Thr | Phe | Leu | Val | Arg | Asp | Ala | Ser | Thr | Lys | Met |      |
|     |     | 595 |     |     |     |     | 600 |     |     |     |     | 605 |     |     |     |      |
| cat | ggt | gat | tat | act | ctt | aca | cta | agg | aaa | ggg | gga | aat | aac | aaa | tta | 1872 |
| His | Gly | Asp | Tyr | Thr | Leu | Thr | Leu | Arg | Lys | Gly | Gly | Asn | Asn | Lys | Leu |      |
|     | 610 |     |     |     |     | 615 |     |     |     |     | 620 |     |     |     |     |      |
| atc | aaa | ata | ttt | cat | cga | gat | ggg | aaa | tat | ggc | ttc | tct | gac | cca | tta | 1920 |
| Ile | Lys | Ile | Phe | His | Arg | Asp | Gly | Lys | Tyr | Gly | Phe | Ser | Asp | Pro | Leu |      |
| 625 |     |     |     |     | 630 |     |     |     |     | 635 |     |     |     |     | 640 |      |
| acc | ttc | agt | tct | gtg | gtt | gaa | tta | ata | aac | cac | tac | cgg | aat | gaa | tct | 1968 |
| Thr | Phe | Ser | Ser | Val | Val | Glu | Leu | Ile | Asn | His | Tyr | Arg | Asn | Glu | Ser |      |
|     |     |     |     |     | 645 |     |     |     |     | 650 |     |     |     |     | 655 |      |
| cta | gct | cag | tat | aat | ccc | aaa | ttg | gat | gtg | aaa | tta | ctt | tat | cca | gta | 2016 |
| Leu | Ala | Gln | Tyr | Asn | Pro | Lys | Leu | Asp | Val | Lys | Leu | Leu | Tyr | Pro | Val |      |
|     |     |     | 660 |     |     |     |     | 665 |     |     |     |     | 670 |     |     |      |
| tcc | aaa | tac | caa | cag | gat | caa | gtt | gtc | aaa | gaa | gat | aat | att | gaa | gct | 2064 |
| Ser | Lys | Tyr | Gln | Gln | Asp | Gln | Val | Val | Lys | Glu | Asp | Asn | Ile | Glu | Ala |      |
|     |     | 675 |     |     |     |     | 680 |     |     |     |     | 685 |     |     |     |      |
| gta | ggg | aaa | aaa | tta | cat | gaa | tat | aac | act | cag | ttt | caa | gaa | aaa | agt | 2112 |
| Val | Gly | Lys | Lys | Leu | His | Glu | Tyr | Asn | Thr | Gln | Phe | Gln | Glu | Lys | Ser |      |
|     | 690 |     |     |     |     | 695 |     |     |     |     | 700 |     |     |     |     |      |
| cga | gaa | tat | gat | aga | tta | tat | gaa | gaa | tat | acc | cgc | aca | tcc | cag | gaa | 2160 |
| Arg | Glu | Tyr | Asp | Arg | Leu | Tyr | Glu | Glu | Tyr | Thr | Arg | Thr | Ser | Gln | Glu |      |
| 705 |     |     |     |     | 710 |     |     |     |     | 715 |     |     |     |     | 720 |      |
| atc | caa | atg | aaa | agg | aca | gct | att | gaa | gca | ttt | aat | gaa | acc | ata | aaa | 2208 |
| Ile | Gln | Met | Lys | Arg | Thr | Ala | Ile | Glu | Ala | Phe | Asn | Glu | Thr | Ile | Lys |      |
|     |     |     |     | 725 |     |     |     |     | 730 |     |     |     |     | 735 |     |      |
| ata | ttt | gaa | gaa | cag | tgc | cag | acc | caa | gag | cgg | tac | agc | aaa | gaa | tac | 2256 |
| Ile | Phe | Glu | Glu | Gln | Cys | Gln | Thr | Gln | Glu | Arg | Tyr | Ser | Lys | Glu | Tyr |      |
|     |     |     | 740 |     |     |     |     | 745 |     |     |     |     | 750 |     |     |      |
| ata | gaa | aag | ttt | aaa | cgt | gaa | ggc | aat | gag | aaa | gaa | ata | caa | agg | att | 2304 |
| Ile | Glu | Lys | Phe | Lys | Arg | Glu | Gly | Asn | Glu | Lys | Glu | Ile | Gln | Arg | Ile |      |
|     |     | 755 |     |     |     |     | 760 |     |     |     |     | 765 |     |     |     |      |
| atg | cat | aat | tat | gat | aag | ttg | aag | tct | cga | atc | agt | gaa | att | att | gac | 2352 |
| Met | His | Asn | Tyr | Asp | Lys | Leu | Lys | Ser | Arg | Ile | Ser | Glu | Ile | Ile | Asp |      |
|     | 770 |     |     |     |     | 775 |     |     |     |     | 780 |     |     |     |     |      |
| agt | aga | aga | aga | ttg | gaa | gaa | gac | ttg | aag | aag | cag | gca | gct | gag | tat | 2400 |
| Ser | Arg | Arg | Arg | Leu | Glu | Glu | Asp | Leu | Lys | Lys | Gln | Ala | Ala | Glu | Tyr |      |
| 785 |     |     |     |     | 790 |     |     |     |     | 795 |     |     |     |     | 800 |      |
| cga | gaa | att | gac | aaa | cgt | atg | aac | agc | att | aaa | cca | gac | ctt | atc | cag | 2448 |
| Arg | Glu | Ile | Asp | Lys | Arg | Met | Asn | Ser | Ile | Lys | Pro | Asp | Leu | Ile | Gln |      |
|     |     |     |     | 805 |     |     |     |     | 810 |     |     |     |     | 815 |     |      |
| ctg | aga | aag | acg | aga | gac | caa | tac | ttg | atg | tgg | tta | act | caa | aaa | ggt | 2496 |
| Leu | Arg | Lys | Thr | Arg | Asp | Gln | Tyr | Leu | Met | Trp | Leu | Thr | Gln | Lys | Gly |      |
|     |     |     | 820 |     |     |     |     | 825 |     |     |     |     | 830 |     |     |      |
| gtt | cgg | caa | aag | aag | ttg | aac | gag | tgg | ttg | ggc | aat | gaa | aac | act | gaa | 2544 |

-continued

```
Val Arg Gln Lys Lys Leu Asn Glu Trp Leu Gly Asn Glu Asn Thr Glu
            835                 840                 845 gac caa tat tca ctg gtg gaa gat gat gaa gat ttg ccc cat cat gat    2592
Asp Gln Tyr Ser Leu Val Glu Asp Asp Glu Asp Leu Pro His His Asp
850                 855                 860 gag aag aca tgg aat gtt gga agc agc aac cga aac aaa gct gaa aac    2640
Glu Lys Thr Trp Asn Val Gly Ser Ser Asn Arg Asn Lys Ala Glu Asn
865                 870                 875                 880 ctg ttg cga ggg aag cga gat ggc act ttt ctt gtc cgg gag agc agt    2688
Leu Leu Arg Gly Lys Arg Asp Gly Thr Phe Leu Val Arg Glu Ser Ser
                885                 890                 895 aaa cag ggc tgc tat gcc tgc tct gta gtg gtg gac ggc gaa gta aag    2736
Lys Gln Gly Cys Tyr Ala Cys Ser Val Val Val Asp Gly Glu Val Lys
            900                 905                 910 cat tgt gtc ata aac aaa aca gca act ggc tat ggc ttt gcc gag ccc    2784
His Cys Val Ile Asn Lys Thr Ala Thr Gly Tyr Gly Phe Ala Glu Pro
        915                 920                 925 tat aac ttg tac agc tct ctg aaa gaa ctg gtg cta cat tac caa cac    2832
Tyr Asn Leu Tyr Ser Ser Leu Lys Glu Leu Val Leu His Tyr Gln His
930                 935                 940 acc tcc ctt gtg cag cac aac gac tcc ctc aat gtc aca cta gcc tac    2880
Thr Ser Leu Val Gln His Asn Asp Ser Leu Asn Val Thr Leu Ala Tyr
945                 950                 955                 960 cca gta tat gca cag cag agg cga tga                                 2907
Pro Val Tyr Ala Gln Gln Arg Arg
                965

<210> SEQ ID NO 49
<211> LENGTH: 968
<212> TYPE: PRT
<213> ORGANISM: Artificial Sequence
<220> FEATURE:
<223> OTHER INFORMATION: EGFP-p85alpha fusion

<400> SEQUENCE: 49

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
```

-continued

```
            180                 185                 190
Pro Val Leu Leu Pro Asp Asn His Tyr Leu Ser Thr Gln Ser Ala Leu
            195                 200                 205
Ser Lys Asp Pro Asn Glu Lys Arg Asp His Met Val Leu Leu Glu Phe
210                 215                 220
Val Thr Ala Ala Gly Ile Thr Leu Gly Met Asp Glu Leu Tyr Lys Ser
225                 230                 235                 240
Gly Leu Arg Ser Met Ser Ala Glu Gly Tyr Gln Tyr Arg Ala Leu Tyr
                245                 250                 255
Asp Tyr Lys Lys Glu Arg Glu Asp Ile Asp Leu His Leu Gly Asp
            260                 265                 270
Ile Leu Thr Val Asn Lys Gly Ser Leu Val Ala Leu Gly Phe Ser Asp
            275                 280                 285
Gly Gln Glu Ala Arg Pro Glu Glu Ile Gly Trp Leu Asn Gly Tyr Asn
            290                 295                 300
Glu Thr Thr Gly Glu Arg Gly Asp Phe Pro Gly Thr Tyr Val Glu Tyr
305                 310                 315                 320
Ile Gly Arg Lys Lys Ile Ser Pro Pro Thr Pro Lys Pro Arg Pro Pro
                325                 330                 335
Arg Pro Leu Pro Val Ala Pro Gly Ser Ser Lys Thr Glu Ala Asp Val
            340                 345                 350
Glu Gln Gln Ala Leu Thr Leu Pro Asp Leu Ala Glu Gln Phe Ala Pro
            355                 360                 365
Pro Asp Ile Ala Pro Pro Leu Leu Ile Lys Leu Val Glu Ala Ile Glu
            370                 375                 380
Lys Lys Gly Leu Glu Cys Ser Thr Leu Tyr Arg Thr Gln Ser Ser Ser
385                 390                 395                 400
Asn Leu Ala Glu Leu Arg Gln Leu Leu Asp Cys Asp Thr Pro Ser Val
                405                 410                 415
Asp Leu Glu Met Ile Asp Val His Val Leu Ala Asp Ala Phe Lys Arg
            420                 425                 430
Tyr Leu Leu Asp Leu Pro Asn Pro Val Ile Pro Ala Ala Val Tyr Ser
            435                 440                 445
Glu Met Ile Ser Leu Ala Pro Glu Val Gln Ser Ser Glu Glu Tyr Ile
            450                 455                 460
Gln Leu Leu Lys Lys Leu Ile Arg Ser Pro Ser Ile Pro His Gln Tyr
465                 470                 475                 480
Trp Leu Thr Leu Gln Tyr Leu Leu Lys His Phe Phe Lys Leu Ser Gln
                485                 490                 495
Thr Ser Ser Lys Asn Leu Leu Asn Ala Arg Val Leu Ser Glu Ile Phe
            500                 505                 510
Ser Pro Met Leu Phe Arg Phe Ser Ala Ala Ser Ser Asp Asn Thr Glu
            515                 520                 525
Asn Leu Ile Lys Val Ile Glu Ile Leu Ile Ser Thr Glu Trp Asn Glu
            530                 535                 540
Arg Gln Pro Ala Pro Ala Leu Pro Pro Lys Pro Lys Pro Thr Thr
545                 550                 555                 560
Val Ala Asn Asn Gly Met Asn Asn Asn Met Ser Leu Gln Asn Ala Glu
                565                 570                 575
Trp Tyr Trp Gly Asp Ile Ser Arg Glu Glu Val Asn Glu Lys Leu Arg
            580                 585                 590
Asp Thr Ala Asp Gly Thr Phe Leu Val Arg Asp Ala Ser Thr Lys Met
            595                 600                 605
```

His Gly Asp Tyr Thr Leu Thr Leu Arg Lys Gly Asn Asn Lys Leu
610                 615                 620

Ile Lys Ile Phe His Arg Asp Gly Lys Tyr Gly Phe Ser Asp Pro Leu
625                 630                 635                 640

Thr Phe Ser Ser Val Val Glu Leu Ile Asn His Tyr Arg Asn Glu Ser
                645                 650                 655

Leu Ala Gln Tyr Asn Pro Lys Leu Asp Val Lys Leu Leu Tyr Pro Val
                660                 665                 670

Ser Lys Tyr Gln Gln Asp Gln Val Val Lys Glu Asp Asn Ile Glu Ala
                675                 680                 685

Val Gly Lys Lys Leu His Glu Tyr Asn Thr Gln Phe Gln Glu Lys Ser
690                 695                 700

Arg Glu Tyr Asp Arg Leu Tyr Glu Glu Tyr Thr Arg Thr Ser Gln Glu
705                 710                 715                 720

Ile Gln Met Lys Arg Thr Ala Ile Glu Ala Phe Asn Glu Thr Ile Lys
                725                 730                 735

Ile Phe Glu Glu Gln Cys Gln Thr Gln Glu Arg Tyr Ser Lys Glu Tyr
                740                 745                 750

Ile Glu Lys Phe Lys Arg Glu Gly Asn Glu Lys Glu Ile Gln Arg Ile
                755                 760                 765

Met His Asn Tyr Asp Lys Leu Lys Ser Arg Ile Ser Glu Ile Ile Asp
770                 775                 780

Ser Arg Arg Arg Leu Glu Glu Asp Leu Lys Lys Gln Ala Ala Glu Tyr
785                 790                 795                 800

Arg Glu Ile Asp Lys Arg Met Asn Ser Ile Lys Pro Asp Leu Ile Gln
                805                 810                 815

Leu Arg Lys Thr Arg Asp Gln Tyr Leu Met Trp Leu Thr Gln Lys Gly
                820                 825                 830

Val Arg Gln Lys Lys Leu Asn Glu Trp Leu Gly Asn Glu Asn Thr Glu
                835                 840                 845

Asp Gln Tyr Ser Leu Val Glu Asp Asp Glu Asp Leu Pro His His Asp
850                 855                 860

Glu Lys Thr Trp Asn Val Gly Ser Ser Asn Arg Asn Lys Ala Glu Asn
865                 870                 875                 880

Leu Leu Arg Gly Lys Arg Asp Gly Thr Phe Leu Val Arg Glu Ser Ser
                885                 890                 895

Lys Gln Gly Cys Tyr Ala Cys Ser Val Val Asp Gly Glu Val Lys
                900                 905                 910

His Cys Val Ile Asn Lys Thr Ala Thr Gly Tyr Gly Phe Ala Glu Pro
                915                 920                 925

Tyr Asn Leu Tyr Ser Ser Leu Lys Glu Leu Val Leu His Tyr Gln His
930                 935                 940

Thr Ser Leu Val Gln His Asn Asp Ser Leu Asn Val Thr Leu Ala Tyr
945                 950                 955                 960

Pro Val Tyr Ala Gln Gln Arg Arg
                965

<210> SEQ ID NO 50
<211> LENGTH: 2160
<212> TYPE: DNA
<213> ORGANISM: Artificial Sequence
<220> FEATURE:
<223> OTHER INFORMATION: EGFP-Smad2 fusion
<220> FEATURE:
<221> NAME/KEY: CDS

<222> LOCATION: (1)..(2157)

<400> SEQUENCE: 50

| | | |
|---|---|---|
| atg gtg agc aag ggc gag gag ctg ttc acc ggg gtg gtg ccc atc ctg<br>Met Val Ser Lys Gly Glu Glu Leu Phe Thr Gly Val Val Pro Ile Leu<br>1                 5                  10               15 | 48 |
| gtc gag ctg gac ggc gac gta aac ggc cac aag ttc agc gtg tcc ggc<br>Val Glu Leu Asp Gly Asp Val Asn Gly His Lys Phe Ser Val Ser Gly<br>               20                  25                  30 | 96 |
| gag ggc gag ggc gat gcc acc tac ggc aag ctg acc ctg aag ttc atc<br>Glu Gly Glu Gly Asp Ala Thr Tyr Gly Lys Leu Thr Leu Lys Phe Ile<br>35                     40                  45 | 144 |
| tgc acc acc ggc aag ctg ccc gtg ccc tgg ccc acc ctc gtg acc acc<br>Cys Thr Thr Gly Lys Leu Pro Val Pro Trp Pro Thr Leu Val Thr Thr<br>50                     55                  60 | 192 |
| ctg acc tac ggc gtg cag tgc ttc agc cgc tac ccc gac cac atg aag<br>Leu Thr Tyr Gly Val Gln Cys Phe Ser Arg Tyr Pro Asp His Met Lys<br>65                     70                  75                  80 | 240 |
| cag cac gac ttc ttc aag tcc gcc atg ccc gaa ggc tac gtc cag gag<br>Gln His Asp Phe Phe Lys Ser Ala Met Pro Glu Gly Tyr Val Gln Glu<br>                     85                  90                  95 | 288 |
| cgc acc atc ttc ttc aag gac gac ggc aac tac aag acc cgc gcc gag<br>Arg Thr Ile Phe Phe Lys Asp Asp Gly Asn Tyr Lys Thr Arg Ala Glu<br>                   100                 105              110 | 336 |
| gtg aag ttc gag ggc gac acc ctg gtg aac cgc atc gag ctg aag ggc<br>Val Lys Phe Glu Gly Asp Thr Leu Val Asn Arg Ile Glu Leu Lys Gly<br>               115                 120              125 | 384 |
| atc gac ttc aag gag gac ggc aac atc ctg ggg cac aag ctg gag tac<br>Ile Asp Phe Lys Glu Asp Gly Asn Ile Leu Gly His Lys Leu Glu Tyr<br>130                   135                 140 | 432 |
| aac tac aac agc cac aac gtc tat atc atg gcc gac aag cag aag aac<br>Asn Tyr Asn Ser His Asn Val Tyr Ile Met Ala Asp Lys Gln Lys Asn<br>145                   150                 155                 160 | 480 |
| ggc atc aag gtg aac ttc aag atc cgc cac aac atc gag gac ggc agc<br>Gly Ile Lys Val Asn Phe Lys Ile Arg His Asn Ile Glu Asp Gly Ser<br>                   165                 170              175 | 528 |
| gtg cag ctc gcc gac cac tac cag cag aac acc ccc atc ggc gac ggc<br>Val Gln Leu Ala Asp His Tyr Gln Gln Asn Thr Pro Ile Gly Asp Gly<br>               180                 185              190 | 576 |
| ccc gtg ctg ctg ccc gac aac cac tac ctg agc acc cag tcc gcc ctg<br>Pro Val Leu Leu Pro Asp Asn His Tyr Leu Ser Thr Gln Ser Ala Leu<br>               195                 200              205 | 624 |
| agc aaa gac ccc aac gag aag cgc gat cac atg gtc ctg ctg gag ttc<br>Ser Lys Asp Pro Asn Glu Lys Arg Asp His Met Val Leu Leu Glu Phe<br>210                   215                 220 | 672 |
| gtg acc gcc gcc ggg atc act ctc ggc atg gac gag ctg tac aag tcc<br>Val Thr Ala Ala Gly Ile Thr Leu Gly Met Asp Glu Leu Tyr Lys Ser<br>225                   230                 235                 240 | 720 |
| gga ctc aga tct cga gct caa gct tcg aat tcg acc atg tcg tcc atc<br>Gly Leu Arg Ser Arg Ala Gln Ala Ser Asn Ser Thr Met Ser Ser Ile<br>               245                 250              255 | 768 |
| ttg cca ttc acg ccg cca gtt gtg aag aga ctg ctg gga tgg aag aag<br>Leu Pro Phe Thr Pro Pro Val Val Lys Arg Leu Leu Gly Trp Lys Lys<br>               260                 265              270 | 816 |
| tca gct ggt ggg tct gga gga gca ggc gga gga gag cag aat ggg cag<br>Ser Ala Gly Gly Ser Gly Gly Ala Gly Gly Gly Glu Gln Asn Gly Gln<br>               275                 280              285 | 864 |
| gaa gaa aag tgt tgt gag aaa gca gtg aaa agt ctg gtg aag aag cta<br>Glu Glu Lys Trp Cys Glu Lys Ala Val Lys Ser Leu Val Lys Lys Leu<br>290                   295                 300 | 912 |

-continued

```
aag aaa aca gga cga tta gat gag ctt gag aaa gcc atc acc act caa      960
Lys Lys Thr Gly Arg Leu Asp Glu Leu Glu Lys Ala Ile Thr Thr Gln
305                 310                 315                 320 aac tgt aat act aaa tgt gtt acc ata cca agc act tgc tct gaa att     1008
Asn Cys Asn Thr Lys Cys Val Thr Ile Pro Ser Thr Cys Ser Glu Ile
                325                 330                 335 tgg gga ctg agt aca cca aat acg ata gat cag tgg gat aca aca ggc     1056
Trp Gly Leu Ser Thr Pro Asn Thr Ile Asp Gln Trp Asp Thr Thr Gly
            340                 345                 350 ctt tac agc ttc tct gaa caa acc agg tct ctt gat ggt cgt ctc cag     1104
Leu Tyr Ser Phe Ser Glu Gln Thr Arg Ser Leu Asp Gly Arg Leu Gln
        355                 360                 365 gta tcc cat cga aaa gga ttg cca cat gtt ata tat tgc cga tta tgg     1152
Val Ser His Arg Lys Gly Leu Pro His Val Ile Tyr Cys Arg Leu Trp
    370                 375                 380 cgc tgg cct gat ctt cac agt cat cat gaa ctc aag gca att gaa aac     1200
Arg Trp Pro Asp Leu His Ser His His Glu Leu Lys Ala Ile Glu Asn
385                 390                 395                 400 tgc gaa tat gct ttt aat ctt aaa aag gat gaa gta tgt gta aac cct     1248
Cys Glu Tyr Ala Phe Asn Leu Lys Lys Asp Glu Val Cys Val Asn Pro
                405                 410                 415 tac cac tat cag aga gtt gag aca cca gtt ttg cct cca gta tta gtg     1296
Tyr His Tyr Gln Arg Val Glu Thr Pro Val Leu Pro Pro Val Leu Val
            420                 425                 430 ccc cga cac acc gag atc cta aca gaa ctt ccg cct ctg gat gac tat     1344
Pro Arg His Thr Glu Ile Leu Thr Glu Leu Pro Pro Leu Asp Asp Tyr
        435                 440                 445 act cac tcc att cca gaa aac act aac ttc cca gca gga att gag cca     1392
Thr His Ser Ile Pro Glu Asn Thr Asn Phe Pro Ala Gly Ile Glu Pro
    450                 455                 460 cag agt aat tat att cca gaa acg cca cct cct gga tat atc agt gaa     1440
Gln Ser Asn Tyr Ile Pro Glu Thr Pro Pro Pro Gly Tyr Ile Ser Glu
465                 470                 475                 480 gat gga gaa aca agt gac caa cag ttg aat caa agt atg gac aca ggc     1488
Asp Gly Glu Thr Ser Asp Gln Gln Leu Asn Gln Ser Met Asp Thr Gly
                485                 490                 495 tct cca gca gaa cta tct cct act act ctt tcc cct gtt aat cat agc     1536
Ser Pro Ala Glu Leu Ser Pro Thr Thr Leu Ser Pro Val Asn His Ser
            500                 505                 510 ttg gat tta cag cca gtt act tac tca gaa cct gca ttt tgg tgt tca     1584
Leu Asp Leu Gln Pro Val Thr Tyr Ser Glu Pro Ala Phe Trp Cys Ser
        515                 520                 525 ata gca tat tat gaa tta aat cag agg gtt gga gaa acc ttc cat gca     1632
Ile Ala Tyr Tyr Glu Leu Asn Gln Arg Val Gly Glu Thr Phe His Ala
    530                 535                 540 tca cag ccc tca ctc act gta gat ggc ttt aca gac cca tca aat tca     1680
Ser Gln Pro Ser Leu Thr Val Asp Gly Phe Thr Asp Pro Ser Asn Ser
545                 550                 555                 560 gag agg ttc tgc tta ggt tta ctc tcc aat gtt aac cga aat gcc acg     1728
Glu Arg Phe Cys Leu Gly Leu Leu Ser Asn Val Asn Arg Asn Ala Thr
                565                 570                 575 gta gaa atg aca aga agg cat ata gga aga gga gtg cgc tta tac tac     1776
Val Glu Met Thr Arg Arg His Ile Gly Arg Gly Val Arg Leu Tyr Tyr
            580                 585                 590 ata ggt ggg gaa gtt ttt gct gag tgc cta agt gat agt gca atc ttt     1824
Ile Gly Gly Glu Val Phe Ala Glu Cys Leu Ser Asp Ser Ala Ile Phe
        595                 600                 605 gtg cag agc ccc aat tgt aat cag aga tat ggc tgg cac cct gca aca     1872
Val Gln Ser Pro Asn Cys Asn Gln Arg Tyr Gly Trp His Pro Ala Thr
```

```
      610               615               620
gtg tgt aaa att cca cca ggc tgt aat ctg aag atc ttc aac aac cag   1920
Val Cys Lys Ile Pro Pro Gly Cys Asn Leu Lys Ile Phe Asn Asn Gln
625             630                 635                 640 gaa ttt gct gct ctt ctg gct cag tct gtt aat cag ggt ttt gaa gcc   1968
Glu Phe Ala Ala Leu Leu Ala Gln Ser Val Asn Gln Gly Phe Glu Ala
                645                 650                 655 gtc tat cag cta act aga atg tgc acc ata aga atg agt ttt gtg aaa   2016
Val Tyr Gln Leu Thr Arg Met Cys Thr Ile Arg Met Ser Phe Val Lys
                660                 665                 670 ggg tgg gga gca gaa tac cga agg cag acg gta aca agt act cct tgc   2064
Gly Trp Gly Ala Glu Tyr Arg Arg Gln Thr Val Thr Ser Thr Pro Cys
            675                 680                 685 tgg att gaa ctt cat ctg aat gga cct cta cag tgg ttg gac aaa gta   2112
Trp Ile Glu Leu His Leu Asn Gly Pro Leu Gln Trp Leu Asp Lys Val
            690                 695                 700 tta act cag atg gga tcc cct tca gtg cgt tgc tca agc atg tca taa   2160
Leu Thr Gln Met Gly Ser Pro Ser Val Arg Cys Ser Ser Met Ser
705                 710                 715
```

<210> SEQ ID NO 51
<211> LENGTH: 719
<212> TYPE: PRT
<213> ORGANISM: Artificial Sequence
<220> FEATURE:
<223> OTHER INFORMATION: EGFP-Smad2 fusion

<400> SEQUENCE: 51

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
        50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Ser
```

-continued

```
            225                 230                 235                 240
Gly Leu Arg Ser Arg Ala Gln Ala Ser Asn Ser Thr Met Ser Ser Ile
                245                 250                 255
Leu Pro Phe Thr Pro Pro Val Val Lys Arg Leu Leu Gly Trp Lys Lys
                260                 265                 270
Ser Ala Gly Gly Ser Gly Gly Ala Gly Gly Glu Gln Asn Gly Gln
                275                 280                 285
Glu Glu Lys Trp Cys Glu Lys Ala Val Lys Ser Leu Val Lys Lys Leu
        290                 295                 300
Lys Lys Thr Gly Arg Leu Asp Glu Leu Glu Lys Ala Ile Thr Thr Gln
305                 310                 315                 320
Asn Cys Asn Thr Lys Cys Val Thr Ile Pro Ser Thr Cys Ser Glu Ile
                325                 330                 335
Trp Gly Leu Ser Thr Pro Asn Thr Ile Asp Gln Trp Asp Thr Thr Gly
                340                 345                 350
Leu Tyr Ser Phe Ser Glu Gln Thr Arg Ser Leu Asp Gly Arg Leu Gln
                355                 360                 365
Val Ser His Arg Lys Gly Leu Pro His Val Ile Tyr Cys Arg Leu Trp
        370                 375                 380
Arg Trp Pro Asp Leu His Ser His His Glu Leu Lys Ala Ile Glu Asn
385                 390                 395                 400
Cys Glu Tyr Ala Phe Asn Leu Lys Lys Asp Glu Val Cys Val Asn Pro
                405                 410                 415
Tyr His Tyr Gln Arg Val Glu Thr Pro Val Leu Pro Pro Val Leu Val
                420                 425                 430
Pro Arg His Thr Glu Ile Leu Thr Glu Leu Pro Pro Leu Asp Asp Tyr
        435                 440                 445
Thr His Ser Ile Pro Glu Asn Thr Asn Phe Pro Ala Gly Ile Glu Pro
        450                 455                 460
Gln Ser Asn Tyr Ile Pro Glu Thr Pro Pro Gly Tyr Ile Ser Glu
465                 470                 475                 480
Asp Gly Glu Thr Ser Asp Gln Gln Leu Asn Gln Ser Met Asp Thr Gly
                485                 490                 495
Ser Pro Ala Glu Leu Ser Pro Thr Thr Leu Ser Pro Val Asn His Ser
        500                 505                 510
Leu Asp Leu Gln Pro Val Thr Tyr Ser Glu Pro Ala Phe Trp Cys Ser
        515                 520                 525
Ile Ala Tyr Tyr Glu Leu Asn Gln Arg Val Gly Glu Thr Phe His Ala
        530                 535                 540
Ser Gln Pro Ser Leu Thr Val Asp Gly Phe Thr Asp Pro Ser Asn Ser
545                 550                 555                 560
Glu Arg Phe Cys Leu Gly Leu Leu Ser Asn Val Asn Arg Asn Ala Thr
                565                 570                 575
Val Glu Met Thr Arg Arg His Ile Gly Arg Gly Val Arg Leu Tyr Tyr
                580                 585                 590
Ile Gly Gly Glu Val Phe Ala Glu Cys Leu Ser Asp Ser Ala Ile Phe
        595                 600                 605
Val Gln Ser Pro Asn Cys Asn Gln Arg Tyr Gly Trp His Pro Ala Thr
        610                 615                 620
Val Cys Lys Ile Pro Pro Gly Cys Asn Leu Lys Ile Phe Asn Asn Gln
625                 630                 635                 640
Glu Phe Ala Ala Leu Leu Ala Gln Ser Val Asn Gln Gly Phe Glu Ala
                645                 650                 655
```

```
Val Tyr Gln Leu Thr Arg Met Cys Thr Ile Arg Met Ser Phe Val Lys
            660                 665                 670

Gly Trp Gly Ala Glu Tyr Arg Arg Gln Thr Val Thr Ser Thr Pro Cys
        675                 680                 685

Trp Ile Glu Leu His Leu Asn Gly Pro Leu Gln Trp Leu Asp Lys Val
    690                 695                 700

Leu Thr Gln Met Gly Ser Pro Ser Val Arg Cys Ser Ser Met Ser
705                 710                 715

<210> SEQ ID NO 52
<211> LENGTH: 2421
<212> TYPE: DNA
<213> ORGANISM: Artificial Sequence
<220> FEATURE:
<223> OTHER INFORMATION: EGFP-Smad4 fusion
<220> FEATURE:
<221> NAME/KEY: CDS
<222> LOCATION: (1)..(2418)

<400> SEQUENCE: 52 atg gtg agc aag ggc gag gag ctg ttc acc ggg gtg gtg ccc atc ctg      48
Met Val Ser Lys Gly Glu Glu Leu Phe Thr Gly Val Val Pro Ile Leu
1               5                   10                  15 gtc gag ctg gac ggc gac gta aac ggc cac aag ttc agc gtg tcc ggc      96
Val Glu Leu Asp Gly Asp Val Asn Gly His Lys Phe Ser Val Ser Gly
            20                  25                  30 gag ggc gag ggc gat gcc acc tac ggc aag ctg acc ctg aag ttc atc     144
Glu Gly Glu Gly Asp Ala Thr Tyr Gly Lys Leu Thr Leu Lys Phe Ile
        35                  40                  45 tgc acc acc ggc aag ctg ccc gtg ccc tgg ccc acc ctc gtg acc acc     192
Cys Thr Thr Gly Lys Leu Pro Val Pro Trp Pro Thr Leu Val Thr Thr
    50                  55                  60 ctg acc tac ggc gtg cag tgc ttc agc cgc tac ccc gac cac atg aag     240
Leu Thr Tyr Gly Val Gln Cys Phe Ser Arg Tyr Pro Asp His Met Lys
65                  70                  75                  80 cag cac gac ttc ttc aag tcc gcc atg ccc gaa ggc tac gtc cag gag     288
Gln His Asp Phe Phe Lys Ser Ala Met Pro Glu Gly Tyr Val Gln Glu
                85                  90                  95 cgc acc atc ttc ttc aag gac gac ggc aac tac aag acc cgc gcc gag     336
Arg Thr Ile Phe Phe Lys Asp Asp Gly Asn Tyr Lys Thr Arg Ala Glu
            100                 105                 110 gtg aag ttc gag ggc gac acc ctg gtg aac cgc atc gag ctg aag ggc     384
Val Lys Phe Glu Gly Asp Thr Leu Val Asn Arg Ile Glu Leu Lys Gly
        115                 120                 125 atc gac ttc aag gag gac ggc aac atc ctg ggg cac aag ctg gag tac     432
Ile Asp Phe Lys Glu Asp Gly Asn Ile Leu Gly His Lys Leu Glu Tyr
    130                 135                 140 aac tac aac agc cac aac gtc tat atc atg gcc gac aag cag aag aac     480
Asn Tyr Asn Ser His Asn Val Tyr Ile Met Ala Asp Lys Gln Lys Asn
145                 150                 155                 160 ggc atc aag gtg aac ttc aag atc cgc cac aac atc gag gac ggc agc     528
Gly Ile Lys Val Asn Phe Lys Ile Arg His Asn Ile Glu Asp Gly Ser
                165                 170                 175 gtg cag ctc gcc gac cac tac cag cag aac acc ccc atc ggc gac ggc     576
Val Gln Leu Ala Asp His Tyr Gln Gln Asn Thr Pro Ile Gly Asp Gly
            180                 185                 190 ccc gtg ctg ctg ccc gac aac cac tac ctg agc acc cag tcc gcc ctg     624
Pro Val Leu Leu Pro Asp Asn His Tyr Leu Ser Thr Gln Ser Ala Leu
        195                 200                 205 agc aaa gac ccc aac gag aag cgc gat cac atg gtc ctg ctg gag ttc     672
```

```
Ser Lys Asp Pro Asn Glu Lys Arg Asp His Met Val Leu Leu Glu Phe
    210                 215                 220 gtg acc gcc gcc ggg atc act ctc ggc atg gac gag ctg tac aag tcc        720
Val Thr Ala Ala Gly Ile Thr Leu Gly Met Asp Glu Leu Tyr Lys Ser
225                 230                 235                 240 gga ctc aga tct cga gct caa gct tcg aat tcg aat tca acc atg gac        768
Gly Leu Arg Ser Arg Ala Gln Ala Ser Asn Ser Asn Ser Thr Met Asp
                245                 250                 255 aat atg tct att acg aat aca cca aca agt aat gat gcc tgt ctg agc        816
Asn Met Ser Ile Thr Asn Thr Pro Thr Ser Asn Asp Ala Cys Leu Ser
            260                 265                 270 att gtg cat agt ttg atg tgc cat aga caa ggt gga gag agt gaa aca        864
Ile Val His Ser Leu Met Cys His Arg Gln Gly Gly Glu Ser Glu Thr
        275                 280                 285 ttt gca aaa aga gca att gaa agt ttg gta aag aag ctg aag gag aaa        912
Phe Ala Lys Arg Ala Ile Glu Ser Leu Val Lys Lys Leu Lys Glu Lys
    290                 295                 300 aaa gat gaa ttg gat tct tta ata aca gct ata act aca aat gga gct        960
Lys Asp Glu Leu Asp Ser Leu Ile Thr Ala Ile Thr Thr Asn Gly Ala
305                 310                 315                 320 cat cct agt aaa tgt gtt acc ata cag aga aca ttg gat ggg agg ctt       1008
His Pro Ser Lys Cys Val Thr Ile Gln Arg Thr Leu Asp Gly Arg Leu
                325                 330                 335 cag gtg gct ggt cgg aaa gga ttt cct cat gtg atc tat gcc cgt ctc       1056
Gln Val Ala Gly Arg Lys Gly Phe Pro His Val Ile Tyr Ala Arg Leu
            340                 345                 350 tgg agg tgg cct gat ctt cac aaa aat gaa cta aaa cat gtt aaa tat       1104
Trp Arg Trp Pro Asp Leu His Lys Asn Glu Leu Lys His Val Lys Tyr
        355                 360                 365 tgt cag tat gcg ttt gac tta aaa tgt gat agt gtc tgt gtg aat cca       1152
Cys Gln Tyr Ala Phe Asp Leu Lys Cys Asp Ser Val Cys Val Asn Pro
    370                 375                 380 tat cac tac gaa cga gtt gta tca cct gga att gat ctc tca gga tta       1200
Tyr His Tyr Glu Arg Val Val Ser Pro Gly Ile Asp Leu Ser Gly Leu
385                 390                 395                 400 aca ctg cag agt aat gct cca tca agt atg atg gtg aag gat gaa tat       1248
Thr Leu Gln Ser Asn Ala Pro Ser Ser Met Met Val Lys Asp Glu Tyr
                405                 410                 415 gtg cat gac ttt gag gga cag cca tcg ttg tcc act gaa gga cat tca       1296
Val His Asp Phe Glu Gly Gln Pro Ser Leu Ser Thr Glu Gly His Ser
            420                 425                 430 att caa acc atc cag cat cca cca agt aat cgt gca tcg aca gag aca       1344
Ile Gln Thr Ile Gln His Pro Pro Ser Asn Arg Ala Ser Thr Glu Thr
        435                 440                 445 tac agc acc cca gct ctg tta gcc cca tct gag tct aat gct acc agc       1392
Tyr Ser Thr Pro Ala Leu Leu Ala Pro Ser Glu Ser Asn Ala Thr Ser
    450                 455                 460 act gcc aac ttt ccc aac att cct gtg gct tcc aca agt cag cct gcc       1440
Thr Ala Asn Phe Pro Asn Ile Pro Val Ala Ser Thr Ser Gln Pro Ala
465                 470                 475                 480 agt ata ctg ggg ggc agc cat agt gaa gga ctg ttg cag ata gca tca       1488
Ser Ile Leu Gly Gly Ser His Ser Glu Gly Leu Leu Gln Ile Ala Ser
                485                 490                 495 ggg cct cag cca gga cag cag cag aat gga ttt act ggt cag cca gct       1536
Gly Pro Gln Pro Gly Gln Gln Gln Asn Gly Phe Thr Gly Gln Pro Ala
            500                 505                 510 act tac cat cat aac agc act acc acc tgg act gga agt agg act gca       1584
Thr Tyr His His Asn Ser Thr Thr Thr Trp Thr Gly Ser Arg Thr Ala
        515                 520                 525
```

| | | |
|---|---|---|
| cca tac aca cct aat ttg cct cac cac caa aac ggc cat ctt cag cac<br>Pro Tyr Thr Pro Asn Leu Pro His His Gln Asn Gly His Leu Gln His<br>530                        535                  540 | | 1632 |
| cac ccg cct atg ccg ccc cat ccc gga cat tac tgg cct gtt cac aat<br>His Pro Pro Met Pro Pro His Pro Gly His Tyr Trp Pro Val His Asn<br>545                        550                  555                  560 | | 1680 |
| gag ctt gca ttc cag cct ccc att tcc aat cat cct gct cct gag tat<br>Glu Leu Ala Phe Gln Pro Pro Ile Ser Asn His Pro Ala Pro Glu Tyr<br>                  565                  570                  575 | | 1728 |
| tgg tgt tcc att gct tac ttt gaa atg gat gtt cag gta gga gag aca<br>Trp Cys Ser Ile Ala Tyr Phe Glu Met Asp Val Gln Val Gly Glu Thr<br>580                        585                  590 | | 1776 |
| ttt aag gtt cct tca agc tgc cct att gtt act gtt gat gga tac gtg<br>Phe Lys Val Pro Ser Ser Cys Pro Ile Val Thr Val Asp Gly Tyr Val<br>                  595                  600                  605 | | 1824 |
| gac cct tct gga gga gat cgc ttt tgt ttg ggt caa ctc tcc aat gtc<br>Asp Pro Ser Gly Gly Asp Arg Phe Cys Leu Gly Gln Leu Ser Asn Val<br>610                        615                  620 | | 1872 |
| cac agg aca gaa gcc att gag aga gca agg ttg cac ata ggc aaa ggt<br>His Arg Thr Glu Ala Ile Glu Arg Ala Arg Leu His Ile Gly Lys Gly<br>625                        630                  635                  640 | | 1920 |
| gtg cag ttg gaa tgt aaa ggt gaa ggt gat gtt tgg gtc agg tgc ctt<br>Val Gln Leu Glu Cys Lys Gly Glu Gly Asp Val Trp Val Arg Cys Leu<br>                  645                  650                  655 | | 1968 |
| agt gac cac gcg gtc ttt gta cag agt tac tac tta gac aga gaa gct<br>Ser Asp His Ala Val Phe Val Gln Ser Tyr Tyr Leu Asp Arg Glu Ala<br>660                        665                  670 | | 2016 |
| ggg cgt gca cct gga gat gct gtt cat aag atc tac cca agt gca tat<br>Gly Arg Ala Pro Gly Asp Ala Val His Lys Ile Tyr Pro Ser Ala Tyr<br>                  675                  680                  685 | | 2064 |
| ata aag gtc ttt gat ttg cgt cag tgt cat cga cag atg cag cag cag<br>Ile Lys Val Phe Asp Leu Arg Gln Cys His Arg Gln Met Gln Gln Gln<br>690                        695                  700 | | 2112 |
| gcg gct act gca caa gct gca gca gct gcc cag gca gca gcc gtg gca<br>Ala Ala Thr Ala Gln Ala Ala Ala Ala Ala Gln Ala Ala Ala Val Ala<br>705                        710                  715                  720 | | 2160 |
| gga aac atc cct ggc cca gga tca gta ggt gga ata gct cca gct atc<br>Gly Asn Ile Pro Gly Pro Gly Ser Val Gly Gly Ile Ala Pro Ala Ile<br>                  725                  730                  735 | | 2208 |
| agt ctg tca gct gct gct gga att ggt gtt gat gac ctt cgt cgc tta<br>Ser Leu Ser Ala Ala Ala Gly Ile Gly Val Asp Asp Leu Arg Arg Leu<br>740                        745                  750 | | 2256 |
| tgc ata ctc agg atg agt ttt gtg aaa ggc tgg gga ccg gat tac cca<br>Cys Ile Leu Arg Met Ser Phe Val Lys Gly Trp Gly Pro Asp Tyr Pro<br>                  755                  760                  765 | | 2304 |
| aga cag agc atc aaa gaa aca cct tgc tgg att gaa att cac tta cac<br>Arg Gln Ser Ile Lys Glu Thr Pro Cys Trp Ile Glu Ile His Leu His<br>770                        775                  780 | | 2352 |
| cgg gcc ctc cag ctc cta gac gaa gta ctt cat acc atg ccg att gca<br>Arg Ala Leu Gln Leu Leu Asp Glu Val Leu His Thr Met Pro Ile Ala<br>785                        790                  795                  800 | | 2400 |
| gac cca caa cct tta gac tga<br>Asp Pro Gln Pro Leu Asp<br>                  805 | | 2421 |

<210> SEQ ID NO 53
<211> LENGTH: 806
<212> TYPE: PRT
<213> ORGANISM: Artificial Sequence
<220> FEATURE:
<223> OTHER INFORMATION: EGFP-Smad4 fusion

```
<400> SEQUENCE: 53

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Ser
225                 230                 235                 240

Gly Leu Arg Ser Arg Ala Gln Ala Ser Asn Ser Asn Ser Thr Met Asp
                245                 250                 255

Asn Met Ser Ile Thr Asn Thr Pro Thr Ser Asn Asp Ala Cys Leu Ser
            260                 265                 270

Ile Val His Ser Leu Met Cys His Arg Gln Gly Gly Glu Ser Glu Thr
        275                 280                 285

Phe Ala Lys Arg Ala Ile Glu Ser Leu Val Lys Lys Leu Lys Glu Lys
    290                 295                 300

Lys Asp Glu Leu Asp Ser Leu Ile Thr Ala Ile Thr Thr Asn Gly Ala
305                 310                 315                 320

His Pro Ser Lys Cys Val Thr Ile Gln Arg Thr Leu Asp Gly Arg Leu
                325                 330                 335

Gln Val Ala Gly Arg Lys Gly Phe Pro His Val Ile Tyr Ala Arg Leu
            340                 345                 350

Trp Arg Trp Pro Asp Leu His Lys Asn Glu Leu Lys His Val Lys Tyr
        355                 360                 365

Cys Gln Tyr Ala Phe Asp Leu Lys Cys Asp Ser Val Cys Val Asn Pro
    370                 375                 380

Tyr His Tyr Glu Arg Val Val Ser Pro Gly Ile Asp Leu Ser Gly Leu
385                 390                 395                 400

Thr Leu Gln Ser Asn Ala Pro Ser Ser Met Met Val Lys Asp Glu Tyr
```

```
                         405                 410                 415
    Val His Asp Phe Glu Gly Gln Pro Ser Leu Ser Thr Glu Gly His Ser
                    420                 425                 430
    Ile Gln Thr Ile Gln His Pro Pro Ser Asn Arg Ala Ser Thr Glu Thr
                435                 440                 445
    Tyr Ser Thr Pro Ala Leu Leu Ala Pro Ser Glu Ser Asn Ala Thr Ser
            450                 455                 460
    Thr Ala Asn Phe Pro Asn Ile Pro Val Ala Ser Thr Ser Gln Pro Ala
    465                 470                 475                 480
    Ser Ile Leu Gly Gly Ser His Ser Glu Gly Leu Leu Gln Ile Ala Ser
                    485                 490                 495
    Gly Pro Gln Pro Gly Gln Gln Asn Gly Phe Thr Gly Gln Pro Ala
                500                 505                 510
    Thr Tyr His His Asn Ser Thr Thr Thr Trp Thr Gly Ser Arg Thr Ala
            515                 520                 525
    Pro Tyr Thr Pro Asn Leu Pro His His Gln Asn Gly His Leu Gln His
    530                 535                 540
    His Pro Pro Met Pro Pro His Pro Gly His Tyr Trp Pro Val His Asn
    545                 550                 555                 560
    Glu Leu Ala Phe Gln Pro Pro Ile Ser Asn His Pro Ala Pro Glu Tyr
                    565                 570                 575
    Trp Cys Ser Ile Ala Tyr Phe Glu Met Asp Val Gln Val Gly Glu Thr
                580                 585                 590
    Phe Lys Val Pro Ser Ser Cys Pro Ile Val Thr Val Asp Gly Tyr Val
                595                 600                 605
    Asp Pro Ser Gly Gly Asp Arg Phe Cys Leu Gly Gln Leu Ser Asn Val
            610                 615                 620
    His Arg Thr Glu Ala Ile Glu Arg Ala Arg Leu His Ile Gly Lys Gly
    625                 630                 635                 640
    Val Gln Leu Glu Cys Lys Gly Glu Gly Asp Val Trp Val Arg Cys Leu
                    645                 650                 655
    Ser Asp His Ala Val Phe Val Gln Ser Tyr Tyr Leu Asp Arg Glu Ala
                660                 665                 670
    Gly Arg Ala Pro Gly Asp Ala Val His Lys Ile Tyr Pro Ser Ala Tyr
            675                 680                 685
    Ile Lys Val Phe Asp Leu Arg Gln Cys His Arg Gln Met Gln Gln Gln
    690                 695                 700
    Ala Ala Thr Ala Gln Ala Ala Ala Ala Gln Ala Ala Val Ala
    705                 710                 715                 720
    Gly Asn Ile Pro Gly Pro Gly Ser Val Gly Ile Ala Pro Ala Ile
                    725                 730                 735
    Ser Leu Ser Ala Ala Gly Ile Gly Val Asp Asp Leu Arg Arg Leu
                740                 745                 750
    Cys Ile Leu Arg Met Ser Phe Val Lys Gly Trp Gly Pro Asp Tyr Pro
            755                 760                 765
    Arg Gln Ser Ile Lys Glu Thr Pro Cys Trp Ile Glu Ile His Leu His
    770                 775                 780
    Arg Ala Leu Gln Leu Leu Asp Glu Val Leu His Thr Met Pro Ile Ala
    785                 790                 795                 800
    Asp Pro Gln Pro Leu Asp
                    805

<210> SEQ ID NO 54
```

-continued

```
<211> LENGTH: 3120
<212> TYPE: DNA
<213> ORGANISM: Artificial Sequence
<220> FEATURE:
<223> OTHER INFORMATION: EGFP-Stat5 fusion
<220> FEATURE:
<221> NAME/KEY: CDS
<222> LOCATION: (1)..(3117)

<400> SEQUENCE: 54 atg gtg agc aag ggc gag gag ctg ttc acc ggg gtg gtg ccc atc ctg      48
Met Val Ser Lys Gly Glu Glu Leu Phe Thr Gly Val Val Pro Ile Leu
1               5                   10                  15 gtc gag ctg gac ggc gac gta aac ggc cac aag ttc agc gtg tcc ggc      96
Val Glu Leu Asp Gly Asp Val Asn Gly His Lys Phe Ser Val Ser Gly
            20                  25                  30 gag ggc gag ggc gat gcc acc tac ggc aag ctg acc ctg aag ttc atc     144
Glu Gly Glu Gly Asp Ala Thr Tyr Gly Lys Leu Thr Leu Lys Phe Ile
        35                  40                  45 tgc acc acc ggc aag ctg ccc gtg ccc tgg ccc acc ctc gtg acc acc     192
Cys Thr Thr Gly Lys Leu Pro Val Pro Trp Pro Thr Leu Val Thr Thr
50                  55                  60 ctg acc tac ggc gtg cag tgc ttc agc cgc tac ccc gac cac atg aag     240
Leu Thr Tyr Gly Val Gln Cys Phe Ser Arg Tyr Pro Asp His Met Lys
65                  70                  75                  80 cag cac gac ttc ttc aag tcc gcc atg ccc gaa ggc tac gtc cag gag     288
Gln His Asp Phe Phe Lys Ser Ala Met Pro Glu Gly Tyr Val Gln Glu
                85                  90                  95 cgc acc atc ttc ttc aag gac gac ggc aac tac aag acc cgc gcc gag     336
Arg Thr Ile Phe Phe Lys Asp Asp Gly Asn Tyr Lys Thr Arg Ala Glu
            100                 105                 110 gtg aag ttc gag ggc gac acc ctg gtg aac cgc atc gag ctg aag ggc     384
Val Lys Phe Glu Gly Asp Thr Leu Val Asn Arg Ile Glu Leu Lys Gly
        115                 120                 125 atc gac ttc aag gag gac ggc aac atc ctg ggg cac aag ctg gag tac     432
Ile Asp Phe Lys Glu Asp Gly Asn Ile Leu Gly His Lys Leu Glu Tyr
130                 135                 140 aac tac aac agc cac aac gtc tat atc atg gcc gac aag cag aag aac     480
Asn Tyr Asn Ser His Asn Val Tyr Ile Met Ala Asp Lys Gln Lys Asn
145                 150                 155                 160 ggc atc aag gtg aac ttc aag atc cgc cac aac atc gag gac ggc agc     528
Gly Ile Lys Val Asn Phe Lys Ile Arg His Asn Ile Glu Asp Gly Ser
                165                 170                 175 gtg cag ctc gcc gac cac tac cag cag aac acc ccc atc ggc gac ggc     576
Val Gln Leu Ala Asp His Tyr Gln Gln Asn Thr Pro Ile Gly Asp Gly
            180                 185                 190 ccc gtg ctg ctg ccc gac aac cac tac ctg agc acc cag tcc gcc ctg     624
Pro Val Leu Leu Pro Asp Asn His Tyr Leu Ser Thr Gln Ser Ala Leu
        195                 200                 205 agc aaa gac ccc aac gag aag cgc gat cac atg gtc ctg ctg gag ttc     672
Ser Lys Asp Pro Asn Glu Lys Arg Asp His Met Val Leu Leu Glu Phe
    210                 215                 220 gtg acc gcc gcc ggg atc act ctc ggc atg gac gag ctg tac aag tcc     720
Val Thr Ala Ala Gly Ile Thr Leu Gly Met Asp Glu Leu Tyr Lys Ser
225                 230                 235                 240 gga ctc aga tct acc atg gcg ggc tgg atc cag gcc cag cag ctg cag     768
Gly Leu Arg Ser Thr Met Ala Gly Trp Ile Gln Ala Gln Gln Leu Gln
                245                 250                 255 gga gac gcg ctg cgc cag atg cag gtg ctg tac ggc cag cac ttc ccc     816
Gly Asp Ala Leu Arg Gln Met Gln Val Leu Tyr Gly Gln His Phe Pro
            260                 265                 270
```

-continued

```
atc gag gtc cgg cac tac ttg gcc cag tgg att gag agc cag cca tgg      864
Ile Glu Val Arg His Tyr Leu Ala Gln Trp Ile Glu Ser Gln Pro Trp
        275                 280                 285 gat gcc att gac ttg gac aat ccc cag gac aga gcc caa gcc acc cag      912
Asp Ala Ile Asp Leu Asp Asn Pro Gln Asp Arg Ala Gln Ala Thr Gln
290                 295                 300 ctc ctg gag ggc ctg gtg cag gag ctg cag aag aag gcg gag cac cag      960
Leu Leu Glu Gly Leu Val Gln Glu Leu Gln Lys Lys Ala Glu His Gln
305                 310                 315                 320 gtg ggg gaa gat ggg ttt tta ctg aag atc aag ctg ggg cac tac gcc     1008
Val Gly Glu Asp Gly Phe Leu Leu Lys Ile Lys Leu Gly His Tyr Ala
                325                 330                 335 acg cag ctc cag aaa aca tat gac cgc tgc ccc ctg gag ctg gtc cgc     1056
Thr Gln Leu Gln Lys Thr Tyr Asp Arg Cys Pro Leu Glu Leu Val Arg
            340                 345                 350 tgc atc cgg cac att ctg tac aat gaa cag agg ctg gtc cga gaa gcc     1104
Cys Ile Arg His Ile Leu Tyr Asn Glu Gln Arg Leu Val Arg Glu Ala
        355                 360                 365 aac aat tgc agc tct ccg gct ggg atc ctg gtt gac gcc atg tcc cag     1152
Asn Asn Cys Ser Ser Pro Ala Gly Ile Leu Val Asp Ala Met Ser Gln
370                 375                 380 aag cac ctt cag atc aac cag aca ttt gag gag ctg cga ctg gtc acg     1200
Lys His Leu Gln Ile Asn Gln Thr Phe Glu Glu Leu Arg Leu Val Thr
385                 390                 395                 400 cag gac aca gag aat gag ctg aag aaa ctg cag cag act cag gag tac     1248
Gln Asp Thr Glu Asn Glu Leu Lys Lys Leu Gln Gln Thr Gln Glu Tyr
                405                 410                 415 ttc atc atc cag tac cag gag agc ctg agg atc caa gct cag ttt gcc     1296
Phe Ile Ile Gln Tyr Gln Glu Ser Leu Arg Ile Gln Ala Gln Phe Ala
            420                 425                 430 cag ctg gcc cag ctg agc ccc cag gag cgt ctg agc cgg gag acg gcc     1344
Gln Leu Ala Gln Leu Ser Pro Gln Glu Arg Leu Ser Arg Glu Thr Ala
        435                 440                 445 ctc cag cag aag cag gtg tct ctg gag gcc tgg ttg cag cgt gag gca     1392
Leu Gln Gln Lys Gln Val Ser Leu Glu Ala Trp Leu Gln Arg Glu Ala
450                 455                 460 cag aca ctg cag cag tac cgc gtg gag ctg gcc gag aag cac cag aag     1440
Gln Thr Leu Gln Gln Tyr Arg Val Glu Leu Ala Glu Lys His Gln Lys
465                 470                 475                 480 acc ctg cag ctg ctg cgg aag cag cag acc atc atc ctg gat gac gag     1488
Thr Leu Gln Leu Leu Arg Lys Gln Gln Thr Ile Ile Leu Asp Asp Glu
                485                 490                 495 ctg atc cag tgg aag cgg cgg cag cag ctg gcc ggg aac ggc ggg ccc     1536
Leu Ile Gln Trp Lys Arg Arg Gln Gln Leu Ala Gly Asn Gly Gly Pro
            500                 505                 510 ccc gag ggc agc ctg gac gtg cta cag tcc tgg tgt gag aag ttg gcc     1584
Pro Glu Gly Ser Leu Asp Val Leu Gln Ser Trp Cys Glu Lys Leu Ala
        515                 520                 525 gag atc atc tgg cag aac cgg cag cag atc cgc agg gct gag cac ctc     1632
Glu Ile Ile Trp Gln Asn Arg Gln Gln Ile Arg Arg Ala Glu His Leu
530                 535                 540 tgc cag cag ctg ccc atc ccc ggc cca gtg gag gag atg ctg gcc gag     1680
Cys Gln Gln Leu Pro Ile Pro Gly Pro Val Glu Glu Met Leu Ala Glu
545                 550                 555                 560 gtc aac gcc acc atc acg gac att atc tca gcc ctg gtg acc agc aca     1728
Val Asn Ala Thr Ile Thr Asp Ile Ile Ser Ala Leu Val Thr Ser Thr
                565                 570                 575 ttc atc att gag aag cag cct cct cag gtc ctg aag acc cag acc aag     1776
Phe Ile Ile Glu Lys Gln Pro Pro Gln Val Leu Lys Thr Gln Thr Lys
            580                 585                 590
```

```
ttt gca gcc acc gta cgc ctg ctg gtg ggc ggg aag ctg aac gtg cac    1824
Phe Ala Ala Thr Val Arg Leu Leu Val Gly Gly Lys Leu Asn Val His
        595                 600                 605 atg aat ccc ccc cag gtg aag gcc acc atc atc agt gag cag cag gcc    1872
Met Asn Pro Pro Gln Val Lys Ala Thr Ile Ile Ser Glu Gln Gln Ala
610                 615                 620 aag tct ctg ctt aaa aat gag aac acc cgc aac gag tgc agt ggt gag    1920
Lys Ser Leu Leu Lys Asn Glu Asn Thr Arg Asn Glu Cys Ser Gly Glu
625                 630                 635                 640 atc ctg aac aac tgc tgc gtg atg gag tac cac caa gcc acg ggc acc    1968
Ile Leu Asn Asn Cys Cys Val Met Glu Tyr His Gln Ala Thr Gly Thr
                645                 650                 655 ctc agt gcc cac ttc agg aac atg tca ctg aag agg atc aag cgt gct    2016
Leu Ser Ala His Phe Arg Asn Met Ser Leu Lys Arg Ile Lys Arg Ala
        660                 665                 670 gac cgg cgg ggt gca gag tcc gtg aca gag gag aag ttc aca gtc ctg    2064
Asp Arg Arg Gly Ala Glu Ser Val Thr Glu Glu Lys Phe Thr Val Leu
    675                 680                 685 ttt gag tct cag ttc agt gtt ggc agc aat gag ctt gtg ttc cag gtg    2112
Phe Glu Ser Gln Phe Ser Val Gly Ser Asn Glu Leu Val Phe Gln Val
690                 695                 700 aag act ctg tcc cta cct gtg gtt gtc atc gtc cac ggc agc cag gac    2160
Lys Thr Leu Ser Leu Pro Val Val Val Ile Val His Gly Ser Gln Asp
705                 710                 715                 720 cac aat gcc acg gct act gtg ctg tgg gac aat gcc ttt gct gag ccg    2208
His Asn Ala Thr Ala Thr Val Leu Trp Asp Asn Ala Phe Ala Glu Pro
                725                 730                 735 ggc agg gtg cca ttt gcc gtg cct gac aaa gtg ctg tgg ccg cag ctg    2256
Gly Arg Val Pro Phe Ala Val Pro Asp Lys Val Leu Trp Pro Gln Leu
        740                 745                 750 tgt gag gcg ctc aac atg aaa ttc aag gcc gaa gtg cag agc aac cgg    2304
Cys Glu Ala Leu Asn Met Lys Phe Lys Ala Glu Val Gln Ser Asn Arg
    755                 760                 765 ggc ctg acc aag gag aac ctc gtg ttc ctg gcg cag aaa ctg ttc aac    2352
Gly Leu Thr Lys Glu Asn Leu Val Phe Leu Ala Gln Lys Leu Phe Asn
770                 775                 780 aac agc agc agc cac ctg gag gac tac agt ggc ctg tcc gtg tcc tgg    2400
Asn Ser Ser Ser His Leu Glu Asp Tyr Ser Gly Leu Ser Val Ser Trp
785                 790                 795                 800 tcc cag ttc aac agg gag aac ttg ccg ggc tgg aac tac acc ttc tgg    2448
Ser Gln Phe Asn Arg Glu Asn Leu Pro Gly Trp Asn Tyr Thr Phe Trp
                805                 810                 815 cag tgg ttt gac ggg gtg atg gag gtg ttg aag aag cac cac aag ccc    2496
Gln Trp Phe Asp Gly Val Met Glu Val Leu Lys Lys His His Lys Pro
        820                 825                 830 cac tgg aat gat ggg gcc atc cta ggt ttt gtg aat aag caa cag gcc    2544
His Trp Asn Asp Gly Ala Ile Leu Gly Phe Val Asn Lys Gln Gln Ala
    835                 840                 845 cac gac ctg ctc atc aac aag ccc gac ggg acc ttg ttg cgc ttt        2592
His Asp Leu Leu Ile Asn Lys Pro Asp Gly Thr Phe Leu Leu Arg Phe
850                 855                 860 agt gac tca gaa atc ggg ggc atc acc atc gcc tgg aag ttt gac tcc    2640
Ser Asp Ser Glu Ile Gly Gly Ile Thr Ile Ala Trp Lys Phe Asp Ser
865                 870                 875                 880 ccg gaa cgc aac ctg tgg aac ctg aaa cca ttc acc acg cgg gat ttc    2688
Pro Glu Arg Asn Leu Trp Asn Leu Lys Pro Phe Thr Thr Arg Asp Phe
                885                 890                 895 tcc atc agg tcc ctg gct gac cgg ctg ggg gac ctg agc tat ctc atc    2736
Ser Ile Arg Ser Leu Ala Asp Arg Leu Gly Asp Leu Ser Tyr Leu Ile
```

```
                    900                 905                 910
tat gtg ttt cct gac cgc ccc aag gat gag gtc ttc tcc aag tac tac      2784
Tyr Val Phe Pro Asp Arg Pro Lys Asp Glu Val Phe Ser Lys Tyr Tyr
        915                 920                 925 act cct gtg ctg gct aaa gct gtt gat gga tat gtg aaa cca cag atc      2832
Thr Pro Val Leu Ala Lys Ala Val Asp Gly Tyr Val Lys Pro Gln Ile
    930                 935                 940 aag caa gtg gtc cct gag ttt gtg aat gca tct gca gat gct ggg ggc      2880
Lys Gln Val Val Pro Glu Phe Val Asn Ala Ser Ala Asp Ala Gly Gly
945                 950                 955                 960 agc agc gcc acg tac atg gac cag gcc ccc tcc cca gct gtg tgc ccc      2928
Ser Ser Ala Thr Tyr Met Asp Gln Ala Pro Ser Pro Ala Val Cys Pro
                965                 970                 975 cag gct ccc tat aac atg tac cca cag aac cct gac cat gta ctc gat      2976
Gln Ala Pro Tyr Asn Met Tyr Pro Gln Asn Pro Asp His Val Leu Asp
            980                 985                 990 cag gat gga gaa ttc gac ctg gat  gag acc atg gat gtg  gcc agg cac    3024
Gln Asp Gly Glu Phe Asp Leu Asp  Glu Thr Met Asp Val  Ala Arg His
        995                 1000                1005 gtg gag gaa ctc tta cgc cga cca atg gac agt ctt  gac tcc cgc         3069
Val Glu Glu Leu Leu Arg Arg Pro Met Asp Ser Leu  Asp Ser Arg
    1010            1015                    1020 ctc tcg ccc cct gcc ggt ctt ttc acc tct gcc aga ggc tcc ctc          3114
Leu Ser Pro Pro Ala Gly Leu Phe Thr Ser Ala Arg Gly Ser Leu
    1025            1030                    1035 tca tga                                                              3120
Ser
```

<210> SEQ ID NO 55
<211> LENGTH: 1039
<212> TYPE: PRT
<213> ORGANISM: Artificial Sequence
<220> FEATURE:
<223> OTHER INFORMATION: EGFP-Stat5 fusion

<400> SEQUENCE: 55

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175
```

-continued

```
Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
            195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys Ser
225                 230                 235                 240

Gly Leu Arg Ser Thr Met Ala Gly Trp Ile Gln Ala Gln Gln Leu Gln
            245                 250                 255

Gly Asp Ala Leu Arg Gln Met Gln Val Leu Tyr Gly Gln His Phe Pro
            260                 265                 270

Ile Glu Val Arg His Tyr Leu Ala Gln Trp Ile Glu Ser Gln Pro Trp
            275                 280                 285

Asp Ala Ile Asp Leu Asp Asn Pro Gln Asp Arg Ala Gln Ala Thr Gln
            290                 295                 300

Leu Leu Glu Gly Leu Val Gln Glu Leu Gln Lys Lys Ala Glu His Gln
305                 310                 315                 320

Val Gly Glu Asp Gly Phe Leu Leu Lys Ile Lys Leu Gly His Tyr Ala
            325                 330                 335

Thr Gln Leu Gln Lys Thr Tyr Asp Arg Cys Pro Leu Glu Leu Val Arg
            340                 345                 350

Cys Ile Arg His Ile Leu Tyr Asn Glu Gln Arg Leu Val Arg Glu Ala
            355                 360                 365

Asn Asn Cys Ser Ser Pro Ala Gly Ile Leu Val Asp Ala Met Ser Gln
370                 375                 380

Lys His Leu Gln Ile Asn Gln Thr Phe Glu Glu Leu Arg Leu Val Thr
385                 390                 395                 400

Gln Asp Thr Glu Asn Glu Leu Lys Lys Leu Gln Gln Thr Gln Glu Tyr
            405                 410                 415

Phe Ile Ile Gln Tyr Gln Glu Ser Leu Arg Ile Gln Ala Gln Phe Ala
            420                 425                 430

Gln Leu Ala Gln Leu Ser Pro Gln Glu Arg Leu Ser Arg Glu Thr Ala
            435                 440                 445

Leu Gln Gln Lys Gln Val Ser Leu Glu Ala Trp Leu Gln Arg Glu Ala
450                 455                 460

Gln Thr Leu Gln Gln Tyr Arg Val Glu Leu Ala Glu Lys His Gln Lys
465                 470                 475                 480

Thr Leu Gln Leu Leu Arg Lys Gln Gln Thr Ile Ile Leu Asp Asp Glu
            485                 490                 495

Leu Ile Gln Trp Lys Arg Arg Gln Gln Leu Ala Gly Asn Gly Gly Pro
            500                 505                 510

Pro Glu Gly Ser Leu Asp Val Leu Gln Ser Trp Cys Glu Lys Leu Ala
            515                 520                 525

Glu Ile Ile Trp Gln Asn Arg Gln Gln Ile Arg Arg Ala Glu His Leu
            530                 535                 540

Cys Gln Gln Leu Pro Ile Pro Gly Pro Val Glu Glu Met Leu Ala Glu
545                 550                 555                 560

Val Asn Ala Thr Ile Thr Asp Ile Ile Ser Ala Leu Val Thr Ser Thr
            565                 570                 575

Phe Ile Ile Glu Lys Gln Pro Pro Gln Val Leu Lys Thr Gln Thr Lys
            580                 585                 590
```

-continued

```
Phe Ala Ala Thr Val Arg Leu Leu Val Gly Gly Lys Leu Asn Val His
            595                 600                 605

Met Asn Pro Pro Gln Val Lys Ala Thr Ile Ile Ser Glu Gln Gln Ala
        610                 615                 620

Lys Ser Leu Leu Lys Asn Glu Asn Thr Arg Asn Glu Cys Ser Gly Glu
625                 630                 635                 640

Ile Leu Asn Asn Cys Cys Val Met Glu Tyr His Gln Ala Thr Gly Thr
                645                 650                 655

Leu Ser Ala His Phe Arg Asn Met Ser Leu Lys Arg Ile Lys Arg Ala
            660                 665                 670

Asp Arg Arg Gly Ala Glu Ser Val Thr Glu Glu Lys Phe Thr Val Leu
        675                 680                 685

Phe Glu Ser Gln Phe Ser Val Gly Ser Asn Glu Leu Val Phe Gln Val
    690                 695                 700

Lys Thr Leu Ser Leu Pro Val Val Ile Val His Gly Ser Gln Asp
705                 710                 715                 720

His Asn Ala Thr Ala Thr Val Leu Trp Asp Asn Ala Phe Ala Glu Pro
                725                 730                 735

Gly Arg Val Pro Phe Ala Val Pro Asp Lys Val Leu Trp Pro Gln Leu
            740                 745                 750

Cys Glu Ala Leu Asn Met Lys Phe Lys Ala Glu Val Gln Ser Asn Arg
        755                 760                 765

Gly Leu Thr Lys Glu Asn Leu Val Phe Leu Ala Gln Lys Leu Phe Asn
    770                 775                 780

Asn Ser Ser Ser His Leu Glu Asp Tyr Ser Gly Leu Ser Val Ser Trp
785                 790                 795                 800

Ser Gln Phe Asn Arg Glu Asn Leu Pro Gly Trp Asn Tyr Thr Phe Trp
                805                 810                 815

Gln Trp Phe Asp Gly Val Met Glu Val Leu Lys Lys His His Lys Pro
            820                 825                 830

His Trp Asn Asp Gly Ala Ile Leu Gly Phe Val Asn Lys Gln Gln Ala
        835                 840                 845

His Asp Leu Leu Ile Asn Lys Pro Asp Gly Thr Phe Leu Leu Arg Phe
    850                 855                 860

Ser Asp Ser Glu Ile Gly Gly Ile Thr Ile Ala Trp Lys Phe Asp Ser
865                 870                 875                 880

Pro Glu Arg Asn Leu Trp Asn Leu Lys Pro Phe Thr Thr Arg Asp Phe
                885                 890                 895

Ser Ile Arg Ser Leu Ala Asp Arg Leu Gly Asp Leu Ser Tyr Leu Ile
            900                 905                 910

Tyr Val Phe Pro Asp Arg Pro Lys Asp Glu Val Phe Ser Lys Tyr Tyr
        915                 920                 925

Thr Pro Val Leu Ala Lys Ala Val Asp Gly Tyr Val Lys Pro Gln Ile
    930                 935                 940

Lys Gln Val Val Pro Glu Phe Val Asn Ala Ser Ala Asp Ala Gly Gly
945                 950                 955                 960

Ser Ser Ala Thr Tyr Met Asp Gln Ala Pro Ser Pro Ala Val Cys Pro
                965                 970                 975

Gln Ala Pro Tyr Asn Met Tyr Pro Gln Asn Pro Asp His Val Leu Asp
            980                 985                 990

Gln Asp Gly Glu Phe Asp Leu Asp Glu Thr Met Asp Val Ala Arg His
        995                 1000                1005

Val Glu  Glu Leu Leu Arg Arg  Pro Met Asp Ser Leu  Asp Ser Arg
```

-continued

```
          1010                1015                1020
Leu Ser  Pro Pro Ala Gly Leu  Phe Thr Ser Ala Arg  Gly Ser Leu
    1025                 1030                1035

Ser

<210> SEQ ID NO 56
<211> LENGTH: 1875
<212> TYPE: DNA
<213> ORGANISM: Artificial Sequence
<220> FEATURE:
<223> OTHER INFORMATION: mERK1-F64L-S65T-GFP fusion
<220> FEATURE:
<221> NAME/KEY: CDS
<222> LOCATION: (1)..(1872)

<400> SEQUENCE: 56 atg gcg gcg gcg gcg gcg gct ccg ggg ggc ggg ggc ggg gag ccc agg      48
Met Ala Ala Ala Ala Ala Ala Pro Gly Gly Gly Gly Gly Glu Pro Arg
1               5                   10                  15 gga act gct ggg gtc gtc ccg gtg gtc ccc ggg gag gtg gag gtg gtg      96
Gly Thr Ala Gly Val Val Pro Val Val Pro Gly Glu Val Glu Val Val
                20                  25                  30 aag ggg cag cca ttc gat gtg ggc cca cgc tac acg cag ctg cag tac     144
Lys Gly Gln Pro Phe Asp Val Gly Pro Arg Tyr Thr Gln Leu Gln Tyr
            35                  40                  45 atc ggc gag ggc gcg tac ggc atg gtc agc tca gct tat gac cac gtg     192
Ile Gly Glu Gly Ala Tyr Gly Met Val Ser Ser Ala Tyr Asp His Val
        50                  55                  60 cgc aag acc aga gtg gcc atc aag aag atc agc ccc ttt gag cat caa     240
Arg Lys Thr Arg Val Ala Ile Lys Lys Ile Ser Pro Phe Glu His Gln
65                  70                  75                  80 acc tac tgt cag cgc acg ctg agg gag atc cag atc ttg ctg cga ttc     288
Thr Tyr Cys Gln Arg Thr Leu Arg Glu Ile Gln Ile Leu Leu Arg Phe
                85                  90                  95 cgc cat gag aat gtt ata ggc atc cga gac atc ctc aga gcg ccc acc     336
Arg His Glu Asn Val Ile Gly Ile Arg Asp Ile Leu Arg Ala Pro Thr
            100                 105                 110 ctg gaa gcc atg aga gat gtt tac att gtt cag gac ctc atg gag aca     384
Leu Glu Ala Met Arg Asp Val Tyr Ile Val Gln Asp Leu Met Glu Thr
        115                 120                 125 gac ctg tac aag ctg ctt aaa agc cag cag ctg agc aat gac cac atc     432
Asp Leu Tyr Lys Leu Leu Lys Ser Gln Gln Leu Ser Asn Asp His Ile
130                 135                 140 tgc tac ttc ctc tac cag atc ctc cgg ggc ctc aag tat ata cac tca     480
Cys Tyr Phe Leu Tyr Gln Ile Leu Arg Gly Leu Lys Tyr Ile His Ser
145                 150                 155                 160 gcc aat gtg ctg cac cgg gac ctg aag cct tcc aat ctg ctt atc aac     528
Ala Asn Val Leu His Arg Asp Leu Lys Pro Ser Asn Leu Leu Ile Asn
                165                 170                 175 acc acc tgc gac ctt aag atc tgt gat ttt ggc ctg gcc cgg att gct     576
Thr Thr Cys Asp Leu Lys Ile Cys Asp Phe Gly Leu Ala Arg Ile Ala
            180                 185                 190 gac cct gag cac gac cac act ggc ttt ctg acg gag tat gtg gcc aca     624
Asp Pro Glu His Asp His Thr Gly Phe Leu Thr Glu Tyr Val Ala Thr
        195                 200                 205 cgc tgg tac cga gcc cca gag atc atg ctt aat tcc aag ggc tac acc     672
Arg Trp Tyr Arg Ala Pro Glu Ile Met Leu Asn Ser Lys Gly Tyr Thr
    210                 215                 220 aaa tcc atc gac atc tgg tct gtg ggc tgc att ctg gct gag atg ctc     720
Lys Ser Ile Asp Ile Trp Ser Val Gly Cys Ile Leu Ala Glu Met Leu
225                 230                 235                 240
```

```
tcc aac cgg ccc atc ttc ccc ggc aag cac tac ctg gac cag ctc aac      768
Ser Asn Arg Pro Ile Phe Pro Gly Lys His Tyr Leu Asp Gln Leu Asn
                245                 250                 255 cac att cta ggt atc ttg ggt tcc cca tcc cag gag gac ctt aat tgc      816
His Ile Leu Gly Ile Leu Gly Ser Pro Ser Gln Glu Asp Leu Asn Cys
        260                 265                 270 atc att aac atg aag gcc cga aac tac ctg cag tct ctg ccc tcg aaa      864
Ile Ile Asn Met Lys Ala Arg Asn Tyr Leu Gln Ser Leu Pro Ser Lys
            275                 280                 285 acc aag gtg gct tgg gcc aag ctc ttt cct aaa tct gac tcc aaa gct      912
Thr Lys Val Ala Trp Ala Lys Leu Phe Pro Lys Ser Asp Ser Lys Ala
    290                 295                 300 ctt gac ctg ctg gac cgg atg tta acc ttc aac cca aac aag cgc atc      960
Leu Asp Leu Leu Asp Arg Met Leu Thr Phe Asn Pro Asn Lys Arg Ile
305                 310                 315                 320 aca gta gag gaa gcg ctg gct cac cct tac ctg gaa cag tac tac gat     1008
Thr Val Glu Glu Ala Leu Ala His Pro Tyr Leu Glu Gln Tyr Tyr Asp
                325                 330                 335 ccg aca gat gag cca gtg gcc gag gag cca ttc acc ttc gac atg gag     1056
Pro Thr Asp Glu Pro Val Ala Glu Glu Pro Phe Thr Phe Asp Met Glu
        340                 345                 350 ctg gat gac ctc ccc aag gag cgg ctg aag gag ttg atc ttc cag gag     1104
Leu Asp Asp Leu Pro Lys Glu Arg Leu Lys Glu Leu Ile Phe Gln Glu
            355                 360                 365 aca gcc cgc ttc cag cca ggg gcg cca gag ggc ccc ggg cgc gcc atg     1152
Thr Ala Arg Phe Gln Pro Gly Ala Pro Glu Gly Pro Gly Arg Ala Met
    370                 375                 380 agt aaa gga gaa gaa ctt ttc act gga gtt gtc cca att ctt gtt gaa     1200
Ser Lys Gly Glu Glu Leu Phe Thr Gly Val Val Pro Ile Leu Val Glu
385                 390                 395                 400 tta gat ggc gat gtt aat ggg caa aaa ttc tct gtt agt gga gag ggt     1248
Leu Asp Gly Asp Val Asn Gly Gln Lys Phe Ser Val Ser Gly Glu Gly
                405                 410                 415 gaa ggt gat gca aca tac gga aaa ctt acc ctt aaa ttt att tgc act     1296
Glu Gly Asp Ala Thr Tyr Gly Lys Leu Thr Leu Lys Phe Ile Cys Thr
        420                 425                 430 act ggg aag cta cct gtt cca tgg cca acg ctt gtc act act ctc act     1344
Thr Gly Lys Leu Pro Val Pro Trp Pro Thr Leu Val Thr Thr Leu Thr
            435                 440                 445 tat ggt gtt caa tgc ttt tct aga tac cca gat cat atg aaa cag cat     1392
Tyr Gly Val Gln Cys Phe Ser Arg Tyr Pro Asp His Met Lys Gln His
    450                 455                 460 gac ttt ttc aag agt gcc atg ccc gaa ggt tat gta cag gaa aga act     1440
Asp Phe Phe Lys Ser Ala Met Pro Glu Gly Tyr Val Gln Glu Arg Thr
465                 470                 475                 480 ata ttt tac aaa gat gac ggg aac tac aag aca cgt gct gaa gtc aag     1488
Ile Phe Tyr Lys Asp Asp Gly Asn Tyr Lys Thr Arg Ala Glu Val Lys
                485                 490                 495 ttt gaa ggt gat acc ctt gtt aat aga atc gag tta aaa ggt att gat     1536
Phe Glu Gly Asp Thr Leu Val Asn Arg Ile Glu Leu Lys Gly Ile Asp
        500                 505                 510 ttt aaa gaa gat gga aac att ctt gga cac aaa atg gaa tac aat tat     1584
Phe Lys Glu Asp Gly Asn Ile Leu Gly His Lys Met Glu Tyr Asn Tyr
            515                 520                 525 aac tca cat aat gta tac atc atg gca gac aaa cca aag aat ggc atc     1632
Asn Ser His Asn Val Tyr Ile Met Ala Asp Lys Pro Lys Asn Gly Ile
    530                 535                 540 aaa gtt aac ttc aaa att aga cac aac att aaa gat gga agc gtt caa     1680
Lys Val Asn Phe Lys Ile Arg His Asn Ile Lys Asp Gly Ser Val Gln
```

-continued

```
545                 550                 555                 560
tta gca gac cat tat caa caa aat act cca att ggc gat ggc cct gtc    1728
Leu Ala Asp His Tyr Gln Gln Asn Thr Pro Ile Gly Asp Gly Pro Val
                565                 570                 575 ctt tta cca gac aac cat tac ctg tcc acg caa tct gcc ctt tcc aaa    1776
Leu Leu Pro Asp Asn His Tyr Leu Ser Thr Gln Ser Ala Leu Ser Lys
                580                 585                 590 gat ccc aac gaa aag aga gat cac atg atc ctt ctt gag ttt gta aca    1824
Asp Pro Asn Glu Lys Arg Asp His Met Ile Leu Leu Glu Phe Val Thr
                595                 600                 605 gct gct ggg att aca cat ggc atg gat gaa cta tac aaa cct cag gag    1872
Ala Ala Gly Ile Thr His Gly Met Asp Glu Leu Tyr Lys Pro Gln Glu
610                 615                 620 taa                                                                 1875
```

<210> SEQ ID NO 57
<211> LENGTH: 624
<212> TYPE: PRT
<213> ORGANISM: Artificial Sequence
<220> FEATURE:
<223> OTHER INFORMATION: mERK1-F64L-S65T-GFP fusion

<400> SEQUENCE: 57

```
Met Ala Ala Ala Ala Ala Pro Gly Gly Gly Gly Glu Pro Arg
1               5                   10                  15

Gly Thr Ala Gly Val Val Pro Val Pro Gly Glu Val Glu Val Val
                20                  25                  30

Lys Gly Gln Pro Phe Asp Val Gly Pro Arg Tyr Thr Gln Leu Gln Tyr
            35                  40                  45

Ile Gly Glu Gly Ala Tyr Gly Met Val Ser Ser Ala Tyr Asp His Val
    50                  55                  60

Arg Lys Thr Arg Val Ala Ile Lys Lys Ile Ser Pro Phe Glu His Gln
65                  70                  75                  80

Thr Tyr Cys Gln Arg Thr Leu Arg Glu Ile Gln Ile Leu Leu Arg Phe
                85                  90                  95

Arg His Glu Asn Val Ile Gly Ile Arg Asp Ile Leu Arg Ala Pro Thr
            100                 105                 110

Leu Glu Ala Met Arg Asp Val Tyr Ile Val Gln Asp Leu Met Glu Thr
        115                 120                 125

Asp Leu Tyr Lys Leu Leu Lys Ser Gln Gln Leu Ser Asn Asp His Ile
    130                 135                 140

Cys Tyr Phe Leu Tyr Gln Ile Leu Arg Gly Leu Lys Tyr Ile His Ser
145                 150                 155                 160

Ala Asn Val Leu His Arg Asp Leu Lys Pro Ser Asn Leu Leu Ile Asn
                165                 170                 175

Thr Thr Cys Asp Leu Lys Ile Cys Asp Phe Gly Leu Ala Arg Ile Ala
            180                 185                 190

Asp Pro Glu His Asp His Thr Gly Phe Leu Thr Glu Tyr Val Ala Thr
        195                 200                 205

Arg Trp Tyr Arg Ala Pro Glu Ile Met Leu Asn Ser Lys Gly Tyr Thr
    210                 215                 220

Lys Ser Ile Asp Ile Trp Ser Val Gly Cys Ile Leu Ala Glu Met Leu
225                 230                 235                 240

Ser Asn Arg Pro Ile Phe Pro Gly Lys His Tyr Leu Asp Gln Leu Asn
                245                 250                 255

His Ile Leu Gly Ile Leu Gly Ser Pro Ser Gln Glu Asp Leu Asn Cys
```

-continued

```
                    260                 265                 270
        Ile Ile Asn Met Lys Ala Arg Asn Tyr Leu Gln Ser Leu Pro Ser Lys
                275                 280                 285

Thr Lys Val Ala Trp Ala Lys Leu Phe Pro Lys Ser Asp Ser Lys Ala
        290                 295                 300

Leu Asp Leu Leu Asp Arg Met Leu Thr Phe Asn Pro Asn Lys Arg Ile
        305                 310                 315                 320

Thr Val Glu Glu Ala Leu Ala His Pro Tyr Leu Gln Gln Tyr Tyr Asp
                        325                 330                 335

Pro Thr Asp Glu Pro Val Ala Glu Glu Pro Phe Thr Phe Asp Met Glu
                        340                 345                 350

Leu Asp Asp Leu Pro Lys Glu Arg Leu Lys Glu Leu Ile Phe Gln Glu
                        355                 360                 365

Thr Ala Arg Phe Gln Pro Gly Ala Pro Glu Gly Pro Gly Arg Ala Met
        370                 375                 380

Ser Lys Gly Glu Glu Leu Phe Thr Gly Val Val Pro Ile Leu Val Glu
        385                 390                 395                 400

Leu Asp Gly Asp Val Asn Gly Gln Lys Phe Ser Val Ser Gly Glu Gly
                        405                 410                 415

Glu Gly Asp Ala Thr Tyr Gly Lys Leu Thr Leu Lys Phe Ile Cys Thr
                        420                 425                 430

Thr Gly Lys Leu Pro Val Pro Trp Pro Thr Leu Val Thr Thr Leu Thr
                        435                 440                 445

Tyr Gly Val Gln Cys Phe Ser Arg Tyr Pro Asp His Met Lys Gln His
                450                 455                 460

Asp Phe Phe Lys Ser Ala Met Pro Glu Gly Tyr Val Gln Glu Arg Thr
        465                 470                 475                 480

Ile Phe Tyr Lys Asp Asp Gly Asn Tyr Lys Thr Arg Ala Glu Val Lys
                        485                 490                 495

Phe Glu Gly Asp Thr Leu Val Asn Arg Ile Glu Leu Lys Gly Ile Asp
                        500                 505                 510

Phe Lys Glu Asp Gly Asn Ile Leu Gly His Lys Met Glu Tyr Asn Tyr
                    515                 520                 525

Asn Ser His Asn Val Tyr Ile Met Ala Asp Lys Pro Lys Asn Gly Ile
        530                 535                 540

Lys Val Asn Phe Lys Ile Arg His Asn Ile Lys Asp Gly Ser Val Gln
        545                 550                 555                 560

Leu Ala Asp His Tyr Gln Gln Asn Thr Pro Ile Gly Asp Gly Pro Val
                        565                 570                 575

Leu Leu Pro Asp Asn His Tyr Leu Ser Thr Gln Ser Ala Leu Ser Lys
                        580                 585                 590

Asp Pro Asn Glu Lys Arg Asp His Met Ile Leu Leu Glu Phe Val Thr
                        595                 600                 605

Ala Ala Gly Ile Thr His Gly Met Asp Glu Leu Tyr Lys Pro Gln Glu
        610                 615                 620

<210> SEQ ID NO 58
<211> LENGTH: 1815
<212> TYPE: DNA
<213> ORGANISM: Artificial Sequence
<220> FEATURE:
<223> OTHER INFORMATION: Erk2-EGFP fusion
<220> FEATURE:
<221> NAME/KEY: CDS
<222> LOCATION: (1)..(1812)
```

-continued

```
<400> SEQUENCE: 58 atg gcg gcg gcg gcg gcg ggc ccg gag atg gtc cgc ggg cag gtg      48
Met Ala Ala Ala Ala Ala Gly Pro Glu Met Val Arg Gly Gln Val
1               5                   10                  15 ttc gac gtg ggg ccg cgc tac act aat ctc tcg tac atc gga gaa ggc  96
Phe Asp Val Gly Pro Arg Tyr Thr Asn Leu Ser Tyr Ile Gly Glu Gly
                20                  25                  30 gcc tac ggc atg gtt tgt tct gct tat gat aat ctc aac aaa gtt cga 144
Ala Tyr Gly Met Val Cys Ser Ala Tyr Asp Asn Leu Asn Lys Val Arg
            35                  40                  45 gtt gct atc aag aaa atc agt cct ttt gag cac cag acc tac tgt cag 192
Val Ala Ile Lys Lys Ile Ser Pro Phe Glu His Gln Thr Tyr Cys Gln
        50                  55                  60 aga acc ctg aga gag ata aaa atc cta ctg cgc ttc aga cat gag aac 240
Arg Thr Leu Arg Glu Ile Lys Ile Leu Leu Arg Phe Arg His Glu Asn
65                  70                  75                  80 atc atc ggc atc aat gac atc atc cgg gca cca acc att gag cag atg 288
Ile Ile Gly Ile Asn Asp Ile Ile Arg Ala Pro Thr Ile Glu Gln Met
                85                  90                  95 aaa gat gta tat ata gta cag gac ctc atg gag aca gat ctt tac aag 336
Lys Asp Val Tyr Ile Val Gln Asp Leu Met Glu Thr Asp Leu Tyr Lys
            100                 105                 110 ctc ttg aag aca cag cac ctc agc aat gat cat atc tgc tat ttt ctt 384
Leu Leu Lys Thr Gln His Leu Ser Asn Asp His Ile Cys Tyr Phe Leu
        115                 120                 125 tat cag atc ctg aga gga tta aag tat ata cat tca gct aat gtt ctg 432
Tyr Gln Ile Leu Arg Gly Leu Lys Tyr Ile His Ser Ala Asn Val Leu
130                 135                 140 cac cgt gac ctc aag cct tcc aac ctc ctg aac acc act tgt gat     480
His Arg Asp Leu Lys Pro Ser Asn Leu Leu Asn Thr Thr Cys Asp
145                 150                 155                 160 ctc aag atc tgt gac ttt ggc ctt gcc cgt gtt gca gat cca gac cat 528
Leu Lys Ile Cys Asp Phe Gly Leu Ala Arg Val Ala Asp Pro Asp His
                165                 170                 175 gat cat aca ggg ttc ttg aca gag tat gta gcc acg cgt tgg tac aga 576
Asp His Thr Gly Phe Leu Thr Glu Tyr Val Ala Thr Arg Trp Tyr Arg
            180                 185                 190 gct cca gaa att atg ttg aat tcc aag ggt tat acc aag tcc att gat 624
Ala Pro Glu Ile Met Leu Asn Ser Lys Gly Tyr Thr Lys Ser Ile Asp
        195                 200                 205 att tgg tct gtg ggc tgc atc ctg gca gag atg cta tcc aac agg cct 672
Ile Trp Ser Val Gly Cys Ile Leu Ala Glu Met Leu Ser Asn Arg Pro
    210                 215                 220 atc ttc cca gga aag cat tac ctt gac cag ctg aat cac atc ctg ggt 720
Ile Phe Pro Gly Lys His Tyr Leu Asp Gln Leu Asn His Ile Leu Gly
225                 230                 235                 240 att ctt gga tct cca tca cag gaa gat ctg aat tgt ata ata aat tta 768
Ile Leu Gly Ser Pro Ser Gln Glu Asp Leu Asn Cys Ile Ile Asn Leu
                245                 250                 255 aaa gct aga aac tat ttg ctt tct ctc ccg cac aaa aat aag gtg ccg 816
Lys Ala Arg Asn Tyr Leu Leu Ser Leu Pro His Lys Asn Lys Val Pro
            260                 265                 270 tgg aac agg ttg ttc cca aac gct gac tcc aaa gct ctg gat tta ctg 864
Trp Asn Arg Leu Phe Pro Asn Ala Asp Ser Lys Ala Leu Asp Leu Leu
        275                 280                 285 gat aaa atg ttg aca ttt aac cct cac aag agg att gaa gtt gaa cag 912
Asp Lys Met Leu Thr Phe Asn Pro His Lys Arg Ile Glu Val Glu Gln
    290                 295                 300 gct ctg gcc cac ccg tac ctg gag cag tat tat gac cca agt gat gag 960
Ala Leu Ala His Pro Tyr Leu Glu Gln Tyr Tyr Asp Pro Ser Asp Glu
```

```
Ala Leu Ala His Pro Tyr Leu Glu Gln Tyr Tyr Asp Pro Ser Asp Glu
305                 310                 315                 320 ccc att gct gaa gca cca ttc aag ttt gac atg gag ctg gac gac tta    1008
Pro Ile Ala Glu Ala Pro Phe Lys Phe Asp Met Glu Leu Asp Asp Leu
                325                 330                 335 cct aag gag aag ctc aaa gaa ctc att ttt gaa gag act gct cga ttc    1056
Pro Lys Glu Lys Leu Lys Glu Leu Ile Phe Glu Glu Thr Ala Arg Phe
            340                 345                 350 cag cca gga tac aga tct atg gat cca ccg gtc gcc acc atg gtg agc    1104
Gln Pro Gly Tyr Arg Ser Met Asp Pro Pro Val Ala Thr Met Val Ser
        355                 360                 365 aag ggc gag gag ctg ttc acc ggg gtg gtg ccc atc ctg gtc gag ctg    1152
Lys Gly Glu Glu Leu Phe Thr Gly Val Val Pro Ile Leu Val Glu Leu
    370                 375                 380 gac ggc gac gta aac ggc cac aag ttc agc gtg tcc ggc gag ggc gag    1200
Asp Gly Asp Val Asn Gly His Lys Phe Ser Val Ser Gly Glu Gly Glu
385                 390                 395                 400 ggc gat gcc acc tac ggc aag ctg acc ctg aag ttc atc tgc acc acc    1248
Gly Asp Ala Thr Tyr Gly Lys Leu Thr Leu Lys Phe Ile Cys Thr Thr
                405                 410                 415 ggc aag ctg ccc gtg ccc tgg ccc acc ctc gtg acc acc ctg acc tac    1296
Gly Lys Leu Pro Val Pro Trp Pro Thr Leu Val Thr Thr Leu Thr Tyr
            420                 425                 430 ggc gtg cag tgc ttc agc cgc tac ccc gac cac atg aag cag cac gac    1344
Gly Val Gln Cys Phe Ser Arg Tyr Pro Asp His Met Lys Gln His Asp
        435                 440                 445 ttc ttc aag tcc gcc atg ccc gaa ggc tac gtc cag gag cgc acc atc    1392
Phe Phe Lys Ser Ala Met Pro Glu Gly Tyr Val Gln Glu Arg Thr Ile
    450                 455                 460 ttc ttc aag gac gac ggc aac tac aag acc cgc gcc gag gtg aag ttc    1440
Phe Phe Lys Asp Asp Gly Asn Tyr Lys Thr Arg Ala Glu Val Lys Phe
465                 470                 475                 480 gag ggc gac acc ctg gtg aac cgc atc gag ctg aag ggc atc gac ttc    1488
Glu Gly Asp Thr Leu Val Asn Arg Ile Glu Leu Lys Gly Ile Asp Phe
                485                 490                 495 aag gag gac ggc aac atc ctg ggg cac aag ctg gag tac aac tac aac    1536
Lys Glu Asp Gly Asn Ile Leu Gly His Lys Leu Glu Tyr Asn Tyr Asn
            500                 505                 510 agc cac aac gtc tat atc atg gcc gac aag cag aag aac ggc atc aag    1584
Ser His Asn Val Tyr Ile Met Ala Asp Lys Gln Lys Asn Gly Ile Lys
        515                 520                 525 gtg aac ttc aag atc cgc cac aac atc gag gac ggc agc gtg cag ctc    1632
Val Asn Phe Lys Ile Arg His Asn Ile Glu Asp Gly Ser Val Gln Leu
    530                 535                 540 gcc gac cac tac cag cag aac acc ccc atc ggc gac ggc ccc gtg ctg    1680
Ala Asp His Tyr Gln Gln Asn Thr Pro Ile Gly Asp Gly Pro Val Leu
545                 550                 555                 560 ctg ccc gac aac cac tac ctg agc acc cag tcc gcc ctg agc aaa gac    1728
Leu Pro Asp Asn His Tyr Leu Ser Thr Gln Ser Ala Leu Ser Lys Asp
                565                 570                 575 ccc aac gag aag cgc gat cac atg gtc ctg ctg gag ttc gtg acc gcc    1776
Pro Asn Glu Lys Arg Asp His Met Val Leu Leu Glu Phe Val Thr Ala
            580                 585                 590 gcc ggg atc act ctc ggc atg gac gag ctg tac aag taa                1815
Ala Gly Ile Thr Leu Gly Met Asp Glu Leu Tyr Lys
        595                 600

<210> SEQ ID NO 59
<211> LENGTH: 604
<212> TYPE: PRT
```

<213> ORGANISM: Artificial Sequence
<220> FEATURE:
<223> OTHER INFORMATION: Erk2-EGFP fusion

<400> SEQUENCE: 59

```
Met Ala Ala Ala Ala Ala Gly Pro Glu Met Val Arg Gly Gln Val
1               5                   10                  15

Phe Asp Val Gly Pro Arg Tyr Thr Asn Leu Ser Tyr Ile Gly Glu Gly
            20                  25                  30

Ala Tyr Gly Met Val Cys Ser Ala Tyr Asp Asn Leu Asn Lys Val Arg
        35                  40                  45

Val Ala Ile Lys Lys Ile Ser Pro Phe Glu His Gln Thr Tyr Cys Gln
    50                  55                  60

Arg Thr Leu Arg Glu Ile Lys Ile Leu Leu Arg Phe Arg His Glu Asn
65                  70                  75                  80

Ile Ile Gly Ile Asn Asp Ile Ile Arg Ala Pro Thr Ile Glu Gln Met
                85                  90                  95

Lys Asp Val Tyr Ile Val Gln Asp Leu Met Glu Thr Asp Leu Tyr Lys
            100                 105                 110

Leu Leu Lys Thr Gln His Leu Ser Asn Asp His Ile Cys Tyr Phe Leu
        115                 120                 125

Tyr Gln Ile Leu Arg Gly Leu Lys Tyr Ile His Ser Ala Asn Val Leu
    130                 135                 140

His Arg Asp Leu Lys Pro Ser Asn Leu Leu Asn Thr Thr Cys Asp
145                 150                 155                 160

Leu Lys Ile Cys Asp Phe Gly Leu Ala Arg Val Ala Asp Pro Asp His
                165                 170                 175

Asp His Thr Gly Phe Leu Thr Glu Tyr Val Ala Thr Arg Trp Tyr Arg
            180                 185                 190

Ala Pro Glu Ile Met Leu Asn Ser Lys Gly Tyr Thr Lys Ser Ile Asp
        195                 200                 205

Ile Trp Ser Val Gly Cys Ile Leu Ala Glu Met Leu Ser Asn Arg Pro
    210                 215                 220

Ile Phe Pro Gly Lys His Tyr Leu Asp Gln Leu Asn His Ile Leu Gly
225                 230                 235                 240

Ile Leu Gly Ser Pro Ser Gln Glu Asp Leu Asn Cys Ile Ile Asn Leu
                245                 250                 255

Lys Ala Arg Asn Tyr Leu Leu Ser Leu Pro His Lys Asn Lys Val Pro
            260                 265                 270

Trp Asn Arg Leu Phe Pro Asn Ala Asp Ser Lys Ala Leu Asp Leu Leu
        275                 280                 285

Asp Lys Met Leu Thr Phe Asn Pro His Lys Arg Ile Glu Val Glu Gln
    290                 295                 300

Ala Leu Ala His Pro Tyr Leu Glu Gln Tyr Tyr Asp Pro Ser Asp Glu
305                 310                 315                 320

Pro Ile Ala Glu Ala Pro Phe Lys Phe Asp Met Glu Leu Asp Asp Leu
                325                 330                 335

Pro Lys Glu Lys Leu Lys Glu Leu Ile Phe Glu Glu Thr Ala Arg Phe
            340                 345                 350

Gln Pro Gly Tyr Arg Ser Met Asp Pro Pro Val Ala Thr Met Val Ser
        355                 360                 365

Lys Gly Glu Glu Leu Phe Thr Gly Val Val Pro Ile Leu Val Glu Leu
    370                 375                 380

Asp Gly Asp Val Asn Gly His Lys Phe Ser Val Ser Gly Glu Gly Glu
```

-continued

```
                      385                 390                 395                 400
        Gly Asp Ala Thr Tyr Gly Lys Leu Thr Leu Lys Phe Ile Cys Thr Thr
                        405                 410                 415

Gly Lys Leu Pro Val Pro Trp Pro Thr Leu Val Thr Thr Leu Thr Tyr
                        420                 425                 430

Gly Val Gln Cys Phe Ser Arg Tyr Pro Asp His Met Lys Gln His Asp
                        435                 440                 445

Phe Phe Lys Ser Ala Met Pro Glu Gly Tyr Val Gln Glu Arg Thr Ile
                        450                 455                 460

Phe Phe Lys Asp Asp Gly Asn Tyr Lys Thr Arg Ala Glu Val Lys Phe
        465                 470                 475                 480

Glu Gly Asp Thr Leu Val Asn Arg Ile Glu Leu Lys Gly Ile Asp Phe
                        485                 490                 495

Lys Glu Asp Gly Asn Ile Leu Gly His Lys Leu Glu Tyr Asn Tyr Asn
                        500                 505                 510

Ser His Asn Val Tyr Ile Met Ala Asp Lys Gln Lys Asn Gly Ile Lys
                        515                 520                 525

Val Asn Phe Lys Ile Arg His Asn Ile Glu Asp Gly Ser Val Gln Leu
                        530                 535                 540

Ala Asp His Tyr Gln Gln Asn Thr Pro Ile Gly Asp Gly Pro Val Leu
        545                 550                 555                 560

Leu Pro Asp Asn His Tyr Leu Ser Thr Gln Ser Ala Leu Ser Lys Asp
                        565                 570                 575

Pro Asn Glu Lys Arg Asp His Met Val Leu Leu Glu Phe Val Thr Ala
                        580                 585                 590

Ala Gly Ile Thr Leu Gly Met Asp Glu Leu Tyr Lys
                        595                 600

<210> SEQ ID NO 60
<211> LENGTH: 2511
<212> TYPE: DNA
<213> ORGANISM: Artificial Sequence
<220> FEATURE:
<223> OTHER INFORMATION: Grk5-EGFP fusion
<220> FEATURE:
<221> NAME/KEY: CDS
<222> LOCATION: (1)..(2508)

<400> SEQUENCE: 60 atg gag ctg gaa aac atc gtg gcc aac acg gtc ttg ctg aaa gcc agg      48
Met Glu Leu Glu Asn Ile Val Ala Asn Thr Val Leu Leu Lys Ala Arg
1               5                   10                  15 gaa ggg ggc gga gga aag cgc aaa ggg aaa agc aag aag tgg aaa gaa      96
Glu Gly Gly Gly Gly Lys Arg Lys Gly Lys Ser Lys Lys Trp Lys Glu
            20                  25                  30 atc ctg aag ttc cct cac att agc cag tgt gaa gac ctc cga agg acc     144
Ile Leu Lys Phe Pro His Ile Ser Gln Cys Glu Asp Leu Arg Arg Thr
        35                  40                  45 ata gac aga gat tac tgc agt tta tgt gac aag cag cca atc ggg agg     192
Ile Asp Arg Asp Tyr Cys Ser Leu Cys Asp Lys Gln Pro Ile Gly Arg
    50                  55                  60 ctg ctt ttc cgg cag ttt tgt gaa acc agg cct ggg ctg gag tgt tac     240
Leu Leu Phe Arg Gln Phe Cys Glu Thr Arg Pro Gly Leu Glu Cys Tyr
65                  70                  75                  80 att cag ttc ctg gac tcc gtg gca gaa tat gaa gtt act cca gat gaa     288
Ile Gln Phe Leu Asp Ser Val Ala Glu Tyr Glu Val Thr Pro Asp Glu
                85                  90                  95 aaa ctg gga gag aaa ggg aag gaa att atg acc aag tac ctc acc cca     336
```

-continued

```
                Lys Leu Gly Glu Lys Gly Lys Glu Ile Met Thr Lys Tyr Leu Thr Pro
                                100                 105                 110 aag tcc cct gtt ttc ata gcc caa gtt ggc caa gac ctg gtc tcc cag              384
Lys Ser Pro Val Phe Ile Ala Gln Val Gly Gln Asp Leu Val Ser Gln
            115                 120                 125 acg gag gag aag ctc cta cag aag ccg tgc aaa gaa ctc ttt tct gcc              432
Thr Glu Glu Lys Leu Leu Gln Lys Pro Cys Lys Glu Leu Phe Ser Ala
        130                 135                 140 tgt gca cag tct gtc cac gag tac ctg agg gga gaa cca ttc cac gaa              480
Cys Ala Gln Ser Val His Glu Tyr Leu Arg Gly Glu Pro Phe His Glu
145                 150                 155                 160 tat ctg gac agc atg ttt ttt gac cgc ttt ctc cag tgg aag tgg ttg              528
Tyr Leu Asp Ser Met Phe Phe Asp Arg Phe Leu Gln Trp Lys Trp Leu
                165                 170                 175 gaa agg caa ccg gtg acc aaa aac act ttc agg cag tat cga gtg cta              576
Glu Arg Gln Pro Val Thr Lys Asn Thr Phe Arg Gln Tyr Arg Val Leu
            180                 185                 190 gga aaa ggg ggc ttc ggg gag gtc tgt gcc tgc cag gtt cgg gcc acg              624
Gly Lys Gly Gly Phe Gly Glu Val Cys Ala Cys Gln Val Arg Ala Thr
        195                 200                 205 ggt aaa atg tat gcc tgc aag cgc ttg gag aag aag agg atc aaa aag              672
Gly Lys Met Tyr Ala Cys Lys Arg Leu Glu Lys Lys Arg Ile Lys Lys
210                 215                 220 agg aaa ggg gag tcc atg gcc ctc aat gag aag cag atc ctc gag aag              720
Arg Lys Gly Glu Ser Met Ala Leu Asn Glu Lys Gln Ile Leu Glu Lys
225                 230                 235                 240 gtc aac agt cag ttt gtg gtc aac ctg gcc tat gcc tac gag acc aag              768
Val Asn Ser Gln Phe Val Val Asn Leu Ala Tyr Ala Tyr Glu Thr Lys
                245                 250                 255 gat gca ctg tgc ttg gtc ctg acc atc atg aat ggg ggt gac ctg aag              816
Asp Ala Leu Cys Leu Val Leu Thr Ile Met Asn Gly Gly Asp Leu Lys
            260                 265                 270 ttc cac atc tac aac atg ggc aac cct ggc ttc gag gag gag cgg gcc              864
Phe His Ile Tyr Asn Met Gly Asn Pro Gly Phe Glu Glu Glu Arg Ala
        275                 280                 285 ttg ttt tat gcg gca gag atc ctc tgc ggc tta gaa gac ctc cac cgt              912
Leu Phe Tyr Ala Ala Glu Ile Leu Cys Gly Leu Glu Asp Leu His Arg
    290                 295                 300 gag aac acc gtc tac cga gat ctg aaa cct gaa aac atc ctg tta gat              960
Glu Asn Thr Val Tyr Arg Asp Leu Lys Pro Glu Asn Ile Leu Leu Asp
305                 310                 315                 320 gat tat ggc cac att agg atc tca gac ctg ggc ttg gct gtg aag atc             1008
Asp Tyr Gly His Ile Arg Ile Ser Asp Leu Gly Leu Ala Val Lys Ile
                325                 330                 335 ccc gag gga gac ctg atc cgc ggc cgg gtg ggc act gtt ggc tac atg             1056
Pro Glu Gly Asp Leu Ile Arg Gly Arg Val Gly Thr Val Gly Tyr Met
            340                 345                 350 gcc ccc gaa gtc ctg aac aac cag agg tac ggc ctg agc ccc gac tac             1104
Ala Pro Glu Val Leu Asn Asn Gln Arg Tyr Gly Leu Ser Pro Asp Tyr
        355                 360                 365 tgg ggc ctt ggc tgc ctc atc tat gag atg atc gag ggc cag tcg ccg             1152
Trp Gly Leu Gly Cys Leu Ile Tyr Glu Met Ile Glu Gly Gln Ser Pro
    370                 375                 380 ttc cgc ggc cgt aag gag aag gtg aag cgg gag gag gtg gac cgc cgg             1200
Phe Arg Gly Arg Lys Glu Lys Val Lys Arg Glu Glu Val Asp Arg Arg
385                 390                 395                 400 gtc ctg gag acg gag gag gtg tac tcc cac aag ttc tcc gag gag gcc             1248
Val Leu Glu Thr Glu Glu Val Tyr Ser His Lys Phe Ser Glu Glu Ala
                405                 410                 415
```

-continued

| | |
|---|---|
| aag tcc atc tgc aag atg ctg ctc acg aaa gat gcg aag cag agg ctg<br>Lys Ser Ile Cys Lys Met Leu Leu Thr Lys Asp Ala Lys Gln Arg Leu<br>420                          425                         430 | 1296 |
| ggc tgc cag gag gag ggg gct gca gag gtc aag aga cac ccc ttc ttc<br>Gly Cys Gln Glu Glu Gly Ala Ala Glu Val Lys Arg His Pro Phe Phe<br>          435                       440                       445 | 1344 |
| agg aac atg aac ttc aag cgc tta gaa gcc ggg atg ttg gac cct ccc<br>Arg Asn Met Asn Phe Lys Arg Leu Glu Ala Gly Met Leu Asp Pro Pro<br>450                          455                       460 | 1392 |
| ttc gtt cca gac ccc cgc gct gtg tac tgt aag gac gtg ctg gac atc<br>Phe Val Pro Asp Pro Arg Ala Val Tyr Cys Lys Asp Val Leu Asp Ile<br>465                         470                       475                       480 | 1440 |
| gag cag ttc tcc act gtg aag ggc gtc aat ctg gac cac aca gac gac<br>Glu Gln Phe Ser Thr Val Lys Gly Val Asn Leu Asp His Thr Asp Asp<br>                   485                       490                       495 | 1488 |
| gac ttc tac tcc aag ttc tcc acg ggc tct gtg tcc atc cca tgg caa<br>Asp Phe Tyr Ser Lys Phe Ser Thr Gly Ser Val Ser Ile Pro Trp Gln<br>500                          505                       510 | 1536 |
| aac gag atg ata gaa aca gaa tgc ttt aag gag ctg aac gtg ttt gga<br>Asn Glu Met Ile Glu Thr Glu Cys Phe Lys Glu Leu Asn Val Phe Gly<br>                   515                       520                       525 | 1584 |
| cct aat ggt acc ctc ccg cca gat ctg aac aga aac cac cct ccg gaa<br>Pro Asn Gly Thr Leu Pro Pro Asp Leu Asn Arg Asn His Pro Pro Glu<br>530                          535                       540 | 1632 |
| ccg ccc aag aaa ggg ctg ctc cag aga ctc ttc aag cgg cag cat cag<br>Pro Pro Lys Lys Gly Leu Leu Gln Arg Leu Phe Lys Arg Gln His Gln<br>545                         550                       555                       560 | 1680 |
| aac aat tcc aag agt tcg ccc agc tcc aag acc agt ttt aac cac cac<br>Asn Asn Ser Lys Ser Ser Pro Ser Ser Lys Thr Ser Phe Asn His His<br>                   565                       570                       575 | 1728 |
| ata aac tca aac cat gtc agc tcg aac tcc acc gga agc agc agg gat<br>Ile Asn Ser Asn His Val Ser Ser Asn Ser Thr Gly Ser Ser Arg Asp<br>580                          585                       590 | 1776 |
| cca ccg gtc gcc acc atg gtg agc aag ggc gag gag ctg ttc acc ggg<br>Pro Pro Val Ala Thr Met Val Ser Lys Gly Glu Glu Leu Phe Thr Gly<br>          595                       600                       605 | 1824 |
| gtg gtg ccc atc ctg gtc gag ctg gac ggc gac gta aac ggc cac aag<br>Val Val Pro Ile Leu Val Glu Leu Asp Gly Asp Val Asn Gly His Lys<br>610                         615                       620 | 1872 |
| ttc agc gtg tcc ggc gag ggc gag ggc gat gcc acc tac ggc aag ctg<br>Phe Ser Val Ser Gly Glu Gly Glu Gly Asp Ala Thr Tyr Gly Lys Leu<br>625                         630                       635                       640 | 1920 |
| acc ctg aag ttc atc tgc acc acc ggc aag ctg ccc gtg ccc tgg ccc<br>Thr Leu Lys Phe Ile Cys Thr Thr Gly Lys Leu Pro Val Pro Trp Pro<br>                   645                       650                       655 | 1968 |
| acc ctc gtg acc acc ctg acc tac ggc gtg cag tgc ttc agc cgc tac<br>Thr Leu Val Thr Thr Leu Thr Tyr Gly Val Gln Cys Phe Ser Arg Tyr<br>660                          665                       670 | 2016 |
| ccc gac cac atg aag cag cac gac ttc ttc aag tcc gcc atg ccc gaa<br>Pro Asp His Met Lys Gln His Asp Phe Phe Lys Ser Ala Met Pro Glu<br>          675                       680                       685 | 2064 |
| ggc tac gtc cag gag cgc acc atc ttc ttc aag gac gac ggc aac tac<br>Gly Tyr Val Gln Glu Arg Thr Ile Phe Phe Lys Asp Asp Gly Asn Tyr<br>690                         695                       700 | 2112 |
| aag acc cgc gcc gag gtg aag ttc gag ggc gac acc ctg gtg aac cgc<br>Lys Thr Arg Ala Glu Val Lys Phe Glu Gly Asp Thr Leu Val Asn Arg<br>705                         710                       715                       720 | 2160 |
| atc gag ctg aag ggc atc gac ttc aag gag gac ggc aac atc ctg ggg<br>Ile Glu Leu Lys Gly Ile Asp Phe Lys Glu Asp Gly Asn Ile Leu Gly<br>                   725                       730                       735 | 2208 |

```
cac aag ctg gag tac aac tac aac agc cac aac gtc tat atc atg gcc    2256
His Lys Leu Glu Tyr Asn Tyr Asn Ser His Asn Val Tyr Ile Met Ala
            740                 745                 750 gac aag cag aag aac ggc atc aag gtg aac ttc aag atc cgc cac aac    2304
Asp Lys Gln Lys Asn Gly Ile Lys Val Asn Phe Lys Ile Arg His Asn
        755                 760                 765 atc gag gac ggc agc gtg cag ctc gcc gac cac tac cag cag aac acc    2352
Ile Glu Asp Gly Ser Val Gln Leu Ala Asp His Tyr Gln Gln Asn Thr
770                 775                 780 ccc atc ggc gac ggc ccc gtg ctg ctg ccc gac aac cac tac ctg agc    2400
Pro Ile Gly Asp Gly Pro Val Leu Leu Pro Asp Asn His Tyr Leu Ser
785                 790                 795                 800 acc cag tcc gcc ctg agc aaa gac ccc aac gag aag cgc gat cac atg    2448
Thr Gln Ser Ala Leu Ser Lys Asp Pro Asn Glu Lys Arg Asp His Met
                805                 810                 815 gtc ctg ctg gag ttc gtg acc gcc gcc ggg atc act ctc ggc atg gac    2496
Val Leu Leu Glu Phe Val Thr Ala Ala Gly Ile Thr Leu Gly Met Asp
            820                 825                 830 gag ctg tac aag taa                                                2511
Glu Leu Tyr Lys
        835

<210> SEQ ID NO 61
<211> LENGTH: 836
<212> TYPE: PRT
<213> ORGANISM: Artificial Sequence
<220> FEATURE:
<223> OTHER INFORMATION: Grk5-EGFP fusion

<400> SEQUENCE: 61

Met Glu Leu Glu Asn Ile Val Ala Asn Thr Val Leu Leu Lys Ala Arg
1               5                   10                  15

Glu Gly Gly Gly Gly Lys Arg Lys Gly Lys Ser Lys Lys Trp Lys Glu
            20                  25                  30

Ile Leu Lys Phe Pro His Ile Ser Gln Cys Glu Asp Leu Arg Arg Thr
        35                  40                  45

Ile Asp Arg Asp Tyr Cys Ser Leu Cys Asp Lys Gln Pro Ile Gly Arg
    50                  55                  60

Leu Leu Phe Arg Gln Phe Cys Glu Thr Arg Pro Gly Leu Glu Cys Tyr
65                  70                  75                  80

Ile Gln Phe Leu Asp Ser Val Ala Glu Tyr Glu Val Thr Pro Asp Glu
                85                  90                  95

Lys Leu Gly Glu Lys Gly Lys Glu Ile Met Thr Lys Tyr Leu Thr Pro
            100                 105                 110

Lys Ser Pro Val Phe Ile Ala Gln Val Gly Gln Asp Leu Val Ser Gln
        115                 120                 125

Thr Glu Glu Lys Leu Leu Gln Lys Pro Cys Lys Glu Leu Phe Ser Ala
    130                 135                 140

Cys Ala Gln Ser Val His Glu Tyr Leu Arg Gly Glu Pro Phe His Glu
145                 150                 155                 160

Tyr Leu Asp Ser Met Phe Phe Asp Arg Phe Leu Gln Trp Lys Trp Leu
                165                 170                 175

Glu Arg Gln Pro Val Thr Lys Asn Thr Phe Arg Gln Tyr Arg Val Leu
            180                 185                 190

Gly Lys Gly Gly Phe Gly Glu Val Cys Ala Cys Gln Val Arg Ala Thr
        195                 200                 205

Gly Lys Met Tyr Ala Cys Lys Arg Leu Glu Lys Lys Arg Ile Lys Lys
```

-continued

```
            210                 215                 220
Arg Lys Gly Glu Ser Met Ala Leu Asn Glu Lys Gln Ile Leu Glu Lys
225                 230                 235                 240

Val Asn Ser Gln Phe Val Val Asn Leu Ala Tyr Ala Tyr Glu Thr Lys
                    245                 250                 255

Asp Ala Leu Cys Leu Val Leu Thr Ile Met Asn Gly Gly Asp Leu Lys
                260                 265                 270

Phe His Ile Tyr Asn Met Gly Asn Pro Gly Phe Glu Glu Arg Ala
            275                 280                 285

Leu Phe Tyr Ala Ala Glu Ile Leu Cys Gly Leu Glu Asp Leu His Arg
290                 295                 300

Glu Asn Thr Val Tyr Arg Asp Leu Lys Pro Glu Asn Ile Leu Leu Asp
305                 310                 315                 320

Asp Tyr Gly His Ile Arg Ile Ser Asp Leu Gly Leu Ala Val Lys Ile
                325                 330                 335

Pro Glu Gly Asp Leu Ile Arg Gly Arg Val Gly Thr Val Gly Tyr Met
                340                 345                 350

Ala Pro Glu Val Leu Asn Asn Gln Arg Tyr Gly Leu Ser Pro Asp Tyr
            355                 360                 365

Trp Gly Leu Gly Cys Leu Ile Tyr Glu Met Ile Glu Gly Gln Ser Pro
370                 375                 380

Phe Arg Gly Arg Lys Glu Lys Val Lys Arg Glu Glu Val Asp Arg Arg
385                 390                 395                 400

Val Leu Glu Thr Glu Glu Val Tyr Ser His Lys Phe Ser Glu Glu Ala
                405                 410                 415

Lys Ser Ile Cys Lys Met Leu Leu Thr Lys Asp Ala Lys Gln Arg Leu
                420                 425                 430

Gly Cys Gln Glu Glu Gly Ala Ala Glu Val Lys Arg His Pro Phe Phe
            435                 440                 445

Arg Asn Met Asn Phe Lys Arg Leu Glu Ala Gly Met Leu Asp Pro Pro
450                 455                 460

Phe Val Pro Asp Pro Arg Ala Val Tyr Cys Lys Asp Val Leu Asp Ile
465                 470                 475                 480

Glu Gln Phe Ser Thr Val Lys Gly Val Asn Leu Asp His Thr Asp Asp
                485                 490                 495

Asp Phe Tyr Ser Lys Phe Ser Thr Gly Ser Val Ser Ile Pro Trp Gln
            500                 505                 510

Asn Glu Met Ile Glu Thr Glu Cys Phe Lys Glu Leu Asn Val Phe Gly
            515                 520                 525

Pro Asn Gly Thr Leu Pro Pro Asp Leu Asn Arg Asn His Pro Pro Glu
            530                 535                 540

Pro Pro Lys Lys Gly Leu Leu Gln Arg Leu Phe Lys Arg Gln His Gln
545                 550                 555                 560

Asn Asn Ser Lys Ser Ser Pro Ser Ser Lys Thr Ser Phe Asn His His
                565                 570                 575

Ile Asn Ser Asn His Val Ser Ser Asn Ser Thr Gly Ser Ser Arg Asp
                580                 585                 590

Pro Pro Val Ala Thr Met Val Ser Lys Gly Glu Glu Leu Phe Thr Gly
            595                 600                 605

Val Val Pro Ile Leu Val Glu Leu Asp Gly Asp Val Asn Gly His Lys
            610                 615                 620

Phe Ser Val Ser Gly Glu Gly Glu Gly Asp Ala Thr Tyr Gly Lys Leu
625                 630                 635                 640
```

```
Thr Leu Lys Phe Ile Cys Thr Thr Gly Lys Leu Pro Val Pro Trp Pro
                645                 650                 655

Thr Leu Val Thr Thr Leu Thr Tyr Gly Val Gln Cys Phe Ser Arg Tyr
            660                 665                 670

Pro Asp His Met Lys Gln His Asp Phe Phe Lys Ser Ala Met Pro Glu
        675                 680                 685

Gly Tyr Val Gln Glu Arg Thr Ile Phe Phe Lys Asp Asp Gly Asn Tyr
    690                 695                 700

Lys Thr Arg Ala Glu Val Lys Phe Glu Gly Asp Thr Leu Val Asn Arg
705                 710                 715                 720

Ile Glu Leu Lys Gly Ile Asp Phe Lys Glu Asp Gly Asn Ile Leu Gly
                725                 730                 735

His Lys Leu Glu Tyr Asn Tyr Asn Ser His Asn Val Tyr Ile Met Ala
            740                 745                 750

Asp Lys Gln Lys Asn Gly Ile Lys Val Asn Phe Lys Ile Arg His Asn
        755                 760                 765

Ile Glu Asp Gly Ser Val Gln Leu Ala Asp His Tyr Gln Gln Asn Thr
    770                 775                 780

Pro Ile Gly Asp Gly Pro Val Leu Leu Pro Asp Asn His Tyr Leu Ser
785                 790                 795                 800

Thr Gln Ser Ala Leu Ser Lys Asp Pro Asn Glu Lys Arg Asp His Met
                805                 810                 815

Val Leu Leu Glu Phe Val Thr Ala Ala Gly Ile Thr Leu Gly Met Asp
            820                 825                 830

Glu Leu Tyr Lys
        835

<210> SEQ ID NO 62
<211> LENGTH: 1893
<212> TYPE: DNA
<213> ORGANISM: Artificial Sequence
<220> FEATURE:
<223> OTHER INFORMATION: Jnk1-EGFP Fusion
<220> FEATURE:
<221> NAME/KEY: CDS
<222> LOCATION: (1)..(1890)

<400> SEQUENCE: 62 atg agc aga agc aag cgt gac aac aat ttt tat agt gta gag att gga      48
Met Ser Arg Ser Lys Arg Asp Asn Asn Phe Tyr Ser Val Glu Ile Gly
1               5                   10                  15 gat tct aca ttc aca gtc ctg aaa cga tat cag aat tta aaa cct ata      96
Asp Ser Thr Phe Thr Val Leu Lys Arg Tyr Gln Asn Leu Lys Pro Ile
            20                  25                  30 ggc tca gga gct caa gga ata gta tgc gca gct tat gat gcc att ctt     144
Gly Ser Gly Ala Gln Gly Ile Val Cys Ala Ala Tyr Asp Ala Ile Leu
        35                  40                  45 gaa aga aat gtt gca atc aag aag cta agc cga cca ttt cag aat cag     192
Glu Arg Asn Val Ala Ile Lys Lys Leu Ser Arg Pro Phe Gln Asn Gln
    50                  55                  60 act cat gcc aag cgg gcc tac aga gag cta gtt ctt atg aaa tgt gtt     240
Thr His Ala Lys Arg Ala Tyr Arg Glu Leu Val Leu Met Lys Cys Val
65                  70                  75                  80 aat cac aaa aat ata att ggc ctt ttg aat gtt ttc aca cca cag aaa     288
Asn His Lys Asn Ile Ile Gly Leu Leu Asn Val Phe Thr Pro Gln Lys
                85                  90                  95 tcc cta gaa gaa ttt caa gat gtt tac ata gtc atg gag ctc atg gat     336
Ser Leu Glu Glu Phe Gln Asp Val Tyr Ile Val Met Glu Leu Met Asp
```

```
            100                 105                 110
gca aat ctt tgc caa gtg att cag atg gag cta gat cat gaa aga atg     384
Ala Asn Leu Cys Gln Val Ile Gln Met Glu Leu Asp His Glu Arg Met
            115                 120                 125 tcc tac ctt ctc tat cag atg ctg tgt gga atc aag cac ctt cat tct     432
Ser Tyr Leu Leu Tyr Gln Met Leu Cys Gly Ile Lys His Leu His Ser
            130                 135                 140 gct gga att att cat cgg gac tta aag ccc agt aat ata gta gta aaa     480
Ala Gly Ile Ile His Arg Asp Leu Lys Pro Ser Asn Ile Val Val Lys
145                 150                 155                 160 tct gat tgc act ttg aag att ctt gac ttc ggt ctg gcc agg act gca     528
Ser Asp Cys Thr Leu Lys Ile Leu Asp Phe Gly Leu Ala Arg Thr Ala
            165                 170                 175 gga acg agt ttt atg atg acg cct tat gta gtg act cgc tac tac aga     576
Gly Thr Ser Phe Met Met Thr Pro Tyr Val Val Thr Arg Tyr Tyr Arg
            180                 185                 190 gca ccc gag gtc atc ctt ggc atg ggc tac aag gaa aac gtg gat tta     624
Ala Pro Glu Val Ile Leu Gly Met Gly Tyr Lys Glu Asn Val Asp Leu
            195                 200                 205 tgg tct gtg ggg tgc att atg gga gaa atg gtt tgc cac aaa atc ctc     672
Trp Ser Val Gly Cys Ile Met Gly Glu Met Val Cys His Lys Ile Leu
            210                 215                 220 ttt cca gga agg gac tat att gat cag tgg aat aaa gtt att gaa cag     720
Phe Pro Gly Arg Asp Tyr Ile Asp Gln Trp Asn Lys Val Ile Glu Gln
225                 230                 235                 240 ctt gga aca cca tgt cct gaa ttc atg aag aaa ctg caa cca aca gta     768
Leu Gly Thr Pro Cys Pro Glu Phe Met Lys Lys Leu Gln Pro Thr Val
            245                 250                 255 agg act tac gtt gaa aac aga cct aaa tat gct gga tat agc ttt gag     816
Arg Thr Tyr Val Glu Asn Arg Pro Lys Tyr Ala Gly Tyr Ser Phe Glu
            260                 265                 270 aaa ctc ttc cct gat gtc ctt ttc cca gct gac tca gaa cac aac aaa     864
Lys Leu Phe Pro Asp Val Leu Phe Pro Ala Asp Ser Glu His Asn Lys
            275                 280                 285 ctt aaa gcc agt cag gca agg gat ttg tta tcc aaa atg ctg gta ata     912
Leu Lys Ala Ser Gln Ala Arg Asp Leu Leu Ser Lys Met Leu Val Ile
            290                 295                 300 gat gca tct aaa agg atc tct gta gat gaa gct ctc caa cac ccg tac     960
Asp Ala Ser Lys Arg Ile Ser Val Asp Glu Ala Leu Gln His Pro Tyr
305                 310                 315                 320 atc aat gtc tgg tat gat cct tct gaa gca gaa gct cca cca cca aag    1008
Ile Asn Val Trp Tyr Asp Pro Ser Glu Ala Glu Ala Pro Pro Pro Lys
            325                 330                 335 atc cct gac aag cag tta gat gaa agg gaa cac aca ata gaa gag tgg    1056
Ile Pro Asp Lys Gln Leu Asp Glu Arg Glu His Thr Ile Glu Glu Trp
            340                 345                 350 aaa gaa ttg ata tat aag gaa gtt atg gac ttg gag gag aga acc aag    1104
Lys Glu Leu Ile Tyr Lys Glu Val Met Asp Leu Glu Glu Arg Thr Lys
            355                 360                 365 aat gga gtt ata cgg ggg cag ccc tct cct tta gca cag gtg cag cag    1152
Asn Gly Val Ile Arg Gly Gln Pro Ser Pro Leu Ala Gln Val Gln Gln
            370                 375                 380 tgg gat cca ccg gtc gcc acc atg gtg agc aag ggc gag gag ctg ttc    1200
Trp Asp Pro Pro Val Ala Thr Met Val Ser Lys Gly Glu Glu Leu Phe
385                 390                 395                 400 acc ggg gtg gtg ccc atc ctg gtc gag ctg gac ggc gac gta aac ggc    1248
Thr Gly Val Val Pro Ile Leu Val Glu Leu Asp Gly Asp Val Asn Gly
            405                 410                 415 cac aag ttc agc gtg tcc ggc gag ggc gag ggc gat gcc acc tac ggc    1296
```

```
                                                                                  -continued His Lys Phe Ser Val Ser Gly Glu Gly Glu Gly Asp Ala Thr Tyr Gly
            420                 425                 430 aag ctg acc ctg aag ttc atc tgc acc acc ggc aag ctg ccc gtg ccc    1344
Lys Leu Thr Leu Lys Phe Ile Cys Thr Thr Gly Lys Leu Pro Val Pro
        435                 440                 445 tgg ccc acc ctc gtg acc acc ctg acc tac ggc gtg cag tgc ttc agc    1392
Trp Pro Thr Leu Val Thr Thr Leu Thr Tyr Gly Val Gln Cys Phe Ser
450                 455                 460 cgc tac ccc gac cac atg aag cag cac gac ttc ttc aag tcc gcc atg    1440
Arg Tyr Pro Asp His Met Lys Gln His Asp Phe Phe Lys Ser Ala Met
465                 470                 475                 480 ccc gaa ggc tac gtc cag gag cgc acc atc ttc ttc aag gac gac ggc    1488
Pro Glu Gly Tyr Val Gln Glu Arg Thr Ile Phe Phe Lys Asp Asp Gly
                485                 490                 495 aac tac aag acc cgc gcc gag gtg aag ttc gag ggc gac acc ctg gtg    1536
Asn Tyr Lys Thr Arg Ala Glu Val Lys Phe Glu Gly Asp Thr Leu Val
            500                 505                 510 aac cgc atc gag ctg aag ggc atc gac ttc aag gag gac ggc aac atc    1584
Asn Arg Ile Glu Leu Lys Gly Ile Asp Phe Lys Glu Asp Gly Asn Ile
        515                 520                 525 ctg ggg cac aag ctg gag tac aac tac aac agc cac aac gtc tat atc    1632
Leu Gly His Lys Leu Glu Tyr Asn Tyr Asn Ser His Asn Val Tyr Ile
    530                 535                 540 atg gcc gac aag cag aag aac ggc atc aag gtg aac ttc aag atc cgc    1680
Met Ala Asp Lys Gln Lys Asn Gly Ile Lys Val Asn Phe Lys Ile Arg
545                 550                 555                 560 cac aac atc gag gac ggc agc gtg cag ctc gcc gac cac tac cag cag    1728
His Asn Ile Glu Asp Gly Ser Val Gln Leu Ala Asp His Tyr Gln Gln
                565                 570                 575 aac acc ccc atc ggc gac ggc ccc gtg ctg ctg ccc gac aac cac tac    1776
Asn Thr Pro Ile Gly Asp Gly Pro Val Leu Leu Pro Asp Asn His Tyr
            580                 585                 590 ctg agc acc cag tcc gcc ctg agc aaa gac ccc aac gag aag cgc gat    1824
Leu Ser Thr Gln Ser Ala Leu Ser Lys Asp Pro Asn Glu Lys Arg Asp
        595                 600                 605 cac atg gtc ctg ctg gag ttc gtg acc gcc gcc ggg atc act ctc ggc    1872
His Met Val Leu Leu Glu Phe Val Thr Ala Ala Gly Ile Thr Leu Gly
    610                 615                 620 atg gac gag ctg tac aag taa                                        1893
Met Asp Glu Leu Tyr Lys
625                 630

<210> SEQ ID NO 63
<211> LENGTH: 630
<212> TYPE: PRT
<213> ORGANISM: Artificial Sequence
<220> FEATURE:
<223> OTHER INFORMATION: Jnk1-EGFP Fusion

<400> SEQUENCE: 63

Met Ser Arg Ser Lys Arg Asp Asn Asn Phe Tyr Ser Val Glu Ile Gly
1               5                   10                  15

Asp Ser Thr Phe Thr Val Leu Lys Arg Tyr Gln Asn Leu Lys Pro Ile
            20                  25                  30

Gly Ser Gly Ala Gln Gly Ile Val Cys Ala Ala Tyr Asp Ala Ile Leu
        35                  40                  45

Glu Arg Asn Val Ala Ile Lys Lys Leu Ser Arg Pro Phe Gln Asn Gln
    50                  55                  60

Thr His Ala Lys Arg Ala Tyr Arg Glu Leu Val Leu Met Lys Cys Val
65                  70                  75                  80
```

```
Asn His Lys Asn Ile Ile Gly Leu Leu Asn Val Phe Thr Pro Gln Lys
                85                  90                  95
Ser Leu Glu Glu Phe Gln Asp Val Tyr Ile Val Met Glu Leu Met Asp
            100                 105                 110
Ala Asn Leu Cys Gln Val Ile Gln Met Glu Leu Asp His Glu Arg Met
        115                 120                 125
Ser Tyr Leu Leu Tyr Gln Met Leu Cys Gly Ile Lys His Leu His Ser
    130                 135                 140
Ala Gly Ile Ile His Arg Asp Leu Lys Pro Ser Asn Ile Val Val Lys
145                 150                 155                 160
Ser Asp Cys Thr Leu Lys Ile Leu Asp Phe Gly Leu Ala Arg Thr Ala
                165                 170                 175
Gly Thr Ser Phe Met Met Thr Pro Tyr Val Val Thr Arg Tyr Tyr Arg
            180                 185                 190
Ala Pro Glu Val Ile Leu Gly Met Gly Tyr Lys Glu Asn Val Asp Leu
        195                 200                 205
Trp Ser Val Gly Cys Ile Met Gly Glu Met Val Cys His Lys Ile Leu
    210                 215                 220
Phe Pro Gly Arg Asp Tyr Ile Asp Gln Trp Asn Lys Val Ile Glu Gln
225                 230                 235                 240
Leu Gly Thr Pro Cys Pro Glu Phe Met Lys Lys Leu Gln Pro Thr Val
                245                 250                 255
Arg Thr Tyr Val Glu Asn Arg Pro Lys Tyr Ala Gly Tyr Ser Phe Glu
            260                 265                 270
Lys Leu Phe Pro Asp Val Leu Phe Pro Ala Asp Ser Glu His Asn Lys
        275                 280                 285
Leu Lys Ala Ser Gln Ala Arg Asp Leu Leu Ser Lys Met Leu Val Ile
    290                 295                 300
Asp Ala Ser Lys Arg Ile Ser Val Asp Glu Ala Leu Gln His Pro Tyr
305                 310                 315                 320
Ile Asn Val Trp Tyr Asp Pro Ser Glu Ala Glu Ala Pro Pro Pro Lys
                325                 330                 335
Ile Pro Asp Lys Gln Leu Asp Glu Arg Glu His Thr Ile Glu Glu Trp
            340                 345                 350
Lys Glu Leu Ile Tyr Lys Glu Val Met Asp Leu Glu Glu Arg Thr Lys
        355                 360                 365
Asn Gly Val Ile Arg Gly Gln Pro Ser Pro Leu Ala Gln Val Gln Gln
    370                 375                 380
Trp Asp Pro Pro Val Ala Thr Met Val Ser Lys Gly Glu Glu Leu Phe
385                 390                 395                 400
Thr Gly Val Val Pro Ile Leu Val Glu Leu Asp Gly Asp Val Asn Gly
                405                 410                 415
His Lys Phe Ser Val Ser Gly Glu Gly Glu Gly Asp Ala Thr Tyr Gly
            420                 425                 430
Lys Leu Thr Leu Lys Phe Ile Cys Thr Thr Gly Lys Leu Pro Val Pro
        435                 440                 445
Trp Pro Thr Leu Val Thr Thr Leu Thr Tyr Gly Val Gln Cys Phe Ser
    450                 455                 460
Arg Tyr Pro Asp His Met Lys Gln His Asp Phe Phe Lys Ser Ala Met
465                 470                 475                 480
Pro Glu Gly Tyr Val Gln Glu Arg Thr Ile Phe Lys Asp Asp Gly
                485                 490                 495
```

```
Asn Tyr Lys Thr Arg Ala Glu Val Lys Phe Glu Gly Asp Thr Leu Val
            500                 505                 510

Asn Arg Ile Glu Leu Lys Gly Ile Asp Phe Lys Glu Asp Gly Asn Ile
            515                 520                 525

Leu Gly His Lys Leu Glu Tyr Asn Tyr Asn Ser His Asn Val Tyr Ile
        530                 535                 540

Met Ala Asp Lys Gln Lys Asn Gly Ile Lys Val Asn Phe Lys Ile Arg
545                 550                 555                 560

His Asn Ile Glu Asp Gly Ser Val Gln Leu Ala Asp His Tyr Gln Gln
                565                 570                 575

Asn Thr Pro Ile Gly Asp Gly Pro Val Leu Leu Pro Asp Asn His Tyr
            580                 585                 590

Leu Ser Thr Gln Ser Ala Leu Ser Lys Asp Pro Asn Glu Lys Arg Asp
            595                 600                 605

His Met Val Leu Leu Glu Phe Val Thr Ala Ala Gly Ile Thr Leu Gly
        610                 615                 620

Met Asp Glu Leu Tyr Lys
625                 630

<210> SEQ ID NO 64
<211> LENGTH: 1821
<212> TYPE: DNA
<213> ORGANISM: Artificial Sequence
<220> FEATURE:
<223> OTHER INFORMATION: p38-EGFP fusion
<220> FEATURE:
<221> NAME/KEY: CDS
<222> LOCATION: (1)..(1818)

<400> SEQUENCE: 64 atg tct cag gag agg ccc acg ttc tac cgg cag gag ctg aac aag aca      48
Met Ser Gln Glu Arg Pro Thr Phe Tyr Arg Gln Glu Leu Asn Lys Thr
1               5                   10                  15 atc tgg gag gtg ccc gag cgt tac cag aac ctg tct cca gtg ggc tct      96
Ile Trp Glu Val Pro Glu Arg Tyr Gln Asn Leu Ser Pro Val Gly Ser
            20                  25                  30 ggc gcc tat ggc tct gtg tgt gct gct ttt gac aca aaa acg ggg tta     144
Gly Ala Tyr Gly Ser Val Cys Ala Ala Phe Asp Thr Lys Thr Gly Leu
        35                  40                  45 cgt gtg gca gtg aag aag ctc tcc aga cca ttt cag tcc atc att cat     192
Arg Val Ala Val Lys Lys Leu Ser Arg Pro Phe Gln Ser Ile Ile His
    50                  55                  60 gcg aaa aga acc tac aga gaa ctg cgg tta ctt aaa cat atg aaa cat     240
Ala Lys Arg Thr Tyr Arg Glu Leu Arg Leu Leu Lys His Met Lys His
65                  70                  75                  80 gaa aat gtg att ggt ctg ttg gac gtt ttt aca cct gca agg tct ctg     288
Glu Asn Val Ile Gly Leu Leu Asp Val Phe Thr Pro Ala Arg Ser Leu
                85                  90                  95 gag gaa ttc aat gat gtg tat ctg gtg acc cat ctc atg ggg gca gat     336
Glu Glu Phe Asn Asp Val Tyr Leu Val Thr His Leu Met Gly Ala Asp
            100                 105                 110 ctg aac aac att gtg aaa tgt cag aag ctt aca gat gac cat gtt cag     384
Leu Asn Asn Ile Val Lys Cys Gln Lys Leu Thr Asp Asp His Val Gln
        115                 120                 125 ttc ctt atc tac caa att ctc cga ggt cta aag tat ata cat tca gct     432
Phe Leu Ile Tyr Gln Ile Leu Arg Gly Leu Lys Tyr Ile His Ser Ala
    130                 135                 140 gac ata att cac agg gac cta aaa cct agt aat cta gct gtg aat gaa     480
Asp Ile Ile His Arg Asp Leu Lys Pro Ser Asn Leu Ala Val Asn Glu
145                 150                 155                 160
```

```
gac tgt gag ctg aag att ctg gat ttt gga ctg gct cgg cac aca gat       528
Asp Cys Glu Leu Lys Ile Leu Asp Phe Gly Leu Ala Arg His Thr Asp
                165                 170                 175 gat gaa atg aca ggc tac gtg gcc act agg tgg tac agg gct cct gag       576
Asp Glu Met Thr Gly Tyr Val Ala Thr Arg Trp Tyr Arg Ala Pro Glu
            180                 185                 190 atc atg ctg aac tgg atg cat tac aac cag aca gtt gat att tgg tca       624
Ile Met Leu Asn Trp Met His Tyr Asn Gln Thr Val Asp Ile Trp Ser
        195                 200                 205 gtg gga tgc ata atg gcc gag ctg ttg act gga aga aca ttg ttt cct       672
Val Gly Cys Ile Met Ala Glu Leu Leu Thr Gly Arg Thr Leu Phe Pro
    210                 215                 220 ggt aca gac cat att gat cag ttg aag ctc att tta aga ctc gtt gga       720
Gly Thr Asp His Ile Asp Gln Leu Lys Leu Ile Leu Arg Leu Val Gly
225                 230                 235                 240 acc cca ggg gct gag ctt ttg aag aaa atc tcc tca gag tct gca aga       768
Thr Pro Gly Ala Glu Leu Leu Lys Lys Ile Ser Ser Glu Ser Ala Arg
                245                 250                 255 aac tat att cag tct ttg act cag atg ccg aag atg aac ttt gcg aat       816
Asn Tyr Ile Gln Ser Leu Thr Gln Met Pro Lys Met Asn Phe Ala Asn
            260                 265                 270 gta ttt att ggt gcc aat ccc ctg gct gtc gac ttg ctg gag aag atg       864
Val Phe Ile Gly Ala Asn Pro Leu Ala Val Asp Leu Leu Glu Lys Met
        275                 280                 285 ctt gta ttg gac tca gat aag aga att aca gcg gcc caa gcc ctt gca       912
Leu Val Leu Asp Ser Asp Lys Arg Ile Thr Ala Ala Gln Ala Leu Ala
    290                 295                 300 cat gcc tac ttt gct cag tac cac gat cct gat gat gaa cca gtg gcc       960
His Ala Tyr Phe Ala Gln Tyr His Asp Pro Asp Asp Glu Pro Val Ala
305                 310                 315                 320 gat cct tat gat cag tcc ttt gaa agc agg gac ctc ctt ata gat gag      1008
Asp Pro Tyr Asp Gln Ser Phe Glu Ser Arg Asp Leu Leu Ile Asp Glu
                325                 330                 335 tgg aaa agc ctg acc tat gat gaa gtc atc agc ttt gtg cca cca ccc      1056
Trp Lys Ser Leu Thr Tyr Asp Glu Val Ile Ser Phe Val Pro Pro Pro
            340                 345                 350 ctt gac caa gaa gag atg gag tcc gag gat cca ccg gtc gcc acc atg      1104
Leu Asp Gln Glu Glu Met Glu Ser Glu Asp Pro Pro Val Ala Thr Met
        355                 360                 365 gtg agc aag ggc gag gag ctg ttc acc ggg gtg gtg ccc atc ctg gtc      1152
Val Ser Lys Gly Glu Glu Leu Phe Thr Gly Val Val Pro Ile Leu Val
    370                 375                 380 gag ctg gac ggc gac gta aac ggc cac aag ttc agc gtg tcc ggc gag      1200
Glu Leu Asp Gly Asp Val Asn Gly His Lys Phe Ser Val Ser Gly Glu
385                 390                 395                 400 ggc gag ggc gat gcc acc tac ggc aag ctg acc ctg aag ttc atc tgc      1248
Gly Glu Gly Asp Ala Thr Tyr Gly Lys Leu Thr Leu Lys Phe Ile Cys
                405                 410                 415 acc acc ggc aag ctg ccc gtg ccc tgg ccc acc ctc gtg acc acc ctg      1296
Thr Thr Gly Lys Leu Pro Val Pro Trp Pro Thr Leu Val Thr Thr Leu
            420                 425                 430 acc tac ggc gtg cag tgc ttc agc cgc tac ccc gac cac atg aag cag      1344
Thr Tyr Gly Val Gln Cys Phe Ser Arg Tyr Pro Asp His Met Lys Gln
        435                 440                 445 cac gac ttc ttc aag tcc gcc atg ccc gaa ggc tac gtc cag gag cgc      1392
His Asp Phe Phe Lys Ser Ala Met Pro Glu Gly Tyr Val Gln Glu Arg
    450                 455                 460 acc atc ttc ttc aag gac gac ggc aac tac aag acc cgc gcc gag gtg      1440
Thr Ile Phe Phe Lys Asp Asp Gly Asn Tyr Lys Thr Arg Ala Glu Val
```

```
                465                 470                 475                 480
aag ttc gag ggc gac acc ctg gtg aac cgc atc gag ctg aag ggc atc         1488
Lys Phe Glu Gly Asp Thr Leu Val Asn Arg Ile Glu Leu Lys Gly Ile
                    485                 490                 495 gac ttc aag gag gac ggc aac atc ctg ggg cac aag ctg gag tac aac         1536
Asp Phe Lys Glu Asp Gly Asn Ile Leu Gly His Lys Leu Glu Tyr Asn
                500                 505                 510 tac aac agc cac aac gtc tat atc atg gcc gac aag cag aag aac ggc         1584
Tyr Asn Ser His Asn Val Tyr Ile Met Ala Asp Lys Gln Lys Asn Gly
            515                 520                 525 atc aag gtg aac ttc aag atc cgc cac aac atc gag gac ggc agc gtg         1632
Ile Lys Val Asn Phe Lys Ile Arg His Asn Ile Glu Asp Gly Ser Val
        530                 535                 540 cag ctc gcc gac cac tac cag cag aac acc ccc atc ggc gac ggc ccc         1680
Gln Leu Ala Asp His Tyr Gln Gln Asn Thr Pro Ile Gly Asp Gly Pro
545                 550                 555                 560 gtg ctg ctg ccc gac aac cac tac ctg agc acc cag tcc gcc ctg agc         1728
Val Leu Leu Pro Asp Asn His Tyr Leu Ser Thr Gln Ser Ala Leu Ser
                565                 570                 575 aaa gac ccc aac gag aag cgc gat cac atg gtc ctg ctg gag ttc gtg         1776
Lys Asp Pro Asn Glu Lys Arg Asp His Met Val Leu Leu Glu Phe Val
            580                 585                 590 acc gcc gcc ggg atc act ctc ggc atg gac gag ctg tac aag taa             1821
Thr Ala Ala Gly Ile Thr Leu Gly Met Asp Glu Leu Tyr Lys
        595                 600                 605
```

<210> SEQ ID NO 65
<211> LENGTH: 606
<212> TYPE: PRT
<213> ORGANISM: Artificial Sequence
<220> FEATURE:
<223> OTHER INFORMATION: p38-EGFP fusion

<400> SEQUENCE: 65

```
Met Ser Gln Glu Arg Pro Thr Phe Tyr Arg Gln Glu Leu Asn Lys Thr
1               5                   10                  15

Ile Trp Glu Val Pro Glu Arg Tyr Gln Asn Leu Ser Pro Val Gly Ser
            20                  25                  30

Gly Ala Tyr Gly Ser Val Cys Ala Ala Phe Asp Thr Lys Thr Gly Leu
        35                  40                  45

Arg Val Ala Val Lys Lys Leu Ser Arg Pro Phe Gln Ser Ile Ile His
    50                  55                  60

Ala Lys Arg Thr Tyr Arg Glu Leu Arg Leu Leu Lys His Met Lys His
65                  70                  75                  80

Glu Asn Val Ile Gly Leu Leu Asp Val Phe Thr Pro Ala Arg Ser Leu
                85                  90                  95

Glu Glu Phe Asn Asp Val Tyr Leu Val Thr His Leu Met Gly Ala Asp
            100                 105                 110

Leu Asn Asn Ile Val Lys Cys Gln Lys Leu Thr Asp Asp His Val Gln
        115                 120                 125

Phe Leu Ile Tyr Gln Ile Leu Arg Gly Leu Lys Tyr Ile His Ser Ala
    130                 135                 140

Asp Ile Ile His Arg Asp Leu Lys Pro Ser Asn Leu Ala Val Asn Glu
145                 150                 155                 160

Asp Cys Glu Leu Lys Ile Leu Asp Phe Gly Leu Ala Arg His Thr Asp
                165                 170                 175

Asp Glu Met Thr Gly Tyr Val Ala Thr Arg Trp Tyr Arg Ala Pro Glu
            180                 185                 190
```

```
Ile Met Leu Asn Trp Met His Tyr Asn Gln Thr Val Asp Ile Trp Ser
        195                 200                 205

Val Gly Cys Ile Met Ala Glu Leu Leu Thr Gly Arg Thr Leu Phe Pro
        210                 215                 220

Gly Thr Asp His Ile Asp Gln Leu Lys Leu Ile Leu Arg Leu Val Gly
225                 230                 235                 240

Thr Pro Gly Ala Glu Leu Leu Lys Lys Ile Ser Ser Glu Ser Ala Arg
                245                 250                 255

Asn Tyr Ile Gln Ser Leu Thr Gln Met Pro Lys Met Asn Phe Ala Asn
            260                 265                 270

Val Phe Ile Gly Ala Asn Pro Leu Ala Val Asp Leu Leu Glu Lys Met
        275                 280                 285

Leu Val Leu Asp Ser Asp Lys Arg Ile Thr Ala Ala Gln Ala Leu Ala
        290                 295                 300

His Ala Tyr Phe Ala Gln Tyr His Asp Pro Asp Asp Glu Pro Val Ala
305                 310                 315                 320

Asp Pro Tyr Asp Gln Ser Phe Glu Ser Arg Asp Leu Leu Ile Asp Glu
                325                 330                 335

Trp Lys Ser Leu Thr Tyr Asp Glu Val Ile Ser Phe Val Pro Pro Pro
            340                 345                 350

Leu Asp Gln Glu Glu Met Glu Ser Glu Asp Pro Pro Val Ala Thr Met
        355                 360                 365

Val Ser Lys Gly Glu Glu Leu Phe Thr Gly Val Val Pro Ile Leu Val
        370                 375                 380

Glu Leu Asp Gly Asp Val Asn Gly His Lys Phe Ser Val Ser Gly Glu
385                 390                 395                 400

Gly Glu Gly Asp Ala Thr Tyr Gly Lys Leu Thr Leu Lys Phe Ile Cys
                405                 410                 415

Thr Thr Gly Lys Leu Pro Val Pro Trp Pro Thr Leu Val Thr Thr Leu
            420                 425                 430

Thr Tyr Gly Val Gln Cys Phe Ser Arg Tyr Pro Asp His Met Lys Gln
        435                 440                 445

His Asp Phe Phe Lys Ser Ala Met Pro Glu Gly Tyr Val Gln Glu Arg
450                 455                 460

Thr Ile Phe Phe Lys Asp Asp Gly Asn Tyr Lys Thr Arg Ala Glu Val
465                 470                 475                 480

Lys Phe Glu Gly Asp Thr Leu Val Asn Arg Ile Glu Leu Lys Gly Ile
                485                 490                 495

Asp Phe Lys Glu Asp Gly Asn Ile Leu Gly His Lys Leu Glu Tyr Asn
            500                 505                 510

Tyr Asn Ser His Asn Val Tyr Ile Met Ala Asp Lys Gln Lys Asn Gly
        515                 520                 525

Ile Lys Val Asn Phe Lys Ile Arg His Asn Ile Glu Asp Gly Ser Val
        530                 535                 540

Gln Leu Ala Asp His Tyr Gln Gln Asn Thr Pro Ile Gly Asp Gly Pro
545                 550                 555                 560

Val Leu Leu Pro Asp Asn His Tyr Leu Ser Thr Gln Ser Ala Leu Ser
                565                 570                 575

Lys Asp Pro Asn Glu Lys Arg Asp His Met Val Leu Leu Glu Phe Val
            580                 585                 590

Thr Ala Ala Gly Ile Thr Leu Gly Met Asp Glu Leu Tyr Lys
        595                 600                 605
```

<210> SEQ ID NO 66
<211> LENGTH: 2913
<212> TYPE: DNA
<213> ORGANISM: Artificial Sequence
<220> FEATURE:
<223> OTHER INFORMATION: p85alpha-EGFP fusion
<220> FEATURE:
<221> NAME/KEY: CDS
<222> LOCATION: (1)..(2910)

<400> SEQUENCE: 66

| | | | | | | | | | | | | | | | | |
|---|---|---|---|---|---|---|---|---|---|---|---|---|---|---|---|---|
| atg | agt | gct | gag | ggg | tac | cag | tac | aga | gcg | ctg | tat | gat | tat | aaa | aag | 48 |
| Met | Ser | Ala | Glu | Gly | Tyr | Gln | Tyr | Arg | Ala | Leu | Tyr | Asp | Tyr | Lys | Lys | |
| 1 | | | | 5 | | | | | 10 | | | | | 15 | | |
| gaa | aga | gaa | gaa | gat | att | gac | ttg | cac | ttg | ggt | gac | ata | ttg | act | gtg | 96 |
| Glu | Arg | Glu | Glu | Asp | Ile | Asp | Leu | His | Leu | Gly | Asp | Ile | Leu | Thr | Val | |
| | | | 20 | | | | | 25 | | | | | 30 | | | |
| aat | aaa | ggg | tcc | tta | gta | gct | ctt | gga | ttc | agt | gat | gga | cag | gaa | gcc | 144 |
| Asn | Lys | Gly | Ser | Leu | Val | Ala | Leu | Gly | Phe | Ser | Asp | Gly | Gln | Glu | Ala | |
| | | 35 | | | | | 40 | | | | | 45 | | | | |
| agg | cct | gaa | gaa | att | ggc | tgg | tta | aat | ggc | tat | aat | gaa | acc | aca | ggg | 192 |
| Arg | Pro | Glu | Glu | Ile | Gly | Trp | Leu | Asn | Gly | Tyr | Asn | Glu | Thr | Thr | Gly | |
| | 50 | | | | | 55 | | | | | 60 | | | | | |
| gaa | agg | ggg | gac | ttt | ccg | gga | act | tac | gta | gaa | tat | att | gga | agg | aaa | 240 |
| Glu | Arg | Gly | Asp | Phe | Pro | Gly | Thr | Tyr | Val | Glu | Tyr | Ile | Gly | Arg | Lys | |
| 65 | | | | | 70 | | | | | 75 | | | | | 80 | |
| aaa | atc | tcg | cct | ccc | aca | cca | aag | ccc | cgg | cca | cct | cgg | cct | ctt | cct | 288 |
| Lys | Ile | Ser | Pro | Pro | Thr | Pro | Lys | Pro | Arg | Pro | Pro | Arg | Pro | Leu | Pro | |
| | | | | 85 | | | | | 90 | | | | | 95 | | |
| gtt | gca | cca | ggt | tct | tcg | aaa | act | gaa | gca | gat | gtt | gaa | caa | caa | gct | 336 |
| Val | Ala | Pro | Gly | Ser | Ser | Lys | Thr | Glu | Ala | Asp | Val | Glu | Gln | Gln | Ala | |
| | | | | 100 | | | | | 105 | | | | | 110 | | |
| ttg | act | ctc | ccg | gat | ctt | gca | gag | cag | ttt | gcc | cct | cct | gac | att | gcc | 384 |
| Leu | Thr | Leu | Pro | Asp | Leu | Ala | Glu | Gln | Phe | Ala | Pro | Pro | Asp | Ile | Ala | |
| | | | 115 | | | | | 120 | | | | | 125 | | | |
| ccg | cct | ctt | ctt | atc | aag | ctc | gtg | gaa | gcc | att | gaa | aag | aaa | ggt | ctg | 432 |
| Pro | Pro | Leu | Leu | Ile | Lys | Leu | Val | Glu | Ala | Ile | Glu | Lys | Lys | Gly | Leu | |
| | | 130 | | | | | 135 | | | | | 140 | | | | |
| gaa | tgt | tca | act | cta | tac | aga | aca | cag | agc | tcc | agc | aac | ctg | gca | gaa | 480 |
| Glu | Cys | Ser | Thr | Leu | Tyr | Arg | Thr | Gln | Ser | Ser | Ser | Asn | Leu | Ala | Glu | |
| 145 | | | | | 150 | | | | | 155 | | | | | 160 | |
| tta | cga | cag | ctt | ctt | gat | tgt | gat | aca | ccc | tcc | gtg | gac | ttg | gaa | atg | 528 |
| Leu | Arg | Gln | Leu | Leu | Asp | Cys | Asp | Thr | Pro | Ser | Val | Asp | Leu | Glu | Met | |
| | | | | 165 | | | | | 170 | | | | | 175 | | |
| atc | gat | gtg | cac | gtt | ttg | gct | gac | gct | ttc | aaa | cgc | tat | ctc | ctg | gac | 576 |
| Ile | Asp | Val | His | Val | Leu | Ala | Asp | Ala | Phe | Lys | Arg | Tyr | Leu | Leu | Asp | |
| | | | | 180 | | | | | 185 | | | | | 190 | | |
| tta | cca | aat | cct | gtc | att | cca | gca | gcc | gtt | tac | agt | gaa | atg | att | tct | 624 |
| Leu | Pro | Asn | Pro | Val | Ile | Pro | Ala | Ala | Val | Tyr | Ser | Glu | Met | Ile | Ser | |
| | | | 195 | | | | | 200 | | | | | 205 | | | |
| tta | gct | cca | gaa | gta | caa | agc | tcc | gaa | gaa | tat | att | cag | cta | ttg | aag | 672 |
| Leu | Ala | Pro | Glu | Val | Gln | Ser | Ser | Glu | Glu | Tyr | Ile | Gln | Leu | Leu | Lys | |
| | | 210 | | | | | 215 | | | | | 220 | | | | |
| aag | ctt | att | agg | tcg | cct | agc | ata | cct | cat | cag | tat | tgg | ctt | acg | ctt | 720 |
| Lys | Leu | Ile | Arg | Ser | Pro | Ser | Ile | Pro | His | Gln | Tyr | Trp | Leu | Thr | Leu | |
| 225 | | | | | 230 | | | | | 235 | | | | | 240 | |
| cag | tat | ttg | tta | aaa | cat | ttc | ttc | aag | ctc | tct | caa | acc | tcc | agc | aaa | 768 |
| Gln | Tyr | Leu | Leu | Lys | His | Phe | Phe | Lys | Leu | Ser | Gln | Thr | Ser | Ser | Lys | |
| | | | | 245 | | | | | 250 | | | | | 255 | | |
| aat | ctg | ttg | aat | gca | aga | gta | ctc | tct | gaa | att | ttc | agc | cct | atg | ctt | 816 |
| Asn | Leu | Leu | Asn | Ala | Arg | Val | Leu | Ser | Glu | Ile | Phe | Ser | Pro | Met | Leu | |

|   |   |   |   |   |   |   |   |   |   |   |   |   |   |   |   |      |
|---|---|---|---|---|---|---|---|---|---|---|---|---|---|---|---|------|
|   |   |   | 260 |   |   |   | 265 |   |   |   | 270 |   |   |   |   |      |
| ttc | aga | ttc | tca | gca | gcc | agc | tct | gat | aat | act | gaa | aac | ctc | ata | aaa | 864  |
| Phe | Arg | Phe | Ser | Ala | Ala | Ser | Ser | Asp | Asn | Thr | Glu | Asn | Leu | Ile | Lys |      |
|   |   | 275 |   |   |   |   | 280 |   |   |   |   | 285 |   |   |   |      |
| gtt | ata | gaa | att | tta | atc | tca | act | gaa | tgg | aat | gaa | cga | cag | cct | gca | 912  |
| Val | Ile | Glu | Ile | Leu | Ile | Ser | Thr | Glu | Trp | Asn | Glu | Arg | Gln | Pro | Ala |      |
|   | 290 |   |   |   |   | 295 |   |   |   |   | 300 |   |   |   |   |      |
| cca | gca | ctg | cct | cct | aaa | cca | cca | aaa | cct | act | act | gta | gcc | aac | aac | 960  |
| Pro | Ala | Leu | Pro | Pro | Lys | Pro | Pro | Lys | Pro | Thr | Thr | Val | Ala | Asn | Asn |      |
| 305 |   |   |   |   | 310 |   |   |   |   | 315 |   |   |   |   | 320 |      |
| ggt | atg | aat | aac | aat | atg | tcc | tta | caa | aat | gct | gaa | tgg | tac | tgg | gga | 1008 |
| Gly | Met | Asn | Asn | Asn | Met | Ser | Leu | Gln | Asn | Ala | Glu | Trp | Tyr | Trp | Gly |      |
|   |   |   |   | 325 |   |   |   |   | 330 |   |   |   |   | 335 |   |      |
| gat | atc | tcg | agg | gaa | gaa | gtg | aat | gaa | aaa | ctt | cga | gat | aca | gca | gac | 1056 |
| Asp | Ile | Ser | Arg | Glu | Glu | Val | Asn | Glu | Lys | Leu | Arg | Asp | Thr | Ala | Asp |      |
|   |   |   | 340 |   |   |   |   | 345 |   |   |   |   | 350 |   |   |      |
| ggg | acc | ttt | ttg | gta | cga | gat | gcg | tct | act | aaa | atg | cat | ggt | gat | tat | 1104 |
| Gly | Thr | Phe | Leu | Val | Arg | Asp | Ala | Ser | Thr | Lys | Met | His | Gly | Asp | Tyr |      |
|   |   | 355 |   |   |   |   | 360 |   |   |   |   | 365 |   |   |   |      |
| act | ctt | aca | cta | agg | aaa | ggg | gga | aat | aac | aaa | tta | atc | aaa | ata | ttt | 1152 |
| Thr | Leu | Thr | Leu | Arg | Lys | Gly | Gly | Asn | Asn | Lys | Leu | Ile | Lys | Ile | Phe |      |
|   | 370 |   |   |   |   | 375 |   |   |   |   | 380 |   |   |   |   |      |
| cat | cga | gat | ggg | aaa | tat | ggc | ttc | tct | gac | cca | tta | acc | ttc | agt | tct | 1200 |
| His | Arg | Asp | Gly | Lys | Tyr | Gly | Phe | Ser | Asp | Pro | Leu | Thr | Phe | Ser | Ser |      |
| 385 |   |   |   |   | 390 |   |   |   |   | 395 |   |   |   |   | 400 |      |
| gtg | gtt | gaa | tta | ata | aac | cac | tac | cgg | aat | gaa | tct | cta | gct | cag | tat | 1248 |
| Val | Val | Glu | Leu | Ile | Asn | His | Tyr | Arg | Asn | Glu | Ser | Leu | Ala | Gln | Tyr |      |
|   |   |   |   | 405 |   |   |   |   | 410 |   |   |   |   | 415 |   |      |
| aat | ccc | aaa | ttg | gat | gtg | aaa | tta | ctt | tat | cca | gta | tcc | aaa | tac | caa | 1296 |
| Asn | Pro | Lys | Leu | Asp | Val | Lys | Leu | Leu | Tyr | Pro | Val | Ser | Lys | Tyr | Gln |      |
|   |   |   | 420 |   |   |   |   | 425 |   |   |   |   | 430 |   |   |      |
| cag | gat | caa | gtt | gtc | aaa | gaa | gat | aat | att | gaa | gct | gta | ggg | aaa | aaa | 1344 |
| Gln | Asp | Gln | Val | Val | Lys | Glu | Asp | Asn | Ile | Glu | Ala | Val | Gly | Lys | Lys |      |
|   |   | 435 |   |   |   |   | 440 |   |   |   |   | 445 |   |   |   |      |
| tta | cat | gaa | tat | aac | act | cag | ttt | caa | gaa | aaa | agt | cga | gaa | tat | gat | 1392 |
| Leu | His | Glu | Tyr | Asn | Thr | Gln | Phe | Gln | Glu | Lys | Ser | Arg | Glu | Tyr | Asp |      |
|   | 450 |   |   |   |   | 455 |   |   |   |   | 460 |   |   |   |   |      |
| aga | tta | tat | gaa | gaa | tat | acc | cgc | aca | tcc | cag | gaa | atc | caa | atg | aaa | 1440 |
| Arg | Leu | Tyr | Glu | Glu | Tyr | Thr | Arg | Thr | Ser | Gln | Glu | Ile | Gln | Met | Lys |      |
| 465 |   |   |   |   | 470 |   |   |   |   | 475 |   |   |   |   | 480 |      |
| agg | aca | gct | att | gaa | gca | ttt | aat | gaa | acc | ata | aaa | ata | ttt | gaa | gaa | 1488 |
| Arg | Thr | Ala | Ile | Glu | Ala | Phe | Asn | Glu | Thr | Ile | Lys | Ile | Phe | Glu | Glu |      |
|   |   |   |   | 485 |   |   |   |   | 490 |   |   |   |   | 495 |   |      |
| cag | tgc | cag | acc | caa | gag | cgg | tac | agc | aaa | gaa | tac | ata | gaa | aag | ttt | 1536 |
| Gln | Cys | Gln | Thr | Gln | Glu | Arg | Tyr | Ser | Lys | Glu | Tyr | Ile | Glu | Lys | Phe |      |
|   |   |   | 500 |   |   |   |   | 505 |   |   |   |   | 510 |   |   |      |
| aaa | cgt | gaa | ggc | aat | gag | aaa | gaa | ata | caa | agg | att | atg | cat | aat | tat | 1584 |
| Lys | Arg | Glu | Gly | Asn | Glu | Lys | Glu | Ile | Gln | Arg | Ile | Met | His | Asn | Tyr |      |
|   |   | 515 |   |   |   |   | 520 |   |   |   |   | 525 |   |   |   |      |
| gat | aag | ttg | aag | tct | cga | atc | agt | gaa | att | att | gac | agt | aga | aga | aga | 1632 |
| Asp | Lys | Leu | Lys | Ser | Arg | Ile | Ser | Glu | Ile | Ile | Asp | Ser | Arg | Arg | Arg |      |
|   | 530 |   |   |   |   | 535 |   |   |   |   | 540 |   |   |   |   |      |
| ttg | gaa | gaa | gac | ttg | aag | aag | cag | gca | gct | gag | tat | cga | gaa | att | gac | 1680 |
| Leu | Glu | Glu | Asp | Leu | Lys | Lys | Gln | Ala | Ala | Glu | Tyr | Arg | Glu | Ile | Asp |      |
| 545 |   |   |   |   | 550 |   |   |   |   | 555 |   |   |   |   | 560 |      |
| aaa | cgt | atg | aac | agc | att | aaa | cca | gac | ctt | atc | cag | ctg | aga | aag | acg | 1728 |
| Lys | Arg | Met | Asn | Ser | Ile | Lys | Pro | Asp | Leu | Ile | Gln | Leu | Arg | Lys | Thr |      |
|   |   |   |   | 565 |   |   |   |   | 570 |   |   |   |   | 575 |   |      |
| aga | gac | caa | tac | ttg | atg | tgg | ttg | act | caa | aaa | ggt | gtt | cgg | caa | aag | 1776 |

-continued

```
                    Arg Asp Gln Tyr Leu Met Trp Leu Thr Gln Lys Gly Val Arg Gln Lys
                            580                 585                 590 aag ttg aac gag tgg ttg ggc aat gaa aac act gaa gac caa tat tca        1824
Lys Leu Asn Glu Trp Leu Gly Asn Glu Asn Thr Glu Asp Gln Tyr Ser
            595                 600                 605 ctg gtg gaa gat gat gaa gat ttg ccc cat cat gat gag aag aca tgg        1872
Leu Val Glu Asp Asp Glu Asp Leu Pro His His Asp Glu Lys Thr Trp
610                 615                 620 aat gtt gga agc agc aac cga aac aaa gct gaa aac ctg ttg cga ggg        1920
Asn Val Gly Ser Ser Asn Arg Asn Lys Ala Glu Asn Leu Leu Arg Gly
625                 630                 635                 640 aag cga gat ggc act ttt ctt gtc cgg gag agc agt aaa cag ggc tgc        1968
Lys Arg Asp Gly Thr Phe Leu Val Arg Glu Ser Ser Lys Gln Gly Cys
                645                 650                 655 tat gcc tgc tct gta gtg gtg gac ggc gaa gta aag cat tgt gtc ata        2016
Tyr Ala Cys Ser Val Val Val Asp Gly Glu Val Lys His Cys Val Ile
            660                 665                 670 aac aaa aca gca act ggc tat ggc ttt gcc gag ccc tat aac ttg tac        2064
Asn Lys Thr Ala Thr Gly Tyr Gly Phe Ala Glu Pro Tyr Asn Leu Tyr
        675                 680                 685 agc tct ctg aaa gaa ctg gtg cta cat tac caa cac acc tcc ctt gtg        2112
Ser Ser Leu Lys Glu Leu Val Leu His Tyr Gln His Thr Ser Leu Val
690                 695                 700 cag cac aac gac tcc ctc aat gtc aca cta gcc tac cca gta tat gca        2160
Gln His Asn Asp Ser Leu Asn Val Thr Leu Ala Tyr Pro Val Tyr Ala
705                 710                 715                 720 cag cag agg cga cag gat cca ccg gtc gcc acc atg gtg agc aag ggc        2208
Gln Gln Arg Arg Gln Asp Pro Pro Val Ala Thr Met Val Ser Lys Gly
                725                 730                 735 gag gag ctg ttc acc ggg gtg gtg ccc atc ctg gtc gag ctg gac ggc        2256
Glu Glu Leu Phe Thr Gly Val Val Pro Ile Leu Val Glu Leu Asp Gly
            740                 745                 750 gac gta aac ggc cac aag ttc agc gtg tcc ggc gag ggc gag ggc gat        2304
Asp Val Asn Gly His Lys Phe Ser Val Ser Gly Glu Gly Glu Gly Asp
        755                 760                 765 gcc acc tac ggc aag ctg acc ctg aag ttc atc tgc acc acc ggc aag        2352
Ala Thr Tyr Gly Lys Leu Thr Leu Lys Phe Ile Cys Thr Thr Gly Lys
770                 775                 780 ctg ccc gtg ccc tgg ccc acc ctc gtg acc acc ctg acc tac ggc gtg        2400
Leu Pro Val Pro Trp Pro Thr Leu Val Thr Thr Leu Thr Tyr Gly Val
785                 790                 795                 800 cag tgc ttc agc cgc tac ccc gac cac atg aag cag cac gac ttc ttc        2448
Gln Cys Phe Ser Arg Tyr Pro Asp His Met Lys Gln His Asp Phe Phe
                805                 810                 815 aag tcc gcc atg ccc gaa ggc tac gtc cag gag cgc acc atc ttc ttc        2496
Lys Ser Ala Met Pro Glu Gly Tyr Val Gln Glu Arg Thr Ile Phe Phe
            820                 825                 830 aag gac gac ggc aac tac aag acc cgc gcc gag gtg aag ttc gag ggc        2544
Lys Asp Asp Gly Asn Tyr Lys Thr Arg Ala Glu Val Lys Phe Glu Gly
        835                 840                 845 gac acc ctg gtg aac cgc atc gag ctg aag ggc atc gac ttc aag gag        2592
Asp Thr Leu Val Asn Arg Ile Glu Leu Lys Gly Ile Asp Phe Lys Glu
850                 855                 860 gac ggc aac atc ctg ggg cac aag ctg gag tac aac tac aac agc cac        2640
Asp Gly Asn Ile Leu Gly His Lys Leu Glu Tyr Asn Tyr Asn Ser His
865                 870                 875                 880 aac gtc tat atc atg gcc gac aag cag aag aac ggc atc aag gtg aac        2688
Asn Val Tyr Ile Met Ala Asp Lys Gln Lys Asn Gly Ile Lys Val Asn
                885                 890                 895
```

```
ttc aag atc cgc cac aac atc gag gac ggc agc gtg cag ctc gcc gac    2736
Phe Lys Ile Arg His Asn Ile Glu Asp Gly Ser Val Gln Leu Ala Asp
        900                 905                 910 cac tac cag cag aac acc ccc atc ggc gac ggc ccc gtg ctg ctg ccc    2784
His Tyr Gln Gln Asn Thr Pro Ile Gly Asp Gly Pro Val Leu Leu Pro
    915                 920                 925 gac aac cac tac ctg agc acc cag tcc gcc ctg agc aaa gac ccc aac    2832
Asp Asn His Tyr Leu Ser Thr Gln Ser Ala Leu Ser Lys Asp Pro Asn
930                 935                 940 gag aag cgc gat cac atg gtc ctg ctg gag ttc gtg acc gcc gcc ggg    2880
Glu Lys Arg Asp His Met Val Leu Leu Glu Phe Val Thr Ala Ala Gly
945                 950                 955                 960 atc act ctc ggc atg gac gag ctg tac aag taa                        2913
Ile Thr Leu Gly Met Asp Glu Leu Tyr Lys
                965                 970

<210> SEQ ID NO 67
<211> LENGTH: 970
<212> TYPE: PRT
<213> ORGANISM: Artificial Sequence
<220> FEATURE:
<223> OTHER INFORMATION: p85alpha-EGFP fusion

<400> SEQUENCE: 67

Met Ser Ala Glu Gly Tyr Gln Tyr Arg Ala Leu Tyr Asp Tyr Lys Lys
1               5                   10                  15

Glu Arg Glu Glu Asp Ile Asp Leu His Leu Gly Asp Ile Leu Thr Val
            20                  25                  30

Asn Lys Gly Ser Leu Val Ala Leu Gly Phe Ser Asp Gly Gln Glu Ala
        35                  40                  45

Arg Pro Glu Glu Ile Gly Trp Leu Asn Gly Tyr Asn Glu Thr Thr Gly
    50                  55                  60

Glu Arg Gly Asp Phe Pro Gly Thr Tyr Val Glu Tyr Ile Gly Arg Lys
65                  70                  75                  80

Lys Ile Ser Pro Pro Thr Pro Lys Pro Arg Pro Pro Arg Pro Leu Pro
                85                  90                  95

Val Ala Pro Gly Ser Ser Lys Thr Glu Ala Asp Val Glu Gln Gln Ala
            100                 105                 110

Leu Thr Leu Pro Asp Leu Ala Glu Gln Phe Ala Pro Pro Asp Ile Ala
        115                 120                 125

Pro Pro Leu Leu Ile Lys Leu Val Glu Ala Ile Glu Lys Lys Gly Leu
    130                 135                 140

Glu Cys Ser Thr Leu Tyr Arg Thr Gln Ser Ser Ser Asn Leu Ala Glu
145                 150                 155                 160

Leu Arg Gln Leu Leu Asp Cys Asp Thr Pro Ser Val Asp Leu Glu Met
                165                 170                 175

Ile Asp Val His Val Leu Ala Asp Ala Phe Lys Arg Tyr Leu Leu Asp
            180                 185                 190

Leu Pro Asn Pro Val Ile Pro Ala Ala Val Tyr Ser Glu Met Ile Ser
        195                 200                 205

Leu Ala Pro Glu Val Gln Ser Ser Glu Glu Tyr Ile Gln Leu Leu Lys
    210                 215                 220

Lys Leu Ile Arg Ser Pro Ser Ile Pro His Gln Tyr Trp Leu Thr Leu
225                 230                 235                 240

Gln Tyr Leu Leu Lys His Phe Phe Lys Leu Ser Gln Thr Ser Ser Lys
                245                 250                 255

Asn Leu Leu Asn Ala Arg Val Leu Ser Glu Ile Phe Ser Pro Met Leu
```

-continued

```
                260                 265                 270
Phe Arg Phe Ser Ala Ala Ser Ser Asp Asn Thr Glu Asn Leu Ile Lys
            275                 280                 285
Val Ile Glu Ile Leu Ile Ser Thr Glu Trp Asn Glu Arg Gln Pro Ala
        290                 295                 300
Pro Ala Leu Pro Pro Lys Pro Pro Lys Pro Thr Thr Val Ala Asn Asn
305                 310                 315                 320
Gly Met Asn Asn Met Ser Leu Gln Asn Ala Glu Trp Tyr Trp Gly
                325                 330                 335
Asp Ile Ser Arg Glu Glu Val Asn Glu Lys Leu Arg Asp Thr Ala Asp
            340                 345                 350
Gly Thr Phe Leu Val Arg Asp Ala Ser Thr Lys Met His Gly Asp Tyr
        355                 360                 365
Thr Leu Thr Leu Arg Lys Gly Gly Asn Asn Lys Leu Ile Lys Ile Phe
        370                 375                 380
His Arg Asp Gly Lys Tyr Gly Phe Ser Asp Pro Leu Thr Phe Ser Ser
385                 390                 395                 400
Val Val Glu Leu Ile Asn His Tyr Arg Asn Glu Ser Leu Ala Gln Tyr
            405                 410                 415
Asn Pro Lys Leu Asp Val Lys Leu Leu Tyr Pro Val Ser Lys Tyr Gln
        420                 425                 430
Gln Asp Gln Val Val Lys Glu Asp Asn Ile Glu Ala Val Gly Lys Lys
        435                 440                 445
Leu His Glu Tyr Asn Thr Gln Phe Gln Glu Lys Ser Arg Glu Tyr Asp
        450                 455                 460
Arg Leu Tyr Glu Glu Tyr Thr Arg Thr Ser Gln Glu Ile Gln Met Lys
465                 470                 475                 480
Arg Thr Ala Ile Glu Ala Phe Asn Glu Thr Ile Lys Ile Phe Glu Glu
            485                 490                 495
Gln Cys Gln Thr Gln Glu Arg Tyr Ser Lys Glu Tyr Ile Glu Lys Phe
        500                 505                 510
Lys Arg Glu Gly Asn Glu Lys Glu Ile Gln Arg Ile Met His Asn Tyr
        515                 520                 525
Asp Lys Leu Lys Ser Arg Ile Ser Glu Ile Ile Asp Ser Arg Arg Arg
530                 535                 540
Leu Glu Glu Asp Leu Lys Lys Gln Ala Ala Glu Tyr Arg Glu Ile Asp
545                 550                 555                 560
Lys Arg Met Asn Ser Ile Lys Pro Asp Leu Ile Gln Leu Arg Lys Thr
                565                 570                 575
Arg Asp Gln Tyr Leu Met Trp Leu Thr Gln Lys Gly Val Arg Gln Lys
            580                 585                 590
Lys Leu Asn Glu Trp Leu Gly Asn Glu Asn Thr Glu Asp Gln Tyr Ser
        595                 600                 605
Leu Val Glu Asp Asp Glu Asp Leu Pro His His Asp Glu Lys Thr Trp
        610                 615                 620
Asn Val Gly Ser Ser Asn Arg Asn Lys Ala Glu Asn Leu Leu Arg Gly
625                 630                 635                 640
Lys Arg Asp Gly Thr Phe Leu Val Arg Glu Ser Ser Lys Gln Gly Cys
                645                 650                 655
Tyr Ala Cys Ser Val Val Val Asp Gly Glu Val Lys His Cys Val Ile
            660                 665                 670
Asn Lys Thr Ala Thr Gly Tyr Gly Phe Ala Glu Pro Tyr Asn Leu Tyr
        675                 680                 685
```

-continued

```
Ser Ser Leu Lys Glu Leu Val Leu His Tyr Gln His Thr Ser Leu Val
    690             695                 700
Gln His Asn Asp Ser Leu Asn Val Thr Leu Ala Tyr Pro Val Tyr Ala
705                 710                 715                 720
Gln Gln Arg Arg Gln Asp Pro Pro Val Ala Thr Met Val Ser Lys Gly
            725                 730                 735
Glu Glu Leu Phe Thr Gly Val Val Pro Ile Leu Val Glu Leu Asp Gly
            740                 745             750
Asp Val Asn Gly His Lys Phe Ser Val Ser Gly Glu Gly Glu Gly Asp
            755                 760                 765
Ala Thr Tyr Gly Lys Leu Thr Leu Lys Phe Ile Cys Thr Thr Gly Lys
    770                 775                 780
Leu Pro Val Pro Trp Pro Thr Leu Val Thr Thr Leu Thr Tyr Gly Val
785                 790                 795                 800
Gln Cys Phe Ser Arg Tyr Pro Asp His Met Lys Gln His Asp Phe Phe
                805                 810                 815
Lys Ser Ala Met Pro Glu Gly Tyr Val Gln Glu Arg Thr Ile Phe Phe
            820                 825                 830
Lys Asp Asp Gly Asn Tyr Lys Thr Arg Ala Glu Val Lys Phe Glu Gly
            835                 840                 845
Asp Thr Leu Val Asn Arg Ile Glu Leu Lys Gly Ile Asp Phe Lys Glu
    850                 855                 860
Asp Gly Asn Ile Leu Gly His Lys Leu Glu Tyr Asn Tyr Asn Ser His
865                 870                 875                 880
Asn Val Tyr Ile Met Ala Asp Lys Gln Lys Asn Gly Ile Lys Val Asn
                885                 890                 895
Phe Lys Ile Arg His Asn Ile Glu Asp Gly Ser Val Gln Leu Ala Asp
            900                 905                 910
His Tyr Gln Gln Asn Thr Pro Ile Gly Asp Gly Pro Val Leu Leu Pro
            915                 920                 925
Asp Asn His Tyr Leu Ser Thr Gln Ser Ala Leu Ser Lys Asp Pro Asn
    930                 935                 940
Glu Lys Arg Asp His Met Val Leu Leu Glu Phe Val Thr Ala Ala Gly
945                 950                 955                 960
Ile Thr Leu Gly Met Asp Glu Leu Tyr Lys
                965                 970
```

```
<210> SEQ ID NO 68
<211> LENGTH: 1788
<212> TYPE: DNA
<213> ORGANISM: Artificial Sequence
<220> FEATURE:
<223> OTHER INFORMATION: Fusion Construct
<220> FEATURE:
<221> NAME/KEY: CDS
<222> LOCATION: (1)..(1785)

<400> SEQUENCE: 68
```

```
atg ggc aac gcc gcc gcc gcc aag aag ggc agc gag cag gag agc gtg       48
Met Gly Asn Ala Ala Ala Ala Lys Lys Gly Ser Glu Gln Glu Ser Val
1               5                   10                  15 aaa gag ttc cta gcc aaa gcc aag gaa gat ttc ctg aaa aaa tgg gaa       96
Lys Glu Phe Leu Ala Lys Ala Lys Glu Asp Phe Leu Lys Lys Trp Glu
            20                  25                  30 gac ccc tct cag aat aca gcc cag ttg gat cag ttt gat aga atc aag     144
Asp Pro Ser Gln Asn Thr Ala Gln Leu Asp Gln Phe Asp Arg Ile Lys
        35                  40                  45
```

```
acc ctt ggc acc ggc tcc ttt ggg cga gtg atg ctg gtg aag cac aag      192
Thr Leu Gly Thr Gly Ser Phe Gly Arg Val Met Leu Val Lys His Lys
        50                  55                  60 gag agt ggg aac cac tac gcc atg aag atc tta gac aag cag aag gtg      240
Glu Ser Gly Asn His Tyr Ala Met Lys Ile Leu Asp Lys Gln Lys Val
65                  70                  75                  80 gtg aag cta aag cag atc gag cac act ctg aat gag aag cgc atc ctg      288
Val Lys Leu Lys Gln Ile Glu His Thr Leu Asn Glu Lys Arg Ile Leu
                85                  90                  95 cag gcc gtc aac ttc ccg ttc ctg gtc aaa ctt gaa ttc tcc ttc aag      336
Gln Ala Val Asn Phe Pro Phe Leu Val Lys Leu Glu Phe Ser Phe Lys
            100                 105                 110 gac aac tca aac ctg tac atg gtc atg gag tat gta gct ggt ggc gag      384
Asp Asn Ser Asn Leu Tyr Met Val Met Glu Tyr Val Ala Gly Gly Glu
        115                 120                 125 atg ttc tcc cac cta cgg cgg att gga agg ttc agc gag ccc cat gcc      432
Met Phe Ser His Leu Arg Arg Ile Gly Arg Phe Ser Glu Pro His Ala
    130                 135                 140 cgt ttc tac gcg gcg cag atc gtc ctg acc ttt gag tat ctg cac tcc      480
Arg Phe Tyr Ala Ala Gln Ile Val Leu Thr Phe Glu Tyr Leu His Ser
145                 150                 155                 160 ctg gac ctc atc tac cgg gac ctg aag ccc gag aat ctt ctc atc gac      528
Leu Asp Leu Ile Tyr Arg Asp Leu Lys Pro Glu Asn Leu Leu Ile Asp
                165                 170                 175 cag cag ggc tat att cag gtg aca gac ttc ggt ttt gcc aag cgt gtg      576
Gln Gln Gly Tyr Ile Gln Val Thr Asp Phe Gly Phe Ala Lys Arg Val
            180                 185                 190 aaa ggc cgt act tgg acc ttg tgt ggg acc cct gag tac ttg gcc ccc      624
Lys Gly Arg Thr Trp Thr Leu Cys Gly Thr Pro Glu Tyr Leu Ala Pro
        195                 200                 205 gag att atc ctg agc aaa ggc tac aac aag gct gtg gac tgg tgg gct      672
Glu Ile Ile Leu Ser Lys Gly Tyr Asn Lys Ala Val Asp Trp Trp Ala
    210                 215                 220 ctc gga gtc ctc atc tac gag atg gct gct ggt tac cca ccc ttc ttc      720
Leu Gly Val Leu Ile Tyr Glu Met Ala Ala Gly Tyr Pro Pro Phe Phe
225                 230                 235                 240 gct gac cag cct atc cag atc tat gag aaa atc gtc tct ggg aag gtg      768
Ala Asp Gln Pro Ile Gln Ile Tyr Glu Lys Ile Val Ser Gly Lys Val
                245                 250                 255 cgg ttc cca tcc cac ttc agc tct gac ttg aag gac ctg ctg cgg aac      816
Arg Phe Pro Ser His Phe Ser Ser Asp Leu Lys Asp Leu Leu Arg Asn
            260                 265                 270 ctt ctg caa gtg gat cta acc aag cgc ttt gga aac ctc aag gac ggg      864
Leu Leu Gln Val Asp Leu Thr Lys Arg Phe Gly Asn Leu Lys Asp Gly
        275                 280                 285 gtc aat gac atc aag aac cac aag tgg ttt gcc acg act gac tgg att      912
Val Asn Asp Ile Lys Asn His Lys Trp Phe Ala Thr Thr Asp Trp Ile
    290                 295                 300 gcc atc tat cag aga aag gtg gaa gct ccc ttc ata cca aag ttt aaa      960
Ala Ile Tyr Gln Arg Lys Val Glu Ala Pro Phe Ile Pro Lys Phe Lys
305                 310                 315                 320 ggc cct ggg gac acg agt aac ttt gac gac tat gag gag gaa gag atc     1008
Gly Pro Gly Asp Thr Ser Asn Phe Asp Asp Tyr Glu Glu Glu Glu Ile
                325                 330                 335 cgg gtc tcc atc aat gag aag tgt ggc aag gag ttt act gag ttt ggg     1056
Arg Val Ser Ile Asn Glu Lys Cys Gly Lys Glu Phe Thr Glu Phe Gly
            340                 345                 350 cgc gcc atg agt aaa gga gaa gaa ctt ttc act gga gtt gtc cca att     1104
Arg Ala Met Ser Lys Gly Glu Glu Leu Phe Thr Gly Val Val Pro Ile
```

```
                                                                                       355                             360                                365
ctt gtt gaa tta gat ggc gat gtt aat ggg caa aaa ttc tct gtt agt              1152
Leu Val Glu Leu Asp Gly Asp Val Asn Gly Gln Lys Phe Ser Val Ser
        370                     375                     380 gga gag ggt gaa ggt gat gca aca tac gga aaa ctt acc ctt aaa ttt              1200
Gly Glu Gly Glu Gly Asp Ala Thr Tyr Gly Lys Leu Thr Leu Lys Phe
385                     390                     395                     400 att tgc act act ggg aag cta cct gtt cca tgg cca acg ctt gtc act              1248
Ile Cys Thr Thr Gly Lys Leu Pro Val Pro Trp Pro Thr Leu Val Thr
                405                     410                     415 act ctc act tat ggt gtt caa tgc ttt tct aga tac cca gat cat atg              1296
Thr Leu Thr Tyr Gly Val Gln Cys Phe Ser Arg Tyr Pro Asp His Met
            420                     425                     430 aaa cag cat gac ttt ttc aag agt gcc atg ccc gaa ggt tat gta cag              1344
Lys Gln His Asp Phe Phe Lys Ser Ala Met Pro Glu Gly Tyr Val Gln
        435                     440                     445 gaa aga act ata ttt tac aaa gat gac ggg aac tac aag aca cgt gct              1392
Glu Arg Thr Ile Phe Tyr Lys Asp Asp Gly Asn Tyr Lys Thr Arg Ala
    450                     455                     460 gaa gtc aag ttt gaa ggt gat acc ctt gtt aat aga atc gag tta aaa              1440
Glu Val Lys Phe Glu Gly Asp Thr Leu Val Asn Arg Ile Glu Leu Lys
465                     470                     475                     480 ggt att gat ttt aaa gaa gat gga aac att ctt gga cac aaa atg gaa              1488
Gly Ile Asp Phe Lys Glu Asp Gly Asn Ile Leu Gly His Lys Met Glu
                485                     490                     495 tac aat tat aac tca cat aat gta tac atc atg gca gac aaa cca aag              1536
Tyr Asn Tyr Asn Ser His Asn Val Tyr Ile Met Ala Asp Lys Pro Lys
            500                     505                     510 aat ggc atc aaa gtt aac ttc aaa att aga cac aac att aaa gat gga              1584
Asn Gly Ile Lys Val Asn Phe Lys Ile Arg His Asn Ile Lys Asp Gly
        515                     520                     525 agc gtt caa tta gca gac cat tat caa caa aat act cca att ggc gat              1632
Ser Val Gln Leu Ala Asp His Tyr Gln Gln Asn Thr Pro Ile Gly Asp
    530                     535                     540 ggc cct gtc ctt tta cca gac aac cat tac ctg tcc acg caa tct gcc              1680
Gly Pro Val Leu Leu Pro Asp Asn His Tyr Leu Ser Thr Gln Ser Ala
545                     550                     555                     560 ctt tcc aaa gat ccc aac gaa aag aga gat cac atg atc ctt ctt gag              1728
Leu Ser Lys Asp Pro Asn Glu Lys Arg Asp His Met Ile Leu Leu Glu
                565                     570                     575 ttt gta aca gct gct ggg att aca cat ggc atg gat gaa cta tac aaa              1776
Phe Val Thr Ala Ala Gly Ile Thr His Gly Met Asp Glu Leu Tyr Lys
            580                     585                     590 cct cag gag taa                                                              1788
Pro Gln Glu
        595

<210> SEQ ID NO 69
<211> LENGTH: 595
<212> TYPE: PRT
<213> ORGANISM: Artificial Sequence
<220> FEATURE:
<223> OTHER INFORMATION: Fusion Construct

<400> SEQUENCE: 69

Met Gly Asn Ala Ala Ala Ala Lys Lys Gly Ser Glu Gln Glu Ser Val
1               5                   10                  15

Lys Glu Phe Leu Ala Lys Ala Lys Glu Asp Phe Leu Lys Lys Trp Glu
            20                  25                  30

Asp Pro Ser Gln Asn Thr Ala Gln Leu Asp Gln Phe Asp Arg Ile Lys
```

```
                 35                  40                  45
Thr Leu Gly Thr Gly Ser Phe Gly Arg Val Met Leu Val Lys His Lys
             50                  55                  60

Glu Ser Gly Asn His Tyr Ala Met Lys Ile Leu Asp Lys Gln Lys Val
 65                  70                  75                  80

Val Lys Leu Lys Gln Ile Glu His Thr Leu Asn Glu Lys Arg Ile Leu
                 85                  90                  95

Gln Ala Val Asn Phe Pro Phe Leu Val Lys Leu Glu Phe Ser Phe Lys
                100                 105                 110

Asp Asn Ser Asn Leu Tyr Met Val Met Glu Tyr Val Ala Gly Gly Glu
            115                 120                 125

Met Phe Ser His Leu Arg Arg Ile Gly Arg Phe Ser Glu Pro His Ala
            130                 135                 140

Arg Phe Tyr Ala Ala Gln Ile Val Leu Thr Phe Glu Tyr Leu His Ser
145                 150                 155                 160

Leu Asp Leu Ile Tyr Arg Asp Leu Lys Pro Glu Asn Leu Leu Ile Asp
                165                 170                 175

Gln Gln Gly Tyr Ile Gln Val Thr Asp Phe Gly Phe Ala Lys Arg Val
            180                 185                 190

Lys Gly Arg Thr Trp Thr Leu Cys Gly Thr Pro Glu Tyr Leu Ala Pro
            195                 200                 205

Glu Ile Ile Leu Ser Lys Gly Tyr Asn Lys Ala Val Asp Trp Trp Ala
            210                 215                 220

Leu Gly Val Leu Ile Tyr Glu Met Ala Ala Gly Tyr Pro Pro Phe Phe
225                 230                 235                 240

Ala Asp Gln Pro Ile Gln Ile Tyr Glu Lys Ile Val Ser Gly Lys Val
                245                 250                 255

Arg Phe Pro Ser His Phe Ser Ser Asp Leu Lys Asp Leu Leu Arg Asn
            260                 265                 270

Leu Leu Gln Val Asp Leu Thr Lys Arg Phe Gly Asn Leu Lys Asp Gly
            275                 280                 285

Val Asn Asp Ile Lys Asn His Lys Trp Phe Ala Thr Thr Asp Trp Ile
290                 295                 300

Ala Ile Tyr Gln Arg Lys Val Glu Ala Pro Phe Ile Pro Lys Phe Lys
305                 310                 315                 320

Gly Pro Gly Asp Thr Ser Asn Phe Asp Asp Tyr Glu Glu Glu Glu Ile
                325                 330                 335

Arg Val Ser Ile Asn Glu Lys Cys Gly Lys Glu Phe Thr Glu Phe Gly
            340                 345                 350

Arg Ala Met Ser Lys Gly Glu Glu Leu Phe Thr Gly Val Val Pro Ile
            355                 360                 365

Leu Val Glu Leu Asp Gly Asp Val Asn Gly Gln Lys Phe Ser Val Ser
            370                 375                 380

Gly Glu Gly Glu Gly Asp Ala Thr Tyr Gly Lys Leu Thr Leu Lys Phe
385                 390                 395                 400

Ile Cys Thr Thr Gly Lys Leu Pro Val Pro Trp Pro Thr Leu Val Thr
                405                 410                 415

Thr Leu Thr Tyr Gly Val Gln Cys Phe Ser Arg Tyr Pro Asp His Met
            420                 425                 430

Lys Gln His Asp Phe Phe Lys Ser Ala Met Pro Glu Gly Tyr Val Gln
            435                 440                 445

Glu Arg Thr Ile Phe Tyr Lys Asp Asp Gly Asn Tyr Lys Thr Arg Ala
450                 455                 460
```

```
Glu Val Lys Phe Glu Gly Asp Thr Leu Val Asn Arg Ile Glu Leu Lys
465                 470                 475                 480

Gly Ile Asp Phe Lys Glu Asp Gly Asn Ile Leu Gly His Lys Met Glu
                485                 490                 495

Tyr Asn Tyr Asn Ser His Asn Val Tyr Ile Met Ala Asp Lys Pro Lys
            500                 505                 510

Asn Gly Ile Lys Val Asn Phe Lys Ile Arg His Asn Ile Lys Asp Gly
        515                 520                 525

Ser Val Gln Leu Ala Asp His Tyr Gln Gln Asn Thr Pro Ile Gly Asp
    530                 535                 540

Gly Pro Val Leu Leu Pro Asp Asn His Tyr Leu Ser Thr Gln Ser Ala
545                 550                 555                 560

Leu Ser Lys Asp Pro Asn Glu Lys Arg Asp His Met Ile Leu Leu Glu
                565                 570                 575

Phe Val Thr Ala Ala Gly Ile Thr His Gly Met Asp Glu Leu Tyr Lys
            580                 585                 590

Pro Gln Glu
        595

<210> SEQ ID NO 70
<211> LENGTH: 2181
<212> TYPE: DNA
<213> ORGANISM: Artificial Sequence
<220> FEATURE:
<223> OTHER INFORMATION: PKB-EGFP fusion
<220> FEATURE:
<221> NAME/KEY: CDS
<222> LOCATION: (1)..(2178)

<400> SEQUENCE: 70 atg agc gac gtg gct att gtg aag gag ggt tgg ctg cac aaa cga ggg     48
Met Ser Asp Val Ala Ile Val Lys Glu Gly Trp Leu His Lys Arg Gly
1               5                   10                  15 gag tac atc aag acc tgg cgg cca cgc tac ttc ctc ctc aag aat gat     96
Glu Tyr Ile Lys Thr Trp Arg Pro Arg Tyr Phe Leu Leu Lys Asn Asp
            20                  25                  30 ggc acc ttc att ggc tac aag gag cgg ccg cag gat gtg gac caa cgt    144
Gly Thr Phe Ile Gly Tyr Lys Glu Arg Pro Gln Asp Val Asp Gln Arg
        35                  40                  45 gag gct ccc ctc aac aac ttc tct gtg gcg cag tgc cag ctg atg aag    192
Glu Ala Pro Leu Asn Asn Phe Ser Val Ala Gln Cys Gln Leu Met Lys
    50                  55                  60 acg gag cgg ccc cgg ccc aac acc ttc atc atc cgc tgc ctg cag tgg    240
Thr Glu Arg Pro Arg Pro Asn Thr Phe Ile Ile Arg Cys Leu Gln Trp
65                  70                  75                  80 acc act gtc atc gaa cgc acc ttc cat gtg gag act cct gag gag cgg    288
Thr Thr Val Ile Glu Arg Thr Phe His Val Glu Thr Pro Glu Glu Arg
                85                  90                  95 gag gag tgg aca acc gcc atc cag act gtg gct gac ggc ctc aag aag    336
Glu Glu Trp Thr Thr Ala Ile Gln Thr Val Ala Asp Gly Leu Lys Lys
            100                 105                 110 cag gag gag gag gag atg gac ttc cgg tcg ggc tca ccc agt gac aac    384
Gln Glu Glu Glu Glu Met Asp Phe Arg Ser Gly Ser Pro Ser Asp Asn
        115                 120                 125 tca ggg gct gaa gag atg gag gtg tcc ctg gcc aag ccc aag cac cgc    432
Ser Gly Ala Glu Glu Met Glu Val Ser Leu Ala Lys Pro Lys His Arg
    130                 135                 140 gtg acc atg aac gag ttt gag tac ctg aag ctg ctg ggc aag ggc act    480
Val Thr Met Asn Glu Phe Glu Tyr Leu Lys Leu Leu Gly Lys Gly Thr
```

```
                                                                              -continued
145                     150                     155                     160
ttc ggc aag gtg atc ctg gtg aag gag aag gcc aca ggc cgc tac tac              528
Phe Gly Lys Val Ile Leu Val Lys Glu Lys Ala Thr Gly Arg Tyr Tyr
                165                     170                     175 gcc atg aag atc ctc aag aag gaa gtc atc gtg gcc aag gac gag gtg              576
Ala Met Lys Ile Leu Lys Lys Glu Val Ile Val Ala Lys Asp Glu Val
            180                     185                     190 gcc cac aca ctc acc gag aac cgc gtc ctg cag aac tcc agg cac ccc              624
Ala His Thr Leu Thr Glu Asn Arg Val Leu Gln Asn Ser Arg His Pro
        195                     200                     205 ttc ctc aca gcc ctg aag tac tct ttc cag acc cac gac cgc ctc tgc              672
Phe Leu Thr Ala Leu Lys Tyr Ser Phe Gln Thr His Asp Arg Leu Cys
    210                     215                     220 ttt gtc atg gag tac gcc aac ggg ggc gag ctg ttc ttc cac ctg tcc              720
Phe Val Met Glu Tyr Ala Asn Gly Gly Glu Leu Phe Phe His Leu Ser
225                     230                     235                     240 cgg gaa cgt gtg ttc tcc gag gac cgg gcc cgc ttc tat ggc gct gag              768
Arg Glu Arg Val Phe Ser Glu Asp Arg Ala Arg Phe Tyr Gly Ala Glu
                245                     250                     255 att gtg tca gcc ctg gac tac ctg cac tcg gag aag aac gtg gtg tac              816
Ile Val Ser Ala Leu Asp Tyr Leu His Ser Glu Lys Asn Val Val Tyr
            260                     265                     270 cgg gac ctc aag ctg gag aac ctc atg ctg gac aag gac ggg cac att              864
Arg Asp Leu Lys Leu Glu Asn Leu Met Leu Asp Lys Asp Gly His Ile
        275                     280                     285 aag atc aca gac ttc ggg ctg tgc aag gag ggg atc aag gac ggt gcc              912
Lys Ile Thr Asp Phe Gly Leu Cys Lys Glu Gly Ile Lys Asp Gly Ala
    290                     295                     300 acc atg aag acc ttt tgc ggc aca cct gag tac ctg gcc ccc gag gtg              960
Thr Met Lys Thr Phe Cys Gly Thr Pro Glu Tyr Leu Ala Pro Glu Val
305                     310                     315                     320 ctg gag gac aat gac tac ggc cgt gca gtg gac tgg tgg ggg ctg ggc             1008
Leu Glu Asp Asn Asp Tyr Gly Arg Ala Val Asp Trp Trp Gly Leu Gly
                325                     330                     335 gtg gtc atg tac gag atg atg tgc ggt cgc ctg ccc ttc tac aac cag             1056
Val Val Met Tyr Glu Met Met Cys Gly Arg Leu Pro Phe Tyr Asn Gln
            340                     345                     350 gac cat gag aag ctt ttt gag ctc atc ctc atg gag gag atc cgc ttc             1104
Asp His Glu Lys Leu Phe Glu Leu Ile Leu Met Glu Glu Ile Arg Phe
        355                     360                     365 ccg cgc acg ctt ggt ccc gag gcc aag tcc ttg ctt tca ggg ctg ctc             1152
Pro Arg Thr Leu Gly Pro Glu Ala Lys Ser Leu Leu Ser Gly Leu Leu
    370                     375                     380 aag aag gac ccc aag cag agg ctt ggc ggg ggc tcc gag gac gcc aag             1200
Lys Lys Asp Pro Lys Gln Arg Leu Gly Gly Gly Ser Glu Asp Ala Lys
385                     390                     395                     400 gag atc atg cag cat cgc ttc ttt gcc ggt atc gtg tgg cag cac gtg             1248
Glu Ile Met Gln His Arg Phe Phe Ala Gly Ile Val Trp Gln His Val
                405                     410                     415 tac gag aag aag ctc agc cca ccc ttc aag ccc cag gtc acg tcg gag             1296
Tyr Glu Lys Lys Leu Ser Pro Pro Phe Lys Pro Gln Val Thr Ser Glu
            420                     425                     430 act gac acc agg tat ttt gat gag gag ttc acg gcc cag atg atc acc             1344
Thr Asp Thr Arg Tyr Phe Asp Glu Glu Phe Thr Ala Gln Met Ile Thr
        435                     440                     445 atc aca cca cct gac caa gat gac agc atg gag tgt gtg gac agc gag             1392
Ile Thr Pro Pro Asp Gln Asp Asp Ser Met Glu Cys Val Asp Ser Glu
    450                     455                     460 cgc agg ccc cac ttc ccc cag ttc tcc tac tcg gcc agc agc acg gcc             1440
```

```
Arg Arg Pro His Phe Pro Gln Phe Ser Tyr Ser Ala Ser Ser Thr Ala
465                 470                 475                 480 tcg gat cca ccg gtc gcc acc atg gtg agc aag ggc gag gag ctg ttc    1488
Ser Asp Pro Pro Val Ala Thr Met Val Ser Lys Gly Glu Glu Leu Phe
                485                 490                 495 acc ggg gtg gtg ccc atc ctg gtc gag ctg gac ggc gac gta aac ggc    1536
Thr Gly Val Val Pro Ile Leu Val Glu Leu Asp Gly Asp Val Asn Gly
            500                 505                 510 cac aag ttc agc gtg tcc ggc gag ggc gag ggc gat gcc acc tac ggc    1584
His Lys Phe Ser Val Ser Gly Glu Gly Glu Gly Asp Ala Thr Tyr Gly
            515                 520                 525 aag ctg acc ctg aag ttc atc tgc acc acc ggc aag ctg ccc gtg ccc    1632
Lys Leu Thr Leu Lys Phe Ile Cys Thr Thr Gly Lys Leu Pro Val Pro
        530                 535                 540 tgg ccc acc ctc gtg acc acc ctg acc tac ggc gtg cag tgc ttc agc    1680
Trp Pro Thr Leu Val Thr Thr Leu Thr Tyr Gly Val Gln Cys Phe Ser
545                 550                 555                 560 cgc tac ccc gac cac atg aag cag cac gac ttc ttc aag tcc gcc atg    1728
Arg Tyr Pro Asp His Met Lys Gln His Asp Phe Phe Lys Ser Ala Met
                565                 570                 575 ccc gaa ggc tac gtc cag gag cgc acc atc ttc ttc aag gac gac ggc    1776
Pro Glu Gly Tyr Val Gln Glu Arg Thr Ile Phe Phe Lys Asp Asp Gly
            580                 585                 590 aac tac aag acc cgc gcc gag gtg aag ttc gag ggc gac acc ctg gtg    1824
Asn Tyr Lys Thr Arg Ala Glu Val Lys Phe Glu Gly Asp Thr Leu Val
        595                 600                 605 aac cgc atc gag ctg aag ggc atc gac ttc aag gag gac ggc aac atc    1872
Asn Arg Ile Glu Leu Lys Gly Ile Asp Phe Lys Glu Asp Gly Asn Ile
610                 615                 620 ctg ggg cac aag ctg gag tac aac tac aac agc cac aac gtc tat atc    1920
Leu Gly His Lys Leu Glu Tyr Asn Tyr Asn Ser His Asn Val Tyr Ile
625                 630                 635                 640 atg gcc gac aag cag aag aac ggc atc aag gtg aac ttc aag atc cgc    1968
Met Ala Asp Lys Gln Lys Asn Gly Ile Lys Val Asn Phe Lys Ile Arg
                645                 650                 655 cac aac atc gag gac ggc agc gtg cag ctc gcc gac cac tac cag cag    2016
His Asn Ile Glu Asp Gly Ser Val Gln Leu Ala Asp His Tyr Gln Gln
            660                 665                 670 aac acc ccc atc ggc gac ggc ccc gtg ctg ctg ccc gac aac cac tac    2064
Asn Thr Pro Ile Gly Asp Gly Pro Val Leu Leu Pro Asp Asn His Tyr
        675                 680                 685 ctg agc acc cag tcc gcc ctg agc aaa gac ccc aac gag aag cgc gat    2112
Leu Ser Thr Gln Ser Ala Leu Ser Lys Asp Pro Asn Glu Lys Arg Asp
690                 695                 700 cac atg gtc ctg ctg gag ttc gtg acc gcc gcc ggg atc act ctc ggc    2160
His Met Val Leu Leu Glu Phe Val Thr Ala Ala Gly Ile Thr Leu Gly
705                 710                 715                 720 atg gac gag ctg tac aag taa                                        2181
Met Asp Glu Leu Tyr Lys
                725

<210> SEQ ID NO 71
<211> LENGTH: 726
<212> TYPE: PRT
<213> ORGANISM: Artificial Sequence
<220> FEATURE:
<223> OTHER INFORMATION: PKB-EGFP fusion

<400> SEQUENCE: 71

Met Ser Asp Val Ala Ile Val Lys Glu Gly Trp Leu His Lys Arg Gly
1               5                   10                  15
```

```
Glu Tyr Ile Lys Thr Trp Arg Pro Arg Tyr Phe Leu Leu Lys Asn Asp
             20                  25                  30

Gly Thr Phe Ile Gly Tyr Lys Glu Arg Pro Gln Asp Val Asp Gln Arg
             35                  40                  45

Glu Ala Pro Leu Asn Asn Phe Ser Val Ala Gln Cys Gln Leu Met Lys
             50                  55                  60

Thr Glu Arg Pro Arg Pro Asn Thr Phe Ile Ile Arg Cys Leu Gln Trp
 65                  70                  75                  80

Thr Thr Val Ile Glu Arg Thr Phe His Val Glu Thr Pro Glu Glu Arg
             85                  90                  95

Glu Glu Trp Thr Thr Ala Ile Gln Thr Val Ala Asp Gly Leu Lys Lys
            100                 105                 110

Gln Glu Glu Glu Met Asp Phe Arg Ser Gly Ser Pro Ser Asp Asn
            115                 120                 125

Ser Gly Ala Glu Glu Met Glu Val Ser Leu Ala Lys Pro Lys His Arg
            130                 135                 140

Val Thr Met Asn Glu Phe Glu Tyr Leu Lys Leu Leu Gly Lys Gly Thr
145                 150                 155                 160

Phe Gly Lys Val Ile Leu Val Lys Glu Lys Ala Thr Gly Arg Tyr Tyr
            165                 170                 175

Ala Met Lys Ile Leu Lys Lys Glu Val Ile Val Ala Lys Asp Glu Val
            180                 185                 190

Ala His Thr Leu Thr Glu Asn Arg Val Leu Gln Asn Ser Arg His Pro
            195                 200                 205

Phe Leu Thr Ala Leu Lys Tyr Ser Phe Gln Thr His Asp Arg Leu Cys
            210                 215                 220

Phe Val Met Glu Tyr Ala Asn Gly Gly Glu Leu Phe Phe His Leu Ser
225                 230                 235                 240

Arg Glu Arg Val Phe Ser Glu Asp Arg Ala Arg Phe Tyr Gly Ala Glu
            245                 250                 255

Ile Val Ser Ala Leu Asp Tyr Leu His Ser Glu Lys Asn Val Val Tyr
            260                 265                 270

Arg Asp Leu Lys Leu Glu Asn Leu Met Leu Asp Lys Asp Gly His Ile
            275                 280                 285

Lys Ile Thr Asp Phe Gly Leu Cys Lys Glu Gly Ile Lys Asp Gly Ala
            290                 295                 300

Thr Met Lys Thr Phe Cys Gly Thr Pro Glu Tyr Leu Ala Pro Glu Val
305                 310                 315                 320

Leu Glu Asp Asn Asp Tyr Gly Arg Ala Val Asp Trp Trp Gly Leu Gly
            325                 330                 335

Val Val Met Tyr Glu Met Met Cys Gly Arg Leu Pro Phe Tyr Asn Gln
            340                 345                 350

Asp His Glu Lys Leu Phe Glu Leu Ile Leu Met Glu Glu Ile Arg Phe
            355                 360                 365

Pro Arg Thr Leu Gly Pro Glu Ala Lys Ser Leu Leu Ser Gly Leu Leu
            370                 375                 380

Lys Lys Asp Pro Lys Gln Arg Leu Gly Gly Gly Ser Glu Asp Ala Lys
385                 390                 395                 400

Glu Ile Met Gln His Arg Phe Phe Ala Gly Ile Val Trp Gln His Val
            405                 410                 415

Tyr Glu Lys Lys Leu Ser Pro Pro Phe Lys Pro Gln Val Thr Ser Glu
            420                 425                 430
```

```
Thr Asp Thr Arg Tyr Phe Asp Glu Glu Phe Thr Ala Gln Met Ile Thr
            435                 440                 445

Ile Thr Pro Pro Asp Gln Asp Asp Ser Met Glu Cys Val Asp Ser Glu
        450                 455                 460

Arg Arg Pro His Phe Pro Gln Phe Ser Tyr Ser Ala Ser Ser Thr Ala
465                 470                 475                 480

Ser Asp Pro Pro Val Ala Thr Met Val Ser Lys Gly Glu Glu Leu Phe
                485                 490                 495

Thr Gly Val Val Pro Ile Leu Val Glu Leu Asp Gly Asp Val Asn Gly
            500                 505                 510

His Lys Phe Ser Val Ser Gly Glu Gly Glu Gly Asp Ala Thr Tyr Gly
        515                 520                 525

Lys Leu Thr Leu Lys Phe Ile Cys Thr Thr Gly Lys Leu Pro Val Pro
    530                 535                 540

Trp Pro Thr Leu Val Thr Thr Leu Thr Tyr Gly Val Gln Cys Phe Ser
545                 550                 555                 560

Arg Tyr Pro Asp His Met Lys Gln His Asp Phe Phe Lys Ser Ala Met
                565                 570                 575

Pro Glu Gly Tyr Val Gln Glu Arg Thr Ile Phe Phe Lys Asp Asp Gly
            580                 585                 590

Asn Tyr Lys Thr Arg Ala Glu Val Lys Phe Glu Gly Asp Thr Leu Val
        595                 600                 605

Asn Arg Ile Glu Leu Lys Gly Ile Asp Phe Lys Glu Asp Gly Asn Ile
610                 615                 620

Leu Gly His Lys Leu Glu Tyr Asn Tyr Asn Ser His Asn Val Tyr Ile
625                 630                 635                 640

Met Ala Asp Lys Gln Lys Asn Gly Ile Lys Val Asn Phe Lys Ile Arg
                645                 650                 655

His Asn Ile Glu Asp Gly Ser Val Gln Leu Ala Asp His Tyr Gln Gln
            660                 665                 670

Asn Thr Pro Ile Gly Asp Gly Pro Val Leu Leu Pro Asp Asn His Tyr
        675                 680                 685

Leu Ser Thr Gln Ser Ala Leu Ser Lys Asp Pro Asn Glu Lys Arg Asp
    690                 695                 700

His Met Val Leu Leu Glu Phe Val Thr Ala Ala Gly Ile Thr Leu Gly
705                 710                 715                 720

Met Asp Glu Leu Tyr Lys
                725

<210> SEQ ID NO 72
<211> LENGTH: 2751
<212> TYPE: DNA
<213> ORGANISM: Artificial Sequence
<220> FEATURE:
<223> OTHER INFORMATION: Fusion construct
<220> FEATURE:
<221> NAME/KEY: CDS
<222> LOCATION: (1)..(2748)

<400> SEQUENCE: 72 atg gct gac gtt tac ccg gcc aac gac tcc acg gcg tct cag gac gtg      48
Met Ala Asp Val Tyr Pro Ala Asn Asp Ser Thr Ala Ser Gln Asp Val
1               5                   10                  15 gcc aac cgc ttc gcc cgc aaa ggg gcg ctg agg cag aag aac gtg cat      96
Ala Asn Arg Phe Ala Arg Lys Gly Ala Leu Arg Gln Lys Asn Val His
            20                  25                  30 gag gtg aaa gac cac aaa ttc atc gcc cgc ttc ttc aag caa ccc acc     144
```

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
| Glu | Val | Lys | Asp | His | Lys | Phe | Ile | Ala | Arg | Phe | Phe | Lys | Gln | Pro | Thr |     |
|     |     | 35  |     |     |     |     | 40  |     |     |     |     | 45  |     |     |     |     |

| | | | | | | | | | | | | | | | | |
|---|---|---|---|---|---|---|---|---|---|---|---|---|---|---|---|---|
| ttc | tgc | agc | cac | tgc | acc | gac | ttc | atc | tgg | ggg | ttt | ggg | aaa | caa | ggc | 192 |
| Phe | Cys | Ser | His | Cys | Thr | Asp | Phe | Ile | Trp | Gly | Phe | Gly | Lys | Gln | Gly |  |
|  |  | 50 |  |  |  |  | 55 |  |  |  |  | 60 |  |  |  |  |

| | | | | | | | | | | | | | | | | |
|---|---|---|---|---|---|---|---|---|---|---|---|---|---|---|---|---|
| ttc | cag | tgc | caa | gtt | tgc | tgt | ttt | gtg | gtt | cat | aag | agg | tgc | cat | gag | 240 |
| Phe | Gln | Cys | Gln | Val | Cys | Cys | Phe | Val | Val | His | Lys | Arg | Cys | His | Glu |  |
| 65 |  |  |  | 70 |  |  |  |  | 75 |  |  |  |  | 80 |  |  |

| | | | | | | | | | | | | | | | | |
|---|---|---|---|---|---|---|---|---|---|---|---|---|---|---|---|---|
| ttc | gtt | acg | ttc | tct | tgt | ccg | ggt | gcg | gat | aag | gga | cct | gac | act | gac | 288 |
| Phe | Val | Thr | Phe | Ser | Cys | Pro | Gly | Ala | Asp | Lys | Gly | Pro | Asp | Thr | Asp |  |
|  |  |  |  | 85 |  |  |  |  | 90 |  |  |  |  | 95 |  |  |

| | | | | | | | | | | | | | | | | |
|---|---|---|---|---|---|---|---|---|---|---|---|---|---|---|---|---|
| gac | ccc | agg | agc | aag | cac | aag | ttc | aaa | atc | cac | aca | tac | gga | agc | cct | 336 |
| Asp | Pro | Arg | Ser | Lys | His | Lys | Phe | Lys | Ile | His | Thr | Tyr | Gly | Ser | Pro |  |
|  |  |  | 100 |  |  |  |  | 105 |  |  |  |  | 110 |  |  |  |

| | | | | | | | | | | | | | | | | |
|---|---|---|---|---|---|---|---|---|---|---|---|---|---|---|---|---|
| acc | ttc | tgt | gat | cac | tgt | ggg | tcc | ctg | ctc | tat | gga | ctt | atc | cac | caa | 384 |
| Thr | Phe | Cys | Asp | His | Cys | Gly | Ser | Leu | Leu | Tyr | Gly | Leu | Ile | His | Gln |  |
|  |  |  | 115 |  |  |  |  | 120 |  |  |  |  | 125 |  |  |  |

| | | | | | | | | | | | | | | | | |
|---|---|---|---|---|---|---|---|---|---|---|---|---|---|---|---|---|
| ggg | atg | aaa | tgt | gac | acc | tgc | gac | atg | aat | gtt | cac | aac | cag | tgt | gtg | 432 |
| Gly | Met | Lys | Cys | Asp | Thr | Cys | Asp | Met | Asn | Val | His | Asn | Gln | Cys | Val |  |
|  | 130 |  |  |  |  | 135 |  |  |  |  | 140 |  |  |  |  |  |

| | | | | | | | | | | | | | | | | |
|---|---|---|---|---|---|---|---|---|---|---|---|---|---|---|---|---|
| atc | aat | gac | cct | agc | ctc | tgc | gga | atg | gat | cac | aca | gag | aag | agg | ggg | 480 |
| Ile | Asn | Asp | Pro | Ser | Leu | Cys | Gly | Met | Asp | His | Thr | Glu | Lys | Arg | Gly |  |
| 145 |  |  |  |  | 150 |  |  |  |  | 155 |  |  |  |  | 160 |  |

| | | | | | | | | | | | | | | | | |
|---|---|---|---|---|---|---|---|---|---|---|---|---|---|---|---|---|
| cgg | att | tat | ctg | aag | gct | gag | gtc | act | gat | gaa | aag | ctc | cac | gtc | acg | 528 |
| Arg | Ile | Tyr | Leu | Lys | Ala | Glu | Val | Thr | Asp | Glu | Lys | Leu | His | Val | Thr |  |
|  |  |  |  | 165 |  |  |  |  | 170 |  |  |  |  | 175 |  |  |

| | | | | | | | | | | | | | | | | |
|---|---|---|---|---|---|---|---|---|---|---|---|---|---|---|---|---|
| gta | cga | gat | gca | aaa | aat | cta | atc | cct | atg | gat | cca | aat | ggg | ctt | tcg | 576 |
| Val | Arg | Asp | Ala | Lys | Asn | Leu | Ile | Pro | Met | Asp | Pro | Asn | Gly | Leu | Ser |  |
|  |  |  | 180 |  |  |  |  | 185 |  |  |  |  | 190 |  |  |  |

| | | | | | | | | | | | | | | | | |
|---|---|---|---|---|---|---|---|---|---|---|---|---|---|---|---|---|
| gat | cct | tat | gtg | aag | ctg | aaa | cta | atc | cct | gac | ccc | aag | aat | gag | agc | 624 |
| Asp | Pro | Tyr | Val | Lys | Leu | Lys | Leu | Ile | Pro | Asp | Pro | Lys | Asn | Glu | Ser |  |
|  |  |  | 195 |  |  |  |  | 200 |  |  |  |  | 205 |  |  |  |

| | | | | | | | | | | | | | | | | |
|---|---|---|---|---|---|---|---|---|---|---|---|---|---|---|---|---|
| aaa | cag | aaa | acc | aaa | acc | atc | cgc | tcc | aac | ctg | aat | cct | cag | tgg | aat | 672 |
| Lys | Gln | Lys | Thr | Lys | Thr | Ile | Arg | Ser | Asn | Leu | Asn | Pro | Gln | Trp | Asn |  |
|  | 210 |  |  |  |  | 215 |  |  |  |  | 220 |  |  |  |  |  |

| | | | | | | | | | | | | | | | | |
|---|---|---|---|---|---|---|---|---|---|---|---|---|---|---|---|---|
| gag | tcc | ttc | acg | ttc | aaa | tta | aaa | cct | tca | gac | aaa | gac | cgg | cga | ctg | 720 |
| Glu | Ser | Phe | Thr | Phe | Lys | Leu | Lys | Pro | Ser | Asp | Lys | Asp | Arg | Arg | Leu |  |
| 225 |  |  |  |  | 230 |  |  |  |  | 235 |  |  |  |  | 240 |  |

| | | | | | | | | | | | | | | | | |
|---|---|---|---|---|---|---|---|---|---|---|---|---|---|---|---|---|
| tct | gta | gaa | atc | tgg | gac | tgg | gat | cgg | acg | act | cgg | aat | gac | ttc | atg | 768 |
| Ser | Val | Glu | Ile | Trp | Asp | Trp | Asp | Arg | Thr | Thr | Arg | Asn | Asp | Phe | Met |  |
|  |  |  |  | 245 |  |  |  |  | 250 |  |  |  |  | 255 |  |  |

| | | | | | | | | | | | | | | | | |
|---|---|---|---|---|---|---|---|---|---|---|---|---|---|---|---|---|
| gga | tcc | ctt | tcc | ttt | ggt | gtc | tca | gag | cta | atg | aag | atg | ccg | gcc | agt | 816 |
| Gly | Ser | Leu | Ser | Phe | Gly | Val | Ser | Glu | Leu | Met | Lys | Met | Pro | Ala | Ser |  |
|  |  |  | 260 |  |  |  |  | 265 |  |  |  |  | 270 |  |  |  |

| | | | | | | | | | | | | | | | | |
|---|---|---|---|---|---|---|---|---|---|---|---|---|---|---|---|---|
| gga | tgg | tat | aaa | gct | cac | aac | caa | gaa | gag | ggc | gaa | tat | tac | aac | gtg | 864 |
| Gly | Trp | Tyr | Lys | Ala | His | Asn | Gln | Glu | Glu | Gly | Glu | Tyr | Tyr | Asn | Val |  |
|  |  | 275 |  |  |  |  | 280 |  |  |  |  | 285 |  |  |  |  |

| | | | | | | | | | | | | | | | | |
|---|---|---|---|---|---|---|---|---|---|---|---|---|---|---|---|---|
| ccc | att | cca | gaa | gga | gat | gaa | gaa | ggc | aac | atg | gaa | ctc | agg | cag | aag | 912 |
| Pro | Ile | Pro | Glu | Gly | Asp | Glu | Glu | Gly | Asn | Met | Glu | Leu | Arg | Gln | Lys |  |
|  | 290 |  |  |  |  | 295 |  |  |  |  | 300 |  |  |  |  |  |

| | | | | | | | | | | | | | | | | |
|---|---|---|---|---|---|---|---|---|---|---|---|---|---|---|---|---|
| ttt | gag | aaa | gcc | aag | cta | ggt | cct | gtt | ggt | aac | aaa | gtc | atc | agc | cct | 960 |
| Phe | Glu | Lys | Ala | Lys | Leu | Gly | Pro | Val | Gly | Asn | Lys | Val | Ile | Ser | Pro |  |
| 305 |  |  |  |  | 310 |  |  |  |  | 315 |  |  |  |  | 320 |  |

| | | | | | | | | | | | | | | | | |
|---|---|---|---|---|---|---|---|---|---|---|---|---|---|---|---|---|
| tca | gaa | gac | aga | aag | caa | cca | tcc | aac | aac | ctg | gac | aga | gtg | aaa | ctc | 1008 |
| Ser | Glu | Asp | Arg | Lys | Gln | Pro | Ser | Asn | Asn | Leu | Asp | Arg | Val | Lys | Leu |  |
|  |  |  | 325 |  |  |  |  | 330 |  |  |  |  | 335 |  |  |  |

| | | | | | | | | | | | | | | | | |
|---|---|---|---|---|---|---|---|---|---|---|---|---|---|---|---|---|
| aca | gac | ttc | aac | ttc | ctc | atg | gtg | ctg | ggg | aag | ggg | agt | ttt | ggg | aag | 1056 |
| Thr | Asp | Phe | Asn | Phe | Leu | Met | Val | Leu | Gly | Lys | Gly | Ser | Phe | Gly | Lys |  |
|  |  | 340 |  |  |  |  | 345 |  |  |  |  | 350 |  |  |  |  |

```
gtg atg ctt gct gac agg aag gga acg gag gaa ctg tac gcc atc aag    1104
Val Met Leu Ala Asp Arg Lys Gly Thr Glu Glu Leu Tyr Ala Ile Lys
        355                 360                 365 atc ctg aag aag gac gtg gtg atc cag gac gac gac gtg gag tgc acc    1152
Ile Leu Lys Lys Asp Val Val Ile Gln Asp Asp Asp Val Glu Cys Thr
370                 375                 380 atg gtg gag aag cgc gtg ctg gcc ctg ctg gac aag ccg cca ttt ctg    1200
Met Val Glu Lys Arg Val Leu Ala Leu Leu Asp Lys Pro Pro Phe Leu
385                 390                 395                 400 aca cag ctg cac tcc tgc ttc cag aca gtg gac cgg ctg tac ttc gtc    1248
Thr Gln Leu His Ser Cys Phe Gln Thr Val Asp Arg Leu Tyr Phe Val
        405                 410                 415 atg gaa tac gtc aac ggc ggg gat ctt atg tac cac att cag caa gtc    1296
Met Glu Tyr Val Asn Gly Gly Asp Leu Met Tyr His Ile Gln Gln Val
        420                 425                 430 ggg aaa ttt aag gag cca caa gca gta ttc tac gca gcc gag atc tcc    1344
Gly Lys Phe Lys Glu Pro Gln Ala Val Phe Tyr Ala Ala Glu Ile Ser
        435                 440                 445 atc gga ctg ttc ttc ctt cat aaa aga ggg atc att tac agg gat ctg    1392
Ile Gly Leu Phe Phe Leu His Lys Arg Gly Ile Ile Tyr Arg Asp Leu
450                 455                 460 aag ctg aac aat gtc atg ctg aac tca gaa ggg cac atc aaa atc gcc    1440
Lys Leu Asn Asn Val Met Leu Asn Ser Glu Gly His Ile Lys Ile Ala
465                 470                 475                 480 gac ttc ggg atg tgc aag gaa cac atg atg gat gga gtc acg acc agg    1488
Asp Phe Gly Met Cys Lys Glu His Met Met Asp Gly Val Thr Thr Arg
            485                 490                 495 acc ttc tgc gga act ccg gac tac att gcc cca gag ata atc gct tac    1536
Thr Phe Cys Gly Thr Pro Asp Tyr Ile Ala Pro Glu Ile Ile Ala Tyr
        500                 505                 510 cag ccg tac ggg aag tct gta gat tgg tgg gcg tac ggt gtg ctg ctg    1584
Gln Pro Tyr Gly Lys Ser Val Asp Trp Trp Ala Tyr Gly Val Leu Leu
        515                 520                 525 tac gag atg cta gcc ggg cag cct ccg ttt gat ggt gaa gat gaa gat    1632
Tyr Glu Met Leu Ala Gly Gln Pro Pro Phe Asp Gly Glu Asp Glu Asp
        530                 535                 540 gaa ctg ttt cag tct ata atg gag cac aac gtg tcc tac ccc aaa tcc    1680
Glu Leu Phe Gln Ser Ile Met Glu His Asn Val Ser Tyr Pro Lys Ser
545                 550                 555                 560 ttg tcc aag gaa gcc gtc tcc atc tgc aaa gga ctt atg acc aaa cag    1728
Leu Ser Lys Glu Ala Val Ser Ile Cys Lys Gly Leu Met Thr Lys Gln
            565                 570                 575 cct gcc aag cga ctg ggc tgc ggg ccc gag gga gag agg gat gtc aga    1776
Pro Ala Lys Arg Leu Gly Cys Gly Pro Glu Gly Glu Arg Asp Val Arg
        580                 585                 590 gag cat gcc ttc ttc agg agg atc gac tgg gag aaa ctg gag aac agg    1824
Glu His Ala Phe Phe Arg Arg Ile Asp Trp Glu Lys Leu Glu Asn Arg
        595                 600                 605 gag atc caa cca cca ttc aag ccc aaa gtg tgt ggc aaa gga gca gaa    1872
Glu Ile Gln Pro Pro Phe Lys Pro Lys Val Cys Gly Lys Gly Ala Glu
610                 615                 620 aac ttt gac aag ttc ttc acg cga gga cag cct gtc tta aca cca cca    1920
Asn Phe Asp Lys Phe Phe Thr Arg Gly Gln Pro Val Leu Thr Pro Pro
625                 630                 635                 640 gat cag ctg gtc att gct aac ata gac caa tct gat ttt gaa ggg ttc    1968
Asp Gln Leu Val Ile Ala Asn Ile Asp Gln Ser Asp Phe Glu Gly Phe
            645                 650                 655 tcg tat gtc aac ccc cag ttt gtg cac cca atc ttg caa agt gca gta    2016
Ser Tyr Val Asn Pro Gln Phe Val His Pro Ile Leu Gln Ser Ala Val
        660                 665                 670
```

-continued

```
ggg cgc gcc atg agt aaa gga gaa gaa ctt ttc act gga gtt gtc cca          2064
Gly Arg Ala Met Ser Lys Gly Glu Glu Leu Phe Thr Gly Val Val Pro
            675                 680                 685 att ctt gtt gaa tta gat ggc gat gtt aat ggg caa aaa ttc tct gtt          2112
Ile Leu Val Glu Leu Asp Gly Asp Val Asn Gly Gln Lys Phe Ser Val
690                 695                 700 agt gga gag ggt gaa ggt gat gca aca tac gga aaa ctt acc ctt aaa          2160
Ser Gly Glu Gly Glu Gly Asp Ala Thr Tyr Gly Lys Leu Thr Leu Lys
705                 710                 715                 720 ttt att tgc act act ggg aag cta cct gtt cca tgg cca acg ctt gtc          2208
Phe Ile Cys Thr Thr Gly Lys Leu Pro Val Pro Trp Pro Thr Leu Val
                725                 730                 735 act act ctc act tat ggt gtt caa tgc ttt tct aga tac cca gat cat          2256
Thr Thr Leu Thr Tyr Gly Val Gln Cys Phe Ser Arg Tyr Pro Asp His
            740                 745                 750 atg aaa cag cat gac ttt ttc aag agt gcc atg ccc gaa ggt tat gta          2304
Met Lys Gln His Asp Phe Phe Lys Ser Ala Met Pro Glu Gly Tyr Val
        755                 760                 765 cag gaa aga act ata ttt tac aaa gat gac ggg aac tac aag aca cgt          2352
Gln Glu Arg Thr Ile Phe Tyr Lys Asp Asp Gly Asn Tyr Lys Thr Arg
    770                 775                 780 gct gaa gtc aag ttt gaa ggt gat acc ctt gtt aat aga atc gag tta          2400
Ala Glu Val Lys Phe Glu Gly Asp Thr Leu Val Asn Arg Ile Glu Leu
785                 790                 795                 800 aaa ggt att gat ttt aaa gaa gat gga aac att ctt gga cac aaa atg          2448
Lys Gly Ile Asp Phe Lys Glu Asp Gly Asn Ile Leu Gly His Lys Met
                805                 810                 815 gaa tac aat tat aac tca cat aat gta tac atc atg gca gac aaa cca          2496
Glu Tyr Asn Tyr Asn Ser His Asn Val Tyr Ile Met Ala Asp Lys Pro
            820                 825                 830 aag aat ggc atc aaa gtt aac ttc aaa att aga cac aac att aaa gat          2544
Lys Asn Gly Ile Lys Val Asn Phe Lys Ile Arg His Asn Ile Lys Asp
        835                 840                 845 gga agc gtt caa tta gca gac cat tat caa caa aat act cca att ggc          2592
Gly Ser Val Gln Leu Ala Asp His Tyr Gln Gln Asn Thr Pro Ile Gly
    850                 855                 860 gat ggc cct gtc ctt tta cca gac aac cat tac ctg tcc acg caa tct          2640
Asp Gly Pro Val Leu Leu Pro Asp Asn His Tyr Leu Ser Thr Gln Ser
865                 870                 875                 880 gcc ctt tcc aaa gat ccc aac gaa aag aga gat cac atg atc ctt ctt          2688
Ala Leu Ser Lys Asp Pro Asn Glu Lys Arg Asp His Met Ile Leu Leu
                885                 890                 895 gag ttt gta aca gct gct ggg att aca cat ggc atg gat gaa cta tac          2736
Glu Phe Val Thr Ala Ala Gly Ile Thr His Gly Met Asp Glu Leu Tyr
            900                 905                 910 aaa cct cag gag taa                                                      2751
Lys Pro Gln Glu
        915
```

<210> SEQ ID NO 73
<211> LENGTH: 916
<212> TYPE: PRT
<213> ORGANISM: Artificial Sequence
<220> FEATURE:
<223> OTHER INFORMATION: Fusion construct

<400> SEQUENCE: 73

Met Ala Asp Val Tyr Pro Ala Asn Asp Ser Thr Ala Ser Gln Asp Val
1               5                   10                  15

Ala Asn Arg Phe Ala Arg Lys Gly Ala Leu Arg Gln Lys Asn Val His

-continued

```
                20                  25                  30
Glu Val Lys Asp His Lys Phe Ile Ala Arg Phe Phe Lys Gln Pro Thr
                35                  40                  45

Phe Cys Ser His Cys Thr Asp Phe Ile Trp Gly Phe Gly Lys Gln Gly
 50                  55                  60

Phe Gln Cys Gln Val Cys Cys Phe Val Val His Lys Arg Cys His Glu
65                   70                  75                  80

Phe Val Thr Phe Ser Cys Pro Gly Ala Asp Lys Gly Pro Asp Thr Asp
                85                  90                  95

Asp Pro Arg Ser Lys His Lys Phe Lys Ile His Thr Tyr Gly Ser Pro
                100                 105                 110

Thr Phe Cys Asp His Cys Gly Ser Leu Leu Tyr Gly Leu Ile His Gln
                115                 120                 125

Gly Met Lys Cys Asp Thr Cys Asp Met Asn Val His Asn Gln Cys Val
                130                 135                 140

Ile Asn Asp Pro Ser Leu Cys Gly Met Asp His Thr Glu Lys Arg Gly
145                 150                 155                 160

Arg Ile Tyr Leu Lys Ala Glu Val Thr Asp Glu Lys Leu His Val Thr
                165                 170                 175

Val Arg Asp Ala Lys Asn Leu Ile Pro Met Asp Pro Asn Gly Leu Ser
                180                 185                 190

Asp Pro Tyr Val Lys Leu Lys Leu Ile Pro Asp Pro Lys Asn Glu Ser
                195                 200                 205

Lys Gln Lys Thr Lys Thr Ile Arg Ser Asn Leu Asn Pro Gln Trp Asn
                210                 215                 220

Glu Ser Phe Thr Phe Lys Leu Lys Pro Ser Asp Lys Asp Arg Arg Leu
225                 230                 235                 240

Ser Val Glu Ile Trp Asp Trp Asp Arg Thr Thr Arg Asn Asp Phe Met
                245                 250                 255

Gly Ser Leu Ser Phe Gly Val Ser Glu Leu Met Lys Met Pro Ala Ser
                260                 265                 270

Gly Trp Tyr Lys Ala His Asn Gln Glu Glu Gly Glu Tyr Tyr Asn Val
                275                 280                 285

Pro Ile Pro Glu Gly Asp Glu Glu Gly Asn Met Glu Leu Arg Gln Lys
                290                 295                 300

Phe Glu Lys Ala Lys Leu Gly Pro Val Gly Asn Lys Val Ile Ser Pro
305                 310                 315                 320

Ser Glu Asp Arg Lys Gln Pro Ser Asn Asn Leu Asp Arg Val Lys Leu
                325                 330                 335

Thr Asp Phe Asn Phe Leu Met Val Leu Gly Lys Gly Ser Phe Gly Lys
                340                 345                 350

Val Met Leu Ala Asp Arg Lys Gly Thr Glu Glu Leu Tyr Ala Ile Lys
                355                 360                 365

Ile Leu Lys Lys Asp Val Val Ile Gln Asp Asp Val Glu Cys Thr
                370                 375                 380

Met Val Glu Lys Arg Val Leu Ala Leu Leu Asp Lys Pro Pro Phe Leu
385                 390                 395                 400

Thr Gln Leu His Ser Cys Phe Gln Thr Val Asp Arg Leu Tyr Phe Val
                405                 410                 415

Met Glu Tyr Val Asn Gly Gly Asp Leu Met Tyr His Ile Gln Gln Val
                420                 425                 430

Gly Lys Phe Lys Glu Pro Gln Ala Val Phe Tyr Ala Ala Glu Ile Ser
                435                 440                 445
```

-continued

```
Ile Gly Leu Phe Phe Leu His Lys Arg Gly Ile Ile Tyr Arg Asp Leu
    450                 455                 460
Lys Leu Asn Asn Val Met Leu Asn Ser Glu Gly His Ile Lys Ile Ala
465                 470                 475                 480
Asp Phe Gly Met Cys Lys Glu His Met Met Asp Gly Val Thr Thr Arg
            485                 490                 495
Thr Phe Cys Gly Thr Pro Asp Tyr Ile Ala Pro Glu Ile Ile Ala Tyr
            500                 505                 510
Gln Pro Tyr Gly Lys Ser Val Asp Trp Trp Ala Tyr Gly Val Leu Leu
        515                 520                 525
Tyr Glu Met Leu Ala Gly Gln Pro Pro Phe Asp Gly Glu Asp Glu Asp
530                 535                 540
Glu Leu Phe Gln Ser Ile Met Glu His Asn Val Ser Tyr Pro Lys Ser
545                 550                 555                 560
Leu Ser Lys Glu Ala Val Ser Ile Cys Lys Gly Leu Met Thr Lys Gln
            565                 570                 575
Pro Ala Lys Arg Leu Gly Cys Gly Pro Glu Gly Glu Arg Asp Val Arg
        580                 585                 590
Glu His Ala Phe Phe Arg Arg Ile Asp Trp Glu Lys Leu Glu Asn Arg
        595                 600                 605
Glu Ile Gln Pro Pro Phe Lys Pro Lys Val Cys Gly Lys Gly Ala Glu
610                 615                 620
Asn Phe Asp Lys Phe Phe Thr Arg Gly Gln Pro Val Leu Thr Pro Pro
625                 630                 635                 640
Asp Gln Leu Val Ile Ala Asn Ile Asp Gln Ser Asp Phe Glu Gly Phe
            645                 650                 655
Ser Tyr Val Asn Pro Gln Phe Val His Pro Ile Leu Gln Ser Ala Val
            660                 665                 670
Gly Arg Ala Met Ser Lys Gly Glu Glu Leu Phe Thr Gly Val Val Pro
        675                 680                 685
Ile Leu Val Glu Leu Asp Gly Asp Val Asn Gly Gln Lys Phe Ser Val
        690                 695                 700
Ser Gly Glu Gly Glu Gly Asp Ala Thr Tyr Gly Lys Leu Thr Leu Lys
705                 710                 715                 720
Phe Ile Cys Thr Thr Gly Lys Leu Pro Val Pro Trp Pro Thr Leu Val
            725                 730                 735
Thr Thr Leu Thr Tyr Gly Val Gln Cys Phe Ser Arg Tyr Pro Asp His
            740                 745                 750
Met Lys Gln His Asp Phe Phe Lys Ser Ala Met Pro Glu Gly Tyr Val
        755                 760                 765
Gln Glu Arg Thr Ile Phe Tyr Lys Asp Asp Gly Asn Tyr Lys Thr Arg
        770                 775                 780
Ala Glu Val Lys Phe Glu Gly Asp Thr Leu Val Asn Arg Ile Glu Leu
785                 790                 795                 800
Lys Gly Ile Asp Phe Lys Glu Asp Gly Asn Ile Leu Gly His Lys Met
            805                 810                 815
Glu Tyr Asn Tyr Asn Ser His Asn Val Tyr Ile Met Ala Asp Lys Pro
            820                 825                 830
Lys Asn Gly Ile Lys Val Asn Phe Lys Ile Arg His Asn Ile Lys Asp
        835                 840                 845
Gly Ser Val Gln Leu Ala Asp His Tyr Gln Gln Asn Thr Pro Ile Gly
850                 855                 860
```

```
Asp Gly Pro Val Leu Leu Pro Asp Asn His Tyr Leu Ser Thr Gln Ser
865                 870                 875                 880

Ala Leu Ser Lys Asp Pro Asn Glu Lys Arg Asp His Met Ile Leu Leu
                885                 890                 895

Glu Phe Val Thr Ala Ala Gly Ile Thr His Gly Met Asp Glu Leu Tyr
                900                 905                 910

Lys Pro Gln Glu
        915

<210> SEQ ID NO 74
<211> LENGTH: 2157
<212> TYPE: DNA
<213> ORGANISM: Artificial Sequence
<220> FEATURE:
<223> OTHER INFORMATION: Smad2-EGFP fusion
<220> FEATURE:
<221> NAME/KEY: CDS
<222> LOCATION: (1)..(2154)

<400> SEQUENCE: 74 atg tcg tcc atc ttg cca ttc acg ccg cca gtt gtg aag aga ctg ctg      48
Met Ser Ser Ile Leu Pro Phe Thr Pro Pro Val Val Lys Arg Leu Leu
1               5                   10                  15 gga tgg aag aag tca gct ggt ggg tct gga gga gca ggc gga gga gag      96
Gly Trp Lys Lys Ser Ala Gly Gly Ser Gly Gly Ala Gly Gly Gly Glu
            20                  25                  30 cag aat ggg cag gaa gaa aag tgg tgt gag aaa gca gtg aaa agt ctg     144
Gln Asn Gly Gln Glu Glu Lys Trp Cys Glu Lys Ala Val Lys Ser Leu
        35                  40                  45 gtg aag aag cta aag aaa aca gga cga tta gat gag ctt gag aaa gcc     192
Val Lys Lys Leu Lys Lys Thr Gly Arg Leu Asp Glu Leu Glu Lys Ala
    50                  55                  60 atc acc act caa aac tgt aat act aaa tgt gtt acc ata cca agc act     240
Ile Thr Thr Gln Asn Cys Asn Thr Lys Cys Val Thr Ile Pro Ser Thr
65                  70                  75                  80 tgc tct gaa att tgg gga ctg agt aca cca aat acg ata gat cag tgg     288
Cys Ser Glu Ile Trp Gly Leu Ser Thr Pro Asn Thr Ile Asp Gln Trp
                85                  90                  95 gat aca aca ggc ctt tac agc ttc tct gaa caa acc agg tct ctt gat     336
Asp Thr Thr Gly Leu Tyr Ser Phe Ser Glu Gln Thr Arg Ser Leu Asp
            100                 105                 110 ggt cgt ctc cag gta tcc cat cga aaa gga ttg cca cat gtt ata tat     384
Gly Arg Leu Gln Val Ser His Arg Lys Gly Leu Pro His Val Ile Tyr
        115                 120                 125 tgc cga tta tgg cgc tgg cct gat ctt cac agt cat cat gaa ctc aag     432
Cys Arg Leu Trp Arg Trp Pro Asp Leu His Ser His His Glu Leu Lys
    130                 135                 140 gca att gaa aac tgc gaa tat gct ttt aat ctt aaa aag gat gaa gta     480
Ala Ile Glu Asn Cys Glu Tyr Ala Phe Asn Leu Lys Lys Asp Glu Val
145                 150                 155                 160 tgt gta aac cct tac cac tat cag aga gtt gag aca cca gtt ttg cct     528
Cys Val Asn Pro Tyr His Tyr Gln Arg Val Glu Thr Pro Val Leu Pro
                165                 170                 175 cca gta tta gtg ccc cga cac acc gag atc cta aca gaa ctt ccg cct     576
Pro Val Leu Val Pro Arg His Thr Glu Ile Leu Thr Glu Leu Pro Pro
            180                 185                 190 ctg gat gac tat act cac tcc att cca gaa aac act aac ttc cca gca     624
Leu Asp Asp Tyr Thr His Ser Ile Pro Glu Asn Thr Asn Phe Pro Ala
        195                 200                 205 gga att gag cca cag agt aat tat att cca gaa acg cca cct cct gga     672
Gly Ile Glu Pro Gln Ser Asn Tyr Ile Pro Glu Thr Pro Pro Pro Gly
```

```
         210                 215                 220
tat atc agt gaa gat gga gaa aca agt gac caa cag ttg aat caa agt      720
Tyr Ile Ser Glu Asp Gly Glu Thr Ser Asp Gln Gln Leu Asn Gln Ser
225                 230                 235                 240 atg gac aca ggc tct cca gca gaa cta tct cct act act ctt tcc cct      768
Met Asp Thr Gly Ser Pro Ala Glu Leu Ser Pro Thr Thr Leu Ser Pro
                245                 250                 255 gtt aat cat agc ttg gat tta cag cca gtt act tac tca gaa cct gca      816
Val Asn His Ser Leu Asp Leu Gln Pro Val Thr Tyr Ser Glu Pro Ala
                260                 265                 270 ttt tgg tgt tca ata gca tat tat gaa tta aat cag agg gtt gga gaa      864
Phe Trp Cys Ser Ile Ala Tyr Tyr Glu Leu Asn Gln Arg Val Gly Glu
            275                 280                 285 acc ttc cat gca tca cag ccc tca ctc act gta gat ggc ttt aca gac      912
Thr Phe His Ala Ser Gln Pro Ser Leu Thr Val Asp Gly Phe Thr Asp
        290                 295                 300 cca tca aat tca gag agg ttc tgc tta ggt tta ctc tcc aat gtt aac      960
Pro Ser Asn Ser Glu Arg Phe Cys Leu Gly Leu Leu Ser Asn Val Asn
305                 310                 315                 320 cga aat gcc acg gta gaa atg aca aga agg cat ata gga aga gga gtg     1008
Arg Asn Ala Thr Val Glu Met Thr Arg Arg His Ile Gly Arg Gly Val
                325                 330                 335 cgc tta tac tac ata ggt ggg gaa gtt ttt gct gag tgc cta agt gat     1056
Arg Leu Tyr Tyr Ile Gly Gly Glu Val Phe Ala Glu Cys Leu Ser Asp
                340                 345                 350 agt gca atc ttt gtg cag agc ccc aat tgt aat cag aga tat ggc tgg     1104
Ser Ala Ile Phe Val Gln Ser Pro Asn Cys Asn Gln Arg Tyr Gly Trp
            355                 360                 365 cac cct gca aca gtg tgt aaa att cca cca ggc tgt aat ctg aag atc     1152
His Pro Ala Thr Val Cys Lys Ile Pro Pro Gly Cys Asn Leu Lys Ile
        370                 375                 380 ttc aac aac cag gaa ttt gct gct ctt ctg gct cag tct gtt aat cag     1200
Phe Asn Asn Gln Glu Phe Ala Ala Leu Leu Ala Gln Ser Val Asn Gln
385                 390                 395                 400 ggt ttt gaa gcc gtc tat cag cta act aga atg tgc acc ata aga atg     1248
Gly Phe Glu Ala Val Tyr Gln Leu Thr Arg Met Cys Thr Ile Arg Met
                405                 410                 415 agt ttt gtg aaa ggg tgg gga gca gaa tac cga agg cag acg gta aca     1296
Ser Phe Val Lys Gly Trp Gly Ala Glu Tyr Arg Arg Gln Thr Val Thr
                420                 425                 430 agt act cct tgc tgg att gaa ctt cat ctg aat gga cct cta cag tgg     1344
Ser Thr Pro Cys Trp Ile Glu Leu His Leu Asn Gly Pro Leu Gln Trp
            435                 440                 445 ttg gac aaa gta tta act cag atg gga tcc cct tca gtg cgt tgc tca     1392
Leu Asp Lys Val Leu Thr Gln Met Gly Ser Pro Ser Val Arg Cys Ser
450                 455                 460 agc atg tca tgg gta ccg cgg gcc cgg gat cca ccg gtc gcc acc atg     1440
Ser Met Ser Trp Val Pro Arg Ala Arg Asp Pro Pro Val Ala Thr Met
465                 470                 475                 480 gtg agc aag ggc gag gag ctg ttc acc ggg gtg gtg ccc atc ctg gtc     1488
Val Ser Lys Gly Glu Glu Leu Phe Thr Gly Val Val Pro Ile Leu Val
                485                 490                 495 gag ctg gac ggc gac gta aac ggc cac aag ttc agc gtg tcc ggc gag     1536
Glu Leu Asp Gly Asp Val Asn Gly His Lys Phe Ser Val Ser Gly Glu
                500                 505                 510 ggc gag ggc gat gcc acc tac ggc aag ctg acc ctg aag ttc atc tgc     1584
Gly Glu Gly Asp Ala Thr Tyr Gly Lys Leu Thr Leu Lys Phe Ile Cys
            515                 520                 525 acc acc ggc aag ctg ccc gtg ccc tgg ccc acc ctc gtg acc acc ctg     1632
```

```
Thr Thr Gly Lys Leu Pro Val Pro Trp Pro Thr Leu Val Thr Thr Leu
            530                 535                 540 acc tac ggc gtg cag tgc ttc agc cgc tac ccc gac cac atg aag cag        1680
Thr Tyr Gly Val Gln Cys Phe Ser Arg Tyr Pro Asp His Met Lys Gln
545                 550                 555                 560 cac gac ttc ttc aag tcc gcc atg ccc gaa ggc tac gtc cag gag cgc        1728
His Asp Phe Phe Lys Ser Ala Met Pro Glu Gly Tyr Val Gln Glu Arg
                565                 570                 575 acc atc ttc ttc aag gac gac ggc aac tac aag acc cgc gcc gag gtg        1776
Thr Ile Phe Phe Lys Asp Asp Gly Asn Tyr Lys Thr Arg Ala Glu Val
            580                 585                 590 aag ttc gag ggc gac acc ctg gtg aac cgc atc gag ctg aag ggc atc        1824
Lys Phe Glu Gly Asp Thr Leu Val Asn Arg Ile Glu Leu Lys Gly Ile
        595                 600                 605 gac ttc aag gag gac ggc aac atc ctg ggg cac aag ctg gag tac aac        1872
Asp Phe Lys Glu Asp Gly Asn Ile Leu Gly His Lys Leu Glu Tyr Asn
610                 615                 620 tac aac agc cac aac gtc tat atc atg gcc gac aag cag aag aac ggc        1920
Tyr Asn Ser His Asn Val Tyr Ile Met Ala Asp Lys Gln Lys Asn Gly
625                 630                 635                 640 atc aag gtg aac ttc aag atc cgc cac aac atc gag gac ggc agc gtg        1968
Ile Lys Val Asn Phe Lys Ile Arg His Asn Ile Glu Asp Gly Ser Val
                645                 650                 655 cag ctc gcc gac cac tac cag cag aac acc ccc atc ggc gac ggc ccc        2016
Gln Leu Ala Asp His Tyr Gln Gln Asn Thr Pro Ile Gly Asp Gly Pro
            660                 665                 670 gtg ctg ctg ccc gac aac cac tac ctg agc acc cag tcc gcc ctg agc        2064
Val Leu Leu Pro Asp Asn His Tyr Leu Ser Thr Gln Ser Ala Leu Ser
        675                 680                 685 aaa gac ccc aac gag aag cgc gat cac atg gtc ctg ctg gag ttc gtg        2112
Lys Asp Pro Asn Glu Lys Arg Asp His Met Val Leu Leu Glu Phe Val
690                 695                 700 acc gcc gcc ggg atc act ctc ggc atg gac gag ctg tac aag taa            2157
Thr Ala Ala Gly Ile Thr Leu Gly Met Asp Glu Leu Tyr Lys
705                 710                 715

<210> SEQ ID NO 75
<211> LENGTH: 718
<212> TYPE: PRT
<213> ORGANISM: Artificial Sequence
<220> FEATURE:
<223> OTHER INFORMATION: Smad2-EGFP fusion

<400> SEQUENCE: 75

Met Ser Ser Ile Leu Pro Phe Thr Pro Pro Val Val Lys Arg Leu Leu
1               5                   10                  15

Gly Trp Lys Lys Ser Ala Gly Gly Ser Gly Gly Ala Gly Gly Gly Glu
            20                  25                  30

Gln Asn Gly Gln Glu Glu Lys Trp Cys Glu Lys Ala Val Lys Ser Leu
        35                  40                  45

Val Lys Lys Leu Lys Lys Thr Gly Arg Leu Asp Glu Leu Glu Lys Ala
50                  55                  60

Ile Thr Thr Gln Asn Cys Asn Thr Lys Cys Val Thr Ile Pro Ser Thr
65                  70                  75                  80

Cys Ser Glu Ile Trp Gly Leu Ser Thr Pro Asn Thr Ile Asp Gln Trp
                85                  90                  95

Asp Thr Thr Gly Leu Tyr Ser Phe Ser Glu Gln Thr Arg Ser Leu Asp
            100                 105                 110

Gly Arg Leu Gln Val Ser His Arg Lys Gly Leu Pro His Val Ile Tyr
```

```
              115                 120                 125
Cys Arg Leu Trp Arg Trp Pro Asp Leu His Ser His His Glu Leu Lys
    130                 135                 140
Ala Ile Glu Asn Cys Glu Tyr Ala Phe Asn Leu Lys Lys Asp Glu Val
145                 150                 155                 160
Cys Val Asn Pro Tyr His Tyr Gln Arg Val Glu Thr Pro Val Leu Pro
                165                 170                 175
Pro Val Leu Val Pro Arg His Thr Glu Ile Leu Thr Glu Leu Pro Pro
            180                 185                 190
Leu Asp Asp Tyr Thr His Ser Ile Pro Glu Asn Thr Asn Phe Pro Ala
        195                 200                 205
Gly Ile Glu Pro Gln Ser Asn Tyr Ile Pro Glu Thr Pro Pro Pro Gly
    210                 215                 220
Tyr Ile Ser Glu Asp Gly Glu Thr Ser Asp Gln Gln Leu Asn Gln Ser
225                 230                 235                 240
Met Asp Thr Gly Ser Pro Ala Glu Leu Ser Pro Thr Thr Leu Ser Pro
                245                 250                 255
Val Asn His Ser Leu Asp Leu Gln Pro Val Thr Tyr Ser Glu Pro Ala
            260                 265                 270
Phe Trp Cys Ser Ile Ala Tyr Tyr Glu Leu Asn Gln Arg Val Gly Glu
        275                 280                 285
Thr Phe His Ala Ser Gln Pro Ser Leu Thr Val Asp Gly Phe Thr Asp
    290                 295                 300
Pro Ser Asn Ser Glu Arg Phe Cys Leu Gly Leu Leu Ser Asn Val Asn
305                 310                 315                 320
Arg Asn Ala Thr Val Glu Met Thr Arg Arg His Ile Gly Arg Gly Val
                325                 330                 335
Arg Leu Tyr Tyr Ile Gly Gly Glu Val Phe Ala Glu Cys Leu Ser Asp
            340                 345                 350
Ser Ala Ile Phe Val Gln Ser Pro Asn Cys Asn Gln Arg Tyr Gly Trp
        355                 360                 365
His Pro Ala Thr Val Cys Lys Ile Pro Pro Gly Cys Asn Leu Lys Ile
    370                 375                 380
Phe Asn Asn Gln Glu Phe Ala Ala Leu Leu Ala Gln Ser Val Asn Gln
385                 390                 395                 400
Gly Phe Glu Ala Val Tyr Gln Leu Thr Arg Met Cys Thr Ile Arg Met
                405                 410                 415
Ser Phe Val Lys Gly Trp Gly Ala Glu Tyr Arg Arg Gln Thr Val Thr
            420                 425                 430
Ser Thr Pro Cys Trp Ile Glu Leu His Leu Asn Gly Pro Leu Gln Trp
        435                 440                 445
Leu Asp Lys Val Leu Thr Gln Met Gly Ser Pro Ser Val Arg Cys Ser
    450                 455                 460
Ser Met Ser Trp Val Pro Arg Ala Arg Asp Pro Pro Val Ala Thr Met
465                 470                 475                 480
Val Ser Lys Gly Glu Glu Leu Phe Thr Gly Val Val Pro Ile Leu Val
                485                 490                 495
Glu Leu Asp Gly Asp Val Asn Gly His Lys Phe Ser Val Ser Gly Glu
            500                 505                 510
Gly Glu Gly Asp Ala Thr Tyr Gly Lys Leu Thr Leu Lys Phe Ile Cys
        515                 520                 525
Thr Thr Gly Lys Leu Pro Val Pro Trp Pro Thr Leu Val Thr Thr Leu
    530                 535                 540
```

-continued

```
Thr Tyr Gly Val Gln Cys Phe Ser Arg Tyr Pro Asp His Met Lys Gln
545                 550                 555                 560

His Asp Phe Phe Lys Ser Ala Met Pro Glu Gly Tyr Val Gln Glu Arg
                565                 570                 575

Thr Ile Phe Phe Lys Asp Asp Gly Asn Tyr Lys Thr Arg Ala Glu Val
                580                 585                 590

Lys Phe Glu Gly Asp Thr Leu Val Asn Arg Ile Glu Leu Lys Gly Ile
                595                 600                 605

Asp Phe Lys Glu Asp Gly Asn Ile Leu Gly His Lys Leu Glu Tyr Asn
                610                 615                 620

Tyr Asn Ser His Asn Val Tyr Ile Met Ala Asp Lys Gln Lys Asn Gly
625                 630                 635                 640

Ile Lys Val Asn Phe Lys Ile Arg His Asn Ile Glu Asp Gly Ser Val
                645                 650                 655

Gln Leu Ala Asp His Tyr Gln Gln Asn Thr Pro Ile Gly Asp Gly Pro
                660                 665                 670

Val Leu Leu Pro Asp Asn His Tyr Leu Ser Thr Gln Ser Ala Leu Ser
                675                 680                 685

Lys Asp Pro Asn Glu Lys Arg Asp His Met Val Leu Leu Glu Phe Val
690                 695                 700

Thr Ala Ala Gly Ile Thr Leu Gly Met Asp Glu Leu Tyr Lys
705                 710                 715

<210> SEQ ID NO 76
<211> LENGTH: 2397
<212> TYPE: DNA
<213> ORGANISM: Artificial Sequence
<220> FEATURE:
<223> OTHER INFORMATION: Smad4-EGFP fusion
<220> FEATURE:
<221> NAME/KEY: CDS
<222> LOCATION: (1)..(2394)

<400> SEQUENCE: 76 atg gac aat atg tct att acg aat aca cca aca agt aat gat gcc tgt        48
Met Asp Asn Met Ser Ile Thr Asn Thr Pro Thr Ser Asn Asp Ala Cys
1               5                   10                  15 ctg agc att gtg cat agt ttg atg tgc cat aga caa ggt gga gag agt        96
Leu Ser Ile Val His Ser Leu Met Cys His Arg Gln Gly Gly Glu Ser
                20                  25                  30 gaa aca ttt gca aaa aga gca att gaa agt ttg gta aag aag ctg aag       144
Glu Thr Phe Ala Lys Arg Ala Ile Glu Ser Leu Val Lys Lys Leu Lys
            35                  40                  45 gag aaa aaa gat gaa ttg gat tct tta ata aca gct ata act aca aat       192
Glu Lys Lys Asp Glu Leu Asp Ser Leu Ile Thr Ala Ile Thr Thr Asn
    50                  55                  60 gga gct cat cct agt aaa tgt gtt acc ata cag aga aca ttg gat ggg       240
Gly Ala His Pro Ser Lys Cys Val Thr Ile Gln Arg Thr Leu Asp Gly
65                  70                  75                  80 agg ctt cag gtg gct ggt cgg aaa gga ttt cct cat gtg atc tat gcc       288
Arg Leu Gln Val Ala Gly Arg Lys Gly Phe Pro His Val Ile Tyr Ala
                85                  90                  95 cgt ctc tgg agg tgg cct gat ctt cac aaa aat gaa cta aaa cat gtt       336
Arg Leu Trp Arg Trp Pro Asp Leu His Lys Asn Glu Leu Lys His Val
                100                 105                 110 aaa tat tgt cag tat gcg ttt gac tta aaa tgt gat agt gtc tgt gtg       384
Lys Tyr Cys Gln Tyr Ala Phe Asp Leu Lys Cys Asp Ser Val Cys Val
            115                 120                 125
```

```
aat cca tat cac tac gaa cga gtt gta tca cct gga att gat ctc tca         432
Asn Pro Tyr His Tyr Glu Arg Val Val Ser Pro Gly Ile Asp Leu Ser
    130                 135                 140 gga tta aca ctg cag agt aat gct cca tca agt atg atg gtg aag gat         480
Gly Leu Thr Leu Gln Ser Asn Ala Pro Ser Ser Met Met Val Lys Asp
145                 150                 155                 160 gaa tat gtg cat gac ttt gag gga cag cca tcg ttg tcc act gaa gga         528
Glu Tyr Val His Asp Phe Glu Gly Gln Pro Ser Leu Ser Thr Glu Gly
                165                 170                 175 cat tca att caa acc atc cag cat cca cca agt aat cgt gca tcg aca         576
His Ser Ile Gln Thr Ile Gln His Pro Pro Ser Asn Arg Ala Ser Thr
            180                 185                 190 gag aca tac agc acc cca gct ctg tta gcc cca tct gag tct aat gct         624
Glu Thr Tyr Ser Thr Pro Ala Leu Leu Ala Pro Ser Glu Ser Asn Ala
        195                 200                 205 acc agc act gcc aac ttt ccc aac att cct gtg gct tcc aca agt cag         672
Thr Ser Thr Ala Asn Phe Pro Asn Ile Pro Val Ala Ser Thr Ser Gln
    210                 215                 220 cct gcc agt ata ctg ggg ggc agc cat agt gaa gga ctg ttg cag ata         720
Pro Ala Ser Ile Leu Gly Gly Ser His Ser Glu Gly Leu Leu Gln Ile
225                 230                 235                 240 gca tca ggg cct cag cca gga cag cag cag aat gga ttt act ggt cag         768
Ala Ser Gly Pro Gln Pro Gly Gln Gln Gln Asn Gly Phe Thr Gly Gln
                245                 250                 255 cca gct act tac cat cat aac agc act acc acc tgg act gga agt agg         816
Pro Ala Thr Tyr His His Asn Ser Thr Thr Thr Trp Thr Gly Ser Arg
            260                 265                 270 act gca cca tac aca cct aat ttg cct cac cac caa aac ggc cat ctt         864
Thr Ala Pro Tyr Thr Pro Asn Leu Pro His His Gln Asn Gly His Leu
        275                 280                 285 cag cac cac ccg cct atg ccg ccc cat ccc gga cat tac tgg cct gtt         912
Gln His His Pro Pro Met Pro Pro His Pro Gly His Tyr Trp Pro Val
    290                 295                 300 cac aat gag ctt gca ttc cag cct ccc att tcc aat cat cct gct cct         960
His Asn Glu Leu Ala Phe Gln Pro Pro Ile Ser Asn His Pro Ala Pro
305                 310                 315                 320 gag tat tgg tgt tcc att gct tac ttt gaa atg gat gtt cag gta gga        1008
Glu Tyr Trp Cys Ser Ile Ala Tyr Phe Glu Met Asp Val Gln Val Gly
                325                 330                 335 gag aca ttt aag gtt cct tca agc tgc cct att gtt act gtt gat gga        1056
Glu Thr Phe Lys Val Pro Ser Ser Cys Pro Ile Val Thr Val Asp Gly
            340                 345                 350 tac gtg gac cct tct gga gga gat cgc ttt tgt ttg ggt caa ctc tcc        1104
Tyr Val Asp Pro Ser Gly Gly Asp Arg Phe Cys Leu Gly Gln Leu Ser
        355                 360                 365 aat gtc cac agg aca gaa gcc att gag aga gca agg ttg cac ata ggc        1152
Asn Val His Arg Thr Glu Ala Ile Glu Arg Ala Arg Leu His Ile Gly
    370                 375                 380 aaa ggt gtg cag ttg gaa tgt aaa ggt gaa ggt gat gtt tgg gtc agg        1200
Lys Gly Val Gln Leu Glu Cys Lys Gly Glu Gly Asp Val Trp Val Arg
385                 390                 395                 400 tgc ctt agt gac cac gcg gtc ttt gta cag agt tac tac tta gac aga        1248
Cys Leu Ser Asp His Ala Val Phe Val Gln Ser Tyr Tyr Leu Asp Arg
                405                 410                 415 gaa gct ggg cgt gca cct gga gat gct gtt cat aag atc tac cca agt        1296
Glu Ala Gly Arg Ala Pro Gly Asp Ala Val His Lys Ile Tyr Pro Ser
            420                 425                 430 gca tat ata aag gtc ttt gat ttg cgt cag tgt cat cga cag atg cag        1344
Ala Tyr Ile Lys Val Phe Asp Leu Arg Gln Cys His Arg Gln Met Gln
        435                 440                 445
```

-continued

| | | | | | | | | | | | | | | | |
|---|---|---|---|---|---|---|---|---|---|---|---|---|---|---|---|
| cag | cag | gcg | gct | act | gca | caa | gct | gca | gca | gct | gcc | cag | gca | gca | gcc | 1392 |
| Gln | Gln | Ala | Ala | Thr | Ala | Gln | Ala | Ala | Ala | Ala | Ala | Gln | Ala | Ala | Ala |
| | 450 | | | | 455 | | | | 460 | | | |

```
cag cag gcg gct act gca caa gct gca gca gct gcc cag gca gca gcc    1392
Gln Gln Ala Ala Thr Ala Gln Ala Ala Ala Ala Ala Gln Ala Ala Ala
    450             455             460 gtg gca gga aac atc cct ggc cca gga tca gta ggt gga ata gct cca    1440
Val Ala Gly Asn Ile Pro Gly Pro Gly Ser Val Gly Gly Ile Ala Pro
465             470             475             480 gct atc agt ctg tca gct gct gct gga att ggt gtt gat gac ctt cgt    1488
Ala Ile Ser Leu Ser Ala Ala Ala Gly Ile Gly Val Asp Asp Leu Arg
                485             490             495 cgc tta tgc ata ctc agg atg agt ttt gtg aaa ggc tgg gga ccg gat    1536
Arg Leu Cys Ile Leu Arg Met Ser Phe Val Lys Gly Trp Gly Pro Asp
            500             505             510 tac cca aga cag agc atc aaa gaa aca cct tgc tgg att gaa att cac    1584
Tyr Pro Arg Gln Ser Ile Lys Glu Thr Pro Cys Trp Ile Glu Ile His
    515             520             525 tta cac cgg gcc ctc cag ctc cta gac gaa gta ctt cat acc atg ccg    1632
Leu His Arg Ala Leu Gln Leu Leu Asp Glu Val Leu His Thr Met Pro
530             535             540 att gca gac cca caa cct tta gac tgg gat cca ccg gtc gcc acc atg    1680
Ile Ala Asp Pro Gln Pro Leu Asp Trp Asp Pro Pro Val Ala Thr Met
545             550             555             560 gtg agc aag ggc gag gag ctg ttc acc ggg gtg gtg ccc atc ctg gtc    1728
Val Ser Lys Gly Glu Glu Leu Phe Thr Gly Val Val Pro Ile Leu Val
                565             570             575 gag ctg gac ggc gac gta aac ggc cac aag ttc agc gtg tcc ggc gag    1776
Glu Leu Asp Gly Asp Val Asn Gly His Lys Phe Ser Val Ser Gly Glu
            580             585             590 ggc gag ggc gat gcc acc tac ggc aag ctg acc ctg aag ttc atc tgc    1824
Gly Glu Gly Asp Ala Thr Tyr Gly Lys Leu Thr Leu Lys Phe Ile Cys
    595             600             605 acc acc ggc aag ctg ccc gtg ccc tgg ccc acc ctc gtg acc acc ctg    1872
Thr Thr Gly Lys Leu Pro Val Pro Trp Pro Thr Leu Val Thr Thr Leu
610             615             620 acc tac ggc gtg cag tgc ttc agc cgc tac ccc gac cac atg aag cag    1920
Thr Tyr Gly Val Gln Cys Phe Ser Arg Tyr Pro Asp His Met Lys Gln
625             630             635             640 cac gac ttc ttc aag tcc gcc atg ccc gaa ggc tac gtc cag gag cgc    1968
His Asp Phe Phe Lys Ser Ala Met Pro Glu Gly Tyr Val Gln Glu Arg
                645             650             655 acc atc ttc ttc aag gac gac ggc aac tac aag acc cgc gcc gag gtg    2016
Thr Ile Phe Phe Lys Asp Asp Gly Asn Tyr Lys Thr Arg Ala Glu Val
            660             665             670 aag ttc gag ggc gac acc ctg gtg aac cgc atc gag ctg aag ggc atc    2064
Lys Phe Glu Gly Asp Thr Leu Val Asn Arg Ile Glu Leu Lys Gly Ile
    675             680             685 gac ttc aag gag gac ggc aac atc ctg ggg cac aag ctg gag tac aac    2112
Asp Phe Lys Glu Asp Gly Asn Ile Leu Gly His Lys Leu Glu Tyr Asn
690             695             700 tac aac agc cac aac gtc tat atc atg gcc gac aag cag aag aac ggc    2160
Tyr Asn Ser His Asn Val Tyr Ile Met Ala Asp Lys Gln Lys Asn Gly
705             710             715             720 atc aag gtg aac ttc aag atc cgc cac aac atc gag gac ggc agc gtg    2208
Ile Lys Val Asn Phe Lys Ile Arg His Asn Ile Glu Asp Gly Ser Val
                725             730             735 cag ctc gcc gac cac tac cag cag aac acc ccc atc ggc gac ggc ccc    2256
Gln Leu Ala Asp His Tyr Gln Gln Asn Thr Pro Ile Gly Asp Gly Pro
            740             745             750 gtg ctg ctg ccc gac aac cac tac ctg agc acc cag tcc gcc ctg agc    2304
Val Leu Leu Pro Asp Asn His Tyr Leu Ser Thr Gln Ser Ala Leu Ser
```

|   |   |   |   |   |   |   |   |   |   |   |   |   |   |   |   |
|---|---|---|---|---|---|---|---|---|---|---|---|---|---|---|---|
| aaa | gac | ccc | aac | gag | aag | cgc | gat | cac | atg | gtc | ctg | ctg | gag | ttc | gtg | 2352 |
| Lys | Asp | Pro | Asn | Glu | Lys | Arg | Asp | His | Met | Val | Leu | Leu | Glu | Phe | Val |
|   | 770 |   |   |   | 775 |   |   |   | 780 |   |   |   |   |   |   |
| acc | gcc | gcc | ggg | atc | act | ctc | ggc | atg | gac | gag | ctg | tac | aag | taa |   | 2397 |
| Thr | Ala | Ala | Gly | Ile | Thr | Leu | Gly | Met | Asp | Glu | Leu | Tyr | Lys |   |   |
| 785 |   |   |   |   | 790 |   |   |   |   | 795 |   |   |   |   |   |

<210> SEQ ID NO 77
<211> LENGTH: 798
<212> TYPE: PRT
<213> ORGANISM: Artificial Sequence
<220> FEATURE:
<223> OTHER INFORMATION: Smad4-EGFP fusion

<400> SEQUENCE: 77

Met Asp Asn Met Ser Ile Thr Asn Thr Pro Thr Ser Asn Asp Ala Cys
1               5                   10                  15

Leu Ser Ile Val His Ser Leu Met Cys His Arg Gln Gly Gly Glu Ser
            20                  25                  30

Glu Thr Phe Ala Lys Arg Ala Ile Glu Ser Leu Val Lys Lys Leu Lys
        35                  40                  45

Glu Lys Lys Asp Glu Leu Asp Ser Leu Ile Thr Ala Ile Thr Thr Asn
    50                  55                  60

Gly Ala His Pro Ser Lys Cys Val Thr Ile Gln Arg Thr Leu Asp Gly
65                  70                  75                  80

Arg Leu Gln Val Ala Gly Arg Lys Gly Phe Pro His Val Ile Tyr Ala
                85                  90                  95

Arg Leu Trp Arg Trp Pro Asp Leu His Lys Asn Glu Leu Lys His Val
            100                 105                 110

Lys Tyr Cys Gln Tyr Ala Phe Asp Leu Lys Cys Asp Ser Val Cys Val
        115                 120                 125

Asn Pro Tyr His Tyr Glu Arg Val Val Ser Pro Gly Ile Asp Leu Ser
    130                 135                 140

Gly Leu Thr Leu Gln Ser Asn Ala Pro Ser Ser Met Met Val Lys Asp
145                 150                 155                 160

Glu Tyr Val His Asp Phe Glu Gly Gln Pro Ser Leu Ser Thr Glu Gly
                165                 170                 175

His Ser Ile Gln Thr Ile Gln His Pro Pro Ser Asn Arg Ala Ser Thr
            180                 185                 190

Glu Thr Tyr Ser Thr Pro Ala Leu Leu Ala Pro Ser Glu Ser Asn Ala
        195                 200                 205

Thr Ser Thr Ala Asn Phe Pro Asn Ile Pro Val Ala Ser Thr Ser Gln
    210                 215                 220

Pro Ala Ser Ile Leu Gly Gly Ser His Ser Glu Gly Leu Leu Gln Ile
225                 230                 235                 240

Ala Ser Gly Pro Gln Pro Gly Gln Gln Asn Gly Phe Thr Gly Gln
                245                 250                 255

Pro Ala Thr Tyr His His Asn Ser Thr Thr Thr Trp Thr Gly Ser Arg
            260                 265                 270

Thr Ala Pro Tyr Thr Pro Asn Leu Pro His His Gln Asn Gly His Leu
        275                 280                 285

Gln His His Pro Pro Met Pro Pro His Pro Gly His Tyr Trp Pro Val
    290                 295                 300

His Asn Glu Leu Ala Phe Gln Pro Pro Ile Ser Asn His Pro Ala Pro
305                 310                 315                 320

-continued

```
Glu Tyr Trp Cys Ser Ile Ala Tyr Phe Glu Met Asp Val Gln Val Gly
                325                 330                 335

Glu Thr Phe Lys Val Pro Ser Ser Cys Pro Ile Val Thr Val Asp Gly
            340                 345                 350

Tyr Val Asp Pro Ser Gly Gly Asp Arg Phe Cys Leu Gly Gln Leu Ser
            355                 360                 365

Asn Val His Arg Thr Glu Ala Ile Glu Arg Ala Arg Leu His Ile Gly
        370                 375                 380

Lys Gly Val Gln Leu Glu Cys Lys Gly Glu Gly Asp Val Trp Val Arg
385                 390                 395                 400

Cys Leu Ser Asp His Ala Val Phe Val Gln Ser Tyr Tyr Leu Asp Arg
            405                 410                 415

Glu Ala Gly Arg Ala Pro Gly Asp Ala Val His Lys Ile Tyr Pro Ser
            420                 425                 430

Ala Tyr Ile Lys Val Phe Asp Leu Arg Gln Cys His Arg Gln Met Gln
            435                 440                 445

Gln Gln Ala Ala Thr Ala Gln Ala Ala Ala Gln Ala Ala Ala
        450                 455                 460

Val Ala Gly Asn Ile Pro Gly Pro Ser Val Gly Ile Ala Pro
465                 470                 475                 480

Ala Ile Ser Leu Ser Ala Ala Gly Ile Gly Val Asp Asp Leu Arg
            485                 490                 495

Arg Leu Cys Ile Leu Arg Met Ser Phe Val Lys Gly Trp Gly Pro Asp
            500                 505                 510

Tyr Pro Arg Gln Ser Ile Lys Glu Thr Pro Cys Trp Ile Glu Ile His
            515                 520                 525

Leu His Arg Ala Leu Gln Leu Leu Asp Glu Val Leu His Thr Met Pro
        530                 535                 540

Ile Ala Asp Pro Gln Pro Leu Asp Trp Asp Pro Val Ala Thr Met
545                 550                 555                 560

Val Ser Lys Gly Glu Glu Leu Phe Thr Gly Val Val Pro Ile Leu Val
            565                 570                 575

Glu Leu Asp Gly Asp Val Asn Gly His Lys Phe Ser Val Ser Gly Glu
            580                 585                 590

Gly Glu Gly Asp Ala Thr Tyr Gly Lys Leu Thr Leu Lys Phe Ile Cys
            595                 600                 605

Thr Thr Gly Lys Leu Pro Val Pro Trp Pro Thr Leu Val Thr Thr Leu
        610                 615                 620

Thr Tyr Gly Val Gln Cys Phe Ser Arg Tyr Pro Asp His Met Lys Gln
625                 630                 635                 640

His Asp Phe Phe Lys Ser Ala Met Pro Glu Gly Tyr Val Gln Glu Arg
            645                 650                 655

Thr Ile Phe Phe Lys Asp Asp Gly Asn Tyr Lys Thr Arg Ala Glu Val
            660                 665                 670

Lys Phe Glu Gly Asp Thr Leu Val Asn Arg Ile Glu Leu Lys Gly Ile
            675                 680                 685

Asp Phe Lys Glu Asp Gly Asn Ile Leu Gly His Lys Leu Glu Tyr Asn
        690                 695                 700

Tyr Asn Ser His Asn Val Tyr Ile Met Ala Asp Lys Gln Lys Asn Gly
705                 710                 715                 720

Ile Lys Val Asn Phe Lys Ile Arg His Asn Ile Glu Asp Gly Ser Val
            725                 730                 735
```

```
Gln Leu Ala Asp His Tyr Gln Gln Asn Thr Pro Ile Gly Asp Gly Pro
        740                 745                 750

Val Leu Leu Pro Asp Asn His Tyr Leu Ser Thr Gln Ser Ala Leu Ser
        755                 760                 765

Lys Asp Pro Asn Glu Lys Arg Asp His Met Val Leu Leu Glu Phe Val
        770                 775                 780

Thr Ala Ala Gly Ile Thr Leu Gly Met Asp Glu Leu Tyr Lys
785                 790                 795

<210> SEQ ID NO 78
<211> LENGTH: 3138
<212> TYPE: DNA
<213> ORGANISM: Artificial Sequence
<220> FEATURE:
<223> OTHER INFORMATION: Stat5-EGFP fusion construct
<220> FEATURE:
<221> NAME/KEY: CDS
<222> LOCATION: (1)..(3135)

<400> SEQUENCE: 78
```

| | |
|---|---|
| atg gcg ggc tgg atc cag gcc cag cag ctg cag gga gac gcg ctg cgc<br>Met Ala Gly Trp Ile Gln Ala Gln Gln Leu Gln Gly Asp Ala Leu Arg<br>1               5                   10                  15 | 48 |
| cag atg cag gtg ctg tac ggc cag cac ttc ccc atc gag gtc cgg cac<br>Gln Met Gln Val Leu Tyr Gly Gln His Phe Pro Ile Glu Val Arg His<br>            20                  25                  30 | 96 |
| tac ttg gcc cag tgg att gag agc cag cca tgg gat gcc att gac ttg<br>Tyr Leu Ala Gln Trp Ile Glu Ser Gln Pro Trp Asp Ala Ile Asp Leu<br>        35                  40                  45 | 144 |
| gac aat ccc cag gac aga gcc caa gcc acc cag ctc ctg gag ggc ctg<br>Asp Asn Pro Gln Asp Arg Ala Gln Ala Thr Gln Leu Leu Glu Gly Leu<br>    50                  55                  60 | 192 |
| gtg cag gag ctg cag aag aag gcg gag cac cag gtg ggg gaa gat ggg<br>Val Gln Glu Leu Gln Lys Lys Ala Glu His Gln Val Gly Glu Asp Gly<br>65                  70                  75                  80 | 240 |
| ttt tta ctg aag atc aag ctg ggg cac tac gcc acg cag ctc cag aaa<br>Phe Leu Leu Lys Ile Lys Leu Gly His Tyr Ala Thr Gln Leu Gln Lys<br>                85                  90                  95 | 288 |
| aca tat gac cgc tgc ccc ctg gag ctg gtc cgc tgc atc cgg cac att<br>Thr Tyr Asp Arg Cys Pro Leu Glu Leu Val Arg Cys Ile Arg His Ile<br>            100                 105                 110 | 336 |
| ctg tac aat gaa cag agg ctg gtc cga gaa gcc aac aat tgc agc tct<br>Leu Tyr Asn Glu Gln Arg Leu Val Arg Glu Ala Asn Asn Cys Ser Ser<br>        115                 120                 125 | 384 |
| ccg gct ggg atc ctg gtt gac gcc atg tcc cag aag cac ctt cag atc<br>Pro Ala Gly Ile Leu Val Asp Ala Met Ser Gln Lys His Leu Gln Ile<br>    130                 135                 140 | 432 |
| aac cag aca ttt gag gag ctg cga ctg gtc acg cag gac aca gag aat<br>Asn Gln Thr Phe Glu Glu Leu Arg Leu Val Thr Gln Asp Thr Glu Asn<br>145                 150                 155                 160 | 480 |
| gag ctg aag aaa ctg cag cag act cag gag tac ttc atc atc cag tac<br>Glu Leu Lys Lys Leu Gln Gln Thr Gln Glu Tyr Phe Ile Ile Gln Tyr<br>                165                 170                 175 | 528 |
| cag gag agc ctg agg atc caa gct cag ttt gcc cag ctg gcc cag ctg<br>Gln Glu Ser Leu Arg Ile Gln Ala Gln Phe Ala Gln Leu Ala Gln Leu<br>            180                 185                 190 | 576 |
| agc ccc cag gag cgt ctg agc cgg gag acg gcc ctc cag cag aag cag<br>Ser Pro Gln Glu Arg Leu Ser Arg Glu Thr Ala Leu Gln Gln Lys Gln<br>        195                 200                 205 | 624 |
| gtg tct ctg gag gcc tgg ttg cag cgt gag gca cag aca ctg cag cag<br>Val Ser Leu Glu Ala Trp Leu Gln Arg Glu Ala Gln Thr Leu Gln Gln | 672 |

```
             210                 215                 220
tac cgc gtg gag ctg gcc gag aag cac cag aag acc ctg cag ctg ctg        720
Tyr Arg Val Glu Leu Ala Glu Lys His Gln Lys Thr Leu Gln Leu Leu
225                 230                 235                 240 cgg aag cag cag acc atc atc ctg gat gac gag ctg atc cag tgg aag        768
Arg Lys Gln Gln Thr Ile Ile Leu Asp Asp Glu Leu Ile Gln Trp Lys
                245                 250                 255 cgg cgg cag cag ctg gcc ggg aac ggc ggg ccc ccc gag ggc agc ctg        816
Arg Arg Gln Gln Leu Ala Gly Asn Gly Gly Pro Pro Glu Gly Ser Leu
                260                 265                 270 gac gtg cta cag tcc tgg tgt gag aag ttg gcc gag atc atc tgg cag        864
Asp Val Leu Gln Ser Trp Cys Glu Lys Leu Ala Glu Ile Ile Trp Gln
                275                 280                 285 aac cgg cag cag atc cgc agg gct gag cac ctc tgc cag cag ctg ccc        912
Asn Arg Gln Gln Ile Arg Arg Ala Glu His Leu Cys Gln Gln Leu Pro
                290                 295                 300 atc ccc ggc cca gtg gag gag atg ctg gcc gag gtc aac gcc acc atc        960
Ile Pro Gly Pro Val Glu Glu Met Leu Ala Glu Val Asn Ala Thr Ile
305                 310                 315                 320 acg gac att atc tca gcc ctg gtg acc agc aca ttc atc att gag aag       1008
Thr Asp Ile Ile Ser Ala Leu Val Thr Ser Thr Phe Ile Ile Glu Lys
                325                 330                 335 cag cct cct cag gtc ctg aag acc cag acc aag ttt gca gcc acc gta       1056
Gln Pro Pro Gln Val Leu Lys Thr Gln Thr Lys Phe Ala Ala Thr Val
                340                 345                 350 cgc ctg ctg gtg ggc ggg aag ctg aac gtg cac atg aat ccc ccc cag       1104
Arg Leu Leu Val Gly Gly Lys Leu Asn Val His Met Asn Pro Pro Gln
                355                 360                 365 gtg aag gcc acc atc atc agt gag cag cag gcc aag tct ctg ctt aaa       1152
Val Lys Ala Thr Ile Ile Ser Glu Gln Gln Ala Lys Ser Leu Leu Lys
                370                 375                 380 aat gag aac acc cgc aac gag tgc agt ggt gag atc ctg aac aac tgc       1200
Asn Glu Asn Thr Arg Asn Glu Cys Ser Gly Glu Ile Leu Asn Asn Cys
385                 390                 395                 400 tgc gtg atg gag tac cac caa gcc acg ggc acc ctc agt gcc cac ttc       1248
Cys Val Met Glu Tyr His Gln Ala Thr Gly Thr Leu Ser Ala His Phe
                405                 410                 415 agg aac atg tca ctg aag agg atc aag cgt gct gac cgg cgg ggt gca       1296
Arg Asn Met Ser Leu Lys Arg Ile Lys Arg Ala Asp Arg Arg Gly Ala
                420                 425                 430 gag tcc gtg aca gag gag aag ttc aca gtc ctg ttt gag tct cag ttc       1344
Glu Ser Val Thr Glu Glu Lys Phe Thr Val Leu Phe Glu Ser Gln Phe
                435                 440                 445 agt gtt ggc agc aat gag ctt gtg ttc cag gtg aag act ctg tcc cta       1392
Ser Val Gly Ser Asn Glu Leu Val Phe Gln Val Lys Thr Leu Ser Leu
                450                 455                 460 cct gtg gtt gtc atc gtc cac ggc agc cag gac cac aat gcc acg gct       1440
Pro Val Val Val Ile Val His Gly Ser Gln Asp His Asn Ala Thr Ala
465                 470                 475                 480 act gtg ctg tgg gac aat gcc ttt gct gag ccg ggc agg gtg cca ttt       1488
Thr Val Leu Trp Asp Asn Ala Phe Ala Glu Pro Gly Arg Val Pro Phe
                485                 490                 495 gcc gtg cct gac aaa gtg ctg tgg ccg cag ctg tgt gag gcg ctc aac       1536
Ala Val Pro Asp Lys Val Leu Trp Pro Gln Leu Cys Glu Ala Leu Asn
                500                 505                 510 atg aaa ttc aag gcc gaa gtg cag agc aac cgg ggc ctg acc aag gag       1584
Met Lys Phe Lys Ala Glu Val Gln Ser Asn Arg Gly Leu Thr Lys Glu
                515                 520                 525 aac ctc gtg ttc ctg gcg cag aaa ctg ttc aac aac agc agc agc cac       1632
```

```
Asn Leu Val Phe Leu Ala Gln Lys Leu Phe Asn Asn Ser Ser Ser His
    530                 535                 540 ctg gag gac tac agt ggc ctg tcc gtg tcc tgg tcc cag ttc aac agg      1680
Leu Glu Asp Tyr Ser Gly Leu Ser Val Ser Trp Ser Gln Phe Asn Arg
545                 550                 555                 560 gag aac ttg ccg ggc tgg aac tac acc ttc tgg cag tgg ttt gac ggg      1728
Glu Asn Leu Pro Gly Trp Asn Tyr Thr Phe Trp Gln Trp Phe Asp Gly
                565                 570                 575 gtg atg gag gtg ttg aag aag cac cac aag ccc cac tgg aat gat ggg      1776
Val Met Glu Val Leu Lys Lys His His Lys Pro His Trp Asn Asp Gly
            580                 585                 590 gcc atc cta ggt ttt gtg aat aag caa cag gcc cac gac ctg ctc atc      1824
Ala Ile Leu Gly Phe Val Asn Lys Gln Gln Ala His Asp Leu Leu Ile
        595                 600                 605 aac aag ccc gac ggg acc ttc ttg ttg cgc ttt agt gac tca gaa atc      1872
Asn Lys Pro Asp Gly Thr Phe Leu Leu Arg Phe Ser Asp Ser Glu Ile
    610                 615                 620 ggg ggc atc acc atc gcc tgg aag ttt gac tcc ccg gaa cgc aac ctg      1920
Gly Gly Ile Thr Ile Ala Trp Lys Phe Asp Ser Pro Glu Arg Asn Leu
625                 630                 635                 640 tgg aac ctg aaa cca ttc acc acg cgg gat ttc tcc atc agg tcc ctg      1968
Trp Asn Leu Lys Pro Phe Thr Thr Arg Asp Phe Ser Ile Arg Ser Leu
                645                 650                 655 gct gac cgg ctg ggg gac ctg agc tat ctc atc tat gtg ttt cct gac      2016
Ala Asp Arg Leu Gly Asp Leu Ser Tyr Leu Ile Tyr Val Phe Pro Asp
            660                 665                 670 cgc ccc aag gat gag gtc ttc tcc aag tac tac act cct gtg ctg gct      2064
Arg Pro Lys Asp Glu Val Phe Ser Lys Tyr Tyr Thr Pro Val Leu Ala
        675                 680                 685 aaa gct gtt gat gga tat gtg aaa cca cag atc aag caa gtg gtc cct      2112
Lys Ala Val Asp Gly Tyr Val Lys Pro Gln Ile Lys Gln Val Val Pro
    690                 695                 700 gag ttt gtg aat gca tct gca gat gct ggg ggc agc agc gcc acg tac      2160
Glu Phe Val Asn Ala Ser Ala Asp Ala Gly Gly Ser Ser Ala Thr Tyr
705                 710                 715                 720 atg gac cag gcc ccc tcc cca gct gtg tgc ccc cag gct ccc tat aac      2208
Met Asp Gln Ala Pro Ser Pro Ala Val Cys Pro Gln Ala Pro Tyr Asn
                725                 730                 735 atg tac cca cag aac cct gac cat gta ctc gat cag gat gga gaa ttc      2256
Met Tyr Pro Gln Asn Pro Asp His Val Leu Asp Gln Asp Gly Glu Phe
            740                 745                 750 gac ctg gat gag acc atg gat gtg gcc agg cac gtg gag gaa ctc tta      2304
Asp Leu Asp Glu Thr Met Asp Val Ala Arg His Val Glu Glu Leu Leu
        755                 760                 765 cgc cga cca atg gac agt ctt gac tcc cgc ctc tcg ccc cct gcc ggt      2352
Arg Arg Pro Met Asp Ser Leu Asp Ser Arg Leu Ser Pro Pro Ala Gly
    770                 775                 780 ctt ttc acc tct gcc aga ggc tcc ctc tca tgg gta ccg cgg gcc cgg      2400
Leu Phe Thr Ser Ala Arg Gly Ser Leu Ser Trp Val Pro Arg Ala Arg
785                 790                 795                 800 gat cca ccg gtc gcc acc atg gtg agc aag ggc gag gag ctg ttc acc      2448
Asp Pro Pro Val Ala Thr Met Val Ser Lys Gly Glu Glu Leu Phe Thr
                805                 810                 815 ggg gtg gtg ccc atc ctg gtc gag ctg gac ggc gac gta aac ggc cac      2496
Gly Val Val Pro Ile Leu Val Glu Leu Asp Gly Asp Val Asn Gly His
            820                 825                 830 aag ttc agc gtg tcc ggc gag ggc gag ggc gat gcc acc tac ggc aag      2544
Lys Phe Ser Val Ser Gly Glu Gly Glu Gly Asp Ala Thr Tyr Gly Lys
        835                 840                 845
```

```
ctg acc ctg aag ttc atc tgc acc acc ggc aag ctg ccc gtg ccc tgg    2592
Leu Thr Leu Lys Phe Ile Cys Thr Thr Gly Lys Leu Pro Val Pro Trp
    850                 855                 860 ccc acc ctc gtg acc acc ctg acc tac ggc gtg cag tgc ttc agc cgc    2640
Pro Thr Leu Val Thr Thr Leu Thr Tyr Gly Val Gln Cys Phe Ser Arg
865                 870                 875                 880 tac ccc gac cac atg aag cag cac gac ttc ttc aag tcc gcc atg ccc    2688
Tyr Pro Asp His Met Lys Gln His Asp Phe Phe Lys Ser Ala Met Pro
                885                 890                 895 gaa ggc tac gtc cag gag cgc acc atc ttc ttc aag gac gac ggc aac    2736
Glu Gly Tyr Val Gln Glu Arg Thr Ile Phe Phe Lys Asp Asp Gly Asn
        900                 905                 910 tac aag acc cgc gcc gag gtg aag ttc gag ggc gac acc ctg gtg aac    2784
Tyr Lys Thr Arg Ala Glu Val Lys Phe Glu Gly Asp Thr Leu Val Asn
            915                 920                 925 cgc atc gag ctg aag ggc atc gac ttc aag gag gac ggc aac atc ctg    2832
Arg Ile Glu Leu Lys Gly Ile Asp Phe Lys Glu Asp Gly Asn Ile Leu
            930                 935                 940 ggg cac aag ctg gag tac aac tac aac agc cac aac gtc tat atc atg    2880
Gly His Lys Leu Glu Tyr Asn Tyr Asn Ser His Asn Val Tyr Ile Met
945                 950                 955                 960 gcc gac aag cag aag aac ggc atc aag gtg aac ttc aag atc cgc cac    2928
Ala Asp Lys Gln Lys Asn Gly Ile Lys Val Asn Phe Lys Ile Arg His
                965                 970                 975 aac atc gag gac ggc agc gtg cag ctc gcc gac cac tac cag cag aac    2976
Asn Ile Glu Asp Gly Ser Val Gln Leu Ala Asp His Tyr Gln Gln Asn
            980                 985                 990 acc ccc atc ggc gac ggc ccc gtg ctg ctg ccc gac aac cac tac ctg    3024
Thr Pro Ile Gly Asp Gly Pro Val Leu Leu Pro Asp Asn His Tyr Leu
            995                 1000                1005 agc acc cag tcc gcc ctg agc aaa gac ccc aac gag aag cgc gat        3069
Ser Thr Gln Ser Ala Leu Ser Lys Asp Pro Asn Glu Lys Arg Asp
    1010                1015                1020 cac atg gtc ctg ctg gag ttc gtg acc gcc gcc ggg atc act ctc        3114
His Met Val Leu Leu Glu Phe Val Thr Ala Ala Gly Ile Thr Leu
1025                1030                1035 ggc atg gac gag ctg tac aag taa                                    3138
Gly Met Asp Glu Leu Tyr Lys
1040            1045

<210> SEQ ID NO 79
<211> LENGTH: 1045
<212> TYPE: PRT
<213> ORGANISM: Artificial Sequence
<220> FEATURE:
<223> OTHER INFORMATION: Stat5-EGFP fusion construct

<400> SEQUENCE: 79

Met Ala Gly Trp Ile Gln Ala Gln Gln Leu Gln Gly Asp Ala Leu Arg
1               5                   10                  15

Gln Met Gln Val Leu Tyr Gly Gln His Phe Pro Ile Glu Val Arg His
            20                  25                  30

Tyr Leu Ala Gln Trp Ile Glu Ser Gln Pro Trp Asp Ala Ile Asp Leu
        35                  40                  45

Asp Asn Pro Gln Asp Arg Ala Gln Ala Thr Gln Leu Leu Glu Gly Leu
    50                  55                  60

Val Gln Glu Leu Gln Lys Lys Ala Glu His Gln Val Gly Glu Asp Gly
65                  70                  75                  80

Phe Leu Leu Lys Ile Lys Leu Gly His Tyr Ala Thr Gln Leu Gln Lys
                85                  90                  95
```

-continued

```
Thr Tyr Asp Arg Cys Pro Leu Glu Leu Val Arg Cys Ile Arg His Ile
                100                 105                 110
Leu Tyr Asn Glu Gln Arg Leu Val Arg Glu Ala Asn Asn Cys Ser Ser
            115                 120                 125
Pro Ala Gly Ile Leu Val Asp Ala Met Ser Gln Lys His Leu Gln Ile
        130                 135                 140
Asn Gln Thr Phe Glu Glu Leu Arg Leu Val Thr Gln Asp Thr Glu Asn
145                 150                 155                 160
Glu Leu Lys Lys Leu Gln Gln Thr Gln Glu Tyr Phe Ile Ile Gln Tyr
                165                 170                 175
Gln Glu Ser Leu Arg Ile Gln Ala Gln Phe Ala Gln Leu Ala Gln Leu
            180                 185                 190
Ser Pro Gln Glu Arg Leu Ser Arg Glu Thr Ala Leu Gln Gln Lys Gln
        195                 200                 205
Val Ser Leu Glu Ala Trp Leu Gln Arg Glu Ala Gln Thr Leu Gln Gln
    210                 215                 220
Tyr Arg Val Glu Leu Ala Glu Lys His Gln Lys Thr Leu Gln Leu Leu
225                 230                 235                 240
Arg Lys Gln Gln Thr Ile Ile Leu Asp Asp Glu Leu Ile Gln Trp Lys
                245                 250                 255
Arg Arg Gln Gln Leu Ala Gly Asn Gly Gly Pro Glu Gly Ser Leu
            260                 265                 270
Asp Val Leu Gln Ser Trp Cys Glu Lys Leu Ala Glu Ile Ile Trp Gln
        275                 280                 285
Asn Arg Gln Gln Ile Arg Arg Ala Glu His Leu Cys Gln Gln Leu Pro
    290                 295                 300
Ile Pro Gly Pro Val Glu Glu Met Leu Ala Glu Val Asn Ala Thr Ile
305                 310                 315                 320
Thr Asp Ile Ile Ser Ala Leu Val Thr Ser Thr Phe Ile Ile Glu Lys
                325                 330                 335
Gln Pro Pro Gln Val Leu Lys Thr Gln Thr Lys Phe Ala Ala Thr Val
            340                 345                 350
Arg Leu Leu Val Gly Gly Lys Leu Asn Val His Met Asn Pro Pro Gln
        355                 360                 365
Val Lys Ala Thr Ile Ile Ser Glu Gln Gln Ala Lys Ser Leu Leu Lys
    370                 375                 380
Asn Glu Asn Thr Arg Asn Glu Cys Ser Gly Glu Ile Leu Asn Asn Cys
385                 390                 395                 400
Cys Val Met Glu Tyr His Gln Ala Thr Gly Thr Leu Ser Ala His Phe
                405                 410                 415
Arg Asn Met Ser Leu Lys Arg Ile Lys Arg Ala Asp Arg Arg Gly Ala
            420                 425                 430
Glu Ser Val Thr Glu Glu Lys Phe Thr Val Leu Phe Glu Ser Gln Phe
        435                 440                 445
Ser Val Gly Ser Asn Glu Leu Val Phe Gln Val Lys Thr Leu Ser Leu
    450                 455                 460
Pro Val Val Val Ile Val His Gly Ser Gln Asp His Asn Ala Thr Ala
465                 470                 475                 480
Thr Val Leu Trp Asp Asn Ala Phe Ala Glu Pro Gly Arg Val Pro Phe
                485                 490                 495
Ala Val Pro Asp Lys Val Leu Trp Pro Gln Leu Cys Glu Ala Leu Asn
            500                 505                 510
```

-continued

```
Met Lys Phe Lys Ala Glu Val Gln Ser Asn Arg Gly Leu Thr Lys Glu
            515                 520                 525

Asn Leu Val Phe Leu Ala Gln Lys Leu Phe Asn Asn Ser Ser Ser His
        530                 535                 540

Leu Glu Asp Tyr Ser Gly Leu Ser Val Ser Trp Ser Gln Phe Asn Arg
545                 550                 555                 560

Glu Asn Leu Pro Gly Trp Asn Tyr Thr Phe Trp Gln Trp Phe Asp Gly
                565                 570                 575

Val Met Glu Val Leu Lys Lys His His Lys Pro His Trp Asn Asp Gly
            580                 585                 590

Ala Ile Leu Gly Phe Val Asn Lys Gln Gln Ala His Asp Leu Leu Ile
        595                 600                 605

Asn Lys Pro Asp Gly Thr Phe Leu Leu Arg Phe Ser Asp Ser Glu Ile
    610                 615                 620

Gly Gly Ile Thr Ile Ala Trp Lys Phe Asp Ser Pro Glu Arg Asn Leu
625                 630                 635                 640

Trp Asn Leu Lys Pro Phe Thr Thr Arg Asp Phe Ser Ile Arg Ser Leu
                645                 650                 655

Ala Asp Arg Leu Gly Asp Leu Ser Tyr Leu Ile Tyr Val Phe Pro Asp
            660                 665                 670

Arg Pro Lys Asp Glu Val Phe Ser Lys Tyr Tyr Thr Pro Val Leu Ala
        675                 680                 685

Lys Ala Val Asp Gly Tyr Val Lys Pro Gln Ile Lys Gln Val Val Pro
690                 695                 700

Glu Phe Val Asn Ala Ser Ala Asp Ala Gly Gly Ser Ser Ala Thr Tyr
705                 710                 715                 720

Met Asp Gln Ala Pro Ser Pro Ala Val Cys Pro Gln Ala Pro Tyr Asn
                725                 730                 735

Met Tyr Pro Gln Asn Pro Asp His Val Leu Asp Gln Asp Gly Glu Phe
            740                 745                 750

Asp Leu Asp Glu Thr Met Asp Val Ala Arg His Val Glu Glu Leu Leu
        755                 760                 765

Arg Arg Pro Met Asp Ser Leu Asp Ser Arg Leu Ser Pro Pro Ala Gly
    770                 775                 780

Leu Phe Thr Ser Ala Arg Gly Ser Leu Ser Trp Val Pro Arg Ala Arg
785                 790                 795                 800

Asp Pro Pro Val Ala Thr Met Val Ser Lys Gly Glu Glu Leu Phe Thr
                805                 810                 815

Gly Val Val Pro Ile Leu Val Glu Leu Asp Gly Asp Val Asn Gly His
            820                 825                 830

Lys Phe Ser Val Ser Gly Glu Gly Glu Gly Asp Ala Thr Tyr Gly Lys
        835                 840                 845

Leu Thr Leu Lys Phe Ile Cys Thr Thr Gly Lys Leu Pro Val Pro Trp
    850                 855                 860

Pro Thr Leu Val Thr Thr Leu Thr Tyr Gly Val Gln Cys Phe Ser Arg
865                 870                 875                 880

Tyr Pro Asp His Met Lys Gln His Asp Phe Phe Lys Ser Ala Met Pro
                885                 890                 895

Glu Gly Tyr Val Gln Glu Arg Thr Ile Phe Phe Lys Asp Asp Gly Asn
            900                 905                 910

Tyr Lys Thr Arg Ala Glu Val Lys Phe Glu Gly Asp Thr Leu Val Asn
        915                 920                 925

Arg Ile Glu Leu Lys Gly Ile Asp Phe Lys Glu Asp Gly Asn Ile Leu
```

```
                930             935             940
Gly His Lys Leu Glu Tyr Asn Tyr Asn Ser His Asn Val Tyr Ile Met
945             950             955             960

Ala Asp Lys Gln Lys Asn Gly Ile Lys Val Asn Phe Lys Ile Arg His
            965             970             975

Asn Ile Glu Asp Gly Ser Val Gln Leu Ala Asp His Tyr Gln Gln Asn
            980             985             990

Thr Pro Ile Gly Asp Gly Pro Val  Leu Leu Pro Asp Asn  His Tyr Leu
            995             1000            1005

Ser Thr  Gln Ser Ala Leu Ser  Lys Asp Pro Asn Glu  Lys Arg Asp
      1010            1015            1020

His Met  Val Leu Leu Glu Phe  Val Thr Ala Ala Gly  Ile Thr Leu
      1025            1030            1035

Gly Met  Asp Glu Leu Tyr Lys
     1040            1045
```

<210> SEQ ID NO 80
<211> LENGTH: 28
<212> TYPE: DNA
<213> ORGANISM: Artificial Sequence
<220> FEATURE:
<223> OTHER INFORMATION: PKB-bottom/+stop Primer

<400> SEQUENCE: 80
tgggatcctc aggccgtgct gctggccg                                28

<210> SEQ ID NO 81
<211> LENGTH: 27
<212> TYPE: DNA
<213> ORGANISM: Artificial Sequence
<220> FEATURE:
<223> OTHER INFORMATION: PKG-top Primer

<400> SEQUENCE: 81
gtctcgaggg agcatgggca ccttgcg                                 27

<210> SEQ ID NO 82
<211> LENGTH: 27
<212> TYPE: DNA
<213> ORGANISM: Artificial Sequence
<220> FEATURE:
<223> OTHER INFORMATION: PKG-bottom/-stop Primer

<400> SEQUENCE: 82
tgggatccga gaagtctata tcccatc                                 27

<210> SEQ ID NO 83
<211> LENGTH: 28
<212> TYPE: DNA
<213> ORGANISM: Artificial Sequence
<220> FEATURE:
<223> OTHER INFORMATION: PKG-bottom/+stop Primer

<400> SEQUENCE: 83
tgggatcctt agaagtctat atcccatc                                28

<210> SEQ ID NO 84
<211> LENGTH: 28
<212> TYPE: DNA
<213> ORGANISM: Artificial Sequence
<220> FEATURE:
<223> OTHER INFORMATION: NFAT-top Primer

```
<400> SEQUENCE: 84
gtctcgagcc atgaacgccc ccgagcgg                                      28

<210> SEQ ID NO 85
<211> LENGTH: 30
<212> TYPE: DNA
<213> ORGANISM: Artificial Sequence
<220> FEATURE:
<223> OTHER INFORMATION: NFAT-bottom/stop Primer

<400> SEQUENCE: 85
gtgaattctc gtctgatttc tggcaggagg                                    30

<210> SEQ ID NO 86
<211> LENGTH: 30
<212> TYPE: DNA
<213> ORGANISM: Artificial Sequence
<220> FEATURE:
<223> OTHER INFORMATION: NFATbottom/+stop Primer

<400> SEQUENCE: 86
gtgaattctt tacgtctgat ttctggcagg                                    30

<210> SEQ ID NO 87
<211> LENGTH: 34
<212> TYPE: DNA
<213> ORGANISM: Artificial Sequence
<220> FEATURE:
<223> OTHER INFORMATION: NFkappaB-top Primer

<400> SEQUENCE: 87
gtctcgagcc atggacgaac tgttccccct catc                               34

<210> SEQ ID NO 88
<211> LENGTH: 31
<212> TYPE: DNA
<213> ORGANISM: Artificial Sequence
<220> FEATURE:
<223> OTHER INFORMATION: NFkappaB-bottom/-stop Primer

<400> SEQUENCE: 88
gtggatccaa ggagctgatc tgactcagca g                                  31

<210> SEQ ID NO 89
<211> LENGTH: 32
<212> TYPE: DNA
<213> ORGANISM: Artificial Sequence
<220> FEATURE:
<223> OTHER INFORMATION: NFkappaB-bottom/+stop Primer

<400> SEQUENCE: 89
gtggatcctt aggagctgat ctgactcagc ag                                 32

<210> SEQ ID NO 90
<211> LENGTH: 32
<212> TYPE: DNA
<213> ORGANISM: Artificial Sequence
<220> FEATURE:
<223> OTHER INFORMATION: ABD-top Primer

<400> SEQUENCE: 90
cctcctaagc ttatcatgga ccattatgat tc                                 32

<210> SEQ ID NO 91
<211> LENGTH: 33
```

-continued

```
<212> TYPE: DNA
<213> ORGANISM: Artificial Sequence
<220> FEATURE:
<223> OTHER INFORMATION: ABD-bottom/-stop Primer

<400> SEQUENCE: 91
cctcctggat ccctgcgcag gatgatggtc cag                            33

<210> SEQ ID NO 92
<211> LENGTH: 45
<212> TYPE: DNA
<213> ORGANISM: Artificial Sequence
<220> FEATURE:
<223> OTHER INFORMATION: RhoA-top Primer

<400> SEQUENCE: 92
ggatggaagc ttcaatggct gccatccgga agaaactggt gattg                45

<210> SEQ ID NO 93
<211> LENGTH: 45
<212> TYPE: DNA
<213> ORGANISM: Artificial Sequence
<220> FEATURE:
<223> OTHER INFORMATION: RhoAbottom/+stop Primer

<400> SEQUENCE: 93
ggatggggat cctcacaaga caaggcaacc agattttttc ttccc                45

<210> SEQ ID NO 94
<211> LENGTH: 29
<212> TYPE: DNA
<213> ORGANISM: Artificial Sequence
<220> FEATURE:
<223> OTHER INFORMATION: VASP-top Primer

<400> SEQUENCE: 94
gggaagcttc catgagcgag acggtcatc                                 29

<210> SEQ ID NO 95
<211> LENGTH: 28
<212> TYPE: DNA
<213> ORGANISM: Artificial Sequence
<220> FEATURE:
<223> OTHER INFORMATION: VASPbottom/+stop Primer

<400> SEQUENCE: 95
cccggatcct cagggagaac ccgcttc                                   28

<210> SEQ ID NO 96
<211> LENGTH: 30
<212> TYPE: DNA
<213> ORGANISM: Artificial Sequence
<220> FEATURE:
<223> OTHER INFORMATION: IKK-top Primer

<400> SEQUENCE: 96
gtgaattcga ccatggagcg gccccggggg                                30

<210> SEQ ID NO 97
<211> LENGTH: 27
<212> TYPE: DNA
<213> ORGANISM: Artificial Sequence
<220> FEATURE:
<223> OTHER INFORMATION: IKK-bottom/-stop Primer

<400> SEQUENCE: 97
```

-continued gtggtaccca ttctgttaac caactcc                                27

<210> SEQ ID NO 98
<211> LENGTH: 28
<212> TYPE: DNA
<213> ORGANISM: Artificial Sequence
<220> FEATURE:
<223> OTHER INFORMATION: IKK-bottom/+stop Primer

<400> SEQUENCE: 98
gtggtacctc attctgttaa ccaactcc                               28

<210> SEQ ID NO 99
<211> LENGTH: 28
<212> TYPE: DNA
<213> ORGANISM: Artificial Sequence
<220> FEATURE:
<223> OTHER INFORMATION: PTP-top Primer

<400> SEQUENCE: 99
gtctcgagag atgctgtccc gtgggtgg                               28

<210> SEQ ID NO 100
<211> LENGTH: 27
<212> TYPE: DNA
<213> ORGANISM: Artificial Sequence
<220> FEATURE:
<223> OTHER INFORMATION: PTP-bottom/-stop Primer

<400> SEQUENCE: 100
gtgaattcgc ttcctcttga gggaacc                                27

<210> SEQ ID NO 101
<211> LENGTH: 27
<212> TYPE: DNA
<213> ORGANISM: Artificial Sequence
<220> FEATURE:
<223> OTHER INFORMATION: PTP-bottom/+stop Primer

<400> SEQUENCE: 101
gtgaattcac ttcctcttga gggaacc                                27

<210> SEQ ID NO 102
<211> LENGTH: 29
<212> TYPE: DNA
<213> ORGANISM: Artificial Sequence
<220> FEATURE:
<223> OTHER INFORMATION: CDK2-top Primer

<400> SEQUENCE: 102
gtctcgagcc atggagaact tccaaaagg                              29

<210> SEQ ID NO 103
<211> LENGTH: 28
<212> TYPE: DNA
<213> ORGANISM: Artificial Sequence
<220> FEATURE:
<223> OTHER INFORMATION: CDK2bottom/-stop Primer

<400> SEQUENCE: 103
gtggatccca gagtcgaaga tggggtac                               28

<210> SEQ ID NO 104
<211> LENGTH: 29
<212> TYPE: DNA
<213> ORGANISM: Artificial Sequence

```
<220> FEATURE:
<223> OTHER INFORMATION: CDK2bottom/+stop Primer

<400> SEQUENCE: 104
gtggatcctc agagtcgaag atggggtac                                     29

<210> SEQ ID NO 105
<211> LENGTH: 30
<212> TYPE: DNA
<213> ORGANISM: Artificial Sequence
<220> FEATURE:
<223> OTHER INFORMATION: Zap70-top Primer

<400> SEQUENCE: 105
gtgaattcgg cgatgccaga ccccgcggcg                                    30

<210> SEQ ID NO 106
<211> LENGTH: 32
<212> TYPE: DNA
<213> ORGANISM: Artificial Sequence
<220> FEATURE:
<223> OTHER INFORMATION: Zap70bottom/-stop Primer

<400> SEQUENCE: 106
gtggatccca ggcacaggca gcctcagcct tc                                 32

<210> SEQ ID NO 107
<211> LENGTH: 33
<212> TYPE: DNA
<213> ORGANISM: Artificial Sequence
<220> FEATURE:
<223> OTHER INFORMATION: Zap70bottom/+stop Primer

<400> SEQUENCE: 107
gtggatcctc aggcacaggc agcctcagcc ttc                                33

<210> SEQ ID NO 108
<211> LENGTH: 2616
<212> TYPE: DNA
<213> ORGANISM: Artificial Sequence
<220> FEATURE:
<223> OTHER INFORMATION: EGFP-Zap70 fusion
<220> FEATURE:
<221> NAME/KEY: CDS
<222> LOCATION: (1)..(2613)

<400> SEQUENCE: 108 atg gtg agc aag ggc gag gag ctg ttc acc ggg gtg gtg ccc atc ctg    48
Met Val Ser Lys Gly Glu Glu Leu Phe Thr Gly Val Val Pro Ile Leu
 1               5                  10                  15 gtc gag ctg gac ggc gac gta aac ggc cac aag ttc agc gtg tcc ggc    96
Val Glu Leu Asp Gly Asp Val Asn Gly His Lys Phe Ser Val Ser Gly
             20                  25                  30 gag ggc gag ggc gat gcc acc tac ggc aag ctg acc ctg aag ttc atc   144
Glu Gly Glu Gly Asp Ala Thr Tyr Gly Lys Leu Thr Leu Lys Phe Ile
         35                  40                  45 tgc acc acc ggc aag ctg ccc gtg ccc tgg ccc acc ctc gtg acc acc   192
Cys Thr Thr Gly Lys Leu Pro Val Pro Trp Pro Thr Leu Val Thr Thr
     50                  55                  60 ctg acc tac ggc gtg cag tgc ttc agc cgc tac ccc gac cac atg aag   240
Leu Thr Tyr Gly Val Gln Cys Phe Ser Arg Tyr Pro Asp His Met Lys
 65                  70                  75                  80 cag cac gac ttc ttc aag tcc gcc atg ccc gaa ggc tac gtc cag gag   288
Gln His Asp Phe Phe Lys Ser Ala Met Pro Glu Gly Tyr Val Gln Glu
                 85                  90                  95
```

```
cgc acc atc ttc ttc aag gac gac ggc aac tac aag acc cgc gcc gag      336
Arg Thr Ile Phe Phe Lys Asp Asp Gly Asn Tyr Lys Thr Arg Ala Glu
        100                 105                 110 gtg aag ttc gag ggc gac acc ctg gtg aac cgc atc gag ctg aag ggc      384
Val Lys Phe Glu Gly Asp Thr Leu Val Asn Arg Ile Glu Leu Lys Gly
            115                 120                 125 atc gac ttc aag gag gac ggc aac atc ctg ggg cac aag ctg gag tac      432
Ile Asp Phe Lys Glu Asp Gly Asn Ile Leu Gly His Lys Leu Glu Tyr
130                 135                 140 aac tac aac agc cac aac gtc tat atc atg gcc gac aag cag aag aac      480
Asn Tyr Asn Ser His Asn Val Tyr Ile Met Ala Asp Lys Gln Lys Asn
145                 150                 155                 160 ggc atc aag gtg aac ttc aag atc cgc cac aac atc gag gac ggc agc      528
Gly Ile Lys Val Asn Phe Lys Ile Arg His Asn Ile Glu Asp Gly Ser
                165                 170                 175 gtg cag ctc gcc gac cac tac cag cag aac acc ccc atc ggc gac ggc      576
Val Gln Leu Ala Asp His Tyr Gln Gln Asn Thr Pro Ile Gly Asp Gly
            180                 185                 190 ccc gtg ctg ctg ccc gac aac cac tac ctg agc acc cag tcc gcc ctg      624
Pro Val Leu Leu Pro Asp Asn His Tyr Leu Ser Thr Gln Ser Ala Leu
        195                 200                 205 agc aaa gac ccc aac gag aag cgc gat cac atg gtc ctg ctg gag ttc      672
Ser Lys Asp Pro Asn Glu Lys Arg Asp His Met Val Leu Leu Glu Phe
    210                 215                 220 gtg acc gcc gcc ggg atc act ctc ggc atg gac gag ctg tac aag tcc      720
Val Thr Ala Ala Gly Ile Thr Leu Gly Met Asp Glu Leu Tyr Lys Ser
225                 230                 235                 240 gga ctc aga tct cga gct caa gct tcg aat tcg gcg atg cca gac ccc      768
Gly Leu Arg Ser Arg Ala Gln Ala Ser Asn Ser Ala Met Pro Asp Pro
                245                 250                 255 gcg gcg cac ctg ccc ttc ttc tac ggc agc atc tcg cgt gcc gag gcc      816
Ala Ala His Leu Pro Phe Phe Tyr Gly Ser Ile Ser Arg Ala Glu Ala
            260                 265                 270 gag gag cac ctg aag ctg gcg ggc atg gcg gac ggg ctc ttc ctg ctg      864
Glu Glu His Leu Lys Leu Ala Gly Met Ala Asp Gly Leu Phe Leu Leu
        275                 280                 285 cgc cag tgc ctg cgc tcg ctg ggc ggc tat gtg ctg tcg ctc gtg cac      912
Arg Gln Cys Leu Arg Ser Leu Gly Gly Tyr Val Leu Ser Leu Val His
    290                 295                 300 gat gtg cgc ttc cac cac ttt ccc atc gag cgc cag ctc aac ggc acc      960
Asp Val Arg Phe His His Phe Pro Ile Glu Arg Gln Leu Asn Gly Thr
305                 310                 315                 320 tac gcc att gcc ggc ggc aaa gcg cac tgt gga ccg gca gag ctc tgc     1008
Tyr Ala Ile Ala Gly Gly Lys Ala His Cys Gly Pro Ala Glu Leu Cys
                325                 330                 335 gag ttc tac tcg cgc gac ccc gac ggg ctg ccc tgc aac ctg cgc aag     1056
Glu Phe Tyr Ser Arg Asp Pro Asp Gly Leu Pro Cys Asn Leu Arg Lys
            340                 345                 350 ccg tgc aac cgg ccg tcg ggc ctc gag ccg cag ccg ggg gtc ttc gac     1104
Pro Cys Asn Arg Pro Ser Gly Leu Glu Pro Gln Pro Gly Val Phe Asp
        355                 360                 365 tgc ctg cga gac gcc atg gtg cgt gac tac gtg cgc cag acg tgg aag     1152
Cys Leu Arg Asp Ala Met Val Arg Asp Tyr Val Arg Gln Thr Trp Lys
    370                 375                 380 ctg gag ggc gag gcc ctg gag cag gcc atc atc agc cag gcc ccg cag     1200
Leu Glu Gly Glu Ala Leu Glu Gln Ala Ile Ile Ser Gln Ala Pro Gln
385                 390                 395                 400 gtg gag aag ctc att gct acg acg gcc cac gag cgg atg ccc tgg tac     1248
Val Glu Lys Leu Ile Ala Thr Thr Ala His Glu Arg Met Pro Trp Tyr
```

-continued

|  |  |  |  |  |  |  |  |  |  |  |  |  |  |  |  |  |
|---|---|---|---|---|---|---|---|---|---|---|---|---|---|---|---|---|
|  |  | 405 |  |  |  | 410 |  |  |  |  | 415 |  |  |  |  |  |
| cac | agc | agc | ctg | acg | cgt | gag | gag | gcc | gag | cgc | aaa | ctt | tac | tct | ggg | 1296 |
| His | Ser | Ser | Leu | Thr | Arg | Glu | Glu | Ala | Glu | Arg | Lys | Leu | Tyr | Ser | Gly |  |
|  |  |  | 420 |  |  |  |  | 425 |  |  |  |  | 430 |  |  |  |
| gcg | cag | acc | gac | ggc | aag | ttc | ctg | ctg | agg | ccg | cgg | aag | gag | cag | ggc | 1344 |
| Ala | Gln | Thr | Asp | Gly | Lys | Phe | Leu | Leu | Arg | Pro | Arg | Lys | Glu | Gln | Gly |  |
|  |  | 435 |  |  |  |  | 440 |  |  |  |  | 445 |  |  |  |  |
| aca | tac | gcc | ctg | tcc | ctc | atc | tat | ggg | aag | acg | gtg | tac | cac | tac | ctc | 1392 |
| Thr | Tyr | Ala | Leu | Ser | Leu | Ile | Tyr | Gly | Lys | Thr | Val | Tyr | His | Tyr | Leu |  |
|  | 450 |  |  |  |  | 455 |  |  |  |  | 460 |  |  |  |  |  |
| atc | agc | caa | gac | aag | gcg | ggc | aag | tac | tgc | att | ccc | gag | ggc | acc | aag | 1440 |
| Ile | Ser | Gln | Asp | Lys | Ala | Gly | Lys | Tyr | Cys | Ile | Pro | Glu | Gly | Thr | Lys |  |
| 465 |  |  |  |  | 470 |  |  |  |  | 475 |  |  |  |  | 480 |  |
| ttt | gac | acg | ctc | tgg | cag | ctg | gtg | gag | tat | ctg | aag | ctg | aag | gcg | gac | 1488 |
| Phe | Asp | Thr | Leu | Trp | Gln | Leu | Val | Glu | Tyr | Leu | Lys | Leu | Lys | Ala | Asp |  |
|  |  |  |  | 485 |  |  |  |  | 490 |  |  |  |  | 495 |  |  |
| ggg | ctc | atc | tac | tgc | ctg | aag | gag | gcc | tgc | ccc | aac | agc | agt | gcc | agc | 1536 |
| Gly | Leu | Ile | Tyr | Cys | Leu | Lys | Glu | Ala | Cys | Pro | Asn | Ser | Ser | Ala | Ser |  |
|  |  |  | 500 |  |  |  |  | 505 |  |  |  |  | 510 |  |  |  |
| aac | gcc | tca | ggg | gct | gct | gct | ccc | aca | ctc | cca | gcc | cac | cca | tcc | acg | 1584 |
| Asn | Ala | Ser | Gly | Ala | Ala | Ala | Pro | Thr | Leu | Pro | Ala | His | Pro | Ser | Thr |  |
|  |  | 515 |  |  |  |  | 520 |  |  |  |  | 525 |  |  |  |  |
| ttg | act | cat | cct | cag | aga | cga | atc | gac | acc | ctc | aac | tca | gat | gga | tac | 1632 |
| Leu | Thr | His | Pro | Gln | Arg | Arg | Ile | Asp | Thr | Leu | Asn | Ser | Asp | Gly | Tyr |  |
|  | 530 |  |  |  |  | 535 |  |  |  |  | 540 |  |  |  |  |  |
| acc | cct | gag | cca | gca | cgc | ata | acg | tcc | cca | gac | aaa | ccg | cgg | ccg | atg | 1680 |
| Thr | Pro | Glu | Pro | Ala | Arg | Ile | Thr | Ser | Pro | Asp | Lys | Pro | Arg | Pro | Met |  |
| 545 |  |  |  |  | 550 |  |  |  |  | 555 |  |  |  |  | 560 |  |
| ccc | atg | gac | acg | agc | gtg | tat | gag | agc | ccc | tac | agc | gac | cca | gag | gag | 1728 |
| Pro | Met | Asp | Thr | Ser | Val | Tyr | Glu | Ser | Pro | Tyr | Ser | Asp | Pro | Glu | Glu |  |
|  |  |  |  | 565 |  |  |  |  | 570 |  |  |  |  | 575 |  |  |
| ctc | aag | gac | aag | aag | ctc | ttc | ctg | aag | cgc | gat | aac | ctc | ctc | ata | gct | 1776 |
| Leu | Lys | Asp | Lys | Lys | Leu | Phe | Leu | Lys | Arg | Asp | Asn | Leu | Leu | Ile | Ala |  |
|  |  |  | 580 |  |  |  |  | 585 |  |  |  |  | 590 |  |  |  |
| gac | att | gaa | ctt | ggc | tgc | ggc | aac | ttt | ggc | tca | gtg | cgc | cag | ggc | gtg | 1824 |
| Asp | Ile | Glu | Leu | Gly | Cys | Gly | Asn | Phe | Gly | Ser | Val | Arg | Gln | Gly | Val |  |
|  |  | 595 |  |  |  |  | 600 |  |  |  |  | 605 |  |  |  |  |
| tac | cgc | atg | cgc | aag | aag | cag | atc | gac | gtg | gcc | atc | aag | gtg | ctg | aag | 1872 |
| Tyr | Arg | Met | Arg | Lys | Lys | Gln | Ile | Asp | Val | Ala | Ile | Lys | Val | Leu | Lys |  |
|  | 610 |  |  |  |  | 615 |  |  |  |  | 620 |  |  |  |  |  |
| cag | ggc | acg | gag | aag | gca | gac | acg | gaa | gag | atg | atg | cgc | gag | gcg | cag | 1920 |
| Gln | Gly | Thr | Glu | Lys | Ala | Asp | Thr | Glu | Glu | Met | Met | Arg | Glu | Ala | Gln |  |
| 625 |  |  |  |  | 630 |  |  |  |  | 635 |  |  |  |  | 640 |  |
| atc | atg | cac | cag | ctg | gac | aac | ccc | tac | atc | gtg | cgg | ctc | att | ggc | gtc | 1968 |
| Ile | Met | His | Gln | Leu | Asp | Asn | Pro | Tyr | Ile | Val | Arg | Leu | Ile | Gly | Val |  |
|  |  |  |  | 645 |  |  |  |  | 650 |  |  |  |  | 655 |  |  |
| tgc | cag | gcc | gag | gcc | ctc | atg | ctg | gtc | atg | gag | atg | gct | ggg | ggc | ggg | 2016 |
| Cys | Gln | Ala | Glu | Ala | Leu | Met | Leu | Val | Met | Glu | Met | Ala | Gly | Gly | Gly |  |
|  |  |  | 660 |  |  |  |  | 665 |  |  |  |  | 670 |  |  |  |
| ccg | ctg | cac | aag | ttc | ctg | gtc | ggc | aag | agg | gag | gag | atc | cct | gtg | agc | 2064 |
| Pro | Leu | His | Lys | Phe | Leu | Val | Gly | Lys | Arg | Glu | Glu | Ile | Pro | Val | Ser |  |
|  |  | 675 |  |  |  |  | 680 |  |  |  |  | 685 |  |  |  |  |
| aat | gtg | gcc | gag | ctg | ctg | cac | cag | gtg | tcc | atg | ggg | atg | aag | tac | ctg | 2112 |
| Asn | Val | Ala | Glu | Leu | Leu | His | Gln | Val | Ser | Met | Gly | Met | Lys | Tyr | Leu |  |
|  | 690 |  |  |  |  | 695 |  |  |  |  | 700 |  |  |  |  |  |
| gag | gag | aag | aac | ttt | gtg | cac | cgt | gac | ctg | gcg | gcc | cgc | aac | gtc | ctg | 2160 |
| Glu | Glu | Lys | Asn | Phe | Val | His | Arg | Asp | Leu | Ala | Ala | Arg | Asn | Val | Leu |  |
| 705 |  |  |  |  | 710 |  |  |  |  | 715 |  |  |  |  | 720 |  |
| ctg | gtt | aac | cgg | cac | tac | gcc | aag | atc | agc | gac | ttt | ggc | ctc | tcc | aaa | 2208 |

-continued

```
                Leu Val Asn Arg His Tyr Ala Lys Ile Ser Asp Phe Gly Leu Ser Lys
                                725                 730                 735 gca ctg ggt gcc gac gac agc tac tac act gcc cgc tca gca ggg aag         2256
Ala Leu Gly Ala Asp Asp Ser Tyr Tyr Thr Ala Arg Ser Ala Gly Lys
            740                 745                 750 tgg ccg ctc aag tgg tac gca ccc gaa tgc atc aac ttc cgc aag ttc         2304
Trp Pro Leu Lys Trp Tyr Ala Pro Glu Cys Ile Asn Phe Arg Lys Phe
        755                 760                 765 tcc agc cgc agc gat gtc tgg agc tat ggg gtc acc atg tgg gag gcc         2352
Ser Ser Arg Ser Asp Val Trp Ser Tyr Gly Val Thr Met Trp Glu Ala
770                 775                 780 ttg tcc tac ggc cag aag ccc tac aag aag atg aaa ggg ccg gag gtc         2400
Leu Ser Tyr Gly Gln Lys Pro Tyr Lys Lys Met Lys Gly Pro Glu Val
785                 790                 795                 800 atg gcc ttc atc gag cag ggc aag cgg atg gag tgc cca cca gag tgt         2448
Met Ala Phe Ile Glu Gln Gly Lys Arg Met Glu Cys Pro Pro Glu Cys
            805                 810                 815 cca ccc gaa ctg tac gca ctc atg agt gac tgc tgg atc tac aag tgg         2496
Pro Pro Glu Leu Tyr Ala Leu Met Ser Asp Cys Trp Ile Tyr Lys Trp
        820                 825                 830 gag gat cgc ccc gac ttc ctg acc gtg gag cag cgc atg cga gcc tgt         2544
Glu Asp Arg Pro Asp Phe Leu Thr Val Glu Gln Arg Met Arg Ala Cys
    835                 840                 845 tac tac agc ctg gcc agc aag gtg gaa ggg ccc cca ggc agc aca cag         2592
Tyr Tyr Ser Leu Ala Ser Lys Val Glu Gly Pro Pro Gly Ser Thr Gln
850                 855                 860 aag gct gag gct gcc tgt gcc tga                                         2616
Lys Ala Glu Ala Ala Cys Ala
865                 870

<210> SEQ ID NO 109
<211> LENGTH: 871
<212> TYPE: PRT
<213> ORGANISM: Artificial Sequence
<220> FEATURE:
<223> OTHER INFORMATION: EGFP-Zap70 fusion

<400> SEQUENCE: 109

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160
```

-continued

```
Gly Ile Lys Val Asn Phe Lys Ile Arg His Asn Ile Glu Asp Gly Ser
                165                 170                 175
Val Gln Leu Ala Asp His Tyr Gln Gln Asn Thr Pro Ile Gly Asp Gly
            180                 185                 190
Pro Val Leu Leu Pro Asp Asn His Tyr Leu Ser Thr Gln Ser Ala Leu
        195                 200                 205
Ser Lys Asp Pro Asn Glu Lys Arg Asp His Met Val Leu Leu Glu Phe
    210                 215                 220
Val Thr Ala Ala Gly Ile Thr Leu Gly Met Asp Glu Leu Tyr Lys Ser
225                 230                 235                 240
Gly Leu Arg Ser Arg Ala Gln Ala Ser Asn Ser Ala Met Pro Asp Pro
                245                 250                 255
Ala Ala His Leu Pro Phe Phe Tyr Gly Ser Ile Ser Arg Ala Glu Ala
            260                 265                 270
Glu Glu His Leu Lys Leu Ala Gly Met Ala Asp Gly Leu Phe Leu Leu
        275                 280                 285
Arg Gln Cys Leu Arg Ser Leu Gly Gly Tyr Val Leu Ser Leu Val His
    290                 295                 300
Asp Val Arg Phe His His Phe Pro Ile Glu Arg Gln Leu Asn Gly Thr
305                 310                 315                 320
Tyr Ala Ile Ala Gly Gly Lys Ala His Cys Gly Pro Ala Glu Leu Cys
                325                 330                 335
Glu Phe Tyr Ser Arg Asp Pro Asp Gly Leu Pro Cys Asn Leu Arg Lys
            340                 345                 350
Pro Cys Asn Arg Pro Ser Gly Leu Glu Pro Gln Pro Gly Val Phe Asp
        355                 360                 365
Cys Leu Arg Asp Ala Met Val Arg Asp Tyr Val Arg Gln Thr Trp Lys
    370                 375                 380
Leu Glu Gly Glu Ala Leu Glu Gln Ala Ile Ile Ser Gln Ala Pro Gln
385                 390                 395                 400
Val Glu Lys Leu Ile Ala Thr Thr Ala His Glu Arg Met Pro Trp Tyr
                405                 410                 415
His Ser Ser Leu Thr Arg Glu Glu Ala Glu Arg Lys Leu Tyr Ser Gly
            420                 425                 430
Ala Gln Thr Asp Gly Lys Phe Leu Leu Arg Pro Arg Lys Glu Gln Gly
        435                 440                 445
Thr Tyr Ala Leu Ser Leu Ile Tyr Gly Lys Thr Val Tyr His Tyr Leu
    450                 455                 460
Ile Ser Gln Asp Lys Ala Gly Lys Tyr Cys Ile Pro Glu Gly Thr Lys
465                 470                 475                 480
Phe Asp Thr Leu Trp Gln Leu Val Glu Tyr Leu Lys Leu Lys Ala Asp
                485                 490                 495
Gly Leu Ile Tyr Cys Leu Lys Glu Ala Cys Pro Asn Ser Ser Ala Ser
            500                 505                 510
Asn Ala Ser Gly Ala Ala Ala Pro Thr Leu Pro Ala His Pro Ser Thr
        515                 520                 525
Leu Thr His Pro Gln Arg Arg Ile Asp Thr Leu Asn Ser Asp Gly Tyr
    530                 535                 540
Thr Pro Glu Pro Ala Arg Ile Thr Ser Pro Asp Lys Pro Arg Pro Met
545                 550                 555                 560
Pro Met Asp Thr Ser Val Tyr Glu Ser Pro Tyr Ser Asp Pro Glu Glu
                565                 570                 575
Leu Lys Asp Lys Lys Leu Phe Leu Lys Arg Asp Asn Leu Leu Ile Ala
```

```
                  580                 585                 590
Asp Ile Glu Leu Gly Cys Gly Asn Phe Gly Ser Val Arg Gln Gly Val
                595                 600                 605

Tyr Arg Met Arg Lys Gln Ile Asp Val Ala Ile Lys Val Leu Lys
    610                 615                 620

Gln Gly Thr Glu Lys Ala Asp Thr Glu Glu Met Met Arg Glu Ala Gln
625                 630                 635                 640

Ile Met His Gln Leu Asp Asn Pro Tyr Ile Val Arg Leu Ile Gly Val
                645                 650                 655

Cys Gln Ala Glu Ala Leu Met Leu Val Met Glu Met Ala Gly Gly Gly
                660                 665                 670

Pro Leu His Lys Phe Leu Val Gly Lys Arg Glu Glu Ile Pro Val Ser
                675                 680                 685

Asn Val Ala Glu Leu Leu His Gln Val Ser Met Gly Met Lys Tyr Leu
                690                 695                 700

Glu Glu Lys Asn Phe Val His Arg Asp Leu Ala Ala Arg Asn Val Leu
705                 710                 715                 720

Leu Val Asn Arg His Tyr Ala Lys Ile Ser Asp Phe Gly Leu Ser Lys
                725                 730                 735

Ala Leu Gly Ala Asp Asp Ser Tyr Tyr Thr Ala Arg Ser Ala Gly Lys
                740                 745                 750

Trp Pro Leu Lys Trp Tyr Ala Pro Glu Cys Ile Asn Phe Arg Lys Phe
                755                 760                 765

Ser Ser Arg Ser Asp Val Trp Ser Tyr Gly Val Thr Met Trp Glu Ala
                770                 775                 780

Leu Ser Tyr Gly Gln Lys Pro Tyr Lys Lys Met Lys Gly Pro Glu Val
785                 790                 795                 800

Met Ala Phe Ile Glu Gln Gly Lys Arg Met Glu Cys Pro Pro Glu Cys
                805                 810                 815

Pro Pro Glu Leu Tyr Ala Leu Met Ser Asp Cys Trp Ile Tyr Lys Trp
                820                 825                 830

Glu Asp Arg Pro Asp Phe Leu Thr Val Glu Gln Arg Met Arg Ala Cys
                835                 840                 845

Tyr Tyr Ser Leu Ala Ser Lys Val Glu Gly Pro Pro Gly Ser Thr Gln
                850                 855                 860

Lys Ala Glu Ala Ala Cys Ala
865                 870

<210> SEQ ID NO 110
<211> LENGTH: 2598
<212> TYPE: DNA
<213> ORGANISM: Artificial Sequence
<220> FEATURE:
<223> OTHER INFORMATION: Zap70-EGFP fusion
<220> FEATURE:
<221> NAME/KEY: CDS
<222> LOCATION: (1)..(2595)

<400> SEQUENCE: 110 atg cca gac ccc gcg gcg cac ctg ccc ttc ttc tac ggc agc atc tcg      48
Met Pro Asp Pro Ala Ala His Leu Pro Phe Phe Tyr Gly Ser Ile Ser
1               5                   10                  15 cgt gcc gag gcc gag gag cac ctg aag ctg gcg ggc atg gcg gac ggg      96
Arg Ala Glu Ala Glu Glu His Leu Lys Leu Ala Gly Met Ala Asp Gly
            20                  25                  30 ctc ttc ctg ctg cgc cag tgc ctg cgc tcg ctg ggc ggc tat gtg ctg     144
Leu Phe Leu Leu Arg Gln Cys Leu Arg Ser Leu Gly Gly Tyr Val Leu
```

|     |     |     |     | 35  |     |     |     |     | 40  |     |     |     |     | 45  |     |     |      |
| --- | --- | --- | --- | --- | --- | --- | --- | --- | --- | --- | --- | --- | --- | --- | --- | --- | ---- |
| tcg | ctc | gtg | cac | gat | gtg | cgc | ttc | cac | cac | ttt | ccc | atc | gag | cgc | cag |     | 192  |
| Ser | Leu | Val | His | Asp | Val | Arg | Phe | His | His | Phe | Pro | Ile | Glu | Arg | Gln |     |      |
|     | 50  |     |     |     | 55  |     |     |     |     | 60  |     |     |     |     |     |     |      |
| ctc | aac | ggc | acc | tac | gcc | att | gcc | ggc | ggc | aaa | gcg | cac | tgt | gga | ccg |     | 240  |
| Leu | Asn | Gly | Thr | Tyr | Ala | Ile | Ala | Gly | Gly | Lys | Ala | His | Cys | Gly | Pro |     |      |
| 65  |     |     |     |     | 70  |     |     |     |     | 75  |     |     |     |     | 80  |     |      |
| gca | gag | ctc | tgc | gag | ttc | tac | tcg | cgc | gac | ccc | gac | ggg | ctg | ccc | tgc |     | 288  |
| Ala | Glu | Leu | Cys | Glu | Phe | Tyr | Ser | Arg | Asp | Pro | Asp | Gly | Leu | Pro | Cys |     |      |
|     |     |     |     |     | 85  |     |     |     |     | 90  |     |     |     |     | 95  |     |      |
| aac | ctg | cgc | aag | ccg | tgc | aac | cgg | ccg | tcg | ggc | ctc | gag | ccg | cag | ccg |     | 336  |
| Asn | Leu | Arg | Lys | Pro | Cys | Asn | Arg | Pro | Ser | Gly | Leu | Glu | Pro | Gln | Pro |     |      |
|     |     |     | 100 |     |     |     |     | 105 |     |     |     |     | 110 |     |     |     |      |
| ggg | gtc | ttc | gac | tgc | ctg | cga | gac | gcc | atg | gtg | cgt | gac | tac | gtg | cgc |     | 384  |
| Gly | Val | Phe | Asp | Cys | Leu | Arg | Asp | Ala | Met | Val | Arg | Asp | Tyr | Val | Arg |     |      |
|     |     | 115 |     |     |     |     | 120 |     |     |     |     | 125 |     |     |     |     |      |
| cag | acg | tgg | aag | ctg | gag | ggc | gag | gcc | ctg | gag | cag | gcc | atc | atc | agc |     | 432  |
| Gln | Thr | Trp | Lys | Leu | Glu | Gly | Glu | Ala | Leu | Glu | Gln | Ala | Ile | Ile | Ser |     |      |
|     | 130 |     |     |     |     | 135 |     |     |     |     | 140 |     |     |     |     |     |      |
| cag | gcc | ccg | cag | gtg | gag | aag | ctc | att | gct | acg | acg | gcc | cac | gag | cgg |     | 480  |
| Gln | Ala | Pro | Gln | Val | Glu | Lys | Leu | Ile | Ala | Thr | Thr | Ala | His | Glu | Arg |     |      |
| 145 |     |     |     |     | 150 |     |     |     |     | 155 |     |     |     |     | 160 |     |      |
| atg | ccc | tgg | tac | cac | agc | agc | ctg | acg | cgt | gag | gag | gcc | gag | cgc | aaa |     | 528  |
| Met | Pro | Trp | Tyr | His | Ser | Ser | Leu | Thr | Arg | Glu | Glu | Ala | Glu | Arg | Lys |     |      |
|     |     |     |     |     | 165 |     |     |     |     | 170 |     |     |     |     | 175 |     |      |
| ctt | tac | tct | ggg | gcg | cag | acc | gac | ggc | aag | ttc | ctg | ctg | agg | ccg | cgg |     | 576  |
| Leu | Tyr | Ser | Gly | Ala | Gln | Thr | Asp | Gly | Lys | Phe | Leu | Leu | Arg | Pro | Arg |     |      |
|     |     |     | 180 |     |     |     |     | 185 |     |     |     |     | 190 |     |     |     |      |
| aag | gag | cag | ggc | aca | tac | gcc | ctg | tcc | ctc | atc | tat | ggg | aag | acg | gtg |     | 624  |
| Lys | Glu | Gln | Gly | Thr | Tyr | Ala | Leu | Ser | Leu | Ile | Tyr | Gly | Lys | Thr | Val |     |      |
|     |     | 195 |     |     |     |     | 200 |     |     |     |     | 205 |     |     |     |     |      |
| tac | cac | tac | ctc | atc | agc | caa | gac | aag | gcg | ggc | aag | tac | tgc | att | ccc |     | 672  |
| Tyr | His | Tyr | Leu | Ile | Ser | Gln | Asp | Lys | Ala | Gly | Lys | Tyr | Cys | Ile | Pro |     |      |
|     | 210 |     |     |     |     | 215 |     |     |     |     | 220 |     |     |     |     |     |      |
| gag | ggc | acc | aag | ttt | gac | acg | ctc | tgg | cag | ctg | gtg | gag | tat | ctg | aag |     | 720  |
| Glu | Gly | Thr | Lys | Phe | Asp | Thr | Leu | Trp | Gln | Leu | Val | Glu | Tyr | Leu | Lys |     |      |
| 225 |     |     |     |     | 230 |     |     |     |     | 235 |     |     |     |     | 240 |     |      |
| ctg | aag | gcg | gac | ggg | ctc | atc | tac | tgc | ctg | aag | gag | gcc | tgc | ccc | aac |     | 768  |
| Leu | Lys | Ala | Asp | Gly | Leu | Ile | Tyr | Cys | Leu | Lys | Glu | Ala | Cys | Pro | Asn |     |      |
|     |     |     |     | 245 |     |     |     |     | 250 |     |     |     |     | 255 |     |     |      |
| agc | agt | gcc | agc | aac | gcc | tca | ggg | gct | gct | gct | ccc | aca | ctc | cca | gcc |     | 816  |
| Ser | Ser | Ala | Ser | Asn | Ala | Ser | Gly | Ala | Ala | Ala | Pro | Thr | Leu | Pro | Ala |     |      |
|     |     |     | 260 |     |     |     |     | 265 |     |     |     |     | 270 |     |     |     |      |
| cac | cca | tcc | acg | ttg | act | cat | cct | cag | aga | cga | atc | gac | acc | ctc | aac |     | 864  |
| His | Pro | Ser | Thr | Leu | Thr | His | Pro | Gln | Arg | Arg | Ile | Asp | Thr | Leu | Asn |     |      |
|     |     | 275 |     |     |     |     | 280 |     |     |     |     | 285 |     |     |     |     |      |
| tca | gat | gga | tac | acc | cct | gag | cca | gca | cgc | ata | acg | tcc | cca | gac | aaa |     | 912  |
| Ser | Asp | Gly | Tyr | Thr | Pro | Glu | Pro | Ala | Arg | Ile | Thr | Ser | Pro | Asp | Lys |     |      |
|     | 290 |     |     |     |     | 295 |     |     |     |     | 300 |     |     |     |     |     |      |
| ccg | cgg | ccg | atg | ccc | atg | gac | acg | agc | gtg | tat | gag | agc | ccc | tac | agc |     | 960  |
| Pro | Arg | Pro | Met | Pro | Met | Asp | Thr | Ser | Val | Tyr | Glu | Ser | Pro | Tyr | Ser |     |      |
| 305 |     |     |     |     | 310 |     |     |     |     | 315 |     |     |     |     | 320 |     |      |
| gac | cca | gag | gag | ctc | aag | gac | aag | aag | ctc | ttc | ctg | aag | cgc | gat | aac |     | 1008 |
| Asp | Pro | Glu | Glu | Leu | Lys | Asp | Lys | Lys | Leu | Phe | Leu | Lys | Arg | Asp | Asn |     |      |
|     |     |     |     | 325 |     |     |     |     | 330 |     |     |     |     | 335 |     |     |      |
| ctc | ctc | ata | gct | gac | att | gaa | ctt | ggc | tgc | ggc | aac | ttt | ggc | tca | gtg |     | 1056 |
| Leu | Leu | Ile | Ala | Asp | Ile | Glu | Leu | Gly | Cys | Gly | Asn | Phe | Gly | Ser | Val |     |      |
|     |     |     | 340 |     |     |     |     | 345 |     |     |     |     | 350 |     |     |     |      |
| cgc | cag | ggc | gtg | tac | cgc | atg | cgc | aag | aag | cag | atc | gac | gtg | gcc | atc |     | 1104 |

```
Arg Gln Gly Val Tyr Arg Met Arg Lys Lys Gln Ile Asp Val Ala Ile
            355                 360                 365 aag gtg ctg aag cag ggc acg gag aag gca gac acg gaa gag atg atg      1152
Lys Val Leu Lys Gln Gly Thr Glu Lys Ala Asp Thr Glu Glu Met Met
        370                 375                 380 cgc gag gcg cag atc atg cac cag ctg gac aac ccc tac atc gtg cgg      1200
Arg Glu Ala Gln Ile Met His Gln Leu Asp Asn Pro Tyr Ile Val Arg
385                 390                 395                 400 ctc att ggc gtc tgc cag gcc gag gcc ctc atg ctg gtc atg gag atg      1248
Leu Ile Gly Val Cys Gln Ala Glu Ala Leu Met Leu Val Met Glu Met
                405                 410                 415 gct ggg ggc ggg ccg ctg cac aag ttc ctg gtc ggc aag agg gag gag      1296
Ala Gly Gly Gly Pro Leu His Lys Phe Leu Val Gly Lys Arg Glu Glu
            420                 425                 430 atc cct gtg agc aat gtg gcc gag ctg ctg cac cag gtg tcc atg ggg      1344
Ile Pro Val Ser Asn Val Ala Glu Leu Leu His Gln Val Ser Met Gly
        435                 440                 445 atg aag tac ctg gag gag aag aac ttt gtg cac cgt gac ctg gcg gcc      1392
Met Lys Tyr Leu Glu Glu Lys Asn Phe Val His Arg Asp Leu Ala Ala
    450                 455                 460 cgc aac gtc ctg ctg gtt aac cgg cac tac gcc aag atc agc gac ttt      1440
Arg Asn Val Leu Leu Val Asn Arg His Tyr Ala Lys Ile Ser Asp Phe
465                 470                 475                 480 ggc ctc tcc aaa gca ctg ggt gcc gac gac agc tac tac act gcc cgc      1488
Gly Leu Ser Lys Ala Leu Gly Ala Asp Asp Ser Tyr Tyr Thr Ala Arg
                485                 490                 495 tca gca ggg aag tgg ccg ctc aag tgg tac gca ccc gaa tgc atc aac      1536
Ser Ala Gly Lys Trp Pro Leu Lys Trp Tyr Ala Pro Glu Cys Ile Asn
            500                 505                 510 ttc cgc aag ttc tcc agc cgc agc gat gtc tgg agc tat ggg gtc acc      1584
Phe Arg Lys Phe Ser Ser Arg Ser Asp Val Trp Ser Tyr Gly Val Thr
        515                 520                 525 atg tgg gag gcc ttg tcc tac ggc cag aag ccc tac aag aag atg aaa      1632
Met Trp Glu Ala Leu Ser Tyr Gly Gln Lys Pro Tyr Lys Lys Met Lys
    530                 535                 540 ggg ccg gag gtc atg gcc ttc atc gag cag ggc aag cgg atg gag tgc      1680
Gly Pro Glu Val Met Ala Phe Ile Glu Gln Gly Lys Arg Met Glu Cys
545                 550                 555                 560 cca cca gag tgt cca ccc gaa ctg tac gca ctc atg agt gac tgc tgg      1728
Pro Pro Glu Cys Pro Pro Glu Leu Tyr Ala Leu Met Ser Asp Cys Trp
                565                 570                 575 atc tac aag tgg gag gat cgc ccc gac ttc ctg acc gtg gag cag cgc      1776
Ile Tyr Lys Trp Glu Asp Arg Pro Asp Phe Leu Thr Val Glu Gln Arg
            580                 585                 590 atg cga gcc tgt tac tac agc ctg gcc agc aag gtg gaa ggg ccc cca      1824
Met Arg Ala Cys Tyr Tyr Ser Leu Ala Ser Lys Val Glu Gly Pro Pro
        595                 600                 605 ggc agc aca cag aag gct gag gct gcc tgt gcc tgg gat cca ccg gtc      1872
Gly Ser Thr Gln Lys Ala Glu Ala Ala Cys Ala Trp Asp Pro Pro Val
    610                 615                 620 gcc acc atg gtg agc aag ggc gag gag ctg ttc acc ggg gtg gtg ccc      1920
Ala Thr Met Val Ser Lys Gly Glu Glu Leu Phe Thr Gly Val Val Pro
625                 630                 635                 640 atc ctg gtc gag ctg gac ggc gac gta aac ggc cac aag ttc agc gtg      1968
Ile Leu Val Glu Leu Asp Gly Asp Val Asn Gly His Lys Phe Ser Val
                645                 650                 655 tcc ggc gag ggc gag ggc gat gcc acc tac ggc aag ctg acc ctg aag      2016
Ser Gly Glu Gly Glu Gly Asp Ala Thr Tyr Gly Lys Leu Thr Leu Lys
            660                 665                 670
```

-continued

```
ttc atc tgc acc acc ggc aag ctg ccc gtg ccc tgg ccc acc ctc gtg    2064
Phe Ile Cys Thr Thr Gly Lys Leu Pro Val Pro Trp Pro Thr Leu Val
        675                 680                 685 acc acc ctg acc tac ggc gtg cag tgc ttc agc cgc tac ccc gac cac    2112
Thr Thr Leu Thr Tyr Gly Val Gln Cys Phe Ser Arg Tyr Pro Asp His
690                 695                 700 atg aag cag cac gac ttc ttc aag tcc gcc atg ccc gaa ggc tac gtc    2160
Met Lys Gln His Asp Phe Phe Lys Ser Ala Met Pro Glu Gly Tyr Val
705                 710                 715                 720 cag gag cgc acc atc ttc ttc aag gac gac ggc aac tac aag acc cgc    2208
Gln Glu Arg Thr Ile Phe Phe Lys Asp Asp Gly Asn Tyr Lys Thr Arg
            725                 730                 735 gcc gag gtg aag ttc gag ggc gac acc ctg gtg aac cgc atc gag ctg    2256
Ala Glu Val Lys Phe Glu Gly Asp Thr Leu Val Asn Arg Ile Glu Leu
        740                 745                 750 aag ggc atc gac ttc aag gag gac ggc aac atc ctg ggg cac aag ctg    2304
Lys Gly Ile Asp Phe Lys Glu Asp Gly Asn Ile Leu Gly His Lys Leu
    755                 760                 765 gag tac aac tac aac agc cac aac gtc tat atc atg gcc gac aag cag    2352
Glu Tyr Asn Tyr Asn Ser His Asn Val Tyr Ile Met Ala Asp Lys Gln
770                 775                 780 aag aac ggc atc aag gtg aac ttc aag atc cgc cac aac atc gag gac    2400
Lys Asn Gly Ile Lys Val Asn Phe Lys Ile Arg His Asn Ile Glu Asp
785                 790                 795                 800 ggc agc gtg cag ctc gcc gac cac tac cag cag aac acc ccc atc ggc    2448
Gly Ser Val Gln Leu Ala Asp His Tyr Gln Gln Asn Thr Pro Ile Gly
            805                 810                 815 gac ggc ccc gtg ctg ctg ccc gac aac cac tac ctg agc acc cag tcc    2496
Asp Gly Pro Val Leu Leu Pro Asp Asn His Tyr Leu Ser Thr Gln Ser
        820                 825                 830 gcc ctg agc aaa gac ccc aac gag aag cgc gat cac atg gtc ctg ctg    2544
Ala Leu Ser Lys Asp Pro Asn Glu Lys Arg Asp His Met Val Leu Leu
    835                 840                 845 gag ttc gtg acc gcc gcc ggg atc act ctc ggc atg gac gag ctg tac    2592
Glu Phe Val Thr Ala Ala Gly Ile Thr Leu Gly Met Asp Glu Leu Tyr
850                 855                 860 aag taa                                                            2598
Lys
865

<210> SEQ ID NO 111
<211> LENGTH: 865
<212> TYPE: PRT
<213> ORGANISM: Artificial Sequence
<220> FEATURE:
<223> OTHER INFORMATION: Zap70-EGFP fusion

<400> SEQUENCE: 111

Met Pro Asp Pro Ala Ala His Leu Pro Phe Phe Tyr Gly Ser Ile Ser
1               5                   10                  15

Arg Ala Glu Ala Glu Glu His Leu Lys Leu Ala Gly Met Ala Asp Gly
            20                  25                  30

Leu Phe Leu Leu Arg Gln Cys Leu Arg Ser Leu Gly Gly Tyr Val Leu
        35                  40                  45

Ser Leu Val His Asp Val Arg Phe His His Phe Pro Ile Glu Arg Gln
    50                  55                  60

Leu Asn Gly Thr Tyr Ala Ile Ala Gly Gly Lys Ala His Cys Gly Pro
65                  70                  75                  80

Ala Glu Leu Cys Glu Phe Tyr Ser Arg Asp Pro Asp Gly Leu Pro Cys
                85                  90                  95
```

-continued

```
Asn Leu Arg Lys Pro Cys Asn Arg Pro Ser Gly Leu Glu Pro Gln Pro
            100                 105                 110
Gly Val Phe Asp Cys Leu Arg Asp Ala Met Val Arg Asp Tyr Val Arg
        115                 120                 125
Gln Thr Trp Lys Leu Glu Gly Glu Ala Leu Glu Gln Ala Ile Ile Ser
        130                 135                 140
Gln Ala Pro Gln Val Glu Lys Leu Ile Ala Thr Ala His Glu Arg
145                 150                 155                 160
Met Pro Trp Tyr His Ser Ser Leu Thr Arg Glu Glu Ala Glu Arg Lys
                165                 170                 175
Leu Tyr Ser Gly Ala Gln Thr Asp Gly Lys Phe Leu Leu Arg Pro Arg
                180                 185                 190
Lys Glu Gln Gly Thr Tyr Ala Leu Ser Leu Ile Tyr Gly Lys Thr Val
            195                 200                 205
Tyr His Tyr Leu Ile Ser Gln Asp Lys Ala Gly Lys Tyr Cys Ile Pro
        210                 215                 220
Glu Gly Thr Lys Phe Asp Thr Leu Trp Gln Leu Val Glu Tyr Leu Lys
225                 230                 235                 240
Leu Lys Ala Asp Gly Leu Ile Tyr Cys Leu Lys Glu Ala Cys Pro Asn
                245                 250                 255
Ser Ser Ala Ser Asn Ala Ser Gly Ala Ala Ala Pro Thr Leu Pro Ala
                260                 265                 270
His Pro Ser Thr Leu Thr His Pro Gln Arg Arg Ile Asp Thr Leu Asn
            275                 280                 285
Ser Asp Gly Tyr Thr Pro Glu Pro Ala Arg Ile Thr Ser Pro Asp Lys
        290                 295                 300
Pro Arg Pro Met Pro Met Asp Thr Ser Val Tyr Glu Ser Pro Tyr Ser
305                 310                 315                 320
Asp Pro Glu Glu Leu Lys Asp Lys Lys Leu Phe Leu Lys Arg Asp Asn
                325                 330                 335
Leu Leu Ile Ala Asp Ile Glu Leu Gly Cys Gly Asn Phe Gly Ser Val
                340                 345                 350
Arg Gln Gly Val Tyr Arg Met Arg Lys Lys Gln Ile Asp Val Ala Ile
        355                 360                 365
Lys Val Leu Lys Gln Gly Thr Glu Lys Ala Asp Thr Glu Glu Met Met
        370                 375                 380
Arg Glu Ala Gln Ile Met His Gln Leu Asp Asn Pro Tyr Ile Val Arg
385                 390                 395                 400
Leu Ile Gly Val Cys Gln Ala Glu Ala Leu Met Leu Val Met Glu Met
                405                 410                 415
Ala Gly Gly Pro Leu His Lys Phe Leu Val Gly Lys Arg Glu Glu
            420                 425                 430
Ile Pro Val Ser Asn Val Ala Glu Leu Leu His Gln Val Ser Met Gly
        435                 440                 445
Met Lys Tyr Leu Glu Glu Lys Asn Phe Val His Arg Asp Leu Ala Ala
        450                 455                 460
Arg Asn Val Leu Leu Val Asn Arg His Tyr Ala Lys Ile Ser Asp Phe
465                 470                 475                 480
Gly Leu Ser Lys Ala Leu Gly Ala Asp Asp Ser Tyr Tyr Thr Ala Arg
                485                 490                 495
Ser Ala Gly Lys Trp Pro Leu Lys Trp Tyr Ala Pro Glu Cys Ile Asn
            500                 505                 510
```

Phe Arg Lys Phe Ser Ser Arg Ser Asp Val Trp Ser Tyr Gly Val Thr
        515                 520                 525

Met Trp Glu Ala Leu Ser Tyr Gly Gln Lys Pro Tyr Lys Met Lys
530                 535                 540

Gly Pro Glu Val Met Ala Phe Ile Glu Gln Gly Lys Arg Met Glu Cys
545                 550                 555                 560

Pro Pro Glu Cys Pro Pro Glu Leu Tyr Ala Leu Met Ser Asp Cys Trp
            565                 570                 575

Ile Tyr Lys Trp Glu Asp Arg Pro Asp Phe Leu Thr Val Glu Gln Arg
            580                 585                 590

Met Arg Ala Cys Tyr Tyr Ser Leu Ala Ser Lys Val Glu Gly Pro Pro
        595                 600                 605

Gly Ser Thr Gln Lys Ala Glu Ala Ala Cys Ala Trp Asp Pro Pro Val
        610                 615                 620

Ala Thr Met Val Ser Lys Gly Glu Glu Leu Phe Thr Gly Val Val Pro
625                 630                 635                 640

Ile Leu Val Glu Leu Asp Gly Asp Val Asn Gly His Lys Phe Ser Val
            645                 650                 655

Ser Gly Glu Gly Glu Gly Asp Ala Thr Tyr Gly Lys Leu Thr Leu Lys
            660                 665                 670

Phe Ile Cys Thr Thr Gly Lys Leu Pro Val Pro Trp Pro Thr Leu Val
        675                 680                 685

Thr Thr Leu Thr Tyr Gly Val Gln Cys Phe Ser Arg Tyr Pro Asp His
        690                 695                 700

Met Lys Gln His Asp Phe Phe Lys Ser Ala Met Pro Glu Gly Tyr Val
705                 710                 715                 720

Gln Glu Arg Thr Ile Phe Phe Lys Asp Asp Gly Asn Tyr Lys Thr Arg
            725                 730                 735

Ala Glu Val Lys Phe Glu Gly Asp Thr Leu Val Asn Arg Ile Glu Leu
            740                 745                 750

Lys Gly Ile Asp Phe Lys Glu Asp Gly Asn Ile Leu Gly His Lys Leu
        755                 760                 765

Glu Tyr Asn Tyr Asn Ser His Asn Val Tyr Ile Met Ala Asp Lys Gln
        770                 775                 780

Lys Asn Gly Ile Lys Val Asn Phe Lys Ile Arg His Asn Ile Glu Asp
785                 790                 795                 800

Gly Ser Val Gln Leu Ala Asp His Tyr Gln Gln Asn Thr Pro Ile Gly
            805                 810                 815

Asp Gly Pro Val Leu Leu Pro Asp Asn His Tyr Leu Ser Thr Gln Ser
            820                 825                 830

Ala Leu Ser Lys Asp Pro Asn Glu Lys Arg Asp His Met Val Leu Leu
        835                 840                 845

Glu Phe Val Thr Ala Ala Gly Ile Thr Leu Gly Met Asp Glu Leu Tyr
        850                 855                 860

Lys
865

<210> SEQ ID NO 112
<211> LENGTH: 1635
<212> TYPE: DNA
<213> ORGANISM: Artificial Sequence
<220> FEATURE:
<223> OTHER INFORMATION: CDK2-EGFP fusion
<220> FEATURE:
<221> NAME/KEY: CDS
<222> LOCATION: (1)..(1632)

-continued

```
<400> SEQUENCE: 112 atg gag aac ttc caa aag gtg gaa aag atc gga gag ggc acg tac gga      48
Met Glu Asn Phe Gln Lys Val Glu Lys Ile Gly Glu Gly Thr Tyr Gly
1               5                   10                  15 gtt gtg tac aaa gcc aga aac aag ttg acg gga gag gtg gtg gcg ctt      96
Val Val Tyr Lys Ala Arg Asn Lys Leu Thr Gly Glu Val Val Ala Leu
                20                  25                  30 aag aaa atc cgc ctg gac act gag act gag ggt gtg ccc agt act gcc     144
Lys Lys Ile Arg Leu Asp Thr Glu Thr Glu Gly Val Pro Ser Thr Ala
            35                  40                  45 atc cga gag atc tct ctg ctt aag gag ctt aac cat cct aat att gtc     192
Ile Arg Glu Ile Ser Leu Leu Lys Glu Leu Asn His Pro Asn Ile Val
        50                  55                  60 aag ctg ctg gat gtc att cac aca gaa aat aaa ctc tac ctg gtt ttt     240
Lys Leu Leu Asp Val Ile His Thr Glu Asn Lys Leu Tyr Leu Val Phe
65                  70                  75                  80 gaa ttt ctg cac caa gat ctc aag aaa ttc atg gat gcc tct gct ctc     288
Glu Phe Leu His Gln Asp Leu Lys Lys Phe Met Asp Ala Ser Ala Leu
                85                  90                  95 act ggc att cct ctt ccc ctc atc aag agc tat ctg ttc cag ctg ctc     336
Thr Gly Ile Pro Leu Pro Leu Ile Lys Ser Tyr Leu Phe Gln Leu Leu
                100                 105                 110 cag ggc cta gct ttc tgc cat tct cat cgg gtc ctc cac cga gac ctt     384
Gln Gly Leu Ala Phe Cys His Ser His Arg Val Leu His Arg Asp Leu
            115                 120                 125 aaa cct cag aat ctg ctt att aac aca gag ggg gcc atc aag cta gca     432
Lys Pro Gln Asn Leu Leu Ile Asn Thr Glu Gly Ala Ile Lys Leu Ala
        130                 135                 140 gac ttt gga cta gcc aga gct ttt gga gtc cct gtt cgt act tac acc     480
Asp Phe Gly Leu Ala Arg Ala Phe Gly Val Pro Val Arg Thr Tyr Thr
145                 150                 155                 160 cat gag gtg gtg acc ctg tgg tac cga gct cct gaa atc ctc ctg ggc     528
His Glu Val Val Thr Leu Trp Tyr Arg Ala Pro Glu Ile Leu Leu Gly
                165                 170                 175 tcg aaa tat tat tcc aca gct gtg gac atc tgg agc ctg ggc tgc atc     576
Ser Lys Tyr Tyr Ser Thr Ala Val Asp Ile Trp Ser Leu Gly Cys Ile
                180                 185                 190 ttt gct gag atg gtg act cgc cgg gcc ctg ttc cct gga gat tct gag     624
Phe Ala Glu Met Val Thr Arg Arg Ala Leu Phe Pro Gly Asp Ser Glu
            195                 200                 205 att gac cag ctc ttc cgg atc ttt cgg act ctg ggg acc cca gat gag     672
Ile Asp Gln Leu Phe Arg Ile Phe Arg Thr Leu Gly Thr Pro Asp Glu
        210                 215                 220 gtg gtg tgg cca gga gtt act tct atg cct gat tac aag cca agt ttc     720
Val Val Trp Pro Gly Val Thr Ser Met Pro Asp Tyr Lys Pro Ser Phe
225                 230                 235                 240 ccc aag tgg gcc cgg caa gat ttt agt aaa gtt gta cct ccc ctg gat     768
Pro Lys Trp Ala Arg Gln Asp Phe Ser Lys Val Val Pro Pro Leu Asp
                245                 250                 255 gaa gat gga cgg agc ttg tta tcg caa atg ctg cac tac gac cct aac     816
Glu Asp Gly Arg Ser Leu Leu Ser Gln Met Leu His Tyr Asp Pro Asn
                260                 265                 270 aag cgg att tcg gcc aag gca gcc ctg gct cac cct ttc ttc cag gat     864
Lys Arg Ile Ser Ala Lys Ala Ala Leu Ala His Pro Phe Phe Gln Asp
            275                 280                 285 gtg acc aag cca gta ccc cat ctt cga ctc tgg gat cca ccg gtc gcc     912
Val Thr Lys Pro Val Pro His Leu Arg Leu Trp Asp Pro Pro Val Ala
        290                 295                 300
```

```
acc atg gtg agc aag ggc gag gag ctg ttc acc ggg gtg gtg ccc atc      960
Thr Met Val Ser Lys Gly Glu Glu Leu Phe Thr Gly Val Val Pro Ile
305                 310                 315                 320 ctg gtc gag ctg gac ggc gac gta aac ggc cac aag ttc agc gtg tcc     1008
Leu Val Glu Leu Asp Gly Asp Val Asn Gly His Lys Phe Ser Val Ser
                325                 330                 335 ggc gag ggc gag ggc gat gcc acc tac ggc aag ctg acc ctg aag ttc     1056
Gly Glu Gly Glu Gly Asp Ala Thr Tyr Gly Lys Leu Thr Leu Lys Phe
            340                 345                 350 atc tgc acc acc ggc aag ctg ccc gtg ccc tgg ccc acc ctc gtg acc     1104
Ile Cys Thr Thr Gly Lys Leu Pro Val Pro Trp Pro Thr Leu Val Thr
        355                 360                 365 acc ctg acc tac ggc gtg cag tgc ttc agc cgc tac ccc gac cac atg     1152
Thr Leu Thr Tyr Gly Val Gln Cys Phe Ser Arg Tyr Pro Asp His Met
    370                 375                 380 aag cag cac gac ttc ttc aag tcc gcc atg ccc gaa ggc tac gtc cag     1200
Lys Gln His Asp Phe Phe Lys Ser Ala Met Pro Glu Gly Tyr Val Gln
385                 390                 395                 400 gag cgc acc atc ttc ttc aag gac gac ggc aac tac aag acc cgc gcc     1248
Glu Arg Thr Ile Phe Phe Lys Asp Asp Gly Asn Tyr Lys Thr Arg Ala
                405                 410                 415 gag gtg aag ttc gag ggc gac acc ctg gtg aac cgc atc gag ctg aag     1296
Glu Val Lys Phe Glu Gly Asp Thr Leu Val Asn Arg Ile Glu Leu Lys
            420                 425                 430 ggc atc gac ttc aag gag gac ggc aac atc ctg ggg cac aag ctg gag     1344
Gly Ile Asp Phe Lys Glu Asp Gly Asn Ile Leu Gly His Lys Leu Glu
        435                 440                 445 tac aac tac aac agc cac aac gtc tat atc atg gcc gac aag cag aag     1392
Tyr Asn Tyr Asn Ser His Asn Val Tyr Ile Met Ala Asp Lys Gln Lys
    450                 455                 460 aac ggc atc aag gtg aac ttc aag atc cgc cac aac atc gag gac ggc     1440
Asn Gly Ile Lys Val Asn Phe Lys Ile Arg His Asn Ile Glu Asp Gly
465                 470                 475                 480 agc gtg cag ctc gcc gac cac tac cag cag aac acc ccc atc ggc gac     1488
Ser Val Gln Leu Ala Asp His Tyr Gln Gln Asn Thr Pro Ile Gly Asp
                485                 490                 495 ggc ccc gtg ctg ctg ccc gac aac cac tac ctg agc acc cag tcc gcc     1536
Gly Pro Val Leu Leu Pro Asp Asn His Tyr Leu Ser Thr Gln Ser Ala
            500                 505                 510 ctg agc aaa gac ccc aac gag aag cgc gat cac atg gtc ctg ctg gag     1584
Leu Ser Lys Asp Pro Asn Glu Lys Arg Asp His Met Val Leu Leu Glu
        515                 520                 525 ttc gtg acc gcc gcc ggg atc act ctc ggc atg gac gag ctg tac aag     1632
Phe Val Thr Ala Ala Gly Ile Thr Leu Gly Met Asp Glu Leu Tyr Lys
    530                 535                 540 taa                                                                  1635
```

<210> SEQ ID NO 113
<211> LENGTH: 544
<212> TYPE: PRT
<213> ORGANISM: Artificial Sequence
<220> FEATURE:
<223> OTHER INFORMATION: CDK2-EGFP fusion

<400> SEQUENCE: 113

Met Glu Asn Phe Gln Lys Val Glu Lys Ile Gly Glu Gly Thr Tyr Gly
1               5                   10                  15

Val Val Tyr Lys Ala Arg Asn Lys Leu Thr Gly Glu Val Val Ala Leu
            20                  25                  30

Lys Lys Ile Arg Leu Asp Thr Glu Thr Glu Gly Val Pro Ser Thr Ala

```
            35                  40                  45
Ile Arg Glu Ile Ser Leu Leu Lys Glu Leu Asn His Pro Asn Ile Val
 50                  55                  60

Lys Leu Leu Asp Val Ile His Thr Glu Asn Lys Leu Tyr Leu Val Phe
 65                  70                  75                  80

Glu Phe Leu His Gln Asp Leu Lys Lys Phe Met Asp Ala Ser Ala Leu
                 85                  90                  95

Thr Gly Ile Pro Leu Pro Leu Ile Lys Ser Tyr Leu Phe Gln Leu Leu
                100                 105                 110

Gln Gly Leu Ala Phe Cys His Ser His Arg Val Leu His Arg Asp Leu
                115                 120                 125

Lys Pro Gln Asn Leu Leu Ile Asn Thr Glu Gly Ala Ile Lys Leu Ala
130                 135                 140

Asp Phe Gly Leu Ala Arg Ala Phe Gly Val Pro Val Arg Thr Tyr Thr
145                 150                 155                 160

His Glu Val Val Thr Leu Trp Tyr Arg Ala Pro Glu Ile Leu Leu Gly
                165                 170                 175

Ser Lys Tyr Tyr Ser Thr Ala Val Asp Ile Trp Ser Leu Gly Cys Ile
                180                 185                 190

Phe Ala Glu Met Val Thr Arg Arg Ala Leu Phe Pro Gly Asp Ser Glu
                195                 200                 205

Ile Asp Gln Leu Phe Arg Ile Phe Arg Thr Leu Gly Thr Pro Asp Glu
210                 215                 220

Val Val Trp Pro Gly Val Thr Ser Met Pro Asp Tyr Lys Pro Ser Phe
225                 230                 235                 240

Pro Lys Trp Ala Arg Gln Asp Phe Ser Lys Val Val Pro Pro Leu Asp
                245                 250                 255

Glu Asp Gly Arg Ser Leu Leu Ser Gln Met Leu His Tyr Asp Pro Asn
                260                 265                 270

Lys Arg Ile Ser Ala Lys Ala Ala Leu Ala His Pro Phe Phe Gln Asp
                275                 280                 285

Val Thr Lys Pro Val Pro His Leu Arg Leu Trp Asp Pro Pro Val Ala
                290                 295                 300

Thr Met Val Ser Lys Gly Glu Glu Leu Phe Thr Gly Val Val Pro Ile
305                 310                 315                 320

Leu Val Glu Leu Asp Gly Asp Val Asn Gly His Lys Phe Ser Val Ser
                325                 330                 335

Gly Glu Gly Glu Gly Asp Ala Thr Tyr Gly Lys Leu Thr Leu Lys Phe
                340                 345                 350

Ile Cys Thr Thr Gly Lys Leu Pro Val Pro Trp Pro Thr Leu Val Thr
                355                 360                 365

Thr Leu Thr Tyr Gly Val Gln Cys Phe Ser Arg Tyr Pro Asp His Met
                370                 375                 380

Lys Gln His Asp Phe Phe Lys Ser Ala Met Pro Glu Gly Tyr Val Gln
385                 390                 395                 400

Glu Arg Thr Ile Phe Phe Lys Asp Asp Gly Asn Tyr Lys Thr Arg Ala
                405                 410                 415

Glu Val Lys Phe Glu Gly Asp Thr Leu Val Asn Arg Ile Glu Leu Lys
                420                 425                 430

Gly Ile Asp Phe Lys Glu Asp Gly Asn Ile Leu Gly His Lys Leu Glu
                435                 440                 445

Tyr Asn Tyr Asn Ser His Asn Val Tyr Ile Met Ala Asp Lys Gln Lys
                450                 455                 460
```

```
Asn Gly Ile Lys Val Asn Phe Lys Ile Arg His Asn Ile Glu Asp Gly
465                 470                 475                 480

Ser Val Gln Leu Ala Asp His Tyr Gln Gln Asn Thr Pro Ile Gly Asp
                485                 490                 495

Gly Pro Val Leu Leu Pro Asp Asn His Tyr Leu Ser Thr Gln Ser Ala
            500                 505                 510

Leu Ser Lys Asp Pro Asn Glu Lys Arg Asp His Met Val Leu Leu Glu
        515                 520                 525

Phe Val Thr Ala Ala Gly Ile Thr Leu Gly Met Asp Glu Leu Tyr Lys
    530                 535                 540

<210> SEQ ID NO 114
<211> LENGTH: 1635
<212> TYPE: DNA
<213> ORGANISM: Artificial Sequence
<220> FEATURE:
<223> OTHER INFORMATION: EGFP-CDK2 fusion
<220> FEATURE:
<221> NAME/KEY: CDS
<222> LOCATION: (1)..(1632)

<400> SEQUENCE: 114
```

| | | | | | | | | | | | | | | | | |
|---|---|---|---|---|---|---|---|---|---|---|---|---|---|---|---|---|
| atg gtg agc aag ggc gag gag ctg ttc acc ggg gtg gtg ccc atc ctg | | | | | | | | | | | | | | | | 48 |
| Met Val Ser Lys Gly Glu Glu Leu Phe Thr Gly Val Val Pro Ile Leu | | | | | | | | | | | | | | | | |
| 1 | | | | 5 | | | | | 10 | | | | | 15 | | |

```
gtc gag ctg gac ggc gac gta aac ggc cac aag ttc agc gtg tcc ggc       96
Val Glu Leu Asp Gly Asp Val Asn Gly His Lys Phe Ser Val Ser Gly
            20                  25                  30 gag ggc gag ggc gat gcc acc tac ggc aag ctg acc ctg aag ttc atc      144
Glu Gly Glu Gly Asp Ala Thr Tyr Gly Lys Leu Thr Leu Lys Phe Ile
        35                  40                  45 tgc acc acc ggc aag ctg ccc gtg ccc tgg ccc acc ctc gtg acc acc      192
Cys Thr Thr Gly Lys Leu Pro Val Pro Trp Pro Thr Leu Val Thr Thr
    50                  55                  60 ctg acc tac ggc gtg cag tgc ttc agc cgc tac ccc gac cac atg aag      240
Leu Thr Tyr Gly Val Gln Cys Phe Ser Arg Tyr Pro Asp His Met Lys
65                  70                  75                  80 cag cac gac ttc ttc aag tcc gcc atg ccc gaa ggc tac gtc cag gag      288
Gln His Asp Phe Phe Lys Ser Ala Met Pro Glu Gly Tyr Val Gln Glu
                85                  90                  95 cgc acc atc ttc ttc aag gac gac ggc aac tac aag acc cgc gcc gag      336
Arg Thr Ile Phe Phe Lys Asp Asp Gly Asn Tyr Lys Thr Arg Ala Glu
            100                 105                 110 gtg aag ttc gag ggc gac acc ctg gtg aac cgc atc gag ctg aag ggc      384
Val Lys Phe Glu Gly Asp Thr Leu Val Asn Arg Ile Glu Leu Lys Gly
        115                 120                 125 atc gac ttc aag gag gac ggc aac atc ctg ggg cac aag ctg gag tac      432
Ile Asp Phe Lys Glu Asp Gly Asn Ile Leu Gly His Lys Leu Glu Tyr
    130                 135                 140 aac tac aac agc cac aac gtc tat atc atg gcc gac aag cag aag aac      480
Asn Tyr Asn Ser His Asn Val Tyr Ile Met Ala Asp Lys Gln Lys Asn
145                 150                 155                 160 ggc atc aag gtg aac ttc aag atc cgc cac aac atc gag gac ggc agc      528
Gly Ile Lys Val Asn Phe Lys Ile Arg His Asn Ile Glu Asp Gly Ser
                165                 170                 175 gtg cag ctc gcc gac cac tac cag cag aac acc ccc atc ggc gac ggc      576
Val Gln Leu Ala Asp His Tyr Gln Gln Asn Thr Pro Ile Gly Asp Gly
            180                 185                 190 ccc gtg ctg ctg ccc gac aac cac tac ctg agc acc cag tcc gcc ctg      624
Pro Val Leu Leu Pro Asp Asn His Tyr Leu Ser Thr Gln Ser Ala Leu
```

```
                195                     200                     205
agc aaa gac ccc aac gag aag cgc gat cac atg gtc ctg ctg gag ttc        672
Ser Lys Asp Pro Asn Glu Lys Arg Asp His Met Val Leu Leu Glu Phe
    210                     215                     220 gtg acc gcc gcc ggg atc act ctc ggc atg gac gag ctg tac aag tcc        720
Val Thr Ala Ala Gly Ile Thr Leu Gly Met Asp Glu Leu Tyr Lys Ser
225                     230                     235                 240 gga ctc aga tct cga gcc atg gag aac ttc caa aag gtg gaa aag atc        768
Gly Leu Arg Ser Arg Ala Met Glu Asn Phe Gln Lys Val Glu Lys Ile
                245                     250                     255 gga gag ggc acg tac gga gtt gtg tac aaa gcc aga aac aag ttg acg        816
Gly Glu Gly Thr Tyr Gly Val Val Tyr Lys Ala Arg Asn Lys Leu Thr
            260                     265                     270 gga gag gtg gtg gcg ctt aag aaa atc cgc ctg gac act gag act gag        864
Gly Glu Val Val Ala Leu Lys Lys Ile Arg Leu Asp Thr Glu Thr Glu
        275                     280                     285 ggt gtg ccc agt act gcc atc cga gag atc tct ctg ctt aag gag ctt        912
Gly Val Pro Ser Thr Ala Ile Arg Glu Ile Ser Leu Leu Lys Glu Leu
    290                     295                     300 aac cat cct aat att gtc aag ctg ctg gat gtc att cac aca gaa aat        960
Asn His Pro Asn Ile Val Lys Leu Leu Asp Val Ile His Thr Glu Asn
305                     310                     315                 320 aaa ctc tac ctg gtt ttt gaa ttt ctg cac caa gat ctc aag aaa ttc       1008
Lys Leu Tyr Leu Val Phe Glu Phe Leu His Gln Asp Leu Lys Lys Phe
                325                     330                     335 atg gat gcc tct gct ctc act ggc att cct ctt ccc ctc atc aag agc       1056
Met Asp Ala Ser Ala Leu Thr Gly Ile Pro Leu Pro Leu Ile Lys Ser
            340                     345                     350 tat ctg ttc cag ctg ctc cag ggc cta gct ttc tgc cat tct cat cgg       1104
Tyr Leu Phe Gln Leu Leu Gln Gly Leu Ala Phe Cys His Ser His Arg
        355                     360                     365 gtc ctc cac cga gac ctt aaa cct cag aat ctg ctt att aac aca gag       1152
Val Leu His Arg Asp Leu Lys Pro Gln Asn Leu Leu Ile Asn Thr Glu
    370                     375                     380 ggg gcc atc aag cta gca gac ttt gga cta gcc aga gct ttt gga gtc       1200
Gly Ala Ile Lys Leu Ala Asp Phe Gly Leu Ala Arg Ala Phe Gly Val
385                     390                     395                 400 cct gtt cgt act tac acc cat gag gtg gtg acc ctg tgg tac cga gct       1248
Pro Val Arg Thr Tyr Thr His Glu Val Val Thr Leu Trp Tyr Arg Ala
                405                     410                     415 cct gaa atc ctc ctg ggc tcg aaa tat tat tcc aca gct gtg gac atc       1296
Pro Glu Ile Leu Leu Gly Ser Lys Tyr Tyr Ser Thr Ala Val Asp Ile
            420                     425                     430 tgg agc ctg ggc tgc atc ttt gct gag atg gtg act cgc cgg gcc ctg       1344
Trp Ser Leu Gly Cys Ile Phe Ala Glu Met Val Thr Arg Arg Ala Leu
        435                     440                     445 ttc cct gga gat tct gag att gac cag ctc ttc cgg atc ttt cgg act       1392
Phe Pro Gly Asp Ser Glu Ile Asp Gln Leu Phe Arg Ile Phe Arg Thr
    450                     455                     460 ctg ggg acc cca gat gag gtg gtg tgg cca gga gtt act tct atg cct       1440
Leu Gly Thr Pro Asp Glu Val Val Trp Pro Gly Val Thr Ser Met Pro
465                     470                     475                 480 gat tac aag cca agt ttc ccc aag tgg gcc cgg caa gat ttt agt aaa       1488
Asp Tyr Lys Pro Ser Phe Pro Lys Trp Ala Arg Gln Asp Phe Ser Lys
                485                     490                     495 gtt gta cct ccc ctg gat gaa gat gga cgg agc ttg tta tcg caa atg       1536
Val Val Pro Pro Leu Asp Glu Asp Gly Arg Ser Leu Leu Ser Gln Met
            500                     505                     510 ctg cac tac gac cct aac aag cgg att tcg gcc aag gca gcc ctg gct       1584
```

-continued

```
Leu His Tyr Asp Pro Asn Lys Arg Ile Ser Ala Lys Ala Ala Leu Ala
        515                 520                 525 cac cct ttc ttc cag gat gtg acc aag cca gta ccc cat ctt cga ctc    1632
His Pro Phe Phe Gln Asp Val Thr Lys Pro Val Pro His Leu Arg Leu
    530                 535                 540 tga                                                                 1635
```

<210> SEQ ID NO 115
<211> LENGTH: 544
<212> TYPE: PRT
<213> ORGANISM: Artificial Sequence
<220> FEATURE:
<223> OTHER INFORMATION: EGFP-CDK2 fusion

<400> SEQUENCE: 115

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Ser
225                 230                 235                 240

Gly Leu Arg Ser Arg Ala Met Glu Asn Phe Gln Lys Val Glu Lys Ile
                245                 250                 255

Gly Glu Gly Thr Tyr Gly Val Val Tyr Lys Ala Arg Asn Lys Leu Thr
            260                 265                 270

Gly Glu Val Val Ala Leu Lys Lys Ile Arg Leu Asp Thr Glu Thr Glu
        275                 280                 285

Gly Val Pro Ser Thr Ala Ile Arg Glu Ile Ser Leu Leu Lys Glu Leu
    290                 295                 300

Asn His Pro Asn Ile Val Lys Leu Leu Asp Val Ile His Thr Glu Asn
305                 310                 315                 320
```

-continued

```
Lys Leu Tyr Leu Val Phe Glu Phe Leu His Gln Asp Leu Lys Lys Phe
                325                 330                 335

Met Asp Ala Ser Ala Leu Thr Gly Ile Pro Leu Pro Leu Ile Lys Ser
            340                 345                 350

Tyr Leu Phe Gln Leu Leu Gln Gly Leu Ala Phe Cys His Ser His Arg
        355                 360                 365

Val Leu His Arg Asp Leu Lys Pro Gln Asn Leu Leu Ile Asn Thr Glu
    370                 375                 380

Gly Ala Ile Lys Leu Ala Asp Phe Gly Leu Ala Arg Ala Phe Gly Val
385                 390                 395                 400

Pro Val Arg Thr Tyr Thr His Glu Val Val Thr Leu Trp Tyr Arg Ala
                405                 410                 415

Pro Glu Ile Leu Leu Gly Ser Lys Tyr Tyr Ser Thr Ala Val Asp Ile
            420                 425                 430

Trp Ser Leu Gly Cys Ile Phe Ala Glu Met Val Thr Arg Arg Ala Leu
        435                 440                 445

Phe Pro Gly Asp Ser Glu Ile Asp Gln Leu Phe Arg Ile Phe Arg Thr
    450                 455                 460

Leu Gly Thr Pro Asp Glu Val Val Trp Pro Gly Val Thr Ser Met Pro
465                 470                 475                 480

Asp Tyr Lys Pro Ser Phe Pro Lys Trp Ala Arg Gln Asp Phe Ser Lys
                485                 490                 495

Val Val Pro Pro Leu Asp Glu Asp Gly Arg Ser Leu Leu Ser Gln Met
            500                 505                 510

Leu His Tyr Asp Pro Asn Lys Arg Ile Ser Ala Lys Ala Ala Leu Ala
        515                 520                 525

His Pro Phe Phe Gln Asp Val Thr Lys Pro Val Pro His Leu Arg Leu
    530                 535                 540

<210> SEQ ID NO 116
<211> LENGTH: 2532
<212> TYPE: DNA
<213> ORGANISM: Artificial Sequence
<220> FEATURE:
<223> OTHER INFORMATION: EGFP-PTP fusion
<220> FEATURE:
<221> NAME/KEY: CDS
<222> LOCATION: (1)..(2529)

<400> SEQUENCE: 116 atg gtg agc aag ggc gag gag ctg ttc acc ggg gtg gtg ccc atc ctg      48
Met Val Ser Lys Gly Glu Glu Leu Phe Thr Gly Val Val Pro Ile Leu
1               5                  10                  15 gtc gag ctg gac ggc gac gta aac ggc cac aag ttc agc gtg tcc ggc      96
Val Glu Leu Asp Gly Asp Val Asn Gly His Lys Phe Ser Val Ser Gly
            20                  25                  30 gag ggc gag ggc gat gcc acc tac ggc aag ctg acc ctg aag ttc atc     144
Glu Gly Glu Gly Asp Ala Thr Tyr Gly Lys Leu Thr Leu Lys Phe Ile
        35                  40                  45 tgc acc acc ggc aag ctg ccc gtg ccc tgg ccc acc ctc gtg acc acc     192
Cys Thr Thr Gly Lys Leu Pro Val Pro Trp Pro Thr Leu Val Thr Thr
    50                  55                  60 ctg acc tac ggc gtg cag tgc ttc agc cgc tac ccc gac cac atg aag     240
Leu Thr Tyr Gly Val Gln Cys Phe Ser Arg Tyr Pro Asp His Met Lys
65                  70                  75                  80 cag cac gac ttc ttc aag tcc gcc atg ccc gaa ggc tac gtc cag gag     288
Gln His Asp Phe Phe Lys Ser Ala Met Pro Glu Gly Tyr Val Gln Glu
                85                  90                  95
```

```
cgc acc atc ttc ttc aag gac gac ggc aac tac aag acc cgc gcc gag      336
Arg Thr Ile Phe Phe Lys Asp Asp Gly Asn Tyr Lys Thr Arg Ala Glu
        100                 105                 110 gtg aag ttc gag ggc gac acc ctg gtg aac cgc atc gag ctg aag ggc      384
Val Lys Phe Glu Gly Asp Thr Leu Val Asn Arg Ile Glu Leu Lys Gly
            115                 120                 125 atc gac ttc aag gag gac ggc aac atc ctg ggg cac aag ctg gag tac      432
Ile Asp Phe Lys Glu Asp Gly Asn Ile Leu Gly His Lys Leu Glu Tyr
130                 135                 140 aac tac aac agc cac aac gtc tat atc atg gcc gac aag cag aag aac      480
Asn Tyr Asn Ser His Asn Val Tyr Ile Met Ala Asp Lys Gln Lys Asn
145                 150                 155                 160 ggc atc aag gtg aac ttc aag atc cgc cac aac atc gag gac ggc agc      528
Gly Ile Lys Val Asn Phe Lys Ile Arg His Asn Ile Glu Asp Gly Ser
                165                 170                 175 gtg cag ctc gcc gac cac tac cag cag aac acc ccc atc ggc gac ggc      576
Val Gln Leu Ala Asp His Tyr Gln Gln Asn Thr Pro Ile Gly Asp Gly
            180                 185                 190 ccc gtg ctg ctg ccc gac aac cac tac ctg agc acc cag tcc gcc ctg      624
Pro Val Leu Leu Pro Asp Asn His Tyr Leu Ser Thr Gln Ser Ala Leu
        195                 200                 205 agc aaa gac ccc aac gag aag cgc gat cac atg gtc ctg ctg gag ttc      672
Ser Lys Asp Pro Asn Glu Lys Arg Asp His Met Val Leu Leu Glu Phe
    210                 215                 220 gtg acc gcc gcc ggg atc act ctc ggc atg gac gag ctg tac aag tcc      720
Val Thr Ala Ala Gly Ile Thr Leu Gly Met Asp Glu Leu Tyr Lys Ser
225                 230                 235                 240 gga ctc aga tct cga gag atg ctg tcc cgt ggg tgg ttt cac cga gac      768
Gly Leu Arg Ser Arg Glu Met Leu Ser Arg Gly Trp Phe His Arg Asp
                245                 250                 255 ctc agt ggg ctg gat gca gag acc ctg ctc aag ggc cga ggt gtc cac      816
Leu Ser Gly Leu Asp Ala Glu Thr Leu Leu Lys Gly Arg Gly Val His
            260                 265                 270 ggt agc ttc ctg gct cgg ccc agt cgc aag aac cag ggt gac ttc tcg      864
Gly Ser Phe Leu Ala Arg Pro Ser Arg Lys Asn Gln Gly Asp Phe Ser
        275                 280                 285 ctc tcc gtc agg gtg ggg gat cag gtg acc cat att cgg atc cag aac      912
Leu Ser Val Arg Val Gly Asp Gln Val Thr His Ile Arg Ile Gln Asn
    290                 295                 300 tca ggg gat ttc tat gac ctg tat gga ggg gag aag ttt gcg act ctg      960
Ser Gly Asp Phe Tyr Asp Leu Tyr Gly Gly Glu Lys Phe Ala Thr Leu
305                 310                 315                 320 aca gag ctg gtg gag tac tac act cag cag cag ggt gtc ctg cag gac     1008
Thr Glu Leu Val Glu Tyr Tyr Thr Gln Gln Gln Gly Val Leu Gln Asp
                325                 330                 335 cgc gac ggc acc atc atc cac ctc aag tac ccg ctg aac tgc tcc gat     1056
Arg Asp Gly Thr Ile Ile His Leu Lys Tyr Pro Leu Asn Cys Ser Asp
            340                 345                 350 ccc act agt gag agg tgg tac cat ggc cac atg tct ggc ggg cag gca     1104
Pro Thr Ser Glu Arg Trp Tyr His Gly His Met Ser Gly Gly Gln Ala
        355                 360                 365 gag acg ctg ctg cag gcc aag ggc gag ccc tgg acg ttt ctt gtg cgt     1152
Glu Thr Leu Leu Gln Ala Lys Gly Glu Pro Trp Thr Phe Leu Val Arg
    370                 375                 380 gag agc ctc agc cag cct gga gac ttc gtg ctt tct gtg ctc agt gac     1200
Glu Ser Leu Ser Gln Pro Gly Asp Phe Val Leu Ser Val Leu Ser Asp
385                 390                 395                 400 cag ccc aag gct ggc cca ggc tcc ccg ctc agg gtc acc cac atc aag     1248
Gln Pro Lys Ala Gly Pro Gly Ser Pro Leu Arg Val Thr His Ile Lys
                405                 410                 415
```

```
gtc atg tgc gag ggt gga cgc tac aca gtg ggt ggt ttg gag acc ttc      1296
Val Met Cys Glu Gly Gly Arg Tyr Thr Val Gly Gly Leu Glu Thr Phe
            420                 425                 430 gac agc ctc acg gac ctg gta gag cat ttc aag aag acg ggg att gag      1344
Asp Ser Leu Thr Asp Leu Val Glu His Phe Lys Lys Thr Gly Ile Glu
            435                 440                 445 gag gcc tca ggc gcc ttt gtc tac ctg cgg cag ccg tac tat gcc acg      1392
Glu Ala Ser Gly Ala Phe Val Tyr Leu Arg Gln Pro Tyr Tyr Ala Thr
            450                 455                 460 agg gtg aat gcg gct gac att gag aac cga gtg ttg gaa ctg aac aag      1440
Arg Val Asn Ala Ala Asp Ile Glu Asn Arg Val Leu Glu Leu Asn Lys
465                 470                 475                 480 aag cag gag tcc gag gat aca gcc aag gct ggc ttc tgg gag gag ttt      1488
Lys Gln Glu Ser Glu Asp Thr Ala Lys Ala Gly Phe Trp Glu Glu Phe
                485                 490                 495 gag agt ttg cag aag cag gag gtg aag aac ttg cac cag cgt ctg gaa      1536
Glu Ser Leu Gln Lys Gln Glu Val Lys Asn Leu His Gln Arg Leu Glu
                500                 505                 510 ggg cag cgg cca gag aac aag ggc aag aac cgc tac aag aac att ctc      1584
Gly Gln Arg Pro Glu Asn Lys Gly Lys Asn Arg Tyr Lys Asn Ile Leu
            515                 520                 525 ccc ttt gac cac agc cga gtg atc ctg cag gga cgg gac agt aac atc      1632
Pro Phe Asp His Ser Arg Val Ile Leu Gln Gly Arg Asp Ser Asn Ile
530                 535                 540 ccc ggg tcc gac tac atc aat gcc aac tac atc aag aac cag ctg cta      1680
Pro Gly Ser Asp Tyr Ile Asn Ala Asn Tyr Ile Lys Asn Gln Leu Leu
545                 550                 555                 560 ggc cct gat gag aac gct aag acc tac atc gcc agc cag ggc tgt ctg      1728
Gly Pro Asp Glu Asn Ala Lys Thr Tyr Ile Ala Ser Gln Gly Cys Leu
                565                 570                 575 gag gcc acg gtc aat gac ttc tgg cag atg gcg tgg cag gag aac agc      1776
Glu Ala Thr Val Asn Asp Phe Trp Gln Met Ala Trp Gln Glu Asn Ser
            580                 585                 590 cgt gtc atc gtc atg acc acc cga gag gtg gag aaa ggc cgg aac aaa      1824
Arg Val Ile Val Met Thr Thr Arg Glu Val Glu Lys Gly Arg Asn Lys
            595                 600                 605 tgc gtc cca tac tgg ccc gag gtg ggc atg cag cgt gct tat ggg ccc      1872
Cys Val Pro Tyr Trp Pro Glu Val Gly Met Gln Arg Ala Tyr Gly Pro
610                 615                 620 tac tct gtg acc aac tgc ggg gag cat gac aca acc gaa tac aaa ctc      1920
Tyr Ser Val Thr Asn Cys Gly Glu His Asp Thr Thr Glu Tyr Lys Leu
625                 630                 635                 640 cgt acc tta cag gtc tcc ccg ctg gac aat gga gac ctg att cgg gag      1968
Arg Thr Leu Gln Val Ser Pro Leu Asp Asn Gly Asp Leu Ile Arg Glu
                645                 650                 655 atc tgg cat tac cag tac ctg agc tgg ccc gac cat ggg gtc ccc agt      2016
Ile Trp His Tyr Gln Tyr Leu Ser Trp Pro Asp His Gly Val Pro Ser
            660                 665                 670 gag cct ggg ggt gtc ctc agc ttc ctg gac cag atc aac cag cgg cag      2064
Glu Pro Gly Gly Val Leu Ser Phe Leu Asp Gln Ile Asn Gln Arg Gln
            675                 680                 685 gaa agt ctg cct cac gca ggg ccc atc atc gtg cac tgc agc gcc ggc      2112
Glu Ser Leu Pro His Ala Gly Pro Ile Ile Val His Cys Ser Ala Gly
            690                 695                 700 atc ggc cgc aca ggc acc atc att gtc atc gac atg ctc atg gag aac      2160
Ile Gly Arg Thr Gly Thr Ile Ile Val Ile Asp Met Leu Met Glu Asn
705                 710                 715                 720 atc tcc acc aag ggc ctg gac tgt gac att gac atc cag aag acc atc      2208
Ile Ser Thr Lys Gly Leu Asp Cys Asp Ile Asp Ile Gln Lys Thr Ile
```

-continued

|  |  |  | 725 |  |  |  | 730 |  |  |  | 735 |  |  |  |  |
|---|---|---|---|---|---|---|---|---|---|---|---|---|---|---|---|
| cag | atg | gtg | cgg | gcg | cag | cgc | tcg | ggc | atg | gtg | cag | acg | gag | gcg | cag | 2256 |
| Gln | Met | Val | Arg | Ala | Gln | Arg | Ser | Gly | Met | Val | Gln | Thr | Glu | Ala | Gln |
|  |  |  | 740 |  |  |  | 745 |  |  |  | 750 |  |  |  |  |

| tac | aag | ttc | atc | tac | gtg | gcc | atc | gcc | cag | ttc | att | gaa | acc | act | aag | 2304 |
| Tyr | Lys | Phe | Ile | Tyr | Val | Ala | Ile | Ala | Gln | Phe | Ile | Glu | Thr | Thr | Lys |
|  |  | 755 |  |  |  |  | 760 |  |  |  |  | 765 |  |  |  |

| aag | aag | ctg | gag | gtc | ctg | cag | tcg | cag | aag | ggc | cag | gag | tcg | gag | tac | 2352 |
| Lys | Lys | Leu | Glu | Val | Leu | Gln | Ser | Gln | Lys | Gly | Gln | Glu | Ser | Glu | Tyr |
| 770 |  |  |  |  | 775 |  |  |  |  | 780 |  |  |  |  |  |

| ggg | aac | atc | acc | tat | ccc | cca | gcc | atg | aag | aat | gcc | cat | gcc | aag | gcc | 2400 |
| Gly | Asn | Ile | Thr | Tyr | Pro | Pro | Ala | Met | Lys | Asn | Ala | His | Ala | Lys | Ala |
| 785 |  |  |  |  | 790 |  |  |  |  | 795 |  |  |  |  | 800 |

| tcc | cgc | acc | tcg | tcc | aaa | cac | aag | gag | gat | gtg | tat | gag | aac | ctg | cac | 2448 |
| Ser | Arg | Thr | Ser | Ser | Lys | His | Lys | Glu | Asp | Val | Tyr | Glu | Asn | Leu | His |
|  |  |  |  | 805 |  |  |  |  | 810 |  |  |  |  | 815 |  |

| act | aag | aac | aag | agg | gag | gag | aaa | gtg | aag | aag | cag | cgg | tca | gca | gac | 2496 |
| Thr | Lys | Asn | Lys | Arg | Glu | Glu | Lys | Val | Lys | Lys | Gln | Arg | Ser | Ala | Asp |
|  |  | 820 |  |  |  |  | 825 |  |  |  |  | 830 |  |  |  |

| aag | gag | aag | agc | aag | ggt | tcc | ctc | aag | agg | aag | tga |  |  |  |  | 2532 |
| Lys | Glu | Lys | Ser | Lys | Gly | Ser | Leu | Lys | Arg | Lys |  |  |  |  |  |
| 835 |  |  |  |  | 840 |  |  |  |  |  |  |  |  |  |  |

<210> SEQ ID NO 117
<211> LENGTH: 843
<212> TYPE: PRT
<213> ORGANISM: Artificial Sequence
<220> FEATURE:
<223> OTHER INFORMATION: EGFP-PTP fusion

<400> SEQUENCE: 117

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
        50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

-continued

```
Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Ser
225                 230                 235                 240

Gly Leu Arg Ser Arg Glu Met Leu Ser Arg Gly Trp Phe His Arg Asp
                245                 250                 255

Leu Ser Gly Leu Asp Ala Glu Thr Leu Leu Lys Gly Arg Gly Val His
                260                 265                 270

Gly Ser Phe Leu Ala Arg Pro Ser Arg Lys Asn Gln Gly Asp Phe Ser
        275                 280                 285

Leu Ser Val Arg Val Gly Asp Gln Val Thr His Ile Arg Ile Gln Asn
    290                 295                 300

Ser Gly Asp Phe Tyr Asp Leu Tyr Gly Gly Glu Lys Phe Ala Thr Leu
305                 310                 315                 320

Thr Glu Leu Val Glu Tyr Tyr Thr Gln Gln Gly Val Leu Gln Asp
                325                 330                 335

Arg Asp Gly Thr Ile Ile His Leu Lys Tyr Pro Leu Asn Cys Ser Asp
                340                 345                 350

Pro Thr Ser Glu Arg Trp Tyr His Gly His Met Ser Gly Gly Gln Ala
        355                 360                 365

Glu Thr Leu Leu Gln Ala Lys Gly Glu Pro Trp Thr Phe Leu Val Arg
    370                 375                 380

Glu Ser Leu Ser Gln Pro Gly Asp Phe Val Leu Ser Val Leu Ser Asp
385                 390                 395                 400

Gln Pro Lys Ala Gly Pro Gly Ser Pro Leu Arg Val Thr His Ile Lys
                405                 410                 415

Val Met Cys Glu Gly Gly Arg Tyr Thr Val Gly Gly Leu Glu Thr Phe
                420                 425                 430

Asp Ser Leu Thr Asp Leu Val Glu His Phe Lys Lys Thr Gly Ile Glu
        435                 440                 445

Glu Ala Ser Gly Ala Phe Val Tyr Leu Arg Gln Pro Tyr Tyr Ala Thr
    450                 455                 460

Arg Val Asn Ala Ala Asp Ile Glu Asn Arg Val Leu Glu Leu Asn Lys
465                 470                 475                 480

Lys Gln Glu Ser Glu Asp Thr Ala Lys Ala Gly Phe Trp Glu Glu Phe
                485                 490                 495

Glu Ser Leu Gln Lys Gln Glu Val Lys Asn Leu His Gln Arg Leu Glu
                500                 505                 510

Gly Gln Arg Pro Glu Asn Lys Gly Lys Asn Arg Tyr Lys Asn Ile Leu
        515                 520                 525

Pro Phe Asp His Ser Arg Val Ile Leu Gln Gly Arg Asp Ser Asn Ile
    530                 535                 540

Pro Gly Ser Asp Tyr Ile Asn Ala Asn Tyr Ile Lys Asn Gln Leu Leu
545                 550                 555                 560

Gly Pro Asp Glu Asn Ala Lys Thr Tyr Ile Ala Ser Gln Gly Cys Leu
                565                 570                 575

Glu Ala Thr Val Asn Asp Phe Trp Gln Met Ala Trp Gln Glu Asn Ser
                580                 585                 590

Arg Val Ile Val Met Thr Thr Arg Glu Val Glu Lys Gly Arg Asn Lys
        595                 600                 605

Cys Val Pro Tyr Trp Pro Glu Val Gly Met Gln Arg Ala Tyr Gly Pro
    610                 615                 620

Tyr Ser Val Thr Asn Cys Gly Glu His Asp Thr Thr Glu Tyr Lys Leu
```

```
625                 630                 635                 640
Arg Thr Leu Gln Val Ser Pro Leu Asp Asn Gly Asp Leu Ile Arg Glu
                        645                 650                 655

Ile Trp His Tyr Gln Tyr Leu Ser Trp Pro Asp His Gly Val Pro Ser
                660                 665                 670

Glu Pro Gly Gly Val Leu Ser Phe Leu Asp Gln Ile Asn Gln Arg Gln
            675                 680                 685

Glu Ser Leu Pro His Ala Gly Pro Ile Ile Val His Cys Ser Ala Gly
        690                 695                 700

Ile Gly Arg Thr Gly Thr Ile Ile Val Ile Asp Met Leu Met Glu Asn
705                 710                 715                 720

Ile Ser Thr Lys Gly Leu Asp Cys Asp Ile Asp Ile Gln Lys Thr Ile
                725                 730                 735

Gln Met Val Arg Ala Gln Arg Ser Gly Met Val Gln Thr Glu Ala Gln
                    740                 745                 750

Tyr Lys Phe Ile Tyr Val Ala Ile Ala Gln Phe Ile Glu Thr Thr Lys
                755                 760                 765

Lys Lys Leu Glu Val Leu Gln Ser Gln Lys Gly Gln Glu Ser Glu Tyr
        770                 775                 780

Gly Asn Ile Thr Tyr Pro Pro Ala Met Lys Asn Ala His Ala Lys Ala
785                 790                 795                 800

Ser Arg Thr Ser Ser Lys His Lys Glu Asp Val Tyr Glu Asn Leu His
                    805                 810                 815

Thr Lys Asn Lys Arg Glu Glu Lys Val Lys Lys Gln Arg Ser Ala Asp
                820                 825                 830

Lys Glu Lys Ser Lys Gly Ser Leu Lys Arg Lys
            835                 840

<210> SEQ ID NO 118
<211> LENGTH: 2562
<212> TYPE: DNA
<213> ORGANISM: Artificial Sequence
<220> FEATURE:
<223> OTHER INFORMATION: PTP-EGFP fusion
<220> FEATURE:
<221> NAME/KEY: CDS
<222> LOCATION: (1)..(2559)

<400> SEQUENCE: 118 atg ctg tcc cgt ggg tgg ttt cac cga gac ctc agt ggg ctg gat gca    48
Met Leu Ser Arg Gly Trp Phe His Arg Asp Leu Ser Gly Leu Asp Ala
1               5                   10                  15 gag acc ctg ctc aag ggc cga ggt gtc cac ggt agc ttc ctg gct cgg    96
Glu Thr Leu Leu Lys Gly Arg Gly Val His Gly Ser Phe Leu Ala Arg
            20                  25                  30 ccc agt cgc aag aac cag ggt gac ttc tcg ctc tcc gtc agg gtg ggg   144
Pro Ser Arg Lys Asn Gln Gly Asp Phe Ser Leu Ser Val Arg Val Gly
        35                  40                  45 gat cag gtg acc cat att cgg atc cag aac tca ggg gat ttc tat gac   192
Asp Gln Val Thr His Ile Arg Ile Gln Asn Ser Gly Asp Phe Tyr Asp
    50                  55                  60 ctg tat gga ggg gag aag ttt gcg act ctg aca gag ctg gtg gag tac   240
Leu Tyr Gly Gly Glu Lys Phe Ala Thr Leu Thr Glu Leu Val Glu Tyr
65                  70                  75                  80 tac act cag cag cag ggt gtc ctg cag gac cgc gac ggc acc atc atc   288
Tyr Thr Gln Gln Gln Gly Val Leu Gln Asp Arg Asp Gly Thr Ile Ile
                85                  90                  95 cac ctc aag tac ccg ctg aac tgc tcc gat ccc act agt gag agg tgg   336
```

```
                His Leu Lys Tyr Pro Leu Asn Cys Ser Asp Pro Thr Ser Glu Arg Trp
                            100                 105                 110 tac cat ggc cac atg tct ggc ggg cag gca gag acg ctg ctg cag gcc          384
Tyr His Gly His Met Ser Gly Gly Gln Ala Glu Thr Leu Leu Gln Ala
            115                 120                 125 aag ggc gag ccc tgg acg ttt ctt gtg cgt gag agc ctc agc cag cct          432
Lys Gly Glu Pro Trp Thr Phe Leu Val Arg Glu Ser Leu Ser Gln Pro
    130                 135                 140 gga gac ttc gtg ctt tct gtg ctc agt gac cag ccc aag gct ggc cca          480
Gly Asp Phe Val Leu Ser Val Leu Ser Asp Gln Pro Lys Ala Gly Pro
145                 150                 155                 160 ggc tcc ccg ctc agg gtc acc cac atc aag gtc atg tgc gag ggt gga          528
Gly Ser Pro Leu Arg Val Thr His Ile Lys Val Met Cys Glu Gly Gly
                165                 170                 175 cgc tac aca gtg ggt ggt ttg gag acc ttc gac agc ctc acg gac ctg          576
Arg Tyr Thr Val Gly Gly Leu Glu Thr Phe Asp Ser Leu Thr Asp Leu
            180                 185                 190 gta gag cat ttc aag aag acg ggg att gag gag gcc tca ggc gcc ttt          624
Val Glu His Phe Lys Lys Thr Gly Ile Glu Glu Ala Ser Gly Ala Phe
        195                 200                 205 gtc tac ctg cgg cag ccg tac tat gcc acg agg gtg aat gcg gct gac          672
Val Tyr Leu Arg Gln Pro Tyr Tyr Ala Thr Arg Val Asn Ala Ala Asp
    210                 215                 220 att gag aac cga gtg ttg gaa ctg aac aag aag cag gag tcc gag gat          720
Ile Glu Asn Arg Val Leu Glu Leu Asn Lys Lys Gln Glu Ser Glu Asp
225                 230                 235                 240 aca gcc aag gct ggc ttc tgg gag gag ttt gag agt ttg cag aag cag          768
Thr Ala Lys Ala Gly Phe Trp Glu Glu Phe Glu Ser Leu Gln Lys Gln
                245                 250                 255 gag gtg aag aac ttg cac cag cgt ctg gaa ggg cag cgg cca gag aac          816
Glu Val Lys Asn Leu His Gln Arg Leu Glu Gly Gln Arg Pro Glu Asn
            260                 265                 270 aag ggc aag aac cgc tac aag aac att ctc ccc ttt gac cac agc cga          864
Lys Gly Lys Asn Arg Tyr Lys Asn Ile Leu Pro Phe Asp His Ser Arg
        275                 280                 285 gtg atc ctg cag gga cgg gac agt aac atc ccc ggg tcc gac tac atc          912
Val Ile Leu Gln Gly Arg Asp Ser Asn Ile Pro Gly Ser Asp Tyr Ile
    290                 295                 300 aat gcc aac tac atc aag aac cag ctg cta ggc cct gat gag aac gct          960
Asn Ala Asn Tyr Ile Lys Asn Gln Leu Leu Gly Pro Asp Glu Asn Ala
305                 310                 315                 320 aag acc tac atc gcc agc cag ggc tgt ctg gag gcc acg gtc aat gac         1008
Lys Thr Tyr Ile Ala Ser Gln Gly Cys Leu Glu Ala Thr Val Asn Asp
                325                 330                 335 ttc tgg cag atg gcg tgg cag gag aac agc cgt gtc atc gtc atg acc         1056
Phe Trp Gln Met Ala Trp Gln Glu Asn Ser Arg Val Ile Val Met Thr
            340                 345                 350 acc cga gag gtg gag aaa ggc cgg aac aaa tgc gtc cca tac tgg ccc         1104
Thr Arg Glu Val Glu Lys Gly Arg Asn Lys Cys Val Pro Tyr Trp Pro
        355                 360                 365 gag gtg ggc atg cag cgt gct tat ggg ccc tac tct gtg acc aac tgc         1152
Glu Val Gly Met Gln Arg Ala Tyr Gly Pro Tyr Ser Val Thr Asn Cys
    370                 375                 380 ggg gag cat gac aca acc gaa tac aaa ctc cgt acc tta cag gtc tcc         1200
Gly Glu His Asp Thr Thr Glu Tyr Lys Leu Arg Thr Leu Gln Val Ser
385                 390                 395                 400 ccg ctg gac aat gga gac ctg att cgg gag atc tgg cat tac cag tac         1248
Pro Leu Asp Asn Gly Asp Leu Ile Arg Glu Ile Trp His Tyr Gln Tyr
                405                 410                 415
```

```
ctg agc tgg ccc gac cat ggg gtc ccc agt gag cct ggg ggt gtc ctc        1296
Leu Ser Trp Pro Asp His Gly Val Pro Ser Glu Pro Gly Gly Val Leu
            420                 425                 430 agc ttc ctg gac cag atc aac cag cgg cag gaa agt ctg cct cac gca        1344
Ser Phe Leu Asp Gln Ile Asn Gln Arg Gln Glu Ser Leu Pro His Ala
                435                 440                 445 ggg ccc atc atc gtg cac tgc agc gcc ggc atc ggc cgc aca ggc acc        1392
Gly Pro Ile Ile Val His Cys Ser Ala Gly Ile Gly Arg Thr Gly Thr
450                 455                 460 atc att gtc atc gac atg ctc atg gag aac atc tcc acc aag ggc ctg        1440
Ile Ile Val Ile Asp Met Leu Met Glu Asn Ile Ser Thr Lys Gly Leu
465                 470                 475                 480 gac tgt gac att gac atc cag aag acc atc cag atg gtg cgg gcg cag        1488
Asp Cys Asp Ile Asp Ile Gln Lys Thr Ile Gln Met Val Arg Ala Gln
                485                 490                 495 cgc tcg ggc atg gtg cag acg gag gcg cag tac aag ttc atc tac gtg        1536
Arg Ser Gly Met Val Gln Thr Glu Ala Gln Tyr Lys Phe Ile Tyr Val
                500                 505                 510 gcc atc gcc cag ttc att gaa acc act aag aag aag ctg gag gtc ctg        1584
Ala Ile Ala Gln Phe Ile Glu Thr Thr Lys Lys Lys Leu Glu Val Leu
                515                 520                 525 cag tcg cag aag ggc cag gag tcg gag tac ggg aac atc acc tat ccc        1632
Gln Ser Gln Lys Gly Gln Glu Ser Glu Tyr Gly Asn Ile Thr Tyr Pro
530                 535                 540 cca gcc atg aag aat gcc cat gcc aag gcc tcc cgc acc tcg tcc aaa        1680
Pro Ala Met Lys Asn Ala His Ala Lys Ala Ser Arg Thr Ser Ser Lys
545                 550                 555                 560 cac aag gag gat gtg tat gag aac ctg cac act aag aac aag agg gag        1728
His Lys Glu Asp Val Tyr Glu Asn Leu His Thr Lys Asn Lys Arg Glu
                565                 570                 575 gag aaa gtg aag aag cag cgg tca gca gac aag gag aag agc aag ggt        1776
Glu Lys Val Lys Lys Gln Arg Ser Ala Asp Lys Glu Lys Ser Lys Gly
                580                 585                 590 tcc ctc aag agg aag cga att ctg cag tcg acg gta ccg cgg gcc cgg        1824
Ser Leu Lys Arg Lys Arg Ile Leu Gln Ser Thr Val Pro Arg Ala Arg
                595                 600                 605 gat cca ccg gtc gcc acc atg gtg agc aag ggc gag gag ctg ttc acc        1872
Asp Pro Pro Val Ala Thr Met Val Ser Lys Gly Glu Glu Leu Phe Thr
610                 615                 620 ggg gtg gtg ccc atc ctg gtc gag ctg gac ggc gac gta aac ggc cac        1920
Gly Val Val Pro Ile Leu Val Glu Leu Asp Gly Asp Val Asn Gly His
625                 630                 635                 640 aag ttc agc gtg tcc ggc gag ggc gag ggc gat gcc acc tac ggc aag        1968
Lys Phe Ser Val Ser Gly Glu Gly Glu Gly Asp Ala Thr Tyr Gly Lys
                645                 650                 655 ctg acc ctg aag ttc atc tgc acc acc ggc aag ctg ccc gtg ccc tgg        2016
Leu Thr Leu Lys Phe Ile Cys Thr Thr Gly Lys Leu Pro Val Pro Trp
                660                 665                 670 ccc acc ctc gtg acc acc ctg acc tac ggc gtg cag tgc ttc agc cgc        2064
Pro Thr Leu Val Thr Thr Leu Thr Tyr Gly Val Gln Cys Phe Ser Arg
                675                 680                 685 tac ccc gac cac atg aag cag cac gac ttc ttc aag tcc gcc atg ccc        2112
Tyr Pro Asp His Met Lys Gln His Asp Phe Phe Lys Ser Ala Met Pro
            690                 695                 700 gaa ggc tac gtc cag gag cgc acc atc ttc ttc aag gac gac ggc aac        2160
Glu Gly Tyr Val Gln Glu Arg Thr Ile Phe Phe Lys Asp Asp Gly Asn
705                 710                 715                 720 tac aag acc cgc gcc gag gtg aag ttc gag ggc gac acc ctg gtg aac        2208
Tyr Lys Thr Arg Ala Glu Val Lys Phe Glu Gly Asp Thr Leu Val Asn
                725                 730                 735
```

```
cgc atc gag ctg aag ggc atc gac ttc aag gag gac ggc aac atc ctg     2256
Arg Ile Glu Leu Lys Gly Ile Asp Phe Lys Glu Asp Gly Asn Ile Leu
            740                 745                 750 ggg cac aag ctg gag tac aac tac aac agc cac aac gtc tat atc atg     2304
Gly His Lys Leu Glu Tyr Asn Tyr Asn Ser His Asn Val Tyr Ile Met
            755                 760                 765 gcc gac aag cag aag aac ggc atc aag gtg aac ttc aag atc cgc cac     2352
Ala Asp Lys Gln Lys Asn Gly Ile Lys Val Asn Phe Lys Ile Arg His
            770                 775                 780 aac atc gag gac ggc agc gtg cag ctc gcc gac cac tac cag cag aac     2400
Asn Ile Glu Asp Gly Ser Val Gln Leu Ala Asp His Tyr Gln Gln Asn
785                 790                 795                 800 acc ccc atc ggc gac ggc ccc gtg ctg ctg ccc gac aac cac tac ctg     2448
Thr Pro Ile Gly Asp Gly Pro Val Leu Leu Pro Asp Asn His Tyr Leu
            805                 810                 815 agc acc cag tcc gcc ctg agc aaa gac ccc aac gag aag cgc gat cac     2496
Ser Thr Gln Ser Ala Leu Ser Lys Asp Pro Asn Glu Lys Arg Asp His
            820                 825                 830 atg gtc ctg ctg gag ttc gtg acc gcc gcc ggg atc act ctc ggc atg     2544
Met Val Leu Leu Glu Phe Val Thr Ala Ala Gly Ile Thr Leu Gly Met
            835                 840                 845 gac gag ctg tac aag taa                                             2562
Asp Glu Leu Tyr Lys
    850

<210> SEQ ID NO 119
<211> LENGTH: 853
<212> TYPE: PRT
<213> ORGANISM: Artificial Sequence
<220> FEATURE:
<223> OTHER INFORMATION: PTP-EGFP fusion

<400> SEQUENCE: 119

Met Leu Ser Arg Gly Trp Phe His Arg Asp Leu Ser Gly Leu Asp Ala
1               5                   10                  15

Glu Thr Leu Leu Lys Gly Arg Gly Val His Gly Ser Phe Leu Ala Arg
            20                  25                  30

Pro Ser Arg Lys Asn Gln Gly Asp Phe Ser Leu Ser Val Arg Val Gly
        35                  40                  45

Asp Gln Val Thr His Ile Arg Ile Gln Asn Ser Gly Asp Phe Tyr Asp
    50                  55                  60

Leu Tyr Gly Gly Glu Lys Phe Ala Thr Leu Thr Glu Leu Val Glu Tyr
65                  70                  75                  80

Tyr Thr Gln Gln Gln Gly Val Leu Gln Asp Arg Asp Gly Thr Ile Ile
            85                  90                  95

His Leu Lys Tyr Pro Leu Asn Cys Ser Asp Pro Thr Ser Glu Arg Trp
            100                 105                 110

Tyr His Gly His Met Ser Gly Gly Gln Ala Glu Thr Leu Leu Gln Ala
        115                 120                 125

Lys Gly Glu Pro Trp Thr Phe Leu Val Arg Glu Ser Leu Ser Gln Pro
    130                 135                 140

Gly Asp Phe Val Leu Ser Val Leu Ser Asp Gln Pro Lys Ala Gly Pro
145                 150                 155                 160

Gly Ser Pro Leu Arg Val Thr His Ile Lys Val Met Cys Glu Gly Gly
            165                 170                 175

Arg Tyr Thr Val Gly Gly Leu Glu Thr Phe Asp Ser Leu Thr Asp Leu
            180                 185                 190
```

-continued

```
Val Glu His Phe Lys Lys Thr Gly Ile Glu Glu Ala Ser Gly Ala Phe
    195                 200                 205
Val Tyr Leu Arg Gln Pro Tyr Tyr Ala Thr Arg Val Asn Ala Ala Asp
    210                 215                 220
Ile Glu Asn Arg Val Leu Glu Leu Asn Lys Lys Gln Glu Ser Glu Asp
225                 230                 235                 240
Thr Ala Lys Ala Gly Phe Trp Glu Glu Phe Glu Ser Leu Gln Lys Gln
                245                 250                 255
Glu Val Lys Asn Leu His Gln Arg Leu Glu Gly Gln Arg Pro Glu Asn
                260                 265                 270
Lys Gly Lys Asn Arg Tyr Lys Asn Ile Leu Pro Phe Asp His Ser Arg
                275                 280                 285
Val Ile Leu Gln Gly Arg Asp Ser Asn Ile Pro Gly Ser Asp Tyr Ile
    290                 295                 300
Asn Ala Asn Tyr Ile Lys Asn Gln Leu Leu Gly Pro Asp Glu Asn Ala
305                 310                 315                 320
Lys Thr Tyr Ile Ala Ser Gln Gly Cys Leu Glu Ala Thr Val Asn Asp
                325                 330                 335
Phe Trp Gln Met Ala Trp Gln Glu Asn Ser Arg Val Ile Val Met Thr
                340                 345                 350
Thr Arg Glu Val Glu Lys Gly Arg Asn Lys Cys Val Pro Tyr Trp Pro
                355                 360                 365
Glu Val Gly Met Gln Arg Ala Tyr Gly Pro Tyr Ser Val Thr Asn Cys
                370                 375                 380
Gly Glu His Asp Thr Thr Glu Tyr Lys Leu Arg Thr Leu Gln Val Ser
385                 390                 395                 400
Pro Leu Asp Asn Gly Asp Leu Ile Arg Glu Ile Trp His Tyr Gln Tyr
                405                 410                 415
Leu Ser Trp Pro Asp His Gly Val Pro Ser Glu Pro Gly Gly Val Leu
                420                 425                 430
Ser Phe Leu Asp Gln Ile Asn Gln Arg Gln Glu Ser Leu Pro His Ala
                435                 440                 445
Gly Pro Ile Ile Val His Cys Ser Ala Gly Ile Gly Arg Thr Gly Thr
                450                 455                 460
Ile Ile Val Ile Asp Met Leu Met Glu Asn Ile Ser Thr Lys Gly Leu
465                 470                 475                 480
Asp Cys Asp Ile Asp Ile Gln Lys Thr Ile Gln Met Val Arg Ala Gln
                485                 490                 495
Arg Ser Gly Met Val Gln Thr Glu Ala Gln Tyr Lys Phe Ile Tyr Val
                500                 505                 510
Ala Ile Ala Gln Phe Ile Glu Thr Thr Lys Lys Lys Leu Glu Val Leu
                515                 520                 525
Gln Ser Gln Lys Gly Gln Glu Ser Glu Tyr Gly Asn Ile Thr Tyr Pro
                530                 535                 540
Pro Ala Met Lys Asn Ala His Ala Lys Ala Ser Arg Thr Ser Ser Lys
545                 550                 555                 560
His Lys Glu Asp Val Tyr Glu Asn Leu His Thr Lys Asn Lys Arg Glu
                565                 570                 575
Glu Lys Val Lys Lys Gln Arg Ser Ala Asp Lys Glu Lys Ser Lys Gly
                580                 585                 590
Ser Leu Lys Arg Lys Arg Ile Leu Gln Ser Thr Val Pro Arg Ala Arg
                595                 600                 605
Asp Pro Pro Val Ala Thr Met Val Ser Lys Gly Glu Glu Leu Phe Thr
```

```
                610                 615                 620
Gly Val Val Pro Ile Leu Val Glu Leu Asp Gly Asp Val Asn Gly His
625                 630                 635                 640

Lys Phe Ser Val Ser Gly Glu Gly Glu Gly Asp Ala Thr Tyr Gly Lys
                645                 650                 655

Leu Thr Leu Lys Phe Ile Cys Thr Thr Gly Lys Leu Pro Val Pro Trp
            660                 665                 670

Pro Thr Leu Val Thr Thr Leu Thr Tyr Gly Val Gln Cys Phe Ser Arg
                675                 680                 685

Tyr Pro Asp His Met Lys Gln His Asp Phe Phe Lys Ser Ala Met Pro
            690                 695                 700

Glu Gly Tyr Val Gln Glu Arg Thr Ile Phe Phe Lys Asp Asp Gly Asn
705                 710                 715                 720

Tyr Lys Thr Arg Ala Glu Val Lys Phe Glu Gly Asp Thr Leu Val Asn
                725                 730                 735

Arg Ile Glu Leu Lys Gly Ile Asp Phe Lys Glu Asp Gly Asn Ile Leu
            740                 745                 750

Gly His Lys Leu Glu Tyr Asn Tyr Asn Ser His Asn Val Tyr Ile Met
            755                 760                 765

Ala Asp Lys Gln Lys Asn Gly Ile Lys Val Asn Phe Lys Ile Arg His
770                 775                 780

Asn Ile Glu Asp Gly Ser Val Gln Leu Ala Asp His Tyr Gln Gln Asn
785                 790                 795                 800

Thr Pro Ile Gly Asp Gly Pro Val Leu Leu Pro Asp Asn His Tyr Leu
            805                 810                 815

Ser Thr Gln Ser Ala Leu Ser Lys Asp Pro Asn Glu Lys Arg Asp His
            820                 825                 830

Met Val Leu Leu Glu Phe Val Thr Ala Ala Gly Ile Thr Leu Gly Met
            835                 840                 845

Asp Glu Leu Tyr Lys
    850

<210> SEQ ID NO 120
<211> LENGTH: 2994
<212> TYPE: DNA
<213> ORGANISM: Artificial Sequence
<220> FEATURE:
<223> OTHER INFORMATION: EGFP-lkappaB-kinase fusion
<220> FEATURE:
<221> NAME/KEY: CDS
<222> LOCATION: (1)..(2991)

<400> SEQUENCE: 120 atg gtg agc aag ggc gag gag ctg ttc acc ggg gtg gtg ccc atc ctg      48
Met Val Ser Lys Gly Glu Glu Leu Phe Thr Gly Val Val Pro Ile Leu
1               5                   10                  15 gtc gag ctg gac ggc gac gta aac ggc cac aag ttc agc gtg tcc ggc      96
Val Glu Leu Asp Gly Asp Val Asn Gly His Lys Phe Ser Val Ser Gly
            20                  25                  30 gag ggc gag ggc gat gcc acc tac ggc aag ctg acc ctg aag ttc atc     144
Glu Gly Glu Gly Asp Ala Thr Tyr Gly Lys Leu Thr Leu Lys Phe Ile
        35                  40                  45 tgc acc acc ggc aag ctg ccc gtg ccc tgg ccc acc ctc gtg acc acc     192
Cys Thr Thr Gly Lys Leu Pro Val Pro Trp Pro Thr Leu Val Thr Thr
    50                  55                  60 ctg acc tac ggc gtg cag tgc ttc agc cgc tac ccc gac cac atg aag     240
Leu Thr Tyr Gly Val Gln Cys Phe Ser Arg Tyr Pro Asp His Met Lys
65                  70                  75                  80
```

```
cag cac gac ttc ttc aag tcc gcc atg ccc gaa ggc tac gtc cag gag        288
Gln His Asp Phe Phe Lys Ser Ala Met Pro Glu Gly Tyr Val Gln Glu
             85                  90                  95 cgc acc atc ttc ttc aag gac gac ggc aac tac aag acc cgc gcc gag        336
Arg Thr Ile Phe Phe Lys Asp Asp Gly Asn Tyr Lys Thr Arg Ala Glu
            100                 105                 110 gtg aag ttc gag ggc gac acc ctg gtg aac cgc atc gag ctg aag ggc        384
Val Lys Phe Glu Gly Asp Thr Leu Val Asn Arg Ile Glu Leu Lys Gly
            115                 120                 125 atc gac ttc aag gag gac ggc aac atc ctg ggg cac aag ctg gag tac        432
Ile Asp Phe Lys Glu Asp Gly Asn Ile Leu Gly His Lys Leu Glu Tyr
130                 135                 140 aac tac aac agc cac aac gtc tat atc atg gcc gac aag cag aag aac        480
Asn Tyr Asn Ser His Asn Val Tyr Ile Met Ala Asp Lys Gln Lys Asn
145                 150                 155                 160 ggc atc aag gtg aac ttc aag atc cgc cac aac atc gag gac ggc agc        528
Gly Ile Lys Val Asn Phe Lys Ile Arg His Asn Ile Glu Asp Gly Ser
                165                 170                 175 gtg cag ctc gcc gac cac tac cag cag aac acc ccc atc ggc gac ggc        576
Val Gln Leu Ala Asp His Tyr Gln Gln Asn Thr Pro Ile Gly Asp Gly
            180                 185                 190 ccc gtg ctg ctg ccc gac aac cac tac ctg agc acc cag tcc gcc ctg        624
Pro Val Leu Leu Pro Asp Asn His Tyr Leu Ser Thr Gln Ser Ala Leu
            195                 200                 205 agc aaa gac ccc aac gag aag cgc gat cac atg gtc ctg ctg gag ttc        672
Ser Lys Asp Pro Asn Glu Lys Arg Asp His Met Val Leu Leu Glu Phe
            210                 215                 220 gtg acc gcc gcc ggg atc act ctc ggc atg gac gag ctg tac aag tcc        720
Val Thr Ala Ala Gly Ile Thr Leu Gly Met Asp Glu Leu Tyr Lys Ser
225                 230                 235                 240 gga ctc aga tct cga gct caa gct tcg aat tcg acc atg gag cgg ccc        768
Gly Leu Arg Ser Arg Ala Gln Ala Ser Asn Ser Thr Met Glu Arg Pro
                245                 250                 255 ccg ggg ctg cgg ccg ggc gcg ggc ggg ccc tgg gag atg cgg gag cgg        816
Pro Gly Leu Arg Pro Gly Ala Gly Gly Pro Trp Glu Met Arg Glu Arg
            260                 265                 270 ctg ggc acc ggc ggc ttc ggg aac gtc tgt ctg tac cag cat cgg gaa        864
Leu Gly Thr Gly Gly Phe Gly Asn Val Cys Leu Tyr Gln His Arg Glu
            275                 280                 285 ctt gat ctc aaa ata gca att aag tct tgt cgc cta gag cta agt acc        912
Leu Asp Leu Lys Ile Ala Ile Lys Ser Cys Arg Leu Glu Leu Ser Thr
290                 295                 300 aaa aac aga gaa cga tgg tgc cat gaa atc cag att atg aag aag ttg        960
Lys Asn Arg Glu Arg Trp Cys His Glu Ile Gln Ile Met Lys Lys Leu
305                 310                 315                 320 aac cat gcc aat gtt gta aag gcc tgt gat gtt cct gaa gaa ttg aat       1008
Asn His Ala Asn Val Val Lys Ala Cys Asp Val Pro Glu Glu Leu Asn
                325                 330                 335 att ttg att cat gat gtg cct ctt cta gca atg gaa tac tgt tct gga       1056
Ile Leu Ile His Asp Val Pro Leu Leu Ala Met Glu Tyr Cys Ser Gly
            340                 345                 350 gga gat ctc cga aag ctg ctc aac aaa cca gaa aat tgt tgt gga ctt       1104
Gly Asp Leu Arg Lys Leu Leu Asn Lys Pro Glu Asn Cys Cys Gly Leu
            355                 360                 365 aaa gaa agc cag ata ctt tct tta cta agt gat ata ggg tct ggg att       1152
Lys Glu Ser Gln Ile Leu Ser Leu Leu Ser Asp Ile Gly Ser Gly Ile
            370                 375                 380 cga tat ttg cat gaa aac aaa att ata cat cga gat cta aaa cct gaa       1200
Arg Tyr Leu His Glu Asn Lys Ile Ile His Arg Asp Leu Lys Pro Glu
```

-continued

```
        385                 390                 395                 400
aac ata gtt ctt cag gat gtt ggt gga aag ata ata cat aaa ata att      1248
Asn Ile Val Leu Gln Asp Val Gly Gly Lys Ile Ile His Lys Ile Ile
                    405                 410                 415 gat ctg gga tat gcc aaa gat gtt gat caa gga agt ctg tgt aca tct      1296
Asp Leu Gly Tyr Ala Lys Asp Val Asp Gln Gly Ser Leu Cys Thr Ser
                420                 425                 430 ttt gtg gga aca ctg cag tat ctg gcc cca gag ctc ttt gag aat aag      1344
Phe Val Gly Thr Leu Gln Tyr Leu Ala Pro Glu Leu Phe Glu Asn Lys
            435                 440                 445 cct tac aca gcc act gtt gat tat tgg agc ttt ggg acc atg gta ttt      1392
Pro Tyr Thr Ala Thr Val Asp Tyr Trp Ser Phe Gly Thr Met Val Phe
        450                 455                 460 gaa tgt att gct gga tat agg cct ttt ttg cat cat ctg cag cca ttt      1440
Glu Cys Ile Ala Gly Tyr Arg Pro Phe Leu His His Leu Gln Pro Phe
465                 470                 475                 480 acc tgg cat gag aag att aag aag aag gat cca aag tgt ata ttt gca      1488
Thr Trp His Glu Lys Ile Lys Lys Lys Asp Pro Lys Cys Ile Phe Ala
                    485                 490                 495 tgt gaa gag atg tca gga gaa gtt cgg ttt agt agc cat tta cct caa      1536
Cys Glu Glu Met Ser Gly Glu Val Arg Phe Ser Ser His Leu Pro Gln
                500                 505                 510 cca aat agc ctt tgt agt tta ata gta gaa ccc atg gaa aac tgg cta      1584
Pro Asn Ser Leu Cys Ser Leu Ile Val Glu Pro Met Glu Asn Trp Leu
            515                 520                 525 cag ttg atg ttg aat tgg gac cct cag cag aga gga gga cct gtt gac      1632
Gln Leu Met Leu Asn Trp Asp Pro Gln Gln Arg Gly Gly Pro Val Asp
        530                 535                 540 ctt act ttg aag cag cca aga tgt ttt gta tta atg gat cac att ttg      1680
Leu Thr Leu Lys Gln Pro Arg Cys Phe Val Leu Met Asp His Ile Leu
545                 550                 555                 560 aat ttg aag ata gta cac atc cta aat atg act tct gca aag ata att      1728
Asn Leu Lys Ile Val His Ile Leu Asn Met Thr Ser Ala Lys Ile Ile
                    565                 570                 575 tct ttt ctg tta cca cct gat gaa agt ctt cat tca cta cag tct cgt      1776
Ser Phe Leu Leu Pro Pro Asp Glu Ser Leu His Ser Leu Gln Ser Arg
                580                 585                 590 att gag cgt gaa act gga ata aat act ggt tct caa gaa ctt ctt tca      1824
Ile Glu Arg Glu Thr Gly Ile Asn Thr Gly Ser Gln Glu Leu Leu Ser
            595                 600                 605 gag aca gga att tct ctg gat cct cgg aaa cca gcc tct caa tgt gtt      1872
Glu Thr Gly Ile Ser Leu Asp Pro Arg Lys Pro Ala Ser Gln Cys Val
        610                 615                 620 cta gat gga gtt aga ggc tgt gat agc tat atg gtt tat ttg ttt gat      1920
Leu Asp Gly Val Arg Gly Cys Asp Ser Tyr Met Val Tyr Leu Phe Asp
625                 630                 635                 640 aaa agt aaa act gta tat gaa ggg cca ttt gct tcc aga agt tta tct      1968
Lys Ser Lys Thr Val Tyr Glu Gly Pro Phe Ala Ser Arg Ser Leu Ser
                    645                 650                 655 gat tgt gta aat tat att gta cag gac agc aaa ata cag ctt cca att      2016
Asp Cys Val Asn Tyr Ile Val Gln Asp Ser Lys Ile Gln Leu Pro Ile
                660                 665                 670 ata cag ctg cgt aaa gtg tgg gct gaa gca gtg cac tat gtg tct gga      2064
Ile Gln Leu Arg Lys Val Trp Ala Glu Ala Val His Tyr Val Ser Gly
            675                 680                 685 cta aaa gaa gac tat agc agg ctc ttt cag gga caa agg gca gca atg      2112
Leu Lys Glu Asp Tyr Ser Arg Leu Phe Gln Gly Gln Arg Ala Ala Met
        690                 695                 700 tta agt ctt ctt aga tat aat gct aac tta aca aaa atg aag aac act      2160
```

```
Leu Ser Leu Leu Arg Tyr Asn Ala Asn Leu Thr Lys Met Lys Asn Thr
705                 710                 715                 720 ttg atc tca gca tca caa caa ctg aaa gct aaa ttg gag ttt ttt cac    2208
Leu Ile Ser Ala Ser Gln Gln Leu Lys Ala Lys Leu Glu Phe Phe His
                725                 730                 735 aaa agc att cag ctt gac ttg gag aga tac agc gag cag atg acg tat    2256
Lys Ser Ile Gln Leu Asp Leu Glu Arg Tyr Ser Glu Gln Met Thr Tyr
            740                 745                 750 ggg ata tct tca gaa aaa atg cta aaa gca tgg aaa gaa atg gaa gaa    2304
Gly Ile Ser Ser Glu Lys Met Leu Lys Ala Trp Lys Glu Met Glu Glu
        755                 760                 765 aag gcc atc cac tat gct gag gtt ggt gtc att gga tac ctg gag gat    2352
Lys Ala Ile His Tyr Ala Glu Val Gly Val Ile Gly Tyr Leu Glu Asp
    770                 775                 780 cag att atg tct ttg cat gct gaa atc atg ggg cta cag aag agc ccc    2400
Gln Ile Met Ser Leu His Ala Glu Ile Met Gly Leu Gln Lys Ser Pro
785                 790                 795                 800 tat gga aga cgt cag gga gac ttg atg gaa tct ctg gaa cag cgt gcc    2448
Tyr Gly Arg Arg Gln Gly Asp Leu Met Glu Ser Leu Glu Gln Arg Ala
                805                 810                 815 att gat cta tat aag cag tta aaa cac aga cct tca gat cac tcc tac    2496
Ile Asp Leu Tyr Lys Gln Leu Lys His Arg Pro Ser Asp His Ser Tyr
            820                 825                 830 agt gac agc aca gag atg gtg aaa atc att gtg cac act gtg cag agt    2544
Ser Asp Ser Thr Glu Met Val Lys Ile Ile Val His Thr Val Gln Ser
        835                 840                 845 cag gac cgt gtg ctc aag gag ctg ttt ggt cat ttg agc aag ttg ttg    2592
Gln Asp Arg Val Leu Lys Glu Leu Phe Gly His Leu Ser Lys Leu Leu
    850                 855                 860 ggc tgt aag cag aag att att gat cta ctc cct aag gtg gaa gtg gcc    2640
Gly Cys Lys Gln Lys Ile Ile Asp Leu Leu Pro Lys Val Glu Val Ala
865                 870                 875                 880 ctc agt aat atc aaa gaa gct gac aat act gtc atg ttc atg cag gga    2688
Leu Ser Asn Ile Lys Glu Ala Asp Asn Thr Val Met Phe Met Gln Gly
                885                 890                 895 aaa agg cag aaa gaa ata tgg cat ctc ctt aaa att gcc tgt aca cag    2736
Lys Arg Gln Lys Glu Ile Trp His Leu Leu Lys Ile Ala Cys Thr Gln
            900                 905                 910 agt tct gcc cgc tct ctt gta gga tcc agt cta gaa ggt gca gta acc    2784
Ser Ser Ala Arg Ser Leu Val Gly Ser Ser Leu Glu Gly Ala Val Thr
        915                 920                 925 cct cag aca tca gca tgg ctg ccc ccg act tca gca gaa cat gat cat    2832
Pro Gln Thr Ser Ala Trp Leu Pro Pro Thr Ser Ala Glu His Asp His
    930                 935                 940 tct ctg tca tgt gtg gta act cct caa gat ggg gag act tca gca caa    2880
Ser Leu Ser Cys Val Val Thr Pro Gln Asp Gly Glu Thr Ser Ala Gln
945                 950                 955                 960 atg ata gaa gaa aat ttg aac tgc ctt ggc cat tta agc act att att    2928
Met Ile Glu Glu Asn Leu Asn Cys Leu Gly His Leu Ser Thr Ile Ile
                965                 970                 975 cat gag gca aat gag gaa cag ggc aat agt atg atg aat ctt gat tgg    2976
His Glu Ala Asn Glu Glu Gln Gly Asn Ser Met Met Asn Leu Asp Trp
            980                 985                 990 agt tgg tta aca gaa tga                                            2994
Ser Trp Leu Thr Glu
        995

<210> SEQ ID NO 121
<211> LENGTH: 997
<212> TYPE: PRT
```

<213> ORGANISM: Artificial Sequence
<220> FEATURE:
<223> OTHER INFORMATION: EGFP-lkappaB-kinase fusion

<400> SEQUENCE: 121

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys Ser
225                 230                 235                 240

Gly Leu Arg Ser Arg Ala Gln Ala Ser Asn Ser Thr Met Glu Arg Pro
                245                 250                 255

Pro Gly Leu Arg Pro Gly Ala Gly Gly Pro Trp Glu Met Arg Glu Arg
            260                 265                 270

Leu Gly Thr Gly Gly Phe Gly Asn Val Cys Leu Tyr Gln His Arg Glu
        275                 280                 285

Leu Asp Leu Lys Ile Ala Ile Lys Ser Cys Arg Leu Glu Leu Ser Thr
290                 295                 300

Lys Asn Arg Glu Arg Trp Cys His Glu Ile Gln Ile Met Lys Lys Leu
305                 310                 315                 320

Asn His Ala Asn Val Val Lys Ala Cys Asp Val Pro Glu Glu Leu Asn
                325                 330                 335

Ile Leu Ile His Asp Val Pro Leu Leu Ala Met Glu Tyr Cys Ser Gly
            340                 345                 350

Gly Asp Leu Arg Lys Leu Leu Asn Lys Pro Glu Asn Cys Cys Gly Leu
        355                 360                 365

Lys Glu Ser Gln Ile Leu Ser Leu Leu Ser Asp Ile Gly Ser Gly Ile
370                 375                 380

Arg Tyr Leu His Glu Asn Lys Ile Ile His Arg Asp Leu Lys Pro Glu
```

```
                385                 390                 395                 400
Asn Ile Val Leu Gln Asp Val Gly Gly Lys Ile Ile His Lys Ile Ile
                405                 410                 415
Asp Leu Gly Tyr Ala Lys Asp Val Asp Gln Gly Ser Leu Cys Thr Ser
            420                 425                 430
Phe Val Gly Thr Leu Gln Tyr Leu Ala Pro Glu Leu Phe Glu Asn Lys
        435                 440                 445
Pro Tyr Thr Ala Thr Val Asp Tyr Trp Ser Phe Gly Thr Met Val Phe
    450                 455                 460
Glu Cys Ile Ala Gly Tyr Arg Pro Phe Leu His Leu Gln Pro Phe
465                 470                 475                 480
Thr Trp His Glu Lys Ile Lys Lys Lys Asp Pro Lys Cys Ile Phe Ala
                485                 490                 495
Cys Glu Glu Met Ser Gly Glu Val Arg Phe Ser Ser His Leu Pro Gln
                500                 505                 510
Pro Asn Ser Leu Cys Ser Leu Ile Val Glu Pro Met Glu Asn Trp Leu
            515                 520                 525
Gln Leu Met Leu Asn Trp Asp Pro Gln Gln Arg Gly Gly Pro Val Asp
        530                 535                 540
Leu Thr Leu Lys Gln Pro Arg Cys Phe Val Leu Met Asp His Ile Leu
545                 550                 555                 560
Asn Leu Lys Ile Val His Ile Leu Asn Met Thr Ser Ala Lys Ile Ile
                565                 570                 575
Ser Phe Leu Leu Pro Pro Asp Glu Ser Leu His Ser Leu Gln Ser Arg
                580                 585                 590
Ile Glu Arg Glu Thr Gly Ile Asn Thr Gly Ser Gln Glu Leu Leu Ser
                595                 600                 605
Glu Thr Gly Ile Ser Leu Asp Pro Arg Lys Pro Ala Ser Gln Cys Val
        610                 615                 620
Leu Asp Gly Val Arg Gly Cys Asp Ser Tyr Met Val Tyr Leu Phe Asp
625                 630                 635                 640
Lys Ser Lys Thr Val Tyr Glu Gly Pro Phe Ala Ser Arg Ser Leu Ser
                645                 650                 655
Asp Cys Val Asn Tyr Ile Val Gln Asp Ser Lys Ile Gln Leu Pro Ile
            660                 665                 670
Ile Gln Leu Arg Lys Val Trp Ala Glu Ala Val His Tyr Val Ser Gly
        675                 680                 685
Leu Lys Glu Asp Tyr Ser Arg Leu Phe Gln Gly Gln Arg Ala Ala Met
    690                 695                 700
Leu Ser Leu Leu Arg Tyr Asn Ala Asn Leu Thr Lys Met Lys Asn Thr
705                 710                 715                 720
Leu Ile Ser Ala Ser Gln Gln Leu Lys Ala Lys Leu Glu Phe Phe His
                725                 730                 735
Lys Ser Ile Gln Leu Asp Leu Glu Arg Tyr Ser Glu Gln Met Thr Tyr
            740                 745                 750
Gly Ile Ser Ser Glu Lys Met Leu Lys Ala Trp Lys Glu Met Glu Glu
        755                 760                 765
Lys Ala Ile His Tyr Ala Glu Val Gly Val Ile Gly Tyr Leu Glu Asp
    770                 775                 780
Gln Ile Met Ser Leu His Ala Glu Ile Met Gly Leu Gln Lys Ser Pro
785                 790                 795                 800
Tyr Gly Arg Arg Gln Gly Asp Leu Met Glu Ser Leu Glu Gln Arg Ala
                805                 810                 815
```

```
Ile Asp Leu Tyr Lys Gln Leu Lys His Arg Pro Ser Asp His Ser Tyr
             820                 825                 830

Ser Asp Ser Thr Glu Met Val Lys Ile Ile Val His Thr Val Gln Ser
         835                 840                 845

Gln Asp Arg Val Leu Lys Glu Leu Phe Gly His Leu Ser Lys Leu Leu
     850                 855                 860

Gly Cys Lys Gln Lys Ile Ile Asp Leu Leu Pro Lys Val Glu Val Ala
865                 870                 875                 880

Leu Ser Asn Ile Lys Glu Ala Asp Asn Thr Val Met Phe Met Gln Gly
                 885                 890                 895

Lys Arg Gln Lys Glu Ile Trp His Leu Leu Lys Ile Ala Cys Thr Gln
             900                 905                 910

Ser Ser Ala Arg Ser Leu Val Gly Ser Ser Leu Glu Gly Ala Val Thr
         915                 920                 925

Pro Gln Thr Ser Ala Trp Leu Pro Pro Thr Ser Ala Glu His Asp His
     930                 935                 940

Ser Leu Ser Cys Val Val Thr Pro Gln Asp Gly Glu Thr Ser Ala Gln
945                 950                 955                 960

Met Ile Glu Glu Asn Leu Asn Cys Leu Gly His Leu Ser Thr Ile Ile
                 965                 970                 975

His Glu Ala Asn Glu Glu Gln Gly Asn Ser Met Met Asn Leu Asp Trp
             980                 985                 990

Ser Trp Leu Thr Glu
         995

<210> SEQ ID NO 122
<211> LENGTH: 2991
<212> TYPE: DNA
<213> ORGANISM: Artificial Sequence
<220> FEATURE:
<223> OTHER INFORMATION: IkappaB-kinase-EGFP fusion
<220> FEATURE:
<221> NAME/KEY: CDS
<222> LOCATION: (1)..(2988)

<400> SEQUENCE: 122 atg gag cgg ccc ccg ggg ctg cgg ccg ggc gcg ggc ggg ccc tgg gag      48
Met Glu Arg Pro Pro Gly Leu Arg Pro Gly Ala Gly Gly Pro Trp Glu
1               5                   10                  15 atg cgg gag cgg ctg ggc acc ggc ggc ttc ggg aac gtc tgt ctg tac      96
Met Arg Glu Arg Leu Gly Thr Gly Gly Phe Gly Asn Val Cys Leu Tyr
                20                  25                  30 cag cat cgg gaa ctt gat ctc aaa ata gca att aag tct tgt cgc cta     144
Gln His Arg Glu Leu Asp Leu Lys Ile Ala Ile Lys Ser Cys Arg Leu
            35                  40                  45 gag cta agt acc aaa aac aga gaa cga tgg tgc cat gaa atc cag att     192
Glu Leu Ser Thr Lys Asn Arg Glu Arg Trp Cys His Glu Ile Gln Ile
        50                  55                  60 atg aag aag ttg aac cat gcc aat gtt gta aag gcc tgt gat gtt cct     240
Met Lys Lys Leu Asn His Ala Asn Val Val Lys Ala Cys Asp Val Pro
65                  70                  75                  80 gaa gaa ttg aat att ttg att cat gat gtg cct ctt cta gca atg gaa     288
Glu Glu Leu Asn Ile Leu Ile His Asp Val Pro Leu Leu Ala Met Glu
                85                  90                  95 tac tgt tct gga gga gat ctc cga aag ctg ctc aac aaa cca gaa aat     336
Tyr Cys Ser Gly Gly Asp Leu Arg Lys Leu Leu Asn Lys Pro Glu Asn
            100                 105                 110 tgt tgt gga ctt aaa gaa agc cag ata ctt tct tta cta agt gat ata     384
```

```
                    Cys Cys Gly Leu Lys Glu Ser Gln Ile Leu Ser Leu Leu Ser Asp Ile
                                115                 120                 125 ggg tct ggg att cga tat ttg cat gaa aac aaa att ata cat cga gat        432
Gly Ser Gly Ile Arg Tyr Leu His Glu Asn Lys Ile Ile His Arg Asp
        130                 135                 140 cta aaa cct gaa aac ata gtt ctt cag gat gtt ggt gga aag ata ata        480
Leu Lys Pro Glu Asn Ile Val Leu Gln Asp Val Gly Gly Lys Ile Ile
145                 150                 155                 160 cat aaa ata att gat ctg gga tat gcc aaa gat gtt gat caa gga agt        528
His Lys Ile Ile Asp Leu Gly Tyr Ala Lys Asp Val Asp Gln Gly Ser
                165                 170                 175 ctg tgt aca tct ttt gtg gga aca ctg cag tat ctg gcc cca gag ctc        576
Leu Cys Thr Ser Phe Val Gly Thr Leu Gln Tyr Leu Ala Pro Glu Leu
        180                 185                 190 ttt gag aat aag cct tac aca gcc act gtt gat tat tgg agc ttt ggg        624
Phe Glu Asn Lys Pro Tyr Thr Ala Thr Val Asp Tyr Trp Ser Phe Gly
                195                 200                 205 acc atg gta ttt gaa tgt att gct gga tat agg cct ttt ttg cat cat        672
Thr Met Val Phe Glu Cys Ile Ala Gly Tyr Arg Pro Phe Leu His His
        210                 215                 220 ctg cag cca ttt acc tgg cat gag aag att aag aag aag gat cca aag        720
Leu Gln Pro Phe Thr Trp His Glu Lys Ile Lys Lys Lys Asp Pro Lys
225                 230                 235                 240 tgt ata ttt gca tgt gaa gag atg tca gga gaa gtt cgg ttt agt agc        768
Cys Ile Phe Ala Cys Glu Glu Met Ser Gly Glu Val Arg Phe Ser Ser
                245                 250                 255 cat tta cct caa cca aat agc ctt tgt agt tta ata gta gaa ccc atg        816
His Leu Pro Gln Pro Asn Ser Leu Cys Ser Leu Ile Val Glu Pro Met
        260                 265                 270 gaa aac tgg cta cag ttg atg ttg aat tgg gac cct cag cag aga gga        864
Glu Asn Trp Leu Gln Leu Met Leu Asn Trp Asp Pro Gln Gln Arg Gly
                275                 280                 285 gga cct gtt gac ctt act ttg aag cag cca aga tgt ttt gta tta atg        912
Gly Pro Val Asp Leu Thr Leu Lys Gln Pro Arg Cys Phe Val Leu Met
        290                 295                 300 gat cac att ttg aat ttg aag ata gta cac atc cta aat atg act tct        960
Asp His Ile Leu Asn Leu Lys Ile Val His Ile Leu Asn Met Thr Ser
305                 310                 315                 320 gca aag ata att tct ttt ctg tta cca cct gat gaa agt ctt cat tca       1008
Ala Lys Ile Ile Ser Phe Leu Leu Pro Pro Asp Glu Ser Leu His Ser
                325                 330                 335 cta cag tct cgt att gag cgt gaa act gga ata aat act ggt tct caa       1056
Leu Gln Ser Arg Ile Glu Arg Glu Thr Gly Ile Asn Thr Gly Ser Gln
        340                 345                 350 gaa ctt ctt tca gag aca gga att tct ctg gat cct cgg aaa cca gcc       1104
Glu Leu Leu Ser Glu Thr Gly Ile Ser Leu Asp Pro Arg Lys Pro Ala
                355                 360                 365 tct caa tgt gtt cta gat gga gtt aga ggc tgt gat agc tat atg gtt       1152
Ser Gln Cys Val Leu Asp Gly Val Arg Gly Cys Asp Ser Tyr Met Val
370                 375                 380 tat ttg ttt gat aaa agt aaa act gta tat gaa ggg cca ttt gct tcc       1200
Tyr Leu Phe Asp Lys Ser Lys Thr Val Tyr Glu Gly Pro Phe Ala Ser
385                 390                 395                 400 aga agt tta tct gat tgt gta aat tat att gta cag gac agc aaa ata       1248
Arg Ser Leu Ser Asp Cys Val Asn Tyr Ile Val Gln Asp Ser Lys Ile
                405                 410                 415 cag ctt cca att ata cag ctg cgt aaa gtg tgg gct gaa gca gtg cac       1296
Gln Leu Pro Ile Ile Gln Leu Arg Lys Val Trp Ala Glu Ala Val His
        420                 425                 430
```

```
tat gtg tct gga cta aaa gaa gac tat agc agg ctc ttt cag gga caa      1344
Tyr Val Ser Gly Leu Lys Glu Asp Tyr Ser Arg Leu Phe Gln Gly Gln
            435                 440                 445 agg gca gca atg tta agt ctt ctt aga tat aat gct aac tta aca aaa      1392
Arg Ala Ala Met Leu Ser Leu Leu Arg Tyr Asn Ala Asn Leu Thr Lys
450                 455                 460 atg aag aac act ttg atc tca gca tca caa caa ctg aaa gct aaa ttg      1440
Met Lys Asn Thr Leu Ile Ser Ala Ser Gln Gln Leu Lys Ala Lys Leu
465                 470                 475                 480 gag ttt ttt cac aaa agc att cag ctt gac ttg gag aga tac agc gag      1488
Glu Phe Phe His Lys Ser Ile Gln Leu Asp Leu Glu Arg Tyr Ser Glu
                485                 490                 495 cag atg acg tat ggg ata tct tca gaa aaa atg cta aaa gca tgg aaa      1536
Gln Met Thr Tyr Gly Ile Ser Ser Glu Lys Met Leu Lys Ala Trp Lys
            500                 505                 510 gaa atg gaa gaa aag gcc atc cac tat gct gag gtt ggt gtc att gga      1584
Glu Met Glu Glu Lys Ala Ile His Tyr Ala Glu Val Gly Val Ile Gly
            515                 520                 525 tac ctg gag gat cag att atg tct ttg cat gct gaa atc atg ggg cta      1632
Tyr Leu Glu Asp Gln Ile Met Ser Leu His Ala Glu Ile Met Gly Leu
530                 535                 540 cag aag agc ccc tat gga aga cgt cag gga gac ttg atg gaa tct ctg      1680
Gln Lys Ser Pro Tyr Gly Arg Arg Gln Gly Asp Leu Met Glu Ser Leu
545                 550                 555                 560 gaa cag cgt gcc att gat cta tat aag cag tta aaa cac aga cct tca      1728
Glu Gln Arg Ala Ile Asp Leu Tyr Lys Gln Leu Lys His Arg Pro Ser
                565                 570                 575 gat cac tcc tac agt gac agc aca gag atg gtg aaa atc att gtg cac      1776
Asp His Ser Tyr Ser Asp Ser Thr Glu Met Val Lys Ile Ile Val His
            580                 585                 590 act gtg cag agt cag gac cgt gtg ctc aag gag ctg ttt ggt cat ttg      1824
Thr Val Gln Ser Gln Asp Arg Val Leu Lys Glu Leu Phe Gly His Leu
            595                 600                 605 agc aag ttg ttg ggc tgt aag cag aag att att gat cta ctc cct aag      1872
Ser Lys Leu Leu Gly Cys Lys Gln Lys Ile Ile Asp Leu Leu Pro Lys
610                 615                 620 gtg gaa gtg gcc ctc agt aat atc aaa gaa gct gac aat act gtc atg      1920
Val Glu Val Ala Leu Ser Asn Ile Lys Glu Ala Asp Asn Thr Val Met
625                 630                 635                 640 ttc atg cag gga aaa agg cag aaa gaa ata tgg cat ctc ctt aaa att      1968
Phe Met Gln Gly Lys Arg Gln Lys Glu Ile Trp His Leu Leu Lys Ile
                645                 650                 655 gcc tgt aca cag agt tct gcc cgc tct ctt gta gga tcc agt cta gaa      2016
Ala Cys Thr Gln Ser Ser Ala Arg Ser Leu Val Gly Ser Ser Leu Glu
            660                 665                 670 ggt gca gta acc cct cag aca tca gca tgg ctg ccc ccg act tca gca      2064
Gly Ala Val Thr Pro Gln Thr Ser Ala Trp Leu Pro Pro Thr Ser Ala
            675                 680                 685 gaa cat gat cat tct ctg tca tgt gtg gta act cct caa gat ggg gag      2112
Glu His Asp His Ser Leu Ser Cys Val Val Thr Pro Gln Asp Gly Glu
690                 695                 700 act tca gca caa atg ata gaa gaa aat ttg aac tgc ctt ggc cat tta      2160
Thr Ser Ala Gln Met Ile Glu Glu Asn Leu Asn Cys Leu Gly His Leu
705                 710                 715                 720 agc act att att cat gag gca aat gag gaa cag ggc aat agt atg atg      2208
Ser Thr Ile Ile His Glu Ala Asn Glu Glu Gln Gly Asn Ser Met Met
                725                 730                 735 aat ctt gat tgg agt tgg tta aca gaa tgg gta ccg cgg gcc cgg gat      2256
Asn Leu Asp Trp Ser Trp Leu Thr Glu Trp Val Pro Arg Ala Arg Asp
            740                 745                 750
```

-continued

| | | |
|---|---|---|
| cca ccg gtc gcc acc atg gtg agc aag ggc gag gag ctg ttc acc ggg<br>Pro Pro Val Ala Thr Met Val Ser Lys Gly Glu Glu Leu Phe Thr Gly<br>          755                      760                      765 | 2304 |
| gtg gtg ccc atc ctg gtc gag ctg gac ggc gac gta aac ggc cac aag<br>Val Val Pro Ile Leu Val Glu Leu Asp Gly Asp Val Asn Gly His Lys<br>770                      775                      780 | 2352 |
| ttc agc gtg tcc ggc gag ggc gag ggc gat gcc acc tac ggc aag ctg<br>Phe Ser Val Ser Gly Glu Gly Glu Gly Asp Ala Thr Tyr Gly Lys Leu<br>785                      790                      795                      800 | 2400 |
| acc ctg aag ttc atc tgc acc acc ggc aag ctg ccc gtg ccc tgg ccc<br>Thr Leu Lys Phe Ile Cys Thr Thr Gly Lys Leu Pro Val Pro Trp Pro<br>                      805                      810                      815 | 2448 |
| acc ctc gtg acc acc ctg acc tac ggc gtg cag tgc ttc agc cgc tac<br>Thr Leu Val Thr Thr Leu Thr Tyr Gly Val Gln Cys Phe Ser Arg Tyr<br>820                      825                      830 | 2496 |
| ccc gac cac atg aag cag cac gac ttc ttc aag tcc gcc atg ccc gaa<br>Pro Asp His Met Lys Gln His Asp Phe Phe Lys Ser Ala Met Pro Glu<br>                      835                      840                      845 | 2544 |
| ggc tac gtc cag gag cgc acc atc ttc ttc aag gac gac ggc aac tac<br>Gly Tyr Val Gln Glu Arg Thr Ile Phe Phe Lys Asp Asp Gly Asn Tyr<br>850                      855                      860 | 2592 |
| aag acc cgc gcc gag gtg aag ttc gag ggc gac acc ctg gtg aac cgc<br>Lys Thr Arg Ala Glu Val Lys Phe Glu Gly Asp Thr Leu Val Asn Arg<br>865                      870                      875                      880 | 2640 |
| atc gag ctg aag ggc atc gac ttc aag gag gac ggc aac atc ctg ggg<br>Ile Glu Leu Lys Gly Ile Asp Phe Lys Glu Asp Gly Asn Ile Leu Gly<br>                      885                      890                      895 | 2688 |
| cac aag ctg gag tac aac tac aac agc cac aac gtc tat atc atg gcc<br>His Lys Leu Glu Tyr Asn Tyr Asn Ser His Asn Val Tyr Ile Met Ala<br>                      900                      905                      910 | 2736 |
| gac aag cag aag aac ggc atc aag gtg aac ttc aag atc cgc cac aac<br>Asp Lys Gln Lys Asn Gly Ile Lys Val Asn Phe Lys Ile Arg His Asn<br>915                      920                      925 | 2784 |
| atc gag gac ggc agc gtg cag ctc gcc gac cac tac cag cag aac acc<br>Ile Glu Asp Gly Ser Val Gln Leu Ala Asp His Tyr Gln Gln Asn Thr<br>                      930                      935                      940 | 2832 |
| ccc atc ggc gac ggc ccc gtg ctg ctg ccc gac aac cac tac ctg agc<br>Pro Ile Gly Asp Gly Pro Val Leu Leu Pro Asp Asn His Tyr Leu Ser<br>945                      950                      955                      960 | 2880 |
| acc cag tcc gcc ctg agc aaa gac ccc aac gag aag cgc gat cac atg<br>Thr Gln Ser Ala Leu Ser Lys Asp Pro Asn Glu Lys Arg Asp His Met<br>                      965                      970                      975 | 2928 |
| gtc ctg ctg gag ttc gtg acc gcc gcc ggg atc act ctc ggc atg gac<br>Val Leu Leu Glu Phe Val Thr Ala Ala Gly Ile Thr Leu Gly Met Asp<br>980                      985                      990 | 2976 |
| gag ctg tac aag taa<br>Glu Leu Tyr Lys<br>          995 | 2991 |

<210> SEQ ID NO 123
<211> LENGTH: 996
<212> TYPE: PRT
<213> ORGANISM: Artificial Sequence
<220> FEATURE:
<223> OTHER INFORMATION: IkappaB-kinase-EGFP fusion

<400> SEQUENCE: 123

Met Glu Arg Pro Pro Gly Leu Arg Pro Gly Ala Gly Gly Pro Trp Glu
1               5                   10                  15

Met Arg Glu Arg Leu Gly Thr Gly Gly Phe Gly Asn Val Cys Leu Tyr

```
                    20                  25                  30
Gln His Arg Glu Leu Asp Leu Lys Ile Ala Ile Lys Ser Cys Arg Leu
                35                  40                  45
Glu Leu Ser Thr Lys Asn Arg Glu Arg Trp Cys His Glu Ile Gln Ile
 50                  55                  60
Met Lys Lys Leu Asn His Ala Asn Val Val Lys Ala Cys Asp Val Pro
 65                  70                  75                  80
Glu Glu Leu Asn Ile Leu Ile His Asp Val Pro Leu Leu Ala Met Glu
                85                  90                  95
Tyr Cys Ser Gly Gly Asp Leu Arg Lys Leu Leu Asn Lys Pro Glu Asn
               100                 105                 110
Cys Cys Gly Leu Lys Glu Ser Gln Ile Leu Ser Leu Leu Ser Asp Ile
               115                 120                 125
Gly Ser Gly Ile Arg Tyr Leu His Glu Asn Lys Ile Ile His Arg Asp
130                 135                 140
Leu Lys Pro Glu Asn Ile Val Leu Gln Asp Val Gly Gly Lys Ile Ile
145                 150                 155                 160
His Lys Ile Ile Asp Leu Gly Tyr Ala Lys Asp Val Asp Gln Gly Ser
               165                 170                 175
Leu Cys Thr Ser Phe Val Gly Thr Leu Gln Tyr Leu Ala Pro Glu Leu
               180                 185                 190
Phe Glu Asn Lys Pro Tyr Thr Ala Thr Val Asp Tyr Trp Ser Phe Gly
               195                 200                 205
Thr Met Val Phe Glu Cys Ile Ala Gly Tyr Arg Pro Phe Leu His His
               210                 215                 220
Leu Gln Pro Phe Thr Trp His Glu Lys Ile Lys Lys Lys Asp Pro Lys
225                 230                 235                 240
Cys Ile Phe Ala Cys Glu Glu Met Ser Gly Glu Val Arg Phe Ser Ser
               245                 250                 255
His Leu Pro Gln Pro Asn Ser Leu Cys Ser Leu Ile Val Glu Pro Met
               260                 265                 270
Glu Asn Trp Leu Gln Leu Met Leu Asn Trp Asp Pro Gln Gln Arg Gly
               275                 280                 285
Gly Pro Val Asp Leu Thr Leu Lys Gln Pro Arg Cys Phe Val Leu Met
               290                 295                 300
Asp His Ile Leu Asn Leu Lys Ile Val His Ile Leu Asn Met Thr Ser
305                 310                 315                 320
Ala Lys Ile Ile Ser Phe Leu Leu Pro Pro Asp Glu Ser Leu His Ser
               325                 330                 335
Leu Gln Ser Arg Ile Glu Arg Glu Thr Gly Ile Asn Thr Gly Ser Gln
               340                 345                 350
Glu Leu Leu Ser Glu Thr Gly Ile Ser Leu Asp Pro Arg Lys Pro Ala
               355                 360                 365
Ser Gln Cys Val Leu Asp Gly Val Arg Gly Cys Asp Ser Tyr Met Val
               370                 375                 380
Tyr Leu Phe Asp Lys Ser Lys Thr Val Tyr Glu Gly Pro Phe Ala Ser
385                 390                 395                 400
Arg Ser Leu Ser Asp Cys Val Asn Tyr Ile Val Gln Asp Ser Lys Ile
               405                 410                 415
Gln Leu Pro Ile Ile Gln Leu Arg Lys Val Trp Ala Glu Ala Val His
               420                 425                 430
Tyr Val Ser Gly Leu Lys Glu Asp Tyr Ser Arg Leu Phe Gln Gly Gln
               435                 440                 445
```

-continued

```
Arg Ala Ala Met Leu Ser Leu Leu Arg Tyr Asn Ala Asn Leu Thr Lys
    450                 455                 460
Met Lys Asn Thr Leu Ile Ser Ala Ser Gln Gln Leu Lys Ala Lys Leu
465                 470                 475                 480
Glu Phe His Lys Ser Ile Gln Leu Asp Leu Glu Arg Tyr Ser Glu
                485                 490                 495
Gln Met Thr Tyr Gly Ile Ser Ser Glu Lys Met Leu Lys Ala Trp Lys
                500                 505                 510
Glu Met Glu Glu Lys Ala Ile His Tyr Ala Glu Val Gly Val Ile Gly
            515                 520                 525
Tyr Leu Glu Asp Gln Ile Met Ser Leu His Ala Glu Ile Met Gly Leu
        530                 535                 540
Gln Lys Ser Pro Tyr Gly Arg Arg Gln Gly Asp Leu Met Glu Ser Leu
545                 550                 555                 560
Glu Gln Arg Ala Ile Asp Leu Tyr Lys Gln Leu Lys His Arg Pro Ser
                565                 570                 575
Asp His Ser Tyr Ser Asp Ser Thr Glu Met Val Lys Ile Ile Val His
                580                 585                 590
Thr Val Gln Ser Gln Asp Arg Val Leu Lys Glu Leu Phe Gly His Leu
            595                 600                 605
Ser Lys Leu Leu Gly Cys Lys Gln Lys Ile Ile Asp Leu Leu Pro Lys
        610                 615                 620
Val Glu Val Ala Leu Ser Asn Ile Lys Glu Ala Asp Asn Thr Val Met
625                 630                 635                 640
Phe Met Gln Gly Lys Arg Gln Lys Glu Ile Trp His Leu Leu Lys Ile
                645                 650                 655
Ala Cys Thr Gln Ser Ser Ala Arg Ser Leu Val Gly Ser Ser Leu Glu
                660                 665                 670
Gly Ala Val Thr Pro Gln Thr Ser Ala Trp Leu Pro Pro Thr Ser Ala
            675                 680                 685
Glu His Asp His Ser Leu Ser Cys Val Val Thr Pro Gln Asp Gly Glu
        690                 695                 700
Thr Ser Ala Gln Met Ile Glu Glu Asn Leu Asn Cys Leu Gly His Leu
705                 710                 715                 720
Ser Thr Ile Ile His Glu Ala Asn Glu Glu Gln Gly Asn Ser Met Met
                725                 730                 735
Asn Leu Asp Trp Ser Trp Leu Thr Glu Trp Val Pro Arg Ala Arg Asp
                740                 745                 750
Pro Pro Val Ala Thr Met Val Ser Lys Gly Glu Glu Leu Phe Thr Gly
            755                 760                 765
Val Val Pro Ile Leu Val Glu Leu Asp Gly Asp Val Asn Gly His Lys
        770                 775                 780
Phe Ser Val Ser Gly Glu Gly Glu Gly Asp Ala Thr Tyr Gly Lys Leu
785                 790                 795                 800
Thr Leu Lys Phe Ile Cys Thr Thr Gly Lys Leu Pro Val Pro Trp Pro
                805                 810                 815
Thr Leu Val Thr Thr Leu Thr Tyr Gly Val Gln Cys Phe Ser Arg Tyr
            820                 825                 830
Pro Asp His Met Lys Gln His Asp Phe Phe Lys Ser Ala Met Pro Glu
        835                 840                 845
Gly Tyr Val Gln Glu Arg Thr Ile Phe Phe Lys Asp Asp Gly Asn Tyr
850                 855                 860
```

```
Lys Thr Arg Ala Glu Val Lys Phe Glu Gly Asp Thr Leu Val Asn Arg
865                 870                 875                 880

Ile Glu Leu Lys Gly Ile Asp Phe Lys Glu Asp Gly Asn Ile Leu Gly
            885                 890                 895

His Lys Leu Glu Tyr Asn Tyr Asn Ser His Asn Val Tyr Ile Met Ala
            900                 905                 910

Asp Lys Gln Lys Asn Gly Ile Lys Val Asn Phe Lys Ile Arg His Asn
            915                 920                 925

Ile Glu Asp Gly Ser Val Gln Leu Ala Asp His Tyr Gln Gln Asn Thr
        930                 935                 940

Pro Ile Gly Asp Gly Pro Val Leu Leu Pro Asp Asn His Tyr Leu Ser
945                 950                 955                 960

Thr Gln Ser Ala Leu Ser Lys Asp Pro Asn Glu Lys Arg Asp His Met
                965                 970                 975

Val Leu Leu Glu Phe Val Thr Ala Ala Gly Ile Thr Leu Gly Met Asp
            980                 985                 990

Glu Leu Tyr Lys
        995

<210> SEQ ID NO 124
<211> LENGTH: 1908
<212> TYPE: DNA
<213> ORGANISM: Artificial Sequence
<220> FEATURE:
<223> OTHER INFORMATION: EGFP-VASP fusion
<220> FEATURE:
<221> NAME/KEY: CDS
<222> LOCATION: (1)..(1905)

<400> SEQUENCE: 124 atg gtg agc aag ggc gag gag ctg ttc acc ggg gtg gtg ccc atc ctg      48
Met Val Ser Lys Gly Glu Glu Leu Phe Thr Gly Val Val Pro Ile Leu
1               5                   10                  15 gtc gag ctg gac ggc gac gta aac ggc cac aag ttc agc gtg tcc ggc      96
Val Glu Leu Asp Gly Asp Val Asn Gly His Lys Phe Ser Val Ser Gly
            20                  25                  30 gag ggc gag ggc gat gcc acc tac ggc aag ctg acc ctg aag ttc atc     144
Glu Gly Glu Gly Asp Ala Thr Tyr Gly Lys Leu Thr Leu Lys Phe Ile
        35                  40                  45 tgc acc acc ggc aag ctg ccc gtg ccc tgg ccc acc ctc gtg acc acc     192
Cys Thr Thr Gly Lys Leu Pro Val Pro Trp Pro Thr Leu Val Thr Thr
50                  55                  60 ctg acc tac ggc gtg cag tgc ttc agc cgc tac ccc gac cac atg aag     240
Leu Thr Tyr Gly Val Gln Cys Phe Ser Arg Tyr Pro Asp His Met Lys
65                  70                  75                  80 cag cac gac ttc ttc aag tcc gcc atg ccc gaa ggc tac gtc cag gag     288
Gln His Asp Phe Phe Lys Ser Ala Met Pro Glu Gly Tyr Val Gln Glu
                85                  90                  95 cgc acc atc ttc ttc aag gac gac ggc aac tac aag acc cgc gcc gag     336
Arg Thr Ile Phe Phe Lys Asp Asp Gly Asn Tyr Lys Thr Arg Ala Glu
            100                 105                 110 gtg aag ttc gag ggc gac acc ctg gtg aac cgc atc gag ctg aag ggc     384
Val Lys Phe Glu Gly Asp Thr Leu Val Asn Arg Ile Glu Leu Lys Gly
        115                 120                 125 atc gac ttc aag gag gac ggc aac atc ctg ggg cac aag ctg gag tac     432
Ile Asp Phe Lys Glu Asp Gly Asn Ile Leu Gly His Lys Leu Glu Tyr
    130                 135                 140 aac tac aac agc cac aac gtc tat atc atg gcc gac aag cag aag aac     480
Asn Tyr Asn Ser His Asn Val Tyr Ile Met Ala Asp Lys Gln Lys Asn
145                 150                 155                 160
```

| | | |
|---|---|---|
| ggc atc aag gtg aac ttc aag atc cgc cac aac atc gag gac ggc agc<br>Gly Ile Lys Val Asn Phe Lys Ile Arg His Asn Ile Glu Asp Gly Ser<br>165                    170                175 | 528 |
| gtg cag ctc gcc gac cac tac cag cag aac acc ccc atc ggc gac ggc<br>Val Gln Leu Ala Asp His Tyr Gln Gln Asn Thr Pro Ile Gly Asp Gly<br>   180                 185                190 | 576 |
| ccc gtg ctg ctg ccc gac aac cac tac ctg agc acc cag tcc gcc ctg<br>Pro Val Leu Leu Pro Asp Asn His Tyr Leu Ser Thr Gln Ser Ala Leu<br>195                    200                205 | 624 |
| agc aaa gac ccc aac gag aag cgc gat cac atg gtc ctg ctg gag ttc<br>Ser Lys Asp Pro Asn Glu Lys Arg Asp His Met Val Leu Leu Glu Phe<br>   210                 215                220 | 672 |
| gtg acc gcc gcc ggg atc act ctc ggc atg gac gag ctg tac aag tcc<br>Val Thr Ala Ala Gly Ile Thr Leu Gly Met Asp Glu Leu Tyr Lys Ser<br>225                    230                235                240 | 720 |
| gga ctc aga tct cga gct caa gct tcc atg agc gag acg gtc atc atg<br>Gly Leu Arg Ser Arg Ala Gln Ala Ser Met Ser Glu Thr Val Ile Met<br>               245                250                255 | 768 |
| agc gag acg gtc atc tgt tcc agc cgg gcc act gtg atg ctt tat gat<br>Ser Glu Thr Val Ile Cys Ser Ser Arg Ala Thr Val Met Leu Tyr Asp<br>        260                265                270 | 816 |
| gat ggc aac aag cga tgg ctc cct gct ggc acg ggt ccc cag gcc ttc<br>Asp Gly Asn Lys Arg Trp Leu Pro Ala Gly Thr Gly Pro Gln Ala Phe<br>      275                280                285 | 864 |
| agc cgc gtc cag atc tac cac aac ccc acg gcc aat tcc ttt cgc gtc<br>Ser Arg Val Gln Ile Tyr His Asn Pro Thr Ala Asn Ser Phe Arg Val<br>290                    295                300 | 912 |
| gtg ggc cgg aag atg cag ccc gac cag cag gtg gtc atc aac tgt gcc<br>Val Gly Arg Lys Met Gln Pro Asp Gln Gln Val Val Ile Asn Cys Ala<br>305                    310                315                320 | 960 |
| atc gtc cgg ggt gtc aag tat aac cag gcc acc ccc aac ttc cat cag<br>Ile Val Arg Gly Val Lys Tyr Asn Gln Ala Thr Pro Asn Phe His Gln<br>               325                330                335 | 1008 |
| tgg cgc gac gct cgc cag gtc tgg ggc ctc aac ttc ggc agc aag gag<br>Trp Arg Asp Ala Arg Gln Val Trp Gly Leu Asn Phe Gly Ser Lys Glu<br>             340                345                350 | 1056 |
| gat gcg gcc cag ttt gcc gcc ggc atg gcc agt gcc cta gag gcg ttg<br>Asp Ala Ala Gln Phe Ala Ala Gly Met Ala Ser Ala Leu Glu Ala Leu<br>      355              360                365 | 1104 |
| gaa gga ggt ggg ccc cct cca ccc cca gca ctt ccc acc tgg tcg gtc<br>Glu Gly Gly Gly Pro Pro Pro Pro Pro Ala Leu Pro Thr Trp Ser Val<br>370                    375                380 | 1152 |
| ccg aac ggc ccc tcc ccg gag gag gtg gag cag cag aaa agg cag cag<br>Pro Asn Gly Pro Ser Pro Glu Glu Val Glu Gln Gln Lys Arg Gln Gln<br>385                    390                395                400 | 1200 |
| ccc ggc ccg tcg gag cac ata gag cgc cgg gtc tcc aat gca gga ggc<br>Pro Gly Pro Ser Glu His Ile Glu Arg Arg Val Ser Asn Ala Gly Gly<br>               405                410                415 | 1248 |
| cca cct gct ccc ccc gct ggg ggt cca ccc cca cca gga cct ccc<br>Pro Pro Ala Pro Pro Ala Gly Gly Pro Pro Pro Pro Gly Pro Pro<br>          420                425                430 | 1296 |
| cct cct cca ggt ccc ccc cca ccc cca ggt ttg ccc cct tcg ggg gtc<br>Pro Pro Pro Gly Pro Pro Pro Pro Gly Leu Pro Pro Ser Gly Val<br>               435                440                445 | 1344 |
| cca gct gca gcg cac gga gca ggg gga gga cca ccc cct gca ccc cct<br>Pro Ala Ala Ala His Gly Ala Gly Gly Gly Pro Pro Pro Ala Pro Pro<br>   450                 455                460 | 1392 |
| ctc ccg gca gca cag ggc cct ggt ggt ggg gga gct ggg gcc cca ggc<br>Leu Pro Ala Ala Gln Gly Pro Gly Gly Gly Gly Ala Gly Ala Pro Gly | 1440 |

| | | | | | | | | | | | | | | | |
|---|---|---|---|---|---|---|---|---|---|---|---|---|---|---|---|
|465| | | | |470| | | | |475| | | | |480|

```
ctg gcc gca gct att gct gga gcc aaa ctc agg aaa gtc agc aag cag      1488
Leu Ala Ala Ala Ile Ala Gly Ala Lys Leu Arg Lys Val Ser Lys Gln
                    485                 490                 495 gag gag gcc tca ggg ggg ccc aca gcc ccc aaa gct gag agt ggt cga      1536
Glu Glu Ala Ser Gly Gly Pro Thr Ala Pro Lys Ala Glu Ser Gly Arg
            500                 505                 510 agc gga ggt ggg gga ctc atg gaa gag atg aac gcc atg ctg gcc cgg      1584
Ser Gly Gly Gly Gly Leu Met Glu Glu Met Asn Ala Met Leu Ala Arg
        515                 520                 525 aga agg aaa gcc acg caa gtt ggg gag aaa acc ccc aag gat gaa tct      1632
Arg Arg Lys Ala Thr Gln Val Gly Glu Lys Thr Pro Lys Asp Glu Ser
    530                 535                 540 gcc aat cag gag gag cca gag gcc aga gtc ccg gcc cag agt gaa tct      1680
Ala Asn Gln Glu Glu Pro Glu Ala Arg Val Pro Ala Gln Ser Glu Ser
545                 550                 555                 560 gtg cgg aga ccc tgg gag aag aac agc aca acc ttg cca agg atg aag      1728
Val Arg Arg Pro Trp Glu Lys Asn Ser Thr Thr Leu Pro Arg Met Lys
                565                 570                 575 tcg tct tct tcg gtg acc act tcc gag acc caa ccc tgc acg ccc agc      1776
Ser Ser Ser Ser Val Thr Thr Ser Glu Thr Gln Pro Cys Thr Pro Ser
            580                 585                 590 tcc agt gat tac tcg gac cta cag agg gtg aaa cag gag ctt ctg gaa      1824
Ser Ser Asp Tyr Ser Asp Leu Gln Arg Val Lys Gln Glu Leu Leu Glu
        595                 600                 605 gag gtg aag aag gaa ttg cag aaa gtg aaa gag gaa atc att gaa gcc      1872
Glu Val Lys Lys Glu Leu Gln Lys Val Lys Glu Glu Ile Ile Glu Ala
    610                 615                 620 ttc gtc cag gag ctg agg aag cgg ggt tct ccc tga                      1908
Phe Val Gln Glu Leu Arg Lys Arg Gly Ser Pro
625                 630                 635

<210> SEQ ID NO 125
<211> LENGTH: 635
<212> TYPE: PRT
<213> ORGANISM: Artificial Sequence
<220> FEATURE:
<223> OTHER INFORMATION: EGFP-VASP fusion

<400> SEQUENCE: 125

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140
```

```
-continued

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
            165                 170                 175

Val Gln Leu Ala Asp His Tyr Gln Gln Asn Thr Pro Ile Gly Asp Gly
        180                 185                 190

Pro Val Leu Leu Pro Asp Asn His Tyr Leu Ser Thr Gln Ser Ala Leu
    195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys Ser
225                 230                 235                 240

Gly Leu Arg Ser Arg Ala Gln Ala Ser Met Ser Glu Thr Val Ile Met
            245                 250                 255

Ser Glu Thr Val Ile Cys Ser Ser Arg Ala Thr Val Met Leu Tyr Asp
        260                 265                 270

Asp Gly Asn Lys Arg Trp Leu Pro Ala Gly Thr Gly Pro Gln Ala Phe
    275                 280                 285

Ser Arg Val Gln Ile Tyr His Asn Pro Thr Ala Asn Ser Phe Arg Val
290                 295                 300

Val Gly Arg Lys Met Gln Pro Asp Gln Val Val Ile Asn Cys Ala
305                 310                 315                 320

Ile Val Arg Gly Val Lys Tyr Asn Gln Ala Thr Pro Asn Phe His Gln
            325                 330                 335

Trp Arg Asp Ala Arg Gln Val Trp Gly Leu Asn Phe Gly Ser Lys Glu
        340                 345                 350

Asp Ala Ala Gln Phe Ala Ala Gly Met Ala Ser Ala Leu Glu Ala Leu
    355                 360                 365

Glu Gly Gly Pro Pro Pro Pro Ala Leu Pro Thr Trp Ser Val
370                 375                 380

Pro Asn Gly Pro Ser Pro Glu Glu Val Glu Gln Gln Lys Arg Gln Gln
385                 390                 395                 400

Pro Gly Pro Ser Glu His Ile Glu Arg Arg Val Ser Asn Ala Gly Gly
            405                 410                 415

Pro Pro Ala Pro Ala Gly Gly Pro Pro Pro Pro Gly Pro Pro
        420                 425                 430

Pro Pro Pro Gly Pro Pro Pro Pro Gly Leu Pro Pro Ser Gly Val
    435                 440                 445

Pro Ala Ala His Gly Ala Gly Gly Pro Pro Ala Pro Pro
450                 455                 460

Leu Pro Ala Ala Gln Gly Pro Gly Gly Gly Ala Gly Ala Pro Gly
465                 470                 475                 480

Leu Ala Ala Ala Ile Ala Gly Ala Lys Leu Arg Lys Val Ser Lys Gln
            485                 490                 495

Glu Glu Ala Ser Gly Gly Pro Thr Ala Pro Lys Ala Glu Ser Gly Arg
        500                 505                 510

Ser Gly Gly Gly Gly Leu Met Glu Glu Met Asn Ala Met Leu Ala Arg
    515                 520                 525

Arg Arg Lys Ala Thr Gln Val Gly Glu Lys Thr Pro Lys Asp Glu Ser
530                 535                 540

Ala Asn Gln Glu Glu Pro Glu Ala Arg Val Pro Ala Gln Ser Glu Ser
545                 550                 555                 560

Val Arg Arg Pro Trp Glu Lys Asn Ser Thr Thr Leu Pro Arg Met Lys
```

|  | 565 |  |  |  | 570 |  |  |  | 575 |  |  |
|---|---|---|---|---|---|---|---|---|---|---|---|

Ser Ser Ser Val Thr Thr Ser Glu Thr Gln Pro Cys Thr Pro Ser
         580                     585                   590

Ser Ser Asp Tyr Ser Asp Leu Gln Arg Val Lys Gln Glu Leu Leu Glu
         595                 600                   605

Glu Val Lys Lys Glu Leu Gln Lys Val Lys Glu Ile Ile Glu Ala
    610                     615                   620

Phe Val Gln Glu Leu Arg Lys Arg Gly Ser Pro
625                 630                 635

<210> SEQ ID NO 126
<211> LENGTH: 1329
<212> TYPE: DNA
<213> ORGANISM: Artificial Sequence
<220> FEATURE:
<223> OTHER INFORMATION: EGFP-RhoA fusion
<220> FEATURE:
<221> NAME/KEY: CDS
<222> LOCATION: (1)..(1326)

<400> SEQUENCE: 126

| atg gtg agc aag ggc gag gag ctg ttc acc ggg gtg gtg ccc atc ctg | 48 |
|---|---|
| Met Val Ser Lys Gly Glu Glu Leu Phe Thr Gly Val Val Pro Ile Leu | |
| 1               5                 10               15 | |
| gtc gag ctg gac ggc gac gta aac ggc cac aag ttc agc gtg tcc ggc | 96 |
| Val Glu Leu Asp Gly Asp Val Asn Gly His Lys Phe Ser Val Ser Gly | |
|            20                     25                  30 | |
| gag ggc gag ggc gat gcc acc tac ggc aag ctg acc ctg aag ttc atc | 144 |
| Glu Gly Glu Gly Asp Ala Thr Tyr Gly Lys Leu Thr Leu Lys Phe Ile | |
|          35                     40                  45 | |
| tgc acc acc ggc aag ctg ccc gtg ccc tgg ccc acc ctc gtg acc acc | 192 |
| Cys Thr Thr Gly Lys Leu Pro Val Pro Trp Pro Thr Leu Val Thr Thr | |
|     50                     55                   60 | |
| ctg acc tac ggc gtg cag tgc ttc agc cgc tac ccc gac cac atg aag | 240 |
| Leu Thr Tyr Gly Val Gln Cys Phe Ser Arg Tyr Pro Asp His Met Lys | |
| 65                  70                  75               80 | |
| cag cac gac ttc ttc aag tcc gcc atg ccc gaa ggc tac gtc cag gag | 288 |
| Gln His Asp Phe Phe Lys Ser Ala Met Pro Glu Gly Tyr Val Gln Glu | |
|                 85                  90               95 | |
| cgc acc atc ttc ttc aag gac gac ggc aac tac aag acc cgc gcc gag | 336 |
| Arg Thr Ile Phe Phe Lys Asp Asp Gly Asn Tyr Lys Thr Arg Ala Glu | |
|                100                 105              110 | |
| gtg aag ttc gag ggc gac acc ctg gtg aac cgc atc gag ctg aag ggc | 384 |
| Val Lys Phe Glu Gly Asp Thr Leu Val Asn Arg Ile Glu Leu Lys Gly | |
|          115                 120              125 | |
| atc gac ttc aag gag gac ggc aac atc ctg ggg cac aag ctg gag tac | 432 |
| Ile Asp Phe Lys Glu Asp Gly Asn Ile Leu Gly His Lys Leu Glu Tyr | |
| 130                  135                 140 | |
| aac tac aac agc cac aac gtc tat atc atg gcc gac aag cag aag aac | 480 |
| Asn Tyr Asn Ser His Asn Val Tyr Ile Met Ala Asp Lys Gln Lys Asn | |
| 145                  150                 155               160 | |
| ggc atc aag gtg aac ttc aag atc cgc cac aac atc gag gac ggc agc | 528 |
| Gly Ile Lys Val Asn Phe Lys Ile Arg His Asn Ile Glu Asp Gly Ser | |
|                165                 170              175 | |
| gtg cag ctc gcc gac cac tac cag cag aac acc ccc atc ggc gac ggc | 576 |
| Val Gln Leu Ala Asp His Tyr Gln Gln Asn Thr Pro Ile Gly Asp Gly | |
|          180                 185              190 | |
| ccc gtg ctg ctg ccc gac aac cac tac ctg agc acc cag tcc gcc ctg | 624 |
| Pro Val Leu Leu Pro Asp Asn His Tyr Leu Ser Thr Gln Ser Ala Leu | |
|          195                 200              205 | |

```
agc aaa gac ccc aac gag aag cgc gat cac atg gtc ctg ctg gag ttc        672
Ser Lys Asp Pro Asn Glu Lys Arg Asp His Met Val Leu Leu Glu Phe
    210                 215                 220 gtg acc gcc gcc ggg atc act ctc ggc atg gac gag ctg tac aag tcc        720
Val Thr Ala Ala Gly Ile Thr Leu Gly Met Asp Glu Leu Tyr Lys Ser
225                 230                 235                 240 gga ctc aga tct cga gct caa gct tca atg gct gcc atc cgg aag aaa        768
Gly Leu Arg Ser Arg Ala Gln Ala Ser Met Ala Ala Ile Arg Lys Lys
                245                 250                 255 ctg gtg att gtt ggt gat gga gcc tgt gga aag aca tgc ttg ctc ata        816
Leu Val Ile Val Gly Asp Gly Ala Cys Gly Lys Thr Cys Leu Leu Ile
            260                 265                 270 gtc ttc agc aag gac cag ttc cca gag gtg tat gtg ccc aca gtg ttt        864
Val Phe Ser Lys Asp Gln Phe Pro Glu Val Tyr Val Pro Thr Val Phe
        275                 280                 285 gag aac tat gtg gca gat atc gag gtg gat gga aag cag gta gag ttg        912
Glu Asn Tyr Val Ala Asp Ile Glu Val Asp Gly Lys Gln Val Glu Leu
    290                 295                 300 gct ttg tgg gac aca gct ggg cag gaa gat tat gat cgc ctg agg ccc        960
Ala Leu Trp Asp Thr Ala Gly Gln Glu Asp Tyr Asp Arg Leu Arg Pro
305                 310                 315                 320 ctc tcc tac cca gat acc gat gtt ata ctg atg tgt ttt tcc atc gac       1008
Leu Ser Tyr Pro Asp Thr Asp Val Ile Leu Met Cys Phe Ser Ile Asp
                325                 330                 335 agc cct gat agt tta gaa aac atc cca gaa aag tgg acc cca gaa gtc       1056
Ser Pro Asp Ser Leu Glu Asn Ile Pro Glu Lys Trp Thr Pro Glu Val
            340                 345                 350 aag cat ttc tgt ccc aac gtg ccc atc atc ctg gtt ggg aat aag aag       1104
Lys His Phe Cys Pro Asn Val Pro Ile Ile Leu Val Gly Asn Lys Lys
        355                 360                 365 gat ctt cgg aat gat gag cac aca agg cgg gag cta gcc aag atg aag       1152
Asp Leu Arg Asn Asp Glu His Thr Arg Arg Glu Leu Ala Lys Met Lys
    370                 375                 380 cag gag ccg gtg aaa cct gaa gaa ggc aga gat atg gca aac agg att       1200
Gln Glu Pro Val Lys Pro Glu Glu Gly Arg Asp Met Ala Asn Arg Ile
385                 390                 395                 400 ggc gct ttt ggg tac atg gag tgt tca gca aag acc aaa gat gga gtg       1248
Gly Ala Phe Gly Tyr Met Glu Cys Ser Ala Lys Thr Lys Asp Gly Val
                405                 410                 415 aga gag gtt ttt gaa atg gct acg aga gct gct ctg caa gct aga cgt       1296
Arg Glu Val Phe Glu Met Ala Thr Arg Ala Ala Leu Gln Ala Arg Arg
            420                 425                 430 ggg aag aaa aaa tct ggt tgc ctt gtc ttg tga                           1329
Gly Lys Lys Lys Ser Gly Cys Leu Val Leu
        435                 440

<210> SEQ ID NO 127
<211> LENGTH: 442
<212> TYPE: PRT
<213> ORGANISM: Artificial Sequence
<220> FEATURE:
<223> OTHER INFORMATION: EGFP-RhoA fusion

<400> SEQUENCE: 127

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45
```

```
Cys Thr Thr Gly Lys Leu Pro Val Pro Trp Pro Thr Leu Val Thr Thr
 50                  55                  60

Leu Thr Tyr Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Ser
225                 230                 235                 240

Gly Leu Arg Ser Arg Ala Gln Ala Ser Met Ala Ala Ile Arg Lys Lys
                245                 250                 255

Leu Val Ile Val Gly Asp Gly Ala Cys Gly Lys Thr Cys Leu Leu Ile
            260                 265                 270

Val Phe Ser Lys Asp Gln Phe Pro Glu Val Tyr Val Pro Thr Val Phe
        275                 280                 285

Glu Asn Tyr Val Ala Asp Ile Glu Val Asp Gly Lys Gln Val Glu Leu
    290                 295                 300

Ala Leu Trp Asp Thr Ala Gly Gln Glu Asp Tyr Asp Arg Leu Arg Pro
305                 310                 315                 320

Leu Ser Tyr Pro Asp Thr Asp Val Ile Leu Met Cys Phe Ser Ile Asp
                325                 330                 335

Ser Pro Asp Ser Leu Glu Asn Ile Pro Glu Lys Trp Thr Pro Glu Val
            340                 345                 350

Lys His Phe Cys Pro Asn Val Pro Ile Ile Leu Val Gly Asn Lys Lys
        355                 360                 365

Asp Leu Arg Asn Asp Glu His Thr Arg Arg Glu Leu Ala Lys Met Lys
    370                 375                 380

Gln Glu Pro Val Lys Pro Glu Glu Gly Arg Asp Met Ala Asn Arg Ile
385                 390                 395                 400

Gly Ala Phe Gly Tyr Met Glu Cys Ser Ala Lys Thr Lys Asp Gly Val
                405                 410                 415

Arg Glu Val Phe Glu Met Ala Thr Arg Ala Ala Leu Gln Ala Arg Arg
            420                 425                 430

Gly Lys Lys Lys Ser Gly Cys Leu Val Leu
        435                 440
```

<210> SEQ ID NO 128
<211> LENGTH: 1140
<212> TYPE: DNA

```
<213> ORGANISM: Artificial Sequence
<220> FEATURE:
<223> OTHER INFORMATION: actin-binding-domain-EGFP fusion
<220> FEATURE:
<221> NAME/KEY: CDS
<222> LOCATION: (1)..(1137)

<400> SEQUENCE: 128
```

| | | | | | | | | | | | | | | | | |
|---|---|---|---|---|---|---|---|---|---|---|---|---|---|---|---|---|
| atg | gac | cat | tat | gat | tct | cag | caa | acc | aac | gat | tac | atg | cag | cca | gaa | 48 |
| Met | Asp | His | Tyr | Asp | Ser | Gln | Gln | Thr | Asn | Asp | Tyr | Met | Gln | Pro | Glu | |
| 1 | | | | 5 | | | | | 10 | | | | | 15 | | |
| gag | gac | tgg | gac | cgg | gac | ctg | ctc | ctg | gac | ccg | gcc | tgg | gag | aag | cag | 96 |
| Glu | Asp | Trp | Asp | Arg | Asp | Leu | Leu | Leu | Asp | Pro | Ala | Trp | Glu | Lys | Gln | |
| | | | 20 | | | | | 25 | | | | | 30 | | | |
| cag | aga | aag | aca | ttc | acg | gca | tgg | tgt | aac | tcc | cac | ctc | cgg | aag | gcg | 144 |
| Gln | Arg | Lys | Thr | Phe | Thr | Ala | Trp | Cys | Asn | Ser | His | Leu | Arg | Lys | Ala | |
| | | 35 | | | | | 40 | | | | | 45 | | | | |
| ggg | aca | cag | atc | gag | aac | atc | gaa | gag | gac | ttc | cgg | gat | ggc | ctg | aag | 192 |
| Gly | Thr | Gln | Ile | Glu | Asn | Ile | Glu | Glu | Asp | Phe | Arg | Asp | Gly | Leu | Lys | |
| | 50 | | | | | 55 | | | | | 60 | | | | | |
| ctc | atg | ctg | ctg | ctg | gag | gtc | atc | tca | ggt | gaa | cgc | ttg | gcc | aag | cca | 240 |
| Leu | Met | Leu | Leu | Leu | Glu | Val | Ile | Ser | Gly | Glu | Arg | Leu | Ala | Lys | Pro | |
| 65 | | | | | 70 | | | | | 75 | | | | | 80 | |
| gag | cga | ggc | aag | atg | aga | gtg | cac | aag | atc | tcc | aac | gtc | aac | aag | gcc | 288 |
| Glu | Arg | Gly | Lys | Met | Arg | Val | His | Lys | Ile | Ser | Asn | Val | Asn | Lys | Ala | |
| | | | | 85 | | | | | 90 | | | | | 95 | | |
| ctg | gat | ttc | ata | gcc | agc | aaa | ggc | gtc | aaa | ctg | gtg | tcc | atc | gga | gcc | 336 |
| Leu | Asp | Phe | Ile | Ala | Ser | Lys | Gly | Val | Lys | Leu | Val | Ser | Ile | Gly | Ala | |
| | | | 100 | | | | | 105 | | | | | 110 | | | |
| gaa | gaa | atc | gtg | gat | ggg | aat | gtg | aag | atg | acc | ctg | ggc | atg | atc | tgg | 384 |
| Glu | Glu | Ile | Val | Asp | Gly | Asn | Val | Lys | Met | Thr | Leu | Gly | Met | Ile | Trp | |
| | | 115 | | | | | 120 | | | | | 125 | | | | |
| acc | atc | atc | ctg | cgc | agg | gat | cca | ccg | gtc | gcc | acc | atg | gtg | agc | aag | 432 |
| Thr | Ile | Ile | Leu | Arg | Arg | Asp | Pro | Pro | Val | Ala | Thr | Met | Val | Ser | Lys | |
| | 130 | | | | | 135 | | | | | 140 | | | | | |
| ggc | gag | gag | ctg | ttc | acc | ggg | gtg | gtg | ccc | atc | ctg | gtc | gag | ctg | gac | 480 |
| Gly | Glu | Glu | Leu | Phe | Thr | Gly | Val | Val | Pro | Ile | Leu | Val | Glu | Leu | Asp | |
| 145 | | | | | 150 | | | | | 155 | | | | | 160 | |
| ggc | gac | gta | aac | ggc | cac | aag | ttc | agc | gtg | tcc | ggc | gag | ggc | gag | ggc | 528 |
| Gly | Asp | Val | Asn | Gly | His | Lys | Phe | Ser | Val | Ser | Gly | Glu | Gly | Glu | Gly | |
| | | | | 165 | | | | | 170 | | | | | 175 | | |
| gat | gcc | acc | tac | ggc | aag | ctg | acc | ctg | aag | ttc | atc | tgc | acc | acc | ggc | 576 |
| Asp | Ala | Thr | Tyr | Gly | Lys | Leu | Thr | Leu | Lys | Phe | Ile | Cys | Thr | Thr | Gly | |
| | | | 180 | | | | | 185 | | | | | 190 | | | |
| aag | ctg | ccc | gtg | ccc | tgg | ccc | acc | ctc | gtg | acc | acc | ctg | acc | tac | ggc | 624 |
| Lys | Leu | Pro | Val | Pro | Trp | Pro | Thr | Leu | Val | Thr | Thr | Leu | Thr | Tyr | Gly | |
| | | 195 | | | | | 200 | | | | | 205 | | | | |
| gtg | cag | tgc | ttc | agc | cgc | tac | ccc | gac | cac | atg | aag | cag | cac | gac | ttc | 672 |
| Val | Gln | Cys | Phe | Ser | Arg | Tyr | Pro | Asp | His | Met | Lys | Gln | His | Asp | Phe | |
| | 210 | | | | | 215 | | | | | 220 | | | | | |
| ttc | aag | tcc | gcc | atg | ccc | gaa | ggc | tac | gtc | cag | gag | cgc | acc | atc | ttc | 720 |
| Phe | Lys | Ser | Ala | Met | Pro | Glu | Gly | Tyr | Val | Gln | Glu | Arg | Thr | Ile | Phe | |
| 225 | | | | | 230 | | | | | 235 | | | | | 240 | |
| ttc | aag | gac | gac | ggc | aac | tac | aag | acc | cgc | gcc | gag | gtg | aag | ttc | gag | 768 |
| Phe | Lys | Asp | Asp | Gly | Asn | Tyr | Lys | Thr | Arg | Ala | Glu | Val | Lys | Phe | Glu | |
| | | | | 245 | | | | | 250 | | | | | 255 | | |
| ggc | gac | acc | ctg | gtg | aac | cgc | atc | gag | ctg | aag | ggc | atc | gac | ttc | aag | 816 |
| Gly | Asp | Thr | Leu | Val | Asn | Arg | Ile | Glu | Leu | Lys | Gly | Ile | Asp | Phe | Lys | |
| | | | 260 | | | | | 265 | | | | | 270 | | | |
| gag | gac | ggc | aac | atc | ctg | ggg | cac | aag | ctg | gag | tac | aac | tac | aac | agc | 864 |
| Glu | Asp | Gly | Asn | Ile | Leu | Gly | His | Lys | Leu | Glu | Tyr | Asn | Tyr | Asn | Ser | |

```
                275                 280                 285
cac aac gtc tat atc atg gcc gac aag cag aag aac ggc atc aag gtg    912
His Asn Val Tyr Ile Met Ala Asp Lys Gln Lys Asn Gly Ile Lys Val
    290                 295                 300 aac ttc aag atc cgc cac aac atc gag gac ggc agc gtg cag ctc gcc    960
Asn Phe Lys Ile Arg His Asn Ile Glu Asp Gly Ser Val Gln Leu Ala
305                 310                 315                 320 gac cac tac cag cag aac acc ccc atc ggc gac ggc ccc gtg ctg ctg   1008
Asp His Tyr Gln Gln Asn Thr Pro Ile Gly Asp Gly Pro Val Leu Leu
                325                 330                 335 ccc gac aac cac tac ctg agc acc cag tcc gcc ctg agc aaa gac ccc   1056
Pro Asp Asn His Tyr Leu Ser Thr Gln Ser Ala Leu Ser Lys Asp Pro
            340                 345                 350 aac gag aag cgc gat cac atg gtc ctg ctg gag ttc gtg acc gcc gcc   1104
Asn Glu Lys Arg Asp His Met Val Leu Leu Glu Phe Val Thr Ala Ala
        355                 360                 365 ggg atc act ctc ggc atg gac gag ctg tac aag taa                   1140
Gly Ile Thr Leu Gly Met Asp Glu Leu Tyr Lys
    370                 375

<210> SEQ ID NO 129
<211> LENGTH: 379
<212> TYPE: PRT
<213> ORGANISM: Artificial Sequence
<220> FEATURE:
<223> OTHER INFORMATION: actin-binding-domain-EGFP fusion

<400> SEQUENCE: 129

Met Asp His Tyr Asp Ser Gln Gln Thr Asn Asp Tyr Met Gln Pro Glu
1               5                   10                  15

Glu Asp Trp Asp Arg Asp Leu Leu Leu Asp Pro Ala Trp Glu Lys Gln
            20                  25                  30

Gln Arg Lys Thr Phe Thr Ala Trp Cys Asn Ser His Leu Arg Lys Ala
        35                  40                  45

Gly Thr Gln Ile Glu Asn Ile Glu Glu Asp Phe Arg Asp Gly Leu Lys
    50                  55                  60

Leu Met Leu Leu Leu Glu Val Ile Ser Gly Glu Arg Leu Ala Lys Pro
65                  70                  75                  80

Glu Arg Gly Lys Met Arg Val His Lys Ile Ser Asn Val Asn Lys Ala
                85                  90                  95

Leu Asp Phe Ile Ala Ser Lys Gly Val Lys Leu Val Ser Ile Gly Ala
            100                 105                 110

Glu Glu Ile Val Asp Gly Asn Val Lys Met Thr Leu Gly Met Ile Trp
        115                 120                 125

Thr Ile Ile Leu Arg Arg Asp Pro Pro Val Ala Thr Met Val Ser Lys
    130                 135                 140

Gly Glu Glu Leu Phe Thr Gly Val Val Pro Ile Leu Val Glu Leu Asp
145                 150                 155                 160

Gly Asp Val Asn Gly His Lys Phe Ser Val Ser Gly Glu Gly Glu Gly
                165                 170                 175

Asp Ala Thr Tyr Gly Lys Leu Thr Leu Lys Phe Ile Cys Thr Thr Gly
            180                 185                 190

Lys Leu Pro Val Pro Trp Pro Thr Leu Val Thr Thr Leu Thr Tyr Gly
        195                 200                 205

Val Gln Cys Phe Ser Arg Tyr Pro Asp His Met Lys Gln His Asp Phe
    210                 215                 220

Phe Lys Ser Ala Met Pro Glu Gly Tyr Val Gln Glu Arg Thr Ile Phe
```

```
                225                 230                 235                 240
        Phe Lys Asp Asp Gly Asn Tyr Lys Thr Arg Ala Glu Val Lys Phe Glu
                        245                 250                 255

Gly Asp Thr Leu Val Asn Arg Ile Glu Leu Lys Gly Ile Asp Phe Lys
                    260                 265                 270

Glu Asp Gly Asn Ile Leu Gly His Lys Leu Glu Tyr Asn Tyr Asn Ser
                    275                 280                 285

His Asn Val Tyr Ile Met Ala Asp Lys Gln Lys Asn Gly Ile Lys Val
                290                 295                 300

Asn Phe Lys Ile Arg His Asn Ile Glu Asp Gly Ser Val Gln Leu Ala
        305                 310                 315                 320

Asp His Tyr Gln Gln Asn Thr Pro Ile Gly Asp Gly Pro Val Leu Leu
                        325                 330                 335

Pro Asp Asn His Tyr Leu Ser Thr Gln Ser Ala Leu Ser Lys Asp Pro
                    340                 345                 350

Asn Glu Lys Arg Asp His Met Val Leu Leu Glu Phe Val Thr Ala Ala
                    355                 360                 365

Gly Ile Thr Leu Gly Met Asp Glu Leu Tyr Lys
                370                 375

<210> SEQ ID NO 130
<211> LENGTH: 3516
<212> TYPE: DNA
<213> ORGANISM: Artificial Sequence
<220> FEATURE:
<223> OTHER INFORMATION: EGFP-NFAT fusion
<220> FEATURE:
<221> NAME/KEY: CDS
<222> LOCATION: (1)..(3513)

<400> SEQUENCE: 130 atg gtg agc aag ggc gag gag ctg ttc acc ggg gtg gtg ccc atc ctg      48
Met Val Ser Lys Gly Glu Glu Leu Phe Thr Gly Val Val Pro Ile Leu
1               5                   10                  15 gtc gag ctg gac ggc gac gta aac ggc cac aag ttc agc gtg tcc ggc      96
Val Glu Leu Asp Gly Asp Val Asn Gly His Lys Phe Ser Val Ser Gly
                20                  25                  30 gag ggc gag ggc gat gcc acc tac ggc aag ctg acc ctg aag ttc atc     144
Glu Gly Glu Gly Asp Ala Thr Tyr Gly Lys Leu Thr Leu Lys Phe Ile
            35                  40                  45 tgc acc acc ggc aag ctg ccc gtg ccc tgg ccc acc ctc gtg acc acc     192
Cys Thr Thr Gly Lys Leu Pro Val Pro Trp Pro Thr Leu Val Thr Thr
        50                  55                  60 ctg acc tac ggc gtg cag tgc ttc agc cgc tac ccc gac cac atg aag     240
Leu Thr Tyr Gly Val Gln Cys Phe Ser Arg Tyr Pro Asp His Met Lys
65                  70                  75                  80 cag cac gac ttc ttc aag tcc gcc atg ccc gaa ggc tac gtc cag gag     288
Gln His Asp Phe Phe Lys Ser Ala Met Pro Glu Gly Tyr Val Gln Glu
                85                  90                  95 cgc acc atc ttc ttc aag gac gac ggc aac tac aag acc cgc gcc gag     336
Arg Thr Ile Phe Phe Lys Asp Asp Gly Asn Tyr Lys Thr Arg Ala Glu
            100                 105                 110 gtg aag ttc gag ggc gac acc ctg gtg aac cgc atc gag ctg aag ggc     384
Val Lys Phe Glu Gly Asp Thr Leu Val Asn Arg Ile Glu Leu Lys Gly
        115                 120                 125 atc gac ttc aag gag gac ggc aac atc ctg ggg cac aag ctg gag tac     432
Ile Asp Phe Lys Glu Asp Gly Asn Ile Leu Gly His Lys Leu Glu Tyr
    130                 135                 140 aac tac aac agc cac aac gtc tat atc atg gcc gac aag cag aag aac     480
```

```
                                                         -continued

Asn Tyr Asn Ser His Asn Val Tyr Ile Met Ala Asp Lys Gln Lys Asn
145                 150                 155                 160 ggc atc aag gtg aac ttc aag atc cgc cac aac atc gag gac ggc agc      528
Gly Ile Lys Val Asn Phe Lys Ile Arg His Asn Ile Glu Asp Gly Ser
                165                 170                 175 gtg cag ctc gcc gac cac tac cag cag aac acc ccc atc ggc gac ggc      576
Val Gln Leu Ala Asp His Tyr Gln Gln Asn Thr Pro Ile Gly Asp Gly
            180                 185                 190 ccc gtg ctg ctg ccc gac aac cac tac ctg agc acc cag tcc gcc ctg      624
Pro Val Leu Leu Pro Asp Asn His Tyr Leu Ser Thr Gln Ser Ala Leu
        195                 200                 205 agc aaa gac ccc aac gag aag cgc gat cac atg gtc ctg ctg gag ttc      672
Ser Lys Asp Pro Asn Glu Lys Arg Asp His Met Val Leu Leu Glu Phe
    210                 215                 220 gtg acc gcc gcc ggg atc act ctc ggc atg gac gag ctg tac aag tcc      720
Val Thr Ala Ala Gly Ile Thr Leu Gly Met Asp Glu Leu Tyr Lys Ser
225                 230                 235                 240 gga ctc aga tct cga gcc atg aac gcc ccc gag cgg cag ccc caa ccc      768
Gly Leu Arg Ser Arg Ala Met Asn Ala Pro Glu Arg Gln Pro Gln Pro
                245                 250                 255 gac ggc ggg gac gcc cca ggc cac gag cct ggg ggc agc ccc caa gac      816
Asp Gly Gly Asp Ala Pro Gly His Glu Pro Gly Gly Ser Pro Gln Asp
            260                 265                 270 gag ctt gac ttc tcc atc ctc ttc gac tat gag tat ttg aat ccg aac      864
Glu Leu Asp Phe Ser Ile Leu Phe Asp Tyr Glu Tyr Leu Asn Pro Asn
        275                 280                 285 gaa gaa gag ccg aat gca cat aag gtc gcc agc cca ccc tcc gga ccc      912
Glu Glu Glu Pro Asn Ala His Lys Val Ala Ser Pro Pro Ser Gly Pro
    290                 295                 300 gca tac ccc gat gat gta atg gac tat ggc ctc aag cca tac agc ccc      960
Ala Tyr Pro Asp Asp Val Met Asp Tyr Gly Leu Lys Pro Tyr Ser Pro
305                 310                 315                 320 ctt gct agt ctc tct ggc gag ccc ccc ggc cga ttc gga gag ccg gat     1008
Leu Ala Ser Leu Ser Gly Glu Pro Pro Gly Arg Phe Gly Glu Pro Asp
                325                 330                 335 agg gta ggg ccg cag aag ttt ctg agc gcg gcc aag cca gca ggg gcc     1056
Arg Val Gly Pro Gln Lys Phe Leu Ser Ala Ala Lys Pro Ala Gly Ala
            340                 345                 350 tcg ggc ctg agc cct cgg atc gag atc act ccg tcc cac gaa ctg atc     1104
Ser Gly Leu Ser Pro Arg Ile Glu Ile Thr Pro Ser His Glu Leu Ile
        355                 360                 365 cag gca gtg ggg ccc ctc cgc atg aga gac gcg ggc ctc ctg gtg gag     1152
Gln Ala Val Gly Pro Leu Arg Met Arg Asp Ala Gly Leu Leu Val Glu
    370                 375                 380 cag cct ccc ctg gcc ggg gtg gcc gcc agc ccc agg ttc acc ctg ccc     1200
Gln Pro Pro Leu Ala Gly Val Ala Ala Ser Pro Arg Phe Thr Leu Pro
385                 390                 395                 400 gtg ccc ggc ttc gag ggc tac cgc gag ccg ctt tgc ttg agc ccc gct     1248
Val Pro Gly Phe Glu Gly Tyr Arg Glu Pro Leu Cys Leu Ser Pro Ala
                405                 410                 415 agc agc ggc tcc tct gcc agc ttc att tct gac acc ttc tcc ccc tac     1296
Ser Ser Gly Ser Ser Ala Ser Phe Ile Ser Asp Thr Phe Ser Pro Tyr
            420                 425                 430 acc tcg ccc tgc gtc tcg ccc aat aac ggc ggg ccc gac gac ctg tgt     1344
Thr Ser Pro Cys Val Ser Pro Asn Asn Gly Gly Pro Asp Asp Leu Cys
        435                 440                 445 ccg cag ttt caa aac atc cct gct cat tat tcc ccc aga acc tcg cca     1392
Pro Gln Phe Gln Asn Ile Pro Ala His Tyr Ser Pro Arg Thr Ser Pro
    450                 455                 460
```

-continued

| | | |
|---|---|---|
| ata atg tca cct cga acc agc ctc gcc gag gac agc tgc ctg ggc cgc<br>Ile Met Ser Pro Arg Thr Ser Leu Ala Glu Asp Ser Cys Leu Gly Arg<br>465                    470                  475                480 | 1440 |
| cac tcg ccc gtg ccc cgt ccg gcc tcc cgc tcc tca tcg cct ggt gcc<br>His Ser Pro Val Pro Arg Pro Ala Ser Arg Ser Ser Ser Pro Gly Ala<br>                  485                  490                495 | 1488 |
| aag cgg agg cat tcg tgc gcc gag gcc ttg gtt gcc ctg ccg ccc gga<br>Lys Arg Arg His Ser Cys Ala Glu Ala Leu Val Ala Leu Pro Pro Gly<br>        500                  505                510 | 1536 |
| gcc tca ccc cag cgc tcc cgg agc ccc tcg ccg cag ccc tca tct cac<br>Ala Ser Pro Gln Arg Ser Arg Ser Pro Ser Pro Gln Pro Ser Ser His<br>515                    520                  525 | 1584 |
| gtg gca ccc cag gac cac ggc tcc ccg gct ggg tac ccc cct gtg gct<br>Val Ala Pro Gln Asp His Gly Ser Pro Ala Gly Tyr Pro Pro Val Ala<br>530                    535                  540 | 1632 |
| ggc tct gcc gtg atc atg gat gcc ctg aac agc ctc gcc acg gac tcg<br>Gly Ser Ala Val Ile Met Asp Ala Leu Asn Ser Leu Ala Thr Asp Ser<br>545                    550                  555                560 | 1680 |
| cct tgt ggg atc ccc ccc aag atg tgg aag acc agc cct gac ccc tcg<br>Pro Cys Gly Ile Pro Pro Lys Met Trp Lys Thr Ser Pro Asp Pro Ser<br>                  565                  570                575 | 1728 |
| ccg gtg tct gcc gcc cca tcc aag gcc ggc ctg cct cgc cac atc tac<br>Pro Val Ser Ala Ala Pro Ser Lys Ala Gly Leu Pro Arg His Ile Tyr<br>        580                  585                590 | 1776 |
| ccg gcc gtg gag ttc ctg ggg ccc tgc gag cag ggc gag agg aga aac<br>Pro Ala Val Glu Phe Leu Gly Pro Cys Glu Gln Gly Glu Arg Arg Asn<br>                  595                  600                605 | 1824 |
| tcg gct cca gaa tcc atc ctg ctg gtt ccg ccc act tgg ccc aag ccg<br>Ser Ala Pro Glu Ser Ile Leu Leu Val Pro Pro Thr Trp Pro Lys Pro<br>610                    615                  620 | 1872 |
| ctg gtg cct gcc att ccc atc tgc agc atc cca gtg act gca tcc ctc<br>Leu Val Pro Ala Ile Pro Ile Cys Ser Ile Pro Val Thr Ala Ser Leu<br>625                    630                  635                640 | 1920 |
| cct cca ctt gag tgg ccg ctg tcc agt cag tca ggc tct tac gag ctg<br>Pro Pro Leu Glu Trp Pro Leu Ser Ser Gln Ser Gly Ser Tyr Glu Leu<br>                  645                  650                655 | 1968 |
| cgg atc gag gtg cag ccc aag cca cat cac cgg gcc cac tat gag aca<br>Arg Ile Glu Val Gln Pro Lys Pro His His Arg Ala His Tyr Glu Thr<br>        660                  665                670 | 2016 |
| gaa ggc agc cga ggg gct gtc aaa gct cca act gga ggc cac cct gtg<br>Glu Gly Ser Arg Gly Ala Val Lys Ala Pro Thr Gly Gly His Pro Val<br>                  675                  680                685 | 2064 |
| gtt cag ctc cat ggc tac atg gaa aac aag cct ctg gga ctt cag atc<br>Val Gln Leu His Gly Tyr Met Glu Asn Lys Pro Leu Gly Leu Gln Ile<br>690                    695                  700 | 2112 |
| ttc att ggg aca gct gat gag cgg atc ctt aag ccg cac gcc ttc tac<br>Phe Ile Gly Thr Ala Asp Glu Arg Ile Leu Lys Pro His Ala Phe Tyr<br>705                    710                  715                720 | 2160 |
| cag gtg cac cga atc acg ggg aaa act gtc acc acc agc tat gag<br>Gln Val His Arg Ile Thr Gly Lys Thr Val Thr Thr Ser Tyr Glu<br>                  725                  730                735 | 2208 |
| aag ata gtg ggc aac acc aaa gtc ctg gag atc ccc ttg gag ccc aaa<br>Lys Ile Val Gly Asn Thr Lys Val Leu Glu Ile Pro Leu Glu Pro Lys<br>        740                  745                750 | 2256 |
| aac aac atg agg gca acc atc gac tgt gcg ggg atc ttg aag ctt aga<br>Asn Asn Met Arg Ala Thr Ile Asp Cys Ala Gly Ile Leu Lys Leu Arg<br>755                    760                  765 | 2304 |
| aac gcc gac att gag ctg cgg aaa ggc gag acg gac att gga aga aag<br>Asn Ala Asp Ile Glu Leu Arg Lys Gly Glu Thr Asp Ile Gly Arg Lys<br>770                    775                  780 | 2352 |

```
aac acg cgg gtg aga ctg gtt ttc cga gtt cac atc cca gag tcc agt      2400
Asn Thr Arg Val Arg Leu Val Phe Arg Val His Ile Pro Glu Ser Ser
785             790                 795                 800 ggc aga atc gtc tct tta cag act gca tct aac ccc atc gag tgc tcc      2448
Gly Arg Ile Val Ser Leu Gln Thr Ala Ser Asn Pro Ile Glu Cys Ser
            805                 810                 815 cag cga tct gct cac gag ctg ccc atg gtt gaa aga caa gac aca gac      2496
Gln Arg Ser Ala His Glu Leu Pro Met Val Glu Arg Gln Asp Thr Asp
        820                 825                 830 agc tgc ctg gtc tat ggc ggc cag caa atg atc ctc acg ggg cag aac      2544
Ser Cys Leu Val Tyr Gly Gly Gln Gln Met Ile Leu Thr Gly Gln Asn
    835                 840                 845 ttt aca tcc gag tcc aaa gtt gtg ttt act gag aag acc aca gat gga      2592
Phe Thr Ser Glu Ser Lys Val Val Phe Thr Glu Lys Thr Thr Asp Gly
850                 855                 860 cag caa att tgg gag atg gaa gcc acg gtg gat aag gac aag agc cag      2640
Gln Gln Ile Trp Glu Met Glu Ala Thr Val Asp Lys Asp Lys Ser Gln
865                 870                 875                 880 ccc aac atg ctt ttt gtt gag atc cct gaa tat cgg aac aag cat atc      2688
Pro Asn Met Leu Phe Val Glu Ile Pro Glu Tyr Arg Asn Lys His Ile
                885                 890                 895 cgc aca cct gta aaa gtg aac ttc tac gtc atc aat ggg aag aga aaa      2736
Arg Thr Pro Val Lys Val Asn Phe Tyr Val Ile Asn Gly Lys Arg Lys
            900                 905                 910 cga agt cag cct cag cac ttt acc tac cac cca gtc cca gcc atc aag      2784
Arg Ser Gln Pro Gln His Phe Thr Tyr His Pro Val Pro Ala Ile Lys
        915                 920                 925 acg gag ccc acg gat gaa tat gac ccc act ctg atc tgc agc ccc acc      2832
Thr Glu Pro Thr Asp Glu Tyr Asp Pro Thr Leu Ile Cys Ser Pro Thr
    930                 935                 940 cat gga ggc ctg ggg agc cag cct tac tac ccc cag cac ccg atg gtg      2880
His Gly Gly Leu Gly Ser Gln Pro Tyr Tyr Pro Gln His Pro Met Val
945                 950                 955                 960 gcc gag tcc ccc tcc tgc ctc gtg gcc acc atg gct ccc tgc cag cag      2928
Ala Glu Ser Pro Ser Cys Leu Val Ala Thr Met Ala Pro Cys Gln Gln
                965                 970                 975 ttc cgc acg ggg ctc tca tcc cct gac gcc cgc tac cag caa cag aac      2976
Phe Arg Thr Gly Leu Ser Ser Pro Asp Ala Arg Tyr Gln Gln Gln Asn
            980                 985                 990 cca gcg gcc gta ctc tac cag cgg  agc aag agc ctg agc  ccc agc ctg    3024
Pro Ala Ala Val Leu Tyr Gln Arg  Ser Lys Ser Leu Ser  Pro Ser Leu
        995                 1000                1005 ctg ggc  tat cag cag ccg gcc  ctc atg gcc gcc ccg  ctg tcc ctt       3069
Leu Gly  Tyr Gln Gln Pro Ala  Leu Met Ala Ala Pro  Leu Ser Leu
    1010                1015                1020 gcg gac  gct cac cgc tct gtg  ctg gtg cac gcc ggc  tcc cag ggc       3114
Ala Asp  Ala His Arg Ser Val  Leu Val His Ala Gly  Ser Gln Gly
1025                1030                1035 cag agc  tca gcc ctg ctc cac  ccc tct ccg acc aac  cag cag gcc       3159
Gln Ser  Ser Ala Leu Leu His  Pro Ser Pro Thr Asn  Gln Gln Ala
    1040                1045                1050 tcg cct  gtg atc cac tac tca  ccc acc aac cag cag  ctg cgc tgc       3204
Ser Pro  Val Ile His Tyr Ser  Pro Thr Asn Gln Gln  Leu Arg Cys
    1055                1060                1065 gga agc  cac cag gag ttc cag  cac atc atg tac tgc  gag aat ttc       3249
Gly Ser  His Gln Glu Phe Gln  His Ile Met Tyr Cys  Glu Asn Phe
    1070                1075                1080 gca cca  ggc acc acc aga cct  ggc ccg ccc ccg gtc  agt caa ggt       3294
Ala Pro  Gly Thr Thr Arg Pro  Gly Pro Pro Pro Val  Ser Gln Gly
```

-continued

```
                    1085                 1090                  1095
cag  agg  ctg  agc  ccg  ggt  tcc  tac  ccc  aca  gtc  att  cag  cag  cag     3339
Gln  Arg  Leu  Ser  Pro  Gly  Ser  Tyr  Pro  Thr  Val  Ile  Gln  Gln  Gln
     1100                 1105                 1110 aat  gcc  acg  agc  caa  aga  gcc  gcc  aaa  aac  gga  ccc  ccg  gtc  agt     3384
Asn  Ala  Thr  Ser  Gln  Arg  Ala  Ala  Lys  Asn  Gly  Pro  Pro  Val  Ser
     1115                 1120                 1125 gac  caa  aag  gaa  gta  tta  cct  gcg  ggg  gtg  acc  att  aaa  cag  gag     3429
Asp  Gln  Lys  Glu  Val  Leu  Pro  Ala  Gly  Val  Thr  Ile  Lys  Gln  Glu
     1130                 1135                 1140 cag  aac  ttg  gac  cag  acc  tac  ttg  gat  gat  gtt  aat  gaa  att  atc     3474
Gln  Asn  Leu  Asp  Gln  Thr  Tyr  Leu  Asp  Asp  Val  Asn  Glu  Ile  Ile
     1145                 1150                 1155 agg  aag  gag  ttt  tca  gga  cct  cct  gcc  aga  aat  cag  acg  taa           3516
Arg  Lys  Glu  Phe  Ser  Gly  Pro  Pro  Ala  Arg  Asn  Gln  Thr
     1160                 1165                 1170
```

<210> SEQ ID NO 131
<211> LENGTH: 1171
<212> TYPE: PRT
<213> ORGANISM: Artificial Sequence
<220> FEATURE:
<223> OTHER INFORMATION: EGFP-NFAT fusion

<400> SEQUENCE: 131

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
        50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Ser
225                 230                 235                 240

Gly Leu Arg Ser Arg Ala Met Asn Ala Pro Glu Arg Gln Pro Gln Pro
                245                 250                 255
```

-continued

```
Asp Gly Gly Asp Ala Pro Gly His Glu Pro Gly Ser Pro Gln Asp
            260                 265                 270

Glu Leu Asp Phe Ser Ile Leu Phe Asp Tyr Glu Tyr Leu Asn Pro Asn
            275                 280                 285

Glu Glu Glu Pro Asn Ala His Lys Val Ala Ser Pro Ser Gly Pro
            290                 295                 300

Ala Tyr Pro Asp Asp Val Met Asp Tyr Gly Leu Lys Pro Tyr Ser Pro
305                 310                 315                 320

Leu Ala Ser Leu Ser Gly Glu Pro Pro Gly Arg Phe Gly Glu Pro Asp
                325                 330                 335

Arg Val Gly Pro Gln Lys Phe Leu Ser Ala Lys Pro Ala Gly Ala
            340                 345                 350

Ser Gly Leu Ser Pro Arg Ile Glu Ile Thr Pro Ser His Glu Leu Ile
            355                 360                 365

Gln Ala Val Gly Pro Leu Arg Met Arg Asp Ala Gly Leu Leu Val Glu
            370                 375                 380

Gln Pro Pro Leu Ala Gly Val Ala Ala Ser Pro Arg Phe Thr Leu Pro
385                 390                 395                 400

Val Pro Gly Phe Glu Gly Tyr Arg Glu Pro Leu Cys Leu Ser Pro Ala
                405                 410                 415

Ser Ser Gly Ser Ser Ala Ser Phe Ile Ser Asp Thr Phe Ser Pro Tyr
                420                 425                 430

Thr Ser Pro Cys Val Ser Pro Asn Asn Gly Gly Pro Asp Asp Leu Cys
            435                 440                 445

Pro Gln Phe Gln Asn Ile Pro Ala His Tyr Ser Pro Arg Thr Ser Pro
450                 455                 460

Ile Met Ser Pro Arg Thr Ser Leu Ala Glu Asp Ser Cys Leu Gly Arg
465                 470                 475                 480

His Ser Pro Val Pro Arg Pro Ala Ser Arg Ser Ser Pro Gly Ala
            485                 490                 495

Lys Arg Arg His Ser Cys Ala Glu Ala Leu Val Ala Leu Pro Pro Gly
            500                 505                 510

Ala Ser Pro Gln Arg Ser Arg Ser Pro Ser Pro Gln Pro Ser Ser His
            515                 520                 525

Val Ala Pro Gln Asp His Gly Ser Pro Ala Gly Tyr Pro Pro Val Ala
            530                 535                 540

Gly Ser Ala Val Ile Met Asp Ala Leu Asn Ser Leu Ala Thr Asp Ser
545                 550                 555                 560

Pro Cys Gly Ile Pro Pro Lys Met Trp Lys Thr Ser Pro Asp Pro Ser
                565                 570                 575

Pro Val Ser Ala Ala Pro Ser Lys Ala Gly Leu Pro Arg His Ile Tyr
            580                 585                 590

Pro Ala Val Glu Phe Leu Gly Pro Cys Glu Gln Gly Glu Arg Arg Asn
            595                 600                 605

Ser Ala Pro Glu Ser Ile Leu Leu Val Pro Pro Thr Trp Pro Lys Pro
            610                 615                 620

Leu Val Pro Ala Ile Pro Ile Cys Ser Ile Pro Val Thr Ala Ser Leu
625                 630                 635                 640

Pro Pro Leu Glu Trp Pro Leu Ser Ser Gln Ser Gly Ser Tyr Glu Leu
                645                 650                 655

Arg Ile Glu Val Gln Pro Lys Pro His His Arg Ala His Tyr Glu Thr
            660                 665                 670
```

-continued

```
Glu Gly Ser Arg Gly Ala Val Lys Ala Pro Thr Gly His Pro Val
            675                 680                 685

Val Gln Leu His Gly Tyr Met Glu Asn Lys Pro Leu Gly Leu Gln Ile
        690                 695                 700

Phe Ile Gly Thr Ala Asp Glu Arg Ile Leu Lys Pro His Ala Phe Tyr
705                 710                 715                 720

Gln Val His Arg Ile Thr Gly Lys Thr Val Thr Thr Ser Tyr Glu
                725                 730                 735

Lys Ile Val Gly Asn Thr Lys Val Leu Glu Ile Pro Leu Glu Pro Lys
                740                 745                 750

Asn Asn Met Arg Ala Thr Ile Asp Cys Ala Gly Ile Leu Lys Leu Arg
            755                 760                 765

Asn Ala Asp Ile Glu Leu Arg Lys Gly Glu Thr Asp Ile Gly Arg Lys
770                 775                 780

Asn Thr Arg Val Arg Leu Val Phe Arg Val His Ile Pro Glu Ser Ser
785                 790                 795                 800

Gly Arg Ile Val Ser Leu Gln Thr Ala Ser Asn Pro Ile Glu Cys Ser
                805                 810                 815

Gln Arg Ser Ala His Glu Leu Pro Met Val Glu Arg Gln Asp Thr Asp
                820                 825                 830

Ser Cys Leu Val Tyr Gly Gly Gln Met Ile Leu Thr Gly Gln Asn
            835                 840                 845

Phe Thr Ser Glu Ser Lys Val Val Phe Thr Glu Lys Thr Thr Asp Gly
850                 855                 860

Gln Gln Ile Trp Glu Met Glu Ala Thr Val Asp Lys Asp Lys Ser Gln
865                 870                 875                 880

Pro Asn Met Leu Phe Val Glu Ile Pro Glu Tyr Arg Asn Lys His Ile
                885                 890                 895

Arg Thr Pro Val Lys Val Asn Phe Tyr Val Ile Asn Gly Lys Arg Lys
            900                 905                 910

Arg Ser Gln Pro Gln His Phe Thr Tyr His Pro Val Pro Ala Ile Lys
        915                 920                 925

Thr Glu Pro Thr Asp Glu Tyr Asp Pro Thr Leu Ile Cys Ser Pro Thr
930                 935                 940

His Gly Gly Leu Gly Ser Gln Pro Tyr Tyr Pro Gln His Pro Met Val
945                 950                 955                 960

Ala Glu Ser Pro Ser Cys Leu Val Ala Thr Met Ala Pro Cys Gln Gln
                965                 970                 975

Phe Arg Thr Gly Leu Ser Ser Pro Asp Ala Arg Tyr Gln Gln Gln Asn
            980                 985                 990

Pro Ala Ala Val Leu Tyr Gln Arg  Ser Lys Ser Leu Ser  Pro Ser Leu
        995                 1000                1005

Leu Gly  Tyr Gln Gln Pro Ala  Leu Met Ala Ala Pro  Leu Ser Leu
        1010                1015                1020

Ala Asp  Ala His Arg Ser Val  Leu Val His Ala Gly  Ser Gln Gly
        1025                1030                1035

Gln Ser  Ser Ala Leu Leu His  Pro Ser Pro Thr Asn  Gln Gln Ala
        1040                1045                1050

Ser Pro  Val Ile His Tyr Ser  Pro Thr Asn Gln Gln  Leu Arg Cys
        1055                1060                1065

Gly Ser  His Gln Glu Phe Gln  His Ile Met Tyr Cys  Glu Asn Phe
        1070                1075                1080

Ala Pro  Gly Thr Thr Arg Pro  Gly Pro Pro Val  Ser Gln Gly
```

-continued

```
                    1085                 1090                 1095
Gln Arg Leu Ser Pro Gly Ser Tyr Pro Thr Val Ile Gln Gln Gln
    1100                1105                1110

Asn Ala Thr Ser Gln Arg Ala Ala Lys Asn Gly Pro Pro Val Ser
    1115                1120                1125

Asp Gln Lys Glu Val Leu Pro Ala Gly Val Thr Ile Lys Gln Glu
    1130                1135                1140

Gln Asn Leu Asp Gln Thr Tyr Leu Asp Asp Val Asn Glu Ile Ile
    1145                1150                1155

Arg Lys Glu Phe Ser Gly Pro Pro Ala Arg Asn Gln Thr
    1160                1165                1170

<210> SEQ ID NO 132
<211> LENGTH: 3546
<212> TYPE: DNA
<213> ORGANISM: Artificial Sequence
<220> FEATURE:
<223> OTHER INFORMATION: NFAT-EGFP fusion
<220> FEATURE:
<221> NAME/KEY: CDS
<222> LOCATION: (1)..(3543)

<400> SEQUENCE: 132 atg aac gcc ccc gag cgg cag ccc caa ccc gac ggc ggg gac gcc cca        48
Met Asn Ala Pro Glu Arg Gln Pro Gln Pro Asp Gly Gly Asp Ala Pro
1               5                   10                  15 ggc cac gag cct ggg ggc agc ccc caa gac gag ctt gac ttc tcc atc        96
Gly His Glu Pro Gly Gly Ser Pro Gln Asp Glu Leu Asp Phe Ser Ile
                20                  25                  30 ctc ttc gac tat gag tat ttg aat ccg aac gaa gaa gag ccg aat gca       144
Leu Phe Asp Tyr Glu Tyr Leu Asn Pro Asn Glu Glu Glu Pro Asn Ala
            35                  40                  45 cat aag gtc gcc agc cca ccc tcc gga ccc gca tac ccc gat gat gta       192
His Lys Val Ala Ser Pro Pro Ser Gly Pro Ala Tyr Pro Asp Asp Val
        50                  55                  60 atg gac tat ggc ctc aag cca tac agc ccc ctt gct agt ctc tct ggc       240
Met Asp Tyr Gly Leu Lys Pro Tyr Ser Pro Leu Ala Ser Leu Ser Gly
65                  70                  75                  80 gag ccc ccc ggc cga ttc gga gag ccg gat agg gta ggg ccg cag aag       288
Glu Pro Pro Gly Arg Phe Gly Glu Pro Asp Arg Val Gly Pro Gln Lys
                85                  90                  95 ttt ctg agc gcg gcc aag cca gca ggg gcc tcg ggc ctg agc cct cgg       336
Phe Leu Ser Ala Ala Lys Pro Ala Gly Ala Ser Gly Leu Ser Pro Arg
                100                 105                 110 atc gag atc act ccg tcc cac gaa ctg atc cag gca gtg ggg ccc ctc       384
Ile Glu Ile Thr Pro Ser His Glu Leu Ile Gln Ala Val Gly Pro Leu
            115                 120                 125 cgc atg aga gac gcg ggc ctc ctg gtg gag cag cct ccc ctg gcc ggg       432
Arg Met Arg Asp Ala Gly Leu Leu Val Glu Gln Pro Pro Leu Ala Gly
        130                 135                 140 gtg gcc gcc agc ccg agg ttc acc ctg ccc gtg ccc ggc ttc gag ggc       480
Val Ala Ala Ser Pro Arg Phe Thr Leu Pro Val Pro Gly Phe Glu Gly
145                 150                 155                 160 tac cgc gag ccg ctt tgc ttg agc ccc gct agc agc ggc tcc tct gcc       528
Tyr Arg Glu Pro Leu Cys Leu Ser Pro Ala Ser Ser Gly Ser Ser Ala
                165                 170                 175 agc ttc att tct gac acc ttc tcc ccc tac acc tcg ccc tgc gtc tcg       576
Ser Phe Ile Ser Asp Thr Phe Ser Pro Tyr Thr Ser Pro Cys Val Ser
                180                 185                 190 ccc aat aac ggc ggg ccc gac gac ctg tgt ccg cag ttt caa aac atc       624
```

```
                Pro Asn Asn Gly Gly Pro Asp Asp Leu Cys Pro Gln Phe Gln Asn Ile
                        195                 200                 205 cct gct cat tat tcc ccc aga acc tcg cca ata atg tca cct cga acc        672
Pro Ala His Tyr Ser Pro Arg Thr Ser Pro Ile Met Ser Pro Arg Thr
210                 215                 220 agc ctc gcc gag gac agc tgc ctg ggc cgc cac tcg ccc gtg ccc cgt        720
Ser Leu Ala Glu Asp Ser Cys Leu Gly Arg His Ser Pro Val Pro Arg
225                 230                 235                 240 ccg gcc tcc cgc tcc tca tcg cct ggt gcc aag cgg agg cat tcg tgc        768
Pro Ala Ser Arg Ser Ser Ser Pro Gly Ala Lys Arg Arg His Ser Cys
                245                 250                 255 gcc gag gcc ttg gtt gcc ctg ccg ccc gga gcc tca ccc cag cgc tcc        816
Ala Glu Ala Leu Val Ala Leu Pro Pro Gly Ala Ser Pro Gln Arg Ser
                260                 265                 270 cgg agc ccc tcg ccg cag ccc tca tct cac gtg gca ccc cag gac cac        864
Arg Ser Pro Ser Pro Gln Pro Ser Ser His Val Ala Pro Gln Asp His
            275                 280                 285 ggc tcc ccg gct ggg tac ccc cct gtg gct ggc tct gcc gtg atc atg        912
Gly Ser Pro Ala Gly Tyr Pro Pro Val Ala Gly Ser Ala Val Ile Met
        290                 295                 300 gat gcc ctg aac agc ctc gcc acg gac tcg cct tgt ggg atc ccc ccc        960
Asp Ala Leu Asn Ser Leu Ala Thr Asp Ser Pro Cys Gly Ile Pro Pro
305                 310                 315                 320 aag atg tgg aag acc agc cct gac ccc tcg ccg gtg tct gcc gcc cca       1008
Lys Met Trp Lys Thr Ser Pro Asp Pro Ser Pro Val Ser Ala Ala Pro
                325                 330                 335 tcc aag gcc ggc ctg cct cgc cac atc tac ccg gcc gtg gag ttc ctg       1056
Ser Lys Ala Gly Leu Pro Arg His Ile Tyr Pro Ala Val Glu Phe Leu
                340                 345                 350 ggg ccc tgc gag cag ggc gag agg aga aac tcg gct cca gaa tcc atc       1104
Gly Pro Cys Glu Gln Gly Glu Arg Arg Asn Ser Ala Pro Glu Ser Ile
            355                 360                 365 ctg ctg gtt ccg ccc act tgg ccc aag ccg ctg gtg cct gcc att ccc       1152
Leu Leu Val Pro Pro Thr Trp Pro Lys Pro Leu Val Pro Ala Ile Pro
370                 375                 380 atc tgc agc atc cca gtg act gca tcc ctc cct cca ctt gag tgg ccg       1200
Ile Cys Ser Ile Pro Val Thr Ala Ser Leu Pro Pro Leu Glu Trp Pro
385                 390                 395                 400 ctg tcc agt cag tca ggc tct tac gag ctg cgg atc gag gtg cag ccc       1248
Leu Ser Ser Gln Ser Gly Ser Tyr Glu Leu Arg Ile Glu Val Gln Pro
                405                 410                 415 aag cca cat cac cgg gcc cac tat gag aca gaa ggc agc cga ggg gct       1296
Lys Pro His His Arg Ala His Tyr Glu Thr Glu Gly Ser Arg Gly Ala
                420                 425                 430 gtc aaa gct cca act gga ggc cac cct gtg gtt cag ctc cat ggc tac       1344
Val Lys Ala Pro Thr Gly Gly His Pro Val Val Gln Leu His Gly Tyr
            435                 440                 445 atg gaa aac aag cct ctg gga ctt cag atc ttc att ggg aca gct gat       1392
Met Glu Asn Lys Pro Leu Gly Leu Gln Ile Phe Ile Gly Thr Ala Asp
        450                 455                 460 gag cgg atc ctt aag ccg cac gcc ttc tac cag gtg cac cga atc acg       1440
Glu Arg Ile Leu Lys Pro His Ala Phe Tyr Gln Val His Arg Ile Thr
465                 470                 475                 480 ggg aaa act gtc acc acc acc agc tat gag aag ata gtg ggc aac acc       1488
Gly Lys Thr Val Thr Thr Thr Ser Tyr Glu Lys Ile Val Gly Asn Thr
                485                 490                 495 aaa gtc ctg gag atc ccc ttg gag ccc aaa aac aac atg agg gca acc       1536
Lys Val Leu Glu Ile Pro Leu Glu Pro Lys Asn Asn Met Arg Ala Thr
                500                 505                 510
```

```
atc gac tgt gcg ggg atc ttg aag ctt aga aac gcc gac att gag ctg      1584
Ile Asp Cys Ala Gly Ile Leu Lys Leu Arg Asn Ala Asp Ile Glu Leu
            515                 520                 525 cgg aaa ggc gag acg gac att gga aga aag aac acg cgg gtg aga ctg      1632
Arg Lys Gly Glu Thr Asp Ile Gly Arg Lys Asn Thr Arg Val Arg Leu
    530                 535                 540 gtt ttc cga gtt cac atc cca gag tcc agt ggc aga atc gtc tct tta      1680
Val Phe Arg Val His Ile Pro Glu Ser Ser Gly Arg Ile Val Ser Leu
545                 550                 555                 560 cag act gca tct aac ccc atc gag tgc tcc cag cga tct gct cac gag      1728
Gln Thr Ala Ser Asn Pro Ile Glu Cys Ser Gln Arg Ser Ala His Glu
                565                 570                 575 ctg ccc atg gtt gaa aga caa gac aca gac agc tgc ctg gtc tat ggc      1776
Leu Pro Met Val Glu Arg Gln Asp Thr Asp Ser Cys Leu Val Tyr Gly
            580                 585                 590 ggc cag caa atg atc ctc acg ggg cag aac ttt aca tcc gag tcc aaa      1824
Gly Gln Gln Met Ile Leu Thr Gly Gln Asn Phe Thr Ser Glu Ser Lys
    595                 600                 605 gtt gtg ttt act gag aag acc aca gat gga cag caa att tgg gag atg      1872
Val Val Phe Thr Glu Lys Thr Thr Asp Gly Gln Gln Ile Trp Glu Met
610                 615                 620 gaa gcc acg gtg gat aag gac aag agc cag ccc aac atg ctt ttt gtt      1920
Glu Ala Thr Val Asp Lys Asp Lys Ser Gln Pro Asn Met Leu Phe Val
625                 630                 635                 640 gag atc cct gaa tat cgg aac aag cat atc cgc aca cct gta aaa gtg      1968
Glu Ile Pro Glu Tyr Arg Asn Lys His Ile Arg Thr Pro Val Lys Val
                645                 650                 655 aac ttc tac gtc atc aat ggg aag aga aaa cga agt cag cct cag cac      2016
Asn Phe Tyr Val Ile Asn Gly Lys Arg Lys Arg Ser Gln Pro Gln His
            660                 665                 670 ttt acc tac cac cca gtc cca gcc atc aag acg gag ccc acg gat gaa      2064
Phe Thr Tyr His Pro Val Pro Ala Ile Lys Thr Glu Pro Thr Asp Glu
    675                 680                 685 tat gac ccc act ctg atc tgc agc ccc acc cat gga ggc ctg ggg agc      2112
Tyr Asp Pro Thr Leu Ile Cys Ser Pro Thr His Gly Gly Leu Gly Ser
690                 695                 700 cag cct tac tac ccc cag cac ccg atg gtg gcc gag tcc ccc tcc tgc      2160
Gln Pro Tyr Tyr Pro Gln His Pro Met Val Ala Glu Ser Pro Ser Cys
705                 710                 715                 720 ctc gtg gcc acc atg gct ccc tgc cag cag ttc cgc acg ggg ctc tca      2208
Leu Val Ala Thr Met Ala Pro Cys Gln Gln Phe Arg Thr Gly Leu Ser
                725                 730                 735 tcc cct gac gcc cgc tac cag caa cag aac cca gcg gcc gta ctc tac      2256
Ser Pro Asp Ala Arg Tyr Gln Gln Gln Asn Pro Ala Ala Val Leu Tyr
            740                 745                 750 cag cgg agc aag agc ctg agc ccc agc ctg ctg ggc tat cag cag ccg      2304
Gln Arg Ser Lys Ser Leu Ser Pro Ser Leu Leu Gly Tyr Gln Gln Pro
    755                 760                 765 gcc ctc atg gcc gcc ccg ctg tcc ctt gcg gac gct cac cgc tct gtg      2352
Ala Leu Met Ala Ala Pro Leu Ser Leu Ala Asp Ala His Arg Ser Val
770                 775                 780 ctg gtg cac gcc ggc tcc cag ggc cag agc tca gcc ctg ctc cac ccc      2400
Leu Val His Ala Gly Ser Gln Gly Gln Ser Ser Ala Leu Leu His Pro
785                 790                 795                 800 tct ccg acc aac cag cag gcc tcg cct gtg atc cac tac tca ccc acc      2448
Ser Pro Thr Asn Gln Gln Ala Ser Pro Val Ile His Tyr Ser Pro Thr
                805                 810                 815 aac cag cag ctg cgc tgc gga agc cac cag gag ttc cag cac atc atg      2496
Asn Gln Gln Leu Arg Cys Gly Ser His Gln Glu Phe Gln His Ile Met
            820                 825                 830
```

-continued

```
tac tgc gag aat ttc gca cca ggc acc acc aga cct ggc ccg ccc ccg      2544
Tyr Cys Glu Asn Phe Ala Pro Gly Thr Thr Arg Pro Gly Pro Pro Pro
        835                 840                 845 gtc agt caa ggt cag agg ctg agc ccg gtt tcc tac ccc aca gtc att      2592
Val Ser Gln Gly Gln Arg Leu Ser Pro Gly Ser Pro Thr Val Ile
850                 855                 860 cag cag cag aat gcc acg agc caa aga gcc gcc aaa aac gga ccc ccg      2640
Gln Gln Gln Asn Ala Thr Ser Gln Arg Ala Ala Lys Asn Gly Pro Pro
865                 870                 875                 880 gtc agt gac caa aag gaa gta tta cct gcg ggg gtg acc att aaa cag      2688
Val Ser Asp Gln Lys Glu Val Leu Pro Ala Gly Val Thr Ile Lys Gln
            885                 890                 895 gag cag aac ttg gac cag acc tac ttg gat gat gtt aat gaa att atc      2736
Glu Gln Asn Leu Asp Gln Thr Tyr Leu Asp Asp Val Asn Glu Ile Ile
                900                 905                 910 agg aag gag ttt tca gga cct cct gcc aga aat cag acg aga att ctg      2784
Arg Lys Glu Phe Ser Gly Pro Pro Ala Arg Asn Gln Thr Arg Ile Leu
            915                 920                 925 cag tcg acg gta ccg cgg gcc cgg gat cca ccg gtc gcc acc atg gtg      2832
Gln Ser Thr Val Pro Arg Ala Arg Asp Pro Pro Val Ala Thr Met Val
930                 935                 940 agc aag ggc gag gag ctg ttc acc ggg gtg gtg ccc atc ctg gtc gag      2880
Ser Lys Gly Glu Glu Leu Phe Thr Gly Val Val Pro Ile Leu Val Glu
945                 950                 955                 960 ctg gac ggc gac gta aac ggc cac aag ttc agc gtg tcc ggc gag ggc      2928
Leu Asp Gly Asp Val Asn Gly His Lys Phe Ser Val Ser Gly Glu Gly
                965                 970                 975 gag ggc gat gcc acc tac ggc aag ctg acc ctg aag ttc atc tgc acc      2976
Glu Gly Asp Ala Thr Tyr Gly Lys Leu Thr Leu Lys Phe Ile Cys Thr
            980                 985                 990 acc ggc aag ctg ccc gtg ccc tgg ccc acc ctc gtg acc acc ctg acc      3024
Thr Gly Lys Leu Pro Val Pro Trp Pro Thr Leu Val Thr Thr Leu Thr
        995                 1000                1005 tac ggc gtg cag tgc ttc agc cgc tac ccc gac cac atg aag cag         3069
Tyr Gly Val Gln Cys Phe Ser Arg Tyr Pro Asp His Met Lys Gln
        1010                1015                1020 cac gac ttc ttc aag tcc gcc atg ccc gaa ggc tac gtc cag gag         3114
His Asp Phe Phe Lys Ser Ala Met Pro Glu Gly Tyr Val Gln Glu
    1025                1030                1035 cgc acc atc ttc ttc aag gac gac ggc aac tac aag acc cgc gcc         3159
Arg Thr Ile Phe Phe Lys Asp Asp Gly Asn Tyr Lys Thr Arg Ala
    1040                1045                1050 gag gtg aag ttc gag ggc gac acc ctg gtg aac cgc atc gag ctg         3204
Glu Val Lys Phe Glu Gly Asp Thr Leu Val Asn Arg Ile Glu Leu
    1055                1060                1065 aag ggc atc gac ttc aag gag gac ggc aac atc ctg ggg cac aag         3249
Lys Gly Ile Asp Phe Lys Glu Asp Gly Asn Ile Leu Gly His Lys
    1070                1075                1080 ctg gag tac aac tac aac agc cac aac gtc tat atc atg gcc gac         3294
Leu Glu Tyr Asn Tyr Asn Ser His Asn Val Tyr Ile Met Ala Asp
    1085                1090                1095 aag cag aag aac ggc atc aag gtg aac ttc aag atc cgc cac aac         3339
Lys Gln Lys Asn Gly Ile Lys Val Asn Phe Lys Ile Arg His Asn
    1100                1105                1110 atc gag gac ggc agc gtg cag ctc gcc gac cac tac cag cag aac         3384
Ile Glu Asp Gly Ser Val Gln Leu Ala Asp His Tyr Gln Gln Asn
    1115                1120                1125 acc ccc atc ggc gac ggc ccc gtg ctg ctg ccc gac aac cac tac         3429
Thr Pro Ile Gly Asp Gly Pro Val Leu Leu Pro Asp Asn His Tyr
```

-continued

```
                1130                1135                1140
ctg agc  acc cag tcc gcc ctg  agc aaa gac ccc aac  gag aag cgc        3474
Leu Ser  Thr Gln Ser Ala Leu  Ser Lys Asp Pro Asn  Glu Lys Arg
    1145                 1150                 1155 gat cac  atg gtc ctg ctg gag  ttc gtg acc gcc gcc  ggg atc act        3519
Asp His  Met Val Leu Leu Glu  Phe Val Thr Ala Ala  Gly Ile Thr
    1160                 1165                 1170 ctc ggc  atg gac gag ctg tac  aag taa                                 3546
Leu Gly  Met Asp Glu Leu Tyr  Lys
    1175                 1180
```

<210> SEQ ID NO 133
<211> LENGTH: 1181
<212> TYPE: PRT
<213> ORGANISM: Artificial Sequence
<220> FEATURE:
<223> OTHER INFORMATION: NFAT-EGFP fusion

<400> SEQUENCE: 133

```
Met Asn Ala Pro Glu Arg Gln Pro Gln Pro Asp Gly Gly Asp Ala Pro
1               5                   10                  15

Gly His Glu Pro Gly Gly Ser Pro Gln Asp Glu Leu Asp Phe Ser Ile
            20                  25                  30

Leu Phe Asp Tyr Glu Tyr Leu Asn Pro Asn Glu Glu Pro Asn Ala
        35                  40                  45

His Lys Val Ala Ser Pro Pro Ser Gly Pro Ala Tyr Pro Asp Asp Val
 50                  55                  60

Met Asp Tyr Gly Leu Lys Pro Tyr Ser Pro Leu Ala Ser Leu Ser Gly
65                  70                  75                  80

Glu Pro Pro Gly Arg Phe Gly Glu Pro Asp Arg Val Gly Pro Gln Lys
                85                  90                  95

Phe Leu Ser Ala Ala Lys Pro Ala Gly Ala Ser Gly Leu Ser Pro Arg
            100                 105                 110

Ile Glu Ile Thr Pro Ser His Glu Leu Ile Gln Ala Val Gly Pro Leu
        115                 120                 125

Arg Met Arg Asp Ala Gly Leu Leu Val Glu Gln Pro Pro Leu Ala Gly
130                 135                 140

Val Ala Ala Ser Pro Arg Phe Thr Leu Pro Val Pro Gly Phe Glu Gly
145                 150                 155                 160

Tyr Arg Glu Pro Leu Cys Leu Ser Pro Ala Ser Ser Gly Ser Ser Ala
                165                 170                 175

Ser Phe Ile Ser Asp Thr Phe Ser Pro Tyr Thr Ser Pro Cys Val Ser
            180                 185                 190

Pro Asn Asn Gly Gly Pro Asp Asp Leu Cys Pro Gln Phe Gln Asn Ile
        195                 200                 205

Pro Ala His Tyr Ser Pro Arg Thr Ser Pro Ile Met Ser Pro Arg Thr
210                 215                 220

Ser Leu Ala Glu Asp Ser Cys Leu Gly Arg His Ser Pro Val Pro Arg
225                 230                 235                 240

Pro Ala Ser Arg Ser Ser Ser Pro Gly Ala Lys Arg Arg His Ser Cys
                245                 250                 255

Ala Glu Ala Leu Val Ala Leu Pro Pro Gly Ala Ser Pro Gln Arg Ser
            260                 265                 270

Arg Ser Pro Ser Pro Gln Pro Ser Ser His Val Ala Pro Gln Asp His
        275                 280                 285

Gly Ser Pro Ala Gly Tyr Pro Pro Val Ala Gly Ser Ala Val Ile Met
```

```
              290                 295                 300
Asp Ala Leu Asn Ser Leu Ala Thr Asp Ser Pro Cys Gly Ile Pro Pro
305                 310                 315                 320
Lys Met Trp Lys Thr Ser Pro Asp Pro Ser Pro Val Ser Ala Ala Pro
                    325                 330                 335
Ser Lys Ala Gly Leu Pro Arg His Ile Tyr Pro Ala Val Glu Phe Leu
                    340                 345                 350
Gly Pro Cys Glu Gln Gly Glu Arg Arg Asn Ser Ala Pro Glu Ser Ile
                    355                 360                 365
Leu Leu Val Pro Pro Thr Trp Pro Lys Pro Leu Val Pro Ala Ile Pro
370                 375                 380
Ile Cys Ser Ile Pro Val Thr Ala Ser Leu Pro Pro Leu Glu Trp Pro
385                 390                 395                 400
Leu Ser Ser Gln Ser Gly Ser Tyr Glu Leu Arg Ile Glu Val Gln Pro
                    405                 410                 415
Lys Pro His His Arg Ala His Tyr Glu Thr Glu Gly Ser Arg Gly Ala
                    420                 425                 430
Val Lys Ala Pro Thr Gly Gly His Pro Val Val Gln Leu His Gly Tyr
                    435                 440                 445
Met Glu Asn Lys Pro Leu Gly Leu Gln Ile Phe Ile Gly Thr Ala Asp
450                 455                 460
Glu Arg Ile Leu Lys Pro His Ala Phe Tyr Gln Val His Arg Ile Thr
465                 470                 475                 480
Gly Lys Thr Val Thr Thr Thr Ser Tyr Glu Lys Ile Val Gly Asn Thr
                    485                 490                 495
Lys Val Leu Glu Ile Pro Leu Glu Pro Lys Asn Asn Met Arg Ala Thr
                    500                 505                 510
Ile Asp Cys Ala Gly Ile Leu Lys Leu Arg Asn Ala Asp Ile Glu Leu
                    515                 520                 525
Arg Lys Gly Glu Thr Asp Ile Gly Arg Lys Asn Thr Arg Val Arg Leu
530                 535                 540
Val Phe Arg Val His Ile Pro Glu Ser Ser Gly Arg Ile Val Ser Leu
545                 550                 555                 560
Gln Thr Ala Ser Asn Pro Ile Glu Cys Ser Gln Arg Ser Ala His Glu
                    565                 570                 575
Leu Pro Met Val Glu Arg Gln Asp Thr Asp Ser Cys Leu Val Tyr Gly
                    580                 585                 590
Gly Gln Gln Met Ile Leu Thr Gly Gln Asn Phe Thr Ser Glu Ser Lys
                    595                 600                 605
Val Val Phe Thr Glu Lys Thr Thr Asp Gly Gln Gln Ile Trp Glu Met
610                 615                 620
Glu Ala Thr Val Asp Lys Asp Lys Ser Gln Pro Asn Met Leu Phe Val
625                 630                 635                 640
Glu Ile Pro Glu Tyr Arg Asn Lys His Ile Arg Thr Pro Val Lys Val
                    645                 650                 655
Asn Phe Tyr Val Ile Asn Gly Lys Arg Lys Arg Ser Gln Pro Gln His
                    660                 665                 670
Phe Thr Tyr His Pro Val Pro Ala Ile Lys Thr Glu Pro Thr Asp Glu
                    675                 680                 685
Tyr Asp Pro Thr Leu Ile Cys Ser Pro Thr His Gly Gly Leu Gly Ser
                    690                 695                 700
Gln Pro Tyr Tyr Pro Gln His Pro Met Val Ala Glu Ser Pro Ser Cys
705                 710                 715                 720
```

-continued

Leu Val Ala Thr Met Ala Pro Cys Gln Gln Phe Arg Thr Gly Leu Ser
            725                 730                 735

Ser Pro Asp Ala Arg Tyr Gln Gln Asn Pro Ala Ala Val Leu Tyr
        740                 745                 750

Gln Arg Ser Lys Ser Leu Ser Pro Ser Leu Leu Gly Tyr Gln Gln Pro
            755                 760                 765

Ala Leu Met Ala Ala Pro Leu Ser Leu Ala Asp Ala His Arg Ser Val
        770                 775                 780

Leu Val His Ala Gly Ser Gln Gly Gln Ser Ser Ala Leu Leu His Pro
785                 790                 795                 800

Ser Pro Thr Asn Gln Gln Ala Ser Pro Val Ile His Tyr Ser Pro Thr
            805                 810                 815

Asn Gln Gln Leu Arg Cys Gly Ser His Gln Glu Phe Gln His Ile Met
            820                 825                 830

Tyr Cys Glu Asn Phe Ala Pro Gly Thr Thr Arg Pro Gly Pro Pro Pro
        835                 840                 845

Val Ser Gln Gly Gln Arg Leu Ser Pro Gly Ser Tyr Pro Thr Val Ile
    850                 855                 860

Gln Gln Gln Asn Ala Thr Ser Gln Arg Ala Ala Lys Asn Gly Pro Pro
865                 870                 875                 880

Val Ser Asp Gln Lys Glu Val Leu Pro Ala Gly Val Thr Ile Lys Gln
            885                 890                 895

Glu Gln Asn Leu Asp Gln Thr Tyr Leu Asp Asp Val Asn Glu Ile Ile
            900                 905                 910

Arg Lys Glu Phe Ser Gly Pro Pro Ala Arg Asn Gln Thr Arg Ile Leu
        915                 920                 925

Gln Ser Thr Val Pro Arg Ala Arg Asp Pro Pro Val Ala Thr Met Val
930                 935                 940

Ser Lys Gly Glu Glu Leu Phe Thr Gly Val Val Pro Ile Leu Val Glu
945                 950                 955                 960

Leu Asp Gly Asp Val Asn Gly His Lys Phe Ser Val Ser Gly Glu Gly
            965                 970                 975

Glu Gly Asp Ala Thr Tyr Gly Lys Leu Thr Leu Lys Phe Ile Cys Thr
        980                 985                 990

Thr Gly Lys Leu Pro Val Pro Trp Pro Thr Leu Val Thr Thr Leu Thr
    995                 1000                1005

Tyr Gly Val Gln Cys Phe Ser Arg Tyr Pro Asp His Met Lys Gln
    1010                1015                1020

His Asp Phe Phe Lys Ser Ala Met Pro Glu Gly Tyr Val Gln Glu
    1025                1030                1035

Arg Thr Ile Phe Phe Lys Asp Gly Asn Tyr Lys Thr Arg Ala
    1040                1045                1050

Glu Val Lys Phe Glu Gly Asp Thr Leu Val Asn Arg Ile Glu Leu
    1055                1060                1065

Lys Gly Ile Asp Phe Lys Glu Asp Gly Asn Ile Leu Gly His Lys
    1070                1075                1080

Leu Glu Tyr Asn Tyr Asn Ser His Asn Val Tyr Ile Met Ala Asp
    1085                1090                1095

Lys Gln Lys Asn Gly Ile Lys Val Asn Phe Lys Ile Arg His Asn
    1100                1105                1110

Ile Glu Asp Gly Ser Val Gln Leu Ala Asp His Tyr Gln Gln Asn
    1115                1120                1125

```
Thr Pro Ile Gly Asp Gly Pro Val Leu Leu Pro Asp Asn His Tyr
    1130            1135                1140

Leu Ser Thr Gln Ser Ala Leu Ser Lys Asp Pro Asn Glu Lys Arg
    1145            1150                1155

Asp His Met Val Leu Leu Glu Phe Val Thr Ala Ala Gly Ile Thr
    1160            1165                1170

Leu Gly Met Asp Glu Leu Tyr Lys
    1175            1180

<210> SEQ ID NO 134
<211> LENGTH: 2802
<212> TYPE: DNA
<213> ORGANISM: Artificial Sequence
<220> FEATURE:
<223> OTHER INFORMATION: EGFP-PKG fusion
<220> FEATURE:
<221> NAME/KEY: CDS
<222> LOCATION: (1)..(2799)

<400> SEQUENCE: 134 atg gtg agc aag ggc gag gag ctg ttc acc ggg gtg gtg ccc atc ctg     48
Met Val Ser Lys Gly Glu Glu Leu Phe Thr Gly Val Val Pro Ile Leu
1               5                   10                  15 gtc gag ctg gac ggc gac gta aac ggc cac aag ttc agc gtg tcc ggc     96
Val Glu Leu Asp Gly Asp Val Asn Gly His Lys Phe Ser Val Ser Gly
            20                  25                  30 gag ggc gag ggc gat gcc acc tac ggc aag ctg acc ctg aag ttc atc    144
Glu Gly Glu Gly Asp Ala Thr Tyr Gly Lys Leu Thr Leu Lys Phe Ile
        35                  40                  45 tgc acc acc ggc aag ctg ccc gtg ccc tgg ccc acc ctc gtg acc acc    192
Cys Thr Thr Gly Lys Leu Pro Val Pro Trp Pro Thr Leu Val Thr Thr
    50                  55                  60 ctg acc tac ggc gtg cag tgc ttc agc cgc tac ccc gac cac atg aag    240
Leu Thr Tyr Gly Val Gln Cys Phe Ser Arg Tyr Pro Asp His Met Lys
65                  70                  75                  80 cag cac gac ttc ttc aag tcc gcc atg ccc gaa ggc tac gtc cag gag    288
Gln His Asp Phe Phe Lys Ser Ala Met Pro Glu Gly Tyr Val Gln Glu
                85                  90                  95 cgc acc atc ttc ttc aag gac gac ggc aac tac aag acc cgc gcc gag    336
Arg Thr Ile Phe Phe Lys Asp Asp Gly Asn Tyr Lys Thr Arg Ala Glu
            100                 105                 110 gtg aag ttc gag ggc gac acc ctg gtg aac cgc atc gag ctg aag ggc    384
Val Lys Phe Glu Gly Asp Thr Leu Val Asn Arg Ile Glu Leu Lys Gly
        115                 120                 125 atc gac ttc aag gag gac ggc aac atc ctg ggg cac aag ctg gag tac    432
Ile Asp Phe Lys Glu Asp Gly Asn Ile Leu Gly His Lys Leu Glu Tyr
    130                 135                 140 aac tac aac agc cac aac gtc tat atc atg gcc gac aag cag aag aac    480
Asn Tyr Asn Ser His Asn Val Tyr Ile Met Ala Asp Lys Gln Lys Asn
145                 150                 155                 160 ggc atc aag gtg aac ttc aag atc cgc cac aac atc gag gac ggc agc    528
Gly Ile Lys Val Asn Phe Lys Ile Arg His Asn Ile Glu Asp Gly Ser
                165                 170                 175 gtg cag ctc gcc gac cac tac cag cag aac acc ccc atc ggc gac ggc    576
Val Gln Leu Ala Asp His Tyr Gln Gln Asn Thr Pro Ile Gly Asp Gly
            180                 185                 190 ccc gtg ctg ctg ccc gac aac cac tac ctg agc acc cag tcc gcc ctg    624
Pro Val Leu Leu Pro Asp Asn His Tyr Leu Ser Thr Gln Ser Ala Leu
        195                 200                 205 agc aaa gac ccc aac gag aag cgc gat cac atg gtc ctg ctg gag ttc    672
Ser Lys Asp Pro Asn Glu Lys Arg Asp His Met Val Leu Leu Glu Phe
    210                 215                 220
```

```
                210                    215                    220
gtg acc gcc gcc ggg atc act ctc ggc atg gac gag ctg tac aag tcc          720
Val Thr Ala Ala Gly Ile Thr Leu Gly Met Asp Glu Leu Tyr Lys Ser
225                 230                    235                    240 gga ctc aga tct cga ggg agc atg ggc acc ttg cgg gat tta cag tac          768
Gly Leu Arg Ser Arg Gly Ser Met Gly Thr Leu Arg Asp Leu Gln Tyr
                    245                    250                    255 gcg ctc cag gag aag atc gag gag ctg agg cag cgg gat gct ctc atc          816
Ala Leu Gln Glu Lys Ile Glu Glu Leu Arg Gln Arg Asp Ala Leu Ile
            260                    265                    270 gac gag ctg gag ctg gag ttg gat cag aag gac gaa ctg atc cag aag          864
Asp Glu Leu Glu Leu Glu Leu Asp Gln Lys Asp Glu Leu Ile Gln Lys
        275                    280                    285 ctg cag aac gag ctg gac aag tac cgc tcg gtg atc cga cca gcc acc          912
Leu Gln Asn Glu Leu Asp Lys Tyr Arg Ser Val Ile Arg Pro Ala Thr
    290                    295                    300 cag cag gcg cag aag cag agc gcg agc acc ttg cag ggc gag ccg cgc          960
Gln Gln Ala Gln Lys Gln Ser Ala Ser Thr Leu Gln Gly Glu Pro Arg
305                    310                    315                    320 acc aag cgg cag gcg atc tcc gcc gag ccc acc gcc ttc gac atc cag         1008
Thr Lys Arg Gln Ala Ile Ser Ala Glu Pro Thr Ala Phe Asp Ile Gln
                    325                    330                    335 gat ctc agc cat gtg acc ctg ccc ttc tac ccc aag agc cca cag tcc         1056
Asp Leu Ser His Val Thr Leu Pro Phe Tyr Pro Lys Ser Pro Gln Ser
            340                    345                    350 aag gat ctt ata aag gaa gct atc ctt gac aat gac ttt atg aag aac         1104
Lys Asp Leu Ile Lys Glu Ala Ile Leu Asp Asn Asp Phe Met Lys Asn
        355                    360                    365 ttg gag ctg tcg cag atc cag gag att gtg gat tgt atg tac ccg gtg         1152
Leu Glu Leu Ser Gln Ile Gln Glu Ile Val Asp Cys Met Tyr Pro Val
    370                    375                    380 gag tat ggc aag gac agt tgc atc atc aaa gaa gga gac gtg ggg tca         1200
Glu Tyr Gly Lys Asp Ser Cys Ile Ile Lys Glu Gly Asp Val Gly Ser
385                    390                    395                    400 ctg gtg tat gtc atg gaa gat ggt aag gtt gaa gtt aca aaa gaa ggt         1248
Leu Val Tyr Val Met Glu Asp Gly Lys Val Glu Val Thr Lys Glu Gly
                    405                    410                    415 gtg aag ttg tgt acc atg ggt cca gga aaa gtg ttt ggg gaa ttg gct         1296
Val Lys Leu Cys Thr Met Gly Pro Gly Lys Val Phe Gly Glu Leu Ala
            420                    425                    430 att ctt tac aac tgt acc cgg aca gcg acc gtc aag act ctt gta aat         1344
Ile Leu Tyr Asn Cys Thr Arg Thr Ala Thr Val Lys Thr Leu Val Asn
        435                    440                    445 gta aaa ctc tgg gcc att gat cga caa tgt ttt caa aca ata atg atg         1392
Val Lys Leu Trp Ala Ile Asp Arg Gln Cys Phe Gln Thr Ile Met Met
    450                    455                    460 agg aca gga ctc atc aag cat acc gag tat atg gaa ttt tta aaa agc         1440
Arg Thr Gly Leu Ile Lys His Thr Glu Tyr Met Glu Phe Leu Lys Ser
465                    470                    475                    480 gtt cca aca ttc cag agc ctt cct gaa gag atc ctc agc aag ctt gct         1488
Val Pro Thr Phe Gln Ser Leu Pro Glu Glu Ile Leu Ser Lys Leu Ala
                    485                    490                    495 gat gtc ctt gaa gag acc cac tat gaa aat gga gaa tat att atc agg         1536
Asp Val Leu Glu Glu Thr His Tyr Glu Asn Gly Glu Tyr Ile Ile Arg
            500                    505                    510 caa ggt gca aga ggg gac acc ttc ttt atc atc agc aaa gga acg gta         1584
Gln Gly Ala Arg Gly Asp Thr Phe Phe Ile Ile Ser Lys Gly Thr Val
        515                    520                    525 aat gtc act cgt gaa gac tca ccg agt gaa gac cca gtc ttt ctt aga         1632
```

```
                                                              -continued

Asn Val Thr Arg Glu Asp Ser Pro Ser Glu Asp Pro Val Phe Leu Arg
        530                 535                 540 act tta gga aaa gga gac tgg ttt gga gag aaa gcc ttg cag ggg gaa      1680
Thr Leu Gly Lys Gly Asp Trp Phe Gly Glu Lys Ala Leu Gln Gly Glu
545                 550                 555                 560 gat gtg aga aca gca aac gta att gct gca gaa gct gta acc tgc ctt      1728
Asp Val Arg Thr Ala Asn Val Ile Ala Ala Glu Ala Val Thr Cys Leu
                565                 570                 575 gtg att gac aga gac tct ttt aaa cat ttg att gga ggg ctg gat gat      1776
Val Ile Asp Arg Asp Ser Phe Lys His Leu Ile Gly Gly Leu Asp Asp
            580                 585                 590 gtt tct aat aaa gca tat gaa gat gca gaa gct aaa gca aaa tat gaa      1824
Val Ser Asn Lys Ala Tyr Glu Asp Ala Glu Ala Lys Ala Lys Tyr Glu
        595                 600                 605 gct gaa gcg gct ttc ttc gcc aac ctg aag ctg tct gat ttc aac atc      1872
Ala Glu Ala Ala Phe Phe Ala Asn Leu Lys Leu Ser Asp Phe Asn Ile
610                 615                 620 att gat acc ctt gga gtt gga ggt ttc gga cga gta gaa ctg gtc cag      1920
Ile Asp Thr Leu Gly Val Gly Gly Phe Gly Arg Val Glu Leu Val Gln
625                 630                 635                 640 ttg aaa agt gaa gaa tcc aaa acg ttt gca atg aag att ctc aag aaa      1968
Leu Lys Ser Glu Glu Ser Lys Thr Phe Ala Met Lys Ile Leu Lys Lys
                645                 650                 655 cgt cac att gtg gac aca aga cag cag gag cac atc cgc tca gag aag      2016
Arg His Ile Val Asp Thr Arg Gln Gln Glu His Ile Arg Ser Glu Lys
            660                 665                 670 cag atc atg cag ggg gct cat tcc gat ttc ata gtg aga ctg tac aga      2064
Gln Ile Met Gln Gly Ala His Ser Asp Phe Ile Val Arg Leu Tyr Arg
        675                 680                 685 aca ttt aag gac agc aaa tat ttg tat atg ttg atg gaa gct tgt cta      2112
Thr Phe Lys Asp Ser Lys Tyr Leu Tyr Met Leu Met Glu Ala Cys Leu
690                 695                 700 ggt gga gag ctc tgg acc att ctc agg gat aga ggt tcg ttt gaa gat      2160
Gly Gly Glu Leu Trp Thr Ile Leu Arg Asp Arg Gly Ser Phe Glu Asp
705                 710                 715                 720 tct aca acc aga ttt tac aca gca tgt gtg gta gaa gct ttt gcc tat      2208
Ser Thr Thr Arg Phe Tyr Thr Ala Cys Val Val Glu Ala Phe Ala Tyr
                725                 730                 735 ctg cat tcc aaa gga atc att tac agg gac ctc aag cca gaa aat ctc      2256
Leu His Ser Lys Gly Ile Ile Tyr Arg Asp Leu Lys Pro Glu Asn Leu
            740                 745                 750 atc cta gat cac cga ggt tat gcc aaa ctg gtt gat ttt ggc ttt gca      2304
Ile Leu Asp His Arg Gly Tyr Ala Lys Leu Val Asp Phe Gly Phe Ala
        755                 760                 765 aag aaa ata gga ttt gga aag aaa aca tgg act ttt tgt ggg act cca      2352
Lys Lys Ile Gly Phe Gly Lys Lys Thr Trp Thr Phe Cys Gly Thr Pro
770                 775                 780 gag tat gta gcc cca gag atc atc ctg aac aaa ggc cat gac att tca      2400
Glu Tyr Val Ala Pro Glu Ile Ile Leu Asn Lys Gly His Asp Ile Ser
785                 790                 795                 800 gcc gac tac tgg tca ctg gga atc cta atg tat gaa ctc ctg act ggc      2448
Ala Asp Tyr Trp Ser Leu Gly Ile Leu Met Tyr Glu Leu Leu Thr Gly
                805                 810                 815 agc cca cct ttc tca ggc cca gat cct atg aaa acc tat aac atc ata      2496
Ser Pro Pro Phe Ser Gly Pro Asp Pro Met Lys Thr Tyr Asn Ile Ile
            820                 825                 830 ttg agg ggg att gac atg ata gaa ttt cca aag aag att gcc aaa aat      2544
Leu Arg Gly Ile Asp Met Ile Glu Phe Pro Lys Lys Ile Ala Lys Asn
        835                 840                 845
```

```
gct gct aat tta att aaa aaa cta tgc agg gac aat cca tca gaa aga    2592
Ala Ala Asn Leu Ile Lys Lys Leu Cys Arg Asp Asn Pro Ser Glu Arg
    850                 855                 860 tta ggg aat ttg aaa aat gga gta aaa gac att caa aag cac aaa tgg    2640
Leu Gly Asn Leu Lys Asn Gly Val Lys Asp Ile Gln Lys His Lys Trp
865                 870                 875                 880 ttt gag ggc ttt aac tgg gaa ggc tta aga aaa ggt acc ttg aca cct    2688
Phe Glu Gly Phe Asn Trp Glu Gly Leu Arg Lys Gly Thr Leu Thr Pro
                885                 890                 895 cct ata ata cca agt gtt gca tca ccc aca gac aca agt aat ttt gac    2736
Pro Ile Ile Pro Ser Val Ala Ser Pro Thr Asp Thr Ser Asn Phe Asp
            900                 905                 910 agt ttc cct gag gac aac gat gaa cca cca cct gat gac aac tca gga    2784
Ser Phe Pro Glu Asp Asn Asp Glu Pro Pro Pro Asp Asp Asn Ser Gly
        915                 920                 925 tgg gat ata gac ttc taa                                            2802
Trp Asp Ile Asp Phe
    930
```

<210> SEQ ID NO 135
<211> LENGTH: 933
<212> TYPE: PRT
<213> ORGANISM: Artificial Sequence
<220> FEATURE:
<223> OTHER INFORMATION: EGFP-PKG fusion

<400> SEQUENCE: 135

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Ser
225                 230                 235                 240
```

-continued

```
Gly Leu Arg Ser Arg Gly Ser Met Gly Thr Leu Arg Asp Leu Gln Tyr
                245                 250                 255

Ala Leu Gln Glu Lys Ile Glu Glu Leu Arg Gln Arg Asp Ala Leu Ile
            260                 265                 270

Asp Glu Leu Glu Leu Glu Leu Asp Gln Lys Asp Glu Leu Ile Gln Lys
        275                 280                 285

Leu Gln Asn Glu Leu Asp Lys Tyr Arg Ser Val Ile Arg Pro Ala Thr
    290                 295                 300

Gln Gln Ala Gln Lys Gln Ser Ala Ser Thr Leu Gln Gly Glu Pro Arg
305                 310                 315                 320

Thr Lys Arg Gln Ala Ile Ser Ala Glu Pro Thr Ala Phe Asp Ile Gln
                325                 330                 335

Asp Leu Ser His Val Thr Leu Pro Phe Tyr Pro Lys Ser Pro Gln Ser
            340                 345                 350

Lys Asp Leu Ile Lys Glu Ala Ile Leu Asp Asn Asp Phe Met Lys Asn
        355                 360                 365

Leu Glu Leu Ser Gln Ile Gln Glu Ile Val Asp Cys Met Tyr Pro Val
    370                 375                 380

Glu Tyr Gly Lys Asp Ser Cys Ile Ile Lys Glu Gly Asp Val Gly Ser
385                 390                 395                 400

Leu Val Tyr Val Met Glu Asp Gly Lys Val Glu Val Thr Lys Glu Gly
                405                 410                 415

Val Lys Leu Cys Thr Met Gly Pro Gly Lys Val Phe Gly Glu Leu Ala
            420                 425                 430

Ile Leu Tyr Asn Cys Thr Arg Thr Ala Thr Val Lys Thr Leu Val Asn
        435                 440                 445

Val Lys Leu Trp Ala Ile Asp Arg Gln Cys Phe Gln Thr Ile Met Met
    450                 455                 460

Arg Thr Gly Leu Ile Lys His Thr Glu Tyr Met Glu Phe Leu Lys Ser
465                 470                 475                 480

Val Pro Thr Phe Gln Ser Leu Pro Glu Glu Ile Leu Ser Lys Leu Ala
                485                 490                 495

Asp Val Leu Glu Glu Thr His Tyr Glu Asn Gly Glu Tyr Ile Ile Arg
            500                 505                 510

Gln Gly Ala Arg Gly Asp Thr Phe Phe Ile Ile Ser Lys Gly Thr Val
        515                 520                 525

Asn Val Thr Arg Glu Asp Ser Pro Ser Glu Asp Pro Val Phe Leu Arg
    530                 535                 540

Thr Leu Gly Lys Gly Asp Trp Phe Gly Glu Lys Ala Leu Gln Gly Glu
545                 550                 555                 560

Asp Val Arg Thr Ala Asn Val Ile Ala Ala Glu Ala Val Thr Cys Leu
                565                 570                 575

Val Ile Asp Arg Asp Ser Phe Lys His Leu Ile Gly Gly Leu Asp Asp
            580                 585                 590

Val Ser Asn Lys Ala Tyr Glu Asp Ala Glu Ala Lys Ala Lys Tyr Glu
        595                 600                 605

Ala Glu Ala Ala Phe Phe Ala Asn Leu Lys Leu Ser Asp Phe Asn Ile
    610                 615                 620

Ile Asp Thr Leu Gly Val Gly Gly Phe Gly Arg Val Glu Leu Val Gln
625                 630                 635                 640

Leu Lys Ser Glu Glu Ser Lys Thr Phe Ala Met Lys Ile Leu Lys Lys
                645                 650                 655

Arg His Ile Val Asp Thr Arg Gln Gln Glu His Ile Arg Ser Glu Lys
```

-continued

```
                          660                 665                 670
        Gln Ile Met Gln Gly Ala His Ser Asp Phe Ile Val Arg Leu Tyr Arg
                      675                 680                 685

Thr Phe Lys Asp Ser Lys Tyr Leu Tyr Met Leu Met Glu Ala Cys Leu
                      690                 695                 700

Gly Gly Glu Leu Trp Thr Ile Leu Arg Asp Arg Gly Ser Phe Glu Asp
        705                 710                 715                 720

Ser Thr Thr Arg Phe Tyr Thr Ala Cys Val Val Glu Ala Phe Ala Tyr
                          725                 730                 735

Leu His Ser Lys Gly Ile Ile Tyr Arg Asp Leu Lys Pro Glu Asn Leu
                      740                 745                 750

Ile Leu Asp His Arg Gly Tyr Ala Lys Leu Val Asp Phe Gly Phe Ala
                      755                 760                 765

Lys Lys Ile Gly Phe Gly Lys Lys Thr Trp Thr Phe Cys Gly Thr Pro
                      770                 775                 780

Glu Tyr Val Ala Pro Glu Ile Ile Leu Asn Lys Gly His Asp Ile Ser
        785                 790                 795                 800

Ala Asp Tyr Trp Ser Leu Gly Ile Leu Met Tyr Glu Leu Leu Thr Gly
                          805                 810                 815

Ser Pro Pro Phe Ser Gly Pro Asp Pro Met Lys Thr Tyr Asn Ile Ile
                      820                 825                 830

Leu Arg Gly Ile Asp Met Ile Glu Phe Pro Lys Lys Ile Ala Lys Asn
                      835                 840                 845

Ala Ala Asn Leu Ile Lys Lys Leu Cys Arg Asp Asn Pro Ser Glu Arg
                      850                 855                 860

Leu Gly Asn Leu Lys Asn Gly Val Lys Asp Ile Gln Lys His Lys Trp
        865                 870                 875                 880

Phe Glu Gly Phe Asn Trp Glu Gly Leu Arg Lys Gly Thr Leu Thr Pro
                          885                 890                 895

Pro Ile Ile Pro Ser Val Ala Ser Pro Thr Asp Thr Ser Asn Phe Asp
                      900                 905                 910

Ser Phe Pro Glu Asp Asn Asp Glu Pro Pro Asp Asp Asn Ser Gly
                      915                 920                 925

Trp Asp Ile Asp Phe
            930

<210> SEQ ID NO 136
<211> LENGTH: 2799
<212> TYPE: DNA
<213> ORGANISM: Artificial Sequence
<220> FEATURE:
<223> OTHER INFORMATION: PKG-EGFP fusion
<220> FEATURE:
<221> NAME/KEY: CDS
<222> LOCATION: (1)..(2796)

<400> SEQUENCE: 136 atg ggc acc ttg cgg gat tta cag tac gcg ctc cag gag aag atc gag        48
Met Gly Thr Leu Arg Asp Leu Gln Tyr Ala Leu Gln Glu Lys Ile Glu
1               5                   10                  15 gag ctg agg cag cgg gat gct ctc atc gac gag ctg gag ctg gag ttg        96
Glu Leu Arg Gln Arg Asp Ala Leu Ile Asp Glu Leu Glu Leu Glu Leu
            20                  25                  30 gat cag aag gac gaa ctg atc cag aag ctg cag aac gag ctg gac aag       144
Asp Gln Lys Asp Glu Leu Ile Gln Lys Leu Gln Asn Glu Leu Asp Lys
        35                  40                  45 tac cgc tcg gtg atc cga cca gcc acc cag cag gcg cag aag cag agc       192
```

```
                                                                         -continued Tyr Arg Ser Val Ile Arg Pro Ala Thr Gln Ala Gln Lys Gln Ser
 50                  55                  60 gcg agc acc ttg cag ggc gag ccg cgc acc aag cgg cag gcg atc tcc          240
Ala Ser Thr Leu Gln Gly Glu Pro Arg Thr Lys Arg Gln Ala Ile Ser
 65                  70                  75                  80 gcc gag ccc acc gcc ttc gac atc cag gat ctc agc cat gtg acc ctg          288
Ala Glu Pro Thr Ala Phe Asp Ile Gln Asp Leu Ser His Val Thr Leu
                 85                  90                  95 ccc ttc tac ccc aag agc cca cag tcc aag gat ctt ata aag gaa gct          336
Pro Phe Tyr Pro Lys Ser Pro Gln Ser Lys Asp Leu Ile Lys Glu Ala
                100                 105                 110 atc ctt gac aat gac ttt atg aag aac ttg gag ctg tcg cag atc cag          384
Ile Leu Asp Asn Asp Phe Met Lys Asn Leu Glu Leu Ser Gln Ile Gln
            115                 120                 125 gag att gtg gat tgt atg tac ccg gtg gag tat ggc aag gac agt tgc          432
Glu Ile Val Asp Cys Met Tyr Pro Val Glu Tyr Gly Lys Asp Ser Cys
130                 135                 140 atc atc aaa gaa gga gac gtg ggg tca ctg gtg tat gtc atg gaa gat          480
Ile Ile Lys Glu Gly Asp Val Gly Ser Leu Val Tyr Val Met Glu Asp
145                 150                 155                 160 ggt aag gtt gaa gtt aca aaa gaa ggt gtg aag ttg tgt acc atg ggt          528
Gly Lys Val Glu Val Thr Lys Glu Gly Val Lys Leu Cys Thr Met Gly
                165                 170                 175 cca gga aaa gtg ttt ggg gaa ttg gct att ctt tac aac tgt acc cgg          576
Pro Gly Lys Val Phe Gly Glu Leu Ala Ile Leu Tyr Asn Cys Thr Arg
                180                 185                 190 aca gcg acc gtc aag act ctt gta aat gta aaa ctc tgg gcc att gat          624
Thr Ala Thr Val Lys Thr Leu Val Asn Val Lys Leu Trp Ala Ile Asp
            195                 200                 205 cga caa tgt ttt caa aca ata atg atg agg aca gga ctc atc aag cat          672
Arg Gln Cys Phe Gln Thr Ile Met Met Arg Thr Gly Leu Ile Lys His
210                 215                 220 acc gag tat atg gaa ttt tta aaa agc gtt cca aca ttc cag agc ctt          720
Thr Glu Tyr Met Glu Phe Leu Lys Ser Val Pro Thr Phe Gln Ser Leu
225                 230                 235                 240 cct gaa gag atc ctc agc aag ctt gct gat gtc ctt gaa gag acc cac          768
Pro Glu Glu Ile Leu Ser Lys Leu Ala Asp Val Leu Glu Glu Thr His
                245                 250                 255 tat gaa aat gga gaa tat att atc agg caa ggt gca aga ggg gac acc          816
Tyr Glu Asn Gly Glu Tyr Ile Ile Arg Gln Gly Ala Arg Gly Asp Thr
                260                 265                 270 ttc ttt atc atc agc aaa gga acg gta aat gtc act cgt gaa gac tca          864
Phe Phe Ile Ile Ser Lys Gly Thr Val Asn Val Thr Arg Glu Asp Ser
            275                 280                 285 ccg agt gaa gac cca gtc ttt ctt aga act tta gga aaa gga gac tgg          912
Pro Ser Glu Asp Pro Val Phe Leu Arg Thr Leu Gly Lys Gly Asp Trp
290                 295                 300 ttt gga gag aaa gcc ttg cag ggg gaa gat gtg aga aca gca aac gta          960
Phe Gly Glu Lys Ala Leu Gln Gly Glu Asp Val Arg Thr Ala Asn Val
305                 310                 315                 320 att gct gca gaa gct gta acc tgc ctt gtg att gac aga gac tct ttt         1008
Ile Ala Ala Glu Ala Val Thr Cys Leu Val Ile Asp Arg Asp Ser Phe
                325                 330                 335 aaa cat ttg att gga ggg ctg gat gat gtt tct aat aaa gca tat gaa         1056
Lys His Leu Ile Gly Gly Leu Asp Asp Val Ser Asn Lys Ala Tyr Glu
                340                 345                 350 gat gca gaa gct aaa gca aaa tat gaa gct gaa gcg gct ttc ttc gcc         1104
Asp Ala Glu Ala Lys Ala Lys Tyr Glu Ala Glu Ala Ala Phe Phe Ala
            355                 360                 365
```

-continued

```
aac ctg aag ctg tct gat ttc aac atc att gat acc ctt gga gtt gga    1152
Asn Leu Lys Leu Ser Asp Phe Asn Ile Ile Asp Thr Leu Gly Val Gly
    370                 375                 380 ggt ttc gga cga gta gaa ctg gtc cag ttg aaa agt gaa gaa tcc aaa    1200
Gly Phe Gly Arg Val Glu Leu Val Gln Leu Lys Ser Glu Glu Ser Lys
385                 390                 395                 400 acg ttt gca atg aag att ctc aag aaa cgt cac att gtg gac aca aga    1248
Thr Phe Ala Met Lys Ile Leu Lys Lys Arg His Ile Val Asp Thr Arg
                405                 410                 415 cag cag gag cac atc cgc tca gag aag cag atc atg cag ggg gct cat    1296
Gln Gln Glu His Ile Arg Ser Glu Lys Gln Ile Met Gln Gly Ala His
            420                 425                 430 tcc gat ttc ata gtg aga ctg tac aga aca ttt aag gac agc aaa tat    1344
Ser Asp Phe Ile Val Arg Leu Tyr Arg Thr Phe Lys Asp Ser Lys Tyr
        435                 440                 445 ttg tat atg ttg atg gaa gct tgt cta ggt gga gag ctc tgg acc att    1392
Leu Tyr Met Leu Met Glu Ala Cys Leu Gly Gly Glu Leu Trp Thr Ile
450                 455                 460 ctc agg gat aga ggt tcg ttt gaa gat tct aca acc aga ttt tac aca    1440
Leu Arg Asp Arg Gly Ser Phe Glu Asp Ser Thr Thr Arg Phe Tyr Thr
465                 470                 475                 480 gca tgt gtg gta gaa gct ttt gcc tat ctg cat tcc aaa gga atc att    1488
Ala Cys Val Val Glu Ala Phe Ala Tyr Leu His Ser Lys Gly Ile Ile
                485                 490                 495 tac agg gac ctc aag cca gaa aat ctc atc cta gat cac cga ggt tat    1536
Tyr Arg Asp Leu Lys Pro Glu Asn Leu Ile Leu Asp His Arg Gly Tyr
            500                 505                 510 gcc aaa ctg gtt gat ttt ggc ttt gca aag aaa ata gga ttt gga aag    1584
Ala Lys Leu Val Asp Phe Gly Phe Ala Lys Lys Ile Gly Phe Gly Lys
        515                 520                 525 aaa aca tgg act ttt tgt ggg act cca gag tat gta gcc cca gag atc    1632
Lys Thr Trp Thr Phe Cys Gly Thr Pro Glu Tyr Val Ala Pro Glu Ile
530                 535                 540 atc ctg aac aaa ggc cat gac att tca gcc gac tac tgg tca ctg gga    1680
Ile Leu Asn Lys Gly His Asp Ile Ser Ala Asp Tyr Trp Ser Leu Gly
545                 550                 555                 560 atc cta atg tat gaa ctc ctg act ggc agc cca cct ttc tca ggc cca    1728
Ile Leu Met Tyr Glu Leu Leu Thr Gly Ser Pro Pro Phe Ser Gly Pro
                565                 570                 575 gat cct atg aaa acc tat aac atc ata ttg agg ggg att gac atg ata    1776
Asp Pro Met Lys Thr Tyr Asn Ile Ile Leu Arg Gly Ile Asp Met Ile
            580                 585                 590 gaa ttt cca aag aag att gcc aaa aat gct gct aat tta att aaa aaa    1824
Glu Phe Pro Lys Lys Ile Ala Lys Asn Ala Ala Asn Leu Ile Lys Lys
        595                 600                 605 cta tgc agg gac aat cca tca gaa aga tta ggg aat ttg aaa aat gga    1872
Leu Cys Arg Asp Asn Pro Ser Glu Arg Leu Gly Asn Leu Lys Asn Gly
610                 615                 620 gta aaa gac att caa aag cac aaa tgg ttt gag ggc ttt aac tgg gaa    1920
Val Lys Asp Ile Gln Lys His Lys Trp Phe Glu Gly Phe Asn Trp Glu
625                 630                 635                 640 ggc tta aga aaa ggt acc ttg aca cct cct ata ata cca agt gtt gca    1968
Gly Leu Arg Lys Gly Thr Leu Thr Pro Pro Ile Ile Pro Ser Val Ala
                645                 650                 655 tca ccc aca gac aca agt aat ttt gac agt ttc cct gag gac aac gat    2016
Ser Pro Thr Asp Thr Ser Asn Phe Asp Ser Phe Pro Glu Asp Asn Asp
            660                 665                 670 gaa cca cca cct gat gac aac tca gga tgg gat ata gac ttc tcg gat    2064
Glu Pro Pro Pro Asp Asp Asn Ser Gly Trp Asp Ile Asp Phe Ser Asp
        675                 680                 685
```

```
cca ccg gtc gcc acc atg gtg agc aag ggc gag gag ctg ttc acc ggg        2112
Pro Pro Val Ala Thr Met Val Ser Lys Gly Glu Glu Leu Phe Thr Gly
    690                 695                 700 gtg gtg ccc atc ctg gtc gag ctg gac ggc gac gta aac ggc cac aag        2160
Val Val Pro Ile Leu Val Glu Leu Asp Gly Asp Val Asn Gly His Lys
705                 710                 715                 720 ttc agc gtg tcc ggc gag ggc gag ggc gat gcc acc tac ggc aag ctg        2208
Phe Ser Val Ser Gly Glu Gly Glu Gly Asp Ala Thr Tyr Gly Lys Leu
                725                 730                 735 acc ctg aag ttc atc tgc acc acc ggc aag ctg ccc gtg ccc tgg ccc        2256
Thr Leu Lys Phe Ile Cys Thr Thr Gly Lys Leu Pro Val Pro Trp Pro
            740                 745                 750 acc ctc gtg acc acc ctg acc tac ggc gtg cag tgc ttc agc cgc tac        2304
Thr Leu Val Thr Thr Leu Thr Tyr Gly Val Gln Cys Phe Ser Arg Tyr
        755                 760                 765 ccc gac cac atg aag cag cac gac ttc ttc aag tcc gcc atg ccc gaa        2352
Pro Asp His Met Lys Gln His Asp Phe Phe Lys Ser Ala Met Pro Glu
    770                 775                 780 ggc tac gtc cag gag cgc acc atc ttc ttc aag gac gac ggc aac tac        2400
Gly Tyr Val Gln Glu Arg Thr Ile Phe Phe Lys Asp Asp Gly Asn Tyr
785                 790                 795                 800 aag acc cgc gcc gag gtg aag ttc gag ggc gac acc ctg gtg aac cgc        2448
Lys Thr Arg Ala Glu Val Lys Phe Glu Gly Asp Thr Leu Val Asn Arg
                805                 810                 815 atc gag ctg aag ggc atc gac ttc aag gag gac ggc aac atc ctg ggg        2496
Ile Glu Leu Lys Gly Ile Asp Phe Lys Glu Asp Gly Asn Ile Leu Gly
            820                 825                 830 cac aag ctg gag tac aac tac aac agc cac aac gtc tat atc atg gcc        2544
His Lys Leu Glu Tyr Asn Tyr Asn Ser His Asn Val Tyr Ile Met Ala
        835                 840                 845 gac aag cag aag aac ggc atc aag gtg aac ttc aag atc cgc cac aac        2592
Asp Lys Gln Lys Asn Gly Ile Lys Val Asn Phe Lys Ile Arg His Asn
    850                 855                 860 atc gag gac ggc agc gtg cag ctc gcc gac cac tac cag cag aac acc        2640
Ile Glu Asp Gly Ser Val Gln Leu Ala Asp His Tyr Gln Gln Asn Thr
865                 870                 875                 880 ccc atc ggc gac ggc ccc gtg ctg ctg ccc gac aac cac tac ctg agc        2688
Pro Ile Gly Asp Gly Pro Val Leu Leu Pro Asp Asn His Tyr Leu Ser
                885                 890                 895 acc cag tcc gcc ctg agc aaa gac ccc aac gag aag cgc gat cac atg        2736
Thr Gln Ser Ala Leu Ser Lys Asp Pro Asn Glu Lys Arg Asp His Met
            900                 905                 910 gtc ctg ctg gag ttc gtg acc gcc gcc ggg atc act ctc ggc atg gac        2784
Val Leu Leu Glu Phe Val Thr Ala Ala Gly Ile Thr Leu Gly Met Asp
        915                 920                 925 gag ctg tac aag taa                                                    2799
Glu Leu Tyr Lys
    930

<210> SEQ ID NO 137
<211> LENGTH: 932
<212> TYPE: PRT
<213> ORGANISM: Artificial Sequence
<220> FEATURE:
<223> OTHER INFORMATION: PKG-EGFP fusion

<400> SEQUENCE: 137

Met Gly Thr Leu Arg Asp Leu Gln Tyr Ala Leu Gln Glu Lys Ile Glu
1               5                   10                  15

Glu Leu Arg Gln Arg Asp Ala Leu Ile Asp Glu Leu Glu Leu Glu Leu
```

-continued

```
                    20                  25                  30
Asp Gln Lys Asp Glu Leu Ile Gln Lys Leu Gln Asn Glu Leu Asp Lys
                35                  40                  45
Tyr Arg Ser Val Ile Arg Pro Ala Thr Gln Gln Ala Gln Lys Gln Ser
 50                  55                  60
Ala Ser Thr Leu Gln Gly Glu Pro Arg Thr Lys Arg Gln Ala Ile Ser
 65                  70                  75                  80
Ala Glu Pro Thr Ala Phe Asp Ile Gln Asp Leu Ser His Val Thr Leu
                85                  90                  95
Pro Phe Tyr Pro Lys Ser Pro Gln Ser Lys Asp Leu Ile Lys Glu Ala
                100                 105                 110
Ile Leu Asp Asn Asp Phe Met Lys Asn Leu Glu Leu Ser Gln Ile Gln
                115                 120                 125
Glu Ile Val Asp Cys Met Tyr Pro Val Glu Tyr Gly Lys Asp Ser Cys
                130                 135                 140
Ile Ile Lys Glu Gly Asp Val Gly Ser Leu Val Tyr Val Met Glu Asp
145                 150                 155                 160
Gly Lys Val Glu Val Thr Lys Glu Gly Val Lys Leu Cys Thr Met Gly
                165                 170                 175
Pro Gly Lys Val Phe Gly Glu Leu Ala Ile Leu Tyr Asn Cys Thr Arg
                180                 185                 190
Thr Ala Thr Val Lys Thr Leu Val Asn Val Lys Leu Trp Ala Ile Asp
                195                 200                 205
Arg Gln Cys Phe Gln Thr Ile Met Met Arg Thr Gly Leu Ile Lys His
                210                 215                 220
Thr Glu Tyr Met Glu Phe Leu Lys Ser Val Pro Thr Phe Gln Ser Leu
225                 230                 235                 240
Pro Glu Glu Ile Leu Ser Lys Leu Ala Asp Val Leu Glu Glu Thr His
                245                 250                 255
Tyr Glu Asn Gly Glu Tyr Ile Ile Arg Gln Gly Ala Arg Gly Asp Thr
                260                 265                 270
Phe Phe Ile Ile Ser Lys Gly Thr Val Asn Val Thr Arg Glu Asp Ser
                275                 280                 285
Pro Ser Glu Asp Pro Val Phe Leu Arg Thr Leu Gly Lys Gly Asp Trp
                290                 295                 300
Phe Gly Glu Lys Ala Leu Gln Gly Glu Asp Val Arg Thr Ala Asn Val
305                 310                 315                 320
Ile Ala Ala Glu Ala Val Thr Cys Leu Val Ile Asp Arg Asp Ser Phe
                325                 330                 335
Lys His Leu Ile Gly Gly Leu Asp Asp Val Ser Asn Lys Ala Tyr Glu
                340                 345                 350
Asp Ala Glu Ala Lys Ala Lys Tyr Glu Ala Glu Ala Ala Phe Phe Ala
                355                 360                 365
Asn Leu Lys Leu Ser Asp Phe Asn Ile Ile Asp Thr Leu Gly Val Gly
                370                 375                 380
Gly Phe Gly Arg Val Glu Leu Val Gln Leu Lys Ser Glu Glu Ser Lys
385                 390                 395                 400
Thr Phe Ala Met Lys Ile Leu Lys Lys Arg His Ile Val Asp Thr Arg
                405                 410                 415
Gln Gln Glu His Ile Arg Ser Glu Lys Gln Ile Met Gln Gly Ala His
                420                 425                 430
Ser Asp Phe Ile Val Arg Leu Tyr Arg Thr Phe Lys Asp Ser Lys Tyr
                435                 440                 445
```

-continued

```
Leu Tyr Met Leu Met Glu Ala Cys Leu Gly Gly Glu Leu Trp Thr Ile
    450                 455                 460
Leu Arg Asp Arg Gly Ser Phe Glu Asp Ser Thr Thr Arg Phe Tyr Thr
465                 470                 475                 480
Ala Cys Val Val Glu Ala Phe Ala Tyr Leu His Ser Lys Gly Ile Ile
                485                 490                 495
Tyr Arg Asp Leu Lys Pro Glu Asn Leu Ile Leu Asp His Arg Gly Tyr
                500                 505                 510
Ala Lys Leu Val Asp Phe Gly Phe Ala Lys Lys Ile Gly Phe Gly Lys
            515                 520                 525
Lys Thr Trp Thr Phe Cys Gly Thr Pro Glu Tyr Val Ala Pro Glu Ile
    530                 535                 540
Ile Leu Asn Lys Gly His Asp Ile Ser Ala Asp Tyr Trp Ser Leu Gly
545                 550                 555                 560
Ile Leu Met Tyr Glu Leu Leu Thr Gly Ser Pro Pro Phe Ser Gly Pro
                565                 570                 575
Asp Pro Met Lys Thr Tyr Asn Ile Ile Leu Arg Gly Ile Asp Met Ile
                580                 585                 590
Glu Phe Pro Lys Lys Ile Ala Lys Asn Ala Ala Asn Leu Ile Lys Lys
            595                 600                 605
Leu Cys Arg Asp Asn Pro Ser Glu Arg Leu Gly Asn Leu Lys Asn Gly
    610                 615                 620
Val Lys Asp Ile Gln Lys His Lys Trp Phe Glu Gly Phe Asn Trp Glu
625                 630                 635                 640
Gly Leu Arg Lys Gly Thr Leu Thr Pro Pro Ile Ile Pro Ser Val Ala
                645                 650                 655
Ser Pro Thr Asp Thr Ser Asn Phe Asp Ser Phe Pro Glu Asp Asn Asp
                660                 665                 670
Glu Pro Pro Pro Asp Asp Asn Ser Gly Trp Asp Ile Asp Phe Ser Asp
            675                 680                 685
Pro Pro Val Ala Thr Met Val Ser Lys Gly Glu Glu Leu Phe Thr Gly
    690                 695                 700
Val Val Pro Ile Leu Val Glu Leu Asp Gly Asp Val Asn Gly His Lys
705                 710                 715                 720
Phe Ser Val Ser Gly Glu Gly Glu Gly Asp Ala Thr Tyr Gly Lys Leu
                725                 730                 735
Thr Leu Lys Phe Ile Cys Thr Thr Gly Lys Leu Pro Val Pro Trp Pro
                740                 745                 750
Thr Leu Val Thr Thr Leu Thr Tyr Gly Val Gln Cys Phe Ser Arg Tyr
            755                 760                 765
Pro Asp His Met Lys Gln His Asp Phe Phe Lys Ser Ala Met Pro Glu
    770                 775                 780
Gly Tyr Val Gln Glu Arg Thr Ile Phe Phe Lys Asp Asp Gly Asn Tyr
785                 790                 795                 800
Lys Thr Arg Ala Glu Val Lys Phe Glu Gly Asp Thr Leu Val Asn Arg
                805                 810                 815
Ile Glu Leu Lys Gly Ile Asp Phe Lys Glu Asp Gly Asn Ile Leu Gly
                820                 825                 830
His Lys Leu Glu Tyr Asn Tyr Asn Ser His Asn Val Tyr Ile Met Ala
            835                 840                 845
Asp Lys Gln Lys Asn Gly Ile Lys Val Asn Phe Lys Ile Arg His Asn
    850                 855                 860
```

-continued

```
Ile Glu Asp Gly Ser Val Gln Leu Ala Asp His Tyr Gln Gln Asn Thr
865                 870                 875                 880

Pro Ile Gly Asp Gly Pro Val Leu Leu Pro Asp Asn His Tyr Leu Ser
            885                 890                 895

Thr Gln Ser Ala Leu Ser Lys Asp Pro Asn Glu Lys Arg Asp His Met
        900                 905                 910

Val Leu Leu Glu Phe Val Thr Ala Ala Gly Ile Thr Leu Gly Met Asp
    915                 920                 925

Glu Leu Tyr Lys
    930

<210> SEQ ID NO 138
<211> LENGTH: 2184
<212> TYPE: DNA
<213> ORGANISM: Artificial Sequence
<220> FEATURE:
<223> OTHER INFORMATION: EGFP-PKB fusion
<220> FEATURE:
<221> NAME/KEY: CDS
<222> LOCATION: (1)..(2181)

<400> SEQUENCE: 138 atg gtg agc aag ggc gag gag ctg ttc acc ggg gtg gtg ccc atc ctg      48
Met Val Ser Lys Gly Glu Glu Leu Phe Thr Gly Val Val Pro Ile Leu
1               5                   10                  15 gtc gag ctg gac ggc gac gta aac ggc cac aag ttc agc gtg tcc ggc      96
Val Glu Leu Asp Gly Asp Val Asn Gly His Lys Phe Ser Val Ser Gly
                20                  25                  30 gag ggc gag ggc gat gcc acc tac ggc aag ctg acc ctg aag ttc atc     144
Glu Gly Glu Gly Asp Ala Thr Tyr Gly Lys Leu Thr Leu Lys Phe Ile
            35                  40                  45 tgc acc acc ggc aag ctg ccc gtg ccc tgg ccc acc ctc gtg acc acc     192
Cys Thr Thr Gly Lys Leu Pro Val Pro Trp Pro Thr Leu Val Thr Thr
        50                  55                  60 ctg acc tac ggc gtg cag tgc ttc agc cgc tac ccc gac cac atg aag     240
Leu Thr Tyr Gly Val Gln Cys Phe Ser Arg Tyr Pro Asp His Met Lys
65                  70                  75                  80 cag cac gac ttc ttc aag tcc gcc atg ccc gaa ggc tac gtc cag gag     288
Gln His Asp Phe Phe Lys Ser Ala Met Pro Glu Gly Tyr Val Gln Glu
                85                  90                  95 cgc acc atc ttc ttc aag gac gac ggc aac tac aag acc cgc gcc gag     336
Arg Thr Ile Phe Phe Lys Asp Asp Gly Asn Tyr Lys Thr Arg Ala Glu
            100                 105                 110 gtg aag ttc gag ggc gac acc ctg gtg aac cgc atc gag ctg aag ggc     384
Val Lys Phe Glu Gly Asp Thr Leu Val Asn Arg Ile Glu Leu Lys Gly
        115                 120                 125 atc gac ttc aag gag gac ggc aac atc ctg ggg cac aag ctg gag tac     432
Ile Asp Phe Lys Glu Asp Gly Asn Ile Leu Gly His Lys Leu Glu Tyr
    130                 135                 140 aac tac aac agc cac aac gtc tat atc atg gcc gac aag cag aag aac     480
Asn Tyr Asn Ser His Asn Val Tyr Ile Met Ala Asp Lys Gln Lys Asn
145                 150                 155                 160 ggc atc aag gtg aac ttc aag atc cgc cac aac atc gag gac ggc agc     528
Gly Ile Lys Val Asn Phe Lys Ile Arg His Asn Ile Glu Asp Gly Ser
                165                 170                 175 gtg cag ctc gcc gac cac tac cag cag aac acc ccc atc ggc gac ggc     576
Val Gln Leu Ala Asp His Tyr Gln Gln Asn Thr Pro Ile Gly Asp Gly
            180                 185                 190 ccc gtg ctg ctg ccc gac aac cac tac ctg agc acc cag tcc gcc ctg     624
Pro Val Leu Leu Pro Asp Asn His Tyr Leu Ser Thr Gln Ser Ala Leu
        195                 200                 205
```

```
agc aaa gac ccc aac gag aag cgc gat cac atg gtc ctg ctg gag ttc      672
Ser Lys Asp Pro Asn Glu Lys Arg Asp His Met Val Leu Leu Glu Phe
    210                 215                 220 gtg acc gcc gcc ggg atc act ctc ggc atg gac gag ctg tac aag tcc      720
Val Thr Ala Ala Gly Ile Thr Leu Gly Met Asp Glu Leu Tyr Lys Ser
225                 230                 235                 240 gga ctc aga tct cga ggc acc atg agc gac gtg gct att gtg aag gag      768
Gly Leu Arg Ser Arg Gly Thr Met Ser Asp Val Ala Ile Val Lys Glu
            245                 250                 255 ggt tgg ctg cac aaa cga ggg gag tac atc aag acc tgg cgg cca cgc      816
Gly Trp Leu His Lys Arg Gly Glu Tyr Ile Lys Thr Trp Arg Pro Arg
        260                 265                 270 tac ttc ctc ctc aag aat gat ggc acc ttc att ggc tac aag gag cgg      864
Tyr Phe Leu Leu Lys Asn Asp Gly Thr Phe Ile Gly Tyr Lys Glu Arg
    275                 280                 285 ccg cag gat gtg gac caa cgt gag gct ccc ctc aac aac ttc tct gtg      912
Pro Gln Asp Val Asp Gln Arg Glu Ala Pro Leu Asn Asn Phe Ser Val
290                 295                 300 gcg cag tgc cag ctg atg aag acg gag cgg ccc cgg ccc aac acc ttc      960
Ala Gln Cys Gln Leu Met Lys Thr Glu Arg Pro Arg Pro Asn Thr Phe
305                 310                 315                 320 atc atc cgc tgc ctg cag tgg acc act gtc atc gaa cgc acc ttc cat     1008
Ile Ile Arg Cys Leu Gln Trp Thr Thr Val Ile Glu Arg Thr Phe His
            325                 330                 335 gtg gag act cct gag gag cgg gag gag tgg aca acc gcc atc cag act     1056
Val Glu Thr Pro Glu Glu Arg Glu Glu Trp Thr Thr Ala Ile Gln Thr
        340                 345                 350 gtg gct gac ggc ctc aag aag cag gag gag gag gag atg gac ttc cgg     1104
Val Ala Asp Gly Leu Lys Lys Gln Glu Glu Glu Glu Met Asp Phe Arg
    355                 360                 365 tcg ggc tca ccc agt gac aac tca ggg gct gaa gag atg gag gtg tcc     1152
Ser Gly Ser Pro Ser Asp Asn Ser Gly Ala Glu Glu Met Glu Val Ser
370                 375                 380 ctg gcc aag ccc aag cac cgc gtg acc atg aac gag ttt gag tac ctg     1200
Leu Ala Lys Pro Lys His Arg Val Thr Met Asn Glu Phe Glu Tyr Leu
385                 390                 395                 400 aag ctg ctg ggc aag ggc act ttc ggc aag gtg atc ctg gtg aag gag     1248
Lys Leu Leu Gly Lys Gly Thr Phe Gly Lys Val Ile Leu Val Lys Glu
            405                 410                 415 aag gcc aca ggc cgc tac tac gcc atg aag atc ctc aag aag gaa gtc     1296
Lys Ala Thr Gly Arg Tyr Tyr Ala Met Lys Ile Leu Lys Lys Glu Val
        420                 425                 430 atc gtg gcc aag gac gag gtg gcc cac aca ctc acc gag aac cgc gtc     1344
Ile Val Ala Lys Asp Glu Val Ala His Thr Leu Thr Glu Asn Arg Val
    435                 440                 445 ctg cag aac tcc agg cac ccc ttc ctc aca gcc ctg aag tac tct ttc     1392
Leu Gln Asn Ser Arg His Pro Phe Leu Thr Ala Leu Lys Tyr Ser Phe
450                 455                 460 cag acc cac gac cgc ctc tgc ttt gtc atg gag tac gcc aac ggg ggc     1440
Gln Thr His Asp Arg Leu Cys Phe Val Met Glu Tyr Ala Asn Gly Gly
465                 470                 475                 480 gag ctg ttc ttc cac ctg tcc cgg gaa cgt gtg ttc tcc gag gac cgg     1488
Glu Leu Phe Phe His Leu Ser Arg Glu Arg Val Phe Ser Glu Asp Arg
            485                 490                 495 gcc cgc ttc tat ggc gct gag att gtg tca gcc ctg gac tac ctg cac     1536
Ala Arg Phe Tyr Gly Ala Glu Ile Val Ser Ala Leu Asp Tyr Leu His
        500                 505                 510 tcg gag aag aac gtg gtg tac cgg gac ctc aag ctg gag aac ctc atg     1584
Ser Glu Lys Asn Val Val Tyr Arg Asp Leu Lys Leu Glu Asn Leu Met
```

```
                 515                 520                 525
ctg gac aag gac ggg cac att aag atc aca gac ttc ggg ctg tgc aag     1632
Leu Asp Lys Asp Gly His Ile Lys Ile Thr Asp Phe Gly Leu Cys Lys
    530                 535                 540 gag ggg atc aag gac ggt gcc acc atg aag acc ttt tgc ggc aca cct     1680
Glu Gly Ile Lys Asp Gly Ala Thr Met Lys Thr Phe Cys Gly Thr Pro
545                 550                 555                 560 gag tac ctg gcc ccc gag gtg ctg gag gac aat gac tac ggc cgt gca     1728
Glu Tyr Leu Ala Pro Glu Val Leu Glu Asp Asn Asp Tyr Gly Arg Ala
                565                 570                 575 gtg gac tgg tgg ggg ctg ggc gtg gtc atg tac gag atg atg tgc ggt     1776
Val Asp Trp Trp Gly Leu Gly Val Val Met Tyr Glu Met Met Cys Gly
            580                 585                 590 cgc ctg ccc ttc tac aac cag gac cat gag aag ctt ttt gag ctc atc     1824
Arg Leu Pro Phe Tyr Asn Gln Asp His Glu Lys Leu Phe Glu Leu Ile
        595                 600                 605 ctc atg gag gag atc cgc ttc ccg cgc acg ctt ggt ccc gag gcc aag     1872
Leu Met Glu Glu Ile Arg Phe Pro Arg Thr Leu Gly Pro Glu Ala Lys
    610                 615                 620 tcc ttg ctt tca ggg ctg ctc aag aag gac ccc aag cag agg ctt ggc     1920
Ser Leu Leu Ser Gly Leu Leu Lys Lys Asp Pro Lys Gln Arg Leu Gly
625                 630                 635                 640 ggg ggc tcc gag gac gcc aag gag atc atg cag cat cgc ttc ttt gcc     1968
Gly Gly Ser Glu Asp Ala Lys Glu Ile Met Gln His Arg Phe Phe Ala
                645                 650                 655 ggt atc gtg tgg cag cac gtg tac gag aag aag ctc agc cca ccc ttc     2016
Gly Ile Val Trp Gln His Val Tyr Glu Lys Lys Leu Ser Pro Pro Phe
            660                 665                 670 aag ccc cag gtc acg tcg gag act gac acc agg tat ttt gat gag gag     2064
Lys Pro Gln Val Thr Ser Glu Thr Asp Thr Arg Tyr Phe Asp Glu Glu
        675                 680                 685 ttc acg gcc cag atg atc acc atc aca cca cct gac caa gat gac agc     2112
Phe Thr Ala Gln Met Ile Thr Ile Thr Pro Pro Asp Gln Asp Asp Ser
    690                 695                 700 atg gag tgt gtg gac agc gag cgc agg ccc cac ttc ccc cag ttc tcc     2160
Met Glu Cys Val Asp Ser Glu Arg Arg Pro His Phe Pro Gln Phe Ser
705                 710                 715                 720 tac tcg gcc agc agc acg gcc tga                                     2184
Tyr Ser Ala Ser Ser Thr Ala
                725

<210> SEQ ID NO 139
<211> LENGTH: 727
<212> TYPE: PRT
<213> ORGANISM: Artificial Sequence
<220> FEATURE:
<223> OTHER INFORMATION: EGFP-PKB fusion

<400> SEQUENCE: 139

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80
```

-continued

```
Gln His Asp Phe Phe Lys Ser Ala Met Pro Glu Gly Tyr Val Gln Glu
             85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Ser
225                 230                 235                 240

Gly Leu Arg Ser Arg Gly Thr Met Ser Asp Val Ala Ile Val Lys Glu
                245                 250                 255

Gly Trp Leu His Lys Arg Gly Glu Tyr Ile Lys Thr Trp Arg Pro Arg
            260                 265                 270

Tyr Phe Leu Leu Lys Asn Asp Gly Thr Phe Ile Gly Tyr Lys Glu Arg
        275                 280                 285

Pro Gln Asp Val Asp Gln Arg Glu Ala Pro Leu Asn Asn Phe Ser Val
    290                 295                 300

Ala Gln Cys Gln Leu Met Lys Thr Glu Arg Pro Arg Pro Asn Thr Phe
305                 310                 315                 320

Ile Ile Arg Cys Leu Gln Trp Thr Thr Val Ile Glu Arg Thr Phe His
                325                 330                 335

Val Glu Thr Pro Glu Glu Arg Glu Glu Trp Thr Thr Ala Ile Gln Thr
            340                 345                 350

Val Ala Asp Gly Leu Lys Lys Gln Glu Glu Glu Met Asp Phe Arg
        355                 360                 365

Ser Gly Ser Pro Ser Asp Asn Ser Gly Ala Glu Glu Met Glu Val Ser
    370                 375                 380

Leu Ala Lys Pro Lys His Arg Val Thr Met Asn Glu Phe Glu Tyr Leu
385                 390                 395                 400

Lys Leu Leu Gly Lys Gly Thr Phe Gly Lys Val Ile Leu Val Lys Glu
                405                 410                 415

Lys Ala Thr Gly Arg Tyr Tyr Ala Met Lys Ile Leu Lys Lys Glu Val
            420                 425                 430

Ile Val Ala Lys Asp Glu Val Ala His Thr Leu Thr Glu Asn Arg Val
        435                 440                 445

Leu Gln Asn Ser Arg His Pro Phe Leu Thr Ala Leu Lys Tyr Ser Phe
    450                 455                 460

Gln Thr His Asp Arg Leu Cys Phe Val Met Glu Tyr Ala Asn Gly Gly
465                 470                 475                 480

Glu Leu Phe Phe His Leu Ser Arg Glu Arg Val Phe Ser Glu Asp Arg
                485                 490                 495

Ala Arg Phe Tyr Gly Ala Glu Ile Val Ser Ala Leu Asp Tyr Leu His
```

```
Ser Glu Lys Asn Val Val Tyr Arg Asp Leu Lys Leu Glu Asn Leu Met
        515                 520                 525

Leu Asp Lys Asp Gly His Ile Lys Ile Thr Asp Phe Gly Leu Cys Lys
    530                 535                 540

Glu Gly Ile Lys Asp Gly Ala Thr Met Lys Thr Phe Cys Gly Thr Pro
545                 550                 555                 560

Glu Tyr Leu Ala Pro Glu Val Leu Glu Asp Asn Asp Tyr Gly Arg Ala
                565                 570                 575

Val Asp Trp Trp Gly Leu Gly Val Val Met Tyr Glu Met Met Cys Gly
            580                 585                 590

Arg Leu Pro Phe Tyr Asn Gln Asp His Glu Lys Leu Phe Glu Leu Ile
        595                 600                 605

Leu Met Glu Glu Ile Arg Phe Pro Arg Thr Leu Gly Pro Glu Ala Lys
    610                 615                 620

Ser Leu Leu Ser Gly Leu Leu Lys Lys Asp Pro Lys Gln Arg Leu Gly
625                 630                 635                 640

Gly Gly Ser Glu Asp Ala Lys Glu Ile Met Gln His Arg Phe Phe Ala
                645                 650                 655

Gly Ile Val Trp Gln His Val Tyr Glu Lys Lys Leu Ser Pro Pro Phe
            660                 665                 670

Lys Pro Gln Val Thr Ser Glu Thr Asp Thr Arg Tyr Phe Asp Glu Glu
        675                 680                 685

Phe Thr Ala Gln Met Ile Thr Ile Thr Pro Pro Asp Gln Asp Asp Ser
    690                 695                 700

Met Glu Cys Val Asp Ser Glu Arg Arg Pro His Phe Pro Gln Phe Ser
705                 710                 715                 720

Tyr Ser Ala Ser Ser Thr Ala
                725

<210> SEQ ID NO 140
<211> LENGTH: 2394
<212> TYPE: DNA
<213> ORGANISM: Artificial Sequence
<220> FEATURE:
<223> OTHER INFORMATION: NFkappaB-EGFP fusion
<220> FEATURE:
<221> NAME/KEY: CDS
<222> LOCATION: (1)..(2391)

<400> SEQUENCE: 140 atg gac gaa ctg ttc ccc ctc atc ttc ccg gca gag cca gcc cag gcc      48
Met Asp Glu Leu Phe Pro Leu Ile Phe Pro Ala Glu Pro Ala Gln Ala
1               5                   10                  15 tct ggc ccc tat gtg gag atc att gag cag ccc aag cag cgg ggc atg      96
Ser Gly Pro Tyr Val Glu Ile Ile Glu Gln Pro Lys Gln Arg Gly Met
            20                  25                  30 cgc ttc cgc tac aag tgc gag ggg cgc tcc gcg ggc agc atc cca ggc     144
Arg Phe Arg Tyr Lys Cys Glu Gly Arg Ser Ala Gly Ser Ile Pro Gly
        35                  40                  45 gag agg agc aca gat acc acc aag acc cac ccc acc atc aag atc aat     192
Glu Arg Ser Thr Asp Thr Thr Lys Thr His Pro Thr Ile Lys Ile Asn
    50                  55                  60 ggc tac aca gga cca ggg aca gtg cgc atc tcc ctg gtc acc aag gac     240
Gly Tyr Thr Gly Pro Gly Thr Val Arg Ile Ser Leu Val Thr Lys Asp
65                  70                  75                  80 cct cct cac cgg cct cac ccc cac gag ctt gta gga aag gac tgc cgg     288
Pro Pro His Arg Pro His Pro His Glu Leu Val Gly Lys Asp Cys Arg
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     | 85  |     |     |     |     | 90  |     |     |     |     |     | 95  |     |      |
| gat | ggc | ttc | tat | gag | gct | gag | ctc | tgc | ccg | gac | cgc | tgc | atc | cac | agt | 336  |
| Asp | Gly | Phe | Tyr | Glu | Ala | Glu | Leu | Cys | Pro | Asp | Arg | Cys | Ile | His | Ser |      |
|     |     |     | 100 |     |     |     |     | 105 |     |     |     |     | 110 |     |     |      |
| ttc | cag | aac | ctg | gga | atc | cag | tgt | gtg | aag | aag | cgg | gac | ctg | gag | cag | 384  |
| Phe | Gln | Asn | Leu | Gly | Ile | Gln | Cys | Val | Lys | Lys | Arg | Asp | Leu | Glu | Gln |      |
|     |     | 115 |     |     |     |     | 120 |     |     |     |     | 125 |     |     |     |      |
| gct | atc | agt | cag | cgc | atc | cag | acc | aac | aac | aac | ccc | ttc | caa | gtt | cct | 432  |
| Ala | Ile | Ser | Gln | Arg | Ile | Gln | Thr | Asn | Asn | Asn | Pro | Phe | Gln | Val | Pro |      |
|     | 130 |     |     |     |     | 135 |     |     |     |     | 140 |     |     |     |     |      |
| ata | gaa | gag | cag | cgt | ggg | gac | tac | gac | ctg | aat | gct | gtg | cgg | ctc | tgc | 480  |
| Ile | Glu | Glu | Gln | Arg | Gly | Asp | Tyr | Asp | Leu | Asn | Ala | Val | Arg | Leu | Cys |      |
| 145 |     |     |     |     | 150 |     |     |     |     | 155 |     |     |     |     | 160 |      |
| ttc | cag | gtg | aca | gtg | cgg | gac | cca | tca | ggc | agg | ccc | ctc | cgc | ctg | ccg | 528  |
| Phe | Gln | Val | Thr | Val | Arg | Asp | Pro | Ser | Gly | Arg | Pro | Leu | Arg | Leu | Pro |      |
|     |     |     |     | 165 |     |     |     |     | 170 |     |     |     |     | 175 |     |      |
| cct | gtc | ctt | cct | cat | ccc | atc | ttt | gac | aat | cgt | gcc | ccc | aac | act | gcc | 576  |
| Pro | Val | Leu | Pro | His | Pro | Ile | Phe | Asp | Asn | Arg | Ala | Pro | Asn | Thr | Ala |      |
|     |     |     | 180 |     |     |     |     | 185 |     |     |     |     | 190 |     |     |      |
| gag | ctc | aag | atc | tgc | cga | gtg | aac | cga | aac | tct | ggc | agc | tgc | ctc | ggt | 624  |
| Glu | Leu | Lys | Ile | Cys | Arg | Val | Asn | Arg | Asn | Ser | Gly | Ser | Cys | Leu | Gly |      |
|     |     | 195 |     |     |     |     | 200 |     |     |     |     | 205 |     |     |     |      |
| ggg | gat | gag | atc | ttc | cta | ctg | tgt | gac | aag | gtg | cag | aaa | gag | gac | att | 672  |
| Gly | Asp | Glu | Ile | Phe | Leu | Leu | Cys | Asp | Lys | Val | Gln | Lys | Glu | Asp | Ile |      |
|     | 210 |     |     |     |     | 215 |     |     |     |     | 220 |     |     |     |     |      |
| gag | gtg | tat | ttc | acg | gga | cca | ggc | tgg | gag | gcc | cga | ggc | tcc | ttt | tcg | 720  |
| Glu | Val | Tyr | Phe | Thr | Gly | Pro | Gly | Trp | Glu | Ala | Arg | Gly | Ser | Phe | Ser |      |
| 225 |     |     |     |     | 230 |     |     |     |     | 235 |     |     |     |     | 240 |      |
| caa | gct | gat | gtg | cac | cga | caa | gtg | gcc | att | gtg | ttc | cgg | acc | cct | ccc | 768  |
| Gln | Ala | Asp | Val | His | Arg | Gln | Val | Ala | Ile | Val | Phe | Arg | Thr | Pro | Pro |      |
|     |     |     |     | 245 |     |     |     |     | 250 |     |     |     |     | 255 |     |      |
| tac | gca | gac | ccc | agc | ctg | cag | gct | cct | gtg | cgt | gtc | tcc | atg | cag | ctg | 816  |
| Tyr | Ala | Asp | Pro | Ser | Leu | Gln | Ala | Pro | Val | Arg | Val | Ser | Met | Gln | Leu |      |
|     |     |     | 260 |     |     |     |     | 265 |     |     |     |     | 270 |     |     |      |
| cgg | cgg | cct | tcc | gac | cgg | gag | ctc | agt | gag | ccc | atg | gaa | ttc | cag | tac | 864  |
| Arg | Arg | Pro | Ser | Asp | Arg | Glu | Leu | Ser | Glu | Pro | Met | Glu | Phe | Gln | Tyr |      |
|     |     | 275 |     |     |     |     | 280 |     |     |     |     | 285 |     |     |     |      |
| ctg | cca | gat | aca | gac | gat | cgt | cac | cgg | att | gag | gag | aaa | cgt | aaa | agg | 912  |
| Leu | Pro | Asp | Thr | Asp | Asp | Arg | His | Arg | Ile | Glu | Glu | Lys | Arg | Lys | Arg |      |
|     | 290 |     |     |     |     | 295 |     |     |     |     | 300 |     |     |     |     |      |
| aca | tat | gag | acc | ttc | aag | agc | atc | atg | aag | aag | agt | cct | ttc | agc | gga | 960  |
| Thr | Tyr | Glu | Thr | Phe | Lys | Ser | Ile | Met | Lys | Lys | Ser | Pro | Phe | Ser | Gly |      |
| 305 |     |     |     |     | 310 |     |     |     |     | 315 |     |     |     |     | 320 |      |
| ccc | acc | gac | ccc | cgg | cct | cca | cct | cga | cgc | att | gct | gtg | cct | tcc | cgc | 1008 |
| Pro | Thr | Asp | Pro | Arg | Pro | Pro | Pro | Arg | Arg | Ile | Ala | Val | Pro | Ser | Arg |      |
|     |     |     |     | 325 |     |     |     |     | 330 |     |     |     |     | 335 |     |      |
| agc | tca | gct | tct | gtc | ccc | aag | cca | gca | ccc | cag | ccc | tat | ccc | ttt | acg | 1056 |
| Ser | Ser | Ala | Ser | Val | Pro | Lys | Pro | Ala | Pro | Gln | Pro | Tyr | Pro | Phe | Thr |      |
|     |     |     | 340 |     |     |     |     | 345 |     |     |     |     | 350 |     |     |      |
| tca | tcc | ctg | agc | acc | atc | aac | tat | gat | gag | ttt | ccc | acc | atg | gtg | ttt | 1104 |
| Ser | Ser | Leu | Ser | Thr | Ile | Asn | Tyr | Asp | Glu | Phe | Pro | Thr | Met | Val | Phe |      |
|     |     | 355 |     |     |     |     | 360 |     |     |     |     | 365 |     |     |     |      |
| cct | tct | ggg | cag | atc | agc | cag | gcc | tcg | gcc | ttg | gcc | ccg | gcc | cct | ccc | 1152 |
| Pro | Ser | Gly | Gln | Ile | Ser | Gln | Ala | Ser | Ala | Leu | Ala | Pro | Ala | Pro | Pro |      |
|     | 370 |     |     |     |     | 375 |     |     |     |     | 380 |     |     |     |     |      |
| caa | gtc | ctg | ccc | cag | gct | cca | gcc | cct | gcc | cct | gct | cca | gcc | atg | gta | 1200 |
| Gln | Val | Leu | Pro | Gln | Ala | Pro | Ala | Pro | Ala | Pro | Ala | Pro | Ala | Met | Val |      |
| 385 |     |     |     |     | 390 |     |     |     |     | 395 |     |     |     |     | 400 |      |
| tca | gct | ctg | gcc | cag | gcc | cca | gcc | cct | gtc | cca | gtc | cta | gcc | cca | ggc | 1248 |

-continued

```
                Ser Ala Leu Ala Gln Ala Pro Ala Pro Val Pro Val Leu Ala Pro Gly
                                405                 410                 415 cct cct cag gct gtg gcc cca cct gcc ccc aag ccc acc cag gct ggg       1296
Pro Pro Gln Ala Val Ala Pro Pro Ala Pro Lys Pro Thr Gln Ala Gly
            420                 425                 430 gaa gga acg ctg tca gag gcc ctg ctg cag ctg cag ttt gat gat gaa       1344
Glu Gly Thr Leu Ser Glu Ala Leu Leu Gln Leu Gln Phe Asp Asp Glu
            435                 440                 445 gac ctg ggg gcc ttg ctt ggc aac agc aca gac cca gct gtg ttc aca       1392
Asp Leu Gly Ala Leu Leu Gly Asn Ser Thr Asp Pro Ala Val Phe Thr
450                 455                 460 gac ctg gca tcc gtc gac aac tcc gag ttt cag cag ctg ctg aac cag       1440
Asp Leu Ala Ser Val Asp Asn Ser Glu Phe Gln Gln Leu Leu Asn Gln
465                 470                 475                 480 ggc ata cct gtg gcc ccc cac aca act gag ccc atg ctg atg gag tac       1488
Gly Ile Pro Val Ala Pro His Thr Thr Glu Pro Met Leu Met Glu Tyr
                485                 490                 495 cct gag gct ata act cgc cta gtg aca ggg gcc cag agg ccc ccc gac       1536
Pro Glu Ala Ile Thr Arg Leu Val Thr Gly Ala Gln Arg Pro Pro Asp
            500                 505                 510 cca gct cct gct cca ctg ggg gcc ccg ggc ctc ccc aat ggc ctc ctt       1584
Pro Ala Pro Ala Pro Leu Gly Ala Pro Gly Leu Pro Asn Gly Leu Leu
            515                 520                 525 tca gga gat gaa gac ttc tcc tcc att gcg gac atg gac ttc tca gcc       1632
Ser Gly Asp Glu Asp Phe Ser Ser Ile Ala Asp Met Asp Phe Ser Ala
530                 535                 540 ctg ctg agt cag atc agc tcc ttg gat cca ccg gtc gcc acc atg gtg       1680
Leu Leu Ser Gln Ile Ser Ser Leu Asp Pro Pro Val Ala Thr Met Val
545                 550                 555                 560 agc aag ggc gag gag ctg ttc acc ggg gtg gtg ccc atc ctg gtc gag       1728
Ser Lys Gly Glu Glu Leu Phe Thr Gly Val Val Pro Ile Leu Val Glu
                565                 570                 575 ctg gac ggc gac gta aac ggc cac aag ttc agc gtg tcc ggc gag ggc       1776
Leu Asp Gly Asp Val Asn Gly His Lys Phe Ser Val Ser Gly Glu Gly
            580                 585                 590 gag ggc gat gcc acc tac ggc aag ctg acc ctg aag ttc atc tgc acc       1824
Glu Gly Asp Ala Thr Tyr Gly Lys Leu Thr Leu Lys Phe Ile Cys Thr
            595                 600                 605 acc ggc aag ctg ccc gtg ccc tgg ccc acc ctc gtg acc acc ctg acc       1872
Thr Gly Lys Leu Pro Val Pro Trp Pro Thr Leu Val Thr Thr Leu Thr
610                 615                 620 tac ggc gtg cag tgc ttc agc cgc tac ccc gac cac atg aag cag cac       1920
Tyr Gly Val Gln Cys Phe Ser Arg Tyr Pro Asp His Met Lys Gln His
625                 630                 635                 640 gac ttc ttc aag tcc gcc atg ccc gaa ggc tac gtc cag gag cgc acc       1968
Asp Phe Phe Lys Ser Ala Met Pro Glu Gly Tyr Val Gln Glu Arg Thr
                645                 650                 655 atc ttc ttc aag gac gac ggc aac tac aag acc cgc gcc gag gtg aag       2016
Ile Phe Phe Lys Asp Asp Gly Asn Tyr Lys Thr Arg Ala Glu Val Lys
            660                 665                 670 ttc gag ggc gac acc ctg gtg aac cgc atc gag ctg aag ggc atc gac       2064
Phe Glu Gly Asp Thr Leu Val Asn Arg Ile Glu Leu Lys Gly Ile Asp
            675                 680                 685 ttc aag gag gac ggc aac atc ctg ggg cac aag ctg gag tac aac tac       2112
Phe Lys Glu Asp Gly Asn Ile Leu Gly His Lys Leu Glu Tyr Asn Tyr
            690                 695                 700 aac agc cac aac gtc tat atc atg gcc gac aag cag aag aac ggc atc       2160
Asn Ser His Asn Val Tyr Ile Met Ala Asp Lys Gln Lys Asn Gly Ile
705                 710                 715                 720
```

```
aag gtg aac ttc aag atc cgc cac aac atc gag gac ggc agc gtg cag      2208
Lys Val Asn Phe Lys Ile Arg His Asn Ile Glu Asp Gly Ser Val Gln
            725                 730                 735 ctc gcc gac cac tac cag cag aac acc ccc atc ggc gac ggc ccc gtg      2256
Leu Ala Asp His Tyr Gln Gln Asn Thr Pro Ile Gly Asp Gly Pro Val
        740                 745                 750 ctg ctg ccc gac aac cac tac ctg agc acc cag tcc gcc ctg agc aaa      2304
Leu Leu Pro Asp Asn His Tyr Leu Ser Thr Gln Ser Ala Leu Ser Lys
    755                 760                 765 gac ccc aac gag aag cgc gat cac atg gtc ctg ctg gag ttc gtg acc      2352
Asp Pro Asn Glu Lys Arg Asp His Met Val Leu Leu Glu Phe Val Thr
770                 775                 780 gcc gcc ggg atc act ctc ggc atg gac gag ctg tac aag taa              2394
Ala Ala Gly Ile Thr Leu Gly Met Asp Glu Leu Tyr Lys
785                 790                 795
```

<210> SEQ ID NO 141
<211> LENGTH: 797
<212> TYPE: PRT
<213> ORGANISM: Artificial Sequence
<220> FEATURE:
<223> OTHER INFORMATION: NFkappaB-EGFP fusion

<400> SEQUENCE: 141

```
Met Asp Glu Leu Phe Pro Leu Ile Phe Pro Ala Glu Pro Ala Gln Ala
1               5                   10                  15

Ser Gly Pro Tyr Val Glu Ile Ile Glu Gln Pro Lys Gln Arg Gly Met
            20                  25                  30

Arg Phe Arg Tyr Lys Cys Glu Gly Arg Ser Ala Gly Ser Ile Pro Gly
        35                  40                  45

Glu Arg Ser Thr Asp Thr Thr Lys Thr His Pro Thr Ile Lys Ile Asn
    50                  55                  60

Gly Tyr Thr Gly Pro Gly Thr Val Arg Ile Ser Leu Val Thr Lys Asp
65                  70                  75                  80

Pro Pro His Arg Pro His Pro His Glu Leu Val Gly Lys Asp Cys Arg
                85                  90                  95

Asp Gly Phe Tyr Glu Ala Glu Leu Cys Pro Asp Arg Cys Ile His Ser
            100                 105                 110

Phe Gln Asn Leu Gly Ile Gln Cys Val Lys Lys Arg Asp Leu Glu Gln
        115                 120                 125

Ala Ile Ser Gln Arg Ile Gln Thr Asn Asn Asn Pro Phe Gln Val Pro
    130                 135                 140

Ile Glu Glu Gln Arg Gly Asp Tyr Asp Leu Asn Ala Val Arg Leu Cys
145                 150                 155                 160

Phe Gln Val Thr Val Arg Asp Pro Ser Gly Arg Pro Leu Arg Leu Pro
                165                 170                 175

Pro Val Leu Pro His Pro Ile Phe Asp Asn Arg Ala Pro Asn Thr Ala
            180                 185                 190

Glu Leu Lys Ile Cys Arg Val Asn Arg Asn Ser Gly Ser Cys Leu Gly
        195                 200                 205

Gly Asp Glu Ile Phe Leu Leu Cys Asp Lys Val Gln Lys Glu Asp Ile
    210                 215                 220

Glu Val Tyr Phe Thr Gly Pro Gly Trp Glu Ala Arg Gly Ser Phe Ser
225                 230                 235                 240

Gln Ala Asp Val His Arg Gln Val Ala Ile Val Phe Arg Thr Pro Pro
                245                 250                 255

Tyr Ala Asp Pro Ser Leu Gln Ala Pro Val Arg Val Ser Met Gln Leu
```

```
                260                 265                 270
Arg Arg Pro Ser Asp Arg Glu Leu Ser Glu Pro Met Glu Phe Gln Tyr
        275                 280                 285
Leu Pro Asp Thr Asp Arg His Arg Ile Glu Glu Lys Arg Lys Arg
290                 295                 300
Thr Tyr Glu Thr Phe Lys Ser Ile Met Lys Lys Ser Pro Phe Ser Gly
305                 310                 315                 320
Pro Thr Asp Pro Arg Pro Pro Arg Ile Ala Val Pro Ser Arg
                325                 330                 335
Ser Ser Ala Ser Val Pro Lys Pro Ala Pro Gln Pro Tyr Pro Phe Thr
        340                 345                 350
Ser Ser Leu Ser Thr Ile Asn Tyr Asp Glu Phe Pro Thr Met Val Phe
        355                 360                 365
Pro Ser Gly Gln Ile Ser Gln Ala Ser Ala Leu Ala Pro Ala Pro Pro
        370                 375                 380
Gln Val Leu Pro Gln Ala Pro Ala Pro Ala Pro Ala Pro Ala Met Val
385                 390                 395                 400
Ser Ala Leu Ala Gln Ala Pro Ala Pro Val Pro Val Leu Ala Pro Gly
                405                 410                 415
Pro Pro Gln Ala Val Ala Pro Pro Ala Pro Lys Pro Thr Gln Ala Gly
                420                 425                 430
Glu Gly Thr Leu Ser Glu Ala Leu Leu Gln Leu Gln Phe Asp Asp Glu
        435                 440                 445
Asp Leu Gly Ala Leu Leu Gly Asn Ser Thr Asp Pro Ala Val Phe Thr
465                 470                 475                 480
Asp Leu Ala Ser Val Asp Asn Ser Glu Phe Gln Gln Leu Leu Asn Gln
465                 470                 475                 480
Gly Ile Pro Val Ala Pro His Thr Thr Glu Pro Met Leu Met Glu Tyr
                485                 490                 495
Pro Glu Ala Ile Thr Arg Leu Val Thr Gly Ala Gln Arg Pro Pro Asp
                500                 505                 510
Pro Ala Pro Ala Pro Leu Gly Ala Pro Gly Leu Pro Asn Gly Leu Leu
                515                 520                 525
Ser Gly Asp Glu Asp Phe Ser Ser Ile Ala Asp Met Asp Phe Ser Ala
        530                 535                 540
Leu Leu Ser Gln Ile Ser Ser Leu Asp Pro Pro Val Ala Thr Met Val
545                 550                 555                 560
Ser Lys Gly Glu Glu Leu Phe Thr Gly Val Val Pro Ile Leu Val Glu
                565                 570                 575
Leu Asp Gly Asp Val Asn Gly His Lys Phe Ser Val Ser Gly Glu Gly
                580                 585                 590
Glu Gly Asp Ala Thr Tyr Gly Lys Leu Thr Leu Lys Phe Ile Cys Thr
        595                 600                 605
Thr Gly Lys Leu Pro Val Pro Trp Pro Thr Leu Val Thr Thr Leu Thr
610                 615                 620
Tyr Gly Val Gln Cys Phe Ser Arg Tyr Pro Asp His Met Lys Gln His
625                 630                 635                 640
Asp Phe Phe Lys Ser Ala Met Pro Glu Gly Tyr Val Gln Glu Arg Thr
                645                 650                 655
Ile Phe Phe Lys Asp Asp Gly Asn Tyr Lys Thr Arg Ala Glu Val Lys
                660                 665                 670
Phe Glu Gly Asp Thr Leu Val Asn Arg Ile Glu Leu Lys Gly Ile Asp
        675                 680                 685
```

-continued

```
Phe Lys Glu Asp Gly Asn Ile Leu Gly His Lys Leu Glu Tyr Asn Tyr
    690                 695                 700
Asn Ser His Asn Val Tyr Ile Met Ala Asp Lys Gln Lys Asn Gly Ile
705                 710                 715                 720
Lys Val Asn Phe Lys Ile Arg His Asn Ile Glu Asp Gly Ser Val Gln
                725                 730                 735
Leu Ala Asp His Tyr Gln Gln Asn Thr Pro Ile Gly Asp Gly Pro Val
            740                 745                 750
Leu Leu Pro Asp Asn His Tyr Leu Ser Thr Gln Ser Ala Leu Ser Lys
        755                 760                 765
Asp Pro Asn Glu Lys Arg Asp His Met Val Leu Leu Glu Phe Val Thr
    770                 775                 780
Ala Ala Gly Ile Thr Leu Gly Met Asp Glu Leu Tyr Lys
785                 790                 795
```

<210> SEQ ID NO 142
<211> LENGTH: 2394
<212> TYPE: DNA
<213> ORGANISM: Artificial Sequence
<220> FEATURE:
<223> OTHER INFORMATION: EGFP-NFkappaB fusion
<220> FEATURE:
<221> NAME/KEY: CDS
<222> LOCATION: (1)..(2391)

<400> SEQUENCE: 142

```
atg gtg agc aag ggc gag gag ctg ttc acc ggg gtg gtg ccc atc ctg      48
Met Val Ser Lys Gly Glu Glu Leu Phe Thr Gly Val Val Pro Ile Leu
1               5                   10                  15 gtc gag ctg gac ggc gac gta aac ggc cac aag ttc agc gtg tcc ggc      96
Val Glu Leu Asp Gly Asp Val Asn Gly His Lys Phe Ser Val Ser Gly
            20                  25                  30 gag ggc gag ggc gat gcc acc tac ggc aag ctg acc ctg aag ttc atc     144
Glu Gly Glu Gly Asp Ala Thr Tyr Gly Lys Leu Thr Leu Lys Phe Ile
        35                  40                  45 tgc acc acc ggc aag ctg ccc gtg ccc tgg ccc acc ctc gtg acc acc     192
Cys Thr Thr Gly Lys Leu Pro Val Pro Trp Pro Thr Leu Val Thr Thr
    50                  55                  60 ctg acc tac ggc gtg cag tgc ttc agc cgc tac ccc gac cac atg aag     240
Leu Thr Tyr Gly Val Gln Cys Phe Ser Arg Tyr Pro Asp His Met Lys
65                  70                  75                  80 cag cac gac ttc ttc aag tcc gcc atg ccc gaa ggc tac gtc cag gag     288
Gln His Asp Phe Phe Lys Ser Ala Met Pro Glu Gly Tyr Val Gln Glu
                85                  90                  95 cgc acc atc ttc ttc aag gac gac ggc aac tac aag acc cgc gcc gag     336
Arg Thr Ile Phe Phe Lys Asp Asp Gly Asn Tyr Lys Thr Arg Ala Glu
            100                 105                 110 gtg aag ttc gag ggc gac acc ctg gtg aac cgc atc gag ctg aag ggc     384
Val Lys Phe Glu Gly Asp Thr Leu Val Asn Arg Ile Glu Leu Lys Gly
        115                 120                 125 atc gac ttc aag gag gac ggc aac atc ctg ggg cac aag ctg gag tac     432
Ile Asp Phe Lys Glu Asp Gly Asn Ile Leu Gly His Lys Leu Glu Tyr
    130                 135                 140 aac tac aac agc cac aac gtc tat atc atg gcc gac aag cag aag aac     480
Asn Tyr Asn Ser His Asn Val Tyr Ile Met Ala Asp Lys Gln Lys Asn
145                 150                 155                 160 ggc atc aag gtg aac ttc aag atc cgc cac aac atc gag gac ggc agc     528
Gly Ile Lys Val Asn Phe Lys Ile Arg His Asn Ile Glu Asp Gly Ser
                165                 170                 175
```

```
gtg cag ctc gcc gac cac tac cag cag aac acc ccc atc ggc gac ggc        576
Val Gln Leu Ala Asp His Tyr Gln Gln Asn Thr Pro Ile Gly Asp Gly
            180                 185                 190 ccc gtg ctg ctg ccc gac aac cac tac ctg agc acc cag tcc gcc ctg        624
Pro Val Leu Leu Pro Asp Asn His Tyr Leu Ser Thr Gln Ser Ala Leu
            195                 200                 205 agc aaa gac ccc aac gag aag cgc gat cac atg gtc ctg ctg gag ttc        672
Ser Lys Asp Pro Asn Glu Lys Arg Asp His Met Val Leu Leu Glu Phe
    210                 215                 220 gtg acc gcc gcc ggg atc act ctc ggc atg gac gag ctg tac aag tcc        720
Val Thr Ala Ala Gly Ile Thr Leu Gly Met Asp Glu Leu Tyr Lys Ser
225                 230                 235                 240 gga ctc aga tct cga gcc atg gac gaa ctg ttc ccc ctc atc ttc ccg        768
Gly Leu Arg Ser Arg Ala Met Asp Glu Leu Phe Pro Leu Ile Phe Pro
                245                 250                 255 gca gag cca gcc cag gcc tct ggc ccc tat gtg gag atc att gag cag        816
Ala Glu Pro Ala Gln Ala Ser Gly Pro Tyr Val Glu Ile Ile Glu Gln
            260                 265                 270 ccc aag cag cgg ggc atg cgc ttc cgc tac aag tgc gag ggg cgc tcc        864
Pro Lys Gln Arg Gly Met Arg Phe Arg Tyr Lys Cys Glu Gly Arg Ser
        275                 280                 285 gcg ggc agc atc cca ggc gag agg agc aca gat acc acc aag acc cac        912
Ala Gly Ser Ile Pro Gly Glu Arg Ser Thr Asp Thr Thr Lys Thr His
    290                 295                 300 ccc acc atc aag atc aat ggc tac aca gga cca ggg aca gtg cgc atc        960
Pro Thr Ile Lys Ile Asn Gly Tyr Thr Gly Pro Gly Thr Val Arg Ile
305                 310                 315                 320 tcc ctg gtc acc aag gac cct cct cac cgg cct cac ccc cac gag ctt       1008
Ser Leu Val Thr Lys Asp Pro Pro His Arg Pro His Pro His Glu Leu
                325                 330                 335 gta gga aag gac tgc cgg gat ggc ttc tat gag gct gag ctc tgc ccg       1056
Val Gly Lys Asp Cys Arg Asp Gly Phe Tyr Glu Ala Glu Leu Cys Pro
            340                 345                 350 gac cgc tgc atc cac agt ttc cag aac ctg gga atc cag tgt gtg aag       1104
Asp Arg Cys Ile His Ser Phe Gln Asn Leu Gly Ile Gln Cys Val Lys
        355                 360                 365 aag cgg gac ctg gag cag gct atc agt cag cgc atc cag acc aac aac       1152
Lys Arg Asp Leu Glu Gln Ala Ile Ser Gln Arg Ile Gln Thr Asn Asn
370                 375                 380 aac ccc ttc caa gtt cct ata gaa gag cag cgt ggg gac tac gac ctg       1200
Asn Pro Phe Gln Val Pro Ile Glu Glu Gln Arg Gly Asp Tyr Asp Leu
385                 390                 395                 400 aat gct gtg cgg ctc tgc ttc cag gtg aca gtg cgg gac cca tca ggc       1248
Asn Ala Val Arg Leu Cys Phe Gln Val Thr Val Arg Asp Pro Ser Gly
                405                 410                 415 agg ccc ctc cgc ctg ccg cct gtc ctt cct cat ccc atc ttt gac aat       1296
Arg Pro Leu Arg Leu Pro Pro Val Leu Pro His Pro Ile Phe Asp Asn
            420                 425                 430 cgt gcc ccc aac act gcc gag ctc aag atc tgc cga gtg aac cga aac       1344
Arg Ala Pro Asn Thr Ala Glu Leu Lys Ile Cys Arg Val Asn Arg Asn
        435                 440                 445 tct ggc agc tgc ctc ggt ggg gat gag atc ttc cta ctg tgt gac aag       1392
Ser Gly Ser Cys Leu Gly Gly Asp Glu Ile Phe Leu Leu Cys Asp Lys
    450                 455                 460 gtg cag aaa gag gac att gag gtg tat ttc acg gga cca ggc tgg gag       1440
Val Gln Lys Glu Asp Ile Glu Val Tyr Phe Thr Gly Pro Gly Trp Glu
465                 470                 475                 480 gcc cga ggc tcc ttt tcg caa gct gat gtg cac cga caa gtg gcc att       1488
Ala Arg Gly Ser Phe Ser Gln Ala Asp Val His Arg Gln Val Ala Ile
                485                 490                 495
```

-continued

```
gtg ttc cgg acc cct ccc tac gca gac ccc agc ctg cag gct cct gtg   1536
Val Phe Arg Thr Pro Pro Tyr Ala Asp Pro Ser Leu Gln Ala Pro Val
            500                 505                 510 cgt gtc tcc atg cag ctg cgg cgg cct tcc gac cgg gag ctc agt gag   1584
Arg Val Ser Met Gln Leu Arg Arg Pro Ser Asp Arg Glu Leu Ser Glu
            515                 520                 525 ccc atg gaa ttc cag tac ctg cca gat aca gac gat cgt cac cgg att   1632
Pro Met Glu Phe Gln Tyr Leu Pro Asp Thr Asp Asp Arg His Arg Ile
            530                 535                 540 gag gag aaa cgt aaa agg aca tat gag acc ttc aag agc atc atg aag   1680
Glu Glu Lys Arg Lys Arg Thr Tyr Glu Thr Phe Lys Ser Ile Met Lys
545                 550                 555                 560 aag agt cct ttc agc gga ccc acc gac ccc cgg cct cca cct cga cgc   1728
Lys Ser Pro Phe Ser Gly Pro Thr Asp Pro Arg Pro Pro Pro Arg Arg
                565                 570                 575 att gct gtg cct tcc cgc agc tca gct tct gtc ccc aag cca gca ccc   1776
Ile Ala Val Pro Ser Arg Ser Ser Ala Ser Val Pro Lys Pro Ala Pro
                580                 585                 590 cag ccc tat ccc ttt acg tca tcc ctg agc acc atc aac tat gat gag   1824
Gln Pro Tyr Pro Phe Thr Ser Ser Leu Ser Thr Ile Asn Tyr Asp Glu
            595                 600                 605 ttt ccc acc atg gtg ttt cct tct ggg cag atc agc cag gcc tcg gcc   1872
Phe Pro Thr Met Val Phe Pro Ser Gly Gln Ile Ser Gln Ala Ser Ala
            610                 615                 620 ttg gcc ccg gcc cct ccc caa gtc ctg ccc cag gct cca gcc cct gcc   1920
Leu Ala Pro Ala Pro Pro Gln Val Leu Pro Gln Ala Pro Ala Pro Ala
625                 630                 635                 640 cct gct cca gcc atg gta tca gct ctg gcc cag gcc cca gcc cct gtc   1968
Pro Ala Pro Ala Met Val Ser Ala Leu Ala Gln Ala Pro Ala Pro Val
                645                 650                 655 cca gtc cta gcc cca ggc cct cct cag gct gtg gcc cca cct gcc ccc   2016
Pro Val Leu Ala Pro Gly Pro Pro Gln Ala Val Ala Pro Pro Ala Pro
                660                 665                 670 aag ccc acc cag gct ggg gaa gga acg ctg tca gag gcc ctg ctg cag   2064
Lys Pro Thr Gln Ala Gly Glu Gly Thr Leu Ser Glu Ala Leu Leu Gln
            675                 680                 685 ctg cag ttt gat gat gaa gac ctg ggg gcc ttg ctt ggc aac agc aca   2112
Leu Gln Phe Asp Asp Glu Asp Leu Gly Ala Leu Leu Gly Asn Ser Thr
690                 695                 700 gac cca gct gtg ttc aca gac ctg gca tcc gtc gac aac tcc gag ttt   2160
Asp Pro Ala Val Phe Thr Asp Leu Ala Ser Val Asp Asn Ser Glu Phe
705                 710                 715                 720 cag cag ctg ctg aac cag ggc ata cct gtg gcc ccc cac aca act gag   2208
Gln Gln Leu Leu Asn Gln Gly Ile Pro Val Ala Pro His Thr Thr Glu
                725                 730                 735 ccc atg ctg atg gag tac cct gag gct ata act cgc cta gtg aca ggg   2256
Pro Met Leu Met Glu Tyr Pro Glu Ala Ile Thr Arg Leu Val Thr Gly
            740                 745                 750 gcc cag agg ccc ccc gac cca gct cct gct cca ctg ggg gcc ccg ggg   2304
Ala Gln Arg Pro Pro Asp Pro Ala Pro Ala Pro Leu Gly Ala Pro Gly
            755                 760                 765 ctc ccc aat ggc ctc ctt tca gga gat gaa gac ttc tcc tcc att gcg   2352
Leu Pro Asn Gly Leu Leu Ser Gly Asp Glu Asp Phe Ser Ser Ile Ala
770                 775                 780 gac atg gac ttc tca gcc ctg ctg agt cag atc agc tcc taa           2394
Asp Met Asp Phe Ser Ala Leu Leu Ser Gln Ile Ser Ser
785                 790                 795
```

<210> SEQ ID NO 143

```
<211> LENGTH: 797
<212> TYPE: PRT
<213> ORGANISM: Artificial Sequence
<220> FEATURE:
<223> OTHER INFORMATION: EGFP-NFkappaB fusion

<400> SEQUENCE: 143
```

| Met | Val | Ser | Lys | Gly | Glu | Glu | Leu | Phe | Thr | Gly | Val | Val | Pro | Ile | Leu |
|---|---|---|---|---|---|---|---|---|---|---|---|---|---|---|---|
| 1 | | | | 5 | | | | | 10 | | | | | 15 | |

| Val | Glu | Leu | Asp | Gly | Asp | Val | Asn | Gly | His | Lys | Phe | Ser | Val | Ser | Gly |
|---|---|---|---|---|---|---|---|---|---|---|---|---|---|---|---|
| | | | 20 | | | | | 25 | | | | | 30 | | |

| Glu | Gly | Glu | Gly | Asp | Ala | Thr | Tyr | Gly | Lys | Leu | Thr | Leu | Lys | Phe | Ile |
|---|---|---|---|---|---|---|---|---|---|---|---|---|---|---|---|
| | | 35 | | | | | 40 | | | | | 45 | | | |

| Cys | Thr | Thr | Gly | Lys | Leu | Pro | Val | Pro | Trp | Pro | Thr | Leu | Val | Thr | Thr |
|---|---|---|---|---|---|---|---|---|---|---|---|---|---|---|---|
| 50 | | | | | 55 | | | | | 60 | | | | | |

| Leu | Thr | Tyr | Gly | Val | Gln | Cys | Phe | Ser | Arg | Tyr | Pro | Asp | His | Met | Lys |
|---|---|---|---|---|---|---|---|---|---|---|---|---|---|---|---|
| 65 | | | | 70 | | | | | 75 | | | | | 80 | |

| Gln | His | Asp | Phe | Phe | Lys | Ser | Ala | Met | Pro | Glu | Gly | Tyr | Val | Gln | Glu |
|---|---|---|---|---|---|---|---|---|---|---|---|---|---|---|---|
| | | | | 85 | | | | | 90 | | | | | 95 | |

| Arg | Thr | Ile | Phe | Phe | Lys | Asp | Asp | Gly | Asn | Tyr | Lys | Thr | Arg | Ala | Glu |
|---|---|---|---|---|---|---|---|---|---|---|---|---|---|---|---|
| | | | 100 | | | | | 105 | | | | | 110 | | |

| Val | Lys | Phe | Glu | Gly | Asp | Thr | Leu | Val | Asn | Arg | Ile | Glu | Leu | Lys | Gly |
|---|---|---|---|---|---|---|---|---|---|---|---|---|---|---|---|
| | | | 115 | | | | | 120 | | | | | 125 | | |

| Ile | Asp | Phe | Lys | Glu | Asp | Gly | Asn | Ile | Leu | Gly | His | Lys | Leu | Glu | Tyr |
|---|---|---|---|---|---|---|---|---|---|---|---|---|---|---|---|
| 130 | | | | | 135 | | | | | 140 | | | | | |

| Asn | Tyr | Asn | Ser | His | Asn | Val | Tyr | Ile | Met | Ala | Asp | Lys | Gln | Lys | Asn |
|---|---|---|---|---|---|---|---|---|---|---|---|---|---|---|---|
| 145 | | | | 150 | | | | | 155 | | | | | 160 | |

| Gly | Ile | Lys | Val | Asn | Phe | Lys | Ile | Arg | His | Asn | Ile | Glu | Asp | Gly | Ser |
|---|---|---|---|---|---|---|---|---|---|---|---|---|---|---|---|
| | | | | 165 | | | | | 170 | | | | | 175 | |

| Val | Gln | Leu | Ala | Asp | His | Tyr | Gln | Gln | Asn | Thr | Pro | Ile | Gly | Asp | Gly |
|---|---|---|---|---|---|---|---|---|---|---|---|---|---|---|---|
| | | | 180 | | | | | 185 | | | | | 190 | | |

| Pro | Val | Leu | Leu | Pro | Asp | Asn | His | Tyr | Leu | Ser | Thr | Gln | Ser | Ala | Leu |
|---|---|---|---|---|---|---|---|---|---|---|---|---|---|---|---|
| | | | 195 | | | | | 200 | | | | | 205 | | |

| Ser | Lys | Asp | Pro | Asn | Glu | Lys | Arg | Asp | His | Met | Val | Leu | Leu | Glu | Phe |
|---|---|---|---|---|---|---|---|---|---|---|---|---|---|---|---|
| 210 | | | | | 215 | | | | | 220 | | | | | |

| Val | Thr | Ala | Ala | Gly | Ile | Thr | Leu | Gly | Met | Asp | Glu | Leu | Tyr | Lys | Ser |
|---|---|---|---|---|---|---|---|---|---|---|---|---|---|---|---|
| 225 | | | | 230 | | | | | 235 | | | | | 240 | |

| Gly | Leu | Arg | Ser | Arg | Ala | Met | Asp | Glu | Leu | Phe | Pro | Leu | Ile | Phe | Pro |
|---|---|---|---|---|---|---|---|---|---|---|---|---|---|---|---|
| | | | | 245 | | | | | 250 | | | | | 255 | |

| Ala | Glu | Pro | Ala | Gln | Ala | Ser | Gly | Pro | Tyr | Val | Glu | Ile | Ile | Glu | Gln |
|---|---|---|---|---|---|---|---|---|---|---|---|---|---|---|---|
| | | | 260 | | | | | 265 | | | | | 270 | | |

| Pro | Lys | Gln | Arg | Gly | Met | Arg | Phe | Arg | Tyr | Lys | Cys | Glu | Gly | Arg | Ser |
|---|---|---|---|---|---|---|---|---|---|---|---|---|---|---|---|
| | | | 275 | | | | | 280 | | | | | 285 | | |

| Ala | Gly | Ser | Ile | Pro | Gly | Glu | Arg | Ser | Thr | Asp | Thr | Thr | Lys | Thr | His |
|---|---|---|---|---|---|---|---|---|---|---|---|---|---|---|---|
| | 290 | | | | | 295 | | | | | 300 | | | | |

| Pro | Thr | Ile | Lys | Ile | Asn | Gly | Tyr | Thr | Gly | Pro | Gly | Thr | Val | Arg | Ile |
|---|---|---|---|---|---|---|---|---|---|---|---|---|---|---|---|
| 305 | | | | | 310 | | | | | 315 | | | | | 320 |

| Ser | Leu | Val | Thr | Lys | Asp | Pro | Pro | His | Arg | Pro | His | Pro | His | Glu | Leu |
|---|---|---|---|---|---|---|---|---|---|---|---|---|---|---|---|
| | | | | 325 | | | | | 330 | | | | | 335 | |

| Val | Gly | Lys | Asp | Cys | Arg | Asp | Gly | Phe | Tyr | Glu | Ala | Glu | Leu | Cys | Pro |
|---|---|---|---|---|---|---|---|---|---|---|---|---|---|---|---|
| | | | 340 | | | | | 345 | | | | | 350 | | |

| Asp | Arg | Cys | Ile | His | Ser | Phe | Gln | Asn | Leu | Gly | Ile | Gln | Cys | Val | Lys |
|---|---|---|---|---|---|---|---|---|---|---|---|---|---|---|---|
| | | 355 | | | | | 360 | | | | | 365 | | | |

| Lys | Arg | Asp | Leu | Glu | Gln | Ala | Ile | Ser | Gln | Arg | Ile | Gln | Thr | Asn | Asn |
|---|---|---|---|---|---|---|---|---|---|---|---|---|---|---|---|
| 370 | | | | | 375 | | | | | 380 | | | | | |

-continued

```
Asn Pro Phe Gln Val Pro Ile Glu Glu Gln Arg Gly Asp Tyr Asp Leu
385                 390                 395                 400
Asn Ala Val Arg Leu Cys Phe Gln Val Thr Val Arg Asp Pro Ser Gly
                405                 410                 415
Arg Pro Leu Arg Leu Pro Pro Val Leu Pro His Pro Ile Phe Asp Asn
            420                 425                 430
Arg Ala Pro Asn Thr Ala Glu Leu Lys Ile Cys Arg Val Asn Arg Asn
        435                 440                 445
Ser Gly Ser Cys Leu Gly Gly Asp Glu Ile Phe Leu Leu Cys Asp Lys
    450                 455                 460
Val Gln Lys Glu Asp Ile Glu Val Tyr Phe Thr Gly Pro Gly Trp Glu
465                 470                 475                 480
Ala Arg Gly Ser Phe Ser Gln Ala Asp Val His Arg Gln Val Ala Ile
                485                 490                 495
Val Phe Arg Thr Pro Pro Tyr Ala Asp Pro Ser Leu Gln Ala Pro Val
            500                 505                 510
Arg Val Ser Met Gln Leu Arg Arg Pro Ser Asp Arg Glu Leu Ser Glu
        515                 520                 525
Pro Met Glu Phe Gln Tyr Leu Pro Asp Thr Asp Asp Arg His Arg Ile
    530                 535                 540
Glu Glu Lys Arg Lys Arg Thr Tyr Glu Thr Phe Lys Ser Ile Met Lys
545                 550                 555                 560
Lys Ser Pro Phe Ser Gly Pro Thr Asp Pro Arg Pro Pro Pro Arg Arg
                565                 570                 575
Ile Ala Val Pro Ser Arg Ser Ser Ala Ser Val Pro Lys Pro Ala Pro
            580                 585                 590
Gln Pro Tyr Pro Phe Thr Ser Ser Leu Ser Thr Ile Asn Tyr Asp Glu
        595                 600                 605
Phe Pro Thr Met Val Phe Pro Ser Gly Gln Ile Ser Gln Ala Ser Ala
    610                 615                 620
Leu Ala Pro Ala Pro Pro Gln Val Leu Pro Gln Ala Pro Ala Pro Ala
625                 630                 635                 640
Pro Ala Pro Ala Met Val Ser Ala Leu Ala Gln Ala Pro Ala Pro Val
                645                 650                 655
Pro Val Leu Ala Pro Gly Pro Pro Gln Ala Val Ala Pro Pro Ala Pro
            660                 665                 670
Lys Pro Thr Gln Ala Gly Glu Gly Thr Leu Ser Glu Ala Leu Leu Gln
        675                 680                 685
Leu Gln Phe Asp Asp Glu Asp Leu Gly Ala Leu Leu Gly Asn Ser Thr
    690                 695                 700
Asp Pro Ala Val Phe Thr Asp Leu Ala Ser Val Asp Asn Ser Glu Phe
705                 710                 715                 720
Gln Gln Leu Leu Asn Gln Gly Ile Pro Val Ala Pro His Thr Thr Glu
                725                 730                 735
Pro Met Leu Met Glu Tyr Pro Glu Ala Ile Thr Arg Leu Val Thr Gly
            740                 745                 750
Ala Gln Arg Pro Pro Asp Pro Ala Pro Leu Gly Ala Pro Gly
        755                 760                 765
Leu Pro Asn Gly Leu Leu Ser Gly Asp Glu Asp Phe Ser Ser Ile Ala
    770                 775                 780
Asp Met Asp Phe Ser Ala Leu Leu Ser Gln Ile Ser Ser
785                 790                 795
```